US009845477B2

(12) United States Patent
Flasinski et al.

(10) Patent No.: US 9,845,477 B2
(45) Date of Patent: Dec. 19, 2017

(54) PLANT REGULATORY ELEMENTS AND USES THEREOF

(75) Inventors: Stanislaw Flasinski, Chesterfield, MO (US); Barrett C. Foat, St. Louis, MO (US); Mohammed Oufattole, St. Louis, MO (US); Randall W. Shultz, St. Louis, MO (US); Xiaoping Wei, St. Louis, MO (US); Wei Wu, St. Louis, MO (US); Shiaw-Pyng Yang, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 668 days.

(21) Appl. No.: 14/117,342

(22) PCT Filed: May 11, 2012

(86) PCT No.: PCT/US2012/037561

§ 371 (c)(1), (2), (4) Date: Oct. 23, 2014

(87) PCT Pub. No.: WO2012/158535

PCT Pub. Date: Nov. 22, 2012

(65) Prior Publication Data

US 2015/0135362 A1 May 14, 2015

Related U.S. Application Data

(60) Provisional application No. 61/485,876, filed on May 13, 2011.

(51) Int. Cl.
*C12N 15/82* (2006.01)
*C07K 14/415* (2006.01)

(52) U.S. Cl.
CPC ........ *C12N 15/8216* (2013.01); *C07K 14/415* (2013.01)

(58) Field of Classification Search
None
See application file for complete search history.

(56) References Cited

U.S. PATENT DOCUMENTS

2004/0055039 A1 3/2004 Yamagata et al.
2012/0084885 A1* 4/2012 Alexandrov ....... C12N 15/8216 800/298

FOREIGN PATENT DOCUMENTS

JP 2001-346580 A 12/2001

OTHER PUBLICATIONS

Potenza et al., In Vitro Cell Dev Biol Plant 40:1-22 (2004).*
Saha et al., In Silico Biol 7(1):7-19 (2007).*
Donald & Cashmore, EMBO J 9:1717-26 (1990).*
Kim et al., Plant Mol Biol 24:105-17 (1994).*
Dolferus et al., Plant Physiol 105:1075-87 (1994).*
Loganantharaj, Int J Bioinf Res Appl 2:36-51 (2006).*
Welsch et al., Planta 216:523-34 (2003).*
Piechulla et al., Plant Mol Biol 38:655-62 (1998).*
Cho & Cosgrove, Plant Cell 14:3237-53 (2002).*
US PTO Written Description Guidelines (2008).*
GenBank Accession No. HN319913, dated Nov. 24, 2010.
GenBank Accession No. JG480182, dated Mar. 16, 2011.
Callis et al., "Introns increase gene expression in cultured maize cells," *Genes Dev.* 1:1183-1200, 1987.
Chee et al., "Expression of a bean storage protein 'phaseolin minigene' in foreign plant tissues," *Gene* 41:47-57, 1986.
Christiansen et al., "Maize polyubiquitin genes: structure, thermal perturbation of expression and transcript splicing, and promoter activity following transfer to protoplasts by electroporation," *Plant Mol. Biol.* 18:675-689, 1992.
Clancy et al., "Splicing of the maize Sh1 first intron is essential for enhancement of gene expression, and a T-rich motif increases expression without affecting splicing," *Plant Physiol.* 130(2):918-929, 2002.
Dean et al., "Sequences downstream of translation start regulate quantitative expression of two petunia rbcS genes," *Plant Cell* 1(2):201-208, 1989.
International Preliminary Report on Patentability regarding PCT Application No. PCT/US2012/037561, dated Nov. 19, 2013.
International Search Report regarding PCT Application No. PCT/US2012/037561, dated Sep. 12, 2012.
Jeon et al., "Tissue-preferential expression of a rice alpha-tubulin gene, OsTubA1, mediated by the first intron," *Plant Physiol.* 123(3):1005-1014, 2000.
Kuhlemeier et al., "Upstream sequences determine the difference in transcript abundance of pea rbcS genes," *Mol. Gen. Genet.* 212:405-411, 1988.
Lasserre et al., "Differential activation of two ACC oxidase gene promoters from melon during plant development and in response to pathogen attack," *Mol. Gen. Genet.* 256(3):211-222, 1997.
Leon et al., "Transient gene expression in protoplasts of *Phaseolus vulgaris* isolated from a cell suspension culture," *Plant Physiol.* 95(3):968-972, 1991.
Mascarenhas et al., "Intron-mediated enhancement of heterologous gene expression in maize," *Plant Mol. Biol.* 15(6):913-920, 1990.
McElroy et al., "Isolation of an efficient actin promoter for use in rice transformation," *Plant Cell* 2(2):163-171, 1990.
Norris et al., "The intron of *Arabidopsis thaliana* polyubiquitin genes is conserved in location and is a quantitative determinant of chimeric gene expression," *Plant Mol. Biol.* 21(5):895-906, 1993.
Rose et al., "Introns act post-transcriptionally to increase expression of the *Arabidopsis thaliana* tryptophan pathway gene PAT1 ," *Plant J.* 11(3):455-464, 1997.

(Continued)

*Primary Examiner* — Cathy Kingdon Worley
*Assistant Examiner* — Russell Boggs
(74) *Attorney, Agent, or Firm* — Dentons US LLP; Carine M. Doyle, Esq.

(57) ABSTRACT

The invention provides DNA molecules and constructs, including their nucleotide sequences, useful for modulating gene expression in plants and plant cells. Transgenic plants, plant cells, plant parts, seeds, and commodity products comprising the DNA molecules operably linked to heterologous transcribable polynucleotides are also provided, as are methods of their use.

14 Claims, 6 Drawing Sheets

(56) References Cited

OTHER PUBLICATIONS

Rose et al., "Intron-mediated enhancement of gene expression independent of unique intron sequences and splicing," *Plant Physiol.* 122(2):535-542, 2000.
Sherf et al., "Dual-luciferase reporter assay: an advanced co-reporter technology integrating firefly and Renilla luciferase assays," *Promega Notes Magazine* No. 57, p. 2, 1996.
Sinibaldi et al., "Intron splicing and intron-mediated enhanced expression in monocots," *Prog. Nucleic Acid Res. Mol. Biol.* (42):229-257, 1992.
Vancanneyt et al., "Construction of an intron-containing marker gene: splicing of the intron in transgenic plants and its use in monitoring early events in Agrobacterium-mediated plant transformation," *Mol. Gen. Genet.* 220(2):245-250, 1990.
Vasil et al., "Increased gene expression by the first intron of maize shrunken-1 locus in grass species," *Plant Physiol.* 91(4):1575-1579, 1989.
Xu et al., "Rice triosephosphate isomerase gene 5' sequence directs β-glucuronidase activity in transgenic tobacco but requires an intron for expression in rice," *Plant Physiol.* 106(2):459-467, 1994.
Yamagata et al., "TGTCACA motif is a novel cis-regulatory enhancer element involved in fruit-specific expression of the *cucumisin gene*," *J. Biol. Chem.* 227(13):11582-11590, 2002.
GenBank Accession No. HN314561, dated Nov. 24, 2010.
GenBank Accession No. JG468661, dated Mar. 16, 2011.
GenBank Accession No. HN298588, dated Nov. 24, 2010.
GenBank Accession No. JG469358, dated Mar. 16, 2011.
GenBank Accession No. HN327993, dated Nov. 24, 2010.
GenBank Accession No. JG467489, dated Mar. 16, 2011.
Office Action regarding Chilean Application No. 201601540, dated Jun. 14, 2017.
GenBank Accession No. LN713263, dated Mar. 5, 2015.
Office Action regarding Eurasian Application No. 201690416, dated Jul. 28, 2017.
GenBank Accession No. HN320890, dated Nov. 23, 2010.

* cited by examiner

```
P-CUCme.Ubq1-1:1:15 (SEQ ID NO: 2)    ATCTGAAAGGAACACCTAGCAAGGGGCTACTCTACAAGCATACTAAGTCTACAAAGCTAG
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    AGTTGTATGGTTATGCAGAAGACCTGGACAAAAGAAGATCACTCGCTGCTTTTACTTTTA
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    TCCTAAGAGGAAATGTGATTTTATGGAAGTTTAACCTATAGCCTGTAGTGGCACTATTCA
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)    CAACAAAAGTAAAGTTTATAGCCATGACTGAAGTTGTTAAAGAAGTCGTCTGGCTAAAAG
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    GACTACTTGAAGAACTTGGCTTCTTTTAACAGTCAGTAAACATCATGTGTGATAGTTAAA
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    GTGCAATACACTTGTCTAAAAATCTGCAATATCACGAAAGAACTAAGCATATTGATGTGA
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------
```

FIG. 1a

```
P-CUCme.Ubq1-1:1:15 (SEQ ID NO: 2)     AGCTATATGTCATTAGAGAAGTCATAGCAAAGAGAAAAGTAACAGTATCAAAGGTTCAGA
P-CUCme.Ubq1-1:1:16 (SEQ ID NO: 6)     ------------------------------------------------------------
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     CAAAAGAAAATGCAGCAGATATGTTGACTAAAATAGTTACTAATGCTAAACTCGAGCACT
P-CUCme.Ubq1-1:1:16 (SEQ ID NO: 6)     ------------------------------------------------------------
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     GCCTACAGTTGCTCAAGGTAATAGACTACTTAAAAGAATAGAATCAGAAGAAATAGTCAT
P-CUCme.Ubq1-1:1:16 (SEQ ID NO: 6)     ------------------------------------------------------------
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     TGGTAGCAATAAAATTCAAGGTGGAGGATTGTTAAAAAGAAGAGTGAATTTTATTACTTA
P-CUCme.Ubq1-1:1:16 (SEQ ID NO: 6)     ------------------------------------------------------------
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     AAGAAAATCTCGGTGAAACTCGAAAGATCTCGATTCGAAACTCTATTGCTTAAGAACCTG
P-CUCme.Ubq1-1:1:16 (SEQ ID NO: 6)     ---------TCGGTGAAACTCGAAAGATCTCGATTCGAAACTCTATTGCTTAAGAACCTG
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     GTGAAGCTCGAGAGATCTTGATACAATCCCAGTGCCCTAACTCTTCAACAAGCTAAGCAA
P-CUCme.Ubq1-1:1:16 (SEQ ID NO: 6)     GTGAAGCTCGAGAGATCTTGATACAATCCCAGTGCCCTAACTCTTCAACAAGCTAAGCAA
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------
```

FIG. 1b

```
P-CUCme.Ubq1-1:1:15 (SEQ ID NO: 2)      GTTGTACTGTGGGGCTCAATCTCGGTTCAATCTCGACGCACCTGATGCTTTGTTCCCTGT
P-CUCme.Ubq1-1:1:16 (SEQ ID NO: 6)      GTTGTACTGTGGGGCTCAATCTCGGTTCAATCTCGACGCACCTGATGCTTTGTTCCCTGT
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      CTACTCGATGAAGAAGCAATTACTTCTCAGGACAACTCGGTACCCCTAAATACAGATTTT
P-CUCme.Ubq1-1:1:16 (SEQ ID NO: 6)      CTACTCGATGAAGAAGCAATTACTTCTCAGGACAACTCGGTACCCCTAAATACAGATTTT
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      GAGCTTCGTGATCCTACAACTGAAATCAAATAGAAAAACTAATAAGTTAGTTAGAGTTTG
P-CUCme.Ubq1-1:1:16 (SEQ ID NO: 6)      GAGCTTCGTGATCCTACAACTGAAATCAAATAGAAAAACTAATAAGTTAGTTAGAGTTTG
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      TTATATTTACTGCCATTAAATAACTCTGTAATGTAAATAATAAACCATTTAACTCAATAT
P-CUCme.Ubq1-1:1:16 (SEQ ID NO: 6)      TTATATTTACTGCCATTAAATAACTCTGTAATGTAAATAATAAACCATTTAACTCAATAT
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      GAAATATAGAATGAGAAAAAGAAAAAGAAAAAGTTAAAGAGAGAGAGGAAGAAAACTCAT
P-CUCme.Ubq1-1:1:16 (SEQ ID NO: 6)      GAAATATAGAATGAGAAAAAGAAAAAGAAAAAGTTAAAGAGAGAGAGGAAGAAAACTCAT
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      TTTCAAATTCTCTATACTTGTTTGATCCTTGAATAAGTTGAATAAAAGCTCTATGGCGGC
P-CUCme.Ubq1-1:1:16 (SEQ ID NO: 6)      TTTCAAATTCTCTATACTTGTTTGATCCTTGAATAAGTTGAATAAAAGCTCTATGGCGGC
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------
```

FIG. 1c

```
P-CUCme.Ubq1-1:1:15 (SEQ ID NO: 2)    TTCAAAGTGGATGTAGGCACTATTAGTCGAACCACAATAAATTTGTTATGTTCTTTTGCT
P-CUCme.Ubq1-1:1:16 (SEQ ID NO: 6)    TTCAAAGTGGATGTAGGCACTATTAGTCGAACCACAATAAATTTGTTATGTTCTTTTGCT
P-CUCme.Ubq1-1:1:17 (SEQ ID NO: 8)    ------------------------AGTCGAACCACAATAAATTTGTTATGTTCTTTTGCT
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    ATTCCTTGTAATCTCCATAAATATTTTCTTACTAAGCTCTAGAAATCTGCTTGTCAAGAG
P-CUCme.Ubq1-1:1:16 (SEQ ID NO: 6)    ATTCCTTGTAATCTCCATAAATATTTTCTTACTAAGCTCTAGAAATCTGCTTGTCAAGAG
P-CUCme.Ubq1-1:1:17 (SEQ ID NO: 8)    ATTCCTTGTAATCTCCATAAATATTTTCTTACTAAGCTCTAGAAATCTGCTTGTCAAGAG
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    ATTAGGTATCATTTATGCCTTTTATATTTCCTTTCGGTTGCATATCTTGAGCTAGTTAAG
P-CUCme.Ubq1-1:1:16 (SEQ ID NO: 6)    ATTAGGTATCATTTATGCCTTTTATATTTCCTTTCGGTTGCATATCTTGAGCTAGTTAAG
P-CUCme.Ubq1-1:1:17 (SEQ ID NO: 8)    ATTAGGTATCATTTATGCCTTTTATATTTCCTTTCGGTTGCATATCTTGAGCTAGTTAAG
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    ATCGAGAGGTTACTGTTGTTGAAACCGAGATTAGTATCTTTGGATTAACACGTGCCTACC
P-CUCme.Ubq1-1:1:16 (SEQ ID NO: 6)    ATCGAGAGGTTACTGTTGTTGAAACCGAGATTAGTATCTTTGGATTAACACGTGCCTACC
P-CUCme.Ubq1-1:1:17 (SEQ ID NO: 8)    ATCGAGAGGTTACTGTTGTTGAAACCGAGATTAGTATCTTTGGATTAACACGTGCCTACC
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    AAAATTTGAAATTTTGTATTTACCCCATTCATTGGATAATAAGCAATTCTTATAGTGTTA
P-CUCme.Ubq1-1:1:16 (SEQ ID NO: 6)    AAAATTTGAAATTTTGTATTTACCCCATTCATTGGATAATAAGCAATTCTTATAGTGTTA
P-CUCme.Ubq1-1:1:17 (SEQ ID NO: 8)    AAAATTTGAAATTTTGTATTTACCCCATTCATTGGATAATAAGCAATTCTTATAGTGTTA
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    TCAATTAAACTCCTATAAAGTGTAATAATTGAATCCATGAACTATTTTCATATGTAATCT
P-CUCme.Ubq1-1:1:16 (SEQ ID NO: 6)    TCAATTAAACTCCTATAAAGTGTAATAATTGAATCCATGAACTATTTTCATATGTAATCT
P-CUCme.Ubq1-1:1:17 (SEQ ID NO: 8)    TCAATTAAACTCCTATAAAGTGTAATAATTGAATCCATGAACTATTTTCATATGTAATCT
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------
```

FIG. 1d

```
P-CUCme.Ubq1-1:1:15 (SEQ ID NO: 2)      TAATAAAATGAATTTAGAAGTTTAATTAAAATAATATATTTTGTATGCTATTTTTCAAAG
P-CUCme.Ubq1-1:1:16 (SEQ ID NO: 6)      TAATAAAATGAATTTAGAAGTTTAATTAAAATAATATATTTTGTATGCTATTTTTCAAAG
P-CUCme.Ubq1-1:1:17 (SEQ ID NO: 8)      TAATAAAATGAATTTAGAAGTTTAATTAAAATAATATATTTTGTATGCTATTTTTCAAAG
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      TTTGAAGAATGTGTTAATTGATACACATACAAAAAATCTAGGTTTTACATGAAAAACTAT
P-CUCme.Ubq1-1:1:16 (SEQ ID NO: 6)      TTTGAAGAATGTGTTAATTGATACACATACAAAAAATCTAGGTTTTACATGAAAAACTAT
P-CUCme.Ubq1-1:1:17 (SEQ ID NO: 8)      TTTGAAGAATGTGTTAATTGATACACATACAAAAAATCTAGGTTTTACATGAAAAACTAT
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      GGAAGTGAAAGATAGCATCTAATATTTTATGACACAAAATGCAAACTAATATATAAAGGA
P-CUCme.Ubq1-1:1:16 (SEQ ID NO: 6)      GGAAGTGAAAGATAGCATCTAATATTTTATGACACAAAATGCAAACTAATATATAAAGGA
P-CUCme.Ubq1-1:1:17 (SEQ ID NO: 8)      GGAAGTGAAAGATAGCATCTAATATTTTATGACACAAAATGCAAACTAATATATAAAGGA
P-CUCme.Ubq1-1:1:18 (SEQ ID NO: 10)     -----------------------------TGACACAAAATGCAAACTAATATATAAAGGA
P-CUCme.Ubq1-1:1:19 (SEQ ID NO: 12)     ------------------------------------------------------------

P-CUCme.Ubq1-1:1:15 (SEQ ID NO: 2)      TTTAATTAATTTTTATAGGTTTCAAATTTGTTAGACTTGTCAAATACAAAATTTTATTGA
P-CUCme.Ubq1-1:1:16 (SEQ ID NO: 6)      TTTAATTAATTTTTATAGGTTTCAAATTTGTTAGACTTGTCAAATACAAAATTTTATTGA
P-CUCme.Ubq1-1:1:17 (SEQ ID NO: 8)      TTTAATTAATTTTTATAGGTTTCAAATTTGTTAGACTTGTCAAATACAAAATTTTATTGA
P-CUCme.Ubq1-1:1:18 (SEQ ID NO: 10)     TTTAATTAATTTTTATAGGTTTCAAATTTGTTAGACTTGTCAAATACAAAATTTTATTGA
P-CUCme.Ubq1-1:1:19 (SEQ ID NO: 12)     ------------------------------------------------------------

P-CUCme.Ubq1-1:1:15 (SEQ ID NO: 2)      ACCAAATACATACAAACATCAAAATTAAGAACAGAAAATCTAAATTCAAATGAAATTTAT
P-CUCme.Ubq1-1:1:16 (SEQ ID NO: 6)      ACCAAATACATACAAACATCAAAATTAAGAACAGAAAATCTAAATTCAAATGAAATTTAT
P-CUCme.Ubq1-1:1:17 (SEQ ID NO: 8)      ACCAAATACATACAAACATCAAAATTAAGAACAGAAAATCTAAATTCAAATGAAATTTAT
P-CUCme.Ubq1-1:1:18 (SEQ ID NO: 10)     ACCAAATACATACAAACATCAAAATTAAGAACAGAAAATCTAAATTCAAATGAAATTTAT
P-CUCme.Ubq1-1:1:19 (SEQ ID NO: 12)     ------------------------------------------------------------

P-CUCme.Ubq1-1:1:15 (SEQ ID NO: 2)      TAATAGAAAAATTAGAAAAAAGAAAAAGAAAATAAAAGGAATCGTATTGTTTTTTCCTTC
P-CUCme.Ubq1-1:1:16 (SEQ ID NO: 6)      TAATAGAAAAATTAGAAAAAAGAAAAAGAAAATAAAAGGAATCGTATTGTTTTTTCCTTC
P-CUCme.Ubq1-1:1:17 (SEQ ID NO: 8)      TAATAGAAAAATTAGAAAAAAGAAAAAGAAAATAAAAGGAATCGTATTGTTTTTTCCTTC
P-CUCme.Ubq1-1:1:18 (SEQ ID NO: 10)     TAATAGAAAAATTAGAAAAAAGAAAAAGAAAATAAAAGGAATCGTATTGTTTTTTCCTTC
P-CUCme.Ubq1-1:1:19 (SEQ ID NO: 12)     ------------------------------------------------------------
```

FIG. 1e

```
P-CUCme.Ubq1-1:1:15 (SEQ ID NO: 2)    CTTTTTCCCATTTGAGAGGTGAATAAAGCTAATTGAGCTGCTCTAACTTCCTAATCTTTA
P-CUCme.Ubq1-1:1:16 (SEQ ID NO: 6)    CTTTTTCCCATTTGAGAGGTGAATAAAGCTAATTGAGCTGCTCTAACTTCCTAATCTTTA
P-CUCme.Ubq1-1:1:17 (SEQ ID NO: 8)    CTTTTTCCCATTTGAGAGGTGAATAAAGCTAATTGAGCTGCTCTAACTTCCTAATCTTTA
P-CUCme.Ubq1-1:1:18 (SEQ ID NO: 10)   CTTTTTCCCATTTGAGAGGTGAATAAAGCTAATTGAGCTGCTCTAACTTCCTAATCTTTA
P-CUCme.Ubq1-1:1:19 (SEQ ID NO: 12)   ------------------------------------------------------------

P-CUCme.Ubq1-1:1:15 (SEQ ID NO: 2)    TGCTTTCCCCATAAAGCTTTCCCAACTGCGCGTAATCGTATAAATGGAAAATTGACCTTT
P-CUCme.Ubq1-1:1:16 (SEQ ID NO: 6)    TGCTTTCCCCATAAAGCTTTCCCAACTGCGCGTAATCGTATAAATGGAAAATTGACCTTT
P-CUCme.Ubq1-1:1:17 (SEQ ID NO: 8)    TGCTTTCCCCATAAAGCTTTCCCAACTGCGCGTAATCGTATAAATGGAAAATTGACCTTT
P-CUCme.Ubq1-1:1:18 (SEQ ID NO: 10)   TGCTTTCCCCATAAAGCTTTCCCAACTGCGCGTAATCGTATAAATGGAAAATTGACCTTT
P-CUCme.Ubq1-1:1:19 (SEQ ID NO: 12)   -----------------------------------TCGTATAAATGGAAAATTGACCTTT

P-CUCme.Ubq1-1:1:15 (SEQ ID NO: 2)    CCAACTAGATTCTTCCAGAACTAAACAATACGTAACACGCAAGTAATCAAAGACACGTTT
P-CUCme.Ubq1-1:1:16 (SEQ ID NO: 6)    CCAACTAGATTCTTCCAGAACTAAACAATACGTAACACGCAAGTAATCAAAGACACGTTT
P-CUCme.Ubq1-1:1:17 (SEQ ID NO: 8)    CCAACTAGATTCTTCCAGAACTAAACAATACGTAACACGCAAGTAATCAAAGACACGTTT
P-CUCme.Ubq1-1:1:18 (SEQ ID NO: 10)   CCAACTAGATTCTTCCAGAACTAAACAATACGTAACACGCAAGTAATCAAAGACACGTTT
P-CUCme.Ubq1-1:1:19 (SEQ ID NO: 12)   CCAACTAGATTCTTCCAGAACTAAACAATACGTAACACGCAAGTAATCAAAGACACGTTT

P-CUCme.Ubq1-1:1:15 (SEQ ID NO: 2)    CATTTTCCTATAGAATATTATAGTTATTCGTGATTAACGGAAGTCGGCAATTTTAGGTAT
P-CUCme.Ubq1-1:1:16 (SEQ ID NO: 6)    CATTTTCCTATAGAATATTATAGTTATTCGTGATTAACGGAAGTCGGCAATTTTAGGTAT
P-CUCme.Ubq1-1:1:17 (SEQ ID NO: 8)    CATTTTCCTATAGAATATTATAGTTATTCGTGATTAACGGAAGTCGGCAATTTTAGGTAT
P-CUCme.Ubq1-1:1:18 (SEQ ID NO: 10)   CATTTTCCTATAGAATATTATAGTTATTCGTGATTAACGGAAGTCGGCAATTTTAGGTAT
P-CUCme.Ubq1-1:1:19 (SEQ ID NO: 12)   CATTTTCCTATAGAATATTATAGTTATTCGTGATTAACGGAAGTCGGCAATTTTAGGTAT

P-CUCme.Ubq1-1:1:15 (SEQ ID NO: 2)    AAATACGTGAATTCTCGAGCGCTAATTT
P-CUCme.Ubq1-1:1:16 (SEQ ID NO: 6)    AAATACGTGAATTCTCGAGCGCTAATTT
P-CUCme.Ubq1-1:1:17 (SEQ ID NO: 8)    AAATACGTGAATTCTCGAGCGCTAATTT
P-CUCme.Ubq1-1:1:18 (SEQ ID NO: 10)   AAATACGTGAATTCTCGAGCGCTAATTT
P-CUCme.Ubq1-1:1:19 (SEQ ID NO: 12)   AAATACGTGAATTCTCGAGCGCTAATTT
```

FIG. 1f

SEQUENCE LISTING

```
<160> NUMBER OF SEQ ID NOS: 212

<210> SEQ ID NO 1
<211> LENGTH: 2611
<212> TYPE: DNA
<213> ORGANISM: Cucumis melo

<400> SEQUENCE: 1

atctgaaagg aacacctagc aaggggctac tctacaagca tactaagtct acaaagctag     60

agttgtatgg ttatgcagaa gacctggaca aaagaagatc actcgctgct tttactttta    120

tcctaagagg aaatgtgatt ttatggaagt ttaacctata gcctgtagtg gcactattca    180

caacaaaagt aaagtttata gccatgactg aagttgttaa agaagtcgtc tggctaaaag    240

gactacttga agaacttggc ttcttttaac agtcagtaaa catcatgtgt gatagttaaa    300

gtgcaataca cttgtctaaa aatctgcaat atcacgaaag aactaagcat attgatgtga    360

agctatatgt cattagagaa gtcatagcaa agagaaaagt aacagtatca aaggttcaga    420

caaaagaaaa tgcagcagat atgttgacta aaatagttac taatgctaaa ctcgagcact    480

gcctacagtt gctcaaggta atagactact taaaagaata gaatcagaag aaatagtcat    540

tggtagcaat aaaattcaag gtggaggatt gttaaaaaga agagtgaatt ttattactta    600

aagaaaatct cggtgaaact cgaaagatct cgattcgaaa ctctattgct taagaacctg    660

gtgaagctcg agagatcttg atacaatccc agtgccctaa ctcttcaaca agctaagcaa    720

gttgtactgt ggggctcaat ctcggttcaa tctcgacgca cctgatgctt tgttccctgt    780

ctactcgatg aagaagcaat tacttctcag gacaactcgg taccccctaaa tacagatttt    840

gagcttcgtg atcctacaac tgaaatcaaa tagaaaaact aataagttag ttagagtttg    900

ttatatttac tgccattaaa taactctgta atgtaaataa taaaccattt aactcaatat    960

gaaatataga atgagaaaaa gaaaaagaaa aagttaaaga gagagaggaa gaaaactcat   1020
```

```
tttcaaattc tctatacttg tttgatcctt gaataagttg aataaaagct ctatggcggc   1080
ttcaaagtgg atgtaggcac tattagtcga accacaataa atttgttatg ttcttttgct   1140
attccttgta atctccataa atattttctt actaagctct agaaatctgc ttgtcaagag   1200
attaggtatc atttatgcct tttatatttc ctttcggttg catatcttga gctagttaag   1260
atcgagaggt tactgttgtt gaaaccgaga ttagtatctt tggattaaca cgtgcctacc   1320
aaaatttgaa attttgtatt taccccattc attggataat aagcaattct tatagtgtta   1380
tcaattaaac tcctataaag tgtaataatt gaatccatga actattttca tatgtaatct   1440
taataaaatg aatttagaag tttaattaaa ataatatatt ttgtatgcta tttttcaaag   1500
tttgaagaat gtgttaattg atacacatac aaaaaatcta ggttttacat gaaaaactat   1560
ggaagtgaaa gatagcatct aatattttat gacacaaaat gcaaactaat atataaagga   1620
tttaattaat ttttataggt ttcaaatttg ttagacttgt caaatacaaa attttattga   1680
accaaataca tacaaacatc aaaattaaga acagaaaatc taaattcaaa tgaaatttat   1740
taatagaaaa attagaaaaa agaaaaagaa aataaaagga atcgtattgt tttttccttc   1800
ctttttccca tttgagaggt gaataaagct aattgagctg ctctaacttc ctaatcttta   1860
tgctttcccc ataaagcttt cccaactgcg cgtaatcgta taaatggaaa attgaccttt   1920
ccaactagat tcttccagaa ctaaacaata cgtaacacgc aagtaatcaa agacacgttt   1980
cattttccta tagaatatta tagttattcg tgattaacgg aagtcggcaa ttttaggtat   2040
aaatacgtga attctcgagc gctaattttc catacagact cgaaatactc taaactttct   2100
catcgcgctt tattcctatt tcgtaattcg ctcttcttca acctctcaag gttttcatct   2160
tttctctatc ttctgttttc agattgcatc ttttcccccct cctgttcgat taattgatgt   2220
ttgaattttc gagaaacgat ttgaagtctt tgttgtattt ttcatttctg ttcgttaggt   2280
aggtcgattt ttaatcgtga tgtccgacgt tgttcggatg attcacattt ggtttttgtc   2340
atcttctttc tatgttgtga ttatcatgat ttttatcttt ttttcttctc aagatttgta   2400
atttatcgat tccccatggt tcttggtttt ttatacatgt attgaatctg gttactagaa   2460
ttatgttctt cgacggacgt ctttcagatt taaattgcat tgtaggaaat atgatttgct   2520
atctgagtaa cgtttttcca gagtattctt gattgcgcga tctatcttca attgttaaat   2580
tgtttttgtt taattggggt catgacaggt g                                  2611
```

<210> SEQ ID NO 2
<211> LENGTH: 2068
<212> TYPE: DNA
<213> ORGANISM: Cucumis melo

<400> SEQUENCE: 2

```
atctgaaagg aacacctagc aaggggctac tctacaagca tactaagtct acaaagctag     60
agttgtatgg ttatgcagaa gacctggaca aaagaagatc actcgctgct tttactttta    120
tcctaagagg aaatgtgatt ttatggaagt ttaacctata gcctgtagtg gcactattca    180
caacaaaagt aaagtttata gccatgactg aagttgttaa agaagtcgtc tggctaaaag    240
gactacttga agaacttggc ttcttttaac agtcagtaaa catcatgtgt gatagttaaa    300
gtgcaataca cttgtctaaa aatctgcaat atcacgaaag aactaagcat attgatgtga    360
agctatatgt cattagagaa gtcatagcaa agagaaaagt aacagtatca aaggttcaga    420
caaaagaaaa tgcagcagat atgttgacta aaatagttac taatgctaaa ctcgagcact    480
gcctacagtt gctcaaggta atagactact taaaagaata gaatcagaag aaatagtcat    540
```

tggtagcaat aaaattcaag gtggaggatt gttaaaaaga agagtgaatt ttattactta 600
aagaaaatct cggtgaaact cgaaagatct cgattcgaaa ctctattgct taagaacctg 660
gtgaagctcg agagatcttg atacaatccc agtgccctaa ctcttcaaca agctaagcaa 720
gttgtactgt ggggctcaat ctcggttcaa tctcgacgca cctgatgctt tgttccctgt 780
ctactcgatg aagaagcaat tacttctcag gacaactcgg taccccctaaa tacagatttt 840 gagcttcgtg atcctacaac tgaaatcaaa tagaaaaact aataagttag ttagagtttg 900
ttatatttac tgccattaaa taactctgta atgtaaataa taaaccattt aactcaatat 960
gaaatataga atgagaaaaa gaaaaagaaa aagttaaaga gagagaggaa gaaaactcat 1020
tttcaaattc tctatacttg tttgatcctt gaataagttg aataaaagct ctatggcggc 1080
ttcaaagtgg atgtaggcac tattagtcga accacaataa atttgttatg ttcttttgct 1140
attccttgta atctccataa atattttctt actaagctct agaaatctgc ttgtcaagag 1200
attaggtatc atttatgcct tttatatttc ctttcggttg catatcttga gctagttaag 1260
atcgagaggt tactgttgtt gaaaccgaga ttagtatctt tggattaaca cgtgcctacc 1320
aaaatttgaa attttgtatt taccccattc attggataat aagcaattct tatagtgtta 1380
tcaattaaac tcctataaag tgtaataatt gaatccatga actattttca tatgtaatct 1440
taataaaatg aatttagaag tttaattaaa ataatatatt ttgtatgcta tttttcaaag 1500
tttgaagaat gtgttaattg atacacatac aaaaaatcta ggttttacat gaaaaactat 1560
ggaagtgaaa gatagcatct aatattttat gacacaaaat gcaaactaat atataaagga 1620
tttaattaat ttttataggt ttcaaatttg ttagacttgt caaatacaaa attttattga 1680
accaaataca tacaaacatc aaaattaaga acagaaaatc taaattcaaa tgaaatttat 1740
taatagaaaa attagaaaaa agaaaaagaa aataaaagga atcgtattgt tttttccttc 1800
ctttttccca tttgagaggt gaataaagct aattgagctg ctctaacttc ctaatcttta 1860
tgctttcccc ataaagcttt cccaactgcg cgtaatcgta taaatggaaa attgaccttt 1920
ccaactagat tcttccagaa ctaaacaata cgtaacacgc aagtaatcaa agacacgttt 1980
cattttccta tagaatatta tagttattcg tgattaacgg aagtcggcaa ttttaggtat 2040
aaatacgtga attctcgagc gctaattt 2068

<210> SEQ ID NO 3
<211> LENGTH: 82
<212> TYPE: DNA
<213> ORGANISM: Cucumis melo

<400> SEQUENCE: 3
tccatacaga ctcgaaatac tctaaacttt ctcatcgcgc tttattccta tttcgtaatt 60
cgctcttctt caacctctca ag 82

<210> SEQ ID NO 4
<211> LENGTH: 461
<212> TYPE: DNA
<213> ORGANISM: Cucumis melo

<400> SEQUENCE: 4
gttttcatct tttctctatc ttctgttttc agattgcatc ttttccccct cctgttcgat 60
taattgatgt ttgaattttc gagaaacgat ttgaagtctt tgttgtattt ttcatttctg 120
ttcgttaggt aggtcgattt ttaatcgtga tgtccgacgt tgttcggatg attcacattt 180

-continued

```
ggtttttgtc atcttctttc tatgttgtga ttatcatgat ttttatcttt ttttcttctc    240

aagatttgta atttatcgat tccccatggt tcttggtttt ttatacatgt attgaatctg    300

gttactagaa ttatgttctt cgacggacgt ctttcagatt taaattgcat tgtaggaaat    360

atgatttgct atctgagtaa cgtttttcca gagtattctt gattgcgcga tctatcttca    420

attgttaaat tgtttttgtt taattggggt catgacaggt g                        461


<210> SEQ ID NO 5
<211> LENGTH: 2002
<212> TYPE: DNA
<213> ORGANISM: Cucumis melo

<400> SEQUENCE: 5

tcggtgaaac tcgaaagatc tcgattcgaa actctattgc ttaagaacct ggtgaagctc     60

gagagatctt gatacaatcc cagtgcccta actcttcaac aagctaagca agttgtactg    120

tggggctcaa tctcggttca atctcgacgc acctgatgct ttgttccctg tctactcgat    180

gaagaagcaa ttacttctca ggacaactcg gtacccctaa atacagattt tgagcttcgt    240

gatcctacaa ctgaaatcaa atagaaaaac taataagtta gttagagttt gttatattta    300

ctgccattaa ataactctgt aatgtaaata ataaaccatt taactcaata tgaaatatag    360

aatgagaaaa agaaaaagaa aaagttaaag agagagagga agaaaactca ttttcaaatt    420

ctctatactt gtttgatcct tgaataagtt gaataaaagc tctatggcgg cttcaaagtg    480

gatgtaggca ctattagtcg aaccacaata aatttgttat gttcttttgc tattccttgt    540

aatctccata aatattttct tactaagctc tagaaatctg cttgtcaaga gattaggtat    600

catttatgcc ttttatattt cctttcggtt gcatatcttg agctagttaa gatcgagagg    660

ttactgttgt tgaaaccgag attagtatct ttggattaac acgtgcctac caaaatttga    720

aattttgtat ttaccccatt cattggataa taagcaattc ttatagtgtt atcaattaaa    780

ctcctataaa gtgtaataat tgaatccatg aactattttc atatgtaatc ttaataaaat    840

gaatttagaa gtttaattaa aataatatat tttgtatgct atttttcaaa gtttgaagaa    900

tgtgttaatt gatacacata caaaaaatct aggttttaca tgaaaaacta tggaagtgaa    960

agatagcatc taatatttta tgacacaaaa tgcaaactaa tatataaagg atttaattaa   1020

tttttatagg tttcaaattt gttagacttg tcaaatacaa aattttattg aaccaaatac   1080

atacaaacat caaaattaag aacagaaaat ctaaattcaa atgaaattta ttaatagaaa   1140

aattagaaaa aagaaaaaga aaataaaagg aatcgtattg ttttttcctt ccttttcccc   1200

atttgagagg tgaataaagc taattgagct gctctaactt cctaatcttt atgctttccc   1260

cataaagctt tcccaactgc gcgtaatcgt ataaatggaa aattgacctt tccaactaga   1320

ttcttccaga actaaacaat acgtaacacg caagtaatca aagacacgtt tcattttcct   1380

atagaatatt atagttattc gtgattaacg gaagtcggca attttaggta taaatacgtg   1440

aattctcgag cgctaatttt ccatacagac tcgaaatact ctaaactttc tcatcgcgct   1500

ttattcctat ttcgtaattc gctcttcttc aacctctcaa ggttttcatc ttttctctat   1560

cttctgtttt cagattgcat cttttccccc tcctgttcga ttaattgatg tttgaatttt   1620

cgagaaacga tttgaagtct ttgttgtatt tttcatttct gttcgttagg taggtcgatt   1680

tttaatcgtg atgtccgacg ttgttcggat gattcacatt tggtttttgt catcttcttt   1740

ctatgttgtg attatcatga tttttatctt tttttcttct caagatttgt aatttatcga   1800

ttccccatgg ttcttggttt tttatacatg tattgaatct ggttactaga attatgttct   1860
```

tcgacggacg tctttcagat ttaaattgca ttgtaggaaa tatgatttgc tatctgagta 1920
acgtttttcc agagtattct tgattgcgcg atctatcttc aattgttaaa ttgtttttgt 1980
ttaattgggg tcatgacagg tg 2002

<210> SEQ ID NO 6
<211> LENGTH: 1459
<212> TYPE: DNA
<213> ORGANISM: Cucumis melo

<400> SEQUENCE: 6
tcggtgaaac tcgaaagatc tcgattcgaa actctattgc ttaagaacct ggtgaagctc 60
gagagatctt gatacaatcc cagtgcccta actcttcaac aagctaagca agttgtactg 120
tggggctcaa tctcggttca atctcgacgc acctgatgct ttgttccctg tctactcgat 180
gaagaagcaa ttacttctca ggacaactcg gtacccctaa atacagattt tgagcttcgt 240
gatcctacaa ctgaaatcaa atagaaaaac taataagtta gttagagttt gttatattta 300
ctgccattaa ataactctgt aatgtaaata ataaaccatt taactcaata tgaaatatag 360
aatgagaaaa agaaaaagaa aaagttaaag agagagagga agaaaactca ttttcaaatt 420
ctctatactt gtttgatcct tgaataagtt gaataaaagc tctatggcgg cttcaaagtg 480
gatgtaggca ctattagtcg aaccacaata aatttgttat gttcttttgc tattccttgt 540
aatctccata aatattttct tactaagctc tagaaatctg cttgtcaaga gattaggtat 600
catttatgcc ttttatattt cctttcggtt gcatatcttg agctagttaa gatcgagagg 660
ttactgttgt tgaaaccgag attagtatct ttggattaac acgtgcctac caaaatttga 720
aattttgtat ttaccccatt cattggataa taagcaattc ttatagtgtt atcaattaaa 780
ctcctataaa gtgtaataat tgaatccatg aactattttc atatgtaatc ttaataaaat 840
gaatttagaa gtttaattaa aataatatat tttgtatgct atttttcaaa gtttgaagaa 900
tgtgttaatt gatacacata caaaaaatct aggttttaca tgaaaaacta tggaagtgaa 960
agatagcatc taatatttta tgacacaaaa tgcaaactaa tatataaagg atttaattaa 1020
tttttatagg tttcaaattt gttagacttg tcaaatacaa aattttattg aaccaaatac 1080
atacaaacat caaaattaag aacagaaaat ctaaattcaa atgaaattta ttaatagaaa 1140
aattagaaaa aagaaaaaga aaataaaagg aatcgtattg ttttttcctt cctttttccc 1200
atttgagagg tgaataaagc taattgagct gctctaactt cctaatcttt atgctttccc 1260
cataaagctt tcccaactgc gcgtaatcgt ataaatggaa aattgacctt tccaactaga 1320
ttcttccaga actaaacaat acgtaacacg caagtaatca aagacacgtt tcattttcct 1380
atagaatatt atagttattc gtgattaacg gaagtcggca attttaggta taaatacgtg 1440
aattctcgag cgctaattt 1459

<210> SEQ ID NO 7
<211> LENGTH: 1507
<212> TYPE: DNA
<213> ORGANISM: Cucumis melo

<400> SEQUENCE: 7
agtcgaacca caataaattt gttatgttct tttgctattc cttgtaatct ccataaatat 60
tttcttacta agctctagaa atctgcttgt caagagatta ggtatcattt atgcctttta 120
tatttccttt cggttgcata tcttgagcta gttaagatcg agaggttact gttgttgaaa 180
ccgagattag tatctttgga ttaacacgtg cctaccaaaa tttgaaattt tgtatttacc 240
ccattcattg gataataagc aattcttata gtgttatcaa ttaaactcct ataaagtgta 300
ataattgaat ccatgaacta ttttcatatg taatcttaat aaaatgaatt tagaagttta 360
attaaaataa tatattttgt atgctatttt tcaaagtttg aagaatgtgt taattgatac 420
acatacaaaa aatctaggtt ttacatgaaa aactatggaa gtgaaagata gcatctaata 480
ttttatgaca caaaatgcaa actaatatat aaaggattta attaattttt ataggtttca 540
aatttgttag acttgtcaaa tacaaaattt tattgaacca aatacataca aacatcaaaa 600
ttaagaacag aaaatctaaa ttcaaatgaa atttattaat agaaaaatta gaaaaaagaa 660
aaagaaaata aaaggaatcg tattgttttt tccttccttt ttcccatttg agaggtgaat 720
aaagctaatt gagctgctct aacttcctaa tctttatgct ttccccataa agctttccca 780
actgcgcgta atcgtataaa tggaaaattg acctttccaa ctagattctt ccagaactaa 840
acaatacgta acacgcaagt aatcaaagac acgtttcatt ttcctataga atattatagt 900
tattcgtgat taacggaagt cggcaatttt aggtataaat acgtgaattc tcgagcgcta 960
attttccata cagactcgaa atactctaaa ctttctcatc gcgctttatt cctatttcgt 1020
aattcgctct tcttcaacct ctcaaggttt tcatcttttc tctatcttct gttttcagat 1080
tgcatctttt ccccctcctg ttcgattaat tgatgtttga attttcgaga aacgatttga 1140
agtctttgtt gtatttttca tttctgttcg ttaggtaggt cgatttttaa tcgtgatgtc 1200
cgacgttgtt cggatgattc acatttggtt tttgtcatct tctttctatg ttgtgattat 1260
catgattttt atcttttttt cttctcaaga tttgtaattt atcgattccc catggttctt 1320
ggttttttat acatgtattg aatctggtta ctagaattat gttcttcgac ggacgtcttt 1380
cagatttaaa ttgcattgta ggaaatatga tttgctatct gagtaacgtt tttccagagt 1440
attcttgatt gcgcgatcta tcttcaattg ttaaattgtt tttgtttaat tggggtcatg 1500
acaggtg 1507

<210> SEQ ID NO 8
<211> LENGTH: 964
<212> TYPE: DNA
<213> ORGANISM: Cucumis melo

<400> SEQUENCE: 8
agtcgaacca caataaattt gttatgttct tttgctattc cttgtaatct ccataaatat 60
tttcttacta agctctagaa atctgcttgt caagagatta ggtatcattt atgcctttta 120
tatttccttt cggttgcata tcttgagcta gttaagatcg agaggttact gttgttgaaa 180
ccgagattag tatctttgga ttaacacgtg cctaccaaaa tttgaaattt tgtatttacc 240
ccattcattg gataataagc aattcttata gtgttatcaa ttaaactcct ataaagtgta 300
ataattgaat ccatgaacta ttttcatatg taatcttaat aaaatgaatt tagaagttta 360
attaaaataa tatattttgt atgctatttt tcaaagtttg aagaatgtgt taattgatac 420
acatacaaaa aatctaggtt ttacatgaaa aactatggaa gtgaaagata gcatctaata 480
ttttatgaca caaaatgcaa actaatatat aaaggattta attaattttt ataggtttca 540
aatttgttag acttgtcaaa tacaaaattt tattgaacca aatacataca aacatcaaaa 600
ttaagaacag aaaatctaaa ttcaaatgaa atttattaat agaaaaatta gaaaaaagaa 660
aaagaaaata aaaggaatcg tattgttttt tccttccttt ttcccatttg agaggtgaat 720
aaagctaatt gagctgctct aacttcctaa tctttatgct ttccccataa agctttccca 780

-continued actgcgcgta atcgtataaa tggaaaattg acctttccaa ctagattctt ccagaactaa 840
acaatacgta acacgcaagt aatcaaagac acgtttcatt ttcctataga atattatagt 900
tattcgtgat taacggaagt cggcaatttt aggtataaat acgtgaattc tcgagcgcta 960
attt 964

<210> SEQ ID NO 9
<211> LENGTH: 1022
<212> TYPE: DNA
<213> ORGANISM: Cucumis melo

<400> SEQUENCE: 9
tgacacaaaa tgcaaactaa tatataaagg atttaattaa tttttatagg tttcaaattt 60
gttagacttg tcaaatacaa aattttattg aaccaaatac atacaaacat caaaattaag 120
aacagaaaat ctaaattcaa atgaaattta ttaatagaaa aattagaaaa aagaaaaaga 180
aaataaaagg aatcgtattg ttttttcctt cctttttccc atttgagagg tgaataaagc 240
taattgagct gctctaactt cctaatcttt atgctttccc cataaagctt tcccaactgc 300
gcgtaatcgt ataaatggaa aattgacctt tccaactaga ttcttccaga actaaacaat 360
acgtaacacg caagtaatca aagacacgtt tcattttcct atagaatatt atagttattc 420
gtgattaacg gaagtcggca attttaggta taaatacgtg aattctcgag cgctaatttt 480
ccatacagac tcgaaatact ctaaactttc tcatcgcgct ttattcctat ttcgtaattc 540
gctcttcttc aacctctcaa ggttttcatc ttttctctat cttctgtttt cagattgcat 600
cttttccccc tcctgttcga ttaattgatg tttgaatttt cgagaaacga tttgaagtct 660
ttgttgtatt tttcatttct gttcgttagg taggtcgatt tttaatcgtg atgtccgacg 720
ttgttcggat gattcacatt tggtttttgt catcttcttt ctatgttgtg attatcatga 780
tttttatctt tttttcttct caagatttgt aatttatcga ttccccatgg ttcttggttt 840
tttatacatg tattgaatct ggttactaga attatgttct tcgacggacg tctttcagat 900
ttaaattgca ttgtaggaaa tatgatttgc tatctgagta acgtttttcc agagtattct 960
tgattgcgcg atctatcttc aattgttaaa ttgtttttgt ttaattgggg tcatgacagg 1020
tg 1022

<210> SEQ ID NO 10
<211> LENGTH: 479
<212> TYPE: DNA
<213> ORGANISM: Cucumis melo

<400> SEQUENCE: 10
tgacacaaaa tgcaaactaa tatataaagg atttaattaa tttttatagg tttcaaattt 60
gttagacttg tcaaatacaa aattttattg aaccaaatac atacaaacat caaaattaag 120
aacagaaaat ctaaattcaa atgaaattta ttaatagaaa aattagaaaa aagaaaaaga 180
aaataaaagg aatcgtattg ttttttcctt cctttttccc atttgagagg tgaataaagc 240
taattgagct gctctaactt cctaatcttt atgctttccc cataaagctt tcccaactgc 300
gcgtaatcgt ataaatggaa aattgacctt tccaactaga ttcttccaga actaaacaat 360
acgtaacacg caagtaatca aagacacgtt tcattttcct atagaatatt atagttattc 420
gtgattaacg gaagtcggca attttaggta taaatacgtg aattctcgag cgctaattt 479

<210> SEQ ID NO 11

<211> LENGTH: 716
<212> TYPE: DNA
<213> ORGANISM: Cucumis melo

<400> SEQUENCE: 11
tcgtataaat ggaaaattga cctttccaac tagattcttc cagaactaaa caatacgtaa 60
cacgcaagta atcaaagaca cgtttcattt tcctatagaa tattatagtt attcgtgatt 120
aacggaagtc ggcaatttta ggtataaata cgtgaattct cgagcgctaa ttttccatac 180
agactcgaaa tactctaaac tttctcatcg cgctttattc ctatttcgta attcgctctt 240
cttcaacctc tcaaggtttt catcttttct ctatcttctg ttttcagatt gcatcttttc 300
cccctcctgt tcgattaatt gatgtttgaa ttttcgagaa acgatttgaa gtctttgttg 360
tatttttcat ttctgttcgt taggtaggtc gatttttaat cgtgatgtcc gacgttgttc 420
ggatgattca catttggttt ttgtcatctt ctttctatgt tgtgattatc atgattttta 480
tctttttttc ttctcaagat ttgtaattta tcgattcccc atggttcttg gtttttttata 540 catgtattga atctggttac tagaattatg ttcttcgacg gacgtctttc agatttaaat 600
tgcattgtag gaaatatgat ttgctatctg agtaacgttt ttccagagta ttcttgattg 660
cgcgatctat cttcaattgt taaattgttt ttgtttaatt ggggtcatga caggtg 716

<210> SEQ ID NO 12
<211> LENGTH: 173
<212> TYPE: DNA
<213> ORGANISM: Cucumis melo

<400> SEQUENCE: 12
tcgtataaat ggaaaattga cctttccaac tagattcttc cagaactaaa caatacgtaa 60
cacgcaagta atcaaagaca cgtttcattt tcctatagaa tattatagtt attcgtgatt 120
aacggaagtc ggcaatttta ggtataaata cgtgaattct cgagcgctaa ttt 173

<210> SEQ ID NO 13
<211> LENGTH: 2000
<212> TYPE: DNA
<213> ORGANISM: Cucumis melo

<400> SEQUENCE: 13
cttattcagc gctttcctgt aaaattaaag acttgatgag ggagaaaaag aaaaccggtt 60
cgcagcttca agaagacggc ttccgaataa gaatcagata ctcgatgatg gggaaacaat 120
aacaaagata tcaaaagaaa tcatgaaaca tagcataaga acgaaaaccc agaggtgaag 180
aacagtgccc aaacgcaact ttacccaaag aacatgtata aaacgtcttc cagacgttca 240
aaataagaaa gtggacaaaa tcaaagctac aaacgatctc caataactag atggaaaaca 300
ctaattgcac tagagatttt gaatgctttg ttgttgattt ataatcctcg acttccaaga 360
aaaagtaaca agtagaaatg aacgaatcag atccgcaatc gaagatctga aggcaagata 420
aggtaaggct aaagaaccat aggaaaacgg taaaaacgtc caaaacagtg tgagaaatat 480
cgcagattca aaggtccgaa ccctaagaac ggtgttatgc agctataaag gtgagaatca 540
aaaccctcta tccataacgt ggacggcgcg gttgaatcat tgtcttgttc cttgaaactg 600
aaggtatgcg agacatagaa ttcgatctca ctattatctt ctaatcaacg acgaagtaaa 660
gaagtgaaat ccagaacaaa gaatggagaa ttggaaatga caagaaaaac ggcagaggaa 720
agtggaaaag tgaaagcgga ctcacctaga tcaatgccct tggctggtcg agcttcagga 780
acctgtcgtc ggagagaaag agaaagagaa aagagcaaga gagagagaga gagagcacaa 840

```
ggagaagaga acgaggacaa tggaggcttt tgtttcgata ctccctgatc tggaattcta    900

taataacata actataaact tctctgggtt ggcccatcat cacgtatatt gggcttttag    960

cccaattatt tgttcactgc tcatgggccg gtgattttgg gctttcttct gggccttggt   1020

acataacaac ccagtatatg acgtattttc ggtgatagct attttcaaga acaccaactt   1080

ttttgttcaa caatgtggag atcaaataac agtatgtata tatacacaaa catatgctca   1140

tttatgaaaa atagaaagaa aaagaatgtt ggtaatttgt tacaaaatta taatttctct   1200

ctctttgttt gatttcatga acggtgtgtt ctatataaaa caatgaaata acataattat   1260

taaaatgatt cttaaaacat gatgatttca atattcatgg tttacatttg gtgggatgat   1320

tcgtttaatt attattgata atgtatagtt attgtgtgtc ccgttttctt tttctttggt   1380

ggaagaaaag aaaaaagtag gaaggcatgt aatattgcga tccttcacgg gacagatcca   1440

ttttccaatg tgatcgagta ctagttaggt ggagagtgga agaatcttcg tgcatgcata   1500

aatcaagtca caacttgcca atttggaaag aatcatgtta tattctacct ttactttcaa   1560

gtagggttaa gtgaattaga ccacaacgaa gcaatcaagt ccaaccaaac tcacttaggt   1620

caagcagttt agtgatatag acaggtcagt ggtcgttttt ttaatactaa gaaatgtcaa   1680

ttctatctag ttgactatta ttcatataga aggagaaaaa tgataactat gattgtccca   1740

caaacaacaa ctaccgatcg atctaaacca acaagtcgat gattggtgcc actttaaatt   1800

taaatctgac gccactcaat tgatgatcac ccctattcaa gcacacaaga acgcatgctc   1860

ttaaaacatt tggtaatatg attggaatta gtacaaaatg tttattcgat ctatacaaac   1920

aactcctttt taacacaaat gttttattgt actttcccgt gaaatggggt tagtaaaact   1980

atggagttaa taaaacataa                                               2000
```

<210> SEQ ID NO 14
<211> LENGTH: 2000
<212> TYPE: DNA
<213> ORGANISM: Cucumis melo

<400> SEQUENCE: 14

```
tataacaaaa tatgtgaaat tagccattat gtttgtcctt tcgttcttct tattcacttc     60

gttgcgattt ctttctatcg tctatcgtct ttcttctttt ttctgttgaa atttattttc    120

atcgtttttc ttctttttcc atcgtgaaaa aaatagtcaa atctaaatga tcgtgtataa    180

agaataaacg atcgtgtaga caaatctaaa tggtcgaata ttaagaaaat tgataggaaa    240

atttattcat tagaaaaatt ttagtaagaa aaattagaaa tgaaagggtt gaaccagaaa    300

gaaataaaag taatagacaa atgaaaattt taaataaaaa gaaatttggg atgggtgcat    360

ttactattta gtcttgagtt ttaattcttt tattacttta cataagatgt attaaattaa    420

agaggtaaga tagaattttt ttttaaaaaa aactatcatt agtaaattta acaaaagtga    480

catagcacca ttttcgttaa aagaataatt gttttatgta gtaaaattgg tagaaatatt    540

ttttaagtat agcaaaatat ctttgtcttt ttatatcttt cactgacaga taataataat    600

ttattaatat atcatttata tagtcccatt ttcggtaaat tttaatattt gaacataaaa    660

cactatttaa aataatgaaa aaaaacttta caaacttttt tatttttatt atatttgtaa    720

atatttctaa aaaattttac atttaaaata atattttcaa ggttaataca gaagaaaaaa    780

aacaaaaaaa gaggaaaagg caatttaaga agaatgacaa gaaaatcggg aggtggtgtg    840

gctaagagga agaagggacc ggttcttcaa gatccaacgc tccacattca atctcacttc    900
```

```
cttcttcaat tccgtcttct ccgtttcctc ctttatatgc ttctctcttt ccctcccttt    960

ctttctctcc ttcaatcaat caatcaatca atcaatcaat cctcccattc ccattacatt   1020

gccaaaaggt tctattctca ttctctacat ccatttccct ttctttcctt cttcttcctc   1080

tgtttcttct tcgtttcctt gattcatttc tctttgtacg ttccttcctt ccttctgcat   1140

tttgattatt ttcttttgtt ttacgtccgg aattgcaatg tggtttatct ttatttctgt   1200

ttttggacgt caagatgcct gttgttttta acattttgat ttgattcatc gttcatggcg   1260

taatcatgtc ttttggaatt gtttgaaatc caaggatcac attgatttca ctattgtttc   1320

atttgttctt ttttgttaat tttgtataat gaatcgtata ggggatcatt tttccattgg   1380

ttctcttgaa aatctttaag agttgcatta tgtatactaa gtctctctta tggcgtctgt   1440

ttgagtgaga attgataaaa gatccatggg aggaagaagt tttctttcat gaggcttggt   1500

tttattcagc tgtttcttct cgttgcaatt tgttgaagaa gggacatggg tatcttttac   1560

atcaaagtat aactaactat ataattcaat ttggttgata aagtagatac atgtaggagt   1620

caaccgattt gagtgtataa taatgttgtt atgtcccttg caacttaatg tagtgcatat   1680

ttgggagtga ttataaaatt gtataaatca ttttatgttt agaatcatct tgaaacacgt   1740

tttttagtat ttaaaaacta atttaatatt tagttttgca cttttaaatg aaatttttgt   1800

ttcactaata ttagttttga ttcattaaat gcatgctcca tcgtaatatt aaaagtaact   1860

agtgatttta accattttat aatcacatgt ctgtgatata gtgaagtgta cggctgcctt   1920

gttgagaatt gttacccttt agaagaaaca caggatgtat ttgatgttta acttgcattt   1980

tcttctggca ggcttagaaa                                               2000
```

<210> SEQ ID NO 15
<211> LENGTH: 1990
<212> TYPE: DNA
<213> ORGANISM: Cucumis melo

<400> SEQUENCE: 15

```
tatttgtaca atgaaaatat ttatttcttt tctcgattct ttaacaaaag ttcaaaatct     60

tttatcataa atacaaatat ttagtaattt aagtttagac taggtgtatc agatgtgcac    120

caagtgtata ttacgtgcat caagtatata tcaaatgtgt accaaacgta tatcacgtgt    180

atcaagtgtg tatcaagtgt ctatttgaag tcaagtgcat taagaatata tcacatgtgt    240

accaaatata tcaaaataaa tactgattga gcatcaagta tgtctattag tagtgtatca    300

agtgtattaa ttaagtttgt agcaaaggtg tatcatgatg tataacgtgt attatgtggg    360

ttggtttttt tttttttttg tcatttttgc aaaagtaatt aagtttgtgt tatgaaccta    420

atttttttaaa tttcttttg tcacgtataa gagacttgaa aataggttta aaaggtctta    480

agggtatttt agtttgactt ttttaaaaag tatttatatg atatttaaaa attagaattt    540

tttagaaaga ataggagttt tataaattat tcttttaaga aaaattgcat cagatgacaa    600

aaaaaattta gaaataagca gcccataata actctttaaa tttgctatca gacgactatc    660

cgagggttat catcttttaa atttgctact tttacaattt agaaaatgta gtgacatgga    720

ccctattatc ataagatttt tttttgctat ttttgcaaac acatgttctt ttaaaatgac    780

ataattattt aaaataaaaa tataaagtta tttgatggat cttttgaacc tatttttaaa    840

agctaaagta ctaaaaagat acatattgaa aacttgaggt caaatgggct attattataa    900

atatgtggac taaaaatgta catttctaaa acttagagac taaatgcaca tatttaaaaa    960

agcatgtgaa ctaaaaaagt cgtttttcct aatattttt tacaacaatg actaaattga   1020
```

```
acctcaaatt tgaagggtgg aaaaccatac taattattca ctaatgaact aaactcattt   1080
gatgatttca agacatatga ggttcattga gtagttgggt ttgaggggat gaaatgagtg   1140
gtggaagaaa gtttatgtaa cgacccaacg aaataggaag gtcatcccaa ggaagtcgca   1200
catccaatga gtaattacca caaaacaacc tctccttttt tctcaaattc ccttttaata   1260
aataatttga ttccccattc cttcctttct cccttggcag ccttctcctt ttttcaaagg   1320
tttttgtttt ttcttttctt ttttaaattt cattcctttg tttctctctt tctttcttca   1380
ttaacattct tcttatttcc tcattactga tcatctcctt ttcttggtat tattcttctt   1440
tcttttctca aagttttgtt tttcattgat gtagatgttt ttgtatcaat caatggaaat   1500
ttgagttttt cttatctcat tgtatcatca ttgagtgtgt gtttatgtta gggatccatt   1560
attaggatgg atgagaatca taatttcatt gctaatctat gaaccatgaa taaagaaatc   1620
taaatccaac atagaagata gaacatttgc attgtgttat gagtaaccag ctctgtcact   1680
tcaattggtt cttctacaca tttgatggca atggctttgt ttgatattcg tgatggcatc   1740
taagcattgg ttcttcctat gtttttcgtt ggctcttggt ttgatttgca attagtgaag   1800
agcatgtttg gaatgaatga gttgaaatca cctttaacat ttttaaaatc actttaaata   1860
ttaaattaat tttgagtgat aaaagtaatt tttaacaatga taaaattact ttcaaatgtg   1920
ggccgaatca aattgtctag aatgtttagg gttctccaac taatagcaat ttatccaaac   1980
agggtaaaaa                                                          1990
```

<210> SEQ ID NO 16
<211> LENGTH: 2005
<212> TYPE: DNA
<213> ORGANISM: Cucumis melo

<400> SEQUENCE: 16

```
ttgttagagg agttagcttt tcagggagtc ggttacaact tacaagacag acaaccatac     60
tgtacaatca atcactactg cctcaaagtc gaaaccattt aataccagtt gagcctcatt    120
gtgactgcat aattttgacc cctaccacga ggtaatttca gttcaaatca attgtatctc    180
tcttctggat atcagtcaag aatctcatgt tctcaagtta tagtacattg ataattactg    240
tgcattttta ttaatttatg agttaaaatc ctgctgatta attcaactaa aggaataaaa    300
tagttattgg catttggatg agaatagaat gtgaatccca tcattcatcg ctagattgga    360
ccgtaattat aagtgagagg gagaaacttc tgttgctatt ccctttttat ttcttaattc    420
atttataaat tgtttttagg ccttttatat atatatattt ctaccatttt tacatttaaa    480
attcttttaa ctttattatg tatggactca aactaacaag ctttatttga taaaattgtt    540
caaactatta tattagtttt atatttgtaa accataaaac aaatccataa aattccacct    600
gcatcactca ctcatgttgt tgaatggtac gaaataaaca atacatgtga aagatgaaaa    660
taagaattgt tctcttatta aatctaaaat ctagattttc tttttagtac atttaacact    720
tcaatgaaag gtctaaaaca ttattgaatg acgtcacgaa ctattacaaa agattattcc    780
gatttatctc aaaaggggtc tatttcacta attttggtgt cccacatctg taaagagaat    840
tttcgtgata tgtgtagata tttaaatata attgaattcg atgaaagcaa agcaagaatc    900
gatatccgta gttattttga tatagatcgg tgataaataa aagacaatat gcataaagtt    960
tgtgggtaca gagtcggcta gttgcaatga ggggtatggc cccaagactt ttccccaacc   1020
ccaacggtca attaatcacc ccaatggggc atcgaatctt ccccaccatt ttccttttct   1080
```

tcgccgactc ttctacccat ctcttttgcc gactctttct cacaggtttg attaaatccc 1140
attcatattc agatacacta tttcaaaata actcgcaaat taatttgttt tttaaatatt 1200
ggtataataa taaaattaat tataaattgt gacctaaaaa gtactttgtg gaagagggga 1260
tatagtctgt ctaatatatt attgattaaa tatataatag aaccataaat gcaaaccact 1320
agaattgtta ataaaaatca acgctctttt aagtctttcc atagaaagaa aggcaaagac 1380
gcgcaacgtc tagaattttc tttataacgg aagctaactc tgttataacg gccgtccaca 1440
taatatggta gatttaaaat gacgtcagca tgtcgcttct aaatttgggt ccaaaggggg 1500
gattcattta tagggaaggg aaacggcaaa tgcaagcata gtgagtaaat acgtggcggc 1560
aaagtaatgg ataattctgc ctctgccgtg acgacattgc ccttccattt cactataaat 1620
acacctcctc tatccctcga tttcttcgca attgaatttc tcttctcatc tctgtcgtag 1680
caaaccaaat cgatttcttc aaaggtattt cttcctttcc tttttttttt tttttttttt 1740
tttttaaatc atgttgttca aactttgaga gatgaaatga ttaggggctt tcaaagtggt 1800
tttcgtttga tatgtttctt agatcgatag ggtttagaat cgagcatcct tgtaggtatc 1860
ctgaggtttg gtggttggat ctgcttaatt tttatgtggt tgcatggaaa attgggattt 1920
tttttttcta attacgtgat tctggaaata ttgatctgtg gttcagatgg aattgaatct 1980
gatctttctg ttttgttctg tatag 2005

<210> SEQ ID NO 17
<211> LENGTH: 2004
<212> TYPE: DNA
<213> ORGANISM: Cucumis melo

<400> SEQUENCE: 17
tagaaaaaaa ttgaagatct tcttaatgct aataataaaa gcatatataa aaaggcttca 60
tattacacaa gcatcttaaa accaaaccga acttgatttg aaattatccc actaattctg 120
tagatttcac caaagtcctt aacctttata ctaacatctg catttgactc tttcatttga 180
cctccaacat attctttctc attttccttc cattcaccac aaaaaccaac aaatacaaaa 240
aaccacaaat acatagaaaa ttaataaaaa aatcaaaatt tcgagatgaa atcattataa 300
actcatccga taactttgag atttgaaacc ttacactata taaagaaact catccgataa 360
ctttgaattc gcatcgaaat tacgtaagtg aagacgaaaa tgtaaatgat tagatgcgaa 420
taacaaaaaa aacataattt ctaaacgtaa aacactatat tcaccttatt atacttgatt 480
attttggaaa agtatgaaat ttgagtgtgg gagaggagcc aaagaattgg aaacttgtta 540
ttaggagtcg ttatgaaaca ttttcaacaa gccaatattc tttcacatac tataatgata 600
tacatagaaa taatacaata atatttttga aattgaggca tttttgtcgt aatttatcta 660
aaaatgtcag ggtagattca tcatgtatac aaatctctcg ctatcaaaac tatataaaaa 720
tcttgtgaat gatttcaatc gaaatggacc gagaaaaaac atcgtaacca cctctaaaat 780
cgataaattt gtttcaattt caaatcccta aaactaaagg tgctactttg tacaatttcc 840
cctgattagg gtgctaaagt taaaccctaa ataaaggtgt gtacgtttcc ggaagtttct 900
agaatcccca gcgaagttct ccaaatcgtg gcttgcagac caaggacccc cattaaaatt 960
cgtttcttcc tctaaacctc ctcccttaat tttggcattt tggtattttg gctcctataa 1020
attcaccccc tccttatccc taatcctttg tcttccaaat tttccttcaa agcctgcttt 1080
tcccatttcg tcgtgctttt tcttcatcta aaggtatatt tcagttctag ttttctttct 1140
ctgttgatct cttggatttg agggacgttt gaagttggct ttgtttaatt ctttgttatt 1200

-continued caatctcttt ttttgttaga gttgttgttt aatcgtttcc cttgttgttt ttctcccttc 1260
tagttcgatt ttagaacgct ttttgtgggt tgattttaat ttctccgttt tcttacatct 1320
ttcacaaaga aacgattgaa atcgtgtttg tttttttcc cacggcatac gttattagat 1380
cttgtagata atgatctcaa tctattgttt agtttttgca aataagaagt tggtttttta 1440
tctccaactt ttatatattc gattcgatga gatgttctac accgttagga tggaaccaag 1500
aagtgaggta agggtgtttg attgaaaaat tgaactgaga agttaaagtt ccttcctaac 1560
tttttaatgg attgtataat tcgttcaatt ccttgtcgtt ccatttttat ttctgtttcg 1620
tttttcgtgt tgctgcgtat cgcttccctt gttgttttcc tcccctattg attttgcgtt 1680
tcttggagtt tctctgtttt ctctcttcat ttttctacaa aaatcaattc tatttttatt 1740
cgttttcaat tcccgagctc cttggaatgt tatccttttc tcctgtgtaa ataagaaccc 1800
gtattcaatc ccagttcata gtttggcttt cccaaataag agcaaaaaga ttgtactgag 1860
aagttgaaga tttcaaaatt ttgtacatga tttcttctaa tttatcaatt tgattggact 1920
ttttgtatat agatttggtt cttgagctat ttatgttatg acgttttcat attgaggcca 1980
tgcgttgaat tggtttctta acag 2004

<210> SEQ ID NO 18
<211> LENGTH: 1935
<212> TYPE: DNA
<213> ORGANISM: Cucumis melo

<400> SEQUENCE: 18
tatacaaatg acaaaatatc gttgaagtcc aaaaaagatt tattgttggt aaatatcgtt 60
aaagttagta aatagatttt agagaaagga gatatagccc ttgtagtaga aacacacaca 120
caaattgaat tagatgtgtt taatgtttaa ttaaattaga tatgagtcaa cttatatcta 180
atataggaca ttattaaaca aataagaaat aagaaacatg aaacaagaaa aacaagaaat 240
agaaacaata tcaaacacat tcctatttct tgttctaaaa aaagaaaaaa catggtacaa 300
gaaataggaa acggaaaaga ggaaacaagg aacaaatgct accaaacggg cctaagtttc 360
taacaaaatg agctaggtgt agtttattgg tatagatagt gactttcaat tattttaaat 420
ttttttatcc atacctccac gtctttagaa tctttcttat ttatatgtga tcttaattca 480
ttcatgtctc aatcttaaaa ttagaacatt acatgttcat catttttttcc ttttgttact 540 gtgtttaatc tttcctaaca agacaaatag tttaacctta atccacacat tattataacc 600
aaattaaaat aatctacctt caaagaaaac attattataa tcttatatta accacaaatt 660
ataataccaa actctaacgc tccaacccaa cctaggaaga atgacaaggc tgtcataatt 720
tagttggttt ggcacgttgt tggaagttct caaaattatg gaaatattta tttccttctt 780
ctttatccat catcctcctt gggagggtga atttgtgtta aaaaagaata gaaactaaag 840
tctaagtggc aggacttaca ttatgtgtgt atgtggaagt aaaattgcag taacagttta 900
caaaaacaac tcatccatga ttcataacca acttaaatga atataatttt ttgcctaaag 960
attttaaatt aatatataag cggaagaatt aacctataac ttcaagttta acaacacaaa 1020
tattatatca tactgattaa ttattggaat gatgtttagg ctttaaacat aaagtattga 1080
gaggctaatt tgagtttaac tcactaaact atcattaccc tttcaaaata gatccaatca 1140
tccatttatt ataatactca atgaaataaa gcaaaagatg agtaaaataa ttcaccatga 1200
acattgataa ttaattttcc cactaagata aactactact cctcaaatct tcatatgtgt 1260

-continued

```
ttttcctttt tgagttgcac tcaaattttc atagttgaaa tttacccatc aaaacaacca   1320

acaatctttc aaattcaaca aacatttgac cttacaccct ttgatgccaa atccttaccc   1380

tctccctctt ccataaaaat tcttatataa accaccatca ctctcacttc tcaattcact   1440

ctcttctcta ctcccaatca cctgacttgc ctcttactcc accgccaggt tccgccccaa   1500

cttccccggt aagttccagt tcttcagatc tggttaccac atttgatttc ttgcttgtat   1560

ttgacgtggg aattttcata tcggcgtttt ttcgaactgg gttttgcttt atgatcatat   1620

tcttgtagta aaatgccatg aatctgttat ttgattccgt ttttttgga gatcggtcta   1680

gctttatggc catattctgg catttaaatg ccatgaatcc gtgatttggt tgaatttcac   1740

ttccgatcca atgtttatgc tgatattgac atctttgcat tcaatgcaga ggagttttgt   1800

ttcgatttat tactgatctc atcacactga tcttgaattt tttatacttt tatgtgtgtg   1860

tgtgtatttt ctttaatatc tatgccaatt gaactatgtg gttaacttca gagtgttctt   1920

gtgggcagtg agaag                                                    1935
```

```
<210> SEQ ID NO 19
<211> LENGTH: 1606
<212> TYPE: DNA
<213> ORGANISM: Cucumis melo

<400> SEQUENCE: 19

atatattgta tcgattcttt agttgctcta tgtttttgtt tgcttcattt gtcgattaaa     60

ctgtaaaatt aatttctttg acaaggaaaa agatataatt taattctata atttattaca    120

atctaatcca tatggtttaa taaaacactg aaaattgttt atgaaaattt tatcgaacta    180

caagaactat taataaagtt tttttaaacc gtaaattgaa tgaattttct ccacggtgta    240

aatttgaaaa cattaattaa ttaattaatt aattttaatt tcaaggtttt ttctgaccca    300

tgaacctatt ttatgatata agttgttcag gggttgcaat agtaaccaaa taaagttgat    360

cagaaaaggt taacaactca tgaaaacttc caaatgcatt tgtgtttcaa ttattttctt    420

aaccctcttt ttttggtaat tttagtttaa aaagtgagtc ggttgatcat tattgttctt    480

taatttcttg ggagaaaaat attaatgttg attatggtga tgagttaagt ccaattcttc    540

atcaaatcat accaaattag gaacaaaaaa aacatcaatt ttaaggtgca aatccatttc    600

taatggctaa aatgtcaagc atcccaccaa accaacaatc tctaaaccca tttttactcc    660

actaatctaa tgtttaataa taatcaacaa ggttttgctc attccttttt tagttaataa    720

tcatttaaca ccaaagctca aaagtaccca cccaatggat caaaatcgag aatatatagc    780

atttaaggat ataaagacta gagataataa taacctagct tagagcttaa agggatacac    840

tagccatcaa gtcaatttgg tagacaatct aaaaacaaat aattcgatga aaataaagtt    900

gtatttttgt gttttcaaac atgttttaag acgaaggttt ttgataaatt tgatctcaat    960

aggtaaacaa tggtaattac tcgattataa ttactcacta aataccaaat cgaatataaa   1020

ttattactaa ttaattatga acatgtttta cattttaaaa aatgaataat ttttttttta   1080

gaatttgtgt tattgaaaat aattttcaaa acaatattga atgaatctta agtgaaatca   1140

atgtattaaa agaacataaa acataatcta gatggtctat cgaacaagct agaaaatatc   1200

ttccataaat ccaatgatta agacaggcag gcaggcatga agataagagg attggattaa   1260

ttggtgattt taagttatga ataaagacac aagaactagc agctctcctc ttcttgtcac   1320

cttcctttgt catccagctc acacaactcc aacttggaat ttgacaggtc tctcttcact   1380

catacattcc cacatgaaat tattaattga atcttcaaca ttgtctttga ttcttcagct   1440
```

```
gcactgtcct tttccaccat ttttttcttc aagataaaga ctaataaact ccttatatat   1500

tcctctcttc ccattcacct gtgcatactc acaaagcaac tgccatttcc ttcttgttta   1560

tctctgtttt tttcttacac atttgttgaa ctttccctct gaaaaa                  1606


<210> SEQ ID NO 20
<211> LENGTH: 1487
<212> TYPE: DNA
<213> ORGANISM: Cucumis melo

<400> SEQUENCE: 20

taatgaattt gtatttgtta gtggattgag tttatatgat attaattttg acccaaacag     60

ttgagtacgt aattaatgtg gcttgcattg aaagtgatat gggcatatag tatgtgtaga    120

atgtagctga cacaacacat taacaaaacc caattttaac tttttctttt tctttttctt    180

ttaattttat atggatcaga tcacatgtca ttttccatta caactcactc tctaccaatc    240

atcccatccc ataggccata ccccataaca tccctttcta aatatctaaa tcatctccct    300

aaattattac atttttttc tctcaaatat aactattcaa ttcataaata ttattctttt    360

tttagctctt attatttcaa ttatgatttt aaatattcct tttcaattta cgacctttta    420

tttaccatat caacatttta attctactca attaaagatc attataatga aatttcaggt    480

ataacaaaat aaataggtgt gatataatga tggactacta atttcactaa tttcgtcatc    540

tgaaataagg acaagttcca actatcacta ttgtgaaaac ctcataactc ctaaaagtgt    600

taaaattgga ccctcaagtt tataataatt ttgcaaattg aatcccaaaa ttaaataatc    660

agtataattt atacgttttg agagtcaaat ttaatatttg aataagcttg aatacttaac    720

ttctaatttt gaaaatttaa aaatgcaact gcgagagtaa cttttgcaat tagccgtcga    780

aacaattaat tatattggtt aatttatgtc tcattctctt ttgatgacca taaagataaa    840

cccatttata atataaatat caagcaaagc taaaacaaaa tctttttttt ttcaaattag    900

atctaaatat gaataaaagc agaactttct agaagtacaa atttgattat ttttcttgag    960

ataaaatttt cgctatgaac ctttttataa taggaaaaag agaaaaagga tggttttata   1020

taaatgtatg ataaaaaggt aataatatcc attgtaatag taaaaaagaa aaaaagaaaa   1080

aaagaaaaag caattttctt tttcatgatt aggaaatata aaaacaaaaa ttggctccca   1140

attgacatct ttaatcttct ttttcttttt cttagaaaat aaaattagtg agagaaggaa   1200

aaaaacgaag ggttgagaga tagagagaga aaaaattgat ttttaattta gtttattttc   1260

ctttttgga gcacaaaata aatagataaa taaaatatta gtttgcaaaa aagcccctcg   1320

agtttatctt atttgctcaa aaaagcaagg ataaatacct cccgacatcc ctgtttatcc   1380

ctctcagttt cataattcca ttggttcgat aagaaaacaa ttctcccaat attcccgctg   1440

tagatctcgt cgattttccg tttgtttccc gggaagatca atcaaag                 1487


<210> SEQ ID NO 21
<211> LENGTH: 1448
<212> TYPE: DNA
<213> ORGANISM: Cucumis melo

<400> SEQUENCE: 21

ggtgtcttgt tgtaaggaaa tggaaagaaa agagaaaggc tcttgttgtt gtccttgttc     60

tgtgtatcga tgaaaatgga tcgacgcgaa gaagatgaag gacgagagtg gggattataa    120

gacagagaaa ctccgaaatt tgagggctaa tatggtaata acaaatggcg ggatactttc    180
```

-continued

```
aatggacgtg gacccattgc ttctttaact caccgtctga tctttatttt acggtcatga    240

tttccctctt tccccaatat ttttgggagg gaaaaccaac tttgtttttg taattttaat    300

catttttcct caaatcgtaa aaaaaaaatt atagattttt tcaaaaatag aaaaaattca    360

tataagaaaa ccaagataaa atattttgaa aaatatccta ttttttactt cttaaaaata    420

attcataaaa gaattattat aaatattaaa aaatatcagt accactatag acaactattt    480

atatagcaca tatagatata tttgttggtt tttctattta gtatttgaaa acaactccaa    540

aaacaataca tttcaatata cctacgaagc atacaaatat aattattaat tttaataagt    600

tcaaaaatat ctaatggcat ccttatttaa tcaatttttt catcgacgtt atacacggta    660

aggatgtcct aatccttgac cattgaaaga cgtttgtttt gataattata tcttttgata    720

tatacaaaca tttatctcat gattagaata gtcacctttt tatttgattt aacgattata    780

cataatattt gaaaattttt aaatccatca acacaatcaa accaaaaatt tcctaactac    840

ataatctaca agagatttac catcttcttt aaacaattgg tcattacgtt tgttaatgtt    900

taaaattaaa tgcaaccata ttgggtgtaa aagccaaaca ttgatttgat tattaaagtt    960

ttttctatat agacttgatg tgtaaaccta ataaccaact tgagctaaat aactttaatt   1020

tctaaaattc attaaactgt cctcatccaa attataaatat caaagatttt tgaaatattt   1080

aaaaattccg aacatgggaa ctactggaac ttggcaataa attcaagcaa gaaagaggaa   1140

aacgatataa tcaaacaatt aaaaaacaac agaaatttat ttaatcaaag gaataatctc   1200

atcttttatt tattgggttt tacttttaat actgtgagtg atgattggaa cattaattaa   1260

catttaagac attaatttgc aacaatcaat caaaattgta taaatccact tgttttgatt   1320

tatttgaacc atcacttttt tttttatata tatatataat atgggagtga aagatcaaac   1380

gtataatcat gaaatgaaag atgggatatc attgaactta attaaatatc attgaactgc   1440

aatttttt                                                            1448
```

<210> SEQ ID NO 22
<211> LENGTH: 1235
<212> TYPE: DNA
<213> ORGANISM: Cucumis melo

<400> SEQUENCE: 22

```
aaattttaat aattaaaatg aacaattttt caagagtaat agagtttgag agatgtcaga     60

gaagtttgag gaagaagata acaagtggga gaagagaata agtttgttgt gtgaaagaga    120

aggggaaatt tcattcaagg gtatattgaa ctttttactc aaattttgta agtctatttt    180

ttccgatcaa tcctaaaatc acacacaccc ttaaaaaatg gattatattt ggcaattttc    240

catgataaac tcatttttaa tttagagtta ttttttcaac gagatattaa cagttttagt    300

tcatatacta attgtaagaa tagtttcttt taagttgaat agaatttttg aaacttttaa    360

tagttcaaaa ggtatttttg aaacaaaata agaatgtttt tgaacttttt ataaaaagaa    420

ttgagatttt tttgaaattt ttgataaaga gaaaagaaaa gaagaaagaa aaaagaaaaa    480

caagtttgta gaactccgtg ggaaaatcgt cgagggccct gtgaaggaat tttgaaatta    540

taatgagggt attttcgtca acaagggaat ttagacatcg tatataagca tcctcaaacc    600

ctataattaa gcccttcaat ccaattgcca ttctccatct ctcgccgcaa gggtttaaga    660

gcagcttctc tcctcaggtt ggggtttccc cctatcttct tcattcttcc tcttctcgat    720

ttctttcttc tatttgctcg atagtctctt atttcttgag cttttgctgt ttttctcctg    780

tacatcctaa catgaattat aacttggttt tgattttgtc ttttacttct gtattaaaca    840
```

```
actttttctta cccttttatt cttctcttct tcttcgtgtc cctgcccttt tgtttttatg    900

ctaattttat gtttctgttt atcaatctat cgaggcgtga cctgtcgttc ttccaatagc    960

gtagatctgc acttaatcta ttctagctga ttggattggt cgtttttcgt ttttttaatt   1020

tattttctct gttctagttc cgataaattt ttttatatat aattaacaag ttctccagcc   1080

aaaagggtta atattgcgtt ggatatttta atttttacgt tatttagatg tgtgaatcta   1140

ataaaattag ggttattcat aaatttcagt aatgatattt tggttatctg ttcttgctgt   1200

tcctgtttcg cagttctttt acctaatatt caagc                               1235
```

<210> SEQ ID NO 23
<211> LENGTH: 2003
<212> TYPE: DNA
<213> ORGANISM: Cucumis melo

<400> SEQUENCE: 23

```
ctagacattt ttgtctaacc tttcaaatgt tttgttttaa tcttccctct cccaaatagt     60

gaaggacatc cagtgtcaac cgtgaacgca tactgtgtca ttcatgaaac aaatcttttt    120

tgtagtgggc attgtcagca tacatagcat gtagaagcta tagacagatg ttgctttgag    180

ttgtatttag ttctctttaa aggaactttg tacaaagtac tgaatgtact ctgttatttg    240

aaatatcaat gaagtcctct taattctttt gagttcccat tccacgttta agttgttagt    300

tgtattcatt ttcgcttact aggtgttctg catgtatctc acagagagac tcacgtgaaa    360

tgtttaggcg gtcacatccc taatgacttt tgaaggggtg tgacacgatc atttgaatat    420

atcacttatc taatagtgac agtggtctat atctttgtct atctgtatag atcattggtt    480

gtttagatat tggtacacta ttgtgtagtg aaaaaaagaag aagaagaaga aaaatataat    540

acttgataat gagaaaagaa taagaaaaaa tattgtcttt atgaaagatg aaaaaatgat    600

gctgaagacg agaaatgacg gaaaaggaat aaattctaga tgaagagatg aagaaattct    660

agaagaacaa atctagaatt tataaatggg ataacaataa agataaatgg gataacaaag    720

aaaaaaaatc aagaaattac ctaaatgttt caatcttgct acgccttaat tagaaaaaga    780

aaagaaacaa aaaagaaaat gcacaaaaat atctatatat atatacacac acaagcacaa    840

gaaaaaaatg aatattggaa aaagacgaaa atgcattatt ttttatttgc gttagcgagt    900

tgttgtgatt ttgtgagcaa gaaaaggata tgcaggagaa ttaagataaa taaggaagat    960

tgaatagaga ttaaaagaga aatatgggaa tagagtgggg atgaaaggtt taaagatagg   1020

gagggaggga gcgagagaga ggagaaacaa acataccttg agaaagggag aatgagagag   1080

ataataaata aatacggtga tttggaactc ataaaaagat taaaaaaaaa aaccttagag   1140

taaagacttt tccatgcatt tcgagaaaat ggaaaagaat attctattct atttgcttgg   1200

acaccaagtt cctttttgtc gcatgcatac gtctatttat ttctgcttgc ttgcataggc   1260

agtttttgtc caaggaaatt cagcaaaggc ggtatcaatt tcgtcaactt agaatccact   1320

cagtactatt tgaagttcct cactaccaat ttgcaccatc caatctcttc tctctccaac   1380

ttcctgccag ggcttaacct ctcttaattc cttatcctta cttgttacct tacctggttc   1440

cactcttcac gtctctctat tctatattgt tttttttca ttcataattt tgttactctc   1500

ttctctgtcc cctttgtctt ggattttatc tctccatata ttcattggaa taatttaagt   1560

tctttgtaga ttttatgaaa ttaccaattt aatttttcaa acagtttttg gatttgttta   1620

atttctcctt ctctaaatcg cgttgacttt atgttatttc gcccttgctc tgttttctct   1680
```

```
gatcataaag tatgtacttg attttatggt gaatgctttc ttgatttaac aaccctggtg   1740

ctgaaatctt ttttaaatcc tacttttgtt gttttacata tgttcttact ctaaaatgag   1800

cgacttattt ccttttattc ttccttcttg attaaggatt taatcgttga agtatgctta   1860

tattgtggaa atttggtttt aattgatcat acgagctagt attactagct tctcggtttc   1920

tttggatgag ttatatgcat atgatgattt caattccaat ttttattttg caacagattg   1980

ttttttgtgg ctgaaattca agt                                           2003
```

<210> SEQ ID NO 24
<211> LENGTH: 2015
<212> TYPE: DNA
<213> ORGANISM: Cucumis melo

<400> SEQUENCE: 24

```
gatcagagta gcagttgagc aaacccaaac caaacccttt atctatacaa tcctctcaaa     60

ataaaattat tgtttaatta ttcccatatc tattatcatt tttccataat tgcattgaga    120

gaaaaaaaaa aaattctagg agacctaaat acaacaacaa ctatttaata atagccccat    180

gtcacattaa ataaaactaa caaaaagttt aatacgtcaa gaaacgatac ttgtggatat    240

tgaggcatgg gtccctcctt ctttgtatat tcaaatctgt ggtctgccat cagataaggc    300

ctttaccata taataagttt tcaaaaaagt aagcaccact tgctgctttt ttaatttaat    360

tatatttaat ctaattattg aaacttatag ttgttttcta tccttattct tttcttctct    420

tcaaacaccc tcctattaat ttaaaataac caaacaacct ttttctttac atagacaaac    480

ttaattagat taaatataac ttgtaattag attaataata tagtttaaaa agaattttat    540

tttaagtaga attattagta aaaatgaatt ttgtggatag atacttggaa tttaagagaa    600

agttaaaaga gagaaaaata tgaaaaggaa ttaaatgatt aaagttgaat gtaagaaatc    660

aataaacata aattccatgt attaaatttt tgtcggtgtg tgaataaata aatatctatt    720

actattagat tacccagctt tgtttataaa aagaaaaaga aaaagttttt aaaatattgg    780

aaaattttgt ataattattg aagaaattgc gtggtctttg caatttgggc atcgttctta    840

tcgcttccaa tgaaggggcc gtttacctcc accactattt ccaacttgtt tttgtaccat    900

tctctatatt tctttgacac ctatattaca cgtgtcttta atccattgga ccttcgtcct    960

actatatttt tacccgaaat gacgaatctg tccttctcat ccacctataa attcacctct   1020

ccggctcctt ccctttcatt cagttttcct ctattcttct ctctatacgt catattcatt   1080

tcttccaagg ttcgtcctcc ttttatcttt cttctttctt tcactttttt tcgctttttt   1140

cttttctttc ggtttttgtt cttttaattt cattcgtttc tttttgttat atggtatgtg   1200

gtatttgttg aattgagatg ttttagggtt tcgatttagg ttttatttct tatcctactt   1260

aagggctatt gtgattttgg agaaaggagt tcttatttgt tttttttttt ttccttttttc   1320

ttatctggca gatgcaaatc ttcgttaaaa ccctaaccgg taagacaatc acccttgagg   1380

ttgagtcgtc tgatacgatc gacaacgtca aggccaagat ccaggacaag gaagggattc   1440

ccccggatca gcaacgtctc atcttcgccg gtaaacaact cgaggatggc cgtaccttgg   1500

ccgactacaa catccagaag gagtccaccc tccaccttgt cctccgtctt cgtggtggca   1560

tgcagatttt cgtgaagacc ctgaccggaa agaccatcac ccttgaggtt gagtcgtctg   1620

acaccattga caacgtgaag gccaagatcc aggacaaaga aggcattccc ccagaccaac   1680

agcgtcttat cttcgctgga aagcaactcg aggatggccg cactttggcc gactacaaca   1740

tccagaagga gtctaccctc cacttggtcc tccgtcttcg tggtggtatg caaattttcg   1800
```

ttaagaccct gacgggtaaa accatcaccc tcgaggtcga atcctctgat accatcgata 1860
acgtcaaggc aaagatccag gacaaggagg gaattccccc agaccaacaa agactcatct 1920
ttgctggtaa gcaattagag gacggccgta cccttgccga ttacaacatc cagaaggagt 1980
ccaccctcca ccttgtgttg cgtcttcgtg gtggt 2015

<210> SEQ ID NO 25
<211> LENGTH: 2006
<212> TYPE: DNA
<213> ORGANISM: Cucumis melo

<400> SEQUENCE: 25
accaccacga agacgcaaca caaggtggag ggtggactcc ttctggatgt tgtaatcggc 60
aagggtacgg ccgtcctcta attgcttacc agcaaagatg agtctttgtt ggtctggggg 120
aattccctcc ttgtcctgga tctttgcctt gacgttatcg atggtatcag aggattcgac 180
ctcgagggtg atggttttac ccgtcagggt cttaacgaaa atttgcatac caccacgaag 240
acggaggacc aagtggaggg tagactcctt ctggatgttg tagtcggcca aagtgcggcc 300
atcctcgagt tgctttccag cgaagataag acgctgttgg tctgggggaa tgccttcttt 360
gtcctggatc ttggccttca cgttgtcaat ggtgtcagac gactcaacct caagggtgat 420
ggtctttccg gtcagggtct tcacgaaaat ctgcatgcca ccacgaagac gcaacacaag 480
gtggagggtg gactccttct ggatgttgta atcggcaagg gtacggccgt cctctaattg 540
cttaccagca aagatgagtc tttgttggtc tgggggaatt ccctccttgt cctggatctt 600
tgccttgacg ttatcgatgg tatcagagga ttcgacctcg agggtgatgg ttttacccgt 660
cagggtctta acgaaatttg cataccacca cgaagacgga ggaccaagtg gagggtagac 720
tccttctgga tgttgtagtc ggccaaagtg cggccatcct cgagttgctt ttccagcgaa 780
gataagacgc tgtttggtct gggggaatgc ctttctttgt cctgggatct tggccttaaa 840
agaacaaaaa ccgaaagaaa agaaaaaagc gaaaaaaagt gaaagaaaga agaaagataa 900
aaggaggacg aaccttggaa gaaatgaata tgacgtatag agagaagaat agaggaaaac 960
tgaatgaaag ggaaggagcc ggagaggtga atttataggt ggatgagaag gacagattcg 1020
tcatttcggg taaaaatata gtaggacgaa ggtccaatgg attaaagaca cgtgtaatat 1080
aggtgtcaaa gaaatataga gaatggtaca aaaacaagtt ggaaatagtg gtggaggtaa 1140
acggcccctt caattggaaa gcgataagaa cgatgcccaa aattgcaaaa gacccacgca 1200
atttcttcaa taattataca aaattttccc aatattaaaa acttttcttt ttctttttat 1260
aaacaaagct gggtaatcta atagtaatag atatttattt attcacacac cgacaaaaat 1320
ttaatacatg gaatttatgt ttattgattt cttacattca actttaatca tttaattcct 1380
tttcatattt ttctctcttt taactttctc ttaaattcca agtatctatc cacaaaattc 1440
atttttacta ataattctac ttaaaataaa attcttttta aactatatta ttaatctaat 1500
tacaagttat atttaatcta attaagtttg tctatgtaaa gaaaaaggtt gtttggttat 1560
tttaaattaa taggagggtg tttgaagaga agaaaagaat aaggatagaa aacaactata 1620
agtttcaata attagattaa atataattaa attaaaaaag cagcaagtgg tgcttacttt 1680
tttgaaaact tattatatgg taaaggcctt atctgatggc agaccacaga tttgaatata 1740
caaagaagga gggacccatg cctcaatatc cacaagtatc ggtttcttga cgtattaaac 1800
tttttgttag ttttatttaa tgtgacatgg ggctattatt aaatagttgt tgttgtattt 1860
aggtctccta gaattttttt tttttctctc aatgcaatta tggaaaaatg ataatagata 1920
tgggaataat taaacaataa ttttattttg agaggattgt atagataaag ggtttggttt 1980
gggtttgctc aactgctact ctgatc 2006

<210> SEQ ID NO 26
<211> LENGTH: 2017
<212> TYPE: DNA
<213> ORGANISM: Cucumis melo

<400> SEQUENCE: 26
atggataagg cagagcttac cactaacctt ctaagatatt ttcgtcgctc ggcatttatt 60
cttggaggga accacaccaa ctccaaaata cccatgaaac ataggaaaaa atggttcata 120
gtctaagttt ccatttcgat tcggtttggt tcggtctttt attttaaaaa caataaatat 180
aaacctacta atttgatgat gacaagttta ctaatgttaa gtaagaattc atcaatacct 240
aagaatttgc aagtttttct taagtttgat ggtaaggatt tcgtaatcct tgaaatacaa 300
caattgtata gaaatgaagc gttgcatttt taacgtctat ataggaacac tattttactc 360
caatcaagtt gtaatttgat agataatagt ttgtataact taatgatgaa gagctttttt 420
ttttatatat aatttttatt aatacgtata gttcaaaatt ggaattagct atcactaaca 480
cgtgcttgcg atagaaacaa caataaattc aattagtgtc gcatgtattt catatggtat 540
tgatgacata agagtagttt gatacgatgg gttacatgga gtgacatgat aattgtatta 600
aatttcaata gttatgatct caagtttggg ttgtgtctca ctttgagctt tttgagaaat 660
tggcctcaag actcgcctaa tttaatgttg cttcaagcta tagatgctta catcgtgtgt 720
atgaaacata ttgcactttg atgcttaaag ttaatatagt gagtaactaa ccagatatta 780
cacgctactc ttttaaaatg gtcaaataag aacatttatt agtatgtgat ataacacgta 840
ccctccaatt acatacaata attgatcaac ccaaatcttg aggtatttaa taataacaaa 900
tacaaaatag atggattata tatctgaata gctaaagaat aaagaatatg tgttatgttg 960
tagttacata gtacaataag tcctctcaaa attagaatgg tataataaaa aataagaggt 1020
acattcttaa agaaaatgtt atcaaaactg ttgcatcata ggcattttgg caggaagaat 1080
agtggaagaa aattcttaaa cctaaattct atcgatatta aatagatttt ataagggata 1140
attgcaaatg tagcaattat atttaaaata attaagtata tagcaacatt ttaaaaaaat 1200
ggcaaatata gcaaaatttg tcaaaatcta tcgatgaccg atagatcatg taagtctatc 1260
actgataaac cataggagtt tatcaacgat agaagtctat caccgataaa ttttgttata 1320
tttataattt ttttaaaata ttgctacata gttaataatt attctaaaaa ttgctattac 1380
caccggtttt taaataggac ctaaatttaa ggtatttgac ataaattttg atgaaccaaa 1440
ctagcccaaa tcaaagaagt ttgggcccaa agcccaacga atccacaaca aacaaagccc 1500
acacaacact tcatgaaaat gattttttca aattttagaa aaaggttata aaatataaaa 1560
aaaataatca aactatccct ggtagctaag tagttattat tatttttatg gatacgaatt 1620
gagtagtatt tattttaaaa taggataatt gatcttagtt tcacttgtga tgaactattt 1680
cactttatta tttgtttgta attcaataaa attagggttt gattgtcaat gataattatt 1740
acaacctcaa tattatactc agtaaagaaa aataaaaatt taaaattgag aaattaatac 1800
caattttttt tgtgaaataa aaggaaaagt aagtaaatat tataaaattt tggacttgga 1860
aattaaaatg cattaataat aatatttagt attattgaat taaaatggac accggaaacc 1920
ctaaaagagg gagtggccac ctataaaagg gaagcactca tctcacccaa acccttgtta 1980

```
ttcccaattg gccgtgcggc aaagaagcct ctcaacc                           2017


<210> SEQ ID NO 27
<211> LENGTH: 1353
<212> TYPE: DNA
<213> ORGANISM: Cucumis melo

<400> SEQUENCE: 27

tgagggtcaa aggaggagga agaacaagaa gtaaatgaag tggagtcatg ggaaaaggaa     60

aacaaatgtg agaaaagaaa gaaagccaga gagggaacat aaaattatta gtcagaatta    120

caacagaaaa tttctgaaga attgagtttg tatgcagcaa taatatattg aacaaataag    180

gagagaagga ggaggggaaa ttcaataaac agcagaggaa gaagaatggc gaaaacccaa    240

tatctaaaac tagttaattc aacaagaagc aacacaatca tttcattaaa aaaagaaaag    300

gtaaagagaa attcccagat tcgttactct agattggtcc aatggagtgg aaagggatgc    360

aatgaaatca gtaatagaaa agaaaagagt taaagtagta ttggtaggta ccgattaaaa    420

atggaaggcg tcggaaggaa acggagagtt caataaaagg aagattcttt gcttcctccg    480

gccatttgat gagaaacaaa aactccgcac ctccaagttc cttccggggg aaggagaaga    540

ctcttctatt ctggggtaca caccctccct tcctgctaca gaatcaaatc taaattattt    600

tggattggaa tggcatggga ttggtctaac ttccaatttc tcgacacaca accccaatct    660

acccgccacc tgtacccagt tttcccaaaa cgcaactcac attgcaattg caattcttgt    720

ctttaataaa tacaaattga tttttctttt tcttttttt tttttttaat aacgattaac     780

cctaaaaaaa ataaagaaaa gaaagccgat cctaaaagta gaattacttt ttttttgttt    840

ttcaaggttc acgtctgtgt ttgcatagac gtgttgtagt cggtgggtgt gtaaattaga    900

gtttgttttt ctcatctctt gttcttttta acgaaatttc aaagatacaa aagcataatg    960

aagaaaagta tacaaagcaa cgtaaactta gcattttgca catgatacaa atttagtcaa   1020

actcaaaccc tggacaacct agcactctct tgggcacgtg gtagatttat gtgaatttcc   1080

ctatttttct tttgaactca caaatgggca aataataata ataaaattta ttgttgattt   1140

ttcttatatt tcaatttatt acctctagtt ttaacctaaa gtttagatgt atataattat   1200

aaatgagcgg tgaaacgggc actgattgat gaatatattg ggccttgggt tggcccaaca   1260

aacctaatgc ccaaatataa aactttggca accatagtta accctaatct gtcaatctac   1320

tctcctcgac tcggtaaacc tgcgactccc aca                               1353


<210> SEQ ID NO 28
<211> LENGTH: 2005
<212> TYPE: DNA
<213> ORGANISM: Cucumis melo

<400> SEQUENCE: 28

cagtgtgctg gaattcgccc ttatccaagg agattaatgt cgagagatta ttatcgaggt     60

ttgaatttat tttgtccaat catatgattc caagagctga ccatcaattc aacagaacat    120

gaaccggaac ctcataccta ttgtaatggt tcacagcatc ctaatacaga acatgaaccg    180

aaacctctta cccattgtaa tggttcacag catctttata cgtattatag gtagtaccat    240

tgaagatgca tttaaatgct gtccatgctc tgttctctaa aaagttggac ttggacttgg    300

acgtcagctg aaagtatgaa atgcactgta gccaacgaag ctatgttttc aggcttcaac    360

atggttttag gaaagtggag gctctttggt tgaagggttg aatgaatgct tttctaattc    420
```

```
cagcatgatc ttcaaatttc gacacaaaaa gcttaagtat tttgttccgt tattctttta    480

atccttgtat tgttatatat tcttttctct gaactgaatg tacgatgatt gcaggggtcg    540

agagcaagtc cgatataatg aaacacgtaa ggacgtgatt gaatgaaaaa ctatgagcag    600

agatacaaag tctaacttac gggatgaacg atgagaggtt tgaccaagag ctgtgacgcc    660

tgtatatttc aacaaaagtt gatgactaac atcacatgtc agagtaatca aagaaatgca    720

gccgcacata tatatatcta tatatatatc gtttagtttt tttttttttt tttttatttt    780

ttttttatc taattatatt ttaattctat tttcctctgc cctcctcccc ctcctcttcc    840

cccacccttc ttctgcacat agtagccaag gattgatcgg tttcttttga ttcgggggga    900

aaatgttgta caatttttgc ttccatagaa gcttgaaagt tttgcagatt atgttgtaaa    960

attacccttg tgtactcaca ctagttcttc tcgtggaaac ttatattaca atggttgagt   1020

tttaaggggc atattcacac tggtaactac cattttctaa tttatgaatg ccgagtttct   1080

ctccatgaaa gacctttcaa atgccctttc ctccgcggtg cgtttgttgt tgtaaatgtg   1140

cagtgtcgtt ggatacacga ttgtgtgaaa gggaaaaggg aatacgatta actcttaaat   1200

tcaaccccta tctccatcag tatcaatcac atttcagcaa ctagctcttg aataacattg   1260

agattcttgt ttaatccacg tactactact actattacta ctatttgaca gccgatatct   1320

caaataacat ccatatttat caaattggta ttttaaggac ttttaatttc ttcgtacata   1380

tttcattata atttaactac tctgaccatc attgaaaatt tcacaaagaa gacattttaa   1440

attgaattga gttgaattaa gttgatataa tggttgaacg ttggatttaa tttataattt   1500

agtggtgtat gggtccattg taataattct taaaaaaaat atcatattct gaattctaaa   1560

gaaccatcta agaccaaaac taaggggtca ccaatgagta tggtaaagtc aacaaagttt   1620

gtctactttt cttatcctta tcatcaagag tgcaatatga tatcaaagat aaattgtacg   1680

tgggcgtcat ccattgggta agaccaagaa gcaaaatatc atagagaagt tgttttagta   1740

gccataggaa ggaaggaagc aaaataataa tatagatttg aaattgtgga tgataaactg   1800

ccaaatggga attcaaaata aactaaataa ataaaataaa aagagaaatc ttgggagttt   1860

ccattttagc caatgaggaa acagatagag atctcatcaa gataaggacc ctattctctt   1920

cttcatctat aaaacaaaaa caaatcaaac cctcatttca ctcattcaaa acaaaaagta   1980

ctccaaagtc aaactaacaa atacg                                         2005
```

<210> SEQ ID NO 29
<211> LENGTH: 1445
<212> TYPE: DNA
<213> ORGANISM: Cucumis melo

<400> SEQUENCE: 29

```
tcccttcagc cacttaacac ttaaaaatct taggaaactc cattggctcc tctttctcca     60

atgaaatttt gacatctgtg ttgttgatag ctcctatatc ctttgagaat ttgatataca    120

cctgtcattt gctgatttgt ggataactgt tagccttttg atattgatac gttccttttt    180

tatgaatttt tgtaaatcca ttcaatttta atgctgtcgt aaatgaaaag ccctttcatt    240

aatgttgttt atatacatat tttaaaatta attcaataac aagtttagtt ctgttagctt    300

ctaggtttgt atctatttta tctattaaag gtatgtttgg gcttcaggtt ggaatggagt    360

agaattgaat gggttgggga gtaaattttc cattcaacaa gttcaatttc aaaatggcta    420

ataagttttg aactcaattt tattttcaat aaattcctta attttttgtt ccttgtttgt    480

aaactattga cttattcgat atattttaaa attgaggtat tttaaaaaaa taatacaata    540
```

```
ttaaaattat ttataaaata taacaaaatt tatgtatagt ttatttgaaa attttactat    600

agtttcattt ttatattatt cctaaccatt tccatttaaa attatttcaa ttatttcttt    660

tattaatata attgaaattt catggattta ttagacacat gatttgaaat tttatgggtt    720

tattaagtat tttctaacac aaaatcgctt ccgcatcgtt ttcaattcat tcagtaatag    780

aagtaatttt ttaaaagaac caaatttgcc aaattttgag ttccataagg actctgaaaa    840

ctcattatgt ctattactct tcactaattg tagagactta aattcaagat aagagacact    900

aattgatgat aattgcccaa aaaataaaaa taaaaatgtt tcttccccat cctcaacctc    960

catgaattca cagagcccaa agattaatta ttgggcccca attcctactc atatatacct   1020

tacagtccct caaagaaatc ttaggaagta atcaatttct gtttattcaa gatgtagcct   1080

cccaaaagaa aaatacatca catcaaattc aaacaaaaat atctacagct agcaaaacct   1140

caaaccgtta aaatttcaag ccacataaat gaaattttca tctgaaaaaa ggacaatcta   1200

tctagacgtt agatttcagc cctaatatga atctgaagca tttggtggac gagaaagagc   1260

catgtaggaa tgcatcaaac aaaggaaaaa tctttgaact ccaatgggat tgaagataca   1320

gataccaatg gataagaatc tgttctcttt gcccactatt taaactcacc aaacccacca   1380

gtatcttcct caccacaaaa tacattccac cgttgatcac aagccttatt ccaccacctc   1440

caaca                                                               1445
```

<210> SEQ ID NO 30
<211> LENGTH: 1282
<212> TYPE: DNA
<213> ORGANISM: Cucumis melo

<400> SEQUENCE: 30

```
tgcaattaag aataagctaa tcttaatgaa gaaaagaaaa tgttctttgt atttgataaa     60

tggtggcgtt ttgggggact ttatatgctt tttttttccc atgagattgg ttatcttcat    120

ttccgtcatg atgtcgccaa gtggcgcttc attgatgata tcttaaaatc tataatgatc    180

atcctctttg ccaatggtgt ggtgacacgt ggaaggactc tccatcttct aaaagattct    240

tcaaataaaa ataaataaat aaagaaaaaa cttgtaagaa gatacatatg tacattttta    300

tatgaaatta atatgagaaa taatcgactt tacagtgact tgatcaaact ttcttatttg    360

tttcatatgt taggttaaat tactaatcaa ttcacgtact ttactagatg agatttcacg    420

tactttactc attgagtcca acggttgatt aacttatttc aagaaaattg attcattcaa    480

ggatgtttcc aactctcata taatttccat gttgttccac ttctatcaag tacaatccta    540

tcgaacacaa gtttgtttaa ctgaagttca ataatcgaga tcaagatagg ccttattatt    600

tcttctagag gttcaagtga tcaatcaaaa aaggtttatc acatgattca ttccaattca    660

actaagctaa taagtggtgt tgcatgatag agtatcggac tagctcgaac ccctatcaat    720

atgataaatg tctatgtata taaataggta cttaacccaa cgaacaatgt gtcttacgtg    780

agaaagcttt tttctaatat acataaaaag cttgcatgac tttttgatga attgtgtttt    840

gataaaacat atttgtgagt atattatctt tataaattta agttataaca acaatgtata    900

ggtgtgagta tgcttttaaa cttaataaaa aaattagaaa aaattacctt tttagtatga    960

aagttttaat gatatatcaa tttgtgtctt tatgatcaaa atgtatactt ttagtctcaa   1020

atgtttataa gaattaactc cttaataatt atcctaaaca atcatgttca aacttggatt   1080

cttattgaca catatttcat tttaatctaa gtttagaaat gaagataatt aggataagga   1140
```

```
tctttagctt atgatatctt atccaatatc ttaaataaat cttcaacacc aagaaatttc   1200

cctattgcgg atatttcaat atcgaatgcc ttggagtatc aaaggcattg gataacaagt   1260

gggacataat tgcgataaaa aa                                            1282


<210> SEQ ID NO 31
<211> LENGTH: 2002
<212> TYPE: DNA
<213> ORGANISM: Cucumis melo

<400> SEQUENCE: 31

ccgtagattg aacttatggc ttcggtcagt tattgagatt ttaattctct ttaacattag     60

gctaatccat gagtttacgt gtgctaacat gttaatatga aaagtatagt agaaaagtaa    120

aataatataa ataaataaat tggattgttt tgaaaagttg aaagattaga atatacataa    180

gattctgaaa tatctcaaat ttttgaccca gcaaactgaa attagccaaa gtaggttgtg    240

ttgtaaataa ttatacttta tattgttctt tttgtataag cttttatgtg tcaatgacaa    300

ttttaacagc taaataattt aaacagaata ttgccaagat gggtggctac aaaaataatt    360

gtaaatagaa cccaataata attagtttaa tcaattatgt ttttattaac ttgtaaatta    420

aatttacact gaaaagttga aagagtttgg aaaatatttt atttgaataa atcaaacaat    480

tgaatactaa tttgcgtaaa atacgtagtt taaaatatat atatatgtat atatatatat    540

atagtgtaat tttcaagtaa taaataaaat gaaaattaaa ggtttaaaaa taagctaatg    600

ggtgcttaaa gtatctacgg aaacgagatt gcattcgact cacgtacgac atgaaaaaga    660

tataaatgaa ttttacatta aaactattaa attgcacata tgattgtcca acaagtaaga    720

agaatcacaa tcaaagtaaa aagaatcaca atcaaaagag aatgtatcta atggatgatg    780

acaatttact taagatttaa gaattaatct aaaaatttag agagaggggt aaagatatca    840

acttttattt accagaacta aaaattatcc ttaggcctca attgctttag taatggatat    900

atatatatat atatacacat ctacctaaca aagctttaat aatagtaata ataaaaattt    960

aaataataaa taaaagaaat cgaccaatat aaaaacatat aaaaaatgta tagttaaaaa   1020

gaaagagaga aagagagaaa gagagaagag tacatgcaag agatttgatt tggaaggagc   1080

acataatagg acaagagaag ggtaattttg gaatttgggt caattattct tagtccaagg   1140

gttacactac aaaaacctaa cagccttcac aaatttttcc ctctttcgct cgcttcgctt   1200

tgcccaaaca ctcgcctcca actccacgga tcagatccga agagtttggc aaaccctagc   1260

ttcctctctt caatctccat ctttttcttc tctaacaatc cacaggtttg tttttcattc   1320

ctttctcttt cgattttgcc ttcctcttct acttattcga ctgcacgaat atggttgtat   1380

gtatgtttcc gccctctttt catatccctt tttgttcctt tagccttgaa ctactctggg   1440

ttttcttttc tttttttact tttttctatt attgtatatc tcaagatttg acgctaatct   1500

ggtctgtggt tgtgggttga gttcgttttt attcgtttgt ttgtttgttt gtttatggcc   1560

atggcttgta attgcttctg taatctacgt gaatctgttt ttgctttgga acgtttttgt   1620

tgttcaactc atacgagaat cgtcgtctat agttgggttg ggtttttttt ttcagtagca   1680

tcttgctttg ggaaaaggtt aatgcggtgt cttttttttt tttttggaga aaaaaagtta   1740

ttagacatcc ctcaactcct tttcctacat tgagacagaa gtttaatgct tgttttcctc   1800

tttatctgga ttgcaagttt ggcttttctg ttacagattt cctttctcag gatagctttg   1860

aacagatttg taatgttgtt ctgtttattc cttggtgggg ttgataaaat ggttatgatt   1920

ttttgtttgt tggcggcata attctggata tttttatctg tttggtctgt gttcatattt   1980
```

gcattgtttt ccacttacag ct 2002

<210> SEQ ID NO 32
<211> LENGTH: 2003
<212> TYPE: DNA
<213> ORGANISM: Cucumis melo

<400> SEQUENCE: 32
tggatcgacc atgacattca aaaaccttta agatatggat cttataaaat aaatgtaaag 60
ggtaaacaat tcttccttgc ttaacccaag ctatatattt tatgcactaa tttaggtatt 120
agagtatatt cagctgaaca ccacctacca atgctagtac tttaatcagt caattctaac 180
ttcgataata tatctcaacc aaattagtga aaaagagtcg taaatgaaaa actatgtacc 240
aagatattct atttgttttt tttatgttta aatatctcaa agataatacc taaaacgttt 300
tctcctcgta caaagattcc tcatttactt tttattgtcg taaactctaa tacaataaac 360
taaaacaagt acaaatacac tagctttaga aatctacttt ttattgaaac caaaaccaat 420
aattcaacat ttcattttca ccgacaaacc tttgtaaaca attgaagtaa tttttgttgg 480
tactatgaat agtaacatca agtcttcaag tgcatcatat caaccaagac atgttcttaa 540
aagcgacact aaaagattta aaaccaaaag catttatgaa atccgaactt aatcaaatcc 600
taaatatttt tcacttaaaa aaaaaaaaat aggaagaaaa attgacataa atgggatatt 660
ttcgttttca aactggcaag ccagcatgca ccacgttgtt gacgtgtcct tccacgtcgg 720
aaaaaaaaat attaccacag taaaaagaga ataaaatgaa agtcgttgac tctcccttag 780
tcggaggaag cgcgtgaagc tgaagccgga ttagaaatcg gcaataaccc cgacacgtca 840
tcgaaatgct agtatcaaat attgtccgtt ggatcttcct tcaccaactc tatttgaacg 900
gccacgatct tccaggtcca acggttcgga agaatctttt cgaaattcca tggctagtcc 960
ctacactcct ccctattggc tccctagggc atcccgaccg gttattccgg ttgccgggaa 1020
ggtggctgga cgctataaat acccgctttg ttcatctcgt agtccttgta ccgttgagct 1080
tcgccttcta atagagctct ggttcggttg gcgtattagc tcgaattctt tctctcttcc 1140
agatctacgc tgccgatttc atcaggtttg cgagctctgt tccaccattt ttcttttcct 1200
gaagctttga gcatgcttgt gattcttcat ttcctcattt ctttgatggt ttatgaaaga 1260
atttagggga attttctctt tttgtattct agtggtactg gtagatttgt ttgaagtttg 1320
tttctcttct tctgagaagt gaattcttcc agatctgaca gttgcttttg atttttttctt 1380 tgggaattag tgaatgatac ttcgatactg ttttttgctc tctgagattc tggatctcgg 1440
gccttggggt tttctattgt cttttggtag ctatgtttcg tttgtcagct tgtatttgtc 1500
attgttgaat ggttcgatcc ggtttgtaaa taaaataaat tttgtaggcg cacttgtttt 1560
ccacggtttt cgtgttacgg tttcatgatt ccctagatct ctggttagaa ctaagttttt 1620
tgtcggtaat tggatttggt aagggactgt tactgtggtt gaattgtaga tccagtcatc 1680
ttctacatga gtgtagggtt ccttagggca gatcttgtgt tttataattt taattttgtt 1740
gtttccctga ttttgaacct gtttggttgt tcagattcgt cgagtcattt ccattcatta 1800
aaagtttcta taattttatt tgaatcttct gaatctgtgc ttgtattacc cagatttcta 1860
taaacctatc ttgatttcaa gtgtgctatg tggtaactgt tgatattttc aagcttaagc 1920
aatactgatg tgactaaaac ttaactaatg aactgaatgt tttttgtaca cgaactaata 1980
tggtgttttg ttatgtttca gag 2003

<210> SEQ ID NO 33
<211> LENGTH: 1372
<212> TYPE: DNA
<213> ORGANISM: Cucumis melo

<400> SEQUENCE: 33
aaataaaacg cggagacaaa cttggacttc cattcccttc ttcttccttt ttcttgtagg 60
aattcttctt tcttccttat aaaattctcg gacccttttt ttttcctttt taattttatt 120
tttccttctg tagttcgttt cttgatttag attttcgaca aaggtacctt ttacaggttt 180
gttccttctc ttcatcgttt actccgattg atgcatttcc tctattttca cttttggatt 240
ggaattatta cgatctatgt tcaatatcgt ttgatccatt ccctagatgg aaattatgtc 300
tctgtaatta tacatagtgt ttgatttgtt tgggaaattt tgtttctttg tgataatgtc 360
ttcatcgatt tgatgatgta tttgtttttt tttttttggt ggaatcgata tgatttatga 420
tttgggtgtt tttttgcttt tgagaattat gatttgatca gagtttttct tattatttct 480
gttgttttgt ttcatttcct gccgttttta aagatgtgtt tagattctgg ttgtttttgt 540
ccttttgatt atgtttttat ttttcatgta gttggaaatc aataggattt cagataattc 600
atttggttgc atagggattt gaggattgga agttcggcac tctataactt tgcagtgaat 660
gatttgggtg aagtttttcc tcttgtttgt gctttcatgc ttcagttgcc tcaaccaata 720
tcgctttttg gaagtcttga aaatctgtag ctttgagctt gtgtttagtt cgcaactgaa 780
gcttcaagga aaaagtaatt tctttcgatt ttcgtaaaag gggggaaaaa ggaagtaatt 840
ctactaaaat tttctcctat gaactcgtag gtcacatagt tgttatttgg tcagttgaca 900
ctctagacta tcttgttacc attccacata actcaaaggt tttaagaata aactcaatat 960
gggaatggtt tcattaggat tgcagagtca ggaacaagag aggttgcttt gcacaagtta 1020
catactttct attcttaggg agaaaagcca gttgtcattg ttcagggaga agattaattt 1080
ggttggaaag atttattgtc cttctgtctt taggttgtca ttggtttgtt ataattaaag 1140
tttcttgttt cctagaaaat agaagttttt ccctatgagt aatgttatac ttcattgtct 1200
tttattttgt gacaagcaaa cagtgattta ttggatgaac tacagttaaa ttctgaatcc 1260
attaattttt ctgaaatcca ttgtgattag aatcatgcaa tgccaactga agaaattttc 1320
accaattatt aaatgaatat gtttatttgc agggtgtttt aaatagatca ag 1372

<210> SEQ ID NO 34
<211> LENGTH: 1122
<212> TYPE: DNA
<213> ORGANISM: Cucumis melo

<400> SEQUENCE: 34
atatatttat tgctagggtt ttccggttcc tgtttgctcc actatttcag ccgcctaggg 60
ttgaaacaac tcattcctcc gatttcagga ttactatctt cctcctcgac cttctccggt 120
aatactttct cttcacaccc cttttgttgt ttgtgatttt taacttcctt tggattgaaa 180
tgcgagatct gtgtgtttct accactcttc tttcttaact tttcgatagt attgcatgtt 240
ccttacttat ggagaggata atgtgtactt agggatatca attttcgttc acagtattca 300
atattcatga cttactgagg tgtgaggagt tttcatttca tagaccgact gatgctatga 360
tctcaagccg agtttgaccc ctgttttttct ttttatattc tttttcttat ttttgtgtca 420
atatattagg tgatcaatga catcctaatc tattattagt gaattgagta ataagaagta 480
aagtcttgtt tatccaattt tttggtttgg atttattact attttgttgg aatgcttgaa 540

```
tgaattctaa tggagtccgt agaaatttgt ttcaggcgtg cgccttttct tctcactaaa    600

tttttcatta ggaatgggtg tatttatttt caggagaatt tgtcgattgg cgatagttgt    660

cttgttcttt ttcatttcct ttataaattc tttatggaaa aaatgtattt gctgcaacct    720

ctgtcttatt acccctattt gaatcaatag agttcctgat ccttcctacg atgtggtttc    780

tggggatttc tctctgggtt cgtgtgatag atgggtgacc gagggaacac cctttattgg    840

aaatgctcct attcttcaga gtcggtttct cattttctca cctttacgct ttgctgctgc    900

tctcattgac agtcgaaccg ttttggaatt cgtgatattg tgtgtatttt ggggatgaaa    960

gttttcttta ataagactag tgacagttca ttattgattg tggagaaatt tatgaccatc   1020

taattttaat ttgaacaagg gaggatgaaa atgattgggc gcattgcatg ttttatccaa   1080

ctagtactca ttttttcttt gttctgatat tcttcaggaa ca                      1122


<210> SEQ ID NO 35
<211> LENGTH: 2017
<212> TYPE: DNA
<213> ORGANISM: Cucumis melo

<400> SEQUENCE: 35

actattggag acgacgaagg aaaactctaa tgtgagctta gaattgaaga tggtgaacaa     60

ttgggagtct tttttaaaaa tctttcgtcg gtatattgaa atttcctttt acactcaaat    120

aacccccctt ttcacgcgtt caacgtcttc aaaccttcct ttttcaatta ttttttcgtt    180

tacattaatg acatttaggt aataagataa attagtggat tcttttgtga aaaatgttag    240

cccatttaag acttttatga aatatattag aaaaaaatca tatagcaatt tatattattc    300

tagttaaaag cccataatag aaactaaccc aacctaaagt aacgtaaaca ttcaataaga    360

gagacaaatt ttaaaataat ttctaattaa aaaaaaaatt gtcaagaccg tccgggtcgg    420

atccaaaata taacccgaac cggccggttt agcatctata taaatacacc tttagggttt    480

ttattctctc aagacttcac cgcatttcca cttctctgag gccacggtca gccattggag    540

cagctcaata atcctttgac tccctactac ggtaagtcga ccttactgct ttcggcttct    600

agtttttca atcctgtcat tagtcctttg gagttcttct gtacatttat gacgttttcg    660

gctcgtgttt tgtttcgcct gtatgtagtg ggtttttcga gttttgtttt tacttttttt    720

tatacttgca ggaattagtt gaaatctatg tacttcatgc cttggataat actcttgatc    780

tgttgtgtta ttcaaaaatg aattgtttta agatggtatt tgagaatggt catgtgagtt    840

ttgcctactt ggttattaaa atgaattgtt ttaggatggt atttgagaat ggtcttctgg    900

gtatttggtt ggaacctttg tgctctgcta tgaattaggg tgttctcccc gttttttttt    960

tttttttct tttggttatt aatatatctt ttatgactac ttattcatat atgatatctt   1020

ttactcgtaa attttgactc atttgaaagt tttatcctta gtcctttctc attcagggtg   1080

taaaggtatg ttgttagggt taaaatagcc tatgcaggaa agttctgtat ttgttctaat   1140

tattgcattt gtgtgcattt gtatctagtt tatttcttgc tgagagtatg cttcattttt   1200

tagtacacat cacttgtgcc actttattat agttgcacat tttgtttat ggagaggatg   1260

aatagcattt agggatgtca attttttatt gagaaaaccc tctctcctac ttaagcttgg   1320

ggaatttttg ttctaaatgt ggtaaacata atacttcttc ttattttaat ttgaatggaa   1380

ggggaagacg aatactaata ttttcaacga accttcacaa cttttttttc ttatttagga   1440

agccatgttt ttcaaaattg tactgtgtga tccacatatt tatcgattat tagtgaatcg   1500
```

aataataatt agagttttat tggtataatt ttgaagttca gacttattac atttgtggaa 1560
agtttggtta caattttcaa ttttattgga atcctaagaa ctttgtgtta acatatattg 1620
agttttcttc tcttttttt tactcattaa gttctctatt aggaatgttt ggttcaatgt 1680
cacatagtcg atagctaaga ccagtgaccc acaaagctat gattgaacga aaaacaagcc 1740
tttcacatct tggtaggaat ttgttatttc tcaatagatt tacagagctg tttcatgtga 1800
tcacaatttt tttctatttt tctgaagttc tctattagga atgggctatc tggttagttg 1860
cttttgagag aacatgtgga ttggtgttgc tcggtttcct tgcctttgta attttgtcct 1920
tggaaaaagc aaaatgatta ggtatcctga tatgcataac atgtttaagc caactagttc 1980
tcactttttt agtgcaaata attgatcttc aggaatc 2017

<210> SEQ ID NO 36
<211> LENGTH: 2000
<212> TYPE: DNA
<213> ORGANISM: Cucumis melo

<400> SEQUENCE: 36
aagttgttga ggctttcaat ccaaccaaat aattgtttcg ttttccacta caatttccta 60
gtactaaggt agcaatggat cgatccatag agaaccattt gatttttcac taaaatcaat 120
ggttgctaag taaccaaggg aggattggtt gaattgattc ctaatttcac ttcaataatt 180
aaagcaatgg caataaaaca aaaattggaa gattgttgaa ttaaatttag caatgagata 240
aatacctagg ccaagactta cgtaggttac tttagattca caactcaatt attgattcat 300
aatgatatta gattccttgc aacatatgaa caaaatctta gttgaccacg tctagagaag 360
ctaatgtgat gttctataaa tcaaatcaat ccttatgtct agattaaaag catcctagag 420
atgaaaatca attggcatta aggtttgagg ctaaagctaa gtcgatcaaa caatttggag 480
ttgtctaatt gattgttcga tgtgatacaa ttctaaacta gttagataaa cgtaattaga 540
atggaattgt caattcaata aatgattcta acttagctta tgttatcttg cagtctaaaa 600
ataacaatta catattagat ctagatctat aacaattaat taaacatgct tggaaaatcg 660
ccaatatttc cgaacacact caatcaaaga aataagtcca aggaaagaat tcattaaatc 720
ttaagattca caggatgaaa atgttcataa catcacacaa gtgtgtgaat caaaagataa 780
gactagaatc tcgagataat agtaccttag ctatgataca tcctcgaaaa catccaacaa 840
aatcaatgaa agtcttgagt caattcgtct agtaaaatac gaagagttca agagaaaatg 900
cctaaaattt agtgccaaaa attgtgtaaa aagtgttggc ggctagggta ataatgcaaa 960
attaagtcac agcaccgcaa caacgtgcaa aacacatgtg ctatactctc gaaaaactct 1020
atagcatcgc agtcaacacg ataccgctac acaacacgtt gtagggctga ggtgtttgca 1080
tgaaattaga ccattctacc ttacagcatc gtgccttctt cgttccattt caattttctt 1140
gccccagttg acacactaaa cctccaatta atctcgttta atataaaaga taattatgat 1200
tttctttatc tacgaacaac attattgtga aaagatataa ggatgatata tcacaatttt 1260
tagggaaaaa aggaaaatat attggcattt attatctcta tcaaatagat gattttacaa 1320
ttatatgtta agatgtttta atccttgcta atgtgaatat ttattttatt tttgttcaca 1380
tgaaacaatg gtattttgta cactccaagt acaatagttt ctttaaaaaa atttaaaatg 1440
atacgtaaat tatctaaatt gacatcttaa ctaagcaaac aaaaatagtt gtttgaaaac 1500
tagacttatt tagtttacaa aaacatgcac cagatatcct cacttaatca ctagctctac 1560
acccaaaata tagactaaat aacttcacat ataatataca aatttaccaa actcaattcg 1620

```
gcatctcaat tggcgaaaga tctttttaac ccaaaagaag acgttggggc attaactttt   1680

caaaatgaac tttggcttca tagtaggaaa ttgggagtga aacatgaggc tgaaaaaggg   1740

ctaacaaaga gagcgatcgt ccacgtggtt ggcagtcaag aggtctttat agaagaggat   1800

gaagaacttg tttcccattg gtccgaaatc tatccaacac cctcctatta gatttccctt   1860

ccagattctc atcttcatga ttcctacttg gctccattta aacccacaat tcaattcaca   1920

atatctccca cacatcctct tcttcatcat atcataaaac acagtccgtt acatacctga   1980

aatcttccat ctcaaaaacc                                                2000


<210> SEQ ID NO 37
<211> LENGTH: 1760
<212> TYPE: DNA
<213> ORGANISM: Cucumis melo
<220> FEATURE:
<221> NAME/KEY: misc_feature
<222> LOCATION: (1)..(1760)
<223> OTHER INFORMATION: n=g, a, t or c.
<220> FEATURE:
<221> NAME/KEY: unsure
<222> LOCATION: (1)..(1760)
<223> OTHER INFORMATION: unsure at all n locations

<400> SEQUENCE: 37

ataatgaata gcaaactacg taagttaagt tttggttact caaatttaaa cgacgtaaaa     60

aaaagaagaa gaaaagaaaa aatacgatgg aaagaaatca cagagaaaaa aagaaaggaa    120

aaaaagaaag acgatggaaa gattaaacga cgtatagaaa gaagaagaaa agaagaaann    180

nnnnnnnnnn nnnnngcagc gaaaaaaaaa gaggaaaaca ataaagatga caaaagaaat    240

cggagcgaag agaagaaaaa gatggaagaa taaacttgaa ttggacaaat tttatggact    300

ttttacatag acactaattt ggttttttttg ttagcttcct acaaattttc ctcttttatt    360

ttatttttgt aaaagtaaat aaatatgtgt cattagtcta attttttgaa cttattttgg    420

gagagataga ggaagacttt aaaaaattat tattactctc cattttaatt ttgagaagag    480

attgtgttgt accattcctc ttattgcttc caatttcttt gagggcagcc ctagcctttg    540

tacaacgcaa gcttcctgta gtatctctat ctctctctct ccctcttccg acggtgatct    600

cttttctctc tctcacattc atcacccgcc gccgccggta gcttctcttt ctctgacgcc    660

accgccgccg gtaatctctc actcgtcgct ctcaacacag agaaatttct gattgagcat    720

caccaggtcc ggcaactaac attccttgct tctgcatctc tttttcttca atttctggta    780

tagttttgat ggatggattg tgtgtattca atcatttatt gtgttttgat ggatgaaccc    840

gtttattatt ctttttatg acttcaagta attgcaactg ggtacttcta tctgcaactt    900

cttggctgaa gtaattttta gttaagtgca aacggacggg ctgggaccga gccaatctaa    960

cgcttatttt atcgaatttt gaggagttgg ttttgtttgg gtttatagct taggaagggt   1020

ttttggtttc gaagaaccta ccatttgaag ggttgggtct aaaatgtcgc ttaattcgac   1080

ccaatatgac tctgaatgtt aaatattgaa tagaaaagaa atgaaatact atccctaacc   1140

tgtctgccaa tttcgtgcaa aaaagcctaa tagccagttt tttctcgccg gcagtacatt   1200

cgccttcccc ttccaagcgc tacggactgt tgctcaatct ccagaatctc tcaattcgca   1260

gggggcaagt tctttccatc aatcatttta tgtatttttg cttctgccct agatcgttca   1320

tctaaagttc tttacctttt tcttctgttt tgttttttgg tgtataactt atttgatggt   1380

gatggattat gattcagtat cattttctta ttttatatca gcaacaaatt tggatttgaa   1440
```

-continued

```
atcatttttt aaataccttt tgatgttaag ggtttaggct tattattatg attcagagtc   1500

attttctacg tgttaaatta gtttactttc caagtatgca gttatgttca agcagttatg   1560

cagtcatttt ctgatgtggg agatagtgct gttttcctta aatgttttct atttaaacca   1620

ttgtgcgctt ggttggtggc cgtgcagata attgcatttc ttttttgga ttggggcagg   1680

ttggttactc tctggtttaa ctttcacaaa gaaccaagac agacatccgt aacttgtttg   1740

cataaagaca ttcaaccaag                                                1760
```

<210> SEQ ID NO 38
<211> LENGTH: 1767
<212> TYPE: DNA
<213> ORGANISM: Cucumis melo
<220> FEATURE:
<221> NAME/KEY: misc_feature
<222> LOCATION: (1)..(1767)
<223> OTHER INFORMATION: n=g, a, t or c.
<220> FEATURE:
<221> NAME/KEY: unsure
<222> LOCATION: (1)..(1767)
<223> OTHER INFORMATION: unsure at all n locations

<400> SEQUENCE: 38

```
aatataaata aatctcatta ctctttatga gctagaaagg atgcctaatg gacctacaga     60

ctagaagcta caacgatatg agattaattg gctaaactca ttaaccacat tatgatatat    120

ttgttaactg tgtgtacact ccactaaaga ctcgcagctg aactcttctc actgtagata    180

tatttatgtg tccacggata tagaccaata ccaataagtt agtccttcac aagtgttcat    240

aacactagct gggtcaaatt actgttttcc ccttgggtta cttctagtcc ttaaatacca    300

atgctcctct aatgaacaac ctgtttaatg tccaaccact aaacagaatc ctttctcatg    360

ccatagagag ggtaagacct tcaagtcctg gatacaccat ttaaaggagc gcttatctat    420

ttaccataaa gtcaagaagg agtgaattcc atcttnnnng attatgttcc cagctcccca    480

cccggttttg tcctcaaaat gataaatata ttgagttgac aatctgacca ctctcacccg    540

tacaaatcaa aagacaatcc ctcgcgaata ggagttcata atatactcat aattaagact    600

aagttatcca tgtcattcta atgaaataga aacccaacta gttaatggag ttacatcttg    660

tggttactat ttcgtggtcg ggtcttatgc aaactcatta catacgatac cctcactcgc    720

atgtcgctta cttgaacatg ttgaataaat gcatttatat tagatacaaa gtaagtcgta    780

tccatagtgt taccaggata agttacctag ccttaaccct atactataga cnnnttaagc    840

tgatcttgaa cattgtttcc tgtatgtctc tacatactgt tcaagactca tcaaacaact    900

caagatgtta atttattgga tttaggttat taagataaaa cgaataatat aattaataac    960

acttcttgaa attataataa tataacactt tattaataac taccaatgaa ttatatttac   1020

tatatacgag ttttaagaca taaaatccaa tataagggtg tatgaactgt taaagatgat   1080

gtgctattct tgttggatat tataggaggt atttagtgga ttatttgtga aagaataagg   1140

aggtacttat gggaagactg ctggaggtta gggaggatct ttgaaaatta ggaagtaggg   1200

atcaacaaaa aaaacgaaag ggaaagctta aagcttaaaa aagaaacgaa ataaagaaaa   1260

atgatttaga ccagcatact aaaatggcaa tgtaatctga ggctaatgta tcaattgaga   1320

actttgtagt cataatgatt aatcccaaac aaattagttt tcaagaaatc aaccccaaat   1380

aaaatgactt aaatattgaa gagtttaaat ggtctaaaat tattgttact gttttttatt   1440

tttggaaaag agacgaaaaa ggaaaaataa gaaacgccca ccgtggggct cgaacccacg   1500

accacaaggt taagagcctt gcgctctacc gactgagcta gacgggcttg gtgtccaaaa   1560
```

```
atccaataat attgaaaata ccatatagtt taatgaactg ggcaattgga ataggcccaa   1620
tatattagat atagcgaccc aattgttagg cgtgtcttct tccaaaaatt ggaggcaaaa   1680
cacaaaccct agcatccgct tctgctcctt tatcgtttct ctcggcgatc aattttcacg   1740
gagctaggtt taatcaagct tcaagca                                       1767
```

<210> SEQ ID NO 39
<211> LENGTH: 2000
<212> TYPE: DNA
<213> ORGANISM: Cucumis melo

<400> SEQUENCE: 39

```
tttaaataaa aataaaaacc atctctttat tttaagtagt taaatgattg tcgtttacta     60
aattaactct agcctatttt aagacggtct ggtcaaaaaa tcgattacga ccgaccaata    120
ttcatctaac ggtcttatta tttttaaaag atatagaaat gtatctcgtt aataaagcca    180
cgacggtctt tttctaataa aaattcaact aaaccatata acaaaattat tgtaccatga    240
aaaacacttt catacataat gcaaaacaac aatagcaaaa aaccaaagag gaaggggaca    300
atttggggaa aagtaatctc aaatttccct ttttgacttt gttctaaatt agtttattga    360
aataaaatct actaatttcc catttccaaa ttaaaatgct taatctttgt ctcattagca    420
ttgctagaac aaattgtctt ctcaaaataa aaataaaaat acaatatcaa ctatttatac    480
ttaattatct aacatttctc caacataaaa agagttatat atatatccta ttttgttctc    540
taatttttcc tctttttttg gtaattaatt ataatattgt cctaacatat tatattagat    600
agcttcgaca aaccgttgct taaaaaaaga aaagagaaat ccaacctaac tcaatccgaa    660
aatatacaaa gtacaaaata attataataa ggtagatggt atatgcatca atgaaataat    720
attgtcaact ttcctcgatg atgatggtaa taataataat aattttatat ttattaggcg    780
taatattttc ctcaatttta gtgtttgtat atactttcat atgtttaatt taagttttaa    840
aatttagtcc ctcaattaac ttgaaattaa ttaaagaatg tgaaaatgtt aatgggtgaa    900
ataaataatt tagagaaaaa ccaaaataaa ttagaggtag ggagtaattt tagaagttca    960
aaaaaaaaaa aaaaataaat tagatgtttg aaagtacaga tttgtttaaa tatgaaccaa   1020
cttcgaatag tctttccatt ttttcttata aaaagtcttt ctgatgtgga tactagttag   1080
agtatcctat caactcatcg atccaaagaa catactttca atcgtaagtc gtccattcta   1140
cttcgatcta aaatgatgct aggtttgctt caccttcacc cttcacaaag acaagtgcag   1200
gtgtgcttcg ctctatcaca tgattttgat tatgtcttca agaacttcac agcggtttta   1260
aaaaaacaag aaagaaaaga gtgagagtgt ttttatgtca gaaacatatg cccaagctta   1320
tgaaacttgt tgatcttgta gcgattgaat aacaaatgga aagtatctca tacaatttct   1380
ctatttttca cttttatcga agaactttgt ctcactaact cgtaatctaa aatacaaact   1440
cttcgactct aatatattaa ctccaaactt catttttcac atctatggaa cagataaagg   1500
tctaattttt taaaaatatg atgggaatta aagtatagta aagagattag cttcatcaat   1560
gggcttggat tggagtccaa agggttagcc caaacccaaa acatagtaaa tccaagccct   1620
ggaacaatga atagcacgga aagtttgtgc tgccggagga gcgtattgga aatgaagggt   1680
ttaggatagt tatggagcag aaaacgacac cgcatcatta aggacggatt tgggatttta   1740
agaatatatt agggacagaa taggaatttg aaaagtagcc ctagccactc aatttggtaa   1800
cagtagcaca aaaattggag gatacctaag gtaagcgaca tggggtaata cacagaattg   1860
```

```
tggctatggc agaattggat agaactccca tttgaggctc tcttttctct taccatttct   1920

acaagataac actactcttc ttcactctcc aaaaccccat cttcttcttc ttctcttagg   1980

ttcctctctc ccttcctcca                                               2000
```

<210> SEQ ID NO 40
<211> LENGTH: 2000
<212> TYPE: DNA
<213> ORGANISM: Cucumis melo

<400> SEQUENCE: 40

```
aattggaacc tgctgatatg aaatgcataa gagaactgaa cctatcagta tcatgcgaaa     60

cctgcagcat agacatacta ccgtgatgtt tcaatttttc aagcaaacaa aatatccaaa    120

aacacacaaa atagaggaaa ataaggcgaa attacaaacc tctctaggat tttcaagatc    180

ttccatattc ctctcagatc cgggtgtaaa gacaaccagt tcgaagttcc aaagctgttg    240

caatactact tgtctaaacg tcatagcaag tatatttttg gacgaggtac ttgaatggaa    300

atcttgagcg agagactttc tgagcttcgt ggccttttcc ttgacttctc tggcaggtaa    360

aaactgttaa cacagtcaac ttaggaatga caaatacaat cggatagcta aattttatct    420

aacgacaata ttccagagag gggagagaga cacattgttt tataacaaga ctcccaattt    480

catgagatga caacatcgca cgacagtcaa acaaaattct aagagaacat caaataatac    540

tagaaacgga catattagtg aaggagctct taaaggtagc cttgaaccag agatgggaac    600

gccatcaaat caatctcatt catcaatcat ggagttaatt gttccgatgg tggaattcaa    660

aatcggtcat agatttttat tttaagaata aaaattaaaa tggaggctcc tgaagctaac    720

atgccaggtg caaaagtttg ggagaacgcg ttcacgtcaa cattcgaatt cagtctcata    780

aatggaaatt gtagcaatga cgaaaaatat tcatagttgt tagtcacgga aatcggttcc    840

ataatacacc accgtcgaat gcgagctaaa acgagcacca aattacgcag tcaggttaaa    900

aaataactaa ccagccgggt cgagacagtg ctgtgttcat cagaaattcc cggaaataca    960

gtctccacaa ccattgcagg catcccagaa tcaaggtgct cagtggcggt ttcaccgcca   1020

tcagccgcag ccgcagtaac agactgccgg aaatcgacgc ctccgaccag agaaagccga   1080

gacaagtcat tctcgtacgt ccggacacag ggaagaatct tctcatcgga ctccagcaca   1140

gcttgaagaa cctcttcctc ggtcgtcgga attggcctcc cagcagagca agagaaggta   1200

gaaaagcaat gccttgagtt tttcagaaca attttgggag tataaattaa gggtatagca   1260

aacagttggc gagctggtat agcctgtata ggagaataat ggataaaaga caaactcaac   1320

gccattggag aaatggccat aaacctctga gcgagtgcta gggttttcgt tttatagtgc   1380

tactagctgt gcgtcgccgg agaagcgatg tctcgtgccc acatcttttt ccctccattt   1440

cttttcgggg ttatttctct atataccctc ccaaaatatt acaattaaaa cagttccatt   1500

ttgttttaaa aaaataataa aaatttattt ctcaataatt ttttttgaaa attgaccgtc   1560

aatttcgtac aatctacttt taaagaaatg attacttcat ggatggtttc taaagggaat   1620

ccaaaattta aaagtttaat taatttagat tatgttttat ataacattga ttaaatgaaa   1680

tatgaaataa ggtgtaagtt gatattagcc ctaatatcaa agatgagggt aaaagtaaaa   1740

taatagtgaa aagatatcca actgattctt gggtaccggt tcgggtaggg tttgggggaa   1800

tccggttggc gttttttgag cacagagaga tgtaaacggg acgggaagaa ataaaggcca   1860

acacaactat aaattctcct ctcggcggaa aggcggagca gcgtccaact tcgcctttca   1920

caaaatttac taagaggggg cttccattct acgtcgattc tgctcctctt ctactttttc   1980
```

ccttctgctt tttgtcgacg 2000

<210> SEQ ID NO 41
<211> LENGTH: 2000
<212> TYPE: DNA
<213> ORGANISM: Cucumis melo

<400> SEQUENCE: 41
ggtctcagac ccataggaat agatcattta ttgccttatg aattagttta tgagtacata 60
ataattgtca accgtataca aatcaacatg aaagaatata atgttgtaca tagtcattcc 120
aagtttacta atattatatt ttaggagtgt tctacaccga acctgtcaca tgtacactgg 180
gtatgctacc cctgaattca atatcataaa gcaactttaa ttgtcaagca ttctcttgac 240
catttgtgac ccatttgctc ctactttttc aatcaataac tatcacaaaa agctagatac 300
cacatgtgat aaactcactg aaatcaggta tatggttacc tgtgcttggt cagcactcaa 360
tcagattcga aggcctagtc tttgtatttc ccccctctg cacactacaa atagtcctcc 420
acgtaaagac ccataacaaa acgcaaacca agtacagaaa atctagccga aatccagacc 480
actcaaacat aacaaatctt ctggtaagtt tgaataaaat ataaaactaa cctaatttaa 540
tcaaataata caataaaatg gaagcaacta acataacata tctaaatatg atcacgtagt 600
aggaaaaaaa aaaacattcc aaaactatta acaatcattc ttaatggtat gggtcaatcc 660
ccattattta ggactataac aagaattcct catacctaat gccacatcct atgtccaacc 720
ctcgagatta cctcgtgagt aatcaatctt attcatcctt atttcaaatt atgtgaaatt 780
tctcatcagg ttgatcatat tgactttcaa tacaacttat gattaatctt tcccttgata 840
taatttcgta tgaaaaggaa gttgacatta tgtgattttc tcataaggta aaccaagtaa 900
acttgacatg acgtcttaac aagtcttggt ttctaagtgt aatttactgc agaaaaaatc 960
ctaaattcta tgacttttcc tatgagattg accaaatcaa ctttacgaga aatcttggga 1020
agccatacct acaaagtctt cccccaagaa attacaattt ctagtaaaga ttgttgaaat 1080
ttaccctcca atttttccgt gaaatttgac aaacttgtaa gaatatcaaa tttgggttgg 1140
atattgacat tccaaaataa gtagttttaa aaaggattta tccaacaata atagaagaaa 1200
aaagatagga aataacatac ccacgtaaat ggaatgtaaa tatttatata ttaggtgtct 1260
tgaacgaccg tcaaacgaaa ataaattgtt catccgaagt tgaaactctt taagtgtaca 1320
tttatctttt cgtaagaata aaatgtaaaa ttaacgtgtg aaaggttggg ttaaataagt 1380
tatgtagaga taatattgaa gatgatagaa taatcacgat cgatgaatta gtatagtccc 1440
agagcggatt taaacctctc tcactttcat gctttctata tatatcaaaa taatttcaag 1500
tagttggttt agtcgtaaaa aagtcaacca atctctttta gataaacctt gagttattaa 1560
aaaattagat caaagataat cgttgaaatt gaaattttaa gagtataatt ataacaaatt 1620
ggaaagttct aaagtagttt ttgcaatatt ctccatcaaa atagagtaga aaaatatttt 1680
agtaattttc ttatcttaat tttagttttg taatagttat taggatggtc ctaagttctc 1740
aatccgcttt tagtccataa aaagaaagaa gagagagaaa aaaagtcccc gatccgcgac 1800
acataccaat ccaaccaatt atgcacaatc catgtgatat cgaacggtca caagaataaa 1860
tgctttctac acacggatca ccatccaacg gcttttcctt ccatctcatc ctctatataa 1920
tctaccaact ctgtcatctt cgacacactt caattatctc agcttttatt tcatcggatt 1980
ttccatcaaa caaggcaaca 2000

<210> SEQ ID NO 42
<211> LENGTH: 2000
<212> TYPE: DNA
<213> ORGANISM: Cucumis melo

<400> SEQUENCE: 42
actccattat ttggtttgat taaagcttcc atctgattaa taaataataa taattataaa 60
ataaaaaaaa gcgagagttc cattaagtaa tattatctac cgaaagagag caactatcac 120
ctcaaacttc aaaaagataa aatagagacg aaacttgacc aagtcaaaca caaaccacaa 180
acaaccgatc tgacagaaag tttgccagaa tcttcaatgt acacgcgaag ataaacaaat 240
aattaaatct cgttcgtctg gataacataa cacagcaaat gaattttttt aatacatatt 300
ttaaaaaaga aatttaaaat tggtagattt tataaatcat ttccaaaggg tttttcttgt 360
tttaaaatgt ttttttgttt aaaataggca gttcatcacc acttgagaag atccaaactg 420
ggcggcaccg gttctgcgac gcttgagggc cgtctccgac tcttcgccgt aggaggccga 480
tttacgcaaa gaataaccgg acaatgttgg acagttttga cgagaagtta aaccgagtaa 540
gggcttatgc ttcttctcaa tgcgctcgtc gtcgtcgtcg gcgacggcgg cagcggtgat 600
ggggacttgc tctgttgcgg ggtgaacatt gggattccga caagaaggtg ggttcttagg 660
gttggaggga aagtggaaag cgttatgggg ttcttgatgc tgttcctgca acttttgctg 720
tttgaggaag cgcttttgga gatctaaaag agaagggcga ccctttttct tcttcttctt 780
catggtggat ttagaaacct cgcccattgt tcttcttccc tttctcgcag gaacgaagcg 840
cagggaggtt aattgatttc agttttcacg gcggagggtg caggatttct aggcacgtgc 900
gaatcgcatg accctatcac gtgcgaatca gtgacggtat aacgtgcatg caaaggaata 960
gaaacacaaa ccgctcttac aattataaaa ctctaaacta aactacgaac gcatctcata 1020
atgggcccac tccatcatcc tatgggcctt ttgaatttta tgtatactat ttttttttt 1080 ttttttttt tctttaatca caatcaattt ttctggtatt tttttaaata ttcaacaaac 1140
tttttgtttt aatgttgtgt atatctaatt aatttagttt tattggatgt catttttttct 1200 atttttgaaa aaactcttaa aaaaaatata aacaaaaaaa gaatggaaaa agaatatcaa 1260
acaaagagag gagagagcaa ccatacctaa aaagtttgaa agtaaaattg aaaaaaagaa 1320
tatacattga gggcagtgtt gaaaatgaaa ttaatgaaaa aggaaagggt acgtaacaat 1380
aaattacatt ttcttgcagg cttaaacgaa ggcccatata tgaaaaggga agcttcgatt 1440
tgggttcagt tatgcgggcc tggggttggt attgggctta attttataaa gaaggcccaa 1500
atgttggaaa gacgggcttt gagagagggt gttcggcttt tgcccgaggg gggtggggga 1560
gtggcaccgc caagcgaaga caacgaatat taggagagaa aacacaaaga ggcggagaga 1620
tggaagagaa tgaggtggac caatgagata agagtgcgca gattattgag gtggcaataa 1680
atttagaatc ccgcctaaat cccagctttc atttcatgcg caattgaatt tcaatttgcc 1740
attcccctcc atagggactt aattatcccc tttttttac tctcataact ccctctcttc 1800
ccaccacgtt cgcttcttcc tccccttcc tcttcaaacc ctaaacctaa cctaacctaa 1860
cctccttccc caacttcttc cgtcggtacg tttcatccat ctcctcccac ttttcatctt 1920
tttttccttc taatttcatc tcttttcttt gtttttcctt ccaattgttg ctgatcccat 1980
actatactgc aggattcgaa 2000

<210> SEQ ID NO 43
<211> LENGTH: 1115

```
<212> TYPE: DNA
<213> ORGANISM: Cucumis melo
<220> FEATURE:
<221> NAME/KEY: misc_feature
<222> LOCATION: (1)..(1115)
<223> OTHER INFORMATION: n=g, a, t or c.
<220> FEATURE:
<221> NAME/KEY: unsure
<222> LOCATION: (1)..(1115)
<223> OTHER INFORMATION: unsure at all n locations

<400> SEQUENCE: 43

aaagaaatca aagcgaaaaa acgaggagga aaagaagaaa aacgannnnn nnnnnnnnnn      60

acataaataa agaatagaaa aataaggaag atgaggaaag aaatcgcaga aaagaaaaag     120

agaaaagaat aaagacaaaa ttgcagggaa agatggagaa gatgaaataa taggaagaag     180

acgaatcgcg agaagaaaat aaagatgaga gggcaaacct gaaatattta aaaaattgct     240

aactttatgg gttttgttac acgggccgta aatagttttg ttacatttat gtaaatttac     300

aatcaattaa ttatacaatt aatcaaattt ccacaaatac aataattgga tattttccca     360

aaatatctaa taagtttcaa tttctaccca tcaaatattt caaccattat taacaccaaa     420

aaattcaaag attaaactta agataattac aaanaaatta ccttaaattt ggggcattac     480

acatttacat tgaactatac aattgtttac cataatcaaa acgatcgttt ttttatgatc     540

gacatgataa tttcctatga tcaacacgat tttttatcat atcaacacct tcatttaaat     600

ttgaagtttt tttcccatcg ttaaaaagaa gtacacgatc ttttagaaga agattacttg     660

cgcgggctga ttaatcgtct gttgactgtg acattttta tatttttcat catgagcctg     720

tatgtctttt ttgtttttat aattgtttta catcgtgtaa atagtttgcc gattagttat     780

atttgttaga aaacactttt tcaaatgtcg aaaatttgat tttgatttat taaaacttta     840

gtaaaggata gtgtttatta cgtatagaat cccaaatttt cacaataatt tttcaaaagt     900

aatccaaaag aaaaaagcaa caataataaa aggctcaaag cgacgtcgtt tagggcaaca     960

gctggggaga agaggacgat ctgaaaaatc atttcttgag cgaagggaaa aggagctcta    1020

ctaaagcagt cgaaaaaaga aaactcaaac ctcgctgcga ctctcgacat tgattctgtt    1080

ttcaattcat tttgccaaag ttaatcgatc cgaac                               1115


<210> SEQ ID NO 44
<211> LENGTH: 2000
<212> TYPE: DNA
<213> ORGANISM: Cucumis melo

<400> SEQUENCE: 44

tatagtttgt aacaatctac tctatgttct ttcaattttg atacatttga atcttaaact      60

ttattgagtt acacaatata gtccttgtat tttaaaattt ataatgactc tatttatatt     120

aatattatag aaatttttgt taaggtttaa taaaaatttt tctgtataaa taaatcgaac     180

acgaagtcta tatttagact gcaatatagt aaaacctgac atctaagttt ggtgaatttt     240

gttttgcttt aaaaactaaa ctattacaat tttaaaaata ttttaattta gttaatgcac     300

attaacttta cggagtaaat ttttacaaga ttgaatatac atagattaaa tagttataaa     360

accaaagatt agagtaaaaa catttaaata gaaagaacta agattttttt aaaacgaaaa     420

tgatactaga tacatatata tgtatctata ttataattac tcattttaac atatagtttt     480

gaaagaacaa agattagttg catgtgttga ttgtttttaa gaaggaaata atttttgaat     540

ggaaaatttt caaaagtttt aaatttgaca ataaactcat atttaaagtg tactacaaat     600
```

```
tttaactttt ggttaaactc cttgtttagt tcaatcatgt aataaattct cattccaaga    660
atcgttttag aaaattttat tgtgcattta ataaaatata gaacatatat ggcatataaa    720
aattgattac ttttttcttt ttttgggacg aaaaacacat tagatataat ctttttttgaa    780
agtttatgaa ctttaaaaat gggttatttt atacggtggt caactttatt ttattgaaat    840
tattgagttt ataaagattg ttatatcatt ttcttcttct ctttcactag aatacaatca    900
aacctatcaa actctctatg acttatttag aattcttttt gttatatttt tgaaattaat    960
aaatgaaaag cttagagtct aaattataac aattaaaatt gaaaattttg caataatttt   1020
atttttagca aaatgacgtt tggtttttgg ggattgggaa tggatcgata ctatcccgat   1080
tccggacaaa gaaaccgacc cgagattcga attttttcca ttcccaaaca gagcacttaa   1140
aatttaagca acgttataac ggcgtcaccg aactaaacgg aaaaatatga agaaaattag   1200
aaaaagaaaa acggaacagt caaacgttac ttcacgtcaa tggcaatatt catttttttt   1260
tttgtttaaa taattgaatt taattaattt ggtttataaa aatagagtcc tcatatatcg   1320
cgaatgcgca tttgatcgtg aaggacagct tctcccttgt gttcaagaga gagagatcta   1380
tcattcttat ttggggccga tctctctatt ctcctctctt ctattccgta agtttttctc   1440
attcattctc ctctctcatt tctctccgag atctgtttac aatccttttg attttcattt   1500
ttcctgcttc gatctgtgct cctggtgatt cccttttcct gttttatctt ttgttgatct   1560
tggaattgat tgttcttttg tgggttttca ttgatttgta ttttctgatc tgggtttctg   1620
ttttctcgcc ttgatgtttt gtatttggat ctgatctgac gtacccttttt tttttttttt   1680
tatttgaatt gcttttccaa tgtttatacc tggattttta ttgatgcatg ggtttaaccg   1740
attggttgga tgcgttttct ttgtgctgga tctaggtgtc cttgttttta atttgaattg   1800
tgggtaaaaa tggcattatt gtaatgtgtt tggagtttga ttttgaatct tggctagttg   1860
atttttgaat tacaaagatc ggatcctctt ctttttttggg ttgtcttaag atttttggct   1920
ggtttaagta tttgatgtcg ttgtatttta aggggtaact gatgccggct tgttgtgttt   1980
gtattcagtt tacttgaaaa                                               2000
```

```
<210> SEQ ID NO 45
<211> LENGTH: 2000
<212> TYPE: DNA
<213> ORGANISM: Cucumis melo
<220> FEATURE:
<221> NAME/KEY: misc_feature
<222> LOCATION: (1)..(1115)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 45

attatctaaa cattaactgc aactaataca gattacagta aatttgaatt atgatgttat     60
ctagagtcat ttgtcttcaa tgatattgac tcagattcaa actttatgaa aatgttaccc    120
tggaaaatat tctaccgcaa aatttcaatc caaagttaaa ggttgaataa tttagaagtt    180
ttctgcgact tccacccact tattatttag aagacctgaa atcaaaatga tagaagatga    240
atataaatat attttttttgc tttaaaattt ataaatcaaa catttgacct agtaattgat    300
aatacataat attatgtgac tcgtaagtaa aaaagaaatt gaaataatat atatatacgg    360
agatcgcaaa aaataaaaat gaaagtaata taaagtaaac gcaaagtaag aaagcaagca    420
ttttcaagta agattgaaac ccccgtccct gggggctcca agataacacg ggtgcccaat    480
```

```
tacccggtac acgacttttg ttgaacaaca ttgaataatt agcccaaatg aaaatatttg    540
tcgacatatc tttcttataa tatgtaaatt agataccaac acaaacactt gtaacaatat    600
cctaactaac ttggttttaa atatatatat atatattatt tttttttcta tttatttatt    660
tnnnnnnnnn nnnnnnnnnn nnnnnnnnta gataccaata tttagtggcg ggtccataaa    720
ttttatatag ggttattata taataaacac taaaaattta gatattatta ttttcaaagt    780
taggccacaa gtaaaagtgg ggatataatt attatactat aaccatattt tggtaaaatt    840
aagtattaaa tatactttaa aattaatatt aaaatataaa aatcgataat gtgtgggata    900
aatttatgga tgtaaatatc aatgttttaa tgttcaaata aataaatagt aaatagaaac    960
aaaacaagaa gtcagtcttt actactaatc gggactaaaa tttgaatttg atttaaaatt   1020
taaaacttaa ataggactaa aaatgttagg acaaaatagt aacaaacacg aaatttaggc   1080
aaagaaatat aattttattt atttattatc attttttta tatatataat tgaaaattga   1140
ttactaaaaa aaacaaagaa cggtaaaacc ctagattaaa atcaaaatag aaannnnnaa   1200
cccgaaagga gaattttgat ttccagagct aaacataaca cgatccaaac ccataaatcc   1260
cgcatcgagt ggaaccgata tcttctcccc ttcgaagttc caactctccg tttccgtctt   1320
tcttttcgat tctccttcaa accctctttt cttcgtcttc ttcaaatctc tacatttcaa   1380
aatcttcgct aatctcttct tccccttctc ttccgatctg accgtgaccc cattcgaagc   1440
ttcttctttc accaagcttt ctctccgcta tcaactttaa ctttcgtcct gtattcctta   1500
gccttccctt gcttttgcag tctccgccac cgaacaattc ctatcccgag ataatcccac   1560
ttttgggtcg tgtttctcac ttattcaaat cgctggttct ttgattttgg gcttatttca   1620
ctctgcatct gctgcgactt ggaggttata acatctctct ctcggtcttg ttaggtatga   1680
aggatttgag atattttcta atctatctga actgggtttt ctttcgcttc cgtttatgag   1740
atgtaatttg ttgttctggg aagttttcag atcctttcta atgggcttct ttaatttaat   1800
ttaaagcttc tttgtttgta cgagatgtca agtcttaatt tctagcaata tcagtatctg   1860
ggttggtggt atttaggatg atcaagtctt ttgttattta atggatgaga acaattattg   1920
tcattgttat tattattttt tggaaaaaaa atcaatgggt tttcactggt tttgttgatc   1980
tttttagata attgaagttc                                               2000
```

<210> SEQ ID NO 46
<211> LENGTH: 2000
<212> TYPE: DNA
<213> ORGANISM: Cucumis melo

<400> SEQUENCE: 46

```
cttctcgatc gcagcaattc aacttcataa acaagtccaa gaacgaagag tttgattccc     60
ctaatttaac ttaattttct ggtgaaaatg gaccatactt ttaattacat attattttgg    120
ttattgcctt ttaaatggtc tattttaatc tctaattttt tttattaaac aatgatggtg    180
aatcttttct aaaagaaaga aaaaacttct ttacaaacta tccaactcta ataacaacac    240
taattataaa ctagtctact acctttatta taacagcaat taaaagaaaa aatcgtattc    300
actgacaaaa attcgttctt ttgaatgctt atcgaatgtt ttaatttttt taaaaaaata    360
tataaatatt tgtaagggaa ggatcagaat taaaactctc tcccctcaat gaaattgaat    420
tatttgtttt tcttgttttt cttttttaa aataaaccta tggatttagt tggtcggtcg    480
aattaaaatc gtgaggtcgc acacgcggtg tcttgtggat tcaaaattat gattatttcc    540
```

atcaccccctt ggctttttcg ctccattcgg ccatgcctta caaatttcgc tccactccca 600
ttcttctctt cctctcctct ttcaactgca ttgaggccga tcctttaggt aaatggttct 660
ctcccatttc atctctaatt cctctgtttc tttttatttt acttgttctt tttccagccg 720
gatcctccat ttctgtggtg aaactgaatt gttcttatcg atttcttgtt tgaattctgt 780
ttttctctgt ttgtgtctgt gtgtgttttt aatttgtttt ggcatgttga agtttaaaga 840
taccaaaagt tgcgcttcac tactttccag tttcgatggt agctgctagt tgtaacgctt 900
acgttcttgg ttttttagtt aaaatttttt tgcttcttgt tgtttactgt ttagcaaaaa 960
gcatggggaa tactaccaaa gtcccgaact taatagatag atgatcatgt gctaagaagt 1020
gcgatacttt ccgtagctga tacgtgacac agtgtctgac atttgtttga cacatattag 1080
aaacttgtta gtataacata tgtgttaaac aggcatagaa cacctgttgt actaaaaaaa 1140
atatttgtat gataataata ataactttga agtgtaaaat atatccagct aagtttttc 1200 aagtatacaa gtgcattaac tcatttcctc ttgattttct tttggtataa aaattatata 1260
tattttgaaa accgtatact ttaataaatg tatccttgtg cattatgtcc tagattttta 1320
gaatatggtg tgttgttgtg tctatatcgt gtcgtatcaa tatctcgtat tcgtatctgt 1380
gtttgttaga tcatatgtat aagcgaggac agctatttct gatgttacaa gaccttcttc 1440
aaattttaca ggaaatcatt caatttgaaa attcaagatt acaaatgcaa tctaaaccaa 1500
acttcaagaa caaaaagtgt tatttgttaa tatccttgcg acctcaccca aagtatctat 1560
tacaaacttc agaaaaaact tcataataag ggttgggttg aaaaaaaaca tgaagaagtc 1620
ccaccccaac ctaactctaa aaagcataaa aaattcaacc caacccaaac cttacaattt 1680
gggttgggta gtccgtgttg ttcgggttgt cgggttattt gaactcctag ttttagctaa 1740
gtgtaaactt atttaaggat gttgaaggtt agcattgatc tttctctctc aaatttggtc 1800
aagaggaatt attttttgag tcattcatat agttccattt tgcttttgag catttgaatt 1860
gtttgttaac tacttctttg attaatatat tcgaaagtga aatttccttg gtttacttta 1920
ttgatcagtg tcccatttta ccagttattt cagttctcct aataaccttc attggacttg 1980
agttcggtta acacaaaaca 2000

<210> SEQ ID NO 47
<211> LENGTH: 2000
<212> TYPE: DNA
<213> ORGANISM: Cucumis melo

<400> SEQUENCE: 47
aatgtatcgt gggcatttat tatgacaata gtgtaaaaat gttgttaaca tatctgtgta 60
ttgtcgatga tgtagatcta ctacgccaat agttatagtt tccatcggta tatctatgaa 120
atgtcaacgc cttaaaatag ttgcatgggc atagacttgt ttttttagaa aaatatgttt 180
tatatttgta ttttttttcac taacatcctt ttggttttgt atctaaacac aactcaaaat 240
atatcaaata ctgaaattca tttcctaaaa aagttacaat tgtttcaaat ataagtcacc 300
tgaatgaagt tcttaaaaca caaagaattg ttccttacaa aattaacata agcaaaatag 360
taagatcgtc caaaataaca aacattacat aaactttaga ccaacttcta atttgtttgc 420
caggaagtga tctccattga aagtttgtct taaaaaacaa ataaaaagaa aataatagaa 480
acatattcaa taaactagta cattttgcac cttacatata tatacaaaaa ctttacctac 540
tttaatttct tgaaaatcta aattttgaat taagaacttt tcttacaacg ccaaaacaat 600
aataacttat aaatcttagt gatggaataa taagttataa ttcattggtt gattgtatca 660
ttaaccattt ctttcttttg gtgtgagaaa cttatccaac taaaaatatt cacaatagta 720
gggcgggttt gtcgtggctt tgtctgaatt tctacaacat gtgtaaatat tttcaactgt 780
tttatcctct aagacaattt tcctaaaaac aatcatgttg ttcacacgag atttccaagg 840
aaatttaatt caaggagttg aacttgtatt tatgttgatt tgatgcctat gcttaatttt 900
aagatttgag aaagcacgtt atatttgtaa agttggagta ttggaagaaa agtttgtatt 960
ttcaaaagaa cctcaatatt cgagatcgac ggttggcttc aaaagttagg aagtctttga 1020
ctcataggag aatcctatct agactttatg caatataaag agagttctgt tttatggact 1080
tagttggata aataattaat ttgattcaac ggtcataatg aaaacatgtg acatcattat 1140
aattaaccaa tttatatctt taatacacat atcaactttt aaatagttct aaattcaatt 1200
atttgtattt atcatcatta attaaataaa taatgtgaca atttgtgatt gatccaaaaa 1260
tttcatattc aatctatact atattagtta agcttaaaat tttactaaat gcttaaagtt 1320
ttggattatc gagcttccta ccaaacaaaa gcctctattg cacatttaaa atatagaata 1380
gtaggtttat ataatatgaa agattgactc ttaagaccat actctatgac ctaatgaaat 1440
cgacatttat gtaattgata attaataatt aataaaaaaa gtgtgacaaa aaagtggaca 1500
taataaaaga aaggaaattg tgaagcatta gcatccgaat ttcgaagaaa acaaagggcg 1560
ccctcagatc aaagaggaca tactataaag tctccacgct atttcaagaa ttggcgtgat 1620
tctcaagcga catttccgta attcaccaca aaaattaaaa acaaaaaaga actcacagat 1680
tctgatttga cttttgaaac cccaaccccc atcatctccc aatttaattt tccctcgata 1740
tttatccaaa ttcagaaaca taatcttgac aattttatgc tccattcttc caatctcagc 1800
cgtacgtttc attcaaactc caattctccc ccactgcgcc ttccactacc tttttccttt 1860
ctattaaagt gtcctcacaa actcacctcc tctctctgtt tctgtctgcg gtaggatcgc 1920
cgactccgga tttacatttc aggggtcgaa gatttgttct ggggtttctt taatttcttt 1980
atatatatac acacacaatc 2000

<210> SEQ ID NO 48
<211> LENGTH: 2000
<212> TYPE: DNA
<213> ORGANISM: Cucumis melo

<400> SEQUENCE: 48
gccaaggaaa atgaattgtc taagaagaag aaagaaaaga aagaacattt tttgcaaggc 60
tacaaatcaa aacttaaatt atccacgtga cacaacaagt tcagagagga aagaaccctc 120
taaaactccc atataccttg gcaataacca tgacaatagc aataaataaa caagtccatg 180
acataaaata aatattgttt tcattaaatc tcaataattc atatgtagtc cgctccgatt 240
atgccacagt catatatcaa gttcagtatt ttaacaattc aagtagacat acataaagct 300
actatggaaa acataaacaa gaatggaaga aggagggtta aggaaacctt tatccctgat 360
ggagtttcag taaaactgag cttgtaggta ttagtacgaa agctgtgaaa tgaacaacct 420
tggccaggta attgaggcac cccaagattt cctttatcaa cactatcaaa gaaagtaaag 480
aaagttatca cttcaaaacc caactcccaa aagcagctca tcattttcca gtaagttaat 540
actttgaaag atcaaaatca aatctacaat caaattagac ttcttaatag ttattgccac 600
gaaccatgca tttgtcacgt tattaagact atggtttgca ataatctcct atctggttgg 660
atcactactt atactaggca cagcataaac taaagtagtt tcccagagaa ggaagaaaca 720

-continued

```
tgaacctggt tgggtccatc ttggcagtaa aggatttaag ggagaagagc aaaccaaaca    780

taagtttatg gtcttgctgg ggattcaatg tccggagagg ccgattccac tccctgtaga    840

acaagcaaac tccattccta ttgaaaatat acatcatatg cacattgttt ccagtcgctg    900

tcggtaccgg aggcgaggga ctaatttctg acccaccaaa gaactgcatg gtttctggaa    960

taaactaaac taaatcaaat caattgtcat ataaaatgat ctacgaatct aagattctaa   1020

caaacccaac atttcactca actctacaat cagtaaccta gcaaagcaac taataattca   1080

atcattccta ataattcatt gaggttaaaa ataaaatagc gaattgtcaa caggtaaaat   1140

ctaacccgac ccaaatcagg aatcactaaa gcaagaagct gtatgactcg atcaaaaata   1200

acccagatgc atttcccttt ggcctctcta cagaaccact caatatagtt agaaacaaat   1260

ctagtgtaaa attgggagtc ctattcatac ataattccaa ggaaaatgga ttttacttat   1320

gcatcgtata agagactgtg agcaggggaa aatggagaga taatcaccaa tgagctggat   1380

ggtgacagat tcaagaagaa gcatcaaaat caaacaacgg agagcagaaa gatacctcaa   1440

agagcagaga ctgcaaagta aaggaagcga tcaattcaac gacgaagctc ttgattcgtc   1500

aggcaatgat tgccggcgac aacaacgtca gcagatcgga gccttacggc accggagacc   1560

cctccgacaa ggacagagtg aacgaacgtc gtttgtgaac ggtgtaagca aatcgatctc   1620

tcggagtcca actccaaagt actgtttcga tatgcattaa tacatttgat ttttgttata   1680

tcaaaaataa atattatatt aaaatttata aacattaaca aaaaaaaatt aatttcacat   1740

aatttaaagg accatttggt aatatataca aaattgcaaa aatcaaattg ggcctatttt   1800

gttgttattg gaggcccaag atgggtggtg ataaatatgg gcctccaaaa gaataagcaa   1860

aaaaccctaa tttcctctct tcctctcttt cccaatacta taaatcttca ccattttcct   1920

gattagggtt tttgttcgtt cttggccgtc cccttcatcg ttcccagaga gagggagaga   1980

gtaagttgca atagtaaaac                                               2000


<210> SEQ ID NO 49
<211> LENGTH: 2000
<212> TYPE: DNA
<213> ORGANISM: Cucumis melo

<400> SEQUENCE: 49

aattagcaaa ttgtatgtaa caacgtcatg aagaggcatt tcatcgaaca atttaatagc     60

agagtcaaga tggcccagtt ttataagttt attgatttct cgattcttaa ggtaaatgag    120

atcgcgagca tggaaatgca gacccaaacg agaatatggg tgtggtaaat ggaccggtga    180

tgttgtggct acaaattcgg attttacagc agtaatagtt ctgacgaagg aagcgaattt    240

agtgaccttt cgcatcacag tttaagctta tcagagacct gaacaagggc tctagctcta    300

caacttagaa aggtttgata tggtccgtga tcgggaggga ccgaataaca ggcgcttaaa    360

ttgttgttca taaagaagag gattgtcgtt gatgtatttt aaccaagaga tgattagtta    420

tccacatcca cagagagaac agaagacggc tttctaaatc tacaccgata aaaataaccc    480

taccactttg tttctttaga aaagggtcac attctttaaa aacattagcg tcgaggatta    540

atagggtata ttgactaatg ctctgtttgg atttcgagaa ataccaattt acaattgatt    600

tcaaattaat tatgttttgt tgttgcacga aagataaaaa gaatttaaaa ttcaaaagga    660

tctcaaatct tatttttaac ttaaaaactt ttatgaccca aacggtttat gtatgattta    720

aaagtagaat acctctgtga attcttaatt ttttttctt tccaattacc acataaatat    780

gaaattttaa atacatttat tttaaatttt atatccgaaa caaaataata atttaaaact    840
```

```
atttctcata tatgaagtgt gattcgatct aaattataaa ataataaaaa tttacatcta    900
gttttgatta tttttttcg ttagatacta aattgttaag aaaataacat ttttaatcca     960
aagttttgaa gaatatatga cttttaaaat ggtatttatc tttttagtgt ctgattttta   1020
aaaaatggat ttcaaaagtt catcaaatag cattgtattt ttattttaaa taattttgac   1080
atttaaaatt agagtaatgg tttataaaag acacttgatc tctaaaacta ttttcttaga   1140
tataaatacg tatgattatt tttaaaaatc aatcaaaata ggtaaattgt aaaaaaaaaa   1200
aaaaatcaca tgaatagtag ttgtaattat gctctcaaac tttcggttat gaaaaataaa   1260
cattttaact tttagacgtg tcaaagttga gtcaagttgg accttcaaag ttatgtagtt   1320
atataaattg taatatatgt ataagcttgt ggattcaatt ttatcattta tgggtccaat   1380
ctctacaatt atcgtaagtc tatgggtcaa ttgtaacaca tgtggagttt aagagctcaa   1440
ttttggacgt ggatgtgttt tgcaaccaac tccacacctt aaaaaggtgt tttttttaa    1500
tttatcaaaa aacaagaatt tagaatcttt aagtttatct ttaaaaatca acggacattt   1560
tgaaaaccaa ttgaaactac tgttataaac ctaacaacta aaagtatatt ttttaagacc   1620
gaaagcataa atccataaaa aaaaaatcca gaactgaaaa tgtaactttt atagttgaaa   1680
atttagctaa attatacata ttaaaattca aggaccatat aaaattaaag tacctgatta   1740
aataataacg aattaatgtt tggtattttt aacctacatt agaaaaaaaa aacaaaagaa   1800
aaacggcata ctatttgtca agcgtccgat gggaagaaaa tccaacggtg agtgttagta   1860
ttgaaatacg cagttctcgt gaatgagcct ggcttagatt tgggaacaag agccaacccc   1920
tttcgaccga gaagccgtcg tcttcaccat attcgcctca accattcgat agccacgttt   1980
gaagaagaat taggattgcc                                               2000
```

<210> SEQ ID NO 50
<211> LENGTH: 2000
<212> TYPE: DNA
<213> ORGANISM: Cucumis melo

<400> SEQUENCE: 50

```
agccaatggt tcaattaaca gctctagttc tagcatggct accgctggta acctttctat     60
gactagagac gtcttggagg tggagggtag ggcacgagga ttgaaaggtg agggtttggt    120
gaaaactcaa gcctttcaaa ttcaagaaag catgcttgac ctagtagcat ctggtgatct    180
tggggaattt gcaatggata ctcataccct tagtcggcat tcgtctcttg gttctgctgg    240
tatatatttt tttctcttgt tttctagtga tattttcttt tatcaatttc cattatgaag    300
atggaatctt atgttctatt ttttcatttg gaatgtaggc tttcacaatg aaaaaattgc    360
taatacgttt ccagaagagg ttgctaaaga cccgtaagtt cttatttctt aacaatttcc    420
tcagtttaac aagttttatt tactaacata tccttagttg tataaatatg aatctattat    480
attaactatt tcatttatct atcttttaac agggtgacca ttcacaacaa agataatact    540
tcattgaaac gccctcctgt ctcacgcact tcggcatccc aggatggatt gtctgtcctg    600
attcctgatc cggttgttag aggaaagaac tcagatggta aataataagt gatccattct    660
gttatcttct ttattcattt tcaattttgt attttgtata tatttatata atattttaga    720
aagataaaag atccatcctg aaactttgtt tcaggtggaa gaccggaccc aactagtatc    780
ttggtgaacc aagaaaacat ggcagccatg aagaaagaga tgcgtttccg gcgctcttct    840
tcttgtagtg acagcgacgt gtcagagact tcttttattg atatgctgaa gaagacagct    900
```

```
ccacaagaat cccatttgac aacggcggga gttccagagc catctgatgg aatgcaggga    960
gggaaaggtg ggaaaaagaa agggaagaag gggagacaga tagatcccgc actactcgga   1020
ttcaaagtca ccagcaaccg aattatgatg ggtgaaatcc aacgcttaga cgattgatcc   1080
attaggcaag atatagaaca gaaattgatt tttttttttt tttttccaat catttttgta   1140
gattgtgcag ttatttgttt tcgtgtttgt ttaaccctct tgtaagttgt tgtatatagg   1200
tttcttagag ttgtcagctg cgttgaaaca tgtggccggt atatgtattc caattctttt   1260
ctttttttccc gcagttgtaa atgatcaaat ttgagttggt caaattacca aacctttgta   1320
caggaacttc gaagagagtt gaaattttat tctttttctt ttttgttctt ttatagagtt   1380
cgagattatt tgtatgaata taatcaaaag caaagcatgt aaaaataaaa tgatttgaaa   1440
gggaggtttt ctatcccatt caatgtgacg aatccaacac ttaaagtaaa tttgaaaact   1500
gtctaattta tatgtatgga atgtaatgct cttcaagaaa ttatcttatc ttctaatatt   1560
taatgggatt cacataaata tgaaatttca acgtttttct tttcctttt  gttgtgagat   1620
taaggatact agataataac cgacctcaac cttttaggcc aagaggtctg gagtctttat   1680
acttgaaaaa agtttacaca tattctaaaa gattaaaagg ttaattgttt ggtaaaacat   1740
taatgatgac gatacttaag gtttcattaa aaaaatattt ggaacaattt gtttataatt   1800
taataaaatt gtaactttga acattttgaa ttacattttg tttttccatt tttacggtcc   1860
tcgaactcat cgatactcac aatggagaaa aatatcacaa tgccgaaaat acccttcttg   1920
ttcccttctt atacaaaagc aacactattg gccttatcaa cggagcagca gctactctcc   1980
tttagcacaa atctccatcc                                               2000
```

<210> SEQ ID NO 51
<211> LENGTH: 2000
<212> TYPE: DNA
<213> ORGANISM: Cucumis melo

<400> SEQUENCE: 51

```
tggtgtaccc acttggtttt ttctcttttt ttcttttagc tttttgctcc taaatttctt     60
gccttagttt tcaaaagctt gtttttattt ttgaaattta accaagtgaa tagaaaaaaa    120
aaagagaaaa caaaagcttt taaaagcttg tttttatttt tgaaatttaa ctaagtgaat    180
aggaaaaaaa gaaaaaagct tataaaattt gacgaaattt gctgtatttt gtacatttta    240
ctatttttct attttaaaaa atgtgtctga acgaaaaact tatattatga gatttaattt    300
tcaaaataaa attataccaa acagacttta gaattgtcaa tcaaatttga caatgattag    360
gtgcattttt taaagttatc ctaaagtttt tttttttttc gtagtcttgc ccttgctttt    420
atcgttaaca aataaaattt tccttatata tatatacaca tttaactact caaggtctgt    480
attttttcca cctgatttat ttaatatttt tttttttgc agaaaatcta tttgtatttt    540
aggggaaaca aatgagtgaa gagatcatca agcaacggtt gcgatgttgc agcggaaaaa    600
tctttggttt gtcatttctt gtgatggggg tttatagggt agtatggtta ttgtatttta    660
ggatgttgat ttttatttta atgagccaag agagagatgt ggattctaaa attgatgatt    720
gatattattg atgtgatata aatatataat tttgtgcgaa aattgctatt ttattttctg    780
tatgctcatt cagatcacac aataatattt gatgtagctt tacttattga caaaatatag    840
gttttaatct tgtgctcata caaacaacag ctatgggtga aattattttc tgattttatt    900
tggcaaagat gatgtcagca ttgtgtaaat ttaatgtgaa ttacacttct gatttcttcc    960
caatgtgccc tctcaaatat tggcaccaag ccatttaatt gtaaatacgg aaaggtcata   1020
```

-continued

```
aatttccatg caagatttat ttcatgttta aaatgattgt gtgaaacaaa atgaaaaaca   1080

agaaattctt acctccaacc tcaaagtagt cgatatgtca aggttcaata tcaattttaa   1140

atatccatga atagctttga tatcttttat aaatgcttgt aatatatata tactaatagc   1200

aatgtctata agttagtttt gagagtaata cttgttatag ataacaatgt tactctattt   1260

accactctac tattgaaagc ttctttttct tccatttatg aattaataac ggtcaagatc   1320

caattgcatg agttactttt aattaattac aatctaaaat gttaatataa gtctaaaatt   1380

gtccaatata tgtgattttt tttttctctc tcaaaccttc ccttcttttc attgaacttg   1440

tggttcaaat ttgatggagg acactgggaa acagcacaat tcaaagagcc aaagattgag   1500

taattttttg atttcagagt tttcatctct tcttcattct acacctttca cttctcatcc   1560

acaactatcc aatcaaccat tgccacgtgg catcaaaaat atccaaaact gaatgagatc   1620

caccacaaag ttcctctcat cactgtttgt catcaactca tcaagaactt catcatcaat   1680

cagaaatcca acatttcaac ttctcttagg aaatgacatt tttaccagtc tccaatgtca   1740

aaaactcaca caaaatccct ctttccaatc taaattttac aaagataaca ggggtaattg   1800

aagaaactta gcagtaagtt aacatattat agctttcatc aacccaagtt tttttggttc   1860

ctttctaaac tgtagtttgt tttcttgatc cattctaaat atttcctctg catgaaaaga   1920

agaaaggaaa agtgaaggcg aaacctgttt tatgcttcag aaaaccaatt cagagtaacc   1980

aaagatctga acttcagacc                                               2000


<210> SEQ ID NO 52
<211> LENGTH: 2000
<212> TYPE: DNA
<213> ORGANISM: Cucumis melo

<400> SEQUENCE: 52

cgctcaaatt actaacatcc ttctctttct tgttcccatt cgactagaga gacactatct     60

tatccacctc agttggctgg gtgaaatcat tgaaactaac ggttgattgt ccagattgtt    120

aaactaccct atgttttatc atcttggtta catttatagg attgtcagaa taataattcc    180

ttttgaaatc atattctaat tggcacagga ctaaaataat gcctttctta agctgtaata    240

attagaatct aaacagtgaa gttagtaact gattgatgac atttccacga ttttcattta    300

tatcctgtgc agctattctg acatcacaaa acatttcttg attttcattt ttacttgtca    360

tccatcagtc aggacgatat cggcgcgctt gttgacgacc ttgtcctaaa tacaaagagg    420

cttatccgag ctacttcaag ggagattgac aagtggaaaa gatgaaatta ctcatttgtt    480

attacattgt acaagtgatc tattaggaag aaccacaatc aaaactgaag aaaaaagaaa    540

cgtgctggct gtctacgtgg cttttagagg tagaatttat gtacaattgt ttagaaagat    600

gtatttaatt gctctaaatc tcatatgcat tggattttga gcaatcttaa aatgccgaat    660

acttaatgta ttatcgtagg ggtccctaga tggcagattt atcatgtcca ttctccagaa    720

agaaagaaaa aaacccttt tattatactt gttcatttta agctttttct ggttgattat    780

aatgtcagta atttaaaaaa aaaaaaaaat tactgtgtat tggcatcggt tatatgttat    840

atacaaccct agttaaaagg taaagttttg ttcattcggt cattagtcat tcctatacga    900

acgtcacatt gtgctttata atttcaatag gttaaaagta ttcaatatag ttttttaagt    960

tacctagtag aggtgatcat tggttgatcg gaatcggttt tttgacaaaa ccgccactga   1020

accgatcata gtcggtttag taaatgttca aatcgacctt gacatcgatg agtaaagatc   1080
```

ggtcggtcgg tttttgtcgg atgggccggt ttaacacttg gaaatactat tttgaaattt 1140
ttcgaaatta atccctcttg ttttcctacc gaccgatttt gggtttggtc ggtcagttcg 1200
attttttcgg cctatcttac tcactcttat tacctaggga ttgaatttca ttttatcctt 1260
agttttaggg ttcttttttt atacttttga aatatttatg tcgatgtcta gagtttaaaa 1320
ataacacttg aaattataat ataatttttt ataattgtta gctataattt tacgtccaaa 1380
tatcaactca ctcgcaactt gtttaatcaa ccaataatat gtgtctggaa tagtaagtat 1440
ataacttgtg gaaaatgact ttaaaagact tttttaaagt atttatttaa tgccaaaata 1500
tctatattta tgtttataca ttaacataca tatccaaagt tacatattag atttgttaaa 1560
taattcaaaa tgagctaaag aaaaaaagaa gttccatata ccaaaataaa atataaaaag 1620
ttgaagacta aaatagagat tttgaaacaa ggtaagttag atttacaaat tgcaatatgg 1680
gagaccaaac caccacataa caaaaatccc aatgtccaaa tggcgcaatt ttgtttagga 1740
tagctcacgt tatccaaatc actcaatcgg agagaccaac ttaaaggcca catctgccac 1800
gtcaccatac tccaccaatc acaacacagc attggatttc tcagcttatg agaccaatca 1860
caaacctgaa tccgacgtgg catgtccaca tccaccagta ccaaccatat agcttctacg 1920
ttctccacat ctaatcttca ccatttacac aatattcttc attcttcttt cctcccttca 1980
atccttcatc ctctccgccc 2000

<210> SEQ ID NO 53
<211> LENGTH: 2000
<212> TYPE: DNA
<213> ORGANISM: Cucumis melo

<400> SEQUENCE: 53
aattctaaca actccggaac caaataattt agcatggatt gaaatataaa tcttcttgac 60
ttgcaaaaaa atcattgtaa tggtcttatg ttggttatag ttagggtatc gaaacgccat 120
acaggaatat gggattaaag ttaacttttg ttcatcaatt tcagcttatg aacttctaaa 180
atatcaattt tacctttgaa cttatatgtt attacccctt tcgattgtgg tatgttaatt 240
aatatctgaa tctcagtcct tatgaaactt ttttatactg tcacaaacat atgaagtttt 300
attgtaagtt cttagaaatc atctaaaaag agtagtttgt tggactattt attttatttt 360
ttcttattaa gttgttttca cgccatttca gtaaaataac tatagtgaat agagaatcaa 420
acttctaatc ttaagttaag gtagtagggt atatgctaat tcaataagat aatccgtgat 480
gcttgacatc tgacttaatt gttataagtt ttaaattttt tattgtaata tttaaaatac 540
tagtttttgg tttctaataa agaaataatt gaacaattac aaatatttat acaaaattaa 600
actagaatat atgatcattt tccttcgtgt tagaaaaagg gaaatatatg tgtgtattta 660
tacatattag atattgtttt actatattcc attttcctca cgggaaatgg aggattgagt 720
gggagataaa cattgtcccc aagagaattg ggaatggaaa tgcaaatgac atggccctcc 780
acaaaattgt tcgcctaaaa atgggctttc tcacttctca ctccgcaaga aaaatatcgt 840
ttcccttcga attattcggg cggcaagatc tcaaaaccac atgtttttct ttctttattt 900
ttcaagccta cattatttat aaaaatataa cttaagcaga gaattatgta aattcaagtc 960
catttttcgc ttcacttagc taaatcatta acaaatctgt aattttgttc ataaattagc 1020
tcaccaatta tgttttagcc cactaaggcc cattagacat ttttattaga aaaacatgaa 1080
ccgttggatc aagatgtgtg ttttcttttc tttttctttt tatttttttt gggttttggt 1140
ggggttttgg tggatcatgg tggatcaatt cgtagcttta gcaacctatt attatatgga 1200
gggaaagggc gtattaatct gttagcgccg tccgggagtt tagctttctt ccccgagcct 1260
cggtcttatc ccctaactcc aaaaccctag cccaaaggta atccactcct tccccctccg 1320
ctcttcatct ttttctattc atcatcttta atctgttctc ccttttggtt cttagattct 1380
tcttttgttg gattctttta atctttactc atggttggcc ttgtaagttt agacgacgtt 1440
tttatacatt ggttaatcct gcttctctat ctattcgcac gctagggttt tcctattgtt 1500
ttctattctg ctctacttct gcaaggttgt gttcttcttc gttcaggtcc ctttttttaa 1560
ccgaaattaa attaatgcaa attcgtttgt gcttctaatt aggaagcctt ttggaacatc 1620
tcgacatttt gattgctgca tttcatttcg ggtatatttc tatgattgaa ggatgtgggt 1680
ctgttcactg catggtcatt acttatgcag ctatgcttat cgagtccatt atgtttgtgc 1740
aatctgtttc cggattcata attttttagt aattgatcag tagatgaaaa aagatattgt 1800
aatattcctt gagtgttgca ccagtcttgg tgggtatctg ctcctgctct ttgcttgtgg 1860
attttacttt tattatatct gtattattcg aaatgttctg ttcttgttat aacttatacc 1920
cgaagatgtg ttcctccccg cgtctagcgt tgtgggttac ttatgatgga catggttttg 1980
attctgtttg gtttgtgcag 2000

<210> SEQ ID NO 54
<211> LENGTH: 1547
<212> TYPE: DNA
<213> ORGANISM: Cucumis melo
<220> FEATURE:
<221> NAME/KEY: misc_feature
<222> LOCATION: (1)..(1547)
<223> OTHER INFORMATION: n=g, a, t or c.
<220> FEATURE:
<221> NAME/KEY: unsure
<222> LOCATION: (1)..(1547)
<223> OTHER INFORMATION: unsure at all n locations

<400> SEQUENCE: 54
ataatgtgtt gatgttgatg atcatgcatg gtatattaat ctcatgatta aagacgttaa 60
gattaatatt cattccatgt ttatgatggg tgttcttagg gttgtaccca tatgggtgtc 120
cctcgggatc accacctttt ttatgactgt atggttctac gagaccacca gtctgtcatg 180
atatgtttat gaatggtacg acggggtcac ttacagccca attgcttaag tgttccttcg 240
ggttcactga agacctattt ttcctaggtt ttcctttgac ttcagcaaaa atcagttttg 300
tcctaggtgt tcctcgagtt cactgaagac tagttttgtc ctaagtgttc ctttaggttt 360
atcgaagatc agatgtgttc ctacagaatc attagattgc aagtgttcgg gaacacatcg 420
gtttaggggt acttctttac atgaacccta atggaaaatt aacagacatc tagcggaatt 480
agtagttggt cccttactga gtatatattt atactcactc tttttatgtt taatatttca 540
ggcaaaggtt aaggtagagg aaagttgacg agtgatagaa aaggatctgt gacatgtcat 600
atggggactc agtttcgttt ctgcttctat gtatcagtgt ttcagtattt tgtttnntaa 660
tgaaaattta gtcttcctct attcaagaaa gtgtctcttg ttattgttta tttttagtaa 720
tgatttcaac ttagtataaa tagttggatc attacaaata atatattggt gatatacttt 780
gtaatgatac attgagttat attattcata tgtttaatat acaaaactgc aatattaaaa 840
aatgaaaatc acgtaataag tatatcaaca aaataataca tatattacaa gcacgtcaca 900
acactaatat acaaaactaa tataaagtaa gatcaaagca aaaccaacgt aaaaaataaa 960
acaaaatcat ttgaaattaa atttaactca aaatacacat cgaagaaagt ggagaaaaat 1020

```
cacaatagag ttaaattact ttgattaata accattatat ttcatattga aaataatatg   1080

tcattagtat tttaaaatca agattaagat aggaagaatg aattgctctt ttcgtataaa   1140

aagggatgat tggggcctta cgaaaggaga aaaatacata tgttatcgaa aaaacaaatt   1200

atttttcttg taagagagaa tgattatatc cttaaaaaaa tgaaagaaag aaacaatcat   1260

ggcattaaaa aggaaaataa ataaattatt aaagggcagt tcgataataa taacaaattc   1320

aacgagagta ttaaaagaaa atgagaattt gcaaaattta aacaaatgtg tatattaagt   1380

acagccaatg caattttcaa attttaattt atttggttta cccaaaattc aatttctaaa   1440

ttgagaggag gatatagtaa attcacacgc attatcccct tcgagtttca tcatctcacc   1500

cattcttgca tacagtgcag ttacaattcc ttcattctgg atagaca                 1547
```

<210> SEQ ID NO 55
<211> LENGTH: 2000
<212> TYPE: DNA
<213> ORGANISM: Cucumis melo

<400> SEQUENCE: 55

```
aaacacttat catgttatgt atcccacatc gaaaagataa aagagacttc atgatcttta     60

catgatatat gagttactcc ttcgactacc attggttttg gagatggatt caacccaata    120

atatgaatct gacccaacaa tggtcaactc aaagagacac catcttgaga tacatgttgt    180

gtacccatat tagatgaatg actatacctc gcaatattta taacatacat gaattacttc    240

tcttactgta atttggtttt gacgtggagc ccatgattat ctaattaacc ataactggta    300

tatgatatat tagtaggtaa cccgaagagg ttctaagata aacacagaat tcaatagaat    360

cagagccttt ccaatgatat ggctttagat gggaatgatt tgaagtataa tcattctacc    420

acacccttta tatttgtctg tcaccagaaa tctcatcttt tcttgaggta ttattcactc    480

gaaaagaggg aggcattttt gggttaccca tctaatgcac gatgaactaa gggaggtcaa    540

gttctgggaa tacagctagg caaccttcac agtggataca ttcgaacaaa tgataaatgt    600

gaaaatgaat catttcatga gtgtgactaa cccaatcatt cctccttcta tatctttgaa    660

tcccacagtg agtcagagta aaagttccag caacaagtcc tacaacccaa attctttagc    720

tatttcttcc accagaacaa aaccaagcaa aaaatcagcc acaaacacag ctcaacaatc    780

tataaaggcc aaaatactaa gacagtcacc attaccacat tgaaagccgt attttccaac    840

agactttgcc tgcaaaatag atcacaaaga cacgatttca cattggacag acgccacagc    900

tccacaatct caatttcaat caaataaaag taaatcaaag ctaaatagca agtgtatggt    960

accacgaaag cagcatggct gacgccactg aggcctgtaa gagagaaaac aaaataagtg   1020

tagaagataa agtgaaatag aaaaatcaat cgataagata gattttcaga ttaccatttt   1080

tacgggaatt gtacggaccc aaacacaaac cccatagagc gccggcctga agatgaacag   1140

gggcaggaaa ttcagaggaa gaaattaaag aaaatgaatc atagtttgag aaattattcg   1200

taaagtttac cgttccgacg cgaatgctgg attcgacggc gagggaagaa caaggaacga   1260

cgccgttgag ttcgtcttcc atcttccaat tctcaatttc cttcggaggt ccgtatgctg   1320

agagctctgt gtctaccaag ttccaaccat actacgtcgt tttggatttt tatttttatt   1380

ttctttcctc tcttttgcca aaaaagaaaa aaatagtatt ccaacctaaa acctcaaaat   1440

aacatatttg ttgtacaaat tataattagt aaacatttgt cattgtgagc ttggtatgta   1500

atattaacac gaactttatc gctaataatt tagacgttaa tgaataattt gagcattgcc   1560

ttcttatatt gttattgtgt ttataatagg attgcttaca atgtaaccta gtatgttgtt   1620
```

```
gagctcgtta actttttgt ttttcttgaa tattcaaagt taaaaaattg tacaagtttt   1680

tggtgacgtt ttcttactac attatcggga tgaagatcaa atatagctta gattagagaa   1740

gataatcatg ttgatttatc gttaaacttt gactacaaaa tccgtttaat ttttttttgg   1800

atgaattagt tatacaattt aaacttaaaa ggggtgaatg aagaaagagg atagttttac   1860

aaattcgaag tgaaatgagt tatttctgct taaagaaaac aaatctcctt cgtgctttaa   1920

aacacaaact caaaacccta aattcagcgc cgattcttca atacatctct gcaggaagtt   1980

agggcaaagc agaagcaaaa                                               2000
```

<210> SEQ ID NO 56
<211> LENGTH: 2000
<212> TYPE: DNA
<213> ORGANISM: Cucumis melo

<400> SEQUENCE: 56

```
acttccaaaa atcagcctca tgggatattt aaagaaaacg taaattaaaa ttagcatcat     60

ttcatattga acaaactaca aaaattaact ctaaaagatg atggtaacta caactaaacc    120

ttcaattttt cattgtaaaa atcgaactct taaacttgtt caaatattaa aatttgaccc    180

tcaaacttaa aagagctaaa aaaagacctt caaatagtaa aagtagaact ctcaagctta    240

tagaattatt acggttatga ttatagccat agatgattca atcgattttc ctccaagatg    300

atggagtata attcttcaaa tctagctgct tagatgttat cacgataatg aaatcatatg    360

ggaactcaac aaaaagaaag cacttaatgt tgaaagacat tattctttgg gtgttgagtt    420

gggcgaactt gatttttatt attaatccgc aaaggacctt ttgagtaagt tgtggcaatc    480

tttattggag tgctaagatt tgttattcga aatttcttgt tttgatattt ttccaactaa    540

aactaatttt tttaagaaat gcaccttcaa ctgatttcat gcgtgtcctt ttgcaagact    600

cgcatgggac ataacacatc atcttatatg gcaaggccta tgtgtcagtg gagatttgac    660

gtcaatttct ttccactgag agtcgtcctc tttgtgatgg cagaactttg gagagtcatc    720

aaaattggtt ctttgaaaat gtttcttatt ttgatttttt tttttgaaag aaatgagagg    780

aataagatat ttttacgagg actctactag tgggtcaatt tgcccgcata tggatatgca    840

taagagtcct tttggagaga aagggtatga tggaaagaca ttgcaaaggc ccgtccacta    900

actttctatt atacaattag gtggaagcca cccatagcaa tgtcttggtt gaacactgat    960

attacttgaa accatgcatt taagatgtga aatctcgact agatgcttta ggaatttgga   1020

ttgtgtctgt tttgttgaat tcaagttcat tcctaaatac catgaagtta agatccttga   1080

agcaatgaag accatttatt tagatcctta attcaaatct ctttactaaa gatgattgtt   1140

tataaatgat caatttgttg aatgatgttc tacttgatat ctctaaagca tctcttttcg   1200

gtgagaagcc cacaacttga atagtattcc ataaatcatc tatttttagt ttctatcatg   1260

ttctttaaca tcaaaacatt ttagcgcact ctcttataac taagacttag aaaaacacga   1320

atcttccttt cttacgatat atatcctaaa tggttttcta tatttgtgcc ttacaatata   1380

atcaattctt tttctatttg atattgtcat aaaataatac tgataacata gtttttatgt   1440

tttattaaca cctaacaaga aatatggaag acgttaatat atcttcaatg tcgatattga   1500

atcattttat ttatgaatat atccacgcgt caaaaaatat tttaatcatt aacttctagg   1560

actaaattca aacattcttg gaaccataga caaaagaaca aaatttgcaa cctcaacaaa   1620

caaaatttta tctttacatt tgcggctaca attcacaaat tcccaaacca tgatagaaag   1680
```

```
gccccaatct cccacgtgat aaacacacat atggcacgtg accaaatcaa aatcatccac   1740

atgatgaaaa cttaatggac agctcggatc ccaacaccca ataaaaagca gccatgaagc   1800

tgacgtggca gatttccccg aaaacctttt aaataataaa caataaaaaa atatatacat   1860

aaccgttggc aacgtttttc cctccacaca ttttcccatt gccttatctt tctttccctc   1920

caaacagcga gggaagaaga atccaatcat cttcttccaa taatttctaa aacgaaattc   1980

tgctcgattt tccctctcca                                               2000
```

<210> SEQ ID NO 57
<211> LENGTH: 2000
<212> TYPE: DNA
<213> ORGANISM: Cucumis melo

<400> SEQUENCE: 57

```
tgggtaacat tatgagtttt attataattt aaatgaagat caaactttaa gttgtagggt     60

caccatagga ataaaatata atcaataagt tagggcccct tagtcccacc tcgtaaagga    120

gttctgtcat acatatacat tatgatatta attctatctc catgagtcat acatgtgatt    180

ttagtacttg taattttcat tctttttcct attataattc attcaagtac tgtcaatatg    240

gttaggtatt gaaattaatt atagactcag atatcatctt cattaatgga aatggaatgt    300

tatattctac ctctcatttt tacacgttga tgataaatta gaagaaaaaa aattattatt    360

tatattgttt taattgtgag atattagttc aaaatgtaat taataaaatg atacgtgtct    420

tataataaaa ttaaacaagt ataattaaat ataaaacaac atacacactc tttaactaaa    480

agacacaact cacctaatgc tcgacttaaa atcactttgt gtcgtaactt aaccatcaaa    540

gcatgttagg gtaaacacaa taaagatgat ttttgagtta tgcatgtcat ataatgtcac    600

ttccaatttg acttatcttg cttgcttgat tcatgtatat aaacaaaaac atgaaaagta    660

gtgtaaggat accaattacc tactgatttt ttttaaaagt agtttgtcta agacgtgtta    720

aattactaac ttagtcacat ttgagtttta gttctaactt attaaacata aagtaggtat    780

ctcccttact catgtgtgtt tcgataatgt caaattccaa tgtttgatta accaaattgg    840

gtaatttaac ataaatattc ataatataat attttttatg gaataccgac atctaaaaag    900

aaatcaaaat gaatattatt aggaggtgag tttttaagag agaggaaaat aataaaatat    960

ggcatcaaca agaacaataa taataagaat agaaatccga caaaggaaga agtggatgcg   1020

tgttagtact attgacattg gcatatgaac ggttgggttg ggcctcaaat aatttgcatt   1080

tctaacttcc aaacacctaa ttcctttttt tttatccata cttgcaaata tatatttata   1140

tatattcaac aagtagttta atttatttga tataccactt taagttttaa attgatggta   1200

gtgtataaat aaataattta ggattaagca tgtctatgaa ccttttgaaa tttgatggag   1260

tatatataaa acagaatact catgggttca ttataaaaat ctaatagtaa atgtattttt   1320

tatttcattt aaacattttc aaacttttaa aaattaaaat tatcttaaaa aacacgtgtg   1380

gtttcgaacc atatggttaa aaatattgag gttctctatt ttgcaaaaaa tttggaaacc   1440

ttcatggaag ttgatataaa ttgttgtaat tagttagtat tttttcttta tttgtggctt   1500

aatcatgcta tgattgatca ttttatcatc atttctataa tgtaaaacaa tatatttgat   1560

gtgtattgta aatttttatg caagagtaga aaattaataa aaaaaaaaga gagaaaaata   1620

attataaagt aatataaagc tattaacatt ttaagaaaaa taatagtgaa aatgaaagtt   1680

tcggacaata attcaataaa gaaatttgta gatttcgatt aaaatttcca aaattaagat   1740

tttcattaac acgtgtgcct cgcaaccgtc tcctacgtta tcccgtaagt agcccaatct   1800
```

```
atcccattct tacacaagcc gtcggcccaa attgattgta ggccatcggc ccactcaaca   1860

cccacaaacc ctagcccctt gctcctcctc ctcctctttt cacggctgct cactccctct   1920

ctttttacac cttctccttc tccttctccg tccctcttcc cttttctgct actatcttca   1980

gcacttgctg agcttcaacc                                                2000


<210> SEQ ID NO 58
<211> LENGTH: 1591
<212> TYPE: DNA
<213> ORGANISM: Cucumis melo
<220> FEATURE:
<221> NAME/KEY: misc_feature
<222> LOCATION: (1)..(1591)
<223> OTHER INFORMATION: n=g, a, t or c.
<220> FEATURE:
<221> NAME/KEY: unsure
<222> LOCATION: (1)..(1591)
<223> OTHER INFORMATION: unsure at all n locations

<400> SEQUENCE: 58

aatgttgatt taccccttgct ttgtttgaat ttcgtcctcg tggacttgac ctttggtctg     60

cttcgtatag gactatttac ggctgccctc atagtccaag tccttgtccg ccttacccta    120

tactctctat ctctagacaa tgtgaagcgg gcccttctat aatattgggc cttgaagttt    180

tgggctttgg atctgccgaa ttgtgttggg tttctctccc aatttatttc atttctttat    240

tcaaataatt ataaatatgg aattttattt tatttaaaat ataaaagtta aaattgaacg    300

aatccaaaaa taatggaatc aaatcgacgt tttaacatat ttttcaatta tgtttttaca    360

ttcattttcg tcctacaaaa atattcccac ctttatttcc tcgatatcgg aggtcacttt    420

gtatgtttca ttcgggtgat gtgatataga tcgagtttct atgcttgatt gactatggaa    480

atatatttta agaagatgtt ataaaagtaa aataaatgtt ttgattgtgg atataattat    540

attttaaaca agatgaggaa taattagatc cgaaccaata atcttgagtc aagagtgtac    600

attgaaagtc gtatattaaa taatggttga gtttataata atattgatag attgcagtta    660

accatatttt ctcaagttgt tgaccaaagt acttatttta taaacagttt agggaatgtt    720

tatgaagttt tgccaagtgt tttgaaccta tatgagtatt gacttaattg gtatataagt    780

gcattaacaa tcaagaggta tttaatttga atcgtcctac ccctatcatg ccaacaaaac    840

aattatatgt ttgtcatatt ttattgaaag tgttttcagc gcaatttagt ttgatttgcg    900

tacaaaacat gtctacacgt atcgagttag tagtaatggt tgctagttaa gactgtgaac    960

taaaacttta aatttacatt aaaaanaaaa acattatggt cgtttggtcc tcatatgtga   1020

ttgatagata ttgattaatg agtatttgtg gttgttgcca acaataaaga tgtagacaag   1080

tgaactatgt tggttgtcaa atcttgtttg tatttgttat gtgtggtttt caccaccaat   1140

gttgtagagt gtcagatcca gaatagcttg atcatttttc atatatatct acagactcaa   1200

ttagtagata aaaactataa gactttgact tatttctctt aaaatgtctc ctcgttctgt   1260

acaatcctca acaacgtttg gtgactttaa aacatcacaa gaatctaaga agaatgatga   1320

attagatgca atgcaaagat ttggacctta attttgttac tttaaacttt atatccgaac   1380

attggaagag gcaagcaaaa agcgcgcttt agaatcgcgg tttctttggg ccgagtgggt   1440

tgctcataac agcggaggtt tgcttttctg ccaagaaaac ccctcaaaga aaaagggctt   1500

aataagcagc tgctccattt ctaagtgggt ttagccttta gcacggaagc gccaattcga   1560

ttcaactctg atacactgca aaaattccgc c                                   1591
```

<210> SEQ ID NO 59
<211> LENGTH: 2000
<212> TYPE: DNA
<213> ORGANISM: Cucumis melo

<400> SEQUENCE: 59
aaagaatgga gcaagctgat attgctaagc aaaagcttct gcatgattgt gaagttcttc 60
accaccgcct tcaagattct actgtcgact ttttcattga gcaggaaaat aaactaattt 120
tggaaactgc ttcgacagct gacgacgcaa tagatctgtt ggcaacatct gataatcaca 180
ttaaccttct tttagcagag gtacttgcgt ttgtttccat tgaaatgcat ttgcatattg 240
aacttcttca tcctgaatgg cacaagtttt tgtccataca aacaggcaaa gcttctggct 300
catgatgcta acaacagcga tgacactgct ggatcagccc gtccaaatgg aactgataaa 360
ggggcagctg accaagtatt aagtaacata ctagcaaata tgcttgtcga aaatgcccga 420
ttaaggatgc agatgaacgc cgtcatccgc tgtgttctaa atgcaaatgg gacaagtgag 480
aaagatgaag atgaatctct caaggaagaa ctgttctaag caagttttta gaggaagaga 540
ttcctgaatg cacatataca atgaccttat actgtcgtgg caagaaatgg gagagctgta 600
gattttgaat aaatgcaaca gatgttgccc attaatttgc aagtcctgac aaatttggtt 660
gtcggaggtg tagaaatgat gtatcaatta aatatttaac aaagtgcctt ttggcttggc 720
taatcatggg catttgaaga ctttgcactt ggtaagagct caaacaaaat ctgggtggct 780
aaatttagtg ttgattaaat ggaatttcac tgatattcat gatctgtctc ttcttccttc 840
attgatatat tatcttctca gtaaactcct gggcctgatg cagaattgct tttaaccatc 900
tgcatacaga gaagaagtaa aaactagctc acgtggataa agggaaattt ctactgacat 960
gttggcatta gaagaaaatt ttgaaagagt tctattacca taacatcatc tacttccgtg 1020
tattattgaa actattattt ctcttacccg gagatattaa attaataaat ttctatttac 1080
attttgaaga tgctcgtgat tattgataaa aatgatgaat cattattttg attacgttac 1140
aaaaaagtca aagagagtaa caaagctatc aacaaaatat tagtaatata tacaaaaaaa 1200
gtgtaaattt aatattaaca ctgagaaata tacacttaag ctaatgggtt aaaatattta 1260
tccattgaat taaatatggt ttttctgtat ttgtgatatt ccaataaata tgaagctgtt 1320
atactgtcaa attcatattc tgcctataca atcaatttca agtcactcaa ttttgcaaaa 1380
ccatatcata ttgagttcaa ataaaatttc atatctatat acataacgaa aatgttatgt 1440
ttttgctttt aatgttttgg gtatctttct aagctacaag aaaatgtaaa aatgataata 1500
agaaatagat tatattaaaa ttattttaca aatcaaattg cggggatagc tcagttggga 1560
gagcgtcaga ctgaagatct gaaggtcgcg tgttcgatcc acgctcaccg caaatttttt 1620
tcttcttttt tttcccttgt gtatcatttt aaatgggctg ttcttacttt gaactgcgga 1680
agcccatgaa agctaggccc aatttagaaa ccgaccatct caagggtcgg ttcgtcattt 1740
atcaagatcc gataacccga ttcgctccat tttagtctct gctctttcat ctccctcacc 1800
cattctcgct tccactgagc gggcaaggga gcttaacccc tcaaagccct agaaaccgcc 1860
attggagaag ctccactagc ttcttcttct atcagcgaac gtattttcgt cttgtataga 1920
cctttcatct ctggaaccga tcggaagttt ggagtttctt ggtctcagtt tgtagattag 1980
ttttatcttg gcgtctcaat 2000

<210> SEQ ID NO 60
<211> LENGTH: 2000

<212> TYPE: DNA
<213> ORGANISM: Cucumis melo

<400> SEQUENCE: 60
gtgcatttaa aataatctag ttgcatgttc taggttcgat ttattatttg gggatttagt 60
tgtgtctgta tgattgaaaa aattaatgtt gatcttgtaa cacaattgtt tttccctcga 120
tgatttgaga ttatttcaac aatttagatc caatgtttaa aaagccacct tggcatcttg 180
ccttcctcat tcgcaacctg cctccagttg aagcctcgag gctcaaagcc cagtgcccta 240
ggacttcttt attaatttta cttaaaaata aagtttgtat ccctaaatgc ataaaatacc 300
cttgtgttta aggctttctg tttcttcgcg tttcacgtca ggtcagacca tgctcagcta 360
tttttccacc attcttcttc ttctctccca aagtctatca agtattttat ttccacacat 420
atattcacct acgccaattt ctttttaaaa ttttatagat atatacagtg cacctcacga 480
aaacaaagtt tgcacttctt cagtttttttg tttcgcctca cacttaagct acaaaaggtt 540
attacgtttt agtaacccac tactcagctt taaaaacact atttgtatca tatgacgtcg 600
cccttatgga ataatttcac ttgattatcg ggttgtttca taaacaatct tactctgttg 660
tacctttgac aggcctggag agcatgcaac tcctctcttg cttgagtttg agtaacaata 720
aaatcggaaa ttttactgca ttggagcctc tgagactgat aaaattctta aaagttttgg 780
atatatcgta caacgagata ggttcgcatt cgatcgacac aaccagatat ctcttctcat 840
ctccactgtc gcattccgaa gaaattgatt tgagcagtga tgaaatggca acaaatttta 900
ctgatatggc aagttactgg gaagcatatt ttctattcaa agatataagc ttgatgcaat 960
tggatataga aggaaacaca atatctagtg aaagtttcaa agcatttctg gtaaagattc 1020
ttcccaaact ccactggctt gatgggaaac gggtacaata gatatggctt aatttatcta 1080
catccaatcc tctgtccatt gtggttgttc atcccctgaa tgtaaaaagg tacgctacga 1140
actagcattg atcctaaatt gaagacattg gttttgattt cttcccaatg caaggttaag 1200
aactaaggat ttgatattgc atccaataag cataggttat ttaagatttt ggtgatagtg 1260
aaaattaggt gacatgtctc gaaagcttaa agggatacat gaggtatgga gatggagatg 1320
gatgtggtta caacatggaa atgaatacgg tgcccagttt tttggactgc tctaaatcaa 1380
attttatcat atacattatg atactgtgtg ccaattgtat ttaaaaaggt actgaacttt 1440
acatttttgt tgtcccaaat tttgaaggat tgtagtttta ataattctta taataactat 1500
caatgttaat taaaaacttc agtatattta caatttttct aaaaatgttt gctatacgtt 1560
tagttattat cttgatcaat tgccccaaga gaaaaattac cctggactat ttcccaaaaa 1620
catcttctag tcgtccatca gctatagttt caaatctgtg tgggcccagt cggcccagtt 1680
cattgggcct gagaatagag atcatgaacc ggacggccca aaccttttttc aggccccagc 1740 caagcctggc ctacaaactt ctaacctaaa accttatccg ttgaagcaat ccaataaaac 1800
aaagccacgt aagcacccag gatctaaaaa tgtatccaaa tccaccaatc tgaggccaca 1860
aatttagcct ctgtggctga atggatgtcg aattacaaga atctctcgat ttcttcctct 1920
taaatccatt tacccttcaa acaaataaac acaaaataaa gaaaaggaga agaaacaatt 1980
gtcgtaatta gcagcaagaa 2000

<210> SEQ ID NO 61
<211> LENGTH: 2000
<212> TYPE: DNA
<213> ORGANISM: Cucumis melo

<400> SEQUENCE: 61
acctagaact tctaaacgat aatctcggaa aaaaaattgg aacaaatcat aataatgaca 60
attaagaagc aagaaccgtt gacaaaagca agatttagag ggagtaaatt tgcatggttt 120
ggtgatgatt atttagttga atttagccta ctcttaggaa gtatccaata atcatacgca 180
aatttcacgt agcatatgaa gcaagtgcat cataataccg cataacctgc ggggttttgt 240
catctcgatt aaacacaatg tgaacatgat gatgtctatg tgtttccagc ttttgttcta 300
atgatgatag acgatagtgt ggtatagttc atatccttga tttaattgtt tccatgtata 360
ctatcgaatt tttaatatat aattaatgta tgaaatcaaa tatcaaataa tgattgtgat 420
ttaatggaat aagatcatgt ctaaaattgg taatagtaat aacgaagaag gaagagaata 480
ataaactacg atttcttgtg aatctcctag ataaattagg ataaaaacta cgagtaagaa 540
tagaataatt atactatata aaataggagt tacaaatttt gtttcttaaa ataccaagct 600
ctgttacaag aaaaaacttt aggtattata tcttcaacat tttgttaatt tgttagagat 660
tttaggatag tttgtcaact atgggtcttc taagaaactt ggtcatcaag caaatctaat 720
gactcgaatt gtccttgatc gatgtgaaag atccaatgac ttcgaattat ctttatgcaa 780
tgtgtaagat ctaattgtca taaattgatc tcatgtgcaa agtgtaagat ccaatgatcc 840
aaaattgtct ccaacaactt cttgaacaat aagataactc tttgaagaat cttgaatatt 900
aattttgaca tagatagatt gatcttgaat attaggaaat aaggaaattt tcttatgtac 960
atgcctgaac tccttcaaca tagcattttg aatcatatct cttctctagt aacttgtata 1020
gttgcaatat attttgcttc tgttgttgat atatcaacac tgattgaagt tttgaaaccc 1080
aacatatagc tctagtggca agagttaaga catatatgtg gtgaatttac ttctatcaag 1140
atcacaatct aagcagatat actttgaaaa taaagttaga ttatccatta tacaatgtaa 1200
tatttacgga ccatttaact cgcttagaaa ttagagttat tttgcaaact ttattgacaa 1260
atatcttcaa aaatttcata caccgtatag acactatcat aagatgttaa agaaaaaaaa 1320
aaggtgaatt ttccatacaa ttaaaaaaaa tcttaaacta taaaggtggt ttcgatacct 1380
ttaaactttg aaaagtttca ttttaattct cgcacttatt gttttaaaac aaacttagta 1440
aaattttcgt ataaatttag aaagaaattt tatatttaca ggtggggaaa attctaaaca 1500
catagatgaa gataaataaa aacacgatca actataaact atacctatta ttaccttcat 1560
ccttaacacc atgcactcaa atattcatta attctctata ttttttcta tcttagcctc 1620
aaaatttact ttcatcctaa acttcgagcc ctcaaatttg cgttatttca ttcacgatat 1680
tccttttta cgttctttca tttatggtat tcttctttac gttcttctat ttacgatatt 1740
cttcttgctt ttatagtgtt ttagatttgt tcataaacaa cgtataaatt gaaaacttta 1800
taaatttagg gcattaaggt ataattgaaa ttaaaaccat atttatagtc attaaccaca 1860
gtattattta tcctttattt attaaaaaaa aaatctactt ttagttttaa atttaggcat 1920
tttacgcaaa gctaattacg acataaaaca ccaaaaggag accccgttcg atcttcacat 1980
cttctcggcc agaaacgacc 2000

<210> SEQ ID NO 62
<211> LENGTH: 2000
<212> TYPE: DNA
<213> ORGANISM: Cucumis melo

<400> SEQUENCE: 62
gcaatggcgg aaataacgta gcagagggca caaacaacga agaggagctt cgttcttcgg 60

-continued

```
tgcgccatct gggaaagtga gaaatggtgg acgaaacaca aacgggggaa tcggattgga    120
tctctcagaa aagaaatggt tggattcgat cacagatcaa tgaagcacat tactcggttt    180
ttcaagaaga ttacaagaac ttgcttcttg aaacctctct tcttctgttt gaaatttttg    240
ggcgtagaat tgaggaccgg agcagtcgcc tgaatttggt cgtcgaatcg attccacgga    300
aacaaaaata tgaagaaacc aaatgaatga cttagcccac tcactacgct tggcgacgtg    360
ttcttcttac gaacggacca atcaaatgcg agcctgatga atatgggcca atcatattat    420
gccacgtaag actttacttt tgcccctgac ctatgggaag aaaattgtgg tcttttctta    480
tgtcaataga agaaaaataa aattatatga aagtcttaaa aggaaaaaaa caaaccatgt    540
taatattact gtttaaaacc ataacacaaa atcaattatt gtttatgttt tgagactccc    600
ttatggtgtt tgctagatag tgtggatttt gtttttgaaa attgtttttg aattttgtta    660
ttcttaagtt tttttatccg aaaatttcat tctagaaaac aaaattatat aaaaccattt    720
taaaacataa tatatcgtgt tatagttttt taatgtaacg ggattacacg gcctattatc    780
aattatataa taagatagat taaataaaca aaaatgattt atatggcttt tttaaaaata    840
aaatttaatc tctaccgctt ataactataa ttaagtcatt ttggtttaat aaaatcatat    900
tatatagtct cactcgtatg tattatttac aaaagatgtc gactttttat caaattatag    960
actaaactat aattttcttc gaggctaaaa ttataattta accaaattta taaatgtaaa   1020
atgtatttat aaataaacga ataatagctt gtcgtcaact atattttagt ggataagtaa   1080
gattagtttt atgatttata aatatatagt ataaaacaca tttaaacatg ttttgttcat   1140
tgcgtttggt tgatatttaa acctagtaac gaaaaagtat taggtattac attaaattag   1200
catccaccta caatgttaaa tttttaagtc agttaataat ttaagagact ctcttcaaca   1260
ttgacttcat gcaacataaa atggtagaaa ttttcacacc attgtttatc gacattacta   1320
cgtaggagaa tggcaaaact ttcttatatg tatgtgtgct tttagatgtg tctttacatc   1380
ccttatcaaa acgaaaacct aattctaacc aaatcaaacc aacccgggtt gttgggttat   1440
tcttacaagc catttgttgg attaaaaaac caaaatagag gatgttcggt tcaagcattt   1500
taaagttttg ggctatttag ttcgaccact ggtttgttca aagtcgggtc ggaccaaacc   1560
gtgagcgatg taaacaacaa aggtctaaat tgggccggga tcagatgggc tgaagatcca   1620
cgattctggt ttccaaccca aggcccaatg aattacaaca aaaaagcgta ctcaggaaat   1680
ccgaatctgg atctcaacgt actctaacct ctcacagttc gccacgtcaa gaaaacacgt   1740
caatacttta ggcgaaaatc aagtgaagaa ttccccacaa taaggaatcg tatatccacg   1800
aaactatcca atcagcttac gccatcggaa gattcggaac aaagcaacag ttcaatggta   1860
tatcataggg tgagaataag tcggttccgc agactagtat ttcttagtca aactttacct   1920
gcttcaatcg gccgccgatt tcccgatatt tacaacattt agttccgatt tttccctcga   1980
agctctgaag tatcgtaaaa                                               2000
```

<210> SEQ ID NO 63
<211> LENGTH: 2000
<212> TYPE: DNA
<213> ORGANISM: Cucumis melo

<400> SEQUENCE: 63

```
gatcaacctt gaaattttcc cacatactgt gttgtaaagt tgtccccaat ttcattcaca     60
aattacctac ttgaggaatc ggcagtaaga agagatcata atgtattttt gctactacac    120
```

-continued

```
tcgcaagtct aatcagagga tttgattaca atatcttgct gctgtaatag attcgttcat    180

aaattaatcc agattgaaaa gtcaagcttt acttcatttt catcgacaat gtagaaattt    240

tgtttataac tttgtactat tgaatctatt gctcctcgat ttgccccctt ggtacgatat    300

caagccatta tttttccaac tcttactcgc aacttcaacg catgaacttg accagcttca    360

acctataatc ttatgcatgt ttttaatgat taaagctgaa atagattgtg aaacgtacct    420

tattctcact accgctgcca aagccaacca agcttccacg ggtacccata aggtccacaa    480

tcatggcact cttggatgac atgtattggt tcctactgtc tcttccgggt tctcttatta    540

atggccccga aagcaacctc tcccggcatt ctcgaaattc ggctcactaa tattctttag    600

ctactaaaac acatgtcctc aaatttctca tttaaatgtg atctgagaaa gtcattcgac    660

ccattttagt ttaaataagc atcaagtcaa aaaccattta acgtgggctt aaaaatttac    720

agcagcgcag cgtacactaa agtttatgaa cgatgaaagt gggtggcaga agaaagcaag    780

aagtccgaga gacatgccaa aaagagtaaa agtcatttgt tggggccttg acagcaaggt    840

tccatatgca tcggtccatt gcagcatggc ggctcaaaat taaattttca cccttgcttt    900

tgcttctcta acctaccctt ctacgcatcg tgtctatctt ccttcacact cattttgtgg    960

taagctttaa cgcaacattt tcttaatgta atttaagctt ggcccaccaa tccctttgaa   1020

aagtttcctc tagatggtgc gtgtcaattt caaattaaca atttgaactt atagttctaa   1080

cccccatatt gtctgccctt tttctcttct tcttcttctt cttctagttt tgttctggtt   1140

taatcttttt cggttttctc tgtgcagggt agtagctttt aagcttagtg attttctctt   1200

gttaacaact ctaagcagtg aattgttaga gacctattat ttcatataaa tactagatga   1260

cttcgactca ttgattaggc tggaagctgt caaaattaaa gagtttgaca aatacccact   1320

aatttggtaa ccaagagcca gcaggaacat ttgtatttat tgagacaagt gaaagtttgt   1380

tattttcttt actcaaaatc tctctttaat tttatagata tagacattac ttggataaga   1440

aagggagttc accggccgga ggttttcctt caaatttaac agtgactgag gtctctttca   1500

gctttgtttt tttggtgtta ttactgtttg ctcaatcctt tgaacgagtg gtgtaacttg   1560

ttaaatgccc acaaattcat gggacgcaat cctttaggag aaaggttggc cactagttat   1620

tggtggttac cgtggctctt agcaacttag catcagaatt tgtcttgaac ttctagtcgt   1680

tgaaaattct cttcatacaa agctaagtct gcttatttgt aggatccata aacatgagat   1740

gataagggtg atgggcctaa gaatgcttga tggaaacatg gtcattggac ttgcttatta   1800

attgaaaaaa ccagccccgt ctctggttag aaccctcatt aggattgtat tgtttcaatt   1860

ctttcagctt gttctggatt ttaaaggctc caatggtttg agatgatagt catggaggtg   1920

ggaaggaatg gacaatacag ttttgaagaa ctgggttatc tcaaatggga aggtgaaatg   1980

tttatgtcag tatttgcttg                                               2000
```

<210> SEQ ID NO 64
<211> LENGTH: 2000
<212> TYPE: DNA
<213> ORGANISM: Cucumis melo

<400> SEQUENCE: 64

```
atcttcaccg ttaaatcgcc gtggttgtta gcggcggcga ggagagagag tgctctttct     60

ctgagaactc ctgccatagt agacctaaag gaagaaagtg gtagtgaaac aaggaatggt    120

gaggagggtg agaattgagg aagtggttag ggctttgaag gaacggggaa ttttatttcc    180

gggaagggaa acaacagggg agaacacagc cggagcggtg tggttgtgag aaaatttaag    240
```

caagcagatg agacgacggc ctggcgccga ggacaggcat atgaatatca cgtggctatg 300
gctatgggaa attgaacgta ggccctttct cattcttata ccaatcttca tttttctatt 360
ttctagggtt tcttttcttt cttttttctt tttcctttt cacattttta tatgtcattg 420
aatttcgaag tttggagtta atatgttgga gtcgtgtatc tatttagctt catgggttat 480
aacattattt tggatgatgt atgatattta atctcaattt aagaaggaaa cgagtaacca 540
aaaaatctta taatgaggtt tgtccatctt ttatgtatta ttctccactt atcacatttg 600
tttgaaataa ataaataaat aaatgttgtg tcacctcaaa cacaaccata tggttcaaat 660
tgaaatttaa cacttgatgg tccctatgtt ccatacgacc taacaaggtc atcttttgat 720
tgtgaggttc atccaacata aagttgttat aaactaagaa tatttcactt atgagtgttt 780
atgtgcacgt tgttggtata ggccataatt ttcaatcatt taaaactttt attaaccatg 840
atttcacatt atcttgatct ctcccattcg aatatgattt tggttcatct atattcccct 900
tataaactca acgttacgtg cctaccagtt ttcgcttggc tcatccccaa cccatatctt 960
actgtggaat gtttttctc tgataccatt tgtattgttt cacaccttcg aatcatattt 1020
tagaatgttg atacagtacc taatgcatgt gatattcccc tccatttgtt gtgacatggc 1080
agcatttgtt cttacttgtg tttgaattgt tttctaagag aaaaaaatga tatctccaca 1140
aaccaacgca catcatttta gcatatcatg tgtctcattc acgtggttct taaaaaaaaa 1200
tcaggacatt atccaataag acgtggtcaa gggatgaacc aaatgaaaat taaaagggca 1260
tgtaatggcc gagttcatga atgcgtcata aatgaatcaa tatcacacta aaataagacc 1320
gatcacaagg gtgtgaaagc atagttaaca ataatataaa aaaaactaaa agctcatatc 1380
tatgccaaca acatacacat tattttcgat tgcttaatcg tatgaacttt aaagttaaac 1440
gtgtttattt taaagttaaa cgtgcttatc ttaaaacaat cttatgttgg acgacctcca 1500
caattttttc cattacgcat gtgagaaaca cattgaaagg actcgaatta gcatgtagag 1560
aatggtgtag cccccattct ataaaagcaa ctcaagatct gaacatgcat tgaaatttca 1620
ctcttcattc ctgacacata cataaagaga agcaagtacg agaatcatcc tctacttttt 1680
attcacaagt tttaagtcaa atttcaactt gatttgtatg tttcaaaacg acacacctac 1740
tcatttaatc ttgagcgtta cttcaattgt ttttatgttt caaaatgtta aaaaagaaaa 1800
aaaaaaaaag ttcaatagtt ttgtaaattg caaaaaaaga gaattacgag tatgcccctg 1860
tacatttaga agaagcgtaa ggtccatatg ggaatcagaa caatcaatcg acggccacat 1920
ctcacgagac ataaacaggg ggagttggag gaatcgacgg agatcggaat ctggtttagg 1980
gttttagcaa aagaagaaca 2000

<210> SEQ ID NO 65
<211> LENGTH: 2000
<212> TYPE: DNA
<213> ORGANISM: Cucumis melo

<400> SEQUENCE: 65
aactcagtga atacgataag aaatttaatt gaagttaaca aactcaaact taaatatttt 60
ttaacacgga caatttaaaa ccaaattcat agtctccttg tatagtgttt agagtgtgtc 120
gcttcattaa acctttctat cgtggaacaa atctcttcta atattttgtc aaaaacctat 180
catcacccaa aatatcatga taattatttg atgaggatca aggcttagag aggaacaagg 240
gaacttttca caagggtgga gagatttagc tattaggttt aactcgttgc ttctaatggt 300

-continued ggatgaataa cgacaaattt taaacaatga acgttatcac gttgaaacta tctacttctc 360
tcaacctact actttatcat aaggtttgaa aagttctatc gaaaatttta aatacataaa 420
acataaaaag gaaaattttc attggagaat tttccatata tgtttaccca caaaactaag 480
gctaattaaa aagctaacct taagactaag gctaaaatgg tatcttatgc tacatttttc 540
agttgctatg ttttgaagca aaagctaatt atttgctaat aatgagatag gcatgtgggt 600
gagtgatgag cttagcctgg cctgcctttg tgtttcttct tattctctta aatatcattg 660
ttcaatcaaa atagttttgt taaatttagc ccatcctcac ttcaacctct tatatttgga 720
ttggccttct ttgtttttg ggcttttgat atttgatgta atggacttca atcatttata 780
gaagccttac cctacagaaa caaacaaaca aaaagaggaa aaaaaaaatg gtgagttggt 840
taataacaac tttctaactc aaccaatata tggtgtgtgt atatatatat atatatcgaa 900
tacaaaatat gaatatgata tgaccacata aaattgttga aagggttgaa aattagtgaa 960
ttggactttt aaattttgta gtgtagtggt ttacctatga tgctcgtaat gttatttaat 1020
tttaaatgtg tttttttttt ttacaaaaaa aagtctcgcg gtgcaagttc aataagttga 1080
tttaaaaaca aatccatcaa aataatgttc gcttgatatg atcgagtata gagccgaatg 1140
tgtatcaaac ataaattcaa actttaatag agtgaaaaat aaatgctacg caaacaaagt 1200
ttttgtatta gcttcttaaa tgtacatata tacttttccg attcaaacac ctccaaaata 1260
aaactcaaaa gttaaaattt agactcagaa aatgagagaa aaagaaaact aaaaacgaat 1320
tctaaagata agcattttca aatataggaa aatgaacaat aaatatttac aaaatagaag 1380
aattgtaaaa aacgacaaat tgacataata cttacaaaac ataacaaaat ttcagattct 1440
atcaatgaca tacactgata tatctttatt agtcatagaa agtctatcat tttataaaatc 1500 caaattttg ttatatattg taaatattta aatttgtttt accatattta aaaattttag 1560
atttatcacc aacaaataac catagatttc aaattttgct ataaatattt ttaaccgttt 1620
atttaccata atttttctat tataaaaaca aaaaaaacaa aaaacagata aaagcgaaga 1680
aaaagtaaga gagcagaaat attttttgat ttaggtttca tttggtaaaa aattgttatt 1740
aaaaaataca aactaatggg aaacaataat aataatttaa ttttttaaa atctaaaaag 1800 aaaatagttg acaacaataa tttaataatt taatacacaa gccagtgtta ttaatctctt 1860
tttttctaac aacgcctttc acgagacatc ctctcaatcc tcgacatcca gtggaaaaac 1920
agtatccctc aaccctcagc tttccccaac cgccctccgt cgttcttctg atcgtcgcca 1980
ccctactccg tcatcggaaa 2000

<210> SEQ ID NO 66
<211> LENGTH: 2000
<212> TYPE: DNA
<213> ORGANISM: Cucumis melo

<400> SEQUENCE: 66
catatattta ttatgttcca cttgataacc attttgtttt tgaaaattaa gtttaaagac 60
gacactaatt ccatcttcaa ctttcttctt ttgttatcaa cattcgacca atagtccaga 120
aaaccaatta agttgttgaa aactaaaaaa aaaaaaaatt cttataaagt tgttttttt 180 ttaaatttgg ttaaaaattt taatcattat acttaaaaaa tatatacacg aatcatagta 240
gaaaattgaa aacaaataaa cttaattcca aatctacttt aaaggctcac tatctgtcaa 300
gaggctttgg tatagttgtc tgtactgatt aagtgtgaga gttcttttaa tatttgtagc 360
tgaccaataa attctttcct ttctttctaa ttttgcttta actccctatc ctattcatac 420

```
acaataaata tacaccatat tctaattgac aatattgttt ggatttgttt gttttcttta    480
cggtaggcaa gaagttgcct agttgttgtc tgacctcaaa accctttgtt gataagagca    540
aacaaagtct agttttccaa aaaaaaaatc accaactcaa ccaaatcttg agccttttac    600
taatttccat cccaaactaa tatctaatca gtgcttacat gtttgagcct tcaactcaat    660
ttaacatcaa aacatcttgc aaccacacct tgacatgagt atgaaaacaa tataggagag    720
aactttagta ttacattgag ttccattatc attgtacatt ctcaaccaac gaaaccaacc    780
caaaacaaaa tagtttttg taacatatga gattaggtat cgtcctagtt aatgatttta    840
caaagttata tgagtattca tttgttgata tagtttgacc ggatcggaca gttggctaca    900
atggtatatt tctataaact aaggtataca atttttcatg tatgttgttt gatattgttt    960
tattattggc acatgtcttt tgtgtccaat agtaataaca aggttgtttc ttatctaaat   1020
aaaataaact cttgccagat aattgaagtt agacttttaa tcaaaacgta atattaaatg   1080
gggatgagaa ataattgatt attaggtaaa cctaacaata aaatctttaa attgtgttag   1140
aatcatttag ttagtcgagt tctacactaa aaaaaattaa aaacactaaa atcatttata   1200
aataaaatat tcaatatctt caaaatgtac taaaacattg aagctcataa aactaatcat   1260
ttttcttttg attaaatttc tctctcatat taccaagaaa cctaagataa cattaccaac   1320
gattcatacc aaaaaaattt attatcattg aacatatctc aaactagtgt attcaataat   1380
ggttagagta gtagttatat taaggtgcca tgagtttgat atttttcttt tttgcctaaa   1440
ttaggttaag ccgtagctag cttgaacaat gctaaagatc ttcttaagag tttcgtagtt   1500
taacgtttat atgataaatt ttattacatc cgaacttgat atttaatttt tgtggctctt   1560
atctgtgttt agtttttctt attctctttt aacttgtagt aatcaaatga aagccatttg   1620
caaatgagga caaatgcatc tgcaagatat atattagcca atctcttgat atttttatgc   1680
tctatgagac aatatattct gccatttgcc catcaaatgg ccataatttc tcaagatttt   1740
tccatttcga gtttgtttca atcttctact ccttttgttt ttcctttgtt caatttttttg   1800
gacctttgat gaaatatctt cataactcct atgacgtggg caccatccat tggttgtcat   1860
ttgataagaa atatgtgtca atggcacaat tcccattcca tttatatatt atatagttcc   1920
taaagccata tccccatgat ttatatcctt cttcaagctc acaattgaac tttaacatta   1980
cttcttccct acacaaagat                                               2000
```

```
<210> SEQ ID NO 67
<211> LENGTH: 2000
<212> TYPE: DNA
<213> ORGANISM: Cucumis melo

<400> SEQUENCE: 67
```

```
aaataatttg tggattttat catattatgt accttagact ttgtaaggtt tataacacaa     60
gatgtggaga aatcccatga tgaacatgga cgttattata tcctttgaaa ctaaaaacaa    120
aggaaaaaaa gacaaatggc tgagtataag aaaaagagaa gaaacaacca aaaagctaaa    180
atgtcatgct ctcatatgta acatatttga attgggattg atttcaagat gtattttaaa    240
ataatttaac acacgataaa ataattctaa caaactcaaa attactctta aacatttact    300
tgatatcttc gacataatga cttttgtttt aatacaactc aaaacataat taaggttggt    360
tttaaatgac aacaaacgaa aaactcgatt ctaatttcaa tactagtctt tgaaagccct    420
aaggagcgtg gttttgaatt gtatagcaag gtttcgaaaa ttttaatcat caaacaatag    480
```

gtatatttac ctgttcctca agtacagtta attcatagct acttgtcgtg cttcctacga 540
caacattgta agacttgcca cacactaatt gaagccgttg ttgaaggtag ttttccatgt 600
atagcttgaa tcgacggatg accaaagagg ttgaagaagg tttgaaaaat aggggaaggg 660
atatacaaag tttgagagtg agagagggag agaaatagaa atagaagaga ctgaaaaatg 720
taaaagaaag gatgaaaaaa tgtggggtaa acgcaaattg gatttttata gtagtatttt 780
gaaaatgcta tagaaaggct atgtatagta gtgcttccaa agttctatat gaatgagaca 840
aatcaaaata tatttttttt gattaattaa ccccaaaaag actcataaaa aaatcttata 900
aatcccacta agatattgca tgttatatgt agtaaaattt atcgttcaaa taaaccttaa 960
acataattca aacgaagaaa gtaaaaattt gaatttctta tcttacatca ttcaaccaaa 1020
caatttccat ataagagatt aaacttctaa ctttaagaga gagatatcca gcatatgcaa 1080
cctaaaccaa cagtgacttt gctatatatt tgcacaaaat gtgggggaca aagttgtaat 1140
ttcggaatat caatgattaa agaaaaggta aaatttaaaa ttcggaagct tgacgtggca 1200
acacggaatg gtgatgatat ttccaactcc tcgcgacttt tagaagttgg cctcaccaac 1260
cgcatatccg cccctttgcc acgtgtcaga ctacaacaac ttccaacaat ttcctttaag 1320
aacaccaaat tatatcaata aatatttaac ttaaattaag aatatatttg ttacaatttt 1380
cctactgagt tagatagata gacagacttg tcaattaact aataagtcca aagtcaattt 1440
actcaacata gatacaattc taatttgagt gtgaaataca tattcaaatc aaaattatta 1500
ttaagaggaa aaactgattt gctttctcaa tttaaaatat aatattttga aaaagaaaca 1560
cacatgtatt atggttttca atatatttac tttcttagtc acctaatctc aaactaattt 1620
ttgaagaaat taaatatata tattatcatt tttattttct tggttatgat attggtatag 1680
aatcaacaaa actacaagtg tcctctcctc tgctatcgat ggggattaga ctctaaactt 1740
gtttagcgat tagtaattat atattagaaa aagtttatgt taatgtggac ccgacaatct 1800
caccaatagg ctcttcactt caccaacccc cgacccattc cctctaataa ttcgacacgg 1860
ctcatccccg gttcgaaccg ggccgacgtc ttcctattta acacacctcc atttcctctt 1920
ccctccgcaa cacaaacaga gacctcaccg gaaaatcaag ttaaagcaaa accaaagaga 1980
agcttcatca ctctccggaa 2000

<210> SEQ ID NO 68
<211> LENGTH: 2000
<212> TYPE: DNA
<213> ORGANISM: Cucumis melo

<400> SEQUENCE: 68
taatagttgc aggtcttgtt taaaatacta atctaggtgt gtaaaacata gaaagtttaa 60
tgtggaattt cttatgagaa cgattaaggc tggtgaatct cgcttggtta aatttgaagt 120
agtttcactt cgatggagac tagacgttta ggcattcgta atttcagaga caacataacg 180
aggctacgtt gggaaaatag ttatgtcatt ttatcataac tgcatacttt gtggtaagga 240
tcatactgat tagtaagtac ggtttccact ctatagtgtt tgagtcaact tctgtgcccc 300
tttactaatc tcacgagaga atccgcctgg tcctgtaaca tttgggtgtc aaagaaactt 360
gtaggaaaga ttccgaccac catggattga atcataagtc aagggccatt agtaaaaacc 420
tctaacttgc tcttgcttta aattttcctc tattctcctt attcgttaag cattgggtgt 480
gggtgctata ctaacttttg tgggttgtta atggcctttg tttctgtaga tagtaaggac 540
ttctactgta aacttgcttt ttgtttgcac tttctcactc tttcattttg ttaaaaaata 600

```
taagacaaca taacagagcg acagagagaa agagagacta accatagcaa ctggagctcc    660
ttgtgaaatt tatccaattc ctcagaagta gacaatatag gcttctttac agcaactttt    720
ctaccatcca accttccttc atacacagta ctctcggccc ctgcatcacc attcgataaa    780
aatccaatat gtcaacagaa cctctcaggc aattgaaccg gaataaatta gtgcagcgtt    840
gagtgcttac ctcgggcaat tggagagagc agcgtgaatg cggaaggttg aagatgaaga    900
ggaatcgaat tgctggagca gcagccctga tgcaggtgtt cggatccata attcccaaat    960
ccatatccgt tttcgtgaag aaatgttgag gaaaaattca ttatgcgttc agtttatacc   1020
attggagagt gggaaagttc gtattgtttt gctaatttcg tcgattctca ggtcttggag   1080
taaaaacgtt gtacccgcca cttcccattg ggccattgtc caatattgtt tgggttgggc   1140
gggtggatga cccaaatttt ggggaagata tgagatttgt ccaactctgt tatcaaatat   1200
gaccaaatga acaaaatatt gacttttttt tttctatatt tttttgaatg aagtataagt   1260
agttgtttta ttttgtttat tttaactcaa aattaccaaa tttggatttc acaaacataa   1320
aatagatttt atacttttta taattcaatc gaaagttgat cgtatatgaa aagaacaatg   1380
aataaagaaa gaaatgtaaa atttatatca acttaattaa aacctcgcaa tacaaaaatc   1440
gagtgaaata gagggtggag gatgagagga agagggagaa gacatccata ccctccatgg   1500
acatgggtag atgtatgggt tgggttgggt tgggttgaat tgggtcaacc catccactcg   1560
gttcatatag acagcattcg ttttataatt tatccaaaat aaaatataat taaaagaaga   1620
aaataaaaga aaaacgaaat ctccaattcg cgtaggaaat taaaaaggaa gagttaattc   1680
aattcgattc tctcccatct tcatcataat tttgcgaaag gatcgtaagt tgtatacttc   1740
tctccttgct gcttttcgaa tcgggataag aatattttct ttttgtcttc cccattccta   1800
ctcttcaaaa ttctctgcat tttctaccca tcacttttac ttcaaccatt tttgttgttg   1860
ggagttccat attttgattt cctctacaac gcctaaactc ttcttcttct tcttcttctt   1920
cttcttcttg gagtgatttt tcagttcaat tttggggatt tcatctattt ctttgatctg   1980
cagcgttgct ggaagttgcg                                               2000

<210> SEQ ID NO 69
<211> LENGTH: 2000
<212> TYPE: DNA
<213> ORGANISM: Cucumis melo

<400> SEQUENCE: 69

agtttattct gttgtagcaa ttcaaagcag tgtgatccag atgagtacat atttggtagt     60
agactcaatt atcattttat ggttgaaaac cacatcctct tctgtcattg ttcatattat    120
tacgaggaaa aaagccacgt cctctttcaa aatttcttcc acaaactctt tcttaaaagg    180
aggaattaga gtttgaaaga ctaattagat cgagaattat tcatattcag attggtacct    240
aattgagtag caaccatcgc agtaggttga agagaaaggt cctcttgttt acgatgtttt    300
gcaagagcaa attcttcaaa tttcaagaga gtatgaagtt cttcaaagat tactgattgt    360
gaacgagtgc gcatagagat gtgaaaatat tgtattcatc tagaaatcaa atgagagtat    420
agatcaacaa atcttcatcg tttactattg aaacacacat ttgcaagttt atctttgatt    480
tttttgcccc tcctcatgta tgaattaata gattcatcaa cttctttgaa atcgattgaa    540
gattagtttt gagattaaca atatttgatc gtaaatttga gtagtgattt tcaagtgcga    600
cccagacttc ctttgatgaa gtacaaccaa caattagggt ttttacagac atagtagcac    660
```

```
tgatcaaggt cataaaagct tgatctttag caatttaatc tttatatata aaagattcaa    720
cattgtcgtc gattgatttt gtattgtaga tgaactagtg gtcgaagaaa tcaaaatcga    780
ttttgaaatc aaaatcgatt ttgctagagc tgtacttatg tcatcaacaa atccatataa    840
atccatatag cttgtgtgct ctcaaaatag tggagaattg gaatttctaa gaaacataat    900
ttgttgattc gagtctgata aatatgaggt acatatattt gtgaggaaga tcaaaaaatt    960
gatttctttt gttcaagaag actcagcgga agccattgat ggagagaaca aaaatcggag   1020
gggatggtta atcatgggtc tttgatctgc tctaatacca tgtgatcttt accaagttgt   1080
gaaaaaataa tctctcattt tctcattaat ttacaataat agaatatggg tatctattac   1140
aacccaattt acagaggaaa tactagctga ttacaacaga atcagtgcca aatcaattat   1200
taaaactaat actcaacact aattaccaaa gaattagtgg ttttttttacc acgaatttat   1260
ggggtaaaaa aagtgaactt ttaccaaatt agtaaaataa aaaaagaaag aaaaaaaaac   1320
gtaatattca aatggatggt gaggcatgaa gaagagtagc ctaaagtaca tgaagagcta   1380
aaagacttat tatcttccat tggtcccatt gaagaccaca aagaaaatat cagtcctttt   1440
tctctttaga gacacaaacc caaagtagaa agaatctttc acaagaatta ggaatttaat   1500
gcaatttttc tttttaaaaa aaatctccaa ttttctatct cattatccac cctttccact   1560
ctaaacttca ctacaatttg atgaaatctg tttccaccaa tcagattgca ccaaattcca   1620
tcaaaaacgc cccatcagat aattatggat gtcttcttct tcctctcttc tttcgtggct   1680
gaaattgaag ctcaactcaa aaatacattt cattttcaaa attccctgat gacccaattc   1740
gccacgtgtc ccttccactc accactaccc acacaaaaca actgcttctc ttcctcttcc   1800
tcttcttctc cattaaattc ccagacccat ccctctgcaa cttcgaatgc aacagaaaga   1860
aaacggacca aaaatccctt gaggaatttc tcatttttga agcataattc aaagattaaa   1920
cccgtattaa ccctcttcat cttaccagag gtttgattta ttgatcgaat tgttttattg   1980
gttttttttc aaggtcacca                                                2000
```

<210> SEQ ID NO 70
<211> LENGTH: 2000
<212> TYPE: DNA
<213> ORGANISM: Cucumis melo

<400> SEQUENCE: 70

```
gcatcttatg gatgtagtca caacatattt atatggattt tctgataatg atatttatat     60
gaaagtccca aaaggattta agatacctaa aacatataaa tcaaattccc ataaactatg    120
ttcaataaag ttacagagat cattgtatgg attgaaaaaa tcatgacgaa tgtgatacaa    180
tcgcctgagt gaatatttag ttaaaaaaat aatatcaata taattcaata tgtccatgcg    240
tttttataaa gaaatcaccg tcaggatttg ctattataac tgtatatgtt gatgatttaa    300
atataattga aattttgaag agttttcaaa ggcaatagaa tattaagaaa gaatttgaga    360
tgaaagatct cagaaaaata aaattttgtc ttgattttca aatcgagcat ctagtaaaag    420
ggatatttgt tcatcaatta acttatacag agaaaatttt aaaaagattt tatatagata    480
aaacacattc attgaacatt ctaatgcaag ttcattcatt aaatgtgaag aaagatattt    540
ttcgacgtcg agatgataat gaagaactcc ttagtccaga agtaccatac cttaatacaa    600
ttggtgcact tattttgtca ataatcaaga ccagatattg cattttctat aaatttatta    660
gctagattca gttctccaac aaaacaacat tggaatgaag ttaaacatat acttcgttat    720
tttcgaggaa caattaatat aagattattt tattcaaata aatcaaattt taacctagtt    780
```

agttttgcat attcttgatt tttatctgat ccacataaat ctagatctca aacaggttat 840
ctattcacat gtggaggaac tgctatatct taacgatcag tgaaacaaat taccataaca 900
gtcaactctt caaaccgtgc tgaaattctt acaattcttg aggcattcat gaggctagcg 960
gagaatgaat atggttaagg tcgatgactc aacacattcg aaaattatgt ggtttgtctt 1020
ctagtaaact ccttccaaca acattatacg aagacaacac aacttgtata gctcaaataa 1080
aatgaggtta tattaaaagt gatagaacaa aacacatctc accgaagttt ttctatactc 1140
atgatcttga agaaaatggt gacatcacag tacaaaaaat ttgttcaaaa gataatttgg 1200
tagatttatt tacaaaatta ttacctactg caacctttga aaaattggtg cacaacattg 1260
gaacgcgacg acttagatat ctcaagtaat gttacatctt acttgccaag ttaactatac 1320
atagtgacat ttggtggagt tgtaagaaac actaatattg gagaaaaatc gaaagaaatt 1380
ggaaaatatg gagaattgaa tttttttag atttttctta ttttctaatt ttaggtttcc 1440
gtattctgat tatgcctcat tttcacaaca ttaataactt taataagatg atttcttggg 1500
ttaagggaaa aaatcatttt tttagagttg cacgtacaaa aatattatca taacatatcg 1560
attataataa accaattcac cgtcaaccta acctaggtag agtttgagtt aaatgttaaa 1620
agaatatcca cccctcaaca ttgtaatccc aactaataaa tcagcaacct aaagtttttt 1680
ttaaaaaact aaaaagaaga gcaatatatt ttttttacta ttattttttt aaagagtgga 1740
tttatttatt aaattaaaaa atgaaaagaa gaaaatttgt tagtttgggt aatccgaaaa 1800
cccgattatt tgggcccgag aaaccgacgt tttgtttatt gttcctcacg gcaataagta 1860
atggcgtgaa tcgaccgcgt gcgcttcaag ctatctagac atttttatat cctccgatta 1920
gaaaccctaa ttcagattct ccgtattacc caccctggaa catctttgaa acgcgaaaag 1980
gtgacccgaa gaaacttgaa 2000

<210> SEQ ID NO 71
<211> LENGTH: 2000
<212> TYPE: DNA
<213> ORGANISM: Cucumis melo

<400> SEQUENCE: 71
taataaagtc gatgatatga attaattaga cggatgggtt atactatagt tattttattg 60
tcttttatag agaatttaac attggtagcg gggaaaatcc gatagatatt ggtgaagagg 120
aattcgttgg tggatgtaaa ggaaagttag tttcgccttg gcacaacgaa gggtttgaat 180
ggaaaatcat gataagttcg actgcctgtt caactaaacg aaagatacca agtcaaacct 240
tagttttctt taaggattta tgatcttagt agtgtatcta tttaaagatt caaaggtatc 300
aatagactat ttatttcaat cgttgtgttg aaatctagga gtatatttaa cgattaactt 360
aaaagatttt gctatcttgt tttgtgtttt tcattttttt gggaaaacct agtgtctttt 420
tattttattt gatacaataa gtattataaa aatgactaga atgactatat acttgatcat 480
tattttgaca tatttgcaat atattaaaaa tgactactta ttttaattac cttcatggtc 540 ttttttaat ttatgaaggg gtgggctcgt gtggcagatg aggcctgtca taattagcct 600
taccttaaat aattgggccg gttctttggg aaatatcggc ccaacctaac ttttcatggg 660
ctcaaatgat gctttatcta atacccatac tttccattac ctttgtatat tgaattagaa 720
tgatagaaaa acatactaca cagttgagtt aggatataaa taaatgcatt gaactatgta 780
ttacatagtt gagaaaaatg agaatgaagt tttgtctttt gaatatatat tctgtgaaag 840

-continued

```
ttagatgtat atagaaatga tgatacttcg gcgtttgttg aagattgagt ggggtgtcaa     900
cctaatcata gttggtttaa gaaaagtttt aattataaga taaccgtttt aagtgactta     960
tgccatattt tgattgcagg ttcacaatga aatgttttaa tttggtgatt agactttgac    1020
aatgtggtaa tttatgttaa gtgagttgtt gtctcgttta ccttgatcat ttgtctctac    1080
tcatttctca ttttgtttca tcccttgtta tatggcatcc attgttgttg tatttgtcat    1140
tgttcacatt cgatgcttaa ctaggtaaga acaacatttt cattttagaa ttggaacgat    1200
agaaattcat aagttttatt tttgaggcac ttggttcatt ttaatcatag aacattagtc    1260
cacaatcgtt tggaataaat ttacactcta tctagatatg gaactcttga caacctctac    1320
caaggaagga tgaaaagcaa aaaaagagta gaaaaacgaa agtagacact ataacaagcc    1380
aattagccca ttgacaaata ttaccacgtt attaaagttc attttaatca tcgtgtcaat    1440
tatcaacctt ataggtcaaa taccatttat aattattttc aaattcaatt aatgaaacaa    1500
gactcaaaaa accaaacaaa tatccaaacc caatatttga gtttagaata taataatttc    1560
atagttagac ttggagacag atttgtacgt atatgttaaa ttaaaaattt aatcaaagta    1620
taaataaatg atttggagtg gcaagaaaat attggccaaa atttcataag aaaaaggaag    1680
aaaataaaaa ggtgtattgg ctaacaaaaa cccaattcca tggggaggag aaaatttgag    1740
tcctcaaaaa aggatttcag atagggaacc aaccaatcaa aacgaaggac gtctccacgt    1800
gtcgctacaa gaggccatct ttccaaaatg agatcgcgga taaacaagcc ttttctgagc    1860
atagaaaaat ggcgaatttt aacaaaaaga aaaatctcag taaagtcatc agctacagct    1920
gctctttgac ggccacttga ttcactattt ccctctcttt ccggcgctga ttctagtgtg    1980
gttgaacttt ctgcaaagaa                                                2000
```

<210> SEQ ID NO 72
<211> LENGTH: 2000
<212> TYPE: DNA
<213> ORGANISM: Cucumis melo

<400> SEQUENCE: 72

```
attacttgaa cttaatccac atttatgtct ttatataaag ttcgaatact cataatatag      60
ccaagaaacc ttgtttattg gattttgagt tttatcataa gcaaatctct tatccaataa     120
caaattatta aacaacactt caacaataac tttattcaac aatatattag tttaacattc     180
acaaatcacg agtattagaa cataaaacgc aacaaagaat ggactaaggt actatattct     240
aacttaggtt gtttaggatt tccatatgtc aatgcttttg tgatttttga actagatttt     300
cttgttagat taattcaatt ctatttttaa atggcttaat atcttatttt cggatgcttg     360
gggattgcta gactaccgct ttgttgaagc aataagttaa atttgtttgt tacaggtatt     420
gatcaatcta acatagaatt gaatttgtat gaatatttag ttagacgctt gaaaactaat     480
tattctacca atgagccgta gatcttaatg caattgttat taatttgaac tttgtatgct     540
tctcatcgat taaatttata tcaagtagtt aattaggaca aatctattgg ctttttcatt     600
taattttgtt aagtaaaagc aacttagaat tttgaaaatg atgaacccat gatccaatac     660
attgaaagag aattttgttt aactcaaact aggattcttc tcacattgat ttcgtataat     720
ttaacttttt caatttatat caatcccccc agggtgaaaa aaatttgttt gaagaattca     780
tgtgctttct aaatctgatc tagacttgcc actaaaatta acttttgata tgtaatttgg     840
ttaaatattt gattcggatt tcgacgacaa acaattgatc aatgtggtat taaattctga     900
tctccatgta agaaatttac acattttcat aagttcaatg ttgacacaaa gagagtaaga     960
```

```
gcattttaaa aaaaaagata cttttaatct tttctaaaaa aacaccaaaa tgccattatg   1020
taaatgtaac ctaaataata aacatttaaa cttagaattc atgcaattag gctttgtatg   1080
ggacattgaa ttgattatta aaatcagtag ttatagaccg tgagttataa tggtttgtat   1140
tagaagcata aattatttta attttgatcg taatagcatg tatttgagat ataaattaat   1200
ttagtttggg tggcaaatag taaacagtaa agcaaaatat aaaaaaatga atttaaaata   1260
gtaagatttg taacaaatga ttaatactat aacaaacgtg gttttaaaat aacgttgatc   1320
gtagctaatt gaacattatt tattgtaaaa ttgagtgttt ttaatatttg gagcctcaaa   1380
cttcgggtgg atcaccacaa tataatcata ttcaaattta aaattttatt tttttatta   1440
attataaata ttgattgtta atagatgctc attatgggcc atctgtcact ccctccgtgc   1500
atatcctacc tgaaacatca tatatcttaa acaatgtcca ttgccatgtg tcactatttt   1560
tacatcccat ccacttgaca aatatgttga agatgcctac ttttttaggg atcatgtaat   1620
ctatctcatg cttgtcaaat tgttcgataa tagtgttaca aaaaatttag taattattat   1680
tattatattt cttcgatatt tatgcttcat atgccattgt gctctccatt tttaccatac   1740
ttaaaaaaat ttcttattat aaattttttc aaaaaaaaat ttactatata gtcatcatct   1800
ttattaaaat taaaattgag aacctgatat ttttgatatt aataatttaa aatttgaatt   1860
aatccacttt aaaattatta ataatttatt cgaatttggg ccttaaggaa gagatacgga   1920
aacaaaccct agatcccatc tatatataaa tcgccacaaa accctacctt tctctcagtt   1980
tctcgtttta gccggcaaaa                                               2000
```

<210> SEQ ID NO 73
<211> LENGTH: 2000
<212> TYPE: DNA
<213> ORGANISM: Cucumis melo

<400> SEQUENCE: 73

```
tgaaaaacta aattaaattg tccttacatg tgtataaaag aaaccttcgg acatttgatc     60
tgagaactat gttaaataat aagatccaaa aaactgaacc ccaacatctt cgaaatcgat    120
ttgatttcaa ttcttaagat aagctacatt caagttacct agatgatcta agaaactaat    180
gattggacaa agttagaaac tcccaataaa ccaatgatct tcaaagcact ctacgatcaa    240
gacagattaa tttttagttt gaatgctttg aacactcgtg cattctatca caagaacaaa    300
aattatacgt tttagaattt tcaaatatca ttcatcccaa tttttatttt aaacgtgaaa    360
attacaactc tatttatact aattaaaata ttaattaaca tgttacaata tttaatttta    420
tgtcatttca actaatgtaa taaataaaaa caaataagac aacgtaaata cacaatttca    480
taaacattta atttcacgac ttttaagttt tctaaataaa ttttcaactt tttcatttga    540
tttaattatg atttctcgga tcatatctat atatatatat atatatgaag ctgagtttta    600
gaaattgtaa attcaaattt ctttaaatgg tacaaattca attagtaaga ggaaaaacag    660
ctaattaaat aatgtgtgat gccccactcc ctaaaacagt gggtttggat cgattaatca    720
actaaaactg accacaaaac aatattcttc tacaacccca ttgatttttt taatcattaa    780
gtgccgattc aaagaaacaa taaacaaaag aagttgaaaa gattgagact tttaaattaa    840
atctgcaaga ttctctccaa actcatgttg tattcaagtg tttaaagctt aaaatatcag    900
taattatgtg ttatttaacg gtgaaaccaa tcaaatcaag caagattctt caatattcaa    960
ttccaaatcc tcaagtttcc atgaaaactt cataacgcct ttatccctcg aaagccaaaa   1020
```

ttcaatttcc tccattcatc ttgcagccct atctactttc caaaagccaa caaataccct 1080
tttaagcagt agccttttgt ttggttgtag taggatcttt gtttctcttc cattttaaca 1140
caagccacag gagaatctct atctctatcc tgcaaccttc atccccacat tgttcttcct 1200
ccattatcgg aaaaacccag tacagggttt gctttccggc cactatccgg ttgttctttg 1260
taagtttttt gggttttcat tatctgggtt tgtggctgct tgtggattca gggtaatgtg 1320
gccatgtttt atagtccaca gccttttttt cttcttttga catgggatta tttctgattc 1380
tatttgtcta ttgttacttt gtgctttttc tggtttgttc ttgtggtcat catttcttat 1440
gcttggaagt tcgaacatga atcaattcaa caactaagtt gagagtgttc gactctctca 1500
tctcattgac cctgatggta tatcttggct tggaagttag aacatgaatc aattgaacag 1560
cttacttgag actcgagagt gttcaactct ttcatctcat tgaccctgat gatatatctt 1620
ggctttggag ttatgaacta tgagagcttg gaggatgaac taaaaagaag ggactatttt 1680
ttgagatgga tatttagttt tagtaattta gctttttttt tttagtacat agtacattaa 1740
ctttgttcgc gaggaaatag tggtcttgtt gacgagcatt tcttaaacaa tgtagttttt 1800
gtctcatctc tttaaaagtt tatggagggg caaacaagtg agatcaatag ttatagtatt 1860
tcaatctata actttggaac agctgatttt taacttttcc tttgtctttt ttttattata 1920
gaacacatta gagtgcgtta gattcttcag ttctgagatt ttgatctttg agtgctctct 1980
tttagcagta gaggcaaaca 2000

<210> SEQ ID NO 74
<211> LENGTH: 2000
<212> TYPE: DNA
<213> ORGANISM: Cucumis melo

<400> SEQUENCE: 74
actttcagta gattttatct cataaaagag tcataaagat aattagtaat gaataaagct 60
ttgtttgaag aaatgtttca ttgcaactga tatttgtcat tgatgtacaa atggctttgt 120
aactctccac tttttctaat ctaaccattt acatacaaaa tatctacgat acactaaaat 180
gaataaagaa atttttttg tcaaaaactg tggggagaat tgctccttgt tctcaaatca 240
ttcatgaact ttgcaattta gaagtaacat caatgaaggc ttcttccttg cagggaattc 300
tcaaacctcc agttgggtgg ctgaatccaa actcttcttc agccttgttg agcaagtcta 360
tgaatgaagg ctgactcaag tacgatattg gaacgaaaaa ccgctttctg tcggtttctc 420
ccacgtacac tggaatgtgg cctttgggaa caatggactg acatcttgct gagacagact 480
gcatcttgag aacttgcttg gcagcggaaa gaagaaccga aggcaaacga attcccatgg 540
ctaaattgga ttgaatcttt ttggaagtgg taaacttcaa tgcttgaatg agaatatgtg 600
aaagatttga agttggagat tagttgtttg tttagagtct atatatagaa tgagaaaaga 660
gaaggtattg tgacatatga atagaagatg ggaaaccaag aaagttgggt tcatcaatgg 720
ctcacatggg ttgctccatt ggttaaggta cattcatttt ctcattggca ccaatttctg 780
gtaagatggc cccatatgtc ataatacgtg aagtcatatt gatctaaaca aaatgggaca 840
caaaaattgt aactatttca attagcatta aaatcatgtc aagaaaacta cattaaatat 900
agatatatta gttaatgatg taataatagt ttcatgtgag atcaaactac gatttttttt 960
tataaataat gttactttta aaaaaatgtc aaaaatatgg tagaagaaaa gctattacaa 1020
aaagttaagt catctactcg gttcataatg cgttatcgtg gatcgggtac acgacaaggc 1080
aatgaagaca tagacccagt ctatgacttc gatgtaaaat gtgggttttt cctaattact 1140

```
cgtaaaaaaa tatttttgaa aacttttctt tttaacaaac ttaaattttg gttaattata   1200
tatataaata ccatctttac tttcttatta tccaaaacaa tttaccatat ataattatat   1260
ttattcaata aataataata taaaatattt agataaacaa aatcaattat ttcaatctta   1320
tatattttaa atatacacta agctaattta aatttacatt ctgaaaattt taattatatt   1380
tctatctaat ttaagatttt aattatattt ctatttaatt taaaatttta atggaaaatt   1440
aaattgtaaa taagaataag agtacaaact tactattttt atttcatttt taatttataa   1500
acttcatctc ttttttcata tatttttaag aaatccaacc ttatatttcg aaatttattt   1560
aaaaaaatta taaaattttt taaactatat ataaataaaa attgtaattt ttgaaataat   1620
ttattaattc ttacaacaaa cttataataa taacaataat aataataata atgagggtac   1680
tcgattctca aaaaaaccga accgatcaaa caacgttaga tcaccaacac agaagtaggg   1740
tttttcatcg gcacataaaa accctcactt cttcttcata aaaaccctca cttcttcttg   1800
acctaattcg cgccgttgat ctccggttcg atcggtttct acgctgtaat ctcaagctat   1860
ctcctacctt atccttccct ctctttttct tcttcttctt cgtatatgca tatcttcaaa   1920
tttgctgctt tttttgtctg attattcatc tgggtttgtt tgcaacagga aggaggaaga   1980
atttcaaatc aagaagaaaa                                               2000
```

<210> SEQ ID NO 75
<211> LENGTH: 2000
<212> TYPE: DNA
<213> ORGANISM: Cucumis melo

<400> SEQUENCE: 75

```
tttattaatc tgaatcattc tgtttcttct gagagtttta ttccttttaa gattctaatt     60
ttattttgga tagttgaatt ttggtgtgct ctctttgccc cttctttatt atacattcct    120
ttatcttaaa aaagccaaaa agttaaaaaa caaaaactaa tcaaaattgt aacatttaca    180
attttatgag catgacattt aaaatatcga ttttgaagtt aagacgttgt attctcacca    240
tcggttttta tctcttccca ttccattaga gtgataggct ttatctttca tcactgtcaa    300
aattcatcca acgtccaaga tctcttctgc aaagagttac ccacaattct ctcagactca    360
ttggcccacc ggataccgag tggatggata gaacctccaa gattgcgaga gcaaaagctc    420
agccaaaact tgcacaaact cacccatggc ttccctctct tgtactacct ccattaatct    480
caccccaaga tccttcaatt ctcgccccca ttcaaattag cttcccattt tcttggtctt    540
cagtccaacc ttcgatggct ctcacccctc tccattggac cctccaatgg gtctagagca    600
acttgctggt tcaatttaag gcaaaatgcc gagggtgcag gcatttatgg cagccagtcc    660
cgagatgatt tcaacagaga tgatgttgag caggttcttt tactaatttc tctcttcttt    720
ctttgtattt tgttttgtga ctttgattgt tgaagagtgg tgtcttttgt ttaattgctg    780
gtttgggctg attcttatgg gtttggagtt gaaattgttc ttaccctctg gctgttctgt    840
tttcttttaa gtattgtgaa ttttcaatgg ctcctttagt gaagatagat gaagaaattt    900
aaattagtaa tttttcgtac cgatgactct cttccagtgg tgttaatgtc aaactaacct    960
tttctttacg tcataaagca cttaatcggt tggaactcag tagacgtctc actcatgttt   1020
gtagccctaa cctaatgcca tggcaatcga aatttatatc gtatccctat tgcgattatt   1080
aaacatcacc ataggtgaga cattcctaac gtgatatact gagttctaga tggttaagtg   1140
ctctgacatt tcacattaac gcctcatccg cactggttag tcgaaagaag aaggtgtttc   1200
```

-continued tgttatgaga ttgtgagaaa ggacctcctt aaacattata accaacctca taacttgtgc 1260
atttgtgtat caaactctgc tttcacataa agaaactaaa acaaggtatc acattgccgt 1320
tatgaaaagt gcatagaact tcctgcttcc ctcaaacaaa acttgcaaat attactgatt 1380
ggccttagcc tttaggtaag ggaagaatca aaagtattcc ttcatccttc tgctttaaaa 1440
atgtgctaaa tgacgttgtc catagtttaa aaactcgacc aaatcgcatt tgtcttacag 1500
tctctcaacc ctttttaagc actctcagag tcaatccaaa tagattccta gttcctaata 1560
tgtaacaaga agagtgatac tatgaaaacc cacaaaaaac ccacaaacat gtgacttgag 1620
ttaagatgac tcccaatccc actgtatcaa gcttttcaaa tagaggaatc acgatgagat 1680
gaacaataat atcccaacgt gctgctatcc caaattagat acagaagtct acttgtggtg 1740
ttcttaatcc aataattcat tatgaaattc ttatataatt tcttaatgag tatcttagaa 1800
ttaatgttac aacttatctc ttattctata tgatagaatc ttaacataag tattcatatt 1860
aagagcaaga ttatgttgat acttctcgaa tcataccaaa aacttggaac catgacatta 1920
acttcattcg tggaaacaag ttttgaagga aaaagaagga ttgacaaatg aacgttatgg 1980
ttgtgcagta ttttaactac 2000

<210> SEQ ID NO 76
<211> LENGTH: 2000
<212> TYPE: DNA
<213> ORGANISM: Cucumis melo

<400> SEQUENCE: 76
atctaaaact gcattttta ctacatacag attcaccttt aggtgctggg gcttccccta 60
tttcatttta tcaatgaaat gtttcttatc tagaaataaa aagaactaca tacagattca 120
caccactgca gaaaggtcaa ataaaacatt catcataatt caaggtaagt aagcataatt 180
ttgtgaaact tatgtgatgc acttaatata tgaacgattg ccccttgttc tctcaaagtc 240
agatcttctt tttcctaaca attgaagaaa gtggaaataa gttaattacc acggccacgc 300
aataatctcc tgatggcctc caatgaaccc cccaaacata atgctgtagg gaatgtcttc 360
ttgcaatcct tcaagacgca caatgtgaga catgcaaaat attaaaaagt gacatcttca 420
aatatagcaa aagaaatcaa aatatttaca aaaaatatag caaagtttca tattttatca 480
attatacaca ctgatcgaca tattttgtaa atattttcaa tagttttgac atctacaata 540
attagttgag attttgtagt caacaggatc cagatttgtg tgttgaaagt tgaaacccat 600
gataagataa aatcccggtt aaatatttca ttttcattct taagtttttg aaaaaggaat 660
agcttggtaa gctacattcc gcatggtaaa caagcataca acttttgttt caaagaacca 720
acaagtacta caaacaaaag agtaattgat ttaatccaag ttaacaatga caaattggta 780
atatttatag gatattagtg agataataca atcaagttcc aaaagatgtt atatttacaa 840
ctatgagcat tcatcttgtt actaccacca agaaaaagta gcggttttcc aatctctgtc 900
aagtatccat ttgagttatg atttcatatt caagactgtc acaaaaaattt cattaaaagg 960 tgcaagtgca acatttcctt aagaaaagga taactgagag atcaatgact ggaattcaca 1020
agttaaaatg aacacaactt cagaacatca caagctaata cctccaaacg gtccaataag 1080
ttttctgcaa cactgtcaac aagcgaatcc tttgggcgca tcaaccaagc agctcggtcc 1140
cgctgttacc aagaaacagc aatttcagca agaacaaaat atagaaatcc tccaagaaaa 1200
ataaacaaac aaataagttc gaaggcacca catatcagaa agcttatgga ggagtacatg 1260
tagtacaaac gctcttgcca tttagtttta cttgttaaaa gtgatttgct cagaataaac 1320
ataaccaaag cagaatccga acatatgaac caatgaatta ataaacccca tcacagaaag 1380
acaagtaata ctcccagaat tgtactctat acagacgacc actacaattt agccacacaa 1440
tatcaccatg ttctctccaa atatatttaa aaaaaaaaaa aaaaaccctc ctattgttgc 1500
ggttaacaca aatagatcaa aaagaagaaa gaaaaaacta aaaggagaca aaggtgttaa 1560
atttggttta cctgtttacg cttaagatca cgatcaaaaa ccttaacctt tgagctgtgc 1620
attccatcac cgattcttcc gtcataatta tcatcaccag tagagaaaga acaacaagga 1680
attgaatttg gaaaatctcg ccatcttgca cttctcaaca ctgagaacga tcttatgatc 1740
gtagacggcg acagccctct catttcacag tcaccgattg aacctcgccg gagagacgga 1800
gggaaatttt gtaaattttt aatgggcctg ggccgtaaag tcgtgtccaa acactcctta 1860
aacggaccaa aaccggcgta gaaatgaaac tatccagata agggacgtgc tatacattta 1920
tccaaacgag gtctcttatc gtatcttgta caagttcgtt gcttttcacg gctgtctcta 1980
gaattttggg ttgggcgaaa 2000

<210> SEQ ID NO 77
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 77
aaacctactc tgtaaatgaa ggtttacatc tcttaaggca gtaccatttc tgccattact 60
tctaccattc ccacgaaacc acctcttttc tctttcattc tccccgtcag gtatgcattt 120
ctcatctcta agtccgccca ctgttttccg actgattttt cgatttttaa ttagtgagtc 180
ggttttattg tttcttattc taagctttct tttactcttt atatttttag atatttaatt 240
tcggatccat tcttcccatc atgcccaatc caaagactgt cgaaagtttt gattgttggt 300
aatgggacat taggtctggg gtttctgttt ttcttatcct ataaattggt tatccttcgt 360
ttcctctatt ttgactttat tccgtagtta ggttagaaga agaaactact gaataatgtt 420
tactatacaa acacctcaaa atagccaagc ctgtcgaaac acatttagct gataagctag 480
ggatgaagag atcaagagat ggttagctca gctgtattgc atctcatggg ggacgggtga 540
aacgaaccag agaagtaata tacacgtttt ttttttaaaa aaaaaaccga ataatttacc 600
tgttcttgct acaattacac cgataagttt tcaacttgag caattacacc gtctaatttg 660
cattgctgaa gaaattggtc tgttccatta ccactgttga ttaaaaagtt ctacttgtca 720
gcacagcatg tccatgtgcc cagatagttc ttgatctttg gaaaaagtgc tatgtttgca 780
tgcttcggta agatgtgagg ttaaaatgag gaggacataa tgttggcata gggaggtcaa 840
aatgtgttaa ttgagagaaa aaatgtggtg gatattggag aggagacatg gaagtagaga 900
gaaagagatg aggagggagg ggtgaaggta aagggaaata gacatacaga aataaagaac 960
tgtgcgagta atgtgttgcg ataagtgaaa gagagaaagc aagagaaaca gtggtagaaa 1020
attgaagtat agagagagat gtagagaggg aaaatatgga gaactacaag ataaaatatc 1080
tttattcttt ctctatctaa gtatttatct ctttagaagt tatctctctt tgtttctgag 1140

-continued

```
tttacccta gtattttctt ttttctttct caagcccttc ctctctaaca caatttctct   1200
ctctctcttc tccctctctc tctgtatctg gctgtggcac tttttttgac ctcttccttt   1260
ctgtctttat ctcctttgaa gacattttga ttttcctaca cccctcaatt ggtcttctac   1320
tcaaactcat ctacttgtta ttatattaaa tgcatgaaat cctaatattt taggaagctg   1380
gagactcatt gtgcgtgcat ctgcttgctt gtagaaagtt ttaaattgaa aggcaagccg   1440
aaggggccta attattcagg ccaggacaat gatgttggtt ttagtttttt gtttttgaaa   1500
nnnnnnnnnn nnnnnnnnnn nnnnnnnnnn nnnnnnnnnn nnnnttttga aactaatttt   1560
tttcttagtt ttcaagactt ggcttggcat ttaaaaacat tggtagaaaa tggataacaa   1620
aaccaagaaa cttacatgtg gaagtagtat ttataaagct tacttatgtg tggaagtagt   1680
gtttagaagc ttaattttta aaagtctata accatatggt catcagtaga gtctcatgca   1740
acttatgttg tgacagtggt gtaattgttc taattaaaaa ttttcgggta caaatgtaaa   1800
aaacattatc gaacagtggt ggtttgtgaa atatgcatta actttttgaa aatttgatgt   1860
gtcatcatat tcattccatg ccgtgccttg tttccctccc agctccttat ccatgctaat   1920
tagattcaga ccattatccc tttggaacag ctatgcttaa ctctgttctt ttctccctct   1980
gtacaacagt atatcaaaaa                                                2000
```

<210> SEQ ID NO 78
<211> LENGTH: 2000
<212> TYPE: DNA
<213> ORGANISM: Cucumis melo

<400> SEQUENCE: 78

```
tagcttgtta attcttgtgt tgaagacgtg tttcaacaaa tctgatgggg tattcatctt     60
aagtgtccac tgaagaatgg gggttctgtg gcagatctgt atgttatgta gtgaaaacaa    120
atctgtaaag ttttttttta cttcgaattt aacgttgctt aagcttctgt gtacagtttt    180
atcactgcct cgaggttatg attattattg gattaaatta caatttagtt tacgtttacc    240
ttggaactgt gtatttcttt tgattgctca acttttctcg gggatttttc aagaattgta    300
tttttaaaat tttaatttat ttggaacatt aagaagttgg ttatttacag atgagatata    360
acactgtgat tggggtggaa aataaacaca gcttcaaaca cggagtgaga tatagttaat    420
tacattacat agtactagag attatataaa tcactccact cacatgagtt ttcatcttaa    480
aagattggaa tttacatctt aacagatgca atcttttaat gtagagttct taacgtgttc    540
tcttacggtt gtatcttttc gttttcatta ttctttggtc aaatcaaaat tagactttat    600
agtttttaat gaaatattgg acacactacg attcatcaaa gtaacccatg atcttataaa    660
gttgtgaaat gtatgtatat tgtctttgat caaactttac gtttaattat atcttgaatt    720
tataattttg tatttaagag atgaatgaat tttagaaaat tctaaagttc ctaggccaaa    780
gttgttatag aagggtaaag aatgctttaa atcatttatt ccataatcat tagttttata    840
atttttattc ttcgtaacta ttttttaaca aaaaaaaaaa aagttatgca tctcttaaat    900
actatctttt aaaagggaaa ttttcataaa taaataaaaa aagacgatag tatacacata    960
aaaaaaactc aaatgattta tagagagttt gatgaatttt gctggattta taaatagttt   1020
agaaaaataa gtattaacct aaaattttgc ctatatctca atggccttct atgtctatgt   1080
tatttcttaa ctaaaatcga aaggatatag gcttatggat tggcttaagc taaaaaatgt   1140
cggtccaaat agttgagatg tcaaacctta aaagtactac gattatgtga ttttcacatg   1200
acatagtgtt ctatggtcaa attttatagc gtacttattc caatccatca ctttttatag   1260
```

aactaaaatt catagttcct attttaatat atatatatat attaaaaaca cacattaaat 1320
gatgatttta tctcttctag gttgattgaa aattactaac taaaaaacac ggtgcctcaa 1380
acctccaacg taaatacgat ttctaagaac tgtgtttttt gtaaacgcca agtgactgat 1440
taaatctctc cattctctgt ttacttctat ttggggttat ttatgctaaa ggatattatt 1500
cattcaatag aataaatgtg agatagtcga gttatattca tagatgttac aatgaggtga 1560
ttcattcctt tgtcaaacaa tgctttctcg actcgtattt tactgtattg gatcgaaatc 1620
cttcttactc gcatggtttg ccttcgttga ttagttttgg tatgaattga tgctttgttt 1680
aagggggaaa atgaaaatgg ttcaattgga ggacaattgt ccaaatttcg ggacattatg 1740
ggttaaacac aaagaagaag tccaacagtg taattttgtt aaagattgcg ttacatttcc 1800
gaaatataaa tgagggtatt ttggggaaag gaaatcaata taggccttgg ccgggtgaga 1860
tgcgaaaaag tctcaaaact gagtgagaag cgtttgagct gggctcgcag ctattgaaaa 1920
agagagaaca aaccctttcg tcgctcttat tttcttcctt tgatctgaaa tttcctgttc 1980
cgatctcgct ttaggacgca 2000

<210> SEQ ID NO 79
<211> LENGTH: 2000
<212> TYPE: DNA
<213> ORGANISM: Cucumis melo

<400> SEQUENCE: 79
aattcattcg ggattgttat gaggtaataa aaaatatctg agtgcgaaca tgataattgg 60
taaagtgaaa aaatgttcag ctattctgtt ctagatacag ggatggaagt gggaacaatg 120
ccaccttgct tattgacaat aaaatgagga gtggcaatat tttgtttctg aataaatatt 180
cactagcata acatattagt gatgattcaa actaaagtgc actaggtcac tagtttcttg 240
attcatcgtg tttggtagta atggtaggta ttgtatctta tagtattgga caaagcttta 300
ccgaccataa attgtggata atgtgcagag aagaattggc agttgaacgt tcctggatat 360
tcaagtgatg agtggaagaa tcacaacaaa aatgtaagaa aattatatta ccctctctaa 420
aacatcattc tattctcctc cctaaaaaat cattctgttt caatttaact ttcaaaattt 480
tgttttagtt taaccatatt gagttttttt tctttttttaa ttatcgtagt tatcatcaag 540
tgatgtccac aagaaacgtt tggacatggt aagttggact tatctcttca agtgtttgct 600
ccatttcttc ttttatcatt tgtctcaaat tttctcttct ggggtttcat cagatacgcc 660
tattgaagga agcctcctgt gtcgaaacaa atgtaaacag ccctaaagag atggtacgac 720
aaggggttgg aatgtcaatt ggtcccaaca ctctaacaag gccttcaccg agttcagaac 780
aactattatc acaaacgtct ggttcacagt tgctgcagca aatgatgagg ttttagtgta 840
ttaactacgt ttgaaactaa tgcttggtag agatcccaac tacttggtga ataaccaacc 900
ccagtgtcag ttcagggata caacaaataa aatgagattt agaggatgcc atatcagagg 960
gaacctggac tggacatctg tgtggagtgg agtgtgatga tttttagtga tacgtctttc 1020
ggaatcaatt tttttaggct gtataatatg aagttgcatt atctggaaca cgggcgtaat 1080
gttaattgta caaaatattt ggcaggtcat attagtatag gccttaagta ttgttgttgt 1140
ctaccatgaa ggacattttc caatttatga ttgataatct ttacttacaa tctcgagtca 1200
tatgaagttt gttgatcagg atcatagcac aattattaca aaaatgaaat agaagatatg 1260
atttttcacc cccccccac cccccccccc cccccccctc ccattcccat cccccctttt 1320
aaactgttac attacaactt gttaactgtt gattttccag atgagagaaa gggcctactt 1380
gtcttgtaca gaaaattcat ccatgacgat aaatgcagat gacctgaacc aaacgtgaca 1440
gtaggggttt cttctatgcc acaaagctcc aagccattca tggtgcgcat gtggtacaga 1500
gaggcttgat ggagcctctt caccttggtc cttagctatc taaaaattgg cttcttatgc 1560
tgatatatct cttcccatgt gcatttggtc cactccactt tcttcgtcga atatccttgg 1620
gttaatcctg aatggtaagc acaacattct tgctaattaa tccctctttt tatcctactt 1680
gccaactgta caagatgagc agaagaagaa ttgcccaatc atgaggtcat taactgcaaa 1740
aaagagaatt tatttctttc tttgagaatc tgatcttctt gagagttcat tgacagccac 1800
atgcatcaca aaatgaaatg ctgtgtggcc ctcattcatt cattcatcaa tcttcctatc 1860
ctgccatttg agtgaatgtt actccaactt gcaggaagct aaattagtac tttttttatat 1920 aaaccctatg aaactcatca agaaaccaca ccatcccaaa aaggaaacga gtgaacaact 1980
agacaactca ccccgaaaaa 2000

<210> SEQ ID NO 80
<211> LENGTH: 2000
<212> TYPE: DNA
<213> ORGANISM: Cucumis melo

<400> SEQUENCE: 80
cagcgatctt cgtagaaact aattcaatgc tagctcatta tttgactttt ctcaggcaag 60
gctccgcgag gaagagaaaa ggtccaattt caggaaccaa gggcatggac aggttccggt 120
cagaagaagc tttttacgta aaccctttgc cagattgttt atgtcaagga gaattaccaa 180
atggaagtac gacttccatt ttcagatagt tcagtagaac atcaaagata aaatgctctt 240
agagagctca atgtatatgc aggcgaccac tcaacgtgtc accagctttg tacatccaat 300
aagccagcta cgatggaacg acggagtgtt tataacctga gttttggtag ttggcggagg 360
cggtgatggt ggtatagaag gaaggtcgag ggatggcaaa ccctttacgc caagtagtgg 420
aagggagtag ttggagatga acacattttg agaagtttcc aagatcactc catttggggg 480
agaggggatg ttggttattt agcacaattg ttttcatgtt ttagtaattt tatccaataa 540
tgagcgaggc attgaagcaa ttaaatttat ttttaatgat tttttcaccc ttccataggc 600
tttttctttt ttcttttcct tttagtttgc aaactttagc tccttttatc ggctgtcgaa 660 ctcattttttg aagttattga atgaaacaca gtttgggctg tgtcagatgg gtggtgaaat 720
tttatacatt ataattacta cataaaatga aatcatattg taattttcta tctatgccac 780
aatttttttt tattgcatca tgaggattaa attgtacgag tccaaatttg tacagtcatg 840
tttttaaagc tttcgagcat tgttactaat gcatggaaag gatcgattat caagtatcct 900
cccaacttca tgaaagttat tatttgtctt ctaaatttgt tttagaaaat gtttaattaa 960
ttatttgaga agaaagttta actaaatcct attggtttcc tctaaggttg tcatacttat 1020
ccaataacaa ttacgtttaa aatcaaaatt attctaatgg tataagacta atgttttaaa 1080
agcataaaat tgatgaggaa ggattggaag taatactatt tattttgaag gtaaacattc 1140
ttgaatgtct gtcctaaaat cactaatgtt ttcttagttt gagactttga gtcgttgaac 1200
ctctccatct ttataaaata taatacgagt ccttcacaat aacttaaaat atatactaaa 1260
tcctaattaa tgaaaaataa ataaataaaa ggtacaaaat cattaaagcc taaaaatcta 1320
ttactccttt aaaacttttc aagggtccct acaaccaatg agaaactacc acgtcatttt 1380
cacaatccgt tcagtgttta gaaaagtcaa atcgcaccgt ccatttatcc actcgtacca 1440
agtacggtag gaatctatct accgtccgat taagcacaaa gaagcacagt aaatgtcaat 1500
cgtgtccatc cgccgccata ccgcacatcc ttcgtccgac cggaaggccc tatataaagt 1560
cctttggttt tccgaatttc tacttcattc gcttttgaaa gatttcccaa tctcttcgtc 1620
ggccaaaatt ctctctcgct tctcaaccct tcttcggctt tttcatccag gtttgtttct 1680
cttctctttt ttcttccttt gttgttcttg gaatatgttt aatttcattt gtttttccat 1740
tcaatttcat gctagatttt acgattaggt tgattttctg ttcgtagatt gtaattgatg 1800
gttagggtta gctttttctc ccattccttc tggaatctgt ttcttgacct tcgaacttcg 1860
ttgataaatc tttagaaaca tttacataac caaacaataa ttgaacaact cgtgttgtta 1920
tgcctatata atagcggtta ggaaactgga aacgccctta taattgaaat cgccttagaa 1980
atttgttttg attcatacag 2000

<210> SEQ ID NO 81
<211> LENGTH: 2000
<212> TYPE: DNA
<213> ORGANISM: Cucumis melo

<400> SEQUENCE: 81
tgtaatgact aaacatacta tagcctattt ggaccgggtc gaaaatccaa attaaccaat 60
ctcccctcag cctcacacca aggataaatc atgtcaacct tctccatttg acatgctagc 120
tggacaaaga gaaatactaa ctcaaattcc atataaatat atctttacga ctccttatca 180
ggtaatttag actcaacaat tagtaataaa tttagtataa tgaatgatag tttccataga 240
tcaattatat catttattga tttgctagat ctagagtgaa cttattgact aatataccaa 300
atataaaata tatcaatgaa cttacccacc aaacataaaa atgtaatatt tatatctaca 360
tgaattttac aataaaaagt gtatcatata aaatacttat atacataaac cctattatat 420
atatatatat ataaaaggaa ggtaagatgg aaaaaattgg aagagaataa tttgacctaa 480
aaaaatcgaa agagaaaaga gtatttaata tataaataaa aagaaaaaga gagaaagaaa 540
aaaatcttgt tcgtcgactc ctcaaaaacc ccagcgtgta gcggttgtga gagaaggaga 600
gctcgtttcc atcacgataa aaccttatct ttctccattc ttctatcttc tcttccggag 660
ctctctccat ttctcagccg ctccccacaa tttcctctaa acacacacat acacgactat 720
ttttccattc aaattccttc acttcgtttt ccattttcct tttctttacc ccacccactc 780
acccacctct cgtcgatgga ctccatggac ttggcccaac aaccgtcgca acagaattca 840
gtctcctcag gttcttcttc cacttcctcc tcctctttta cgtcttctac cgttgattcc 900
catgtcgata ctccctctct cgatgaacct gagatggggg ttgctgaaat taaaactagt 960
gtagttgccg atgggggtgg tagtgatggt gctggttccg aaactgaagg gtttttgagt 1020
ggggaggagg aatttgagtc tgcttcagat agaccaattg tgggttatcc agaggaagag 1080
tccatcggga agtccgccca aggggctgat actggtactt cttttgtggg ttattctcaa 1140
ctttctgctc cggttagtgt taggccaatt gcgaaggttt ctgttgatag tgacgttgag 1200
gaggaggatg aggaggagga ggaggaggag gatgaccttc aggtggatga gaacttgagg 1260
ggaaaggagg aaattgagga taaagtgggt ggagaagatg tttttgttga gagtaagaag 1320
gggaaggaag ttgaggttcc agtggaaaag gaggagacta ttgttgtatc tgatggaaac 1380
aagaatttgg atgatgtggt gaatgatgat gatgatgcca gtcaagtgca ggaaagaaca 1440
attgagttgt cggggaactc aaaagagggc aatgtgcctg aaagcttagt agctgaagat 1500

-continued

```
gttggctctg tgcccgagga atctgttgat ggtgggaagc aggtgtcaga aggggatgaa   1560

ttgaatgatg tgacagttaa acagtcacaa aatgaggctt cagatggaaa aaagaagcag   1620

agttggataa agaaactctg gcgtctggga agcaggctgg taaagggatt gacttgagtg   1680

agaaggtggt tgctgaggat gtagagcaat tgaaagaaca ggaaacacct ggttcttctt   1740

ctgacgagaa agctgttttg ggagaccaag caagctctaa gcttgtgaaa ctagcagatg   1800

aaaaacaaga agaggagacc tctgcggctg agaagcaggt agatgtggag gtcaaattga   1860

atgacacggt ggctgctgct gaagatggag agcagttaaa aaatttagaa actgattctc   1920

ctgttgacga caaaattgtt ctagctgatg acgaaaactc taaggtttta gaaccagcag   1980

atggaggaca agaagcagaa                                               2000
```

<210> SEQ ID NO 82
<211> LENGTH: 1072
<212> TYPE: DNA
<213> ORGANISM: Cucumis melo

<400> SEQUENCE: 82

```
tttaatatgg tatcagagca aatggtccag agaggtcttg tgttcaagcc cctgcattta     60

cgtttccttc ccaattaaaa ttgtttccac ttgttgggct tttcaaatat ttcaagccca    120

caagtgaggg ggagtgttag tgtatataat taaatttgcc ttcttcaacc actagctgaa    180

gtttgtgggt gaattggtgg tttaatagta actatatcat gcaattagct tttttgagtt    240

caacaatatc tgtggtggag atttgaaatc gagattatga tgccttaacc atgtgaacta    300

tgcttaggtt gacaactata tcatgcaact atcgaaaaca tcatctctaa tttataggtc    360

ttttttaaca tagttgaagt ttcaatattc tatatgaaca cagctggcta tttaaattac    420

catattgaaa agcagcactt gaaatgcttc taaaaattaa tgccaattag aagtgtttat    480

gattctaatt ggttaacatt actgaacaca gattagttat agttattgaa agaataaaaa    540

ttgtaaaatg ccgaactaat accaaatgga tgggtagtct gcaaatttta ccaaatggta    600

ctacagctgg tgatgaactt agaaggggta aaggtatagt gtaactgtct aagttaatgc    660

cataaaggta tagtgtaact gtctaagtta atgccattag cagatcaagt ccgttgtatt    720

atgtactgaa cacatttttt aatcgtatag ttctaaatcc tataatctgt cgaccaagtt    780

ttaggtttgt taggctgaaa gttcatgcaa atctaggtgc ttttttgtac taattgtttg    840

agattcagaa attgtatctc aatgttctcc atgattatgt gcgtgtattt gcaaacagct    900

ctttggtttt ttcttcttct tctgacaagg atagtcaaat caattacagg acataatttc    960

aagatttaag gagagaaagc aagggaaaga ttcacgggag tggactgagt ttccaagcag   1020

agttgcagtg caattaaatg atactcatcc aacccttgca attcctgaac tg           1072
```

<210> SEQ ID NO 83
<211> LENGTH: 1730
<212> TYPE: DNA
<213> ORGANISM: Cucumis melo

<400> SEQUENCE: 83

```
gttcaactcc acaagtcaaa tttttttgga aatctcgtgt gaacacttgt gaaacacttt     60

atttttatat taaaagaaac aagaagattt aagatgagaa tcccgtattt gtttggttga    120

aggacaatga aattggtaaa tatatcccat cgaaaaataa tcaaatctag acacaaaaat    180

ttaaagttaa aacttactta ataatcagct ggagcatagt ttaatttgaa tgaaaataaa    240

aatcctaaac tagagaagtt tcttatggta ttgaaaggcc agtttagaaa gcccaatagc    300
```

gtgggttttt cttggaccca tgtgtatgtc tcactcatga aattaaatta attggcctcc 360
acattcacct ctctcctccc aattcccata actcaatttt agacctctta aatgaaacat 420
atcatatttt cataaacttc ttttttacgt tacttatgag attaaaagac tttaaataaa 480
gtgtcaattt atattatagt agatgagatg gagtgtgtgt ctttgtgccc tccttggggc 540
ccaaggacta agtaaggatg aaagggcaaa gaaatacaaa atagaagaga gtagaaagaa 600
aatgaaatgg aatatatagt aagggttatc gtttatggtt attatgaggg aagggctgaa 660
attgataatg aacctatcct tatcttccct tcttcacctc tcattttgct tgaaattaca 720
aatgactttt ttttcaatta ttttgtgtgt acatccaaat gtggtatgca catatgggcc 780
tcccattaac ttgtgatcca aattaattct tttgcaacct aagttgaaat taaacacttt 840
tacctctctt tttttcccta acaattttac tttcattgtt agatggttga ttatcttgac 900
atgtaacaaa aagttctctc atgtcaagat agaaaaatcg aatatttgat tttgagattg 960
ataatattat aatatcagtt gagctatact cattttaact atcagtaaag cttcattaac 1020
atatttttta tttagtaaac taagattaat ataaatagaa tcttactttc attatatact 1080
ttgacgagac ttaaaaccta tttagcgcat gatttttaaa agttggtagg attttaaccc 1140
ttgaaaaatt ggtcattcgg gaatcaaaac attagtttcc ctttgagcat ttattttttaa 1200
agcacttcaa aagctaaatt agtagcatta aaaaaaaaag tcaaatagta tatatatata 1260
ccaaaacttt gtttttcaaa actatatttt aaaccaacat tctttttttt ttattattta 1320
ttactaatta agtgcagatt atagtggttc tcttttgtag ttggatcaaa tatttcattc 1380
tttttgaca ataacaaaag ttaaaatact cattaaatgc taaaaacttc catactaaca 1440
ttattgaacc attaaatata tgagcaacga aagtataggt aagaatttat attgttgttg 1500
tttagtttgg aaatagaaaa tggaccaatg ggtgagcttg gtttaagtta gggttcttgt 1560
ggttggatga taatgaaata aaatggccaa aattttaatg gagaagaaga tccctttaag 1620
ttcaaccact aatggagtct tttaggatca attcacaacc cctttctcct tctgccacgt 1680
gtcatctcag ctaatctcaa ctgtgtggtt gttgagaaat tttgaaactc 1730

<210> SEQ ID NO 84
<211> LENGTH: 2000
<212> TYPE: DNA
<213> ORGANISM: Cucumis melo

<400> SEQUENCE: 84
aactagacta gcgagtgcac aaccaaatta caaaatcctt aacagagaca accatctatc 60
tcctttaaag caacaataac atcaaccgaa ttagaatcca caatcagtaa agacgatgcc 120
gacaccaatg accaaaaccg atcaaatata gcttattacg gaccattact tcaacagtta 180
catcaacaaa aaaaaaaaat taaacattgc taataaaatc tgaaaatgag gaaaaagaga 240
ttaaaagttt tgaagataga aagaataaat ctgaaatgtt ctaatttgat atataagaaa 300
tatgaggtaa tatgacgaaa gcattttgat agttttcacc aactcccttt gtgaaaggat 360
acatccaacc aattttacaa tttctgttca aattttgtcc acctaccctt ctcttctgcc 420
ccccaaggct gctttctttc ttttattatt tgctaaatta ccaaaaacta ttttcgaatt 480
aaaccatcta tttcaattat atacgtcatt cgaattttaa cttaattaac attagtatat 540
gtttcggatc aaggatagtg gtataaatca tcctaatttc aatttgtatt tagaaaagtt 600
caattatact taaaacttct aaaaatttta tattttaaat ttggatataa attaaattta 660

-continued agatttatgg aaggtaaata attagagcaa aacaaacttc aaactatatg gaaaatagaa 720
aaggaatatt ttagccaaac aaaaacactt attatattta ttttgttttt tgtttttttt 780
aatttaacaa tttttttttt tattggttga atgtgtttct ccactggtga gtctccaact 840
ttgacctgca aagggtctat atagcgagtt tcacgagcac ctaaccaata tctgtgtaat 900
aattcccatt tttctttcat acccacttca tttgatcatc tttttcacaa ccccggatct 960
ctaattcttg ggaatttgcc tctttctcga tccatttcca ccgtaattga aaaatattca 1020
ggtttgattt cttctgggtt ttcattcaac tgtctaactt cattatgccc tttatgtgtt 1080
tgttgaaagc cccccaccca ccatcgttca atgcggtttc tttacctttt gttcggtttc 1140
aacgatgatt tagaagttat agatggatgc taattgtttc gttgttggtt tgatccactg 1200
atctgccttt gattggcata aaaggagatt ctagatcttg ttttgatgtt gtgatttatg 1260
gatattattg ttatagtcgt ggaagttttt cttgtcgttc tgcggtatat ggttgtttta 1320 tttttgagt ggtaaattga gcagattgtg aacttttggg ttttatggtg aaagcatgaa 1380
ttagtaaatg tagagctgct gaaacaaaat ggaggtttgc tagacctctt tgtgaattct 1440
taatggtcag cctccatctt aagaggctaa gtccaaaaat ttaaggcagt cttttgttat 1500
tgttacaaag gacaagaaat aacagaggag ttattttaat tgaatcaagt tggaaagaag 1560
tactacttca tgcttctttc aaaagcaggt caaagtgctt taaagtcttc ttatttattt 1620
attttttcct gaatcaattt aaactaatga tagaaagaag tgttttttaa tgggttatta 1680
taagtaacat caatttttaa ccattccaaa agttacatca aattcatcat agtgtgagtt 1740
tacgaatttt ggaagttgta attttaagtt aatacttctt ttaaggaaat gtacactttg 1800
catgttgtgt tcataagggg tatttctttg acaaacgcag caaccacccc ttaatgaaaa 1860
ctacaccacg gtggttggtt ttttcttgtt attttttac ttggaattta caataagttg 1920
ttatattcgg atatatggca aagcagatat ctgtttttat ccgaaacctc ataaatcttg 1980
aatgtgcagc aggtaaaaac 2000

<210> SEQ ID NO 85
<211> LENGTH: 1020
<212> TYPE: DNA
<213> ORGANISM: Cucumis melo

<400> SEQUENCE: 85
tcattgatga agaaggaaac tttaagccaa ttcgacaact tatccattca acaactttcc 60
accttcagac attcagattc aactataata taacataaat tgatagtcaa gtcttttttg 120
agacaaccat aaatcatctt agcttcgaga actgtcactt ccttaaattg gtgaatatat 180
cacattccat ccattcaaaa ctttgttttc gaacttttac tgtagttatg aatcaataaa 240
ttgggagaga tattgtttaa aaagagagag catatttgtt tctattattt actctctcct 300
aagagagggt taattagtct ataaatgatc tattcttctc gtccattgaa attttgttat 360
cctaaattta tgaatacttc tacccaaaat aaagactttt ttttttgaaa agtgtcaaaa 420
aaacataaag aaattgacaa aacattcatt tttagtggat ttttacggac gtaaatagtt 480
tgttttgttt cttttaataa tacaattttt ttactttaaa aaatattttt gttataaaac 540
caccgtattt ttattcaatt ttaataaata aataaatgaa agaatataaa aaagaggaag 600
gaaaaagaag ccaacgaacc aacggttgcc acgtatcaaa ggtctaaagt gcgcaaaacg 660
aggccttcgg aaaccaaaat gcgtggcttc aattggagca agtaaacatg gaaaccacgt 720
ccattgtaac gcttcctgat ctcttcttta caaccgttgg attcgagtac tttttctcaa 780
cgattaacga ctgagtggac ctccacttgc ttctgttcca cgcgcgtggg attgacgtgt 840
ggtccacgca actcttctcg ataggatcat tcgagaacat cctttactta aaccgcctct 900
ctctgcctca atttctcgtc acttccttct ccttctttac cctttccact gcggctgatt 960
cttcttcgcc ttttattctc tcgtacgccg ccatattctt cacttctttt tccggcgaca 1020

<210> SEQ ID NO 86
<211> LENGTH: 2000
<212> TYPE: DNA
<213> ORGANISM: Cucumis melo
<400> SEQUENCE: 86
aaatcatctt ctcccatttg catgtgttaa cgcctaatgt agtacattta ccatgattcc 60
tagaataaga ccgattttac caacgagaag ttgctttcaa cttgctacaa tatacataac 120
atttctttgg tacgttattg atgagaagag gtataaagca tttcacagta ttctctcagc 180
aactcattag tttaaaaaaa aattaaagga atatttgaat atcgggggat gaattaagta 240
tagcctcaca atttgccagc tccttctcct tagcggctgc caacctccga agctttgcag 300
cctgtgcaaa tgtagacggt ctacaagaac ataaaagcaa atgaatacga tccccatgac 360
agccataaca gttgcaaaca atcatataga atgaatgatt tgagcctttt ttttttgtaa 420
gatgatttga gccgaattaa cagtgtctaa tgctgaatcg agctggaaaa tactacttac 480
tgagataagg tgctagcctc cctcagaagt tgctttattg atttgcgcaa ctccaattcc 540
acctggctgt tggaacctcc ctgaaaagta cacgcatgat ggaaacatga ttgtttcaaa 600
acaaacaagt tgacaagatt gaacggataa caattataac atagcaaatt cccagacatt 660
aaaactgaaa atgtcaatag atctccacat taaatgcatc acgtccctaa actaatcaaa 720
tcaaatgtct tcaatccaat atcgtaaact taacgaagca cagttaggca tattgcattc 780
tcaagtctgt caacgaaata ctgaaacgcg ctacagccca aacctcaaaa ttttcaacta 840
taaataacaa gctttgaatt gaaaaacaaa cggaatgata gaaaatacaa acacgaaaaa 900
attccgacgg gaaaaagaaa atcaaacgaa aaggcgaacc ttcttcaggt gctccagcca 960
tctagcgaga aactgaaaac cgataacgat aaagaaaata aatggagcgg caatggagct 1020
tccatgctct acgattcctt ccgcttccat ttccatttcc agaggacttt tctgccacaa 1080
cggtgaatta atcaaacaaa gaaactccgt tcatcgtcgc aattcgacgg aggttattct 1140
ggaagaagtt gagatcgtaa ttgggctacg aatatcatca aaggggcttc aataaaaggt 1200
ctctcaaaac ccaaggccca aaaaaacgaa aagcccagcc caattagtgg agaatcaaaa 1260
cgctgcgttg tagatacaaa tatcttagga aagggaacca agttacgaaa atacccctga 1320
gtagtgagat caatgattac ctcaacgacg cgttaatcgt tttatcacgt ttattgtgat 1380
aagttccgca ctaaggaagg gacgagttgt aggaagggag gggtaaactg gtgatttcgc 1440
attcaaacaa cgggctttaa ctcacgtgtc cggatctgtt gagagggaac aattcacagc 1500
gaggaaattg caaataacac acaaaggaaa cacaaaagag cggaaagcaa atgtgaagag 1560
acgaagagta gccaatgaga aaaaaggacg aggatcgatg acatggcaaa agatttttga 1620
aatcccgcct aaacccggag tttcaattga tatcgcgatt tatctctccc tctctttaac 1680
gaaaccgact cccttcatat ccctctctct cgctccctct tcacttcaaa gggcttttcc 1740
ttctttccac ataaacacac gcactcgaag ccaatctcaa aaccgcatca cacgaaccaa 1800
actaagccta acccaatttt ttctcctcat atttcactct cacactcttt ccttatcttc 1860
ttcttccccc aaaccctaga gttttacagg taaactccca atctctccgc cgctccctcg 1920
ctcgattctc cttcgtttct ccgccttttt tcttataatc attacctgtt ttctccttcc 1980
ctctatctgc aggattcatc 2000

<210> SEQ ID NO 87
<211> LENGTH: 2000
<212> TYPE: DNA
<213> ORGANISM: Cucumis melo

<400> SEQUENCE: 87
gtgtagagtg agtgacggtg gccgacagtt cgtaacattt agttgttagt gagagacggt 60
gagacgtttg gtaacaaact ttgtttttag ttcaatcatt gctttgtttt ctctttcttt 120
tccttaatgt ctaatgtttt catcttcctt tctttatttc ttacccaatt tccgaatcaa 180
attttaattt ctaaaaaagt atttaaaaaa aaaaaaaaaa ttagtcgctt tattcgagaa 240
tttcataatc aacctaattt tcaaaattaa tcatcaatct ggaaactttt ttattttttt 300
tctcctttgg attatcctgt atgaaagtca acatactttg cactccttga gaatattttt 360
agtggtgttt tttttttctc ttaataaata aaaaagttta catctataat aatcaagatt 420
ccttggcagg tgtcactgtc aaaataattc ctatttgttg aagttgaaaa taatttaact 480
ataaacttta tttgaacgtc aaaaaaagaa aaaaaaaaga tatatgaatt cacccattcc 540
ataatttaac tatataactt tatttgaatg ttgaaaaaga aaaaaatgaa gacaaagcaa 600
attcacctgt tgccattacg acaaaatttc aaatgcgttt tattttgttt ttatgtccac 660
aagattctct atttgtattc tgcgaaatta aagtcacggg cttcgcacgt gtgtgattaa 720
tagtatttgt aaaagggcat gtagtcgaac aggatgggaa ttaaaggaga ttatgaatgg 780
gttgggtcgg gaaggcccat ttctataatg aattgatggg ccgtcaagga catttgtcta 840
cataaagggc atggaccatg aagttaagcc cacttcctaa acgagttcct tagtgtgtct 900
acattcatat ttaaatcatc tttaattcag aattttcacc atcatcaaat aatgtcttat 960
aaacctccca ttttatagtt taattatgga ttctaataaa aaatctctaa cttcaaagtg 1020
gataattttt tttttttttt aagttgaacc atgttcattc atttaattac atggaataaa 1080
aataacgtaa tttaggttaa aagttgagag gataagatga agttgaaaaa ttacaacaag 1140
ttaagaaggg aatatgaaga agaagaattc aaaattgaga acataataaa ggaattaggt 1200
ccaaagctgt aaagactagg agaaacgagt agagaaggga aggactcgtt tttcaaagaa 1260
aagaaaagtg tggaaaagga aaaaggttca ttaggggtgg tgaggaaatg gatggatatg 1320
gaatgatgat gatgagaaag aacagcacgg gaagtttccg agtagttgcc ttttgcatat 1380
accaacaagt tatctaataa aatgttttga ttaattacat taatttattc aattgattta 1440
tcggaaattt ccatactctt cacgtgatat gcacgtggtc ttcccatgtt ctaatatttt 1500
ttgtttttga aaatttgaat tcctactctg ttttgttatt ctgctcattt aactactcaa 1560
atattttagt ttgtagatat aactttgtaa atttttatta taacattttg taaatatttt 1620
aaattgtgcc catagattat gagtagataa atttacgaat taaaaaaagt ttaattctca 1680
cttcaattta attttttttt attattatcc aaatctattt gtcgcagtgg ggaaaacggg 1740
gacgtacggc cgattggagt ccaattagtg gatgtgaaac gtggacggta gagatgcaat 1800
atgaagctgg acatcaactt tgcgaaggaa ttgttccttc tttccctctg acgcttgtcc 1860
cgttattgct cgttttaaag caattcgagc tccgcgttgt ctcttccctc acgttttcct 1920
ttcaatccca ctgctcctcc tttcaccaat aaaacaaaaa cgcctcaaag aagaagaagc 1980
aacgaccaga aacctcaaaa 2000

<210> SEQ ID NO 88
<211> LENGTH: 2000
<212> TYPE: DNA
<213> ORGANISM: Cucumis melo

<400> SEQUENCE: 88
gttcgagcat gtgaatgtct tctgttgttt gatgttagaa ggaaagagat gggttaggga 60
gttcctgttg atgtctagta ggttcttttt tttttctctt gtgcaatgta acatagtaac 120
ttcgctgcaa agcagctctt atccttagaa tacgaaaatc ttctgttttt tgttatgttt 180
ctaactttat cccttcttga ttttaacttt tgagttaaat tccatctctc tgactttgct 240
ttgtggtatt ctgtttctgt tgtatgataa ttcttatgga actcctatgc tctctctcat 300
tgccttcttt ttcggctgtt acttaattac tttcttcact tgaaatttat agcttctctc 360
acaaatttga gctcattcaa gtatcaaaat tacacccatc tcataccata tttctatctc 420
tgaaggagga tttttcccct tttaaggagg gtagattgac aaagctgata gggtgagaca 480
atttaataac tcaggtcaga tgaattatac attgaagaac tctcatccag ggccagtgct 540
ttgtttataa caagatgatt aatgtgttgc tatcaaaact ttgctggttc actaaaaaaa 600
actcttggtc cttgaaagta ggcttttact agttttagct ttaatgcaca tctgtatgtc 660
aaccacgaac tccatttttc ttacttgatg catgtgcaac tttagcagct ttctaagttc 720
atatcaaagc aaatgtacct ttattcctat tgtaattcct tttctgcttt cctcttttat 780
gaattgtcaa aaatatggac aggaaagtaa gctgagcacc aacaggttgt accccttttt 840
catgtcttga aaatgaacta ccaggacaca aatcagatga tgattgttgg gagaaggaat 900
gtaagattat tcgttctgtt tgatataaga gatgtaagtt cacatgtctt acaacttttt 960
gaaatttgtg tgtcgcttat gtgcagattc ctgtatgtca ttagtggcat ttgtaagcta 1020
caattgttga atttttgtat tattatctta aaaggaaatg acaaaaggta taatcaaatc 1080
aagctgaacc taaaagaagg tacaggtttt tagtattatg catgaagaag gtttttcatg 1140
tctcttctgc catttggatt ttgtctgtga caagggacta agacactaca catgatgctg 1200
gaaactgcaa gagtgttttt accctaataa gattaaaacg tgaaaagcaa ttagattttc 1260
gtgcatatct atctttttgt gcattccacc aaactgttcg atcataactt gtcaagatct 1320
tgctttttcc ttttttttat aaatatttta atatccttct aatgtgaatg gtgaaaagag 1380
atgcacaaag ataagtgata ctatagatgt atctaagtat taccccttata cctttgccac 1440 gtaagattag atacgagaag agaaaaaaat ctatgagtta gtaatagggc aacaataaac 1500
cacagaaaaa ccaattaata cctttcctca ttgtctaata atatctaaaa gaaacttctt 1560
ttcatgttaa tgaaccaaac tatgttgtgc tatagcatga gcacattatt tctacccttt 1620
agacaagtga tgagaatgga caatatttcg actgagttca ccagaatgta accaacggtt 1680
ttgcatttgt aatatgaatt tgaaagtttg agattcctta tacgaggacc ttttttcatg 1740
tatctaacaa cacgagaacc accaaaatga gaagggagtt ggtccaagcc aaaagaattt 1800
tgacctccat gaaaatccag atagtggggc atccttatct aaacaatcag aacctgaagt 1860
ccgacgtagc cttatccaca tttcaacttc aaaaacactc cctctaagat cctttcgaac 1920
caccaaaatc taagaaaatt tctcttcctc atcctcctcc gacacaaaat ctagcttcaa 1980
tttcattcct ctgtaaaaac 2000

<210> SEQ ID NO 89
<211> LENGTH: 2000
<212> TYPE: DNA
<213> ORGANISM: Cucumis melo

<400> SEQUENCE: 89
attcgtcttc gcattatcag taaatttatc attttaagag tttgttcttt tttaaaaaaa 60
attaatcatt tcgataaagt tggagaattc aaaaatttct ccaaataatt tataaaaact 120
ttcggttata tatcgaaaaa attaacatgg tattaaaacg atcataactc aattaacata 180
aacactccct ctcaacttta ataccaaatt tctttattaa cgcaaaattt aaaatttgtt 240
tttaaaattt tcacataaca taatagaaat acttttcttt atggcaaaaa tacaataatc 300
aaaattgatt gatggtgaca ggacaccaca caatattttt aaattttgaa tatacgaact 360
atataataag atatttatga gattcccatc ctaaagattc ctagagattt ccttgtgtac 420
aatattacac aagtatcttg gaagtccaaa gtcctgagaa aaaagctatg tataaagtaa 480
tgtgtttgtc gtaggaaatt tacttcattc gtgtcattag ctttttattg aaaaaaaaaa 540
ttaggtatat cttagtgaat ctcacttaat cgttgtcgat agttattctt ttaatatcat 600
tatatactaa aatataacaa tattgaaaag ctaaaactgt atataaaaaa aatgttacct 660
ctaaactttt atcgtttatt taaaagataa atatattctt tcaaaactta caatcaacat 720
cctacgacta tcattatagg tacaaatctt ttcatgttta cacaaaaatt agatttttaa 780
atggtgtaat gatgatatat aacgaaattt tgaatgatta ctatttgagg ttaccattgt 840
aattggtcgt gttgtttgaa atttaatttt attagaaaat ttgtcaaaag tagcaaaaat 900
gaataaacta tttaaacttt aggataaaat caagtgttat gagtttttgt ctagtttata 960
tatttttatt tttattgaaa accctttttcc tatcttttca ttacttcaaa atagttttaa 1020
aatgtctatt aaggctaaag ttagtataaa taaaatttcg gaaatttttt ttcgaaaaaa 1080
attgataaat tatttatatt ttatattaaa gtcaaaattt attacgcgta gatgtttatc 1140
aaattttctt tctttttgtt gataattttc caaaatttgg ataatttttt aaaatagtaa 1200
aattattaaa aaatgaaaac aaactattta taccttaagc aagaaatact aaaaaggcaa 1260
aaattcattt acttcatgaa gcgtaaaaat taaatatttt accacttttt gttatttttt 1320
accatctcta tcaattattt gtaaaaagaa aactacaaaa ttagatgttt tttcttttttt 1380 aaggtttaat caatattaaa atttcttaaa ttggcagaca agttggtgtt ggtaattacg 1440
aataaatccc gaattgacta aaaataaatt cttctccaag taaaatagac acgtggatga 1500
agaaataagt gaatcaaagg catccacagt tcaataaatg gaaaaaacta ctttctgctg 1560
actcattcat aagttttcat aaaatttcat aagaaaggcc aaagggctta tgaaagtgaa 1620
tgtcatagca gtaaatgaag cacagcgcca ttgaaagaca actcaaattg catgcaaacc 1680
cacataatta ttcaacaaac ccacatcaaa tttcccataa agatcaattc tttagggggt 1740
tcaattaccc aaaagtgagg tagttgaaaa ccattaaaca acaagaaatc aacaattttg 1800
taatttgttt gtacagaagt aagagataaa atcatcgtta accattcctt tatttcgtaa 1860
tacaacccat caaccatctc tctctctctc tctctctctc tctcggcctt tatctttctc 1920
ttcctcaatt aatttaagta ctacccaagt gagctaaaag caagttcagt ggacagtgtt 1980
gtaagaacca ctacagaaaa 2000

<210> SEQ ID NO 90
<211> LENGTH: 2000

<212> TYPE: DNA
<213> ORGANISM: Cucumis melo

<400> SEQUENCE: 90
aatcatcagg tctccttcca atgaaaccga cgacaacgac agtgtcggaa aagcgaggaa 60
gggatggcga aggcgaggaa ggagaaaacg aagtagaggg ttccggtaaa gcagaatgag 120
gagggagagg agttggggaa ggtgaagagg aagaggaagt gggagttgat aatggtggcg 180
gccggataag tactcggaca gaggaggaat tgggtacgtc catggatgag agaaaatttt 240
gagctttcag atgcaactga aaactgcttc actgctttca cttccgatga ccgccgaggg 300
gaaacttatt ttttccttgc ccttttttgcc tcctcaatat tttcctttta ccatttcctt 360
tccaaattta tttttctatg ttttgatttt atgttttgtt atatttttga tttactttta 420
cgttattttt aaatattttt gatttaattt tgttatattt gaaaacaaga tattcattat 480
atactgtaaa tcttacttta ttattgttta aatgtcgttt tggtaattca aaattaagtt 540
gaataaacac aatattttaa atattatttt agtaaaataa tttttaggtt ggagaatggc 600
aaaagaaaca aaggattgaa agactgaacc catatttgag gatagaagtc aaagccaatg 660
tcaataagtg aaactcactt ggaccaaaat accaatttta gttttatatt tttaattgtt 720
caatcttagt ttccatactt tcaatgcata ttaaacttat agttcattat tctttttcaa 780
taaatcttaa cattttacta caaattttta aaatgtttca catactttat ttttttacat 840
gaaaatgatt gttattgttt aatccatttc aataaaatta aaatttgaaa agctaaaaat 900
tcaagaatta tcgatagaca attacaattt tgtcccatta aaattatcaa attgaagtgg 960
ctacacaatg gaatggtaaa tcctttattc ttgtattggt gtgatttgga ttgagatatg 1020
aaacattata atctaaagga acatgtttaa accgaacatc acgtattttg tctttcaaaa 1080
tttcgtaagt ttgtaggttg tttttttttt gtcattttat atagttacaa ttatttaagt 1140
cagatcggat aaattttgtt atacaccaat aggaaactaa aaattccaca aggagtatga 1200
atgacctcct acgggagcat taatgaaaat gaccaagggt taaaaaatgg taagaaaaat 1260
gttcttcact aatgacaatt cctcgtgaaa gtactaacat gttcttaaaa tgcttgcaag 1320
catatatgtc accaagaatt ctcattcatt cctctggctt ctttctctca tttctcatca 1380
acattaatat gacacacttt ttccttcttc tttttgtatg tgtttataat cttactcatt 1440
ccttattctc attgtcactc aacgattcca acaagcaata tgggaacaaa cgaaggaaga 1500
agagaaaaat acactaagaa gaagagatga acaaagttgc attagaacaa ggcgtagaat 1560
atcaaagaat tcaaaataaa aaggaaaaaa agattactag acgagagaga acgagacttg 1620
aaaagaatta gaataatttc ggtaatttta cattggacga cgaaagcaaa tgacaaaaac 1680
aatttttttt tcaaaaacat agctcaaatt tcatttagat ctttcatccc aaatggcata 1740
atttctctaa tttcacatac accacaaata taatgatgac tgattaaacg aagtaaatta 1800
caataggact aaatatataa ttaaacttct taaattgagt ttgagataaa acctttgaag 1860
ccacgagggg tcgggtcggg ggcgaaagag acatgccata taagcagttg gttgctgtaa 1920
agtggcacac gcatatctac tggaagcctc catttccaat ctcccattat cccattatca 1980
tcggcagttc cccatagcta 2000

<210> SEQ ID NO 91
<211> LENGTH: 2000
<212> TYPE: DNA
<213> ORGANISM: Cucumis melo

<400> SEQUENCE: 91

```
ctttcctgac ccaataagag atcaaatcac tgtctcctgt agcctttccc ttgccgctct     60
attattgaca tttgggccta ccttcccccc cccccttct cccgattcat cacccttggg    120
ccttggccca ttaaaacatt acccagctcc ttactacttt ttaataacta tcacgtctat    180
tccttcgcaa gtgggtggaa gcgaatattt ataccaatta tcttttggtt gatcatgtag    240
ccaaaatttg gctcaccaaa ctcgtacaaa gacatttact tgttttccac tgtagatttt    300
aattttggaa gaagagatca gttgccaata gattgaatta atgcatttat gtacactttc    360
atacttaact tttggcaaag agttgaaagc aaggttttaa agaataaaat gaacttactt    420
tttttacaaa tctcatgatt tacgctagct caaacttagg atttctttcg tttgaaaaat    480
tggaccaaat atatatacaa tagattgaat aggagtcttt taaaatactg gcctcaaaga    540
aatagacaag ttagctaggt cgggataatt gcctcactca ttcttcacct cagagatgcc    600
tctcctccta ggcatgtttt ctaccctcat aatttaattc actcattttt gcttccttat    660
tgattagtaa aagtaccgat ttgccttctt ttctatgttg acaagttccc actagaaaac    720
aaattagatt atgagtttat aggaaagaat taaacacaaa tacataagtc aaattgtgaa    780
gtatcaagat aggctgttag gacagaaagt tcaaatttgg aaaacaaata tatatgttat    840
tgagttgtca tcttcttaga taatgataaa atgtgaactt ttgacacata taataaatag    900
catgttcttg ataaatagtt ttccattaaa acaataagct attattggat gatagaaact    960
cccctgggac tacaagaaaa agctaaaata gaatcagcat taaaacttcc tttaatagga   1020
tcgttatccc aaataacaac tccatctcaa aacacttcta aagaagtagt taaagaataa   1080
caatgtatat tagttatgga tgttgatgat agagaacttg gattttagct aaatttagaa   1140
tcttaaaaag ggaaggaaga aaaaaggaac aaaataaaaa gataacagta tgattactcc   1200
aacttgtgat gaacagtacc actcatggta tgtcaaacat atacatagaa tgagaacaat   1260
ttagatcaat taatttactc atttatcctt cttgctacag attgttgaga aaatagaaaa   1320
acaaattaaa gtaggaaaaa aaagaataaa tggggaatta tggaaccaaa atatcaagaa   1380
aaaggagggg caataaatta aagaggaata gtgtaggcct tctcacagtg gaagtattag   1440
cgtttaagtc agtaccttac ctttatttgt tttcatacta agttctttct ctttcatgtt   1500
aataaatttt caatcgatcc atctattcaa aatggtgtgt tttattagga agaaaggtaa   1560
tttcatacaa gaaggctaaa aaatagttga cagctgtggg atttgaaccc acgccctttc   1620
ggaccagagc ctaaatctgg cgccttagac cactcggcca aactgtcgga attgtgagtt   1680
gaataactaa gatgatcgga aatgtgacga aataaattgg gctaaagaaa agaaaagccc   1740
aaacaatgaa gaacaattcg gcccacttaa tttcacgcgc atggcacgtg taaagaaatc   1800
ccaatctgtt ctactaggtg gtggtggtgg cgaggcgaag caaagcaaag caagatcagc   1860
cttatcaaat tgtgtggtga agaatgaaga ttgtataatg tagatagaaa aagatccccc   1920
cattcccatt cccattccct tttctgaatc cgccattgtt atctctctca gacctccata   1980
acctccattt ctacccagcc                                                2000
```

<210> SEQ ID NO 92
<211> LENGTH: 2000
<212> TYPE: DNA
<213> ORGANISM: Cucumis melo

<400> SEQUENCE: 92

```
cttctaaaca tcctcaatgt tcgattttga tcaaggtcgt ttgcttctaa acatcctcaa     60
```

-continued

```
tgttcgattt tgatcaagag gtcgtttctc tatagtaaac atctgttaca ccttccattt    120

ctgttattca atttttccaa ttttattgag cagtttattt atttccgtaa ctactttgca    180

tcggaggcga tcatcagttt ttaaggtaca aaactagatt atatataatt atgaagcaca    240

gcaaagtata aaattttgaa gatgaaattg attggacctt gtgaacagaa ctctaaagag    300

aaaatgcatc agatagtctg gatcgttaga atttgaaatt taaatttcta tcttccacta    360

aagatatctc tgttttgcaa actaatgttc ctcattctaa acagagaatg ccagtggtat    420

tttgttcgtt ttttgcgaat atgattaaat tacccatttt atttgcatat tttatttatt    480

ctcatatcag ctccaaaaga atatgatccc tttttcctcg ataagaaaaa atatttaata    540

ctttcaactt catgcattgt gagactgccc atttgttttg tttaaagtag caccaacttc    600

tcaattgtat aagtttgtga ttttttttct atctaaattg acttgaatta tttttagata    660

taattaaatt aattgctttt aagagcaagt taaattaagg tttcgtaagg atatggatta    720

aatttaatta agaattggct tcttgctcta aatacaaatt agagtgagat ttgaaatagg    780

aggaaaaaga gagtatggtt acaaaggata tgaaagatca aatttcaaac ctttgccaac    840

tgaggctttt cagaactctt aaaccatcac agttttttct ttgcccaaat gaaatcaaac    900

attaagaaac agtgataacg aaaacgaatt atccctatgc caaccgtgac agatgatagg    960

caagaaaccc acgattagtc tctcatccgg attgttccaa caaatgaaaa agcgttttct   1020

gagactacac aaacaacaaa cacagagtta gatagttcaa gcaaatgatt ctagcagatt   1080

agaggataag gtttcttatt aaatgtttga atacattcta accaaaaacc aaaaacccta   1140

tttgcaaatc agcttatgta aaccaaaaac atatttacta agaattcaga atttcgctgc   1200

ttgaaatttg aaggatacca tataaaacaa taatagattc cccaatcgt gttcagtagc    1260

tcaatatagg caccgtgcaa aaggttgttt gttgtaagat taatgaacaa acacccgtgt   1320

ctgattttaa tgccaattca aactctaatt caaaaaccct acaaagacct aattgcagat   1380

aatgggatta gaaattttaa aaaatgtcga ccgggcattg tatcttaaaa ctattaagtt   1440

tcaaggatct tcctccggta acaaaatatc ggctccatgc ggcagacgga tcgccattaa   1500

aacggcgcct gctgctgact cgatgataga gccaattcag aataaccaac ccatttcatc   1560

gaaattttta aagagagaga aaataaacga ttcaagatat caaacgcatt tcgcttctat   1620

tgaaggagaa gacaatgaaa atcaaaacaa atcggaaatt aaagttaaag aagaaggaga   1680

taatctcagg acggacggaa gataattcta aaggtgcgat tcggttgaaa tttatagagg   1740

atttgtgaag gaaccctaaa ttctgattgt gaattttatc ggaaagaccg gagaggaagc   1800

ccattgtgtg aggcccaaag taactgatct gggccttttt tagtttcagc ccaaacggaa   1860

gcgacacgtc gtttctatgt agagccaaga gcgtgccacg tcaacagacg acgtcggtta   1920

gtaggaataa taccgatttg tggatttaag aattgttcat ttcggtttgt atcggaagtt   1980

ctgaatcttg atccgtggca                                                2000
```

<210> SEQ ID NO 93
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)

<223> OTHER INFORMATION: unsure at all n locations

<400> SEQUENCE: 93
aagtagaaat tcagcgaaaa atgcagatgg tttcatagac aataaaaagc aggaacaagc 60
gcagagaatg gttaatcctc cagaaaatgt gataaaaggc gccaccaaga ccagtaatcc 120
ctttaccaat cacagaatac tcaacaagaa aagcgattcc agcaaaaacg aagatgaaac 180
tctcacttac aagaagaggg tcgacatttt cccgcaaaac gatgagaatg gcgagtgccc 240
agaagaagaa aatggccagt gattgctggg agaatgcgaa tctgtaagtg gggtttccgg 300
aaaaagcgag aaaaaggaaa atttcagaga aggcgacgat ggggaggagg aggatgaggg 360
aatataaatc gaaatttttc catttcggtt ctgataaata ccaggttttt gatcggtaaa 420
gagatgggtt gttgaggtaa atggaggaag aacagaggag gcgacgaagg ccaatgggga 480
tgaggaaaag ggaggcggag agatgcgttg ctagtgatgc cattgaaagg gcttttgaat 540
ttgttgaagc attcagattc ttctctgtct atggttccgt agattgttct ccaattcttc 600
cattgggaag acggagttcg gtggctgaac gttgacccta acaagtttga tcacgttgat 660
ccgttcaatg ttaaacagct cgatgatttt cgtctaaaaa agaagtgatt tttttttaa 720
ccttttttatt attgaacaaa aaaaagatct gtttatacca tagtttacgt tcttccacat 780
gagaagtttt ataatagttt atagaatcta tccaaattgt gttttattgg gtttcgattt 840
tatagaaatg tcatatcaaa aaaaaattta aaaatgataa aaatcattat aattatttta 900
tgaaattttt actgtgactt aattagatta taaaccgacc attctttaat cattattttg 960
gatgtctatc gtatgtgtat ttatagatgt caaacatgag agcatagatt taaaaaacaa 1020
atagcttaaa caaacaacaa taacttttta tctttcagaa aagnnnnnnn nnnnnnnnnn 1080
nnnnnnnnnn nnnnaagaaa agaaaagaaa agaagtcttg aaaaaagtat taaatttcac 1140
aataaatttt ttaaaataaa atacattaaa tggggatgag gaagaaacaa ctaagagtcc 1200
aagaagagaa ataaaaaatg agaggtggtg ttttttttgg tatgttaatc aaattatggt 1260
ctccacatac aagaaatgaa gccacgttaa tgacccaaca acactaacac atcaattctt 1320
aaaattcaat tccttctttt cttcccttcc aaaattatgg gtcctccaac ttacaaatta 1380
acaattgact ttagctaact atgtttttta aatataaaaa acgaatacaa gtcagtttaa 1440
taggacttga agattgtata aaccaatatt agacaatcaa aacaatcaat tttaggttca 1500
ttcccaacga tacatcaatt tggattagat taatttttca ttatggtttg atagagtgga 1560
tttagtttta gtggaatgca gggagggaaa agtaatttga aagaaaagga atgaggttgg 1620
tcaattccga agcctaggta tccaaataca agaatccata tcaaatttat gaacacctag 1680
aaaataatag taattttaat aataaaatgg agaaatgggg tccggtcgtc ctcttcctcg 1740
cggcggagat gaagccaccg cgataagaga aagagaccct tttcaataca attcaacaat 1800
cacatgaatt attccaattc acatctctgc ttttgaaact aaactaaacg ccaaaaaccc 1860
ttctgtggct cataagtttc ctctctcaaa tctccgattt ccctcaccca catcccacat 1920
ttcgcatcca aataaaaaag ggacacggac aacaagaagg agtttttaat tcagtagtgc 1980
ctctggaaga agctgtttca 2000

<210> SEQ ID NO 94
<211> LENGTH: 2000
<212> TYPE: DNA
<213> ORGANISM: Cucumis melo

<400> SEQUENCE: 94

```
ttagtgaaag ttcaagatgt aattcactct ctttaacaag gttgtttctt tgcttcacta     60
cgcatcaatt caaatattta gatattgatg tttaagctta atctcctatc ttagctcaga    120
acaaaattgt caaaatctca ttcttatttg tctacctggt aactttgctg ctatagttat    180
ttgtgggaga ttgtagcaaa tgactgtaga tcgaaaccat ttcagcatca atttcgaccc    240
actcttctcg tcaacaactt gatcggcagc ttcgacattc ttcaagcgcc agcttctatt    300
ggatctttag ctcaaccaca tcttcgtctt tgaattgcat gtgagctgtt gggctccttt    360
cttttgtgct tatcagttgg gagattatta ctataaatac aaagcctcac gggtatttta    420
agacacaaca aaaaattaaa agtctctcct ctgaatcacc acttccattt tctataaatt    480
ttgttctgag caacttttgt ttgtttctat ttcttattct gaagagtgca tgtttgagta    540
tggggagtaa tgttaacctt gaggaacaat tggcaacacg attggcacct cggtcaatca    600
tagttgcttt taggacagtg gttcgtcaca acacaacaat ttattttaag ttcaacattc    660
tcattctttt cttctacagt attcaaagtt atagtgttta tttctcttat tgttccttta    720
gttaacaatc taccctttaa ctaaagtaac aacttaaaag taaaatggat tattctactt    780
tttcttaatt gttactttta aaggtttaag aactgaattg ttactccgat gaaagtctaa    840
agaccaatag tggtttctat ccttaaaaaa ctattcaatg aaatttatgc taaaaaaata    900
atcactaatt catcgtgagc ttccaaacca cttgaaatta gctcaatgag attgtaactt    960
ggtcgggatc tcatcaaagg gatggtcttg gctagattct taaagatcat tttagaaagt   1020
agatcatgaa aggttgcaaa gatgctagaa acaactgggt tgtcgacgtt ttggaagcta   1080
aagcggtgat gattgacgta atagatatca ctaaacattg gcacaatcat acttggaaat   1140
agcttctata gatatattcc attttgtaag gtcttaaaga caagaacaaa gctacctata   1200
agcttgtatc ttagtttcct cttgcgatct tcttgtcgag agatgacttt ccggttttgg   1260
gttgtgtctt tgtttgtttt tctttataaa aaagtcaaaa caaaataaat ttggattaat   1320
tatcctcgta ctgaaatcaa ttggtttgga actaagtaac aataggatac atgcggcgca   1380
ccggatcatg ccattctccc tctttaaata tcaaagcaga tccctaaacc ctaacaaaga   1440
tccaaatatc aaacctcccc tcttactaca cgctccggca cctccaaaac tccatctcga   1500
ggtttgtcac ttttatgttc ttgtttttct ttatttagaa tatgatgatg attagaccga   1560
tggctatttt ctttaaatgc ctttactcct ctgactagag tggtctgtac tctgaatcag   1620
agggttcatt tcgaatcttc gaacgttgta tttcgcttca aaagctagac ttttcccaat   1680
ttacttgaac ttattgtaat tttagtgcta gcccattgat cttggtctcc aatgccactc   1740
tctgttccga ataactgccg attattgagg ggtttttttt ggacttcatg atttcgagtt   1800
gttgtaaaat gattggggat tcatttaaat atgaaatata tccatcgttt atctcaaaag   1860
tatatatctt aagataaacc atgaacaaga agtttccgat ctaattccca tgggttgtct   1920
aacgagttat tctcaacaga ttacgaactg ataactagac gtttgaattt tggcacagag   1980
agaaatcgca tcactttgaa                                               2000
```

```
<210> SEQ ID NO 95
<211> LENGTH: 2000
<212> TYPE: DNA
<213> ORGANISM: Cucumis melo

<400> SEQUENCE: 95

taaatgggaa attggaaact aacttgaaac gaccacaaac catggggact taaaaaagtg     60
```

-continued

```
ataatctaac aaaggcttta cactcctttt tcataataaa gaacaaaaag aaagctcaag    120

agcaatcaag tttatcataa ctaattaaag tcaaacacta catttctcaa aagaatgata    180

taaaatgacc aaacatctag ctgctttaca gtgtaatgaa cacccaccat taaaggaacc    240

aaggcaactg aataaattgg taacttaatt gccctccaaa tcagagtccc cataccaaca    300

tcctcttccc cattctcttg gggcatcgaa tcaacctcca tcgctttaca ttccgataac    360

aaacctctaa aacggacatt tctgcacaac cccaattgcg ttctacgact cccgcaggca    420

aatttatgag catcagtcga caaactcgat gaatttaaac gacccagatg aaagctgtga    480

tagtagaaga gtcaagaaga taaatggggc taaacgataa ggttttgaaa gaagatgtag    540

ttgccattgt gaagtggtac ttgccttgga gtaatggtgg tgaaggagag gtggtcgttg    600

agtttgttct ttagggcgcc gagttgggtg ggtatgcaga ctatggaggc cattggcatc    660

acatagctga agatgaaact gcagagtgaa gctgcttgtt gaagcagagg atggattaat    720

taaagtggga cgattttagt tgtgtcttat cttcttcaac tttatgtttc ctcttggttt    780

gacacggttt taccattatc gctaccattt taagtaacaa tagtagtgat gaatgggtaa    840

aatataaatc ttattccatt gttagaacct tcgacaagtt ttccattatg tgtggctgtg    900

tttgacccac caactcgagt agagttgaat ttgtttggtc tactatattt acaaactaat    960

attaaataac aaaactctat taatttcatc ggtgttcact gttgaaatat atacatttag   1020

tatgaatctt tatctatttc tctcttaccc ttcctctaac atttctagtg cctccatcat   1080

caattgtcat caacgacgaa atgtgacgat aactatagtc aacgagtatt tccaccttac   1140

tttgacaata ttcattgcca caatatgctc ttgacgacct ctagcactcc acgtatgata   1200

aagactacat ttgatgacca attaaggaaa tcgtatttga caccacattc caatggctat   1260

ctctagtgat caatttcgac tatcacttgt ggttatcgac tttcaaccat ttctaacgac   1320

taacttgacg accatcttaa tcaatcatat actagaaaaa caaaaaaaaa aataactcat   1380

caaatggaaa catttttaaa tgcaattttg aaactaccac ttctctgtat ttaatagtaa   1440

tttgacatta acaaaaacac ttttaagtac ataaaaaacc aaacaaactt gtatataaaa   1500

cacttttgaa aaaaacggat gtaaccaaac acacaagtat ttttctttta gattatgttt   1560

taaaagatag aaataaaaat attaaaagaa aagcaccttt ttacaaacat gtaaatccaa   1620

atcaaacatg ctatttttta atactaaaag aaatagaaaa aacatgttaa acatatccat   1680

tagcaaaata aagtgaaatt ccaagaatta gaaagatggt ttgaaaattg attttataaa   1740

gcgaagaaaa accttttttcc ccaaaagaat aatattctta ttttggaaaa aacagaaaac   1800

aaaaaatgtg acaaaaagtt acattcctgc ggatttgacc ctctggtggc tgcattcgaa   1860

tctttgattt cgaataactg aagtaaacat taaccaaagt ccgtcgaaat cttccttttt   1920

ttcatttggg attccctcaa tcttcatcac caccatcacc atcctccact ttcactctgt   1980

ttccctccaa acatcaaaaa                                               2000
```

```
<210> SEQ ID NO 96
<211> LENGTH: 1373
<212> TYPE: DNA
<213> ORGANISM: Cucumis melo

<400> SEQUENCE: 96

tttaaatgtt actttgatat gatctatgtt tagatttgaa gtatttttct catcattaaa     60

aagaactaca cgatcgtatt catttagaag aagaattgta cgtacgcgtg tagccgatta    120

atcacgtgtt gagtgaaaca ttttttatat ttttgctaat agacctatat attgttttca    180
```

```
tttttaaaat tgatatgtaa atattttggt ttgttatata tatatatttt ttttggaaaa    240
aaaactcctt tatttatttg tcgttaagta ttaatttctt tttttagtac ttttattacc    300
attgtggcct tgttttgctc ctcaatttag atatttatta tttgtggttt atttatttct    360
tttgttttcg ggacaagtga tgtttgggat attaaagtaa aggaaaaaaa agagagatat    420
tttgattgtc aaaatgtcag aaatatctaa acccggagct tctgccacgt aggcatcact    480
ttcattacct tttataaaaa gtacgaattg aaccttcatg acactgctcc cctgctccct    540
tatataaaac ccaatcctct tccatgctca gtattatctt cactctttgc tcgaaccgcg    600
tgtttaacag ataagattca actcacaagc attcatcgct aggttcttcc aaacaaaaac    660
cctacatctt ttccatttcg cctccttaat tctctcatat ttctgtatct taatccattc    720
taaaactaca ttttaatgca ctgccttgtg ttctgtattc cactatctgt tatcgtttta    780
ttgcgttttc tttgatcaga tcgctttgtt gttgcatgaa ctgctgagtt cgtttgatga    840
ttttgtttgc gcttcagttt tcatcgtttg ccgtccagat tgtttgattg gcgagagtga    900
agtgaaaatt ctgtatgata ttggagcgtt tcgtgtaaaa tctgtcttgt ttttctatta    960
tctgtatttt agtgatttgt ttttcgttga cgattttgta tgacgtaaag atattgtcca   1020
ttttaaagga ttttcttcca ctggttacta gagatcttag attgagcttt cattcggctg   1080
tattttgatg atgctttttg tgtttttttt tcctttcttt ctttagcttt tgcggactca   1140
tggagtcttt ttctgaacga catcttaaga tgtttaagat gcttatttgc tttttttctat   1200
ttttggtatg acggggtcga gtctgatttt gaacgacatg ttaatattta tgatattttt   1260
gaagctagtt gtgcttgatt ctgaaaattg cttttgatac acgagaaact tttttgtttt   1320
cttcaatggt aggattttga ccattattat tattattttt taaaagatca aat          1373
```

<210> SEQ ID NO 97
<211> LENGTH: 2000
<212> TYPE: DNA
<213> ORGANISM: Cucumis melo

<400> SEQUENCE: 97

```
ccgaattcgc tattgggctg cataacttta tcacttgctg ggagactgca atttgtttgt     60
ttagtgctat gtagttttca agtttactag gctagtatgt ttgtattgcc tgagagtgtg    120
catcatgagg tggataaaat tcttaggtct tatttttgga ggggtaagga ggatggtaga    180
gggggtgtta aggtggcatg agcggaggtg tgtcttcctt ttgaggaggg caggcttgcc    240
atccatgatg ggccttcttg gaaatattgc tatgtctatg aagattcttt ggtcgctatt    300
ggcgaattct ggttctcttt ggtggcttag gtggaggctt acattcttaa ggggaggtcg    360
ttatggacga ttgatagtga ggttggttga tattgtgtct tcgggctatc ttgtgtaagt    420
gggatagttt gaaagcactt gttcctatgg aggtggggga tgggagaagg tgtagagttt    480
ggcttgatac gtagttgcat ggcggtccta tccttgatta ggttggggag agggtgcttt    540
atgacgcgac gagtcggagt gaggcttgac tttctaattt tcttggtcat gatgaggagt    600
ggaggtggcc acgagtttct ttggagttgg ttaacttatg ggatacggtt cagactgttt    660
gttcgtgtct tagtgttagt gataggtgag tatgaattcc tgacagtcat ggtggttttt    720
cgaccgcgaa tgtgtgggat actctctgtc ctcgaagtag tcaggttcct tggactggtt    780
tattgtgggg tagggggga ttgttttcca aaacatttct ttttgagttt gacttgccat    840
caaagatagg ttgttctttt tgtagttctt tcttttggtg ctttttgttt ctatggatcc    900
```

```
tgtgagggtt ttctgctctc gtgccttaaa ctcaggctgt gaggtcctcc ttgttatggt    960

ataataatat taccttttca aacaaaaaaa aaacaaattg attcagaatg attttttttt   1020

ctttcttttg tatttattct atgtttcctt attcaggcta ctagatttga atatgttatt   1080

tgttacttcc ttttctaaca aaattagtta taattaattt tatttggttt ctttaaaaag   1140

tgtggggttg aagcttcttg cagaatatag gatcacaaat gcctaataca cttctttcta   1200

cttctttgtt ttgcagcagg gtatgaaaaa acaaattaat atgtattttt tatacttctt   1260

tctcgtatgc attattcttc ttttgtttct gttggctttg cattgtagcc gttttcttgt   1320

tcttgtctca ttttttctct acctttttgtt tcttctctaa attcctttta tgttcatttt   1380

tcataatgcg gatttttttca aaaaagaaaa ttatagttgt tagttgtgtt tgatgagaaa   1440

caagaaaaga gagtgaaaag agaaaagagg tagaagagaa aagaaaagaa gaatctgagt   1500

agaggaaaaa aattgaacaa aaaagttgga attgtgttgg atgaagtgag agcaagaact   1560

aaattttgtt tgagcgtcaa gcccccaccc cacacgtttc taagaacaag atggtaattt   1620

taaatacaac taatataagc aaaatacaat ttctcgagga aataggaaac ttcattccag   1680

gcttcaaagg aaaaaagaaa aaaaaagaaa aagaaagtaa aacgattaga acgtgaattg   1740

cacgtcacta gacaaaacca tcttttggta gagaaaaaca cgtgattaca aaaaacaaac   1800

gaaacccaaa taaatatata tagaaaaaaa ataaataaaa gaaatagaaa aatctaaaaa   1860

aattgggtta gcgggcaaac aagaaaccct tgtttcgatc ccccaaaacc cccccaccct   1920

ttctcccatc ttctttcttc ttcttccctt ccccattttt gaagaaccaa ccagcacctc   1980

tgaccaacat ttgcttaccc                                                2000
```

<210> SEQ ID NO 98
<211> LENGTH: 2000
<212> TYPE: DNA
<213> ORGANISM: Cucumis melo

<400> SEQUENCE: 98

```
tagtttggtt cataggttat agtttccaaa tttgttaggc tatcattaat caaacacaat     60

acttctcttg taggatggct gcccccctata gtactttttt aacttaggag aaggatataa    120

taattatatt ccttttagaa aatataataa taattgtgta gtgctttgat ataccttaaa    180

ttagctactc acgtttttag gaggaagctt ccgttgcttt tcatggtgtt atgatctttt    240

ttattttata aaggactgaa ctttaaaatt tctctttcat ctattttgga ttggattcca    300

tctattttat acgggaagtg aactctaaga tttctcttca cctattgtga atcggactcc    360

gtcatgtagg tcaagactac gacagataag aatagacttc cacgaaagaa agtggtcaat    420

cgagatggct atatttggct ctttcagctc aatttcttct tttttccttg catgttcttc    480

cgttggtaca tttcttgcac ttttttttgtt ctcacatgac taatgtattc caagtttatc    540

attggcattg tgcctctttt aggcttgtaa actctcgatc caaaattatc taggacatat    600

gtttcctagt gaagaaatac tagtatattc cttatgtcaa tatgtcaaaa ttttcaattt    660

cttaaccttt gagtaaatca atattatatt tttatggagg ttatttataa ttggaaaaaa    720

gttacaccca tctcaaccct aattaacacc aaatgaaatt gtaccatgcg gcacaatatt    780

tttttgtgag ttttttgcaa agagaaacaa agtagcagac aaagaacaaa cattccccca    840

aaaacagcag agaataccta agagagaatg ctctctcgta aaaaataata cccaagaatc    900

ttcccaaaaa gagggagtaa aagagtccaa aacaaacgaa ccgaagattg acaagaaggg    960

cactctcgcc ctccactgcg ccgctaaatt gtaagaagca tattttcttg agttaacata   1020
```

-continued

```
ggaataggtg taactcaaga gaaatgtaat tcgtagaatt gaactttgta tattaattta   1080

tatggtgttg tagatacaat ctttagtatt tactcatttg gtgctttctc tcaaatacaa   1140

tttaaactta gaacttttg atcttcgatt ttcaggaagt tggagttgca aatcaattcg   1200

agtttcaatc tctggaattt aataaaagtt tgatcttcca agttttcaat ctttcagaag   1260

acgatgatct tgatatggat aaaaaattgc acatcatgag agctttttga agtttaaatc   1320

ttcaattctc tagagcttaa attcttcctt aaaccaaaga tcaccaaatg aatgacaaat   1380

gtctctattt atcgaaaaat ttcatagact tttagatggg cttaggcaca ttacttgttg   1440

ggcttggact tgggcttatt tgcttggcgg gctcatgctc gagcccatta tttctttggc   1500

ctatttttca tgaggggctt gaacttggtt gtatacgaaa aaacttgact acctaaatct   1560

aatcaaatta taatcatcac aattttgacg tgttacgatt taattggcca aaaattcttg   1620

ttcaacactt gtctctaatc attttcctat ataatttaac taaaatattt aactttaagt   1680

aacttaaaag atatagttta attcgaatca aaatacaaat acaatttcgt ctatctattc   1740

ccatcataaa tgttgattga gattcatatt ataaacttct ttcaggaaaa gaaagaggaa   1800

aattcaccta aaccacgttt tcctattttg gtaagaatcc ccaaaccata aatcattcca   1860

aaattatttt ttttagaaaa aagaaattca catggcgtaa aatttcagcc ccgtgagata   1920

ttttcgaacc cccagataca atctacaccg tgaaaacaaa atcggacggt ggagattgct   1980

ataatgtccg tttagaggca                                               2000
```

<210> SEQ ID NO 99
<211> LENGTH: 2000
<212> TYPE: DNA
<213> ORGANISM: Cucumis melo

<400> SEQUENCE: 99

```
acactttgaa agtccatttg agagattagg gtaaatttga gtgaggatgg cgtgatgaca     60

acgataaaag tgaaaaatgt cagatccaag agagactcaa aagtgaatga cgtgaagaca    120

atcggaatcg aaattgaaaa atcagatttt aaattatctt aaaccacata ttaattaaat    180

ttcgattcca gtttcaattt ggtttgctgt gataaaacta aattcttaat tgtacctaat    240

tttctattaa ataaataggt aaaaaaagta tagtaaaaat attggcgtcg cccggactcg    300

aaccggagac cttcagtgtg ttagactgac gtgataacca actacaccac gacaccgttt    360

tgttacatga gtaaaatgtt tcctatttgt ctaatattat tattactact actacttctt    420

cttcttcttc gagaaaaacc aatttctatg ggtttaaatt tccaaattga tgttgagtgt    480

atcaataata tagcactcac atgctactta acaaaaatca attctttctt tttagttaaa    540

accttttctt ttatatttag tgaaaggatt aagctatgtt ctacgttaaa ttgttataaa    600

caaaatttga ttgttactta tcgagattaa tttatttaag tggatatgtt ggaatatgtt    660

actaaaatga taattgatag tgatacgtcg agtttatgct aaacacattt tgatatggtt    720

ttctttttca atataataat ttgacattaa ttacattttt ttttcatata ctctcaagaa    780

tgtttatttt tattatgtac ttttaaaaat taagattttt tatggtttta tccataaatt    840

tgtttcattt tttaatcgaa attttagtat tagactttag ttgttaaaga tcctaaaata    900

tagtcattat attttattaa agagtctccg tcacgtgtat aaattaaaat agtcttaacc    960

gttaaaagta tagtgaacaa aatttctaac aagaattgga tcggagtaga agggtgattg   1020

attcaacatg atccttgtgc cattattgtt gttactcaag ggacgttcat caatagataa   1080
```

```
cttgaaatca aaatggcata aactattgct cagttgaaag gttgtttgtt gattgaagag   1140

ttaggtttgg atatttgggt ggaagccaat ggccttgtcg tggttaataa ggtgctttca   1200

tttaattttg cactctctcc tcatggggtt tattacacta aagtggttca tttaattgag   1260

agcatattgg acgaaaataa acaattaaga ctaaggacga aagtaatatt taaacattat   1320

tttaagaaaa agtcatttta attcctaagt tctttttag tataattttc atttgtttgc    1380

tatattttaa aaggttacgc ttttatcaat aattctttag tttagttttc atttgaccta   1440

taaattttaa aatatcacct ttttcctttt atattttggg tttaattttc cttccttgca   1500

ttttcatatt ttacactaat acctttaaac aactaaggct tactcctagt ctttgaaggt   1560

taaacgttga gtttcaacta attgatttaa tcatctaaaa ttttgagatt tttttaaaag   1620

caatgattag gtgcagtctt ctgcttccca tttatttatc acgtaaaaaa attataaaaa   1680

aatcattttt taaaattgtt acctgacaat tttttgagtg caactcgaac tgcctatcgt   1740

tgtaacccga ctgtacctaa atattttcaa tattttaaaa cctttgatta aatgataaac   1800

aaattaaaac taagggggaa attacatttt ccttaattta aaaacaattt tgttgataag   1860

atggggcctg gcccatgagg ttttgggctg ggccttttcg aatcgtctat ttataatgag   1920

caaacgagtc tgagcttcga agaaatcccc tttttttcac ttgcgaaaga gacgaacaaa   1980

cgcaaaacag tcgaaggaag                                               2000
```

<210> SEQ ID NO 100
<211> LENGTH: 2000
<212> TYPE: DNA
<213> ORGANISM: Cucumis melo

<400> SEQUENCE: 100

```
tgttggcaat gatttctttc agaaactttt gccaccttaa tgcttgcgta gtttcaaact     60

aaatgctgat tgctgtcagt aactgattaa attttgattt aagtatagta gctgccttat    120

tgtgttaaca agtttctcca tcattttttg cattgacttg atgatttgac ttcttttggg    180

tcatatcttt gattctttcc atgtttgaaa gttctaattt agatgttggt ttgtatagcc    240

attgagaagt ttaattggca aaacatttta tagcgacctt gacatagaag aagatgatat    300

cttcgtttct gatggtgcaa aatgtgacat aacacgactt caggtatgat ttgttttagt    360

ttggaacatc tttcatccat gtaatatttt tattttcctc atttttttg aactttaatg     420

ttggttacta accttagtta aatatgtaag atagcctggt aatcgtatct ttcatcttgt    480

tactatttaa cttctcttcc caattttggc agcttgtttt tggatccaac gtgtcgatgg    540

cagtgcagga cccatcatac ccggtgattt tctcttctca ttaatgaaaa ctttcgatga    600

ttaattggta cactaataat attttgcctg tccacctata tatcagacat ttacttaaat    660

gatcatttga aaaatatcaa gctcttgggc aatcattttg tgtgtctcat ctttactgtt    720

gtgcttgaat gagtgaccac gatggataga ctttttgaga aagatccctt tgttaatggg    780

tctttttgt tgtattcttt gtcggaaagc ggaggaaacc cagatcatct tatttaggag     840

tcttagtttg tgaggtctat gtggaatttt ctttcaaaag ttttgatgtt gtacttgctt    900

gctagaggga tgttcatttg atgattagag agtttctcct ctagttgcct ttcaaagaga    960

aatgacaact attgtgggtt ggcctagtac taaaatagga gacatagtct caataactaa   1020

ctaagaagtc atgggttcta tccatggtgg ccacctacct aggaattaat tttctatgag   1080

tttctttgac atccaaatgt agtagggtta gacgggttgt cccgtgagat tagtttaggt   1140

gagtgtaagt tggtttggac actcatggat ataataaaag agaaatgttg ttttctattt   1200
```

```
tgtggtttgt gggtgtgtca tgtgtgcttt gttgtggaat ctttaaggaa agaggaacca   1260

caaaccctat tgaggtttgg ttcttggtga agagtgtgag gtttcatgtt ctgggcttcg   1320

gtttcaaaga ctatttgtaa ttattcactc tcacttagtt gcaaacactt tcttttgagg   1380

gtttccgtgg gcttggtttt ctgtatgctg ttgtgttttt ttcacttttt ccctcaatgg   1440

atgcaattct ttattcaaaa gaaaatcttt actcttgaat ttgcatatgc accctttgat   1500

aacttttggt aggttagtca cttcagatca aaccacaaat aataatatat tttgttttcg   1560

caaaacttag aaaatatatt tttgatatca gtctgttggt ccattctccc acttattggt   1620

ttatgttttt ttggtagtta tgaagtaaca tccaaaggcc tgtattgttt aggctgtaga   1680

actttataca aacctctgct aagtcaattc ctaatcaaga atttgtggaa ctgtaggctt   1740

atgtggactc gagtgtcatc ttggggcaga ctggacagta ccagaaggat gttgagaaat   1800

atggcaatat tgaatacatg aggtgtacac cagaaaatgg atttttttccc gatctatcta   1860

aggttcctcg aacagatatc atatttttct gttcaccaaa caatcctact ggctcatctg   1920

caactaggga acagttgacc caacttgtgc agtttgacta aaagaatgga tcaattatag   1980

tctatgattc agcatatgca                                                2000
```

<210> SEQ ID NO 101
<211> LENGTH: 1078
<212> TYPE: DNA
<213> ORGANISM: Cucumis melo
<220> FEATURE:
<221> NAME/KEY: unsure
<222> LOCATION: (1)..(1078)
<223> OTHER INFORMATION: unsure at all n locations

<400> SEQUENCE: 101

```
ataatattaa tttcatttaa aaataacttg aattttttcc tcctatattt atcatgcatt     60

tttacaaatc cacgttcgaa aatcccatta atcataggag ttaaattgtc atcacttgat    120

ttgaatattt attttttttt aaaattaata aataaataat gtcacgaaaa tgataaaaat    180

gcaaagtatc gaatttaaaa attaaacaga acaaaattta aaaattaaat gataaaaata    240

aatataaaat ataggtggat gttaaagata ataatttaaa tctttatcta tcatcaaatg    300

acgatcctcc aatggaaaaa gaaaaaaaaa actttattct ttacctcaaa ctcctcgcta    360

aaaagtaaca atggtaagat aaaactttat tttaaattat tcttccactt gcaagcaaag    420

taaatagtta tttgattctt acacaaaaga gaatttttac tttttacttt tcattagtta    480

tatataactt tataatacat ttccctctca tggaatttaa aactaccatt tgagcaaaat    540

attttaaact aaagaaaaat atgaaactta aaactatgtg acagggatga taatgacgtt    600

tactccaaat tttcatttta aattaacgta cgttatttta taagtatatg tcaaaatttt    660

aaggatctat tttattagac aattcaaatt atatgttgtg ctttcatatt ttgttaaatt    720

caataaatat gcctttggtt gattatacta tttttctaat taactctgga gacatttcaa    780

aagatttttt atttatttat ttaagaaaat atattaatat ggtcaataga tatgtattat    840

gcacatgata taaaaannnn nnnnnnngta ataatattat tacataatta aattctttca    900

tcttcctaac agagagagag gatcgtcctc tcagcgacgc tgatcccaac tgttccagta    960

ccaaatctct gtgtcccaat ccaacagatc cttcttttaa gctaaaccca ccattttttt   1020

tttttctgga aacccatttc ttatctctcg ccggaccttc agattttacc tcaaaacc     1078
```

<210> SEQ ID NO 102

<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 102
cactatctat catagataaa taagtgatag atctaaacga tcatttacca aagtctcaaa 60
gatcatgtac caatatctaa acgagtttgg tacaagattg tataccaaaa tcatttgatt 120
tgatacaaga tcgtgtacca aaattgttta gatttgatac aatatcatgt acaagatagt 180
gtatcaatat ttaaacaatt aatcgtctat cctagataaa caaagataaa ccactaggaa 240
atcgcacgaa gagaaataga ggaagtgaag aaaaaaatta ctcatataaa ttgatgaaaa 300
atgttatcct tctctaatat ggttttaatt tttgcactag gaaatcacac attaatgatt 360
ataatacaaa gtcctacaaa gagatctgaa ttgattcatt tgtgaaactt tacaatttta 420
atcgatacaa ttattaactt aagagtgtaa ttgatttaag ctacaaggtt taagcaaaaa 480
actaaaacat aaacagaagt caaacttttc ttaatttttg agtttagtga gctacttatt 540
tattgggtag ctttagaaaa gtcaaacttg aattgtcatt tttaagtatg atcaaactta 600
atttaaccca aacttctgtt gtaggtgaat tagcagctag tttgtatata ttgactgatt 660
tacaaattct tattttaatt aattttaacc atccattaaa atggagagtt atagttattc 720
aaggatttta actactctca aaatcatcaa gatcacttgc atatttagta taagttcaag 780
gacttaagtc cttattgata ttttcatcat catctggaaa actaatcaaa taatcatgtt 840
gatgcaactt agatgattaa gattaaagct aagacttttg aaatgataaa gaatataaat 900
aaaaaaggaa gttttttaaa aatataacaa ataggtaaaa tatttacatt atataaaaca 960
attctagaaa cgaaaaaaac ccacggtctc acaatgaaaa atacaaaaaa taccctagtc 1020
aatagcaatt aatcagccag cttgcgcgaa gaatattctt ttaaacgact gtgtactaca 1080
atttcaacga ataatccagt attgtttagg tcatgacacg atcatgtagt tctattttaa 1140
cgatgggaaa aaaggttttg aatttaaatg atcgtattga tcatgaaaaa caactatgtt 1200
gattacgata agcgatcatg tagtccaatg taaatgaatt tcaagtctaa cgatcatgtt 1260
gaccatgcta aacgattgtg ttagctatgg taagcaattg tgtagatcat gtcaacacga 1320
tcgtttagat cattttaaac gatgtgaaaa agactnnnnn nnnnnnnnnn nnnnnnnnnn 1380
nnnnnccatg ataaacgatt gtgttgacaa tggtaaaaga ttgtgttgac gatgataaac 1440
gattgtgttg ataatggtaa agatcgtgtt gacgatggta aacgatcggc taaatcatgt 1500
caaaatgata tttagacgat gtagatattt ttgaatatga gaaagatgaa gtgactttaa 1560
agatgaagta gcttttaggt caaaagcaaa taaaaacata taaaaacata cgaggaaaag 1620
ttaacatatt tttagtctat tcagactcat ccaaatttta attgtgtcat caaatctcaa 1680
tccacagctc tcaccttgat taaatacata acatatctaa gatcttataa ttaagttcat 1740
gaacgtatct aactttttaa ttcattgatc tgccttgctt agttcaagtt acataccctc 1800
ttgcttaaaa aaaaaagtta cataccctct tgcttaaaaa aaaaaagtta tataccctct 1860
ttgacaaata tcaaaggaga aaaagacaaa aactgacatt ggcttcccat catccagaga 1920
aaagaaagaa aagccgcgcg ggttgtttat ccacttgttt cccttattat cctcatcgat 1980

```
tccaagtttt gaactcaaca                                              2000


<210> SEQ ID NO 103
<211> LENGTH: 2000
<212> TYPE: DNA
<213> ORGANISM: Cucumis melo

<400> SEQUENCE: 103

ttcctattta aattaactgg ttttcttaga aaataacaga attcctgtgt ggaatcccgg     60

ctctaatcca aatttcatag ggatgaaaaa tgaaatgggg agtagacatg gagatgggga    120

gtggcattcc tgacctcacc ccgtccccgt ggacatcttt ggtgacagaa tcatcccatc    180

caaatcaatc tgtgggcaaa tttcaacact cacaacaagt tgaaagactt tgttttgtaa    240

tgtatttcga gttcaactca catgtggttg tatagtctac catttcaaac ccactccaaa    300

taagaaaaaa atataaaaaa acatatttta gaaccccaca acattttttt tatttgaaac    360

aaacaaatat ctccacgtgt ttctgtttga tctcaaattg tacaaaaggg agacaaacaa    420

gagcaactta atcgtgtggt cgaaagttca taaaaaacgt tgtttttcat tactattatt    480

acatcaacca atgcgatctc aatcttgtga agatttttct tccatgtgtg agtcatttct    540

tctcgatctt aattatcttc tcacaatcca tttattatag cataatctaa gttaatttag    600

attcaaaact atacaataat aataattaag aaaattacaa atttaaatag caaaagaacc    660

atttgttctt tatagtttct acactaactt ttgaaaaggt taaggttatt ggaaatcttt    720

ttctggggca tttttctcca attctacaat agacaatttt ttttaattaa ttaattaatt    780

aaatttaaag tttaccttgg agtagtcaat aattaatttt tatgcacatt tgtcttttat    840

atgattgaat gtaacaaaca ataacttatt cttcttcttt tattctattg ttttgatgca    900

aacccacaat atttaatgag ctcatagtta tgtgtttgct ttactaatta attattttct    960

tttcataaaa taaaaaaact tgtacaatat aaactctatt atcattgaat ttttagtact   1020

taatttaaac gtactaaaat aaaatacatc attctgactg acgatccatg taaataaaat   1080

ctaaaaataa aagaaaaatg tcagaaatag caaattgaca aaatatttac aagccatagc   1140

aaaatttcat attctaccga taacaaacat ttgatagaca ttgatattct tctgtcagtg   1200

gtattggtag acagtgatag aagtctatca atttctatca tcgatagaat tcaaaatttt   1260

gttatagatc gtaaatattt taatttattt gttactttta aaaatgtctc aatataaaaa   1320

ttattaaata aacattaatt ttttattttt caattttaat atctaagctc ataaatatta   1380

actttaccca ttatttattt ggtttcttac cgcttaaatg ttgcaaaaat attttaaatt   1440

ttatttttga aatttggtta aattcgtttt tacttaaaaa tttccgtgat aaaaatattc   1500

gaatttttta ggtttttata agatttaaaa gtaaactaca taaatgaaat cgttattttc   1560

taattctcaa tttaactttt ttatactttt taattaccaa atggaaacat gaaattttaa   1620

atatatttat tttaaatctt actcgttaca aacaaaacaa taaatttaaa attatttttc   1680

cgagttttaa attacaagat ttaaaattaa tttttcaaca agaccaaaag aattgtaagt   1740

ttcgaataaa aaggtttctt tttgggctat aaagtccaat ttcctataaa agaatttgat   1800

caattggagc ccaaagtcag atccattaac ttttgggccc aaatagaaca atgaaaagaa   1860

agcccaaaag ctgacccacc aattaacctt attattaggg ttttgctctc tcttttaaca   1920

tccgaaaatc aggactctct tgccgctttt ctcttcgccg tcgccttctt cgagcttcaa   1980

gtctcccatc ctcttcagcc                                              2000
```

<210> SEQ ID NO 104
<211> LENGTH: 1974
<212> TYPE: DNA
<213> ORGANISM: Cucumis melo

<400> SEQUENCE: 104
tttgctattt tcgtttcatg tgggaaaaat agtatagtat gtttacgtct taaattattt 60
caaattccta gctaggaatt aaaactttaa tatatccaaa acgtttctta tttattataa 120
agatctgcaa tagcacaatg ccaatttctc ttctttgaaa tccaggttca aatcccggtt 180
gcggaataat gttttgctat tttcgtttca tgtggaaaaa atagtatagt atgtttacgt 240
cttaaattat tacaaattcc tagctaggaa ttaaaacttt aatatatcca aaacgttcct 300
tgtttattac aaagatctac actagcacaa cggtaggtag tttctcttct ttgaaatcca 360
aaatctttgc tattttcatt tcattttcaa attgaatgca tagctttaga ttgtagtaaa 420
cattgtatat atatgtttag gttgtgctaa ctttaaatgt acaaaattca aaatgtaata 480
gaattagatg tacatgataa agagttgcaa tatttagatt aaaatataag aatttaaatg 540
taagacttgc atatatcaaa aaaagatttc tttataaaca atattttttt atacaatttg 600
aaggcaactt attgttactc atgggcttga tccaaacttt tgttgtcttc actaaaattc 660
ctctaaatag ttcaacataa agttgttcat gagaaaactc attaagatat attccaacat 720
tatgaattgt ttgtccttgt attttgttaa ttgtcattgc aaagtataaa tgaatggaga 780
tttgttttct tttgaacttg aatagatatc cattatcatt tggtgggttt aatggtattc 840
atggaagaaa aatttatttt tctgcataat cacccattat tatttcagca tgtataaatat 900 ttttgctaaa taattgacat actaatcttg tctcgttaca caatccatta gatgaatcca 960
aatttttcaa taacaacgtt ggtaaaaaaa atcaagacag ccttttatat agtaaaaaaa 1020
atgttacaac aacttttcaa cgttcaagtc tttaaatttg tattgttgat tagaattaat 1080
aagatatttg atttgcaaca aatttctaaa atgtaaataa aaaaccattt gcattcaaac 1140
tctttacatc caatacttta attccttcgc atcctatact ttaattccac tcacttaaat 1200
ataattaatt aaaaatatag tggataaatg aaaaccaatt tgcatttaat ttttatatat 1260
gcatacttta attccactaa acttcgttag aattaattca aaaagttgtg ggagagaatg 1320
tgcattttat catattacaa gaaaaataaa attaaaaaag aatttaccat aaagtcatta 1380
aacaaaattc aaaggttgaa tggagagaat aaaatttctg cacgctttga tatatacaag 1440
atatttaaaa ttaaaaaaat agttttaaag agaatgtttc taaattatta ttctaacttt 1500
aaatataatt actcataatt atacttattt ttttttaaat ttagaaacta aaatgataca 1560
ttctcgaaaa ctataatcaa acgagttaat gttataaact ttgaaaacta ttttttgttt 1620
ttaaactctg catagcaaat agcatataga ggttttttaa aaaataataa taattaaaaa 1680
aacattaaag gcaaaatcta ttattccttg atttgtgtat agggtgtaaa tattttgtta 1740
ctgtgttatt tttaaccatt tgcgcactga tacggactaa aaggtaaaaa cataattttc 1800
tcgaattgtt attagaaaac tggggaagaa aaaggaaatc aaatcgcgcg aggtgggatt 1860
tgacccggga acctaagact agctcggtgt ggtgttgaaa tccacgcgtt gttcaccgat 1920
tttcttcata acaaacgcac ccaggctacg gcagtcttcg aagctctctc aatc 1974

<210> SEQ ID NO 105
<211> LENGTH: 2000
<212> TYPE: DNA
<213> ORGANISM: Cucumis melo

<400> SEQUENCE: 105

```
gtcgtcgagc agagctctgg cagttaccct acaacccgga gcacgataac tgcagtgatc     60
cctatcctca gcatcagtta aatgggccga ttcaaaactt ttatgggcct cagcccactt    120
ccacttacaa ctattacaaa catggatacg atagtcacga tcaggcccat catcttaatt    180
actccacaca ttccaatatc ttcggccgcc aaactgcctc cgtttttagc gacgaaaatg    240
tccataattg ctctattatg taataaggct aaacactaat catctatccc tttaaatctt    300
gaatttttgt aataaaacca atctatactt tttgccatag tttatttcta gaaaagttta    360
gaatacattg aagatttgag aaacttgtct acaaggcatc aacaaaacta cgtgaaaatg    420
acaaattgga aacaaataaa aatatcttat gtttgagtat atggaatgaa gggattgatg    480
taataaaact taacgtcaag tgttaatatt acgctatagt tattttcttg ttgtagtaat    540
tttctcttag ttaatttttt tattattgaa ataagtgata aattttctaa taagaacgta    600
aagatttaaa cctctaatta agttaaaaaa aaaaacttga attattgttt gagttatgag    660
gtaacgtaaa agacaactta aattttaaag tcaaaccgaa aggaaaagag ttaaataccc    720
acaaatggat caaagaagtt aataacacac acgcacgttg ggaagcttaa aaattagcaa    780
caaacaagca atcattggtg tgggacagta ttgaaattcc acaaaactac aagggtatat    840
tggaaaatcc aatttattta tttatttttt aataggaatt aaatttactg taaaaaaatg    900
taagaccgtc gattgacaat tggtggactg tgaaacgtgg caaaagttaa ttggcgaaaa    960
ggagaggaaa gattttctct tttcattata atgaaaaaaa ttaatgatag tacacgtggc   1020
aaaaaagtat tggagagaaa tttccgggaa ttatctctaa tacgcggcta atttggatgt   1080
caattttgca aagaccagaa tctttttgaa cagcgaagaa gaacaaatat atagacatac   1140
aataataaat aaaaataaaa atatattaag cataagagaa aaagaagatt tgaaggttat   1200
attgaagtga tattgttggt ttctccattt ctgtgggtct gactctgcct ctctcttttc   1260
gagccagaac caccaaaacg aaaaaaccca cacactgtat agcaaaccct aattctttgg   1320
tctcagatcg cccatggctt ccactaaaga acgcgacaac ttcgtttaca tcgctaagct   1380
cgccgagcag gccgagcggt ttattgtatt ggttttccta ccttcctttc cacttttttt   1440
ttttgggttt gcttctcatt tctattttat gcttttctta atttgtgttt tacttttcac   1500
tctctctttg ctcagatcgt atttcttctg gttgtttaat tttgtgttta tgtttttttga   1560
cttcggattt aagccacgat cgcttgcctt tttgtgtact attttcagaa gtgttgttat   1620
gtttatccgt ttacacgatc tgtttgaaat ttatggaaat ttagtttgct tataattttg   1680
ctacatttct attgtttagc ttctcgagca gttttttttt tttttggccg atccattgat   1740
ttatactgtt tttctgtctg atctgtttta tttaatggag aatactcttt ttttgcgaag   1800
cttggtagct catttttcac tcatacttac acagactact tggtcattgt ttttatctgt   1860
aagcacaaag caaattcaag tttctgcctg ttctttcttt gcttgtcaaa cgacaaaact   1920
atgtttgtag ttgcttttgg atgatagatg gtgattctga ttttaattta cgttttcctg   1980
ctgttttttt tttaaaagaa                                                2000
```

<210> SEQ ID NO 106
<211> LENGTH: 1643
<212> TYPE: DNA
<213> ORGANISM: Cucumis melo

<400> SEQUENCE: 106

```
tccattggcc ctctcaaacc tttatgtgca tatcactaat atggttgaat atgtatatct     60
tctttctcga atagatgatt cttggtggtt tcaataatca tttagcaaat ccagaaattg    120
ggacctcaag ttcggttgcc gtggaaatag ctaaattaac tctgaaatcc tcaaactgaa    180
atgtgagaat aatcacgatg aatctgaacc gtcaacggcg gaacatagca acagtaatca    240
gaattaccaa atttcaattg ggggaattcc tttgtatgat ccttccttgg gcctaacagg    300
gattcttgat ttgaacctct cttcttcgta aaaattacac aaaatattta gctgctagag    360
ctagacaaaa caagatttag attggaaaaa caacaatgca gctcccaaat tgcaatccta    420
attccactat ttcttttttc tttttctttt ttttaatctt aggattcaat tcatcattca    480
tcaattttat tgttactgct cattgatgac caatgttttg gattttgtgt gtcaaatatt    540
ttagtttata tatggtgaaa agataaaatg aatagtttca aattttgtgt tttatgaatt    600
cctcactacc tctttctttc actaatacgt atgaaatgtg tatggttgtt tataaataag    660
atggatggat gttttgattt tgatttgaat gttaatgtta cttaaattat agattttaac    720
catttgaatg aaatatggag agaacagttt ttatatgtaa aaacaaatta atgtgagaaa    780
gaaataaata gcaatgcctt tcttcactaa taaatgtatt tatatttttt attaacaaaa    840
taaaatttat attaattatt agtgtatgag gtgtgttctt gtacaaagga aagtattgca    900
aaattacaaa aatggaaagt tgaaattact gcactcattt gctaaaatca aattagttaa    960
ttatagaacg aaaaataaat aaataagttg tatttgatga tcctagataa ataacttttg   1020
aagaataaag atcaactatt taaaaaaaat atgtgtatca caaaaaagaa tagagaaaaa   1080
aatcacaaaa atcacatccc aaattataat aattcatatt ataataattt atataccaaa   1140
cataaactat aataatcacg tattattata actcatagac tataataact cactccacgt   1200
cccgtagtta ttaaataaaa gaaagtaacg gtaacattaa cattataact tcgccctcat   1260
ttatggcaag gaaaaattgg ggggattggc aagtattata tttgtttatg gaaaactttt   1320
gtgaaggtgg aaaatagaga gagccaaatt aacaaaaata ataacaaaat caaagggtgt   1380
agaattcatc cagtttgaga gcggaagatt agatgggtga agaaaggatt attctagaac   1440
cctagcccac gtgtcataat ccaaccctca ccttttcttc aaaaaccctt tctttcttct   1500
ccctccccta tatctccttc ttcgaccacc aaactctttt ctctcaattt cccagcatct   1560
tcttcatttt tcattcttaa ttcaacccat ttcttctctc ttttcgtttc tattttcatc   1620
gtttctctat aatttctccc tta                                           1643
```

<210> SEQ ID NO 107
<211> LENGTH: 2000
<212> TYPE: DNA
<213> ORGANISM: Cucumis melo

<400> SEQUENCE: 107

```
ggatgggcaa tcgtgcgaca cttgttctac tcgattaaca aattagccgt gtaaaatcca     60
aaaattgtgg acaatttacg gtatgatgta gcccctcttc acgttcttaa gaaatttttt    120
ataaaatgag aaagggaaag gaaatcattg aaaagatcat aaaagaaagc attgaagact    180
gttaattgca aagaaagctt agcttaaaaa gagtgcaaca aggcttagtt ggggatttaa    240
ctactatgtc tcccttattg tacattttga atatttttat ccttggcaga cttgcatatg    300
aaaatgtcga aacgtcacac actaggtcga caacataaaa atgaaagcaa tagagcaata    360
gattaaacta agtagaaaac ataaagacaa ggtgatttga aggtatttgg atatgtggcc    420
ataggcaaat aacgcgctgg acaagcatgt tcatgacata tgacactttg cacgcatgct    480
```

```
caatgtggat atatcagcat ggcgcacgtg cctcactcgg acacataaac atggtatgcg    540
cggcatcatg tgcgcacgcc ttacacgacc aacgagctag gtgtagtcca agcacacacg    600
cgatgggcaa acgtgcctat ggctgcccct ggcgcagaca gtctcgaaag atgcatgtcc    660
atcctaggcc catctagaca cgtccaaaag ttccaatgac ggtccaaaag gatacaatac    720
ctttagaagt gtcatggtag gtctagaatg ttctagagtc atttgtaaat tgttaaactg    780
ccttatatct tctagatata caggtcctcg gccgaccttc aaagcaccta ggtcggttag    840
gaaagctata aatagatgta aggtggctta tttgtaatca ccctaaaatc ttggcataac    900
ctagccaagt aagacaacct tgcctcatca tttgtacaca aggtaccttt acaaatggta    960
ataccctggc aaaggactac actcatttgt atacaacttg tacacaagca atcttggaac   1020
gcaaagtact cttccaagaa gtgtcaagct aagctccatc attctcacaa aatgatctct   1080
cttgcctttc aactatctta aatcttctac tgccatattc tttctcatag tgcttagtgc   1140
actaacctct caaaggctta cttggctacg tgggcgttaa tattagtcaa gtgttgtacg   1200
tttggttagt tgaaaaatct aaccacgtga caatagacaa acatcaattt tattttattt   1260
tagagtctca ccaagttctt aaataaaatg tttattgtaa gacaaacaaa aatgaaaata   1320
tgttattata gtgatataga attttcacta ttagtacaag atataaaagc gaaaggaaga   1380
atgaatgaac actcaacatt tagaaagtgt tttgagtaaa gaagtaaata gtgagaaata   1440
acgagtacaa atgtgtggaa agttataaac ttctaagatc tacagaacaa aagattgata   1500
agatataaaa ttgatgttag gataggagct acaaactcct ttgaccaaat atcgagcagg   1560
attcacaagt catactctct tactctacca aattcattag aagtacataa tgggcatgca   1620
tgtgaacgaa ttaaaaaatt ggtattttta tttttatatt ttaaaaaaat tggatgaatt   1680
ggcaatggcc atgaatgaac cagttgttaa agtttagagg acaaaaccca aaagagagaa   1740
gtgtacctca taaaaaacaa atccaccaat tgagaatcac ataaattata ggaagacgtg   1800
tcactctatc ggccgatcct caaactcttc caccaaatcc acatgcacaa tctccttctc   1860
ttcccttcca ccatacactc aaaatcccac tgatcttctt cttcataaaa acccatataa   1920
tcataaatta atttcctcaa gtttttcttt tccaattaaa caaacaactc tgcaaaagag   1980
gcctttcttc caccatttcc                                               2000
```

```
<210> SEQ ID NO 108
<211> LENGTH: 2000
<212> TYPE: DNA
<213> ORGANISM: Cucumis melo

<400> SEQUENCE: 108
```

```
agacgaagaa gaagacaggg tgtgatcatt taagaatatg cgttttaact ctgccctttt     60
tagggctttt ttcttttatt tatttgcctt ttttctcgct cctagggttt ttccctccat    120
tgaattagaa ggatgactgg gccacagact tatgatgggc ttcacggtca ttatttgaaa    180
gtgtgatatt ctaaaaaaaa taaaaactca tttgaattaa aatagggttt ccctccatgg    240
gagtatgaaa gacttttaat tgaattgggg tttttaaacc ctaaattgaa ctaaatatat    300
ttttatgatt tttacaaaaa ttaatactac aaaacaaatt atgattaata aaatttgttg    360
atatttttca aaaaacaatt atataataaa acaaactaaa tattcaattt ggtattttta    420
accatgctat aggaaaagat tcatatgggc atcaaaatga agcaagaaca tggcaaagca    480
agttgggtga agataagtat tgtcctaaat cgaaggacga ggcaataaac tcgatatctc    540
```

```
gaagagtctc caggtcaaca tcacaacgcc tgcacaaacc aaatattatt atatatatag    600
ccatcgttta ctataagact atgtatttac gaaaaattct atattgtttt cgacgattac    660
atttatatta tataggaata aaatacaaac ttttcgaaaa gtcatatatc ccaccatata    720
aagatcaaac gtggtagatt gaaaacatta tacagtatat tctctatttt tttctcataa    780
aacttattac gctttgtcaa gttataaaga ttaatggttt tggtatattg tgctaacttc    840
gtccatttgt tgtgaaatta cattttcact acttttttcc acattgcacc atttttcata    900
tgttttattt ccattatctc gtagaatatg agcaaagaaa aagattaaag atgaaatttt    960
tcaacgtgtg agagaaacat cattaaaggt tacttaataa ggaattagaa aaaagagcat   1020
gaacctagaa caacaagata caaaatatca aagacaaaag agttcgatgg agagctagaa   1080
agataaatca agattttgta aaagaaaagt gctcggtggg gaactagaaa aatgttatag   1140
aagctagaaa gataagccga taatttgtaa actataagag gccgtttaga ggaagagttg   1200
ggttgtgaaa tgttagtgtt atgataaaac tattgttatg tttggggaaa gagtttaaaa   1260
aggtactttt atgataaaat atgtctggga taagagttga aaaacgtagt tttatgggag   1320
agttgaagat atagggttat gaagagttaa aaaaggtata agaaaaggag agagagagag   1380
ggaatagggg ttatgatcat agtcttaaaa cagaattatc ataacccaat ccaagtgata   1440
acccttggac caaacgacct aaaatatcaa agagaaaact gtttggtgag gaactataaa   1500
aatgttatag aagctaaaaa tacgaactag aaagataagc ggagccaatt ataagggttg   1560
gttaagtgta gggtttattt atttgagggg aatgataatt taagatataa attaatagaa   1620
tggcaagttt tgtaagaaaa attaataaca actcgataaa cttttgtttg tgttggtaga   1680
gaaaacatgg gccacaaaca tgagcccaaa tgtggagaag cccagctgat aatttaattt   1740
taaaaataat aaagattaga ttatttttgt tcgcccaaaa ttcggcgcgg ctaggaggtt   1800
gcttataaat ggaaataaat ggaaagggtg ttaggtctcg aacaagtgtg cgacggtatt   1860
ttaaaggtcg gccacgttga ggcggccctt ttcactcctt tttcctcgct cgtattcaat   1920
ctagggtttt aggtttccaa cttctcttcc tccccttccc cttccccttc cccttccttc   1980
tctactcatc actattctca                                               2000
```

<210> SEQ ID NO 109
<211> LENGTH: 2000
<212> TYPE: DNA
<213> ORGANISM: Cucumis melo

<400> SEQUENCE: 109

```
atgggtagtt ttcaaattaa tccgaccttt gaagtacttt ggtttttaaa ataatttttt     60
atcatctgaa atcactccat agacttatgt taccgtaaat cattattctt tacaaatgat    120
ttgattttac ttaaaagtat attatttcaa acacgttata ggtattatga agttttaccg    180
tcaacaatta tagttagtaa gccaactatt tataaaaatt taaaaaggaa tatttgaagc    240
atggtgcatg atgtatgttc ttctctctct taagttgact atcaaaactt aatcatgctc    300
agaataacat acctcacata gcatgtgcaa tttaatctaa gcaattcaaa attcattaac    360
aataattcat acacactaca aagtcatacc acctatgtca cccaagaact actattattg    420
taacaagtca aataagaagt ccctatccta tccatcctaa gatggagtaa tttttctttt    480
ccttaaattt ttggaaagaa gaatattgaa attcaggaca ttaaatcaaa gctgttcgga    540
gataaatgaa ccattcttca agtaaaattc atatttgtca tcatgcaaac aaatattgaa    600
aacatgatat caagaaaaag aacaaattat ttaaaaacat cataccgcac atcaaactta    660
```

aaataacctt ttgtgcatat caaacttaaa ataacttttc tcaacaaatt aaagcgacat 720
aaaattgata atttttgttt ttttttaaa tatatattca agaaaatcga caaatccaaa 780
tgacaagttg ttcacctgta tattaaaaaa aacaataatg aaaatttgaa aggagagatg 840
agaaaaaaaa aatcaatcca tcaatccaac ttgaattttt gggtcgacag catatcccta 900
attataatag gaagcaccct actttttta caaaagtatc gaaattatta gtcgaaaatc 960
ttaattagag tccaaattgg atgcagcaag gatagtttta aatccaatta atagcatgcc 1020
taatgctatt acaaatatat tttggattat acataaatag aaaaaaaaaa gtgaacttcc 1080
agactcaaat agattttact ctattgttat aaaaactata cattaaaatt agatgtagag 1140
aatgagagct caaaaccaag aaaagtaaat gataaaaggg aaacaggagg tgaaaagaaa 1200
aggtgatacc gcggatttga tgtggctctc ggtttttgcc tcccaagcaa tccccattgc 1260
ccatctcctc tacaccaacc cacttttctc cctttctttc tttctttctt tctaaaactt 1320
ttgttttcca attttgacct ctcttcttgg gcccacttac taacaaatca aaaccaattt 1380
tcattttttt ttcttttctc tattcccttc cacaaataag aaaaaacttt atataaatca 1440
atacaagaat gacatttatt ataatagtat atactataag gtgggaggga tggcaattgc 1500
caattgtata agtaactatt aatagacagt aaaactttga aatagaaggt atttagatgt 1560
ctgagggtaa acttataaca ttttatgaaa tctaaaaact aaaattaaaa ttattgggac 1620
aatataaact ttagacataa gaagaaaaca tatttttgtt aataatttaa caaagaacac 1680
aacaagaatg gtagagtgtt gattaagagt gagcataata gacaaaaaaa aatatagtca 1740
atcagccaaa atagacggtg gttggtcgga gatgaagaga gtttcaatct aatcagttgg 1800
taaaaaattc aaacatcgtc acattcttta aaacttttaa aggtttaaat ctgctaagat 1860
ttatcgaaca atgacctatt tgtactactt tatgattgac atcaatttaa atatttaccg 1920
gtgaatttag taacgattag ggcgagagcg gttttaaaaa caggagtgga gtagtggaca 1980
aggagggggc ggaccaaccg 2000

<210> SEQ ID NO 110
<211> LENGTH: 2000
<212> TYPE: DNA
<213> ORGANISM: Cucumis melo

<400> SEQUENCE: 110
ataatactat aaaacaaata aattttaatt aagttgtttt tactttcata ttatactaac 60
aagaacagtt tgttaagttt tatatgtatt tataaaagat atatgagtta ttggttaatc 120
tataatatca atgtcgaatc tctaacaaat attttagtgt ctagacctta tgtaaaaatc 180
agaagtgacg ctcaatattt ggaaacagga atcattggga tacgtggaaa tcaatctttc 240
tgacattgtt acaaacaaaa gaataaacga aaagtatcac cttatagact caaagaatgg 300
aaggattcag attgagttgc aatggaggac ttcatcctga agtacctata tatttttctt 360
cttggttagt ttttcagtct tctcttctat ggatcaagtg gggaatacag caagagacaa 420
gaaagacatt ttcctataca aattcatttt attattcttt cattgtctct ataaataaag 480
aggcatttaa atccttttcc taatttaggt ttggtatcaa tattttgttt gtaacagagt 540
aatagaacca aaatatttca ttatgttact tgaaatgttg atttttttgt gcccattctc 600
ttctgagtcg acaagtgaga gtagatatga aagtagctta catttatatt ttaagagttt 660
ggaatctctt accttaaata ttttctaaaa gaatatcgtt gtgggaatat gatttttcta 720

-continued

```
ttttataaat ttgacactat cgatcaattt aaacacgacg tataatttta gttttatttt    780
tagaaaaata agctttttag tttaagtttt tttttacgta attactattg aatccctaaa    840
gttttaaaat gctatagctt tactcttata ctttgagttt agtttgtata tatggtcgat    900
aaattttaag attatgtacc gtaattctaa gttaaaacat tgctcacctc ttgtcctcaa    960
agttaatgta aatgaaatta taatactcat acataataga actttttttt attcttaatt   1020
atgcaaaaag aatagtgaag gttaatttag ttataatcag ttctagaaaa ttaacacaaa   1080
cattctaaaa gtagtttgaa attgagataa aatgaaagtc aaattcaaaa caacgaaata   1140
aagttataaa tatgaaactt tgaaaaatat agataaaatt agaactacgc atgaaaactc   1200
taagacaaat agacaattct cgagatagaa gtttgaaatc gaaatctggg gaaggaaaaa   1260
tctttacatt tccattttat tcctatatct actaataagt tttgtattaa aaaagaacat   1320
caaatagagt aaataactgc acactaaaca acactcaccc aaccacccca tatctcaatg   1380
agaaatctta atgtgaacta caaagctagg gacagaaaaa tgattcatta gattccagaa   1440
caataataat tatgattaca ttttggattc attagattcc aaaataataa taattatgat   1500
tacatttggt gtttgaccta tttatttatt tattttatat aaatattttg tcgaagagat   1560
agaaaaaagg atgcatttaa attaaaaaag aaaaattata ttgataaaga agaagatggc   1620
gggctgacaa gagaagaccg ggaggctgat gtggcaatgg gaattccaat tttccaatca   1680
aaaactaaaa acaaaaaaga aaaaaaaaaa gcaaaataat tttggttcac tgaaaatttt   1740
catataaata catgtggcgg ttgatggccc aaaggatgag ctttgaaggt cgcattatca   1800
aaagtttggg gaagcagatt tttgctaact tcgaggtact ctcctctcct ctcctctcct   1860
cactttcctt tctctctata ctaactataa tttccattcc tcctccatca ataatttctt   1920
catcctcttc cttagctaat ctctctcttc tctaccagtc aaacgccctc ccttttggtg   1980
ctctctagcc tcctcctccc                                                2000
```

```
<210> SEQ ID NO 111
<211> LENGTH: 2000
<212> TYPE: DNA
<213> ORGANISM: Cucumis melo

<400> SEQUENCE: 111
```

```
ttctctctct cttttaatct acaacgtatc caattatatg gagaaagttg aggttgttgg     60
atttaattca ttttttcaca ttttttaggg ttaaaatcta aaaacacatt tcgattttgc    120
gactgttcaa ggcgtatatg tttctttaaa tattatagtt gaaattacga tcaaattctt    180
acgctggtta agaaagagaa aatcgtagga gagaaattgt gagcatataa gtgaaaataa    240
cctcctagag tttttttggat ttttgagcga aacaaaagta aggttgtaac gatttatgtc    300
taaaatgaac aatgtcatat cattgtggga atatgtgtga atgataaatt atcacaactt    360
ccaacaatga gtatcacaat acatatcatt gatgggtttt gagaaaatga gggttgactt    420
ggacatgaca acttgataga cttataactg tgtggtgtac ttataagaaa tcggaagttg    480
gtttaaaagg agaatcattt gcgtcgacaa gatgattatt attgcaaaag atgcaaccaa    540
ggtatgtcga tacataggct agataaaaag aagatcaagt aatgatataa ctatgtctct    600
gttgatatgt ttttaagtga aataaaaaac aaaactatta atcctatacc taaaatgaac    660
catatcgtac tatattagaa aagaataatg tacctcttga tagaaactta tagtaaaagt    720
gattaataaa atatcactag agagatacgt aaatacttcg ttatcataat ttattttact    780
tataaatgaa ctataacaaa aagtatttat atccacaaaa tcaacgttaa gaatattagg    840
```

```
gcgtcgaaga agacgccaaa ctattttaat ataggttacg tttggtatct catctacata    900

acaatctttt gctttcaaat acactcaata aagtaaatgg aatgattttt tgttttctaa    960

ttttgtcatt aaaaacagtg ttttacattg tacttgaatt tgtgacatat aatgatatat   1020

ttctttttac aatacccaaa atcaacagta aaaaaacaaa tacttacttc ttttcattca   1080

aatttttcat atgcttttga ccgttattag cctttagtag tttatcgtaa atagattgtg   1140

atatttttat caagaagttt tattttttaa aataaatttc ctttttcata accacaaaaa   1200

gcacccttgc aaaatcaata tttcattttg gaccgggttg acattaggtg ctttaaggat   1260

cggcccaatc tagattcaat aatctcagta aggcccactt gtaaaccaca aaaaggcatg   1320

gcccaccgag cccactatgc caatagttgg gcctttcttt cgcaaatgca cgcagctaat   1380

taaggcttca ttacttaata atcagtaatt aattttgctc caaaacgggt caaagagcga   1440

cccgacccgc gaatatgtat ctgggccgtt gattatttta gtagtaatct caaccgttca   1500

gtcggtcctt ttatatgtct gtcctccctc gtaatcaatt cttagggttt tctagggttt   1560

ttagttcttc tctacgcttg gttggaagtg cccttcctct cattcttcct gctttactac   1620

aggttttcaa tcttcaacaa tttaaatctc aacatttaat ttgttttgca cattgattca   1680

agtgtgtttt ttttctttcg tttgggcttt tgttgattga aattactcaa gaaattgcag   1740

ccacaaggat agtctaaaaa tgcatttgat ttagtgtagg tgctgctctc tttttgtga   1800

ttgttcttag cttacttgga gctgtatgtt aatgctagag ttcattgagt atcaatgctc   1860

aattacagat agttttgttt tgtaatttcc acatatattt tcgtatttgt gaaattaagc   1920

tcgtttgttt tcattgtttg ttggcaattt atgttttatg ttatgccaac gattcatgat   1980

ttgtagcttg actcgaaagg                                               2000


<210> SEQ ID NO 112
<211> LENGTH: 1027
<212> TYPE: DNA
<213> ORGANISM: Cucumis melo

<400> SEQUENCE: 112

ggggggggtt gtcttcctca aactctgtta tcgaaattag gtttacattt agtatctggt     60

tgacgttttg attgtattcc tgggcctgaa atatgataaa taaatatgac cattgaagtt    120

ggtgtttatt ctgggtttct atcattaaga gggtgtgaac ttacgaggga accaagaaag    180

ggatggaaat aggaatattt agaatagtag gaagctcaaa tgaattattt cgttcgataa    240

ggcggagtga atataaataa tatgcaagga gatgcggaga atattaccca ccttatgaga    300

gagagccaca aatcagaaaa cagtaacaaa tataacaaat caaacaacac catttgcaag    360

cgaattcaaa cgtttttcgg gtatgttgtt ccattaccac attcaaacat gaattgaaac    420

ctgagctctt gggcacttta attttatttt caacacatta cgtttaaatt gccgagtggt    480

caatatcatg tattgcttag tactaggtgg atacaaacct tacatataag gtcaaagtat    540

tgtgggcatg atataaatgc tctagcatat tggtctcata gagtttttta tacttttaca    600

tatccattaa tgagataagt taatgtttca acattaaatt tttagttaat atgaattcta    660

gatgcatttg ttatacaaat ggtctgatgt atttgaggtt ctgaatgtca aataggattg    720

tagtttattc acgttgaata ttgtaaagag ttaggacgtt tttttaagat tagatgatgg    780

gtgccatatg ctaccccata cgccaacaat tataatgaaa attatatttt gtcatttggt    840

atttaacaat ttttttaaa aaataagcta ataacgcata gaattcctga gatttaaaca    900
```

```
actttctgta atttcttttc tatgtactaa ttgttataga acctgtgatg tgcttgtcca     960

tcatgcagat tacaacgact ttgaacataa cttcaaaatt gttgataatg gtagccgagt    1020

ttttgcc                                                              1027


<210> SEQ ID NO 113
<211> LENGTH: 2000
<212> TYPE: DNA
<213> ORGANISM: Cucumis melo

<400> SEQUENCE: 113

agccaaagtt taatatgatt caatcttgca caaatgcagg ttacccaaat ggttaaggtt      60

aagacaggca acaccactct agcagttggt gatggtgcaa acgatgttgg aatgatccaa     120

gaagcggata tcgggatcgg tattagtggt gtagaaggga tgcaggtaaa tttaaaacag     180

atcccagctg gagtgataaa atatagcttt cattcatctc aattttgttt tatacttctt     240

atctttctga atttcaggcg gtcatgtcaa gtgatattgc aatcgcacag ttccgatact     300

tggagcggct gctccttgtg catggacatt ggtgttacag aaggatctct tccatggtac     360

attatgatct ataaatatta ctttatatta gcttcttagt gagaatcatc cagattaatg     420

tgcaactata cagtctcaac atcattttca gcttgaaaat ctttgaaata tgtcgaactc     480

atcgcatttt atatatggca gatatgctat ttcttctaca agaacattgt ttttgggttc     540

actctattct tctttgagat gtatgcatca ttctccggcc aaactgtata caacgactgg     600

ttcctttctt tgtataacgt cttttttact tctctccctg tgattgcttt gggagtgttt     660

gaccaagacg tctcatcccg gtactgtctt aaggtaagtt caactttcct ttatttcatt     720

ggtgcaatct tttgccttcc ttaagtacaa tatcaaatgg ctcattgccc tcaacatttt     780

tggattttca gttctcactt ttataccaag aaggtgtcca aaatgtgtta tttagttggg     840

ttcgaatttt cggatgggtg ttcaatgggc tactcagttc tgtcatcata ttcttctttt     900

gtgttggggc aatggaccat caagctttcc gcaacagcgg agaggtcgtc gggctggaaa     960

ttcttggtgc caccatgtac acttgtgttg tttgggttgt aaactgccaa atggcattgt    1020

ccatcagtta cttcacctat attcaacatc tcttcatctg gggcagcatc attctttggt    1080

atttattcct catggcatat ggagctataa acccagccat atccaccaca gcatttcagg    1140

tattcattga ggcctgcgcc ccggcaccat cattttggat cctcacacta ttggctcttg    1200

gagcttccct tcttccatac ttcgtctttt catcgatcca aatgcgattc ttcccaatgt    1260

atcatcaaat gattcaatgg ataaaagctg acggacaatc gaacgatcca gaatactgtc    1320

aggtagtgag acagaggtca ttacgtcaca caaccgtcgg ttacacagct cggttcgaag    1380

catcaaagca ttttgaagaa ttctcagaaa tcaagagtca ctaggtttga tgattagatc    1440

gtagaaagat tcaaaacatt ttttctacgt aaagtttctt ctcagtgtat atatatatat    1500

acatttatat atttatacaa catgtgtaca taagattctt gtgtagtttt gatctccttg    1560

tagcttaagt gaccattccc aattcaaatg gtcaaaaatt ttcttccttt catgaaattt    1620

ttaggaaata agccaattgt agtattcaat cgtatatttc aaatagtcat tgagaagttc    1680

taactctact atagttctca attataagta tgatggtttt gtcttattca tcttgtagta    1740

gaaacaaaag aataaattta cgaaggatga agcattgtta ttttaattat aatttgggaa    1800

atttggagcc acgaaatgaa atccaatttt gtgccaagta gatgtgcaac aatgggcaaa    1860

gaatcacttt ttctttttca taattttccc ttccaacact caccactaat tcatcacctc    1920

aatcctcttc ttcttcttct tcttcttctt cttcttcttc actcgccttt gggttgaggt    1980
```

tggctctgtt acagtcatcc 2000

<210> SEQ ID NO 114
<211> LENGTH: 2000
<212> TYPE: DNA
<213> ORGANISM: Cucumis melo

<400> SEQUENCE: 114
aaaagagtca tagtgaaaaa agctgagatc ataatagttt caccctaaac acaacttata 60
ataacacata ctatcataat atacacacca aacacagact ctatagtctt cactctaaac 120
gcagattaca atagtctgca ccccaaacgt agactattat aatcttctga ctattataat 180
actcttttca cttatcgccc caaacgtccc ctaagagaac aaagataggt tataaaagag 240
agatgagggt ttatattatg caacaagtat aaggttctag aacgatgtag tcttcaaagt 300
aacgaaagca ataggctaca cgagaaaaat atttttaaaa tatagtgctt tccctaaact 360
agatttcaat gacaaattat tataaaaaat agaatcatta atccaacatg gcttgcatgt 420
cacaccttgg ccaaaactga agacggatgt catactcgac ttcaatatat ttttttaatt 480
aattttcatg tgacaacaca taaatattta aaatttagat tgggttggat tttttttcaa 540
gtgggtccca aaatactctt caaacccaaa ccaacccaac ttgtttaccc atctaataat 600
aacccaccag gttcaagaag acgaaccgaa ccgaaccgat ccggtctaac tttgtttcat 660
acttaagtcg aacttagcgg tacttttggt tcggttctcg gtttccccaa acagagccac 720
tcaaaattag atttagggtt ccgttcgcaa ttttcagcgc atttttattt gaatcggtcg 780
tttgttgaac acgttctctc tcagctggtt tagggttcat cgttctctct tctcgcgcta 840
tatctttctc tctctcaggt tcgtttcttt ctcttaggcc attttatcag aaagatcctc 900
ttcgtttctc cgattttctt tccgtgttcg ccctcggttt ctcagcagac gtaggaagtt 960
tggtttccgt ttagtgaatc tgtttggggt attacgaatg atattttgta ctgggctttc 1020
cgcatagtct ttttctttct aggaatatat gcatctgaga atttatttgt ttggcttttc 1080
tttataaagt atgaggacat atacatctcg attgctaatc cttgattata atcttttttt 1140
ttctatgttg tttgaatctg tttttttttt tttaatttct aggtttttttg aatctaaaaa 1200 tgtatttctt ggatgaattg catactgttg aattagaagt ttattgatta gattgttgat 1260
atttgcccta agttccatgg ataggtttgc gtctttcacc ttttcgtttg ctttttcttt 1320
tggctgacga catcttacat agcctctgct ctaaaaggtg ccatgatttt ttttcctggc 1380
tttatctgag tttgcgcaat ttagatttga agtgatgatt tgtctaaata taaatatcta 1440
tcggccatac tattttttgt tattttgagt ttttcaagga tgactgctag agaatgaaaa 1500
atcttgaaaa cattgtgttt tgaagttcaa ggatcttgta gttttgttct tttctagact 1560
atctcatttg atatagccct ttaaatttaa tcaaaatttg ttaatattca aatcctcgga 1620
cattttaatt atttatctaa atagttgttt aggcattact caggttgccc actattttaa 1680
gcttagaagc ctactctggt tgacctaaag tttgcatgct atttgcctta tttcgcacga 1740
ctctaaactg ttatagacat ctttttttcag ccttcaggta aatgaacaca aaaaggagtg 1800
aaagtctgac ttctgtgtga tggtctttta atcaattata gggattaaga tggttttttt 1860
attcattgta taaatattaa attagaatga tgacaaccaa taatattaaa actgacaatg 1920
gaaggttcct tatattattt ggagtgtaca ttacaacagc ctgattcttg gcttggcagg 1980
ttcctgatca ccttgtaaac 2000

<210> SEQ ID NO 115
<211> LENGTH: 2000
<212> TYPE: DNA
<213> ORGANISM: Cucumis melo

<400> SEQUENCE: 115
aatgtaaata gtttataaac ttaagataaa attggtaatt gtttaataca aatacaaatt 60
gttaaatgaa atgacacacc ttgagcaatt ttcttttcta atcttctctt atagattaat 120
tttatttaat catgaaggtt agaatttctt tagcattatt tatttattta tttattagaa 180
aaagatagtt tgtgtatatt ttatatcata aagtttcaga agaaaccata aaattaatgg 240
agaataataa aaggtgggga tctctaacat ttttgccata aacaaatcac taagttaaga 300
atatgacact aaacttcttc taatttaata ttatatacaa agattttaaa attataaagt 360
aagagccttg aattgtagct aatttaagaa tatgctctaa gttttttaaa atcacttttg 420
ccctacggtt attatttatt tttttgttga aatatgttta atccaaatca atttcaatcg 480
aacatagtca aggatatgac tgcggattcg tatattagtt gattttgaaa cgattaaatg 540
tttgaaatat tgtagtttag gaacaattac aattataaca atcagattca aaattttagt 600
atatacagta acatttaaaa gaataataaa tatatcaaaa tctatcgaca atagacttct 660
cttcatagat aaattatcag ggtctgactt ctctcataga taaattatca gggtctatta 720
gcaatagact aaatccttga tggtttatca ttggtagacc aaaagagttt attagtgtga 780
tagactttac tacataattt gcaatttgtt taaaatgttg ttatacattt ggttgctatc 840
cttaacatta caatccataa catttgtcgt gtctttaact tgaattgatt gttatctgtg 900
ataaaaagag atgatcactt tttgtcatga gatttgaaca attgatgtta aaagtggtaa 960
ttaatgtacc attcactaac caatgtcaat atttattttg tttaataaaa agaaaaagga 1020
gattgtgaca ttagttttat actcttttct aaacataggt ttggtttgtg ttagatttgg 1080
cctacactta gctcaaatcc actctttata aaattccctt acttattaca agttatattt 1140
tcactccaat cataatcttt taaaggataa tatttgtatt agaagatacg acacatgtag 1200
aagataattc ttttttaacc aaaacaacat acaatttcga ggatatgaca aattaccttt 1260
tctattttta actatttgat cttcaagtcc catctaaaca tcaaatgaaa gttgattagg 1320
ttaaagaatt ggacaattag agaaggaatg gagaatcaaa cctctaactt ttaaggaatt 1380
aggtcattca cattttcatt gagctaagct cacattaaca agatcaatat tacttgtatg 1440
tagttaattc agatgtgaat ccttgaggtt tcaaaagtga cactttagtt cgaggtttaa 1500
aaaatattta tatatataca catgttacaa cccaaattta aggtatatat ataaatatat 1560
ataatttaat tatcttgaat tataattacc ttaaattact taaagtaaag attggtttat 1620
ttatgattaa gttatgatga atgttaagta atttgaaaat ttgaagttta gaggattgtt 1680
aattcacttc attgtgggcc tcattaattg gcccattaaa tctccatatg ggcctgtcta 1740
gggcttcatt tccccaagct tccaactgta atggcggcca cagttctctc ctccatctcc 1800
tctcttctta cctacttatt atgttaatat ctacgttttc cagattcatt ttctttttat 1860
ttgtattatt ctaaatctcc agaactgctt agctgctctg gtttttgggg attttagggg 1920
gctcgatctg gtgggtttac ggttaaattt tgcagctttt cgaggtcctt ttcggcttcc 1980
attttgtcgg aagttacaaa 2000

<210> SEQ ID NO 116
<211> LENGTH: 2000

<212> TYPE: DNA
<213> ORGANISM: Cucumis melo

<400> SEQUENCE: 116
acacttgtaa tgttgagcag ggtaacttat ggtaaatttg acatgagctg gcgcacaaag 60
gcctagcatg ctcggagctg tttttccatg gagtcaatgc ttgatcgcat tattggctat 120
attctaaatg aaactaaaat tattgatggg ttccatctgt ttggatacca actttataca 180
caggtgtttt tctatttatg agtgtaaagt ttgatttgct tcatcatcgt atattcaacg 240
tagagtttct tagttaatcc aatccatatg cctcaactat catgctcttt tccctgtaat 300
tgaatgtttt ttttggtgtc cacatggtca tggaggtttt gttctgcact agcttcacga 360
tgctactaaa catgatgatg aagcttgagt ttatttattt cttagtactt tgtgatgaaa 420
aaaaagtaga agaaaacggt agaaaattgg aatggatacg gtacaatgga tgggttgtgc 480
taagtcacgt ctcgtggata caactacaat tagttatttt gttttgtaga tttcatatta 540
gcatttcctt ctgaatagtt gaaatcacca tagaatgtgt actgatgttt tgtgatttta 600
gtgcttcggt ataatttgaa cgctttacaa gtaaaaattt cctcaggtaa acgagtcttc 660
cgaagtactt gttcataaaa tgttcttgtg tgggagagtt gattggagag gatcatggtc 720
aaattcttct tggtgtgttt tatataaggt tttaatgatt ctttgaaatt gtaatgtttc 780
cttagttttt ttaagtgata ctggtgggtt ttccttggaa taaatattaa gggctgaaac 840
ttaggaatta tatggatttg agggaggttt gtggattctc aaatcaaatc aaaccaaaac 900
cagataattt taaattctag aattttgaag ttactatttg tgtttagaaa taaaaagaaa 960
gaatatcgct tctttgtcct tccaatattc tttagaacca aaagagaacc aaaattatat 1020
ataaaagagt cgataaaatc aaatatatat ctataatata gtttattatt atttttcatt 1080
tgctatcaat aagaatttg aaatgtaata tttgctccaa attatattaa aaacagctgt 1140
tgaaatttca acaaaatgag aatttgtact ctggattttg ttattagttt ttttttcaat 1200
atcttaaact atttcttaaa tattctcatt gcgagtcctt ccatttacat agaactaaaa 1260
atggattgag tttggttaga gaataatccc aatcttactc atatttttag gttgattaga 1320
ttggtaattt gattagcggt taagttattg ggttgtattg tttcataaat tcgatagatt 1380
acatcgatgg caatgtagtg tggaacataa aaaataatga aataccagcg gaacacaatg 1440
gagactgaaa aggatagacg atcgaagatg atgaaatgag aagctgacaa caatgagggg 1500
cgtgagttga gaagccgaga caagagggag agagtgagtc ggaaagagat gtggggcgtt 1560
acaagttgtg ttgaacaaag tgaggtcaaa tttaaattta ctatttgcta aattaataat 1620
aaaataaaat ataaatataa acatataaat atatatatga ttgggttggg ttgatacaaa 1680
atttctaacc ctaactcgat aaagcaaaat gcaacccaaa ttttaaatta accagatcgg 1740
gttattctta tcctaacctt aggacagtga ttacttaatc tgtacgcagg ggcaattttg 1800
acctttgata aactctccca ttttgttttc ttttttcggc aattttccct ccctctctag 1860
tctcttctgt tctcagttca gctctctagg gttttgtcga acagccattt ctaagtgtac 1920
atctcctctc aatttccctc gctttattcc attttttcac gtactatcgg cggatccttt 1980
gagctccaac tctctcatcc 2000

<210> SEQ ID NO 117
<211> LENGTH: 1025
<212> TYPE: DNA
<213> ORGANISM: Cucumis melo

<400> SEQUENCE: 117

```
tttttcttac ttcattatcg aacaataatt tgatttccaa gcgacccttt caaattcaaa     60
caaacccatt tctcctctca gccagagcaa gtgattgaac tgctgcgctg cgcgtgacct    120
gttatcttct ccgtttttct taccgccgcc cgcccctcac ggcggagtag tttcaccgcc    180
gacccatttc gccggccgcc ggcggtgttt cgattcctct tgttttgtcc cttttcgtct    240
taccagtttt ctctctgtct acattgtgtg ctcgttaaca gccagctgta tagccactgc    300
tttttttatt gactcttgaa acagagagat aggggagatt ctgtatagtc ccactgtttc    360
tgctcaactt tttcggttta atgtctgttt ctatattcga ttcttcgttt tatgttcgtg    420
attcgatatt gcttttgctt ggaatcgttt agaggcaagt gattgtctct gcttttgcta    480
tgtagttact ctgttttttt tccctttctc tctctctctc tctccccccc tctttctcaa    540
aagggggttg gttttttat cgtcggagga tgttgggttg atcttttgat agggtctgtt     600
gactaattta gctggtgttc ttggtctgct gaatccgaac ttctcttagt tttagagttt    660
tcgatgttgt tggtttacac tgattcttct tcgtttgttt gggattattt ttgacaggac    720
tatagtgttt aactgctagc tgccatggaa catgcagaat ctgcggtgag tttttagaat    780
aaacttgttc ggttggtgag aaaagcatgg gaaagaggag ggggaggttt ttctttatgt    840
caaatatttt ctcaaactca ggttttagaa taaaaaagcc tttgtttctt aaccaaatag    900
tttatttgat aatcagctgt tttgttttag ctccctcatc tcattttcgg aaatcttagt    960
tatcagttta atcaactctg tgttctatga tgctcatttg tacttaggca aaggttataa   1020
agaac                                                               1025
```

<210> SEQ ID NO 118
<211> LENGTH: 2000
<212> TYPE: DNA
<213> ORGANISM: Cucumis melo

<400> SEQUENCE: 118

```
tgcattttat cagagatgaa attgaaaaag gaagaataaa cacgtactgt aaaatcaaaa     60
cataagaaac ccagctgact tagcttgtta attaaccaaa caaagtttga gcattgtcta    120
aattaaagtt gttcaacttg actgttgtag ggttattaat ttttcttgaa aagaaaacgc    180
agcatataat attaaaggag tattttgtct cgagggggaa gattattggt taaaagtata    240
tatggtgtga cataattaaa tactttgtaa ctaaaaaata aaacataatg ggaagttatc    300
tctaccaatt tttttgttaa agggctgaat atataacctc caacattact tagttactga    360
tatatcagtt tctctagccg tcaacagtac tacatagttg ctgatcataa atagaagaaa    420
caagttagaa attttgtgaa gagaaaggcg agattatgtg atttttgctt tgtataattt    480
tgaaaaccct tgatataagg aagttccttg ttgctgcatg ccttcttaga gatcagcagt    540
tactgtatgt ctatatataa ttctctctct caatattttt ttctgttctt gagcttgatt    600
gtttactgct tcagaaatct tctttacaac tactactgta tttggaagtt ttagttccat    660
atatatttct attttttttaa tgatttcaaa tcttgttgtt tcaaacagta ctctcctaat   720
tacaaataca ataaaattat atctagcatt acaattttac aaagtccttt tcttgtgaaa    780
aataaattac gtgagacttt gtaaatggta ttttgaatgt attaaggtac tatatgacac    840
ttagaattgc tttgctttag ctctaaccat gggttcaaat gtaaagttaa aaataaaaca    900
atcaactatt taaggtttta cttaaaaatg taattatttg tcaaaataag cataataatt    960
gagtagtaat ttacatatat tgcctccaca tttgagatca aaactagaga tgttcatttt   1020
```

cttagatata ttattaagct aagaatgaga gaatgggtga ggggaaaagt gaacggaggc 1080
aggaagacca aatcacccat tcctgaaaat ggaaggatta aaattgcaat tttccttgca 1140
atttaatacc aacatgattt tgtatatata tatttgaaga ggggttttaa aaaaatataa 1200
caaactgtta aaatatttac actatataca acaatcgtta agataaaaaa actcataggt 1260
ccacaatgaa aaatataaca aatgtcatag tcaacacgcg attaatcagc cacactcacg 1320
ttcgagtaat cttcttctga atgattgtgt attacagtca aaatacacaa tcgtagagtt 1380
cttttctaat gatgttgaaa aatacttcaa atttagggtt tagggtttag ggtttaatga 1440
tcgtgttaac cgtgaaaaat aatcgtgtta atcaatggaa aacgatcgtg ttgattatga 1500
taagtgatcg tgtagtccaa tgtaaacgat cgtgtttgac tatgttaaat gatcactatg 1560
gtaagtgatc gtttaaatca tataaacacg acgatcatgt agttcttttt aaaagatgga 1620
aaaagaattc aaatgcaaac gttcgtgtta acaatgacaa atcattgttt agatcatgtc 1680
aaaattaata tttaaacgat ctattgatat tcttaaatag gaggaagatg aagtagttct 1740
aaagaatact gtcgaaaaca ataaagatag aatatgatat ttaaattaaa aaataaatga 1800
tatcggaaga gaagatgaat aaatcagaga aacagatata aaaggggaag tgactgatcc 1860
tccaaatcta aaagataaaa atattttaca tgactctgta aactttggtt tcttttgcta 1920
ggcagtaaat atttgagggt tttggtattg tatttgtggc ggaatggagt aagtgggcct 1980
ggcattgggc cgtatacgta 2000

<210> SEQ ID NO 119
<211> LENGTH: 2000
<212> TYPE: DNA
<213> ORGANISM: Cucumis melo

<400> SEQUENCE: 119
tcattccaga aaaggtaatc tttgattttg agaagttaat ttgaatttta ttttaaggga 60
attcaggcag caagattaat catctggctt cctggaaaaa ggtcaagttt tctcaatcag 120 aagggggggct aggtttgggc agtttaaaaa ataaaaaaaa taaggccctc tttctttact 180
aaataaatgg tgttggaggt ttttgaaaga agactccaca ttgtggggta agttatcaaa 240
agtatccatg gcttcaaaaa aatttaattg gcagactcta aacaaactag aaaatagcct 300
tagaagttcg tggatcatgg gaaagttgag ttggcaactt tcaaaacaga gaacgaaagg 360
agagtaactt tctggacaga ttcgtggatt agtgatctcc ctcttaaata tccatttcca 420
aatatattca gattagctca acaacccaat gattcaatta ctgcgcactg ggattatgtc 480
actaattctt ggtcattagt attttgaaga ttgctaaaag atgaagaaat tcaagatttc 540
caaaggcttt taacactcaa atcctagaaa gtaatagact tggatgatag aagagtttgg 600
tcattaaaaa cctcaggcca tttttcagtt aagtcccttt cgaagcacct ctctccttct 660
tcacctttgg aaaaagatta ctttaaagca ccttggaaaa ccaggagtcc aagaagaata 720
aatgttctgg tttggattat agcagtgggt tctctaaact gttatgagac tatataaagg 780
aagcttccta atatgtgttt actaccttta gtgtgctcca tttgcttgaa aaacagtgag 840
ctcctaatac acttattcat tttttgtccc ttctcatcta cttgttggtt tagcatattt 900
tctatgctca aacaacttgg gtctttgatg gttcattaaa caccaacgtt gttcctaatt 960
ttttaggggg tccttattta tatatatata tataaaaaaa acttttctaa tttgggttaa 1020
tttgataaaa gcactcctag ctgagatttg gtttgaatgt aaccaatgca tcttccatga 1080

```
taaaagagag agagagagat tgggttgaca ttgtagacaa ttctaaaaga aacgtggtag   1140

cttggtgttc ttcaaatgca gaattcaaat gcaggatatc tacttattgg actaccttca   1200

tatgaagaga ttcaatgcag tttcccccga ctactagttt agaatttgtg tttttgtagt   1260

tttaatgggc tgtaatatgt atttctacct ttaagttttt acttttcagt cttgcttctg   1320

tctaccatag gtagtattgt tattttgggt atttactttt gtcttttcat gaccttagtc   1380

ttgttcttgt attttggata taatgagggt gctatcgggg tatcaaccta gttgagatgt   1440

tcgagtgcac ctactgatcc ccttatttgt aggcttctct attattctca atgtataact   1500

ctcttgtact ttgagtttat caataataaa gaagcttgtc tcattctaaa aaaacaaaaa   1560

ggaaaaggaa gataattgct cctaatcgtt gaaattacta ctaattactc ttaattactc   1620

caaatgatcg tataacatac atttataatt tttaactttc ttttcctttt taaataccaa   1680

cattaaattt taaatacatc cattaatttg aaattagttt tcaaattcca aatcgaaaga   1740

tttaaagtcc tttgaatcca aagggagaat gagcccatcc aagcaagttt ttgtgtcgta   1800

gttgcatatt ttaagtcgtt tcatattagc ctcgagtttg gcttaatgac ttggtggtgt   1860

ctagtgcagg cttgtggcga ctggcgagcg tggttctaaa gataaggttt gcattcgctc   1920

cttctccctc cctttcacta cttcatatcc atttcctttc tcgatttctc gtcttccctt   1980

ctgaattccc cattccagcc                                               2000
```

<210> SEQ ID NO 120
<211> LENGTH: 2000
<212> TYPE: DNA
<213> ORGANISM: Cucumis melo

<400> SEQUENCE: 120

```
atttatttgt ttagagataa gacgcacatg agaatatgag atggattcca ctccactcac     60

actccaattt ctacctatcc tattactgtt tactattatc attccacccc tcgacccctc    120

attcttcttc tcaccttact tttttatgat ttactactac ttcattttgg atcacaatct    180

gatcaatgct gggtgggctg ccctcggcct gtcaccaggc ccagcccact tccaaattaa    240

acctcttggc ccaccgccca ttgtccccat cccattccat ttaatattcc caaccttccc    300

tttttctttc ccaatgcgat gcttctccaa tataccttc ctgccctcca tgtttccttt    360

ttactgcttt cttatattta taacacacct tctacagtct tttggctggg aatgctgcgt    420

atgtgaatga gattcaagat ttcgttgatg ttatttgagt ctctatattc ataagttttg    480

ttcttagttt tctctagacc aactgcaaga gttagcgttc catatgctca taagtttcag    540

atttctgctg tgtggtttga agacagtcat cgatccatgg gtgaattcgg ctttttatta    600

ttattattat tattatttat tgttgtctta cttttctatt tgaatcttcc tatcttttta    660

ctcattgttg gactctaata attcttgcta aacacaatct ccatttttat tggacatttt    720

aaatcccatc tcaactcata attttagtta ccttccacca tcaccatatc caaatccgaa    780

ataaactcaa ataaaatcct tcacgtgcat gtgctctcca tatatttttt ctacatggta    840

aaaataaaat gaaaacaatc taaatttaat aaaataacat atatggcaga cttttattga    900

tgtagagact gggtgttgta caagaacagt gcagccaaga aaaaaaaaat acttccaatg    960

aatcgtacat tttaaggatt atgaaactaa ctagttccaa ccattttttc acgaccacgt   1020

gcttgttaaa cacgcaagta gaatcaaaat gtgggcttct tcgctttata taactgtgaa   1080

tcattctcca aaaagggaag gggatctcat tccctaattc aataaagaaa aagaaaaatg   1140

ctagcgaact tcatccatct cattcctttt acctatttca tgagatgccc attgtatata   1200
```

```
agtatttttt ttttttttat ttcattttac ttagtttact cctcacctct aaaaaaaatt   1260
aggagagttt gctaaatcca ttctcaaact tagctttatt tttttaattt tatttaacct   1320
cgtcgtggat gttaacctca aatgtcagtt ctttttattc tatttattga tgttataatt   1380
tactttagga ttccaatttt ataaaaataa gaatacaaat aaagataaag agtgtgaaag   1440
ccagaaagaa aaaaaggaaa tcgtaatatg ggtaaaattg gtacaaattg ggtcccgtta   1500
aatattaact caaaaaatgc gagaaaatgg tagaaaagga aatagggggt aagagcaaag   1560
tagtggaagg agagcattga acatattctc tagtttttgc acttggatct aaacacgagg   1620
aattataggt ttattcattt actaattaca taaataggat tggattttaa aatttgaccg   1680
agtgattatg catatttgat agagttagaa aatagtggtg gggcaggtac aagttacaag   1740
taatgtataa gagatatgat gagcatatta ggaaactata gatttaaatt cgtccgtaaa   1800
taaataatta gaaatataat attcgagtgg aagggtatta gggttaggcg aaaccaattg   1860
cagttgcacc tataaaaccc cttttacgcc tccacccgct tcaacagcgg tctcggcgtc   1920
tacaactaca cactacacac tacacactac acactacaca gttgcagacc agaagcataa   1980
cgtaacgccg gtccacaaaa                                                2000
```

<210> SEQ ID NO 121
<211> LENGTH: 2000
<212> TYPE: DNA
<213> ORGANISM: Cucumis melo

<400> SEQUENCE: 121

```
tgaagagccg gaaaagcatg gcaaggtcaa ggcatttcag caagaatacg aggatgaatt     60
ctgggtttgt aagtccggtt cttcttcgga gttgtggttc gaatttcaaa cggccatgag    120
gagccctaca gcttaggaag cttcaggtct gagactctga ctccgacaga aattgctgat    180
ttttgtgtgt gttttgaata accattgtat gagtatgatt ggttgtatag gtttgaaatg    240
agggaaagtg atccatctcc ttgttgtctt tgcaggaaag gctcatattc gaccaagaac    300
gctttgtcat tgctttcgat aatcatagaa tccacaatgg tttggcatat tagcaaacaa    360
atcttcttta ggcattgcag acagaaaatt ggagagtaag ttattataat taaggattct    420
aaatgagtaa gaataataag atcaggcaaa gattggaaga actaaagcgt ttagtatttt    480
gtgtggtaca gaagaattgt aattagatac gtagtctaga gaagcagatg gtgagatttg    540
tgaaagacaa atgttagtgg agagtgaaga gtgtttctca acaaccgaca tagaaggatt    600
ctcagaaaat gagaaagatt tttattgcgc aaaatagctc ccatatcatc atatgccgtt    660
gccattccct ctggggttgc atgtaatgag taatggaaag ctgtagacag gctaacttca    720
ccctttgtct tgggtatagg gtgcattttt ggtcactcca ttttaagttt tctaataata    780
aaaggatgaa gaaaagatat tgaaaaacag ctcaggtttt aaagttgtca cacttgagaa    840
taatgcattt aacagttaga attttgcatc aacgtctttc aaatagaaaa gtaaaggaga    900
gtctagtttg agctggatag ctaaactggt ttaatcatat cttctatcaa gtggttagag    960
ttttagacct cccaacttta tatgtcgttg ccctaacaat gttgatggat gtttagtcct   1020
aagctctaac attgtccccg tatcatattt cataatagaa tgtactgagt aatggaaaac   1080
tagagaggta ggaagttgga cgaactttga atctatattg attttactat agtctttctt   1140
ccaagtctta atgagagctt tagctaaagt ttttcaaaaa ctcaaaagaa gtttttgttt   1200
tccaattctt cgatccatag attgtcaaga tggctataat atccttgaag ttaatagcct   1260
```

tcaaagtttc atagctttta tcctatgatc tttagaaatt caagagttat attctttaga 1320
actacagaac tttgatcttc gattcttcac ctcttccaga acctttatag tagagtttct 1380
tgaccttaca tgggcttggg attgggcctg gctacttatg ggcttagaga ttgaccttgg 1440
gtttaagcac attcgtttta cttggcccaa ttttcttaaa cttctgcaaa atcctaatta 1500
actaacacct caacaaaagt ccagtattaa atggggcata taaacaaaag ttaaacaaaa 1560
ttgtcgtaca gaatcctaat ttgctaacct cagcaaattt tatgccattc gtccttgtgt 1620
atctaattag tgttaatttg aggaaatata ataatataga cgtaggacgg atattggtat 1680
ttggtgcaac atcctccgaa ccaattcctg gaaagtaatt ggggcaacaa gataatgtta 1740
tcgtcagttt caagtgcaaa acttgccacg tggaacagcg gcaacatgat atctcaaata 1800
tggacctctc acccggtcaa gcttccacca ccaccaccac ctccgtattc taaaataaag 1860
tcaggaacaa gaacagacac accttaacaa aaccaatatt cttcatctct atctctctct 1920
catttcagca tagaagagag ctgagtaaaa ggaaaaaact tcaatcaaat ttgacagaga 1980
agagcccaag agaaaaccaa 2000

<210> SEQ ID NO 122
<211> LENGTH: 2000
<212> TYPE: DNA
<213> ORGANISM: Cucumis melo

<400> SEQUENCE: 122
agatgaacca gaaagatgga aaatctactt ggggttcagc agtgagtttg gaaaagagag 60
aactatttga agaaagagca gaaaccatct tgctaatact taaacaccgc ttccctggaa 120
ttccacaatc ttcactagac atcagcaaaa ttcagttcaa ccgggtaaaa gaacgctcct 180
tccttgtcta taatctcatc taaaattatc aacaatccaa acacaattta tacaaactaa 240
aatgaaagct tctcaacttt aggctacaaa aacagatgct tattataatt ctgcccaaca 300
atatcttctc ctaaataaga tgatatatgt tttttgccca tataatcaaa taggaaataa 360
caatcctgtg cccatttctt tggagtgtga gatcataaaa cactgtctaa aacaacatgt 420
ccaaacatat cgtaaatacc tagtttcata gtgtgatgaa ccaccacaaa caaacttact 480
ctttggtgaa ctgcaggacg tggggcacgc cgttttagag agctactcca gaatactgga 540
aagcttagcc ttcacagtga tgtcacgaat tgaagacgta ctccacgccg ataggttaac 600
tcagaaccca tcacaaatag caacaaggag gaaaccgacg agcgaacccc caatggagaa 660
atcagaagag ttgaacaaca acggcccaga aacgccagct tcaatgacgc tgttggattt 720
catggggtgg ggacaggatc aaaacgagtt ggagatgaag aaggaatggt ttgggaattc 780
agatgattta aacgcggatt cagatctgaa acaagggaat aagccaggga atatagtgac 840
gaacaagagg gtttcatacc tggagaattt gagcgctgtg agaagtccaa cggcgcgcca 900
ttgaagaaga agaatagata gagagatgat ttggaggcaa aattccatga tttcagttat 960
atacattcct tttgtgtaaa taggaagaag aagaaggaga atgagatcaa ccccattttt 1020
ttctctcttc ttttttaat ttggattttg gaatcacaac tctttgtgtt tgtgtaaaac 1080
caaaattgtt ctatgtatca tttgtatcaa ttaatgtagt cattttagat tcatacattc 1140
aaaaatatca actccatttt ccaactacta tcttcctcca tctcacctct aatcataatt 1200
caaagcggat acaaattcat gttagaatga aagattcgag tatagcctat tccattgatc 1260
aaatgcatgt atctatacta ttgacacttt tcaactcaag tcatgcttga acaattgttt 1320
tttataaatg ttaattacaa gagtgtacac aaatcgagtt gggaaaaaat atgaaccaac 1380

```
ccaaaccaaa aactttgagt tggaccgaat ttgaataaat aattcaattt tcattatttt   1440

tatatagttt ttcaaccaaa ttttttatct tttttttctc aaatttcaag tttacaataa   1500

tgtccattca aaagtttaaa ttttcatatt tcgaacattg aagttggaag gtccaaacga   1560

aagaactaaa tgattatgac acatgtctag ggtttatata tattgttgag ttgagtaatc   1620

caagtttttg aaacaccact agttatttat gttaaataat taactgagta ctcgactttc   1680

ttagttcgag aatatttttt agaaaaaaga agagaggatg tgtttagaaa taatagcaag   1740

ttagggtgtt ggtgagtgag aaatattttg ggatcttctt gtaatagtta ttaagaagat   1800

ttttcaaaga atttgagagt taaagaaata ataataataa ataagtaaac atttaatagt   1860

aaacgacatg tcgttttata cagcatcgta tttacttacc atgtgctcat tcacacacga   1920

ttcctcctcc tcctcctccc gttcatctct tcttatcttc gtcttcttca tttcggataa   1980

cacaaaaatc cctaaaaaaa                                                2000
```

<210> SEQ ID NO 123
<211> LENGTH: 2000
<212> TYPE: DNA
<213> ORGANISM: Cucumis melo

<400> SEQUENCE: 123

```
tcattttcgt ttggttaaag aatatatcat cgtttctttt ataaaatgtt tttgtagaat     60

taatcttcga gtacttctca taaaaacatt ttttttaatt acatagagtc agtaataatt    120

agaactatct caaaccaaag tactataaca tttcaaacca taacactgta tttttttagaa    180

aagttattgt aaaggataga attacaaaaa tattatagca tatgaaacat tattgttata    240

ttttataaat attccatata caatataatt gattctagat gtctctaaaa atagggaagc    300

atatgtgtta ataactaaat ttaaaaatta aaaaattact cgattactgt ttatttattt    360

atgtgttgag gctatacata ctatatttta gtaattattt taaaattaaa aacaaaatca    420

catggctaat agaaacgata gatatctagt agtaaaattt tgttatattt ataataagtt    480

gtcttatttt acttaatgta actacaaata tctcactgtt attttccttt ttttttcagc    540

ttattggttt atatgtttag aaaatttggt aaaatatttg tgtagctgcg gttatcatgt    600

atcaacttaa ctatgtaatc tatgaaaaaa tagtcattct ttaaaaaaaa aatgaaaagt    660

taaaaaagaa aaaaaggata aatttataac aatattcttt aattgaattt tatcatttga    720

ttcaaagata ttcttatact tttaaaagct gcaatgttat ttatgaaatt gttttaaaat    780

tacatttata atgaaaaaat ctttaaaaat gtagaaaaat caaggcttag aattgtattg    840

tcatttccat caaggagagg atgtaatttt ttctttatca ctttatttga atcctcaaat    900

tttcgataag tatatatttt gacatttgag aatatttttg tttactttaa atttaaagtt    960

atttttaaaa caaatgaaac aaaatattca taacgtggat caaatcacca taatttagaa   1020

agcgttcttt tgaaacatga ccccaaaact ttagaagata aattacaatt tgaactattt   1080

tgaaaatggt agcaaggaga caggtaaaaa aagaccacat aaatcacttt aggctttaaa   1140

gaaacaatgt taattggaga aagattcatt ggcatataat tttgaaatat gattgtattt   1200

tatatttcaa atcatattcc atgaatttat ctatctttgc ttgtagtcta aatcatgcaa   1260

actttgaaaa taacaatgtt attgtatcaa aatttaaaag tttaaaacat ataattgatt   1320

aaataaagaa aaatatttag aaatgttgta tgccaatagg tattatgtaa taaattataa   1380

atgatataat attaaaaaca ataattcata ccattttttta aacataaaaa catgcttagt   1440
```

```
agattagtta taaacagttt caagtaatat ttaaaagaga gtcataagta gttttataat   1500

ttataaaata caatatcaaa cgtacttaaa actaattgct tttaacttca aatctaaatt   1560

aagaataaga aaagggagag tgggaaagag caaaatgaga gaaaatgtcg aaaatacgcc   1620

caacggttcg gaccggtcca tttttgtccc gcgcaatggt aaaaatagat taggttacga   1680

caatcaccat gatgatgagg atgatgatga tcatagcaat tcaagaagca tagggcccca   1740

cttttggccc tcttattttc tcttctctta cttactttaa agaatctaac tgtcctccat   1800

taccccgccg atcaatgctc tatttttctc tctctttttt cttttcttta ttaaacaata   1860

ataacaaaaa ccatcaaatt ttcaaaattt tgaattatat tcccttaaca caaaacactc   1920

tcctcttttc ctttctctta taaatacaag tggagctcca cacacttgtc attttgtacc   1980

cttcttcccc aacctcccaa                                                2000
```

<210> SEQ ID NO 124
<211> LENGTH: 2000
<212> TYPE: DNA
<213> ORGANISM: Cucumis melo

<400> SEQUENCE: 124

```
gggcttccat tggcctcctt cccgtcgccg tagtgagaga aaaaagaaag aaaggggaga     60

ggcagaagaa tttgagagat ggatcgagga gaggttttgg aatgaatggg aaatttgaag    120

gaagaggttt aaacataaaa gtgaggcacg tgcgagaatg caaatattta cggggctaaa    180

aatgggagag ccaacggatt caccccagta aaaaggtaaa ttcaaacacg tttatgcctt    240

tttacctttt tctttctttt tttaacacct atagatgtaa gatatttcat attcttaact    300

ttctctttct cttttctttt ttgttttact atttcccttt cgttggctaa taataaaaat    360

tgatggatac agtatatttg gtatgtcatc ataaatttag agaaggtatt aagattttgt    420

gacataaaaa cccaatttct tttaatgaga ttcttagaaa ttttattgaa gagaattata    480

aactttacgt aaattaggta aagtctttcc ctccttctcg atagaagttg ataataaaca    540

tagcatacct agataaaagt ttgggaacat ttttgttgtt tggagggttg aaaaaaatta    600

agaaatttca atttggttag gatttgatgt cttgattttt tgaaatataa actttcaatt    660

ccaaatggtc ggacttggaa cctaacaaat cgtgttttca attttacctt gatattttag    720

atgtgtgaga ctccattaag tattctcttc gctctcttct tactatttct ctgttttgct    780

atcgaacgat attttttta aaagatttat tttttaattg gtggaatgtt tgtatgagag    840

tatataagtt aaggtaaaca aataataatt ggttatttag caatcttcct agtcaataag    900

caaaacagac ctaacatgca tcaaagaaac aaaatcaaaa ccttaaaata tcatggttgg    960

gcgttgattt ttttttcttt ttaatgtttg aaaatgtggg ctttgggtgc cgcagtcgta   1020

tggttgtagg gatttctttt aagaaaatta ttttatattg tattcgtttt gatctgaaga   1080

tatcaattat acaataattg gaatataagg agtaatttaa ctttgttcgt gattgttttc   1140

tactttattc gatgtgtatt ttggaattaa atatgatttc aaatgatttt gtttatttct   1200

ttttattgat tttgttttga ttttactttg tatcaatttt gaatatcaat gtagtgatgt   1260

gcttgtatta aatgtattgg ttgataaatt tactatgcaa attttttttc aaaatttatg   1320

caattcattg tagtattatt aactatatca acacatcagt aaagtgaatc attatcaagt   1380

atatcaatta agttacaaag tgtatatatc aataatgtat caagtttatc agtagcactt   1440

taagcatata aagtgtattt aatcaattaa ctgtaccagt gaatcttact agatgtattt   1500

gcagtacatc cgacgtatca aacatatcat gtgtatcata tgtttaaatt tgttgagtat   1560
```

attagtgaaa cataacaagt ttattagtag tgcatcaagt atatcaaatt tatcagttaa 1620
acatttaagt ctactaagaa aaaatgagtg caataaaaat tatttttcgg atatataaaa 1680
aaatattgag tgtatcgaag agttccatgg tgcatcaaat atataaagat aaaaaaatat 1740
caagaaatat taaatgtata tccatatatc aagaaacaaa cctaacatgt atttcgtgat 1800
ccaacaaccg gactggaaga caaatttcgg cccgggactt tcatagtcca aataaaggcc 1860
cattaaactt aacctgggcc caaattaatt tgtaaatttt aagtataaaa agaagagaaa 1920
ccctagggtt tccttcattc accaggcctt cctatcccct tcccttcccc ccctccccat 1980
tcccattttt gccggccgcc 2000

<210> SEQ ID NO 125
<211> LENGTH: 2000
<212> TYPE: DNA
<213> ORGANISM: Cucumis melo

<400> SEQUENCE: 125
ggacttatgg ggaatgggtt caagtgatgg taactagcta cttcagattt aatatcctaa 60
attgccttgg caacccaatt caaatgtatt aggattagat aggtgttttg tgaggatagt 120
taataaggtg cttgcaagtt ggtgtcgaca ttcccaaatg tgaagggaaa aaaaccccaa 180
tctttggtct caactggact ttggttcatt gcagttgaaa ataaattatt ttagttcaaa 240
ccaataaaac acatttttta aaatctttgg atatttgttt cttaaagttc ctgaaacagc 300
ccaccaagtc catagcaatt aggaaggcat aagttagagc tagtatgctt ggcatggttg 360
ggggtgggtt accttgttat gtaaattcat agaaatattc atatcttgtg ctaaaagtca 420
aatggaaaga gggtgattgc tgtgatgctg tctaatacaa agtgctagaa gccatatgga 480
gaaagggtat ttctacagtg tctaataagt taattacata ataaatttct aggttatgag 540
aatccaatcc gcatgaattt aaggactgca cacttgctcc atttgcaaca tgtgtaccac 600
tttagaatca tatttcacct gagttcatta ttcaactaga ttaatgtatc tcttttggtg 660
ttacatgttt ttaagaacat aattatttta gtttactgtc ggagagaagc aagtactggt 720
tatgcatggt tctagtgagc ctaatagagt aaggctatgg tttgggcatt tggaagtttt 780
agtggattag aattttgaag gcaaagctaa ggatcataca cgcccttctt cccttttgac 840
cagttggaga tctatcatgt aactctattg tcttgggctt cggccttatt ttataaattt 900
catatatcaa tgaaatttat ttcctataaa aaaaagaaaa aagaaaaaaa gctaaggatt 960
ttaatatcat tgttagtttc tttaattttt ttctttggga agtgtgcatg tagagctcct 1020
ttgaaagaga aaaagcaaag aactcttgaa tgtaaaatct ctatgtttga gttttatagt 1080
agcgtaccac attcacttca tggtgatgta gttatagttt tcctatggaa tatggctatt 1140
aatttttgcg aggctcttat tttatagttc ttttggggtg ttctttcctg taccccctcc 1200
cctttttgtg agaaggggag gtttctgtgg ctagctgggt tggtttagat ttgtggacct 1260
tttttgtgag aggaaccata gaacctttttg atgaggacct cgagcactat ttgatcattt 1320
ataagtttcc ataggctttt gtaattacct ttttggtctt attttaattg gagtcccctt 1380
cctccccttt tgttggcttt tttgttgtat ggttgggcat tctttcgtta gggaagtttg 1440
ataattcaca taataaacat acaataaaca accatcaata caatcaacaa gcaggattag 1500
tgtaatactg taaatgtctt ttattttctt tactcctttt ttcttttgag gtctatgata 1560
attgatatcc aacagtgtat tggccaaaat gatttatcat ggtcagtacc ttaggggttt 1620

```
gacttccaat ccaggattta aggtttgaga ccagatattc tgtgcctcaa ggccctcaac   1680

aaccttctca tggctttttc ctgtatacat attattatat aaagttataa ccaataaaag   1740

ggacaggtca aatcctctta atatatgcga aaatcaacct aatgtctact gtataccttc   1800

tcaatcgcca ccttcctcct gctgtcatcc aaggtagggc cttattgtat cagctagctc   1860

cctttactta tttatttatt ttttgaagtg cgcagtttgt ttgtttacct tgttatagga   1920

aattcaatct attctcattt tattggtgca ttcgtctcag aaattcttgt acggtttcag   1980

gttatcatct acccttgtag                                               2000
```

<210> SEQ ID NO 126
<211> LENGTH: 1397
<212> TYPE: DNA
<213> ORGANISM: Cucumis melo

<400> SEQUENCE: 126

```
tatatatatt aacttttaaa attttgaaaa cgtcatagat aaattatata caaaataaaa     60

agtttgatta tttacgaaag ttaaaaagtt tatccgaaag ttgactcaac gataaaaaca    120

ctaaatatca cttttagaga tgatgatatt atacataaac atacgaactt acgcgtcaaa    180

cttttatact aacacaagat caaaacaact ttgttgagta gtgagaattt tatctgctga    240

tatggttgaa acttgggaag caagcagagg aagttccatt cattaccaaa atccattttg    300

tattcatcaa aatatgaagt ttagcgactt gataaagtca agtcaagtgg tcctatcgat    360

ttgttaatgt caatgtttgg ttttgaattt gatacctatt agacaatgat atataatttt    420

aagtatggtt tacactgtga tgctttatat atttttaaat gtaaaatatt agaacttgta    480

atttcaataa attttaaaaa tgattttgtg ttatttcctt ttttaaattg aaatatcaat    540

gtatcaatat tgcgtcatag agtattgcaa cacaacctta tgttaaattg tttattgctt    600

attgctctaa ttcaactcct tcatcaaatg tgcacagaat ttaaacaaga aaaagagtag    660

gtgctttttt actaaaatat actaaaagct ttttatacca aatcttatga caaaatcatt    720

ccaacaaaat gactatttaa atataagatc gaatccctaa tttaaaaaaa aaaaatcaaa    780

gatgttaatt tctattatta aactcacttt agcgtagcta acaaaaaaag gaaaaatgag    840

aggctacaaa gcttgagccc tctgcctccc tttattgcat tgtttgaaat tagatcaata    900

ctttgtattt ttttcaaaat gaaaaatcgt acatagaatt aattctatgg acaaaaaatc    960

agagaaggaa ataatctaga ataaaattcg atttttaacc caaaaaaaaa aaaaaaactc   1020

gattctgatt tttgtaagca atcacccaaa ttaccataaa taaatggtat tcaattactc   1080

aattatggat attttagaaa tgataaattt ttattcataa actcttttct ttctctttca   1140

aaaagaaaaa aattagcata aacttcaatg acatttattt attcttcttc gtttggagtc   1200

aaaagtttaa attgagcatc agtccagccc aaaagcccac gaagaagccc aagaatcttc   1260

agctttttcg ttcaaacgtc cctttttggt ttataaaatt aaagaaaata aaaactaaat   1320

ttatttgtta tttaacaaaa catttttggt taagacattc tctttgatta tttttcttcc   1380

attcttcgtc gtcaatc                                                  1397
```

<210> SEQ ID NO 127
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, c or t.

<220> FEATURE:
<221> NAME/KEY: unsure
<222> LOCATION: (1)..(2000)
<223> OTHER INFORMATION: unsure at all n locations

<400> SEQUENCE: 127
tttatattta tgaaaatgaa gtctctaaac aatttttcta ctcccaaatt tgttgatttt 60
tctgcctatt ctttatcggt gctttaaaaa atgaaaccaa atttcaaaac taaaaaaacc 120
aagcttttaa aaaaatgtta ggttattttt gaaattcaac taaatgttga actcttttac 180
ttattaaata ggcaaattat tgaaataaat ttagagcaag taagcttaat ttttaaaact 240
aatatactta ccaaatcgag gactaaaata ttcaaatact ctttaaaatt aagattaaca 300
ttaatcactt tgttatgttt aaaaagttgc agtgtcactt gaaccttttt aaattaatat 360
aatgaaaatg aatccaactc aatatatata atatctatat tattaatctc gatgtcagat 420
gtttgatacg cacatatctc aaaaattata cctcaactaa catcggtgca cgatgtatta 480
tttcgtgagg ataaaaatcg tttttagtat aaattgatgg aaagattatt tgaattactg 540
aaaaatgcac cggtacatta tttgaaactt ccccttcatt taaagaggct aatattagaa 600
aaagacacgc tgaggctatt tttacaatta atgtgggctg ttgacttggc ccagcccaaa 660
acataaaccc taaagtagca caaacaaacg cctctttctt cttgaaaccg catattaagc 720
gttttatcac ttctcaccac ctctcattcc tcctcttccg cacgttgttt cgctcctcaa 780
cgggagtgcc ttccctttgc tctccctcca ggttcttctt ccttctcatc tcatttccaa 840
gtaatttcat tccgtttctt ttctcttaat cgtatcttgt tcagactctt tcgcgttttt 900
ttttagttgc gccttaccag atctgtgttt tcactcgttt ctattcgata catgcttcca 960
agatccattt cttaatcgca tgtattcggt tgattggatg attgtctttt tgtaagtttt 1020
gattactttt ttggaatgga tcggttgaac caacggggtt taagtcgatg gaagtaggtt 1080
atgttaaaga tttgcttctt ttttttatg aagatgtgtg tgttcttttt ctttgctaga 1140
tgatgttatt atttgattgt tttaacagtc gtgttttgtt tttctgcagt ttatagtcct 1200
cggtcttttg aagacttgtc aagatggtta gtacacctct tgtcatcgtg attttgattg 1260
agtgatgtgt taagtgcttc tttaggttac agctaacgcg attttttata ttcaattgtg 1320
cctgtgcagg tgaagtttac agcagaagag ctccgtcgga ttatggacta taagcataac 1380
attcgtaata tgtctgttat tgctcacgtc gatcatggta agctacttag tttaagttta 1440
tttatgccga gcgtctattt aagaagatta acatcttagc tttcatttat tgtttatttg 1500
gtaagcatcg tttctttttc tccgaggaac tgtacatgtc agttcacatg acaataaaac 1560
gatcttcctt ggacattagt ttttgaagtt caattagacg ccaaattttg ttggttaaaa 1620
gatgcttgtg gagcatatgg acctaatgga atcagtactt tttgatggat ggacttgtct 1680
tttgttcttt tattttcaaa agaaattgca tgtgcaatta catcatcttt gatcgaaaga 1740
ttgggtaatt gggtaattgg ggtaaagaca tgttgtaaaa actaatgtta attatcaatt 1800
accattatat accttattta gtgcttattt atatcctttt tccccatttc agggaagtcc 1860
actctcacag attctcttgt ggctgctgcc ggtatcattg cacaagaagt tgcnnngatg 1920
tacgaatgac agatactcgt caagatgagg cagagcgtgg tatcaccatt aaatctactg 1980
gaatctccct ctactatgag 2000

<210> SEQ ID NO 128
<211> LENGTH: 1657
<212> TYPE: DNA

<213> ORGANISM: Cucumis melo

<400> SEQUENCE: 128

```
ggcaaaatgg agagaaaaaa gtttctccct attgccacat ttatatatag tatatagata     60
tatactatag acatgatgga gaatcataag ataaggtaag gctgaggaag attttgacga    120
tatagaatgg aaaattttga agatataaaa tggaagattt tgaaaatata gaataagatc    180
atcaaatgat agcaaaaaaa tccaaatgag tcagatgaaa cactacgcca aattttcatc    240
actccaaaat tgttgcaaag gagattgatt aatagggtat tatacacaat catatttttc    300
gtagcatgat aattggttaa taattagaca taatggcaat caattagtta actaatacaa    360
cattttaggt agcaatatta aaattggaga tccggaaaaa aactaaaaac tcagaaaaat    420
cttgggcaaa atgagcacgg tttatcaaat ttttaggctt ttttggtaca attttgtcta    480
ggatgaaacg agatccataa ttttctttga gaagataaaa aaaattaaga tttggtgtaa    540
gatttgggaa gatttgaata attttttttaa aagaaaaaat aagatttgga aaatggtaga    600
ataacggtct aatgtctccc aagatgcacc gggaaagcaa aaaacaacca aaacaataaa    660
taaattggaa aattttaata ttttaggaaa atctcgatgt caatttcgtc taagattgga    720
tcgagaaaaa cagttttacg agtttttaaa aaatgtgtta tatttaaaaa taaaatcaaa    780
attgtgctac ttttgtcaat ttcccaagat aaaaaatgtat gcttccacgt aaaaagtaac    840
attactaccc ttctttcatt taatctctat atttggaaat gtcgcactag ttcttggtag    900
ctaatatttg gatactaatt atcttatatg acaaaatatt taatgtactt ttttttttaca    960
acaaatattg aatgaactta aataatcttt tcactgcaat gaaaaaagat aaattagagc   1020
atcccaaaaa gatgaaaagt tcgaaagtct gctaactaca ttgaaaaaca aagcatttaa   1080
ttcttcaaac ttgatagttc aattaaattt ctaccaacta actcaagtaa atctattatt   1140
agtgtttgag tgaggctatg aactctaaga ctaagcctat aagtttggtt aaatttaatt   1200
ataccagccc ttttgtaagt aatttgattt gaaaggtaag acgtaatacc gattacccaa   1260
cccaaaatta ctgtgaatga gttaaaaaat aaaattagtt gaattttaaa taaaaagcat   1320
accaataaga cgatgacaca tgtacaaaat cttagaagga gaagcttcat ttgaggacaa   1380
aaaagagtgt gtggagtgag aagaaagaat agtcacgaat attgctgact gtgcaacaaa   1440
tgtacatttg gcaccaatca aaacctataa aaccttatcc aaaaatcaat aatctcatcc   1500
cttcttcgct gttcttcccc aatccaaacc ccaaccattc tcctccacac acacacacac   1560
tcacatacac aaatccttcc aacattattc tatacccact tcccaattct cattgcattt   1620
cacaatcatt gttctaactc acttacaacc tccatca                            1657
```

<210> SEQ ID NO 129
<211> LENGTH: 2000
<212> TYPE: DNA
<213> ORGANISM: Cucumis melo

<400> SEQUENCE: 129

```
atgaacgaag gagaatatcg gataatgaag aggagatcca tgaatcacag agaatgaatg     60
aaggagaccc acgtgaatta aatagaacga aggagaatga agagaaagga tgaatacttc    120
ttttctttaa ttttaaccta atcgggtgaa tcaaactcaa atcgaaactg gtttagttcg    180
attatgtttg gtaccattgt cttttaaacc gatcaaacct gaaccaaacg aatcggtacg    240
gttttttgca cccctaattt atatcatgtg aaaggtttta agttaagggt cagctagtgt    300
cgtttagagg gaatgatatt ggttgacttc atgtcgtctc ttggatcaag agtaggagat    360
```

tcgggagggg tgtgacgaaa tcaaccccga gattgtccta cagatggcat gtaaaatgca 420
tcatatctcg ggactccttc tacaaactcg agaaaaatgt ctcttgagat tcttcttcta 480
cacagcccca aattgatgaa atgactgaga ttctttgaaa gacaccacat gcattaactg 540
aaactaatgt tgtacatcta aaaaactaca tcacgccacc aactaaaaag ttttccattt 600
gcctgatttc aaactaaaaa caaaagactt aaacgataaa ctaaaaacta aaccacaaac 660
aatgaaatcg ttaaaagtgc accttgagag atttaagaga gtaaatgagt tcacatagtt 720
ttttgaagga aaaatcacta aaacaagttg gattgtagga gcgaaattgt tcactcctta 780
accgaaatta gcaaaatgtt tggagtttag cgtttttaga gaatatgtaa cgttatgaat 840
aataagggta ttttggtaat ttgatatatc cctttatttt caaattttta ataaaaaaca 900
cacatcttgg tgacacactc gactgaaaag gaccaagata tttccttgaa agattttttt 960
ttttaaattg ggaaagaatc ttggggtcga tctcgatcga gattgatcga gaaaaataga 1020
attacgagtt ttctaaaact gtgcttttga aatatcacac caaaaaagcg ttatttctca 1080
aaatttccca agtttatatg tgggggttat tgcgagttag cttttgatgg gtttgctttt 1140
gggtgtttgt atataggttt gaaatgtacc tttaatgtcg atttttgaag aaaggtacct 1200
ttattgttta aaattgacat tgtaccttca tatttgattt cagtttaaaa ttgatattaa 1260
ttatccgcat tttaaaaacc aacatcaaac atccatgttc atttcttttc aaatttaagc 1320
ttgaggatga cttcgtgaaa ctttttgagc aaacacgttt atcggttgtt caaagtaaat 1380
caccttcaca aatttaagct tgaggacgac tttgtgaaat ttcggcaagc aaaaatcaga 1440
caaatctctt caatcttttt tgagcaaaca cactttatct ctgctgaaat gagcacaagg 1500
tttagggttt tgagaatatc tagcatttag gctttcaatg gtattttggt catttgagaa 1560
taccatttat tttgaaattt taaaacaaaa acctaccatc ttggtgacga tcatttaggc 1620
cgagatgtat tgaaaaatta tgttaaaatg agtttttcaa atttgattag aacctcgtgt 1680
tgaggtcgac cgaaattgac cgagaaaaat aaatttacga atttttttc aaaatgtgct 1740 acttttaaaa tataaaacta aatgggttac ttctcaaaag ctaaccgaaa ctattagtta 1800
tattgcggaa atatcaattt cgcccaattt tagtcatcca gagcctgact catcgaattt 1860
aggagattct agacgttgca ttcaggagat ttttatccgt tgtcgccgac tctctttact 1920
gatctacatt gtacttcatt gctgaactca acgagtcaac tcaatcgttt ctagatttgg 1980
aagaatctgc ttcagcgacg 2000

<210> SEQ ID NO 130
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 130
aaaaggcgaa aaaaaagtta gcttcccgag aaggagaaga cgaggaagag tttgacttcc 60
cggggagata aagtttgtgt ctcgagggaa tctctaatct ggagttgacc gtcgacttat 120
gtgtcgagcc tggatttagt tgcatggtgc gacaaagcga taaggcggca tatgtaaagt 180

```
agtaattcaa aactagcggt taaagaaata atcagccaaa aaatttagta caaatacggg    240
tggaggccct aagtgaagtg ctgctattca gaggttttgg caaaagagtg caaagagttg    300
agttgtgcag agaaagtact aggtgaggag aggcgtttgg aaaagaaaag gatcaaacat    360
ttgcatgagt gatattctta aactaaacac tcttgtgtga gtgacttgcc taagctaaac    420
actcttgcat gagtaacttt cttaaactaa acgttttgta atgttttctt aatggattct    480
tttcgagtct gagttatgct taacacgttt tgtttctctc gtgttattgt tgttgttgtt    540
tgaaaagaga aaactattgt tttctatgtg ctgattgtga tgaatgtgtg cgaaccatta    600
gccttaatcc tatcaagtga atagtgatta tgtggtgtgt gcacataatg taaatgacat    660
tgtgtggatg gccagtgcaa caagaaatga atcagaaagc ttcccaaata ctgtgaatgg    720
agtgaacatc acactagctc aatggcaaga tattggcgat agtgaatcac aataggcttg    780
acaaggggaa ggattcatgt tcttggttga aaggaataag agaggctaat gtgagatttc    840
tgtgatttgc aaaatgaggc gttggaagac acgtttgaga aatgaaaacg aattagtgct    900
tgacttgtat tcctaaaaaa gttgtccaat atcttcaatc actaaatatt tgatgtgcct    960
aagttttcct tccttagttg ttgaggcgtt gaggccgagt aaggaaagat aagataatta   1020
tgacgttgaa aagctggtca agttatccat ctttggatgg tttaaagtta ttacatgtag   1080
ggagggttgc attccaattt tgtgtgtgag atgagtctta ttttcgagat gggttgctag   1140
gcgatcaagg agaagtataa gaaatgagtt cttatactct tgaacaactt gacacgaaga   1200
ataacatcct agtggatgaa ggaaggtgat ggaacttaaa gtttaggttt tattttnnnn   1260
nnnnnnnnnn nnnnnaaatg taattgtaaa gtattagatc aagtaataaa acagagttgt   1320
gttttctatt tttgctgtgt tgggttgtgt atctttattg tgcttatggc ctagttgcta   1380
aagagttaag gttattacct aaatgtttta cggtgtgttg agttgtaaag atctcctgag   1440
ttaaagttgg aattttgtat tggagattgt tttgagaagt ttagcttact aattgtttaa   1500
ctcattaggt gtctaagcga cacgcctcct tttggtcgca tgaagtggct agcagggtgg   1560
ggcggaccgg ggtggggtgt gataataaac ctaaaaaatc acccagataa gcctaaatta   1620
tacgttgaag ttaaacttac aatttgatta gaagaagaag gaatatctga tttggacatg   1680
aattaattac aaatacggcg ccaatcatac aaagcacatg taagatcaac gcattctaca   1740
ctcaatctca gccgttgatt gctttcaatc cttcaaaaag aaaaaaagaa gggcagttcg   1800
ggcagagtca tacctacccg ttgactataa aagcaactac aaatcgaaaa cctccatttc   1860
tccgttacca ttacagagaa aatcaaagaa atttggcgtt gagagattgg gagagaggtt   1920
tctctttcta gggttgcttc ttcttcttca tcctccattg ttgcaaattt cacttccttc   1980
tcctcttgtt ctcatctccc                                               2000
```

<210> SEQ ID NO 131
<211> LENGTH: 2000
<212> TYPE: DNA
<213> ORGANISM: Cucumis melo

<400> SEQUENCE: 131

```
atagagtaac caatatgccc ttttcagcag ccaaagtttt ctatgggcag acttaatcaa     60
ttaaggttcc tattgaggcc ccactcttag tgaaaagcct agacccttct ttccaacatg    120
tctcaattgg tcacctccat caaaagcttc tatcatttaa tctaaaagca tactcttttt    180
tcctttttaa atttcatttt gatggtctat atttgaaaat aataatcact acaacgacga    240
cacgttgttt tcaaactatt attttgtatg aattaataat tttttaata gtatagttgt    300
```

-continued

```
tttacttatg gaatctatac gtttaatcga ttcggtcaca tctatttact ttgatgtttt    360

tgttatttta tttagacgtg gttgtaaaga gtttaaagca atggagaaga aattgatgct    420

ttccaaagca atacaaattt atatatacct tcaaatgaga ctaacattag acaatacata    480

aactataata aacattttga aagtacatag atcaaaatga accaaagtcg aaaaagtaca    540

attatcaaat tagtttttaa accttggata aacttcagca ttcaaacttt gtatttcttt    600

tttttttcga tcgatatata tagtgataga agattttttt tttctgttta ttatttttga    660

cgatacgttg agtagaagaa tcgaacatca aacctttaaa tcaataatat atattttacg    720

actcaatatc tagccatcaa tattttaaaa tagcaattat tattcactaa attatgttag    780

agattggatg tcatacaaca attgttaaag attatttgtc tagtttgttc aattaatcaa    840

gagagcatta agcattaaag tcaattattg tgataagatg cttttgcact atgtaactaa    900

aaatagttgg atacaccatt taaggcccta catgcaaacc atgataggcc cacaaaaaaa    960

aatctctttt tggaaacaat ggtcaaataa tttctttcaa ataataataa taattacaac   1020

aaataaatac ataaaccaaa ttactaaact aatgtatcaa gttctagaga aaacaaaatt   1080

atgccctttc aagttgcaac atcccctact ataatttttc ttcaaatttt ccatttaata   1140

taatccaatt ctaaacatgg aaaagaaatg taacaatatt tacattattt caatctttcc   1200

tatattcatc gactaatttt aataagacgt gaaatcaaca tttttctaaa ctcgttgatg   1260

tcataaaaaa taaacttaaa ttatgtacaa gatcgtctat taaattatgt ataacacgtg   1320

tggtgtatga gtaatagaaa ctttaaactc ttgatcaagg acatgtacct ataaataaat   1380

agatttcttt aagtcttgac tattaaccaa cttgtattca gtaaggttaa agtgatctat   1440

tatcatacta aatacacaag tttatttcga gtatgaatgc aaagaatcaa agatatatgg   1500

tttaaacaaa atctattata ccaataaaaa aggttaacca tatgcaataa aaactaaaaa   1560

gtctattgct caaatctctt tcgagaccat attaaaaatg ttagtttaat tgacgtatgt   1620

atttattgga tttatctaat aacattttaa gagattgttg caaatatagc tattagattc   1680

aaaataatta agtatatagc aaagtctgtc aaattctatc gatgatagga ctatgttaaa   1740

attgttgttc gatcgttggt aaactataaa aatctacgac aataaactac tattcaaaaa   1800

tttttttacta cccaaatttt aaatccatct catggatcga gtcaagccca cttctaaatt   1860

gggccacgaa tattgattgt gaagctcaat aatcccatac gtatggctga aaacgcatta   1920

cgaacgaacg cccttcaact atccaaatcc gaacccaccc aaattccggt taggcttctt   1980

ctccgagatc gacgaccgcg                                                2000
```

<210> SEQ ID NO 132
<211> LENGTH: 2000
<212> TYPE: DNA
<213> ORGANISM: Cucumis melo

<400> SEQUENCE: 132

```
tgcagctgca caaaagattc caaatgatat aacataatag tttatgaaaa tttaatgcat     60

ttaatttccc cttccacaga agacactata tttttcaact acccaacaat accaataatt    120

atcattatta ttatacctct aattagtaat tagtcacaac ataaacagct attctcatta    180

atacatataa tcaacaactt cataaattct taaatttgta tgtgtacttg atgggtgtag    240

atttaagaag tccaagagtt tgacaccctt tgttaaaatg atatacaaat tcctgcaaat    300

taaatttacc attggtatga ttgttgttgg agtggtcaca acactaattt actaattagc    360
```

```
ttcgtattta acatagttgg ccatgcgagg aggtagcttt tgaacttcca ataacctggc    420

ttggaaggac gtcgataaac agaataacaa ctatgctaaa ttttgaataa tatactttat    480

atatattata taaagacgac aaagttgagg agcatccgtc ccctacattt gttggtgctc    540

atatcatcct attgcatatg ccttttacca atgaaaccct atctccttaa ttatttctac    600

tccacactca taattatcat tcatttattt tcatgcatga ctttctttta ccaaatttag    660

tttccaatta aactccatta actaccaaca atcaactcca ataacgtaac tcacattcat    720

tctaaccaat tgtttggatt gactcgagaa aaaaaaatgt tttttctaac tcatttttac    780

ttatacattt aaaaattctt ttggaagtga tcgtcaaaca ttttgatatt tttttccttt    840

taaaatgact tattttttaa aaaacttaaa tattcaaaaa ggttttccaa atgaatgtaa    900

ttaattactc aacatagatc tccattaatc attattatat gtaacaatag taattcaaag    960

taaaaaaaaa attatgtgga gtgcaaagat gaaaattttg acctatttta catgatttga   1020

actatatgtt tatgcgtacc tatgatttaa ctcttatata cacatatttt tgtctcaatt   1080

taatttaatt ttacgatttt cttgaataat tttattctct aaccactttt gaaaaacatt   1140

ttttaaactt tagaaaagaa tatctttacc aaacttaatt caatatatga aaatagctaa   1200

ataaaattta aaaaacagat aaccaccctt tgataactgt agctgatatt attaattaat   1260

tgtcatattt atatttgcaa tatgaaaaag gagatgtcat gagttttttt ttttttaatc   1320

aatctaatgc aattttctta aatttaatta atgtgaaggt gagagagaga ggcaatttca   1380

aattttaggt aagtattatg aataaggtta cttaacatta ttttaattta attttacatt   1440

atgttttatt tgaatttttt taaagactct catttttcca ttttggaact tttggaaaag   1500

aaaattttac ttcaatctct tatgcaagca agttaaaact acatttgtct tttcatggga   1560

tttttaagga gatgtgtggg gaaatacaat aagccttttt ttatttgcaa tttgctaaat   1620

gtgtattctt ccaattggct aattattaaa gtgaaattta gattgaaaaa agagataaaa   1680

ttgaattgaa gttgtataga tgggttagga atatgaaaat tgtttgagat atagtgagta   1740

ttggttttat ccaatgccat gtcatagggg tggaatccaa atgaaccaat gagaatcact   1800

caaaagaaaa cagatataat gcactatcca aacctaaaac taaaagccac acattgctca   1860

tccattcact cccattctca aaaccacaca aaaataaata tcaaatcaat ctctttccct   1920

tttccatata taccactttc ccctctcttc gcctctttga ttattaccca ccaaatattc   1980

ccatatatct tacaacaacc                                               2000
```

```
<210> SEQ ID NO 133
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 133

aagcttgttt gaccctattt ttaatgtctt aacacaggat tatgaacaaa agaagaaact     60

agtgaatcac agaggaactc acgcaaagac taggtgagaa gatcatatca aaatgagaga    120

ataagttcgc tagaagataa aagtggtagt tgaagttgat gtgacttgac caagaggcag    180

cttctggtgt tgatatattc agaagactag atttcctgcc taaatctacc tatataaaga    240
```

```
actccatctc cattaagaaa atgaggcctg aatggaccac ccaagtggtc gactgtgtga    300
agagccaaat gtttgtgaac tgcccatgag tgcctgaaag gcccgatcct agagagtggt    360
gggaaggagc agcctttcca ccatctgtaa agtctttctt catcttctcc agttagttta    420
agagtgaaag tttgaggttg agtgaagaag attccattcc tatctttttc taactggtaa    480
tgtcatttct attctttcca tttttgtata tttctttgta atgtatttnn ncatattgta    540
cagtggccta agacctatat tctttaatac atttcatgtt tatatctttt caatctatca    600
cgtttgttat tattcatctg tccttgtgct attggtagct taagatttat gataagttct    660
tgataagaag gttagcttat atttcttatg tgtgttagtt gtgagctatt ttcatcacct    720
ggctagtgta tattgcaaac tacctgagag ggtaagtagc aaagatatgg cttaggcgca    780
caaggaggag tttggagaca aaatccacat tggcaagata acttccatca tttgtgtctc    840
aaaaggagaa caagtgtggg tattaagcat tgagatgttg tgacccttaa acgagaagct    900
atataagtct tagtgaaggt cgtttggatc tcgagaggtg agcaagtgtg gtgtttaaag    960
acaccgagag gtgctcgtct taatcataag ctcgttaact aagttatatt gcattaggga   1020
tattttattg cttaatttct tggtaatgca cgaacttttt ttcacccatt cttttatgcc   1080
agctagttca caattccatc tcgcatccat tttaatcccc ctttacagat tctccggtgt   1140
agataagtag atatagttta aacttacatg ctttcacact atatatttta ttcttttata   1200
ctacctaaat gcctagtgaa gcctagaact aagctttgat atcgattccc tgcattcgac   1260
tctaaatcgc ccatataaac ctattgtttc gcttacactt gggcaagcaa taggaaaact   1320
tgtactcaac gaggacttat gagttacatg atgacgagat acatagagag catctaatat   1380
gcattgacca tgatcattga ctcttcatgt agatttaaat acctttcagc ttaattagat   1440
agaagatata taataaagcc attccattag tttaaaagaa ttaagttaga ggtagttgaa   1500
atgctttata agtgggggtt aattctattt tagctgtaat gctgagctga tctcaagcca   1560
aggttgcctt gagatatccc cgagtttaaa aacagaagct aaaatggaaa ctaaaaacta   1620
agacatataa actttttagt tacttttagg gaaatatctt agctataaat taaagaatat   1680
gaccaacatg gaagttcctc catcactttt ccaccaactc attttattgg gggttagtca   1740
ttttaaggcc aattagttta aattaaagtt caatctcagt gatgcactag gccgagagag   1800
accgagataa atcattcaaa tattttttta aatttgggaa gaatcttgag gtcgagattg   1860
atcctgagaa aaacaaaatt acgagttttt taaaactgtg aaatataaaa caaaaaagtg   1920
ctagttttgt caattcccat ttatcttgct cattgttgat acaagatcat taaaagttta   1980
tggataaatg ttggttgaga                                               2000
```

<210> SEQ ID NO 134
<211> LENGTH: 1696
<212> TYPE: DNA
<213> ORGANISM: Cucumis melo

<400> SEQUENCE: 134

```
tatatatata tataaaaaga ggaatacaat taagacatcc cattgttaat aaggggtgga     60
ataaattggg aaattaccat tcgagaaatc attgacgaga gcaaatatgt caaagtagaa    120
aattagtcat ctcaaaagaa tgtaatcgtt acaaaaatta aaagtacgta aatttaatca    180
tcgttacaaa aattaaaaga atataaatta caccgttaca caataatacc aacaatccat    240
ttataatatg ttgtttttat ttcaactttg aataaaattt gaactctttg ataaaatttg    300
```

tttaaaataa atttaaaacc atttcaaaag ctatttttat attatccaaa tacatatatt 360
cttttctttt tccaaaatga cttgtttcta aattcgaaca tccaaaaatt aaaacataac 420
atttttagta tattaagaat tataaattaa gagataaaat attcaatact attataataa 480
aatcggtgtt ttcagtaatt gtatttgtac aagtaaataa aattaatagt aaaattttta 540
atatataaac aagttttaaa agaaacttaa agatataaaa aataaattga aataaaattc 600
aaacccatca acaaataaag aaaataaaga tggttttatt gaaatgaatg aactaaaatt 660
tgaaggaggc aaaagtaagt acaccaaaaa tagaatacta aaatggtaga ggacaataat 720
tgcatatgtt tggtagattt ttcattaact atcataccaa ttaacaataa tgaaataaac 780
tttctcgttg atattgatta caatcgtaat agggcaaccc actgtttaac ttgtcaaagt 840
tttcttaact ttattatttt tgactttatt tgtttgtttt attgattaga ttgatagatt 900
atatatttta atcatattat ttatagtaca acaactacga ggtaagtgat tgaagcttta 960
gtctctaaga acaaaggttc gacctaattt tttagtctgt ttttatttga catattttgt 1020
ccattgatag aattactatc acttaagtta aatgtattat tattgcaaac cactaattct 1080
acgtaaaatc tctaagtagc aagtgttatg tcaataaaat agcaattttt tttttaccaa 1140
ttacacacat catggtgata attattatca tgcacgggta aatttttaat tataaaattt 1200
caactttcaa aattatacca atactaaatt tattacaaaa gttattttag gtaaattata 1260
aaaacttgat aacaattaca agtacattct aaaactttca ataataaaga ttgaatcatc 1320
caattcatcc aaatgttaaa tttataatcc gatttcaaga agaaaattaa aaactcaatt 1380
tttatgaaaa tgtaactaca accacaacca tattaaacaa aaactcacaa tttgtccata 1440
ttttttaagt taaaaatata ggtttaggat tcaaatattt ataaaataaa ataaaatgaa 1500
actatttgaa aacatagttt aaaaaagaag aagaagaagt gttaaataaa gtcccatttt 1560
ttaaaaaaat atcaagaccg atattaatat tatatatata tagaaatgta cacaaagtta 1620
aaaaaaagta tcctataaat atctaagttt ctccccgtct agccttcgcc aaccttatct 1680
caaaaactcg gaagcc 1696

<210> SEQ ID NO 135
<211> LENGTH: 2000
<212> TYPE: DNA
<213> ORGANISM: Cucumis melo

<400> SEQUENCE: 135
tttacatatt tatgaacatt ttcctatttt tgtaaatatc ttgattcaag atttttgttc 60
gatatattta aaaataaact tattttaaat tcatacttct ttctccttct atatgattat 120
ataagtattg tagttactat agattaaact cataacctcc tagttagata ttgagattat 180
tactttcttt tattatcggg ccagtacaga aacgctttta tgacgattac attcgtcatt 240
cgtcacttat ttgtgcatta aagttggcat tgtaatgttt gtttttacat gattctctat 300
tccatagatt tcctttatcc ttttccttgc atttgagtgg ccctttccta agatgtattc 360
ttcggacttt caaataaata aagattagaa gcattttttct cttcaatatt gacttcatcc 420
ttaatcctta agccttaagc ggaggctaaa aaggctttat ttgcctcgaa tcccaactaa 480
ttctccctct catgcccatt tcaatctctt gcctaattgt taattaatgg gtcaaatttc 540
gtattgaatt tcaattttgg atcaatccta cgattatctc aattaggggt caaaattaat 600
ggttgatgta ggagcaagtg gaagacacaa ttttggtgta gcaattggag cttcatcatc 660
aacaacatga gatttaatcc cgtggttgca gttaaatggt gtagaagaag tagtcaacac 720

```
aacccaaggt gaagaagagg gagacaagag aagtggttga ggttgtggct ctatttgcct    780
atggcagcct tcacctcttc tctctcgctc cctctccgtt tcaatccctt atccccttcc    840
tctccccgcc attttcttct tctcttcttc ttccctccac caatttcacc tcccgattct    900
ctgccctaac catctcttcc tcctccttgc actccgcctc cgacaatttc gatcatgcca    960
aaagctcccc tttttcatct aaggtctgat tcatttctgt tgtttgttta actcaatttg   1020
tcttagttat attcaatcgg gattttgctt gcttgtggaa ttaattttcg tttattaagt   1080
ggaagatatg ggtatgcttg gtgacactgt atttactgtt aaatttcaaa caatcctacc   1140
aaattttggt ttaaattgag tatttttagt tccttcttgg taaattggat ttgcgaatga   1200
ttaacttaac tatgttggca cttcgttgta agaccgttaa ctatttagct tccttacggg   1260
taatgatgtt tagaaggggg gtgcttggtc cactaagtgg agttaagtct atggtaaaca   1320
tgttggcatt agtaagtttt tggtaaacat gttggcatta gtaagttttt ggtaaacacg   1380
ttggcattag taagtttttg gtaaacatgt tggcattagt aagtttttgt ttgtgatgta   1440
gagttgtaag attgagttct ttaataattt gagttgtaag attgaattct tcgataactg   1500
tgaaaagtat attaagaaag taagatagag ttacttgata aatttgaata gtggagatag   1560
gggcaagatt gagttccttg ataaaagtat aataaagtaa atgtgcaact cttgcctata   1620
tacagcttag caggaactct tacttttgtg tgtcatgtat tcttattggt tcgttcttat   1680
tgcatttagt agatagtgga tcccagtgaa cttttttaat cgctagaatg gcgccttaaa   1740
aagttagttg gagcttctac ttgttggttg gtatggtgcg gttgcaagta tttttccttt   1800
ctatgattat gtttttagat ctaaatttta aagcactcga tgaatgctga tgcttgatat   1860
gttttctgtg ttaaattctt ttgttgatga atattatttc catttttcag aaatcagttc   1920
tttcatcttt gatacaagag atagagccgt tagatgtaag cttaattcaa aaagatgttc   1980
cacctactac tgtggatgct                                               2000
```

<210> SEQ ID NO 136
<211> LENGTH: 2000
<212> TYPE: DNA
<213> ORGANISM: Cucumis melo

<400> SEQUENCE: 136

```
ttcttgatta gcttggtgtg ctgttgtata tcatatttgg tgcgagcata acttaccctt     60
ggctaccttg catctaccct aagtggttta gtcagattgt atgatttgag gtatttcgtt    120
tctttgttgc tctaagtggc tttgagcttc tactgaggga acctaggacg tctcttcttt    180
ttgggatctt ttttctcgag tagttggatg cctagttggt ttttttgttc ctttactcaa    240
gtcctttgtt tgtcatttga tcgtgtcaaa gtccaaatgc tttctattgc aattcagtat    300
cttaaaaaac tgttctttgt tgatttatgt aaatgacata ctgtatgtat aaaaggacag    360
aatgctacca tttcttgaag tttctggcac ttaccctgat aatcgttacg gtaattatta    420
tgtgcagatt gacggcaata acgcagctag cacatcatgg tatgatattt gtacctcttg    480
ggtacacatt tgggagtaag atgatggaaa tgaatgaggt gaaaggtggc tctccttatg    540
gtgctggaac ctttgcagcc gatggaactc gacacccgac tgagttggag cttgaacagg    600
ctttttacca aggtaagtat gttgctgagt taaccaagaa actcaaaaac taatgccatg    660
tttgaaatgt tgttgggtat ttgaaaacgt gttattacac tagcacactt ttactgtact    720
tccttccaac atctattatt cagcttctca catcatggct atataaataa aggttaatgg    780
```

-continued aagttactaa aaatgatgta aatctatcac attgttaata ctcctgtaat tatattgatt 840
gatgaacaat tcgatcacca tcttttgtta tttaaaatta aacttgtaat atgtattcga 900
acgtttttag ctttattgca tgcttattat ttcactgttt taaaactatc tttagacttc 960
aaatcaaatt ctgaaaaaca aaattaagtt ttcacataca ttatgtcatg aatataaaat 1020
tttagatatt ttagttcatt ttactatatt taaaaatgtt ttattattat taattttgta 1080
aaacaaccat gatcgtttat taattgaatt gtcacaatta agccattatt ttttttttta 1140
ctttcctttt tcccatcaat ttctttattt tctaaaaatt attggcctcc cagactcttt 1200
gttatttgca aataatgagt ctaatcataa tagaatttca ttgataaaac caatcatagc 1260
gagtcttaaa accaatcata gcgagtcgta attataaata ttattgaatt gctcttggtc 1320
cagtttagct agaattatga atttgatcaa attttctgtt atcattaccg tataacaata 1380
aatgataaaa ttcaaaaaaa aaaaagaaag aaaattgata tgttaacgac aatggtaatg 1440
ataaccataa ttgtaatggt aaccgtaact acaatacata atttttgaat ccaatgagat 1500
gaatcactta cttagttgat ttgcgtacca aattatagaa caccaatcat ttttgtaatt 1560
aggattgatt tactagcgtt agattagaga aaagcttggc ttatttctaa ttcctcctcc 1620
ctcttccact cattttgtcc ttaactaaaa catagtgata gttccctttt tcttttagag 1680
aaaagaaaag aaaagaaaag aaaaagagtg ttaattggta atacataata acatatcaca 1740
tacataaata aatcatgccg agttcgcctt agaaacgacg ccgtttaaag taagtcaaca 1800
agtcaacact gacagctaat ttccgcaata aatacgtaaa aatgaaaaga aaattaaaaa 1860
acgatataat ataaatagaa gcaagaggct cccatcacaa gatcccattc gcaaccacat 1920
tccggccttg aggcttcaaa aaatcgaagg aaaacactct ctgtatctct cccctctacc 1980
caccgattcc gtcgcggccg 2000

<210> SEQ ID NO 137
<211> LENGTH: 1575
<212> TYPE: DNA
<213> ORGANISM: Cucumis melo

<400> SEQUENCE: 137
atatatatat atataattta actaaataaa caaatgaaag aaaaaagtga gttcccattc 60
ggaaaatgca gatggatcca tttcttcaaa tattaaaaaa taaaaaaataa aataaaataa 120 cttaaatatg caaatagaaa gaattttaat ttctggatta tccatatggg acaattttta 180
aaactcattt attttatttt ttttatttat ttgattttga tatatctatg gggaaatttt 240
tcgtaataat tttcgaaaaa atattgcaat atatcatttg atcagatcgg tattattaaa 300
tctctatcac atttggtctt aaattatcca aagattcctt taagataatt tagataacca 360
tctacagatc actactataa tcaacaaaag gaacaactta aattatttaa acaaattcat 420
taatattaga ctttgtgctt cattagaaaa tgatcttatc acaaccacaa ccatagtggt 480
ggtttaaaat tttattttaa actcttatta gtattatttt aattcatact taatcaaact 540
aattacttta aaaaacatat atatataaat aagttaaatc attcccccctt atctaaataa 600 cataaaaaaa aattgtttac tctacaagaa gtttgtatat atatatgctc ggtactattt 660
agcatcttta taataaaatt tctaaatcaa ttttttatat ctctttatta aatgtatagt 720
catcaaaaaa tttaacgaga taatgtgtca aagatttatt ttattaacgt tcataaatat 780
caaattatac ttagcttata attgaaaaca tgttcgataa atataagtaa ataaaatttt 840
atttttttta aatattacaa aataaactaa ataagttata aatatgacaa taaacattat 900
atattttatt atatttataa atacttaata atttagtcgt ttaaaataat tttcttaatt 960
ttcaaaacat gtttcatatg ttaataataa ataaatggaa aaccttccaa aagaagaaaa 1020
aaagatatct taaaatttaa aaattgagat tttgaggatc aataattaat aaaagaagga 1080
ttaataaggg tgaaattaaa tcccaaaaag aaaattgaaa atgaagaaaa gaaaagtgaa 1140
gaaataattg aacgtgggaa gtggattcga tgtctccaga gaacaagcga aaggagacga 1200
aatccacata atttgcacgt tacgtgtccc tatcaaccgt agacacgtgt caacatctca 1260
acaccctacg ccgaattgct tcgctggatc tggacggtca tcggataaca gcggcaacca 1320
attaatattt ccccttatat ttcacagcct ggccatgtcc accaatcacg ttcaactatt 1380
aattcatttt tcatttcctt tttctttttt tttttaattc ccctcaatta ttaccgacaa 1440
cctgttgtag ccggttaacc ctaccctcca acgttccatt ataaggccta gaaaatggac 1500
gtgaaaatgg agtactacaa actacaatta attttaaaga attttaattt taaagttctc 1560
taattactat tagcc 1575

<210> SEQ ID NO 138
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 138
ccgtcgggaa cctctgctct gacataatta atattcatgt atttcctgat acccatgcaa 60
gtcgtcggga aatatgttac caattttcga cgccagacga gaatcgttag gaacaagtgt 120
caccatgccc aacttcttgt atggggcatc aggataagtt aaatttcttt tttagttgtg 180
aactattccc gacgccataa acctagatgt cggaaatgtc ttcttgtttt tcgacggctt 240
cgtgaatctt cgaaaaaacg taagattaaa ataatgtttt cgacgagttc cgacctgtgc 300
aaaacgacat cgggaatagg tatttattcc aacgttctag cttctgacat ctagaaccct 360
tcaatttctt gtagtgccag tgcaaagatt gacactctta aacgatggga cttgtcaaat 420
agatgttgcg cagatatcca taggttatct aaggttttgt tttgttacct aagttatcat 480
caaacttctt catgaattct cttagctatt tctaagtacc taagttctcc tctatccact 540
aggattgtct ctcttaaagt caagggtggc tgttggtagg atgtagactt tgtcggcatt 600
ggtctaccaa tttaatctct tatatcccta aagacctaga ctccatggtc tccacctatt 660
tccataaatg tacccataac atcattaaat gaaattatta ctcaagtaca aaaaaattgt 720
ttaattttat tgataaaaac catatgtgaa aaaatagatg acatttttaa aagcttgtaa 780
acagtgtgtg aaataagtat cctaagtgaa ggctattaat ttaacttaaa cacaataatt 840
attattgttt taatgatgaa aataattaac ttatataacc aattttcatc aacacataca 900
taccttttgt ataaacattt atttgaacac aaatgagaga caaatagaca tttttatttg 960
gtaattttct cagcattatt aattatcatt ttcagatatc ttaattgaaa tttctgaata 1020
attttttatt tttcggattt tcacattata atattttgaa ttagttagtt gaaaaccaaa 1080
gccagcatca gtgaaaactc attaatacat gtaaaatact aaaattgttt ttttaaactt 1140

-continued

```
ctcaaagaaa aaaagtctta atttttattt tcttaacttg acataaaaat cattggtgtt   1200

gtttttaata aagtaaatgt taaagtagac tcagttaaaa acgaaaaaaa aagttaaagt   1260

ggactcaaca cttggagtaa acattttttt taaaaaaaat taatcctaaa attatgatta   1320

taatttttat ttggcttaaa tatttcaaaa tgtgttacac atggtttagt ttcaatttag   1380

ttgttacaaa atttattatt gtatttgaat ttttgataga ctaattaaaa tttgaaaatc   1440

aatttattta tacagttgtt tttcttttaa tgatgtaaat agaggtctaa tgattttaac   1500

ttgtaagggt taatttttct tatgatctaa tgtaattcaa tgagcattaa ttttagaaga   1560

aaatgtgtac ttattttgtg taaaaataaa ttataataac aatttttttca ttttggtata   1620

acgtatgatt aagttccatg aaaaaacaaa ataaaaaaga ataaaatatt tttccattta   1680

aagaaaaaca ataataaaaa tggagggatt caataggaat ttcggagggc ccacttccca   1740

attccaactc cccactcact cactcactca cnnnnnnnnn nnnnnnnnnn nnnnnnnnnn   1800

nnnnnnnnnn nntttttttt attattatat tagaaattaa taattattgt ttatttcgct   1860

gtcaaataaa aataaaattg tggggcaggt gcagctcacg tgcctcctca cattgacacc   1920

acatttaaac actttcattt tcaaaggctg ctgctttata ttcttcacaa aaacttcctc   1980

ttccctttct cacactacta                                                2000
```

<210> SEQ ID NO 139
<211> LENGTH: 1006
<212> TYPE: DNA
<213> ORGANISM: Cucumis melo

<400> SEQUENCE: 139

```
ataataataa taaatacata aaataaaaaa ataataatag taatgaaaat caatagaata     60

attttaaaat cgggaaggaa gtcgtgtaca atccttgcac gttggagagt caaatggcct    120

aagtggtgat gtggaagtcg tgtaccgggt acacgatttt cctacaagtc aataataata    180

atatggttat tttttttcta gtttagggtt catgacaaaa gattgttcag tcgactggat    240

gtagacaaat ctaaaaaata aattaaaatc taatatgaaa actagtttta atttccaaat    300

tattaagggt tgaattcgac caataaataa taataatacg gttattttga aatttaggaa    360

attgaataaa gttgttaaaa tcttcaagca aattgttaag ccccgagata ttaagaagag    420

gtaataatag aggattctat atttataaca tgttaaaatt aattgcaaac tcataaatgc    480

atcacacaga ttaacaacat aggagggact tccgataaaa gtgcaaatat tgaaataatt    540

acagttcgcg aacatgagta ttttaatatt ttataaaata gtatgcacgt gtatttttgc    600

caaaagaaaa aaagaataga ttttgccatt tttcaaagtg actctcggtt atatctttta    660

tggcgattgt attttatagc gtatgttgtt tgtagttaac ccatttctca ttggcaaatt    720

caatcgtggg ccacaacgtt tgggcatagc ttcaatttgg attaactcaa ttatgtctga    780

atgggttgga ctagttcgga ctcttcggct gggccagaat cagattcggg ccgcaatctg    840

ttcatttcac acctatatcc aaacaccccc aaaatcgata cccatcaaac cctaactctc    900

aataaccccc atatataaat tccttcttta gggtttttca tcctcataca ctctcaaacc    960

tccggtcatt ctcattttcc ctgccgcttc ttcaataacc ctaatc                  1006
```

<210> SEQ ID NO 140
<211> LENGTH: 2000
<212> TYPE: DNA
<213> ORGANISM: Cucumis melo

<400> SEQUENCE: 140

-continued

```
aaggagtaga ctctcaagtc cactattcta acttcttacc cgaaagagcc aaaacttttc     60
attcaaattc aactagaaag ttattattga tctatcaatt tgattttaat ctacaggcgt    120
gcgttgcaat ttgggaaggg attgagtttg taactggagt acgggcaacc tcattgaatt    180
ctcttcgatc aacgtgggga tgaagttctt tcaccagttg gagtctggaa aaacttttgc    240
tagactaacc tattgctact gcctttttggt gaaatctttg tgctctaata ttaaaaagac    300
tccaactttg aatcgttaat tataaactag tgttatttgc ttgtaaatct tacttatagt    360
ttgaaatgag tgcttggcga aagtgttgtt caaatcggta cgtgtaagtt taaagattct    420
tatttcagct ttgaatcaga tcagagtctt ttaaacttaa tcaaccgaca ccaccacacc    480
ccactcttgt tcttctccac gtgggagttc ccaaattggt tgatttgtta tctctttgaa    540
tcatctcaaa tcaagaaatt tcagaacagg tttggggaaa tttgataaac tacactctct    600
tgctcgaact ttgcaaggtt tttactgttt gttatatgat tcaatattcc catttcttct    660
aattggatga actgttgaaa attggaaatg ctcagctgcc aagttttttt ccgaaatagg    720
tataaattca aagattcaat cagtgtgggt ttacccaaaa aaccaatggg gtaagtccat    780
tttggactca tgtggagggc acatgtttag gcaaagcctt atctctttgc cagtgggctc    840
acaatcaata cggacaagac aagaaatgct tcctaacacc gtcattgtca gcgaccatgt    900
gagctttcag caaattggat ccttcaagta actcacgtga aagatattta gtgattgact    960
taattactct ccccttcctg tttatctaaa ttaggcgaat agatccaaag tgggtatttt   1020
tggagatcat ttatctgttt cctgttcttg tttatcgttt ataattattg attgtttttc   1080
tggctcaagt aaaacgagga ctttgacatt tcaatacccc ctttttttgtt ttctggtagg   1140
tagcgctaag tgggtttctg atatcgtact gaaaaagtta tagttttgct agaacactcg   1200
atagatttta gcttttgtat tgattttttt gttgatattt cctggtttca gtgaatgaat   1260
gatattcttt tatgacggtt gttgtgaaga ctcataagtt tgtctcagat cttcagttat   1320
actcttgaag cttcttcgtt catacttcaa cagttcttgt acattttacc ccctctgttc   1380
ctctttccat cggcttgtga atctgtgatt gtaaattgtg ctgatgattg tttttaagct   1440
gttgagatgg cgttggggtt gtgtcctaat ttgagactgg tcaacttgat catttggggt   1500
agtgatggcc ttcttttcta tatcattctg tgaagagtac tttctaaccg attttgttaa   1560
aaacacatgt cggattgctt gcttgttttg tggtgtttct gatttgtgat atgatttgat   1620
taatctctga tcgagttgtt atgaatttga ttgacagcaa ttgggggacc atggaatcat   1680
tgtggttcct ctcatagatt ttgatttctg aggtgttgag aaggctttaa ccttttttgtc   1740
actgaaatgg atggtggaag ctctgaatcc ccagatatgg gttgtaacaa gaccatagta   1800
tggtttcgta ggacctcagg attgaggaca accctgcttt agctgctgct gctaggaatg   1860
gttttgtata tcctgtgtac atatggtgtc ctaaagaaga gggacaattc tatcctggtc   1920
gggtatcgag gtggtggttg aagcaatccc ttgcccattt gaaacagtct cttaaatcac   1980
ttggtgctga cctagtgctg                                                2000
```

```
<210> SEQ ID NO 141
<211> LENGTH: 1556
<212> TYPE: DNA
<213> ORGANISM: Cucumis melo

<400> SEQUENCE: 141

ttttagtcat tatacttcaa catctcgttg gttttaggtt tttggaaagc aaacctacaa     60
```

-continued

```
aacacactct ttcattcatt ggttttaagt tttgttgaca actttttagg agtgctttga    120
ctaagatttc aaagtcttgt acttaaaatg atgcatacta tcgtaaaatt agtataagag    180
actagatttt taaaaaagaa gaagatcggt ggaagtatgt tctaatttct aagtttttca    240
acacttacaa atttattgaa aaacagctgt cggtacatgc acacatacta tttatggatc    300
tacaattcca agcatagaag agtttagtat atatccaaat tcttattttt aaggggaaaa    360
aatgaacgaa agaatgcatt gtattctcgc ttttgtcgtg ataacgtatg attttcaagc    420
tctttcgtcg aaaaacatca acaaacaaac aagctaagtg taatctaaat aatcttcaac    480
atccttggaa atttattgaa aaataaagat ggctagcaat gcatactttt tatggatcta    540
tatcccattt caaccgtaga agattcaaag tattcgaatt cttaaaaaaa caaaacaaac    600
tgccttgtta agataaaatg gaattagaat gaaattttca aaattgaagt ggggccttgt    660
aaaagaataa actttgtttg aaaattaatt tccatcgttg gttggtagat gtgtccttaa    720
ttgaaaaagt ggaagaaatg aaggatgaat atgaaagttc tgaaaagaat atggacggaa    780
ttggaaaaaa caaaaaacct aatttcataa attaaccaga atctaaacat tgggggatga    840
agggagcgga ggccattcat gtaattggcc gtacagattc atggtttaac aaaagccaca    900
acgactccca ttcttccacc acagaaattt cctctcctcc taaattcact tatctctttc    960
tatataattg cttcgttccc caactttcta tcttcgtgca gccccattca atcccccatt   1020
ttacccactt cgtcttctcc tttctccttc gtcttccagt tccgttttcc ccatctgggt   1080
tctcctgatt tctctttaaa atcaactacc catgttcgac tttgaggaac tggtgcgttg   1140
gaattgagct ttcgaaggag atttattgtt tttatcacaa cccatctgct cgaggtaagg   1200
ggtaaaaccc gggttcgtca ggctgtagac atcacggcta tacacgtagt ttcccggtcg   1260
ttctttcatg tccgggctgt acgacggaag ggttgtataa ctccgacaaa cccttcgccg   1320
cacggcggac gtggtgcttt gccttccgaa ggtggtagtc cttctgatct tctttttctc   1380
gccggcggtg gattctcttg cttcttctct tcttcgtatt agctttgcaa cgagtccgtt   1440
tgtgttttag ctctaccggt ttaggatttg acatcagcaa gtttctgttt tgcgtttctt   1500
tgttttgggt ggggagattt tggtgttggg tttggtttga attagaagca gacgat       1556
```

<210> SEQ ID NO 142
<211> LENGTH: 2000
<212> TYPE: DNA
<213> ORGANISM: Cucumis melo

<400> SEQUENCE: 142

```
gagtacctaa tctaaactaa ttaactcgct caccctctta tttactgccc catactaatg     60
atcctaatag attgtttggt tgggttgata aattctcttt aaaattatca agttttccaa    120
tttttgccac ctaagttgtt ttcttacaaa aaataaaaaa taaaaaaagg caatgttatt    180
tctcgtatgc attaattgat tgattttctc aactaaccct tcaatttgac tttatatgta    240
ataatagtgt aaaatatata cgcacatacc tacatatgac caacaataaa aacgataaca    300
ttaaattcag acagaaataa aaattacgat tatgatttta ataaatataa atgcacataa    360
ataaaattta cagttcatag aaaaatccga tgtaatgaag tttaaatcgt tagttatttt    420
atttcgtaaa ataccaattt atgatttgca tgacaaattt ttaaaatata acttatgaaa    480
ttaaaagttg gttttgagaa aacattcaag actttattac aaccaaacaa aaattttatt    540
gagttttgtt tcattaaaaa aattattaaa ttacaaatat ttggacttac gtaatttgtt    600
ttctttcttt ttagggtaga aaaatatgat agattaaaag gattcgaaat caaactttat    660
```

atcaatttcc ttttaaataa ttatttcttt ccaaatttag tttttatatg atagcctaag 720
tctccatcat aagaaacaac gttaattata ataaaaaatg gatgtagatt caccaatatt 780
ttccaactat attattactt tcacgtttac attaaaatta aatccacaca ataatataat 840
agttttcttt gtttgattca aagtttctct tggttaaaat taaatttcga aatgataata 900
aataaactcg tgattaataa actttaattt aaatttcaaa cttaggtgtc taataaattc 960
ctatattttg tatcacaact tttcaattat gtgcaataaa ttttctaatg atttattatt 1020
ttttttaaga atgtaaagtt gattatattc atattaaaca taagattgaa aagagagagt 1080
tgattatata ccgagtagcc gacagtcatt ggaagcatta acccattatc atctccggcg 1140
agcaaaagca aggatctaca aacaaacatg acaattaata tgaaactcat caatccacgt 1200
atccaaacat tccatatgtt agacatggaa gagcaataat tacaaagctc tctcatcgtc 1260
tccgatcact ccatttatcg tacaaatccg tctttcttca ccttaatcat tttccccgaa 1320
attcatccca ctgtttcgca acaaaatcca agtttggaaa gatgagtttg tttttagtga 1380
tcaaggaaag gacaaagaat gtagcattgg caatgacggg caaacaagag aggtgtggct 1440
aaacttatac atgcttttgt ttggtgaaag gttaaagcga agaacgccaa agacagagga 1500
aaccgtataa aatatgagta aatgtcaatg ctaatgaatg ggcagaggtg aagcggtcgt 1560
ctatggctgg agaagggcag atgtgaaaca atatgaggta gacgaaggtg gagacaaaac 1620
aatttagtaa agtcaaaaca attcatccat atcctaatcc aattatattt ctttaaaaag 1680
tttaagtatc aaaattggac tgcttgatca tctatcaagt tatttttgaa ctttatttta 1740
aaaagtttaa gattattaat aaaaatgtaa tgtttaaagt ggttagtgct ttggaagcca 1800
ttacgtccta tggattatgt ggtgtgttgg gctactctct atttggacat gttttgacgt 1860
accgtgcgaa gtcctgactc tatttgtaaa acgtcacccg gcaaaaaccc aacttaaaaa 1920
acagaacttt atttcattta atttgcgggg tttatccgga aagaattgtg agagctctct 1980
tgtgtttggt ttgcttatct 2000

<210> SEQ ID NO 143
<211> LENGTH: 2000
<212> TYPE: DNA
<213> ORGANISM: Cucumis melo

<400> SEQUENCE: 143
gtaatgcaat attagcaatt attttggagc aatacaaaca actaggtttg gatcaaatat 60
cacgaaatac aggagcaata acattaacaa caaataaatg cacgaagttt tttttttga 120 acaaacactt aactctctcc aaaccaaaac gagctaagtt agacctaaaa aaacaaagta 180
tcggaataca atatagctta aacaaaaatc atgtttagat tattggttag gttcatctaa 240
actagtggtt agccattttt caaaagaaaa atatgatttg tccttgctaa ttttccaaat 300
ctatatttta aaagtatcac tctcgtcata attttccata gctcaattaa tactaatctc 360
acggtagctt ttaattgttc ttgacaagta atggattaac ttaaaacatt tatataactt 420
tgtaggtatt attttataga aaaattagtt tatacgtgaa aacttcttaa atatctaact 480
acaatcaaat acctagatta cataatgtat ttttcataat atttatacat tatatttgaa 540
aaaggactct catttctttt attggtatct acgcagaaat taagattttc gagttgcgac 600
atctcaatca acgaaccagc taagaagacc ggcaaattcc aaacgtatcc ttcgggaagc 660
actgagtgtt tccacgtcaa taacaaaata ttgacccaat aaatttcagc cacgtagaaa 720
caaagcaatg aaagccgtcg gattctccac atcggctacc gtatgccgtt aagatcatca 780
agtagacttc taattcccat gtcttccgtg ggggccagaa atggaaaatt gaaatcgctt 840
tatccacgtc aagctaacaa aaaacaacca ataataattc gccacgtttt ctcattagaa 900
aagtgcaccg ttggatcatc cacgttggca acatagatcg atccgatgga cttatataaa 960
tttgggtagc tcgtcgagaa atcagatcag tgatcgaagc tactggaagt ttttgctaag 1020
aaccatgagg aagtggacga tcgcttctgc tcttctcctt ctttgcattc tctctctcgt 1080
tcccgatgaa ggtgtgattt cgtttcttcc ttcagcagtt tgatttattt gttggaatgt 1140
aaactgaatg cattgcatta tcttaatcac gagggctgat gctttaattt ttgggggttc 1200
gaggagaaat ttggatgaga ttcgagcttc gtttgaactg cgaaggtttg atggtgatat 1260
ttctattgtg tttgaatttt caggtcctag atttcatgcc aaggccgacg gtgatgccga 1320
cgaggttgta gatccaccaa aggttgagga aaaaatcggc gccgttccac atggtctttc 1380
cactgattct gatgttgtta agaggttcgt gaatgtctaa tctcgttgat acacgcttca 1440
agtatagatt tgtccacttc gggaaaaaaa attatcgaac cttcttttga atgttgattc 1500
agagagtcgg agtcaatctc gaagagatct cttcgcagta gcggggagaa atttgagttc 1560
caagctgagg tgtctcggct catggatatt atcatcaatt ccttatatag taacaaagac 1620
attttcctaa gagaattgat ctccaacgct tctgatgtaa gttcactctg cctcttctca 1680
cttcattaga tctagtaatc tcattgttag atttgtgtta gttaataatg gcgtctctgc 1740
atttcaggcg ttggataaga ttaggttcct ttccctaacc gacaaagaga tattgggtga 1800
gggagacaac tcgaagctgg agattcaagt gagttcgacc ttcatactga catattgttt 1860
tcttattacc tcgctgaaaa aagctgctcg ttctggttga tgaaccttgc atacttttat 1920
tgttgtccat aaatcaaata tcgcagatta agttggacaa agcaaacaaa atcctttcaa 1980
ttcgcgacag aggtattggt 2000

<210> SEQ ID NO 144
<211> LENGTH: 1337
<212> TYPE: DNA
<213> ORGANISM: Cucumis melo

<400> SEQUENCE: 144 tttttttaa ttttcttttt gcagattgtg gggctgatcg tccacgatat gattccactt 60
tggctacgag gggtgtcggg caccttgtcc gtaagggcac tggtgggaga tcgtctgtta 120
ggtaacctag ccctagcttt ttcgtgtttg gattcttcta tttaattgtt ggcttgatgt 180
tgtagatgta atgctgggtt tgagtgcttt gaaatgttga gggaaattta agaaatttaa 240
tgggatgaag atgaacagtg gtacttcaag cctcaaattg aattaaaatt attttaaaca 300
tcctaaattg gtatgactaa gtattgctaa acatgatagt catataaaag cgcaaaagaa 360
aagaaaaatc acccctctac taggattggt ttattctatg gatttttgcc ttcagtgttc 420
ttgaagtcac aataataaaa gtagtaatag ttgcagtcac aactcaaacc tttatatgtt 480
ttttaagatt gtggtaaata ttgttttgat cattagacaa gacatagaga ttttaagtct 540
ctgggccttt tcacgaagcc ataagcctct tatggttcag caaaggcata ctcaaggcta 600
gaagttaaaa aagccttgcc ttgagatgta attctgaata ccttttttaaa acatttggta 660 cttcaaattt ataagtttat tagtggaaaa tataatcttt cagtctcttt tttagctgaa 720
atacttatac cttttttccc cattgtcatt gatttcttaa ttcatatgca gaggaaagga 780
ctaattagat atactttgtt ttattgagta atctaaaaga tgtggcacta cccactatga 840
acattttgac gtcattccag cttttatggg atattgaagc aggcaatttt aatctgagct 900
ggtttctctg tcgctgtcag ataatccttg tttgtgctta tgtgttctct ttcaagcatg 960
cacattagga ttctcaggca gatcagatca ttgatattta attcaatttg tggatttagt 1020
ttgtagtgaa tacactaaat tctgtctctg gtttctctga tcttactgtt ttattacaaa 1080
attgttttgc agtgggattg ttgctactgt cttcggagct actggattcc ttggccgata 1140
tgttgtacag caactaggta ataggtgaac ataaatggta ctagcattcg actttctttt 1200
tgcttagata tgtaatttat tacgtttctc tataccttct actactagtg ggttttggca 1260
gctttggctc tattcttgat ttttatatca attttatgct aagcatgatt ttggaaatga 1320
attgtgtttc agctaaa 1337

<210> SEQ ID NO 145
<211> LENGTH: 2000
<212> TYPE: DNA
<213> ORGANISM: Cucumis melo

<400> SEQUENCE: 145
atatgtgacg attaattacc taaaaattaa ttatttacat agggttagtc aagttgtccc 60
gtgagactag ttgaggtgag cataagttga tccgaaagct cacaaaaata taaaatacgt 120
caatctccat gctttcataa aaataacaat ttgattctca tgactactca ttcacttatc 180
gtaaactctt ttaaagaata ttaagagcgt attagtgtag tgggctagtt tgttacaaaa 240
gttggcgaca aatagatgaa attagagtta tctcgagatt cgacgagggt taaaaagagc 300
atttgcttta ccctgtattt tcatcgtagt tcatatttat ttatattcaa attctatcaa 360
gttaaggcca cgtatattcc aagaaaacat aatccattaa tggtaatatg aaaaatgagt 420
tttaatttga tcatgttgtc ggcattatgt aatcacaaag atatctaaag ctcaatgtta 480
aatctaatta atggaggccg ataatccaat tatatttgaa aattaagtgg aacctacggt 540
gagatatttg tactatcaca attacaatta ctcttacttg ttcggaaaag aaattttgta 600
aacatgtcaa aattatcgtt actattccaa atattgtcac tgacctgaac attgtcaaaa 660
agaaataaat aaataaaata atattagata atgtaaaata aaccacctaa actttaatct 720
attatggtcg caaatgcttt gataacacat aaaccgattg atccgtcaat gaaattttac 780
cataatcttt attatggatc gataaatatg acttaatttt cttttaaaaa agtgtttttt 840
aatttaaaaa aaaaaaagga aaggaaaggg ggaggggcaa aggttctaga gtgttccaaa 900
taggacaatg gaggagggtc tccaatggag ggaggagcca aatccaacgg ccaacaattg 960
ctggaagctt caggagccta catgattctt gggttcgttt ttctctcctc ttcctatcca 1020
tccttttgaa atttgctata aagaaaccta cttctcttct ccttacaaaa aatccatttt 1080
acactctctg taataccccc agttttgcct cactcgcagc gctcatttct caccctctta 1140
tccaaatcaa tccttctccc tctaaaccct aaaacccctt tgcacctccg ccgttttctt 1200
gtaagattcc ccctctcttt tcattctgtt ggactttctt atccttttac tttactgggt 1260
catgcttaca tttctatttg ggttttgttt ttgcttgccg attcagtctt ctgtattgtg 1320
ttttgagctt tctgactgtt ttggctttct gggtttcaat tgttggtgta gacttatcga 1380
ttgattcgtt tgttttgtgt cctttcattt ctgggttttg atttctttaa catttcttc 1440 atgggttttg gattttgggt cttcttcttg tgtgcatctc tgtagcttgc tgattcattt 1500
gtatctcgtg tttatctatt tgtttgagtt cctgacatgt gggtttttgt tgttgtctga 1560
gaattatgtg tcaaatgtca attgtcaatt cctatgttct tgaatttgtt tatgtcattt 1620
cctttctggg ttttctctgt tcaatcttgc tacatgggtt ttgggttttc ttacccttgt 1680
tgtgtgtagt tttagctgat ttttgtttat gcttactgat tcggttctgt attctcgatg 1740
atttgcttac ctggtttttt atgtcgtttg agaattgtgt gtcaattcct ttgttgttga 1800
ttttgtttgt catttctggt ttgacattcc atccaatcct ctctgctcta agtctacttg 1860
gttttcaatt catgaatttc catcagacgc attgtcggcc ccctgctcta tttgtttaca 1920
attctggttg tgaagttgtt tcagtttgaa ctaattgatg gtctggtgat tacgttctgt 1980
atcagtttgg aagagggtaa 2000

<210> SEQ ID NO 146
<211> LENGTH: 1212
<212> TYPE: DNA
<213> ORGANISM: Cucumis melo

<400> SEQUENCE: 146
atatatatat atataatgga ataggctatt tgatttagat gaaagctatt acgtcctggg 60
gtttacatca taatctctat tataatgtta atcgagaaac tttataaagg ttaactcatt 120
atctctcttg tcttcagttt attattgttg tttttatatc ggtggaattc cacctttcac 180
caactctcaa gctgtggtgt gaatctatgg gattaatcta gggcgaataa gggagctgag 240
tattttctat ttgtggaatt aaatctatag tacacaaaac atttgctcaa ctactaagga 300
tatgaaaacc cttggctctg ccaacatggc ttatagaaag tatctgaaaa cgttcaccac 360
tttgcaattt caacaataag tgtaaattct tttcctattg ttgttattta gtcgatttga 420
tcgttgtaca atatttgctg taacatgttt gatttttggc cattttagtg ttcacaagaa 480
gatattgttt gttataagaa tctacctgat ccttttcaat tgttattcaa tatattgcct 540
actccgttga cagcaggtcc atgcagagga acaagttcta aagttcaaac tcgatgctga 600
tattcttcag gtactacttt tctgttttca caagtttgtt gtttcaatag ttctaagaca 660
gtgacactca tccctttatc tccgtaaccc aattcattaa cgatgacttt tgatcggttt 720
gaagaaaaaa tttataacac tttctcatct cgttcccttt ggattttcag tttttaaaat 780
tgcatctata tgtattcttt tgttatcaaa ttttacttga taatgacttt taaattgtac 840
taactcattt agatgtgaat attaataatt ttaaacttca tttctgacgt ctaatactaa 900
taaaataata ataacaatta tccttcttaa ttaaatatgg tttacctacc ggtctattgt 960
tctgaactgg atatattcaa tttgttttat ctgaataatc ttttgaggtt gagttatcaa 1020
gagcctgttt aacttaccta aagcatttct aacctgaact atgccccata tgaatacttc 1080
attttcttta ttctattgta aaacattgtt gttattataa tttgaaacgc ctgtaatagt 1140
ttttacgatg tcttgcagga gtctatcgtt cggcatgtaa acgaacaccc acaggctggc 1200
tggaaagcta cc 1212

<210> SEQ ID NO 147
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 147

```
acatagtatt aataaattag ggaatgactt agttatttaa tttaagcggt agtaaatatt      60
attaactttt gttcgttgtg ttattttact ttcaaaacgt tcatcttgat ctttatcctt     120
tctaatattt atttatttta gttaatatca aaaaactaaa tttaatttat acgttaagtt     180
acaacttcat ttatttcaat ctaaaacttt tagaattaca ctttattcac taaaaaatta     240
ctcgtaaatg caaccattcc aaaaaggttt caatattata taaaatatca taatttttcg     300
aacattctta aaataaatta aacaaaatag tagttttcat atacataaaa ttcgaataaa     360
tcctcataca aaaattttaa atttgaatca tcacattgtt ttattttaga taatcaatca     420
aataatttag gaaaagagaa gaaagaaaag taaaaggaag ttgaaggtat tttatttagt     480
gatagaatta taaaataggg tattttagaa ataaaaacac aaatatataa aaatacagaa     540
attgatgcat ttaatggaac actatttgac aatcaataag aaagaaaaaa aagaannnnn     600
nnnaaaaaaa gaaaaaagag aaaaggtttg gtattgggtt tgtgggattt tattaataaa     660
tgaaataaaa aaaaaagaaa gaaaaattta attgattaat ttggtgggag aatattacaa     720
tgaaacccca ctttgtgaac aaatacattg catttgggtt gtaatcaagt gtacatgcat     780
ctacccaaac ctttcttgaa ctcaccataa atccttcttt tagaccgctt cgacttccca     840
atttttcttc actttttttc ccccttctct ctcttcctcc gtttcccccc cccttttttt     900
tccctatctc atagggtttc catccacctt cttcttcttc cgttctctca tgcattgtca     960
ttcacaatct cattctgaat tcctcttgat cttcttcatc ttcatttcct ccttattttt    1020
tgctctcttt cgagggtttt tcggttcatt tccgtccaga ttccaccacc tcccgtggtt    1080
ttttcaccca tactcatgtc gaagctcttc gccttttccg gtaagtttat ggatttttac    1140
tgattttttt tttttgtttg ttttgccttt ctttggattt gacttagatt gggtagctgg    1200
tagggttaag cgtcgtgttt tgtatgggtg tttggattgt tatttggatc gtagggaaag    1260
atttggaatt attggtttta gtttttgggg gtttcttgat tcgccaggtg gcggatcatg    1320
gcttggtatg aattgtgagg gaatatggat ttgggtttct ttctattagg attgttttat    1380
tgtgttgatt gattggctat tttattgtct tgaacagtcc atgccagatg taagtttctt    1440
gaaaagagat atcgtagttt gaagatgggt ttacctttta agtgatgtgt atgtgttgtt    1500
gatctgtcgt tcccgtacag atttagattt gaggtttaga ataagagagc acatcaatag    1560
taaatattaa agggtcaaat atagttttgc agagattgct tcttgttttt ctctgttgat    1620
aaattttcga tcttttgatc tagaagttga ggggtatttt ggtctgagga tttatttgtg    1680
atgttggatg atgtatctaa cttgtagttc ttgttgttga aatttcaggt agtgaagatt    1740
tttgcactgg agggtcaata tacccaaatc ccaaggactc cagtttattc ttgtcccttc    1800
ctcaccacgt tgatgtctat tttcctcctc gaaagaggtc tcgcatcact gctccatttg    1860
tgtttggtgg agaagaagtt gaatcaaaag caaatgtttc tatcgagatt cttccggatg    1920
agtgcctgtt tgagattttc agacggttgt ctggtggcaa agaaaggagt gcctgcgcaa    1980
ccgtttctaa acgatggcta                                                2000
```

<210> SEQ ID NO 148
<211> LENGTH: 1254
<212> TYPE: DNA
<213> ORGANISM: Cucumis melo
<220> FEATURE:
<221> NAME/KEY: misc_feature
<222> LOCATION: (1)..(1254)

<223> OTHER INFORMATION: n=g, a, t or c.
<220> FEATURE:
<221> NAME/KEY: unsure
<222> LOCATION: (1)..(1254)
<223> OTHER INFORMATION: unsure at all n locations

<400> SEQUENCE: 148

```
tcataaatat atatataaaa aaacaaatat tataacctac cttttgcaaa tgataaaatt     60

gtaaagtctc gtgccgataa tgtgttataa aataaaagaa caaagaaact aaataagaac    120

aatgcaacaa nnnnnnnnnn nnnaatagag aagagaggaa gaaggggaaa caattaaaaa    180

ctcaattgta gtgtgactta cacaaatgca acacatatat ctatttatag gacatatcat    240

ggtatatgtt atattatgaa attcaatgaa atgaatgtta caataaagaa ttgaatgaga    300

gttgtatgaa aattgtaacc ttcataaatt atggatatct actcttataa tatatcatta    360

tatttataat gtatactata tgtttgtatt ttaataagaa aattatccca ttggatttgc    420

gatcttagat ctaacctact aaacaaatat tccaacgaag aggaacgaga tgagaacgcc    480

gttctaacct acgcaatatc aatcgtttct tcgctgctac tttacgcctc aagttcctac    540

ccttcaagtt tcatcttcaa cgatcaaccc aacgattaac ccactgcacc accttatctc    600

ttgttggtgt catctaatcc atcttcttcc tgcatcttct gcaaatgctc tcaggttctt    660

tcctctctct tgtgcacaaa ctgatcaccc atgttgttcg ccggaaaatg attcagattc    720

ttcgtatctt gcctgcattg tctttgacta taatatgatt gaaattcact tgttgattgg    780

ttttcaattg ttaattaccg ttggttttgc tgtttagtga tagtatatta tgaggttttt    840

gttcgttttc gggtttttgg atgtgatttc atcctataga atgaagagta tgcaacgtat    900

gctgtcacct tgcgggggaa atggtacacg tggacccgaa atggagctag gttttgatac    960

gtgcagtttg agttttggtt ttgggaggat ttggcattcg ttatatgaat tttgtaatta   1020

actatgccgt ttgattgtta tttataacgg tgcattgctt tttgaggttt agaatttgga   1080

cttaacgcct ctttctattc atggttattg gttttatttc ttcctttttg ttgactgaga   1140

ttggtcgtag aactcgttgc ctgtctatgt tttaatgttg gcctgatttt gaatttctaa   1200

tccatgacta agtatttctt tattgtcttg atatagttga ttgaatcatc aatc         1254
```

<210> SEQ ID NO 149
<211> LENGTH: 2000
<212> TYPE: DNA
<213> ORGANISM: Cucumis melo

<400> SEQUENCE: 149

```
cattttaaat tgacctttca tgaaaaatcg tatgtttttg gtgtgatttt gagtataata     60

aaaatgattt taaccatttg aaaatcactt taaattacac ctaatgggtg actgaggttt    120

tagctttcgt ctttgtttag ctctaaattt gcatggcaag ttttccattc caatgattga    180

tgtggcttgt aatagttgaa atatatatat atatatatga ggtatcaaaa tccccagcct    240

tgtgttaggt tgaatatgga gggagtgggg agttattttt cctgctctta ccccgttcct    300

aattcccacc ttgtttacta tgtgttattg ttattgccat atttactatg tacataatat    360

ttcgattaga aattttattg tttaaccatt agacaatttt atatgtctaa accataggtt    420

tgaacaaacc atttagatta tatatatgtt gacaattaga ttgatagggc aattattttg    480

tttatcctaa aaatggtaaa taatgttctt aaacttggtt ctttgtgaaa taccttcaac    540

tttcaaagtt tttaataata ttcttacgct tataaaaaga aaaaaaggat aagttgaaaa    600

aagaatactt ctatgataag ttttagatgg aaactattta ctttttcatt taaaaaatac    660
```

```
ttttcaaatt tatgaagttc caaaagtatg acttaaagaa atagttatac ccttattgat    720
aatatacgac aaaaacaacg caatatttcg ttacaaaaat aaatctagct gcattactat    780
cttactttaa agatactctt atcgtctatc taaactacct tactctagaa ttaataatta    840
agttcctttt actttataaa tataacttat tcctactatt agtatatatt tatattggta    900
tctaatagct aattttgaat tttgttccaa aaaaaaaata tcgctgagtt ttgttttgaa    960
gtcttttttt ttttttaaat atatattttc gattaaagct agatgttgca gttgatatgt   1020
agatttaaaa gaaatgtgtg agatcgttta taactatata gaagattaag catttattac   1080
ttcaaaatat atcgttaaaa ttattcacat aaccaatttt tactcatcaa atattatgtc   1140
agagaaaaga aaaacgaaaa agaaaaccta cttcaacgga caaagaagtc cttagttcaa   1200
atcttcaaac ctttatttgt attaaaaaat ggcatataaa ttttttcaat ttttacgcat   1260
tacctgttgc gtgaaaaaca ttgatttaat agaaaagaac tgtcctttca gttttgtttt   1320
tttaaaacca atttcgaaat tcaagaatag aaacaaaact ttaagtctag aggatcacta   1380
aaatctatca taaggctaga aatacatctt gtaatctgca gtaggcattt gccgggatga   1440
caattttctg gtgcttggat taagaaaaaa gaaaaaaaga aaaaagaaaa aaaaatggtg   1500
aggacttaga ggccataatg agtttggcat tgggcccaca gtaggatgag taaattataa   1560
ttgggagaaa atgagcatag ggtgtggagg ggaaaaggag aaggctaaaa cactatcaca   1620
aatcacacag tagaagatac acagaagaag taaccacagc cattcattga gtgagaggct   1680
atccataatc tcatcctctt acccttctca tcattcattc aaagccattc aactcaacat   1740
cccactctta gttaaccaac aaaatatata tacatccttc tcaatttccc ttctctctac   1800
tgctttaatc ttttgcttct tcttcttctt cttcttcttc ttctgctttc tcaataccct   1860
caaccatggc tacggctact ctatcagtag ccaaaccatc tattcaggtt cctccattac   1920
taaacaccat cctctttccc ttccactctt ctttaatttt ttgtatctga taaacattac   1980
tgcattttct tgcatagcag                                               2000
```

<210> SEQ ID NO 150
<211> LENGTH: 1680
<212> TYPE: DNA
<213> ORGANISM: Cucumis melo

<400> SEQUENCE: 150

```
tttttatgaa gggagttgtt attttccttt gggatttgga gggatatgat atatatcctt     60
tttttgcaat ttgatgacag aattctgctt ttagagactt ttcaaactgt ttcgtaatga    120
atttgatggg ttgggggtgg cttagttcaa tactttgtgg gttgaaaatt ttgatttgca    180
ataaatgaaa gccaaaaatg tggggaagct ttcagttcaa gtaagttaag ggaaaactgc    240
agaatatctg gcttgaaata agagatgtct tcgaaggtta atagttttac attgactttt    300
ttaaaaaaaa gattatatta taagtacaaa tatgggtgga tgtgaactta tattattcaa    360
agagactaat ataagttttg ggcgcttaat attttatatt ttcatttagc agtcaaagat    420
gtataagaaa actttggtaa tgcattttat actagtttat ttatgtagga tgtaggatct    480
atcgaataat acaacatatt tttaaatgat gtgtacaatt gtgaaaaaaa aaggaacata    540
cagtattgta gaaactaaaa tattttctaa gatatatcga gatgtaaaaa aaatgaatgg    600
atgtcaattc cagcataact taattgttga actaaaaaca aaaagaagaa ataaaggggg    660
caatggtttg atcctcatgc cccacatgaa agtcaaagtt atgtaaaggt tccgtgtagg    720
```

-continued

```
atatccttcc tcctaataag gggagatagg attttatgag ggtgccaaca gctcagaatt    780

ccaaattccc aaaataccct cttgcttgaa aatttcaaac tcttctgttt ttgccttgtg    840

taccattcac tattccgatg cgtacagttc attaaccaca caagttctcc ttttgcaggc    900

aggtttagct aaacttattg gacttgctgg agagaccaat gttcaggtaa gatcttattt    960

gttataatga actcacaaac taatttagat tagccaaaga attctgtttc tgaagaaaga   1020

gaggatgaaa atcatctcat accaaatttc tttcttttt tggaattatg tcttcacatt   1080

tattcatttt ccttgtcaac agggtgaaga gcaaaagaaa ctggatgtgc tctcaaatga   1140

agtctttatc aaagctttgg tcagcagtgg cagaactgta agctgctatc taatcataca   1200

aatgacacga caaaaatatc tggtgactta ctctaatagt tgacaaattg gtggcagtgt   1260

attcttgttt ctgaagaaga tgaagagcca acatatgtcg agccatctcg gcgtggaagg   1320

tttgttttcc attcttgatg atttttgtct aatgcttaca attatcatca gtatcaactc   1380

ctcttacttt gttttaattt taatgttatt tcttcttatt ttccaatgac aaaggtattc   1440

tgtggtgttc gatccactgg atggttcctc caacattgat tgtggtgttt ccattggaac   1500

ggtaacatcc ctatgctacc ttctgaatga gatttcaaat atttttggta taatttcttt   1560

ccaataagct gagtgtatga ttgtttgaat atctactttt tcatgtagat ttttggaatt   1620

tatcacttga acgacagcca cgaacctaac ctagaagacg tcttgcaacc tggaaagaat   1680
```

```
<210> SEQ ID NO 151
<211> LENGTH: 1524
<212> TYPE: DNA
<213> ORGANISM: Cucumis melo

<400> SEQUENCE: 151

tatatatata tatataggta atgagtaaag aaatgaaaaa gaatgagttg aagaatcaca     60

cccttaccat tctatttgaa actcgtgagt cttgtagact tttacatgtc ttctccttca    120

cttaatatca ttctggattt tgattatatg tatctttatt tctaaacagc ttggacagat    180

ttattattgt tagaatacct tgaatatgtt ttctggtgct tagaacgatc atacatgggt    240

ttttctaggg ttagaggagt gcgctataca taaactttct agttctagag gcattgctgt    300

aatcttaagt ttaacagttt ctctttaata acaaaaactg ctcttcccct acggtttaag    360

ttttctcctt atcttaacag ttataattat gaaaaatgat ggaaccaaaa caaagttctg    420

ttaaaatttg actaattgat tgaatgaact tttgtttcca agattcttaa tttgtaaagt    480

aataatgttc ttacaaatca ttattttgat gtctgagtta taacccttaa gcttggtggt    540

tcatattcca ttcaggtgaa gaagattgtg agtgaaagct gttcccaaga ggttttagaa    600

gtggcgttaa actccatctc atccctaatt accatcctct cctccatgtc atcgtctacc    660

aaactccatt cttcactttg atggtataag aaagtgaatt agatttggga ttgagcttca    720

aaacatgtat gatgatgtga atatttactc gtgtaaataa tataacatgt tgtattcttg    780

cttgtttctc tttgctcatc ttcgttttgt taagagcaaa gaaaagctta cgagcatgaa    840

catgtgcaaa tttatgaagg tcaatgggct tcgtaatttt ttttccccat tgatttaacg    900

atttatggaa gatggatata gtaaatttag gttaagctgt acaaaaccag agaattttca    960

ttatagtaaa tactttacaa ttttcaatta gctacaataa acaccgtttc aaaatctccc   1020

tcatttgcta ccatatttac tattcgatat ttatcatttt ttttattcct gttgtaatgt   1080

ctactatttt tcttttaaac tattacacca caaacacata ctattataat tcaaattaaa   1140

ataatcacta gtataactca actataataa ctcagatgat ttcattccat gaaagtggta   1200
```

attataaata tttaatatct tatatgataa ggataactat ctatttggtg aaaccaaatc 1260
acaatgatgc agtggtaagt gctttggact ttgaatctct tttttatagt atttcattct 1320
tttttcaacg aagcagcatc atgggccttg aatggaggcc agctagaacg agcccattac 1380
atttgacaga gcatctcttc ggcccatgag cccaaacact attcatcttg ttaaaccacg 1440
aacaaatcga gactgccgag agtgtaagag aattgagtaa tttttttcga gacacaggga 1500
gtttagagag taagtcggag aaca 1524

<210> SEQ ID NO 152
<211> LENGTH: 1851
<212> TYPE: DNA
<213> ORGANISM: Cucumis melo

<400> SEQUENCE: 152
ttgggtcgtt acaatatcac tgtttaaact taagtttatt tttatttatt tttttatttt 60
ttaatctttt tcccttcttc ctttcatctt ccattcattt atacaaaaat aaataatgag 120
aaaattactt ttcacttttg agtttaatta tttttaagtt ctaaaatcta cattttaatc 180
tttaaattta aaaaaaaaag gatttacaag attcttgagt aatttattat tattattatt 240
ttgaacgtaa atataacctt ttacaaaatc taaatgagtg tttgggacaa tgagttgatt 300
attataagta ttgaattata ataatttttt gtggggtata gactatttta atttgaagaa 360
taataggtac gtgtttgaaa tataaattat gttagttggg aaagaaaata gtaaatatcg 420
tagaaaaaaa taaaataaat gaacaataag aatataaaat atggtaataa attgggactt 480
tgaaataatg gtaataatta attaattaat tgaaagctac aaaacaatgt tcacttcatt 540
gctatagttc taaacagact aacaatctca atcaatgacc taatgggtca ggccattata 600
ttgggctcaa atagattttg gcaaaacgaa tcgaaagccc aatggggcct atattatgta 660
gggccgaaat gaatttcaac gaaaggaacc caaagcccaa taggcccaaa ttgagactta 720
caaaggcgca tgttagcatg aagagagaat tgaaagctta aacagcgcca tcacaaaaca 780
tttgcatttt cgtgttgaaa tcgcatttgg gccgtaaacc aatgaaacac aaaacaaaca 840
aatcctggaa tagcctcaac ggttctggaa gaagaagaat cttctggaac ctccaatccc 900
acaataaaaa tcaaacccta aactcttaca ttcagctctt tgcttacctt atcccaacaa 960
accttcacca acgctctacc ggaactaaaa cccctccgac ctcccacttc cgacttacga 1020
cctctgttgc ctgaacatgg cgtctgccaa tgctctttct tccgcttcta ttctatgttc 1080
ttctcacaag gtacttcact tataaccccc tcatttcttc cttgtatttt tcacaattcc 1140
tctttggaaa tgatgatatc tagattgtag tagttgggat tgtatgttag gtagagattt 1200
tgtggagtta gctgagagcg gctgagaata ctaatatatc gtttccagta gcttacgttg 1260
cgtttttcta atgttgcaga gcttgagaaa ggtgaatcaa acgcagaaca acagagtaaa 1320
ttacagacag gctggtagta gatttgttgt gagagccact gcaaaggaga tagcattcga 1380
ccagagttct agaactgcac ttcagtctgg gattgataag cttgctaatg cagttggttt 1440
gactcttgga cctaggggta actttctgtt tatatttatt tatgaattgg ttagtattgg 1500
atgttgttct aatattgaaa tccctacagg atatattcat cacatttata gattcgtgtt 1560
atggttatgt tgagaaattt gggttcttca cataattctc aatcttgttg tgatattttg 1620
tatttgaagg gaggaatgtg gtgttggatg agtttggtag tcccaaagtg gttaatgatg 1680
gtgtgacaat tgctcgggca attgagttac ctgatcccat ggaaaatgct ggtgcagctt 1740

```
taattagaga ggttggtttt ttatactttg ttatgaagca aaattttctc atctatcgat   1800
tattgaagtc ttattagttc ttacattgcg ttgacaagta ttctatatgt c            1851
```

<210> SEQ ID NO 153
<211> LENGTH: 2000
<212> TYPE: DNA
<213> ORGANISM: Cucumis melo

<400> SEQUENCE: 153

```
actaattaat agtaatttgt atgggatata tgtatatgtg tgtataacag gaactacaga     60
gatagagatt cactttctag aaataaagtt gactgccatt ggagtttatt tggagccttc    120
agttgtggag catttgcaac aatggaaggg aaaagctgct aaggacttag tggaagatga    180
tgacttcttt caggctattg tttctggtat ctccctagtt atcctatttt taactatact    240
atctcatcac attcctaaat gtgaattact tgacgatctg ttcaaacata tatatttcat    300
tgtttgatcg taatgtttca tatttatgat gtttcatata ctacctcgtc acacgtgcaa    360
aggatttaga tccgttcaaa catatttcat tattggatcg taatgtttca tatctatgat    420
gtttcttata ctatcgcatc acacatgaga tccattcaaa catatctcat tgttagaaag    480
attatacatt atttcaattc aaatagctct aaccaatgac aaaattagat tcgtcccgtt    540
tagcttattc tatatatata gatagataga tagatagata gtatggatat gcttgtgata    600
agtgtttttt tcttcttttt tttttctttt tttgtttttt ttctttttttt gtcactttct   660 aaattatcta tctcacagtt agctagttgg cggggtgatg acttttggtg tgtcagtcta    720
gtgagaagtt tgggggttat ttttattttc gaaagcttcc taattgaatg acttgtaaag    780
gttaatgttt atgtttttgt acatgttttt catgaactat tggttttaca agagttacaa    840
ttctatttat ttgtgtaaga aagatcatat cacattttta cccctggtgt gttcgtttta    900
tgttcttgat ttgcttttttg tttttcaata atttacgggg aaagagagaa taaaattttc   960
tttctccgat ctccgcattc aatttttttt tttttgaaag gtgcattcaa tttttttgtg   1020
cttattaaat attcacttac atcttttgtt ttgtttattt ttttattttc atctttctta   1080
tatgaaaata aaatattttt tagtacaaca atagaacctc ttgttaccat tgaaatgaat   1140
tacaggaaat taaaactttt actttttatt tgagagaatt aaaagagtag tttttaaata   1200
taacaaaacg actttcgcaa tagatccaga tgatcattta ttaacaattt tctaattaaa   1260
attgttacta aattttaaca attattaaaa aatattaatt gaaaaacacg tgtatatata   1320
taggaacatt ttcaattata gccaaaagtt ataattattt actctataaa attctttaga   1380
gtctatttaa cctttttgtt aaattttgtt aatagtttta ctttgccatt cataaaaatt   1440
tctcatatta tatacagtga gaattttata agtctcaaaa gtcaaagatt tgattaaaaa   1500
aaaaagaaat gaaagcatat ctaaatatat tatttatact ttgaaaatta cttccgaagc   1560
aaaatgtaaa accgttataa gtgaacttag aatccaaaaa catatattaa attaagttta   1620
aattatataa caacaccttt ggattttgtc attttctaaa atacctttta tcatttcaat   1680
aattgtaaaa tgagtcctaa attttcacaa atgtttcaaa aatatttgga ggagacaatt   1740
ccttgagaat ttcaaagata tattaaagag gacgtattga cccaaatctt ttgttctatg   1800
tcactatgat caccctttta tatcacaatt tatttccatc tacaattcta aagaatttat   1860
aatttaaaag tagtttcaaa atgtttctaa attttcgagg gtaatatttt aacttttgga   1920
agtacggaaa gttaatcaaa tctttgtctc aaaatctcaa ctaataactg gaattgggaa   1980
agctaaagtc tagaccttaa                                                2000
```

<210> SEQ ID NO 154
<211> LENGTH: 1288
<212> TYPE: DNA
<213> ORGANISM: Cucumis melo
<220> FEATURE:
<221> NAME/KEY: misc_feature
<222> LOCATION: (1)..(1288)
<223> OTHER INFORMATION: n=g, a, t or c.
<220> FEATURE:
<221> NAME/KEY: unsure
<222> LOCATION: (1)..(1288)
<223> OTHER INFORMATION: unsure at all n locations

<400> SEQUENCE: 154
cgagaagtac ccggcgttgg tcaccggatt tttcttcttc atgtggtggg tttaattgtt 60
ggtcacgtgt tttgcacggc gaaggccggg tggtaattat tacgttgcgg caagtttgag 120
cttggttgtg tgaaattacc gtgttgtcct ttctgttttg taggtacttt ttgaacgtga 180
ttttcaatat cctcaataag aagatatata attacttccc ctatccatag tatgtatttc 240
caatttacat tttcatccct gtatttttct tcttcttctt cttnnnnttt ttttttaat 300 attgttatta atatttgttt acgttccagt tttgtgtcgg tgatccattt agttgttggg 360
gttgtgtact gtttgataag ctgggcagtg ggtcttccta agcgagcagt aagtcaactc 420
tttctatagc ccaatatgcc aattttgtct ttttctttca ttaaaattgt tatttttaac 480
tttttcatac ccaatttagt ttttttagtc tgtttattag tcttgttttc ttcaaattta 540
gtagtattgg tagtctaatt ggtagggctg ttttgaaagt aattacctaa tataatgagt 600
atttagattg agacagtact atagtctaaa cgatgtcatt gcagttttga ttgaaatttt 660
ttctccttta tttatttcga aaatgacaat ataacttctg taatctttgt aaccatgttt 720
atttgaagct acgttgtaaa ggggaaaaag aaaaggaaag tgtaaaatgg tcaaataaat 780
tatattttta agtgaataga ttatataatg tgcggtaaaa tatagcactc acaagtaaat 840
gcaacttagt aatctaaaga ttgaactatc aattcatgaa tttttttata attagcatgg 900
ttttctatag tttttgggag tctgtttttc aatgaaaata ttgccagtat ggtaatcttg 960
tatgacaatg tattttctaa agtatggata taattaaatt ttctttaatt tatcggctta 1020
aacttttcgt tgtactaaaa atctaggata ggacgtttaa tatttgaacc tttgtaatgc 1080
catttaatca ccgattaata tagatctaac tattgaaact tcttcaaaag ttttaatcca 1140
acggatggct aagagtgtta aaatattgat acaattaaat ttatcgtagc ttaagctttg 1200
acagtgtcaa aagctaattc agttattttc tctgcccttg gtataagggt aactctgttc 1260
tctctatttc acacaagtga ttgctaac 1288

<210> SEQ ID NO 155
<211> LENGTH: 2000
<212> TYPE: DNA
<213> ORGANISM: Cucumis melo

<400> SEQUENCE: 155
ttatgtttta ttaactccat agttttacta accccatttc acgggaaagt acaataaaac 60
atttgtgtta aaaaggagtt gtttgtatag atcgaataaa cattttgtac taattccaat 120
catattacca aatgttttaa gagcatgcgt tcttgtgtgc ttgaataggg gtgatcatca 180
attgagtggc gtcagattta aatttaaagt ggcaccaatc atcgacttgt tggtttagat 240
cgatcggtag ttgttgtttg tgggacaatc atagttatca tttttctcct tctatatgaa 300

```
taatagtcaa ctagatagaa ttgacatttc ttagtattaa aaaaacgacc actgacctgt    360

ctatatcact aaactgcttg acctaagtga gtttggttgg acttgattgc ttcgttgtgg    420

tctaattcac ttaaccctac ttgaaagtaa aggtagaata taacatgatt ctttccaaat    480

tggcaagttg tgacttgatt tatgcatgca cgaagattct tccactctcc acctaactag    540

tactcgatca cattggaaaa tggatctgtc ccgtgaagga tcgcaatatt acatgccttc    600

ctactttttt cttttcttcc accaaagaaa aagaaaacgg gacacacaat aactatacat    660

tatcaataat aattaaacga atcatcccac caaatgtaaa ccatgaatat tgaaatcatc    720

atgttttaag aatcatttta ataattatgt tatttcattg ttttatatag aacacaccgt    780

tcatgaaatc aaacaaagag agagaaatta taattttgta acaaattacc aacattcttt    840

ttctttctat ttttcataaa tgagcatatg tttgtgtata tatacatact gttatttgat    900

ctccacattg ttgaacaaaa aagttggtgt tcttgaaaat agctatcacc gaaaatacgt    960

catatactgg gttgttatgt accaaggccc agaagaaagc ccaaaatcac cggcccatga   1020

gcagtgaaca aataattggg ctaaaagccc aatatacgtg atgatgggcc aacccagaga   1080

agtttatagt tatgttatta tagaattcca gatcagggag tatcgaaaca aaagcctcca   1140

ttgtcctcgt tctcttctcc ttgtgctctc tctctctctc tcttgctctt ttctctttct   1200

ctttctctcc gacgacaggt tcctgaagct cgaccagcca agggcattga tctaggtgag   1260

tccgctttca cttttccact ttcctctgcc gtttttcttg tcatttccaa ttctccattc   1320

tttgttctgg atttcacttc tttacttcgt cgttgattag aagataatag tgagatcgaa   1380

ttctatgtct cgcatacctt cagtttcaag gaacaagaca atgattcaac cgcgccgtcc   1440

acgttatgga tagagggttt tgattctcac ctttatagct gcataacacc gttcttaggg   1500

ttcggacctt tgaatctgcg atatttctca cactgttttg gacgttttta ccgttttcct   1560

atggttcttt agccttacct tatcttgcct tcagatcttc gattgcggat ctgattcgtt   1620

catttctact tgttactttt tcttggaagt cgaggattat aaatcaacaa caaagcattc   1680

aaaatctcta gtgcaattag tgttttccat ctagttattg gagatcgttt gtagctttga   1740

ttttgtccac tttcttattt tgaacgtctg gaagacgttt tatacatgtt ctttgggtaa   1800

agttgcgttt gggcactgtt cttcacctct gggttttcgt tcttatgcta tgtttcatga   1860

tttcttttga tatctttgtt attgtttccc catcatcgag tatctgattc ttattcggaa   1920

gccgtcttct tgaagctgcg aaccggtttt ctttttctcc ctcatcaagt ctttaatttt   1980

acaggaaagc gctgaataag                                               2000
```

<210> SEQ ID NO 156
<211> LENGTH: 2011
<212> TYPE: DNA
<213> ORGANISM: Cucumis melo

<400> SEQUENCE: 156

```
ttgttagagg agttagcttt tcagggagtc ggttacaact tacaagacag acaaccatac     60

tgtacaatca atcactactg cctcaaagtc gaaaccattt aataccagtt gagcctcatt    120

gtgactgcat aattttgacc cctaccacga ggtaatttca gttcaaatca attgtatctc    180

tcttctggat atcagtcaag aatctcatgt tctcaagtta tagtacattg ataattactg    240

tgcattttta ttaatttatg agttaaaatc ctgctgatta attcaactaa aggaataaaa    300

tagttattgg catttggatg agaatagaat gtgaatccca tcattcatcg ctagattgga    360

ccgtaattat aagtgagagg gagaaacttc tgttgctatt cccttttat ttcttaattc    420
```

```
atttataaat tgtttttagg ccttttatat atatatattt ctaccatttt tacatttaaa    480

attcttttaa ctttattatg tatggactca aactaacaag ctttatttga taaaattgtt    540

caaactatta tattagtttt atatttgtaa accataaaac aaatccataa aattccacct    600

gcatcactca ctcatgttgt tgaatggtac gaaataaaca atacatgtga aagatgaaaa    660

taagaattgt tctcttatta aatctaaaat ctagattttc tttttagtac atttaacact    720

tcaatgaaag gtctaaaaca ttattgaatg acgtcacgaa ctattacaaa agattattcc    780

gatttatctc aaaaggggtc tatttcacta attttggtgt cccacatctg taaagagaat    840

tttcgtgata tgtgtagata tttaaatata attgaattcg atgaaagcaa agcaagaatc    900

gatatccgta gttattttga tatagatcgg tgataaataa aagacaatat gcataaagtt    960

tgtgggtaca gagtcggcta gttgcaatga ggggtatggc cccaagactt ttccccaacc   1020

ccaacggtca attaatcacc ccaatggggc atcgaatctt ccccaccatt ttccttttct   1080

tcgccgactc ttctacccat ctcttttgcc gactctttct cacaggtttg attaaatccc   1140

attcatattc agatacacta tttcaaaata ctcgcaaatt aatttgtttt tttaaatatt   1200

ggtataataa taaaattaat tataaattgt gacctaaaaa gtactttgtg gaagagggga   1260

tatagtctgt ctaatatatt attgattaaa tatataatag aaccataaat gcaaaccact   1320

agaattgtta ataaaaatca acgctctttt aagtctttcc atagaaagaa aggcaaagac   1380

gcgcaacgtc tagaattttc tttataacgg aagctaactc tgttataacg gccgtcccaca   1440

taatatggta gatttaaaat gacgtcagca tgtcgcttct aaatttgggt ccaaaggggg   1500

gattcattta tagggaaggg aaacggcaaa tgcaagcata gtgagtaaat acgtggcggc   1560

aaagtaatgg ataattctgc ctctgccgtg acgacattgc ccttccattt cactataaat   1620

acacctcctc tatccctcga tttcttcgca attgaatttc tcttctcatc tctgtcgtag   1680

caaaccaaat cgatttcttc aaaggtattt cttcctttcc tttttttttt tttttttttt   1740

tttttaaatc atgttgttca aactttgaga gatgaaatga ttaggggctt tcaaagtggt   1800

tttcgtttga tatgtttctt agatcgatag ggtttagaat cgagcatcct tgtaggtatc   1860

ctgaggtttg gtggttggat ctgcttaatt tttatgtggt tgcatggaaa attgggattt   1920

tttttttcta attacgtgat tctggaaata ttgatctgtg gttcagatgg aattgaatct   1980

gatctttctg ttttgttctg tataggtggg c                                  2011
```

<210> SEQ ID NO 157
<211> LENGTH: 1698
<212> TYPE: DNA
<213> ORGANISM: Cucumis melo

<400> SEQUENCE: 157

```
ttgttagagg agttagcttt tcagggagtc ggttacaact tacaagacag acaaccatac     60

tgtacaatca atcactactg cctcaaagtc gaaaccattt aataccagtt gagcctcatt    120

gtgactgcat aattttgacc cctaccacga ggtaatttca gttcaaatca attgtatctc    180

tcttctggat atcagtcaag aatctcatgt tctcaagtta tagtacattg ataattactg    240

tgcattttta ttaatttatg agttaaaatc ctgctgatta attcaactaa aggaataaaa    300

tagttattgg catttggatg agaatagaat gtgaatccca tcattcatcg ctagattgga    360

ccgtaattat aagtgagagg gagaaacttc tgttgctatt cccttttttat ttcttaattc    420

atttataaat tgtttttagg ccttttatat atatatattt ctaccatttt tacatttaaa    480
```

attcttttaa ctttattatg tatggactca aactaacaag ctttatttga taaaattgtt 540
caaactatta tattagtttt atatttgtaa accataaaac aaatccataa aattccacct 600
gcatcactca ctcatgttgt tgaatggtac gaaataaaca atacatgtga aagatgaaaa 660
taagaattgt tctcttatta aatctaaaat ctagattttc tttttagtac atttaacact 720
tcaatgaaag gtctaaaaca ttattgaatg acgtcacgaa ctattacaaa agattattcc 780
gatttatctc aaaaggggtc tatttcacta attttggtgt cccacatctg taaagagaat 840
tttcgtgata tgtgtagata tttaaatata attgaattcg atgaaagcaa agcaagaatc 900
gatatccgta gttattttga tatagatcgg tgataaataa aagacaatat gcataaagtt 960
tgtgggtaca gagtcggcta gttgcaatga ggggtatggc cccaagactt ttccccaacc 1020
ccaacggtca attaatcacc ccaatggggc atcgaatctt ccccaccatt ttccttttct 1080
tcgccgactc ttctacccat ctcttttgcc gactctttct cacaggtttg attaaatccc 1140
attcatattc agatacacta tttcaaaata ctcgcaaatt aatttgtttt tttaaatatt 1200
ggtataataa taaaattaat tataaattgt gacctaaaaa gtactttgtg gaagagggga 1260
tatagtctgt ctaatatatt attgattaaa tatataatag aaccataaat gcaaaccact 1320
agaattgtta ataaaaatca acgctctttt aagtctttcc atagaaagaa aggcaaagac 1380
gcgcaacgtc tagaattttc tttataacgg aagctaactc tgttataacg gccgtccaca 1440
taatatggta gatttaaaat gacgtcagca tgtcgcttct aaatttgggt ccaaaggggg 1500
gattcattta tagggaaggg aaacggcaaa tgcaagcata gtgagtaaat acgtggcggc 1560
aaagtaatgg ataattctgc ctctgccgtg acgacattgc ccttccattt cactataaat 1620
acacctcctc tatccctcga tttcttcgca attgaatttc tcttctcatc tctgtcgtag 1680
caaaccaaat cgatttct 1698

<210> SEQ ID NO 158
<211> LENGTH: 313
<212> TYPE: DNA
<213> ORGANISM: Cucumis melo

<400> SEQUENCE: 158
tcaaaggtat ttcttccttt cctttttttt tttttttttt tttttttaaa tcatgttgtt 60
caaactttga gagatgaaat gattaggggc tttcaaagtg gttttcgttt gatatgtttc 120
ttagatcgat agggtttaga atcgagcatc cttgtaggta tcctgaggtt tggtggttgg 180
atctgcttaa tttttatgtg gttgcatgga aaattgggat ttttttttc taattacgtg 240 attctggaaa tattgatctg tggttcagat ggaattgaat ctgatctttc tgttttgttc 300
tgtataggtg ggc 313

<210> SEQ ID NO 159
<211> LENGTH: 2010
<212> TYPE: DNA
<213> ORGANISM: Cucumis melo

<400> SEQUENCE: 159
tagaaaaaaa ttgaagatct tcttaatgct aataataaaa gcatatataa aaaggcttca 60
tattacacaa gcatcttaaa accaaaccga acttgatttg aaattatccc actaattctg 120
tagatttcac caaagtcctt aacctttata ctaacatctg catttgactc tttcatttga 180
cctccaacat attctttctc attttccttc cattcaccac aaaaaccaac aaatacaaaa 240
aaccacaaat acatagaaaa ttaataaaaa aatcaaaatt tcgagatgaa atcattataa 300
actcatccga taactttgag atttgaaacc ttacactata taaagaaact catccgataa 360
ctttgaattc gcatcgaaat tacgtaagtg aagacgaaaa tgtaaatgat tagatgcgaa 420
taacaaaaaa aacataattt ctaaacgtaa aacactatat tcaccttatt atacttgatt 480
attttggaaa agtatgaaat ttgagtgtgg gagaggagcc aaagaattgg aaacttgtta 540
ttaggagtcg ttatgaaaca ttttcaacaa gccaatattc tttcacatac tataatgata 600
tacatagaaa taatacaata atatttttga aattgaggca tttttgtcgt aatttatcta 660
aaaatgtcag ggtagattca tcatgtatac aaatctctcg ctatcaaaac tatataaaaa 720
tcttgtgaat gatttcaatc gaaatggacc gagaaaaaac atcgtaacca cctctaaaat 780
cgataaattt gtttcaattt caaatcccta aaactaaagg tgctactttg tacaatttcc 840
cctgattagg gtgctaaagt taaaccctaa ataaaggtgt gtacgtttcc ggaagtttct 900
agaatcccca gcgaagttct ccaaatcgtg gcttgcagac caaggacccc cattaaaatt 960
cgtttcttcc tctaaacctc ctcccttaat tttggcattt tggtattttg gctcctataa 1020
attcaccccc tccttatccc taatcctttg tcttccaaat tttccttcaa agcctgcttt 1080
tcccatttcg tcgtgctttt tcttcatcta aaggtatatt tcagttctag ttttctttct 1140
ctgttgatct cttggatttg agggacgttt gaagttggct ttgtttaatt ctttgttatt 1200
caatctcttt ttttgttaga gttgttgttt aatcgtttcc cttgttgttt ttctcccttc 1260
tagttcgatt ttagaacgct ttttgtgggt tgattttaat ttctccgttt tcttacatct 1320
ttcacaaaga aacgattgaa atcgtgtttg tttttttttcc cacggcatac gttattagat 1380
cttgtagata atgatctcaa tctattgttt agtttttgca aataagaagt tggtttttta 1440
tctccaactt ttatatattc gattcgatga gatgttctac accgttagga tggaaccaag 1500
aagtgaggta agggtgtttg attgaaaaat tgaactgaga agttaaagtt ccttcctaac 1560
tttttaatgg attgtataat tcgttcaatt ccttgtcgtt ccatttttat ttctgtttcg 1620
tttttcgtgt tgctgcgtat cgcttccctt gttgttttcc tcccctattg attttgcgtt 1680
tcttggagtt tctctgtttt ctctcttcat ttttctacaa aaatcaattc tatttttatt 1740
cgttttcaat tcccgagctc cttggaatgt tatccttttc tcctgtgtaa ataagaaccc 1800
gtattcaatc ccagttcata gtttggcttt cccaaataag agcaaaaaga ttgtactgag 1860
aagttgaaga tttcaaaatt ttgtacatga tttcttctaa tttatcaatt tgattggact 1920
ttttgtatat agatttggtt cttgagctat ttatgttatg acgttttcat attgaggcca 1980
tgcgttgaat tggtttctta acaggtgggc 2010

<210> SEQ ID NO 160
<211> LENGTH: 1107
<212> TYPE: DNA
<213> ORGANISM: Cucumis melo

<400> SEQUENCE: 160
tagaaaaaaa ttgaagatct tcttaatgct aataataaaa gcatatataa aaaggcttca 60
tattacacaa gcatcttaaa accaaaccga acttgatttg aaattatccc actaattctg 120
tagatttcac caaagtcctt aacctttata ctaacatctg catttgactc tttcatttga 180
cctccaacat attctttctc attttccttc cattcaccac aaaaaccaac aaatacaaaa 240
aaccacaaat acatagaaaa ttaataaaaa aatcaaaatt tcgagatgaa atcattataa 300
actcatccga taactttgag atttgaaacc ttacactata taaagaaact catccgataa 360
ctttgaattc gcatcgaaat tacgtaagtg aagacgaaaa tgtaaatgat tagatgcgaa 420
taacaaaaaa aacataattt ctaaacgtaa aacactatat tcaccttatt atacttgatt 480
attttggaaa agtatgaaat ttgagtgtgg gagaggagcc aaagaattgg aaacttgtta 540
ttaggagtcg ttatgaaaca ttttcaacaa gccaatattc tttcacatac tataatgata 600
tacatagaaa taatacaata atatttttga aattgaggca tttttgtcgt aatttatcta 660
aaaatgtcag ggtagattca tcatgtatac aaatctctcg ctatcaaaac tatataaaaa 720
tcttgtgaat gatttcaatc gaaatggacc gagaaaaaac atcgtaacca cctctaaaat 780
cgataaattt gtttcaattt caaatcccta aaactaaagg tgctactttg tacaatttcc 840
cctgattagg gtgctaaagt taaaccctaa ataaaggtgt gtacgtttcc ggaagtttct 900
agaatcccca gcgaagttct ccaaatcgtg gcttgcagac caaggacccc cattaaaatt 960
cgtttcttcc tctaaacctc ctcccttaat tttggcattt tggtattttg gctcctataa 1020
attcaccccc tccttatccc taatcctttg tcttccaaat tttccttcaa agcctgcttt 1080
tcccatttcg tcgtgctttt tcttcat 1107

<210> SEQ ID NO 161
<211> LENGTH: 903
<212> TYPE: DNA
<213> ORGANISM: Cucumis melo

<400> SEQUENCE: 161
ctaaaggtat atttcagttc tagttttctt tctctgttga tctcttggat ttgagggacg 60
tttgaagttg gctttgttta attctttgtt attcaatctc tttttttgtt agagttgttg 120
tttaatcgtt tcccttgttg tttttctccc ttctagttcg attttagaac gctttttgtg 180
ggttgatttt aatttctccg ttttcttaca tctttcacaa agaaacgatt gaaatcgtgt 240
ttgttttttt tcccacggca tacgttatta gatcttgtag ataatgatct caatctattg 300
tttagttttt gcaaataaga agttggtttt ttatctccaa cttttatata ttcgattcga 360
tgagatgttc tacaccgtta ggatggaacc aagaagtgag gtaagggtgt ttgattgaaa 420
aattgaactg agaagttaaa gttccttcct aactttttaa tggattgtat aattcgttca 480
attccttgtc gttccatttt tatttctgtt tcgtttttcg tgttgctgcg tatcgcttcc 540
cttgttgttt tcctccccta ttgattttgc gtttcttgga gtttctctgt tttctctctt 600
catttttcta caaaaatcaa ttctattttt attcgttttc aattcccgag ctccttggaa 660
tgttatcctt ttctcctgtg taaataagaa cccgtattca atcccagttc atagtttggc 720
tttcccaaat aagagcaaaa agattgtact gagaagttga agatttcaaa attttgtaca 780
tgatttcttc taatttatca atttgattgg actttttgta tatagatttg gttcttgagc 840
tatttatgtt atgacgtttt catattgagg ccatgcgttg aattggtttc ttaacaggtg 900
ggc 903

<210> SEQ ID NO 162
<211> LENGTH: 1235
<212> TYPE: DNA
<213> ORGANISM: Cucumis melo

<400> SEQUENCE: 162
aaattttaat aattaaaatg aacaattttt caagagtaat agagtttgag agatgtcaga 60
gaagtttgag gaagaagata acaagtggga gaagagaata agtttgttgt gtgaaagaga 120
aggggaaatt tcattcaagg gtatattgaa ctttttactc aaattttgta agtctatttt 180

-continued ttccgatcaa tcctaaaatc acacacaccc ttaaaaaatg gattatattt ggcaattttc 240
catgataaac tcatttttaa tttagagtta ttttttcaac gagatattaa cagttttagt 300
tcatatacta attgtaagaa tagtttcttt taagttgaat agaatttttg aaacttttaa 360
tagttcaaaa ggtatttttg aaacaaaata agaatgtttt tgaacttttt ataaaaagaa 420
ttgagatttt tttgaaattt ttgataaaga gaaaagaaaa gaagaaagaa aaaagaaaaa 480
caagtttgta gaactccgtg ggaaaatcgt cgagggccct gtgaaggaat tttgaaatta 540
taatgagggt attttcgtca acaagggaat ttagacatcg tatataagca tcctcaaacc 600
ctataattaa gcccttcaat ccaattgcca ttctccatct ctcgccgcaa gggtttaaga 660
gcagcttctc tcctcaggtt ggggtttccc cctatcttct tcattcttcc tcttctcgat 720
ttctttcttc tatttgctcg atagtctctt atttcttgag cttttgctgt ttttctcctg 780
tacatcctaa catgaattat aacttggttt tgattttgtc ttttacttct gtattaaaca 840
acttttctta ccctttttatt cttctcttct tcttcgtgtc cctgcccttt tgtttttatg 900
ctaattttat gtttctgttt atcaatctat cgaggcgtga cctgtcgttc ttccaatagc 960
gtagatctgc acttaatcta ttctagctga ttggattggt cgtttttcgt ttttttaatt 1020
tattttctct gttctagttc cgataaattt ttttatatat aattaacaag ttctccagcc 1080
aaaagggtta atattgcgtt ggatatttta atttttacgt tatttagatg tgtgaatcta 1140
ataaaattag ggttattcat aaatttcagt aatgatattt tggttatctg ttcttgctgt 1200
tcctgtttcg cagttctttt acctaatatt caagc 1235

<210> SEQ ID NO 163
<211> LENGTH: 617
<212> TYPE: DNA
<213> ORGANISM: Cucumis melo

<400> SEQUENCE: 163
aaattttaat aattaaaatg aacaattttt caagagtaat agagtttgag agatgtcaga 60
gaagtttgag gaagaagata acaagtggga gaagagaata agtttgttgt gtgaaagaga 120
aggggaaatt tcattcaagg gtatattgaa ctttttactc aaattttgta agtctatttt 180
ttccgatcaa tcctaaaatc acacacaccc ttaaaaaatg gattatattt ggcaattttc 240
catgataaac tcatttttaa tttagagtta ttttttcaac gagatattaa cagttttagt 300
tcatatacta attgtaagaa tagtttcttt taagttgaat agaatttttg aaacttttaa 360
tagttcaaaa ggtatttttg aaacaaaata agaatgtttt tgaacttttt ataaaaagaa 420
ttgagatttt tttgaaattt ttgataaaga gaaaagaaaa gaagaaagaa aaaagaaaaa 480
caagtttgta gaactccgtg ggaaaatcgt cgagggccct gtgaaggaat tttgaaatta 540
taatgagggt attttcgtca acaagggaat ttagacatcg tatataagca tcctcaaacc 600
ctataattaa gcccttc 617

<210> SEQ ID NO 164
<211> LENGTH: 54
<212> TYPE: DNA
<213> ORGANISM: Cucumis melo

<400> SEQUENCE: 164
aatccaattg ccattctcca tctctcgccg caagggttta agagcagctt ctct 54

<210> SEQ ID NO 165

<211> LENGTH: 545
<212> TYPE: DNA
<213> ORGANISM: Cucumis melo

<400> SEQUENCE: 165
cctcaggttg gggtttcccc ctatcttctt cattcttcct cttctcgatt tctttcttct 60
atttgctcga tagtctctta tttcttgagc ttttgctgtt tttctcctgt acatcctaac 120
atgaattata acttggtttt gattttgtct tttacttctg tattaaacaa cttttcttac 180
ccttttattc ttctcttctt cttcgtgtcc ctgccctttt gtttttatgc taattttatg 240
tttctgttta tcaatctatc gaggcgtgac ctgtcgttct tccaatagcg tagatctgca 300
cttaatctat tctagctgat tggattggtc gtttttcgtt tttttaattt attttctctg 360
ttctagttcc gataaatttt tttatatata attaacaagt tctccagcca aaagggttaa 420
tattgcgttg gatattttaa tttttacgtt atttagatgt gtgaatctaa taaaattagg 480
gttattcata aatttcagta atgatatttt ggttatctgt tcttgctgtt cctgtttcgc 540
agttc 545

<210> SEQ ID NO 166
<211> LENGTH: 19
<212> TYPE: DNA
<213> ORGANISM: Cucumis melo

<400> SEQUENCE: 166
ttttacctaa tattcaagc 19

<210> SEQ ID NO 167
<211> LENGTH: 2003
<212> TYPE: DNA
<213> ORGANISM: Cucumis melo

<400> SEQUENCE: 167
cagtgtgctg gaattcgccc ttatccaagg agattaatgt cgagagatta ttatcgaggt 60
ttgaatttat tttgtccaat catatgattc caagagctga ccatcaattc aacagaacat 120
gaaccggaac ctcataccta ttgtaatggt tcacagcatc ctaatacaga acatgaaccg 180
aaacctctta cccattgtaa tggttcacag catctttata cgtattatag gtagtaccat 240
tgaagatgca tttaaatgct gtccatgctc tgttctctaa aaagttggac ttggacttgg 300
acgtcagctg aaagtatgaa atgcactgta gccaacgaag ctatgttttc aggcttcaac 360
atggttttag gaaagtggag gctctttggt tgaagggttg aatgaatgct tttctaattc 420
cagcatgatc ttcaaatttc gacacaaaaa gcttaagtat tttgttccgt tattctttta 480
atccttgtat tgttatatat tcttttctct gaactgaatg tacgatgatt gcaggggtcg 540
agagcaagtc cgatataatg aaacacgtaa ggacgtgatt gaatgaaaaa ctatgagcag 600
agatacaaag tctaacttac gggatgaacg atgagaggtt tgaccaagag ctgtgacgcc 660
tgtatatttc aacaaaagtt gatgactaac atcacatgtc agagtaatca aagaaatgca 720
gccgcacata tatatatcta tatatatatc gagttttttt tttttttttt tttttttttt 780
tttttttatc taatatattt taatctattt tcctctgccc tcctccccct cctcttcccc 840
cacccttctt ctgcacatag tagccaagga ttgatcggtt tcttttgatt cggggggaaa 900
atgttgtaca atttttgctt ccatagaagc ttgaaagttt tgcagattat gttgtaaaat 960
tacccttgtg tactcacact agttcttctc gtggaaactt atattacaat ggttgagttt 1020
taaggggcat attcacactg gtaactacca ttttctaatt tatgaatgcc gagtttctct 1080

```
ccatgaaaga cctttcaaat gccctttcct ccgcggtgcg tttgttgttg taaatgtgca   1140
gtgtcgttgg atacacgatt gtgtgaaagg gaaaagggaa tacgattaac tcttaaattc   1200
aacccctatc tccatcagta tcaatcacat ttcagcaact agctcttgaa taacattgag   1260
attcttgttt aatccacgta ctactactac tattactact atttgacagt tgatatctca   1320
aataacatcc atatttatca aattggtatt ttaaggactt ttaatttctt cgtacatatt   1380
tcattataat ttaactactc tgaccatcat tgaaaatttc acaaagaaga cattttaaat   1440
tgaattgagt tgaattaagt tgatataatg gttgaacgtt ggatttaatt tataatttag   1500
tggtgtatgg gtccattgta ataattctta aaaaaaatat catattctga attctaaaga   1560
accatctaag accaaaacta aggggtcacc aatgagtatg gtaaagtcaa caaagtttgt   1620
ctacttttct tatccttatc atcaagagtg caatatgata tcaaagataa attgtacgtg   1680
ggcgtcatcc attgggtaag accaagaagc aaaatatcat agagaagttg ttttagtagc   1740
cataggaagg aaggaagcaa aataataata tagatttgaa attgtggatg ataaactgcc   1800
aaatgggaat tcaaaataaa ctaaataaat aaaataaaaa gagaaatctt gggagtttcc   1860
attttagcca atgaggaaac agatagagat ctcatcaaga taaggaccct attctcttct   1920
tcatctataa aacaaaaaca aatcaaaccc tcatttcact cattcaaaac aaaaagtact   1980
ccaaagtcaa actaacaaat acg                                           2003
```

<210> SEQ ID NO 168
<211> LENGTH: 2004
<212> TYPE: DNA
<213> ORGANISM: Cucumis melo

<400> SEQUENCE: 168

```
tggatcgacc atgacattca aaaaccttta agatatggat cttataaaat aaatgtaaag     60
ggtaaacaat tcttccttgc ttaacccaag ctatatattt tatgcactaa tttaggtatt    120
agagtatatt cagctgaaca ccacctacca atgctagtac tttaatcagt caattctaac    180
ttcgataata tatctcaacc aaattagtga aaaagagtcg taaatgaaaa actatgtacc    240
aagatattct atttgttttt tttatgttta aatatctcaa agataatacc taaaacgttt    300
tctcctcgta caaagattcc tcatttactt tttattgtcg taaactctaa tacaataaac    360
taaaacaagt acaaatacac tagctttaga aatctacttt ttattgaaac caaaaccaat    420
aattcaacat ttcattttca ccgacaaacc tttgtaaaca attgaagtaa tttttgttgg    480
tactatgaat agtaacatca agtcttcaag tgcatcatat caaccaagac atgttcttaa    540
aagcgacact aaaagattta aaaccaaaag catttatgaa atccgaactt aatcaaatcc    600
taaatatttt tcacttaaaa aaaaaaaaat aggaagaaaa attgacataa atgggatatt    660
ttcgttttca aactggcaag ccagcatgca ccacgttgtt gacgtgtcct tccacgtcgg    720
aaaaaaaaat attaccacag taaaaagaga ataaaatgaa agtcgttgac tctcccttag    780
tcggaggaag cgcgtgaagc tgaagccgga ttagaaatcg gcaataaccc cgacacgtca    840
tcgaaatgct agtatcaaat attgtccgtt ggatcttcct tcaccaactc tatttgaacg    900
gccacgatct tccaggtcca acggttcgga agaatctttt cgaaattcca tggctagtcc    960
ctacactcct ccctattggc tccctagggc atcccgaccg gttattccgg ttgccgggaa   1020
ggtggctgga cgctataaat acccgctttg ttcatctcgt agtccttgta ccgttgagct   1080
tcgccttcta atagagctct ggttcggttg gcgtattagc tcgaattctt tctctcttcc   1140
```

-continued

```
agatctacgc tgccgatttc atcaggtttg cgagctctgt tccaccattt ttcttttcct   1200

gaagctttga gcatgcttgt gattcttcat ttcctcattt ctttgatggt ttatgaaaga   1260

atttagggga attttctctt tttgtattct agtggtactg gtagatttgt ttgaagtttg   1320

tttctcttct tctgagaagt gaattcttcc agatctgaca gttgcttttg atttttttctt   1380

tgggaattag tgaatgatac ttcgatactg tttttttgctc tctgagattc tggatctcgg   1440

gccttggggt tttctattgt cttttggtag ctatgtttcg tttgtcagct tgtatttgtc   1500

attgttgaat ggttcgatcc ggtttgtaaa taaaataaat tttgtaggcg cacttgtttt   1560

ccacggtttt cgtgttacgg tttcatgatt ccctagatct ctggttagaa ctaagttttt   1620

tgtcggtaat tggatttggt aagggactgt tactgtggtt gaattgtaga tccagtcatc   1680

ttctacatga gtgtagggtt ccttagggca gatcttgtgt tttataattt taattttgtt   1740

gtttccctga ttttgaacct gtttggttgt tcagattcgt cgagtcattt ccattcatta   1800

aaagtttcta taattttatt tgaatcttct gaatctgtgc ttgtattacc cagatttcta   1860

taaacctatc ttgatttcaa gtgtgctatg tggtaactgt tgatattttc aagcttaagc   1920

aatactgatg tgactaaaac ttaactaatg aactgaatgt tttttgtaca cgaactaata   1980

tggtgttttg ttatgtttca gagg                                           2004
```

<210> SEQ ID NO 169
<211> LENGTH: 1067
<212> TYPE: DNA
<213> ORGANISM: Cucumis melo

<400> SEQUENCE: 169

```
tggatcgacc atgacattca aaaaccttta agatatggat cttataaaat aaatgtaaag     60

ggtaaacaat tcttccttgc ttaacccaag ctatatattt tatgcactaa tttaggtatt    120

agagtatatt cagctgaaca ccacctacca atgctagtac tttaatcagt caattctaac    180

ttcgataata tatctcaacc aaattagtga aaaagagtcg taaatgaaaa actatgtacc    240

aagatattct atttgttttt tttatgttta aatatctcaa agataatacc taaaacgttt    300

tctcctcgta caaagattcc tcatttactt tttattgtcg taaactctaa tacaataaac    360

taaaacaagt acaaatacac tagctttaga aatctacttt ttattgaaac caaaaccaat    420

aattcaacat ttcattttca ccgacaaacc tttgtaaaca attgaagtaa tttttgttgg    480

tactatgaat agtaacatca agtcttcaag tgcatcatat caaccaagac atgttcttaa    540

aagcgacact aaaagattta aaaccaaaag catttatgaa atccgaactt aatcaaatcc    600

taaatatttt tcacttaaaa aaaaaaaaat aggaagaaaa attgacataa atgggatatt    660

ttcgttttca aactggcaag ccagcatgca ccacgttgtt gacgtgtcct tccacgtcgg    720

aaaaaaaaat attaccacag taaaaagaga ataaaatgaa agtcgttgac tctcccttag    780

tcggaggaag cgcgtgaagc tgaagccgga ttagaaatcg gcaataaccc cgacacgtca    840

tcgaaatgct agtatcaaat attgtccgtt ggatcttcct tcaccaactc tatttgaacg    900

gccacgatct tccaggtcca acggttcgga agaatctttt cgaaattcca tggctagtcc    960

ctacactcct ccctattggc tccctagggc atcccgaccg gttattccgg ttgccgggaa   1020

ggtggctgga cgctataaat acccgctttg ttcatctcgt agtcctt                 1067
```

<210> SEQ ID NO 170
<211> LENGTH: 92
<212> TYPE: DNA
<213> ORGANISM: Cucumis melo

<400> SEQUENCE: 170
gtaccgttga gcttcgcctt ctaatagagc tctggttcgg ttggcgtatt agctcgaatt 60
ctttctctct tccagatcta cgctgccgat tt 92

<210> SEQ ID NO 171
<211> LENGTH: 845
<212> TYPE: DNA
<213> ORGANISM: Cucumis melo

<400> SEQUENCE: 171
catcaggttt gcgagctctg ttccaccatt tttcttttcc tgaagctttg agcatgcttg 60
tgattcttca tttcctcatt tctttgatgg tttatgaaag aatttagggg aattttctct 120
ttttgtattc tagtggtact ggtagatttg tttgaagttt gtttctcttc ttctgagaag 180
tgaattcttc cagatctgac agttgctttt gatttttttct ttgggaatta gtgaatgata 240
cttcgatact gttttttgct ctctgagatt ctggatctcg ggccttgggg ttttctattg 300
tcttttggta gctatgtttc gtttgtcagc ttgtatttgt cattgttgaa tggttcgatc 360
cggtttgtaa ataaaataaa ttttgtaggc gcacttgttt tccacggttt tcgtgttacg 420
gtttcatgat tccctagatc tctggttaga actaagtttt ttgtcggtaa ttggatttgg 480
taagggactg ttactgtggt tgaattgtag atccagtcat cttctacatg agtgtagggt 540
tccttagggc agatcttgtg ttttataatt ttaattttgt tgtttccctg attttgaacc 600
tgtttggttg ttcagattcg tcgagtcatt tccattcatt aaaagtttct ataattttat 660
ttgaatcttc tgaatctgtg cttgtattac ccagatttct ataaacctat cttgatttca 720
agtgtgctat gtggtaactg ttgatatttt caagcttaag caatactgat gtgactaaaa 780
cttaactaat gaactgaatg ttttttgtac acgaactaat atggtgtttt gttatgtttc 840
agagg 845

<210> SEQ ID NO 172
<211> LENGTH: 2018
<212> TYPE: DNA
<213> ORGANISM: Cucumis melo

<400> SEQUENCE: 172
actattggag acgacgaagg aaaactctaa tgtgagctta gaattgaaga tggtgaacaa 60
ttgggagtct tttttaaaaa tctttcgtcg gtatattgaa atttcctttt acactcaaat 120 aaccccccctt ttcacgcgtt caacgtcttc aaaccttcct ttttcaatta ttttttcgtt 180
tacattaatg acatttaggt aataagataa attagtggat tcttttgtga aaaatgttag 240
cccatttaag acttttatga aatatattag aaaaaaaatca tatagcaatt tatattattc 300
tagttaaaag cccataatag aaactaaccc aacctaaagt aacgtaaaca ttcaataaga 360
gagacaaatt ttaaaataat ttctaattaa aaaaaaaatt gtcaagaccg tccgggtcgg 420
atccaaaata taacccgaac cggccggttt agcatctata taaatacacc tttagggttt 480
ttattctctc aagacttcac cgcatttcca cttctctgag gccacggtca gccattggag 540
cagctcaata atcctttgac tccctactac ggtaagtcga ccttactgct ttcggcttct 600
agttttttca atcctgtcat tagtcctttg gagttcttct gtacatttat gacgttttcg 660
gctcgtgttt tgtttcgcct gtatgtagtg ggtttttcga gttttgtttt tactttttttt 720 tatacttgca ggaattagtt gaaatctatg tacttcatgc cttggataat actcttgatc 780

```
tgttgtgtta ttcaaaaatg aattgtttta agatggtatt tgagaatggt catgtgagtt    840

ttgcctactt ggttattaaa atgaattgtt ttaggatggt atttgagaat ggtcttctgg    900

gtatttggtt ggaacctttg tgctctgcta tgaattaggg tgttctcccc gttttttttt    960

tttttttct tttggttatt aatatatctt ttatgactac ttattcatat atgatatctt   1020

ttactcgtaa attttgactc atttgaaagt tttatcctta gtcctttctc attcagggtg   1080

taaaggtatg ttgttagggt taaaatagcc tatgcaggaa agttctgtat ttgttctaat   1140

tattgcattt gtgtgcattt gtatctagtt tatttcttgc tgagagtatg cttcattttt   1200

tagtacacat cacttgtgcc actttattat agttgcacat ttttgtttat ggagaggatg   1260

aatagcattt agggatgtca attttttatt gagaaaaccc tctctcctac ttaagcttgg   1320

ggaattttttg ttctaaatgt ggtaaacata atacttcttc ttattttaat ttgaatggaa   1380

ggggaagacg aatactaata ttttcaacga accttcacaa cttttttttc ttatttagga   1440

agccatgttt ttcaaaattg tactgtgtga tccacatatt tatcgattat tagtgaatcg   1500

aataataatt agagttttat tggtataatt ttgaagttca gacttattac atttgtggaa   1560

agtttggtta caattttcaa ttttattgga atcctaagaa ctttgtgtta acatatattg   1620

agttttcttc tcttttttttt tactcattaa gttctctatt aggaatgttt ggttcaatgt   1680

cacatagtcg atagctaaga ccagtgaccc acaaagctat gattgaacga aaaacaagcc   1740

tttcacatct tggtaggaat ttgttatttc tcaatagatt tacagagctg tttcatgtga   1800

tcacaatttt tttctatttt tctgaagttc tctattagga atgggctatc tggttagttg   1860

cttttgagag aacatgtgga ttggtgttgc tcggtttcct tgcctttgta attttgtcct   1920

tggaaaaagc aaaatgatta ggtatcctga tatgcataac atgtttaagc caactagttc   1980

tcactttttt agtgcaaata attgatcttc aggaatcg                          2018
```

<210> SEQ ID NO 173
<211> LENGTH: 565
<212> TYPE: DNA
<213> ORGANISM: Cucumis melo

<400> SEQUENCE: 173

```
actattggag acgacgaagg aaaactctaa tgtgagctta gaattgaaga tggtgaacaa     60

ttgggagtct tttttaaaaa tctttcgtcg gtatattgaa atttcctttt acactcaaat    120

aaccccccctt ttcacgcgtt caacgtcttc aaaccttcct ttttcaatta ttttttcgtt    180

tacattaatg acatttaggt aataagataa attagtggat tcttttgtga aaaatgttag    240

cccatttaag acttttatga aatatattag aaaaaaatca tatagcaatt tatattattc    300

tagttaaaag cccataatag aaactaaccc aacctaaagt aacgtaaaca ttcaataaga    360

gagacaaatt ttaaaataat ttctaattaa aaaaaaaatt gtcaagaccg tccgggtcgg    420

atccaaaata taacccgaac cggccggttt agcatctata taaatacacc tttagggttt    480

ttattctctc aagacttcac cgcatttcca cttctctgag gccacggtca gccattggag    540

cagctcaata atcctttgac tccct                                          565
```

<210> SEQ ID NO 174
<211> LENGTH: 1453
<212> TYPE: DNA
<213> ORGANISM: Cucumis melo

<400> SEQUENCE: 174

```
actacggtaa gtcgacctta ctgctttcgg cttctagttt tttcaatcct gtcattagtc     60
```

-continued ctttggagtt cttctgtaca tttatgacgt tttcggctcg tgttttgttt cgcctgtatg 120
tagtgggttt ttcgagtttt gtttttactt ttttttatac ttgcaggaat tagttgaaat 180
ctatgtactt catgccttgg ataatactct tgatctgttg tgttattcaa aaatgaattg 240
ttttaagatg gtatttgaga atggtcatgt gagttttgcc tacttggtta ttaaaatgaa 300
ttgttttagg atggtatttg agaatggtct tctgggtatt tggttggaac ctttgtgctc 360
tgctatgaat tagggtgttc tccccgtttt tttttttttt tttcttttgg ttattaatat 420
atcttttatg actacttatt catatatgat atcttttact cgtaaatttt gactcatttg 480
aaagttttat ccttagtcct ttctcattca gggtgtaaag gtatgttgtt agggttaaaa 540
tagcctatgc aggaaagttc tgtatttgtt ctaattattg catttgtgtg catttgtatc 600
tagtttattt cttgctgaga gtatgcttca ttttttagta cacatcactt gtgccacttt 660
attatagttg cacattttttg tttatggaga ggatgaatag catttaggga tgtcaatttt 720
ttattgagaa aaccctctct cctacttaag cttggggaat ttttgttcta aatgtggtaa 780
acataatact tcttcttatt ttaatttgaa tggaagggga agacgaatac taatattttc 840
aacgaacctt cacaactttt ttttcttatt taggaagcca tgtttttcaa aattgtactg 900
tgtgatccac atatttatcg attattagtg aatcgaataa taattagagt tttattggta 960
taattttgaa gttcagactt attacatttg tggaaagttt ggttacaatt ttcaatttta 1020
ttggaatcct aagaactttg tgttaacata tattgagttt tcttctcttt ttttttactc 1080
attaagttct ctattaggaa tgtttggttc aatgtcacat agtcgatagc taagaccagt 1140
gacccacaaa gctatgattg aacgaaaaac aagcctttca catcttggta ggaatttgtt 1200
atttctcaat agatttacag agctgtttca tgtgatcaca attttttttct atttttctga 1260 agttctctat taggaatggg ctatctggtt agttgctttt gagagaacat gtggattggt 1320
gttgctcggt ttccttgcct ttgtaatttt gtccttggaa aaagcaaaat gattaggtat 1380
cctgatatgc ataacatgtt taagccaact agttctcact tttttagtgc aaataattga 1440
tcttcaggaa tcg 1453

<210> SEQ ID NO 175
<211> LENGTH: 1999
<212> TYPE: DNA
<213> ORGANISM: Cucumis melo

<400> SEQUENCE: 175
ggtctcagac ccataggaat agatcattta ttgccttatg aattagttta tgagtacata 60
ataattgtca accgtataca aatcaacatg aaagaatata atgttgtaca tagtcattcc 120
aagtttacta atattatatt ttaggagtgt tctacaccga acctgtcaca tgtacactgg 180
gtatgctacc cctgaattca atatcataaa gcaactttaa ttgtcaagca ttctcttgac 240
catttgtgac ccatttgctc ctactttttc aatcaataac tatcacaaaa agctagatac 300
cacatgtgat aaactcactg aaatcaggta tatggttacc tgtgcttggt cagcactcaa 360
tcagattcga aggcctagtc tttgtatttc cccccctctg cacactacaa atagtcctcc 420
acgtaaagac ccataacaaa acgcaaacca agtacagaaa atctagccga aatccagacc 480
actcaaacat aacaaatctt ctggtaagtt tgaataaaat ataaaactaa cctatttaat 540
caaataatac aataaaatgg aagcaactaa cataacatat ctaaatatga tcacgtagta 600
ggaaaaaaaa aaacattcca aaactattaa caatcattct taatggtatg ggtcaatccc 660

-continued

```
cattatttag gactataaca agaattcctc atacctaatg ccacatccta tgtccaaccc    720
tcgagattac ctcgtgagta atcaatctta ttcatcctta tttcaaatta tgtgaaattt    780
ctcatcaggt tgatcatatt gactttcaat acaacttatg attaatcttt cccttgatat    840
aatttcgtat gaaaaggaag ttgacattat gtgattttct cataaggtaa accaagtaaa    900
cttgacatga cgtcttaaca agtcttggtt tctaagtgta atttactgca gaaaaaatcc    960
taaattctat gacttttcct atgagattga ccaaatcaac tttacgagaa atcttgggaa   1020
gccataccta caaagtcttc ccccaagaaa ttacaatttc tagtaaagat tgttgaaatt   1080
taccctccaa tttttccgtg aaaatttgac aaacttgtaa gaatatcaaa tttgggttgg   1140
atattgacat tccaaaataa gtagttttaa aaaggattta tccaacaata atagaagaaa   1200
aaagatagga aataacatac ccacgtaaat ggaatgtaaa tatttatata ttaggtgtct   1260
tgaacgaccg tcaaacgaaa ataaattgtt catccgaagt tgaaactctt taagtgtaca   1320
tttatctttt cgtaagaata aaatgtaaaa ttaacgtgtg aaaggttggg ttaaataagt   1380
tatgtagaga taatattgaa gatgatagaa taatcacgat cgatgaatta gtatagtccc   1440
agagcggatt taaacctctc tcactttcat gctttctata tatatcaaaa taatttcaag   1500
tagttggttt agtcgtaaaa aagtcaacca atctctttta gataaacctt gagttattaa   1560
aaaattagat caaagataat cgttgaaatt gaaattttaa gagtataatt ataacaaatt   1620
ggaaagttct aaagtagttt ttgcaatatt ctccatcaaa atagagtaga aaaatatttt   1680
agtaattttc ttatcttaat tttagttttg taatagttat taggatggtc ctaagttctc   1740
aatccgcttt tagtccataa aaagaaagaa gagagagaaa aaaagtcccc gatccgcgac   1800
acataccaat ccaaccaatt atgcacaatc catgtgatat cgaacggtca caagaataaa   1860
tgctttctac acacggatca ccatccaacg gctttccttc catctcatcc tctatataat   1920
ctaccaactc tgtcatcttc gacacacttc aattatctca gcttttattt catcggattt   1980
tccatcaaac aaggcaaca                                                1999
```

<210> SEQ ID NO 176
<211> LENGTH: 2004
<212> TYPE: DNA
<213> ORGANISM: Cucumis melo

<400> SEQUENCE: 176

```
tatagtttgt aacaatctac tctatgttct ttcaattttg atacatttga atcttaaact     60
ttattgagtt acacaatata gtccttgtat ttttaaaatt tataatgact ctatttatat    120
taatattata gaaatttttg ttaaggttta ataaaaattt ttctgtataa ataaatcgaa    180
cacgaagtct atatttagac tgcaatatag taaaacctga catctaagtt tggtgaattt    240
tgttttgctt taaaaactaa actattacaa ttttaaaaat attttaattt agttaatgca    300
cattaacttt acggagtaaa tttttacaag attgaatata catagattaa atagttataa    360
aaccaaagat tagagtaaaa aacatttaaa tagaaagaac taagattttt ttaaaacgaa    420
aatgatacta gatacatata tatgtatcta tattataatt actcatttta acatatagtt    480
ttgaaagaac aaagattagt tgcatgtgtt gattgttttt aagaaggaaa taatttttga    540
atggaaaatt ttcaaaagtt ttaaatttga caataaactc atatttaaag tgtactacaa    600
attttaactt ttggttaaac tccttgttta gttcaatcat gtaataaatt ctcattccaa    660
gaatcgtttt agaaaatttt attgtgcatt taataaaata tagaacatat atggcatata    720
aaaattgatt actttttttct ttttttggga cgaaaaacac attagatata atcttttttg    780
```

aaagtttatg aactttaaaa atgggttatt ttatacggtg gtcaacttta ttttattgaa 840
attattgagt ttataaagat tgttatatca ttttcttctt ctctttcact agaatacaat 900
caaacctatc aaactctcta tgacttattt agaattcttt ttgttatatt tttgaaatta 960
ataaatgaaa agcttagagt ctaaattata acaattaaaa ttgaaaattt tgcaataatt 1020
ttatttttag caaaatgacg tttggttttt ggggattggg aatggatcga tactatcccg 1080
attccggaca aagaaaccga cccgagattc gaattttttc cattcccaaa cagagcactt 1140
aaaatttaag caacgttata acggcgtcac cgaactaaac ggaaaaatat gaagaaaatt 1200
agaaaaagaa aaacggaaca gtcaaacgtt acttcacgtc aatggcaata ttcatttttt 1260
tttttgttta aataattgaa tttaattaat ttggtttata aaaatagagt cctcatatat 1320
cgcgaatgcg catttgatcg tgaaggacag cttctccctt gtgttcaaga gagagagatc 1380
tatcattctt atttggggcc gatctctcta ttctcctctc ttctattccg taagtttttc 1440
tcattcattc tcctctctca tttctctccg agatctgttt acaatccttt tgattttcat 1500
ttttcctgct tcgatctgtg ctcctggtga ttccctttc ctgttttatc ttttgttgat 1560
cttggaattg attgttcttt tgtgggtttt cattgatttg tattttctga tctgggtttc 1620
tgttttctcg ccttgatgtt ttgtatttgg atctgatctg acgacccttt tttttttttt 1680
tttttatttg aattgctttt ccaatgttta tacctggatt tttattgatg catgggttta 1740
accgattggt tggatgcgtt ttctttgtgc tggatctagg tgtccttgtt tttaatttga 1800
attgtgggta aaaatggcat tattgtaatg tgtttggagt ttgattttga atcttggcta 1860
gttgattttt gaattacaaa gatcggatcc tcttctttt tgggttgtct taagattttt 1920
ggctggttta agtatttgat gtcgttgtat tttaaggggt aactgatgcc ggcttgttgt 1980
gtttgtattc agtttacttg aaaa 2004

<210> SEQ ID NO 177
<211> LENGTH: 2005
<212> TYPE: DNA
<213> ORGANISM: Cucumis melo

<400> SEQUENCE: 177
aattagcaaa ttgtatgtaa caacgtcatg aagaggcatt tcatcgaaca atttaatagc 60
agagtcaaga tggcccagtt ttataagttt attgatttct cgattcttaa ggtaaatgag 120
atcgcgagca tggaaatgca gacccaaacg agaatatggg tgtggtaaat ggaccggtga 180
tgttgtggct acaaattcgg attttacagc agtaatagtt ctgacgaagg aagcgaattt 240
agtgaccttt cgcatcacag tttaagctta tcagagacct gaacaagggc tctagctcta 300
caacttagaa aggtttgata tggtccgtga tcgggaggga ccgaataaca ggcgcttaaa 360
ttgttgttca taaagaagag gattgtcgtt gatgtatttt aaccaagaga tgattagtta 420
tccacatcca cagagagaac agaagacggc tttctaaatc tacaccgata aaaataaccc 480
taccactttg tttctttaga aaagggtcac attctttaaa aacattagcg tcgaggatta 540
atagggtata ttgactaatg ctctgtttgg atttcgagaa ataccaattt acaattgatt 600
tcaaattaat tatgttttgt tgttgcacga aagataaaaa gaatttaaaa ttcaaaagga 660
tctcaaatct tatttttaac ttaaaaactt ttatgaccca aacggtttat gtatgattta 720
aaagtagaat acctctgtga attcttaatt tttttttctt tccaattacc acataaatat 780
gaaattttaa atacatttat tttaaatttt atatccgaaa caaaataata atttaaaact 840

```
atttctcata tatgaagtgt gattcgatct aaattataaa ataataaaaa tttacatcta    900
gttttgatta ttttttttc gttagatact aaattgttaa gaaaataaca tttttaatcc    960
aaagttttga agaatatatg acttttaaaa tggtatttat ctttttagtg tctgattttt   1020
aaaaaatgga tttcaaaagt tcatcaaata gcattgtatt tttattttaa ataattttga   1080
catttaaaat tagagtaatg gtttataaaa gacacttgat ctctaaaact attttcttag   1140
atataaatac gtatgattat ttttaaaaat caatcaaaat aggtaaattg taaaaaaaaa   1200
aaaaaaatca taaaacatga tagtagttgt aattatgctc tcaaactttc ggttatgaaa   1260
aataaacatt ttaactttta gacgtgtcaa agttgagtca agttggacct tcaaagttat   1320
gtagttatat aaattgtaat atatgtataa gcttgtggat tcaattttat catttatggg   1380
tccaatctct acaattatcg taagtctatg ggtcaattgt aacacatgtg gagtttaaga   1440
gctcaatttt ggacgtggat gtgttttgca accaactcca caccttaaaa aggtgttttt   1500
ttttaattta tcaaaaaaca agaatttaga atctttaagt ttatctttaa aaatcaacgg   1560
acattttgaa aaccaattga aactactgtt ataaacctaa caactaaaag tatatttttt   1620
aagaccgaaa gcataaatcc ataaaaaaaa aatccagaac tgaaaatgta acttttatag   1680
ttgaaaattt agctaaatta tacatattaa aattcaagga ccatataaaa ttaaagtacc   1740
tgattaaata ataacgaatt aatgtttggt atttttaacc tacattagaa aaaaaaaaca   1800
aaagaaaaac ggcatactat ttgtcaagcg tccgatggga agaaaatcca acggtgagtg   1860
ttagtattga aatacgcagt tctcgtgaat gagcctggct tagatttggg aacaagagcc   1920
aaccccttc gaccgagaag ccgtcgtctt caccatattc gcctcaacca ttcgatagcc    1980
acgtttgaag aagaatagga ttgcc                                         2005
```

<210> SEQ ID NO 178
<211> LENGTH: 1978
<212> TYPE: DNA
<213> ORGANISM: Cucumis melo

<400> SEQUENCE: 178

```
aattctaaca actccggaac aaataattta gcatggattg aaatataaat cttcttgact     60
tgcaaaaaaa tcattgtaat ggtcttatgt tggttatagt tagggtatcg aaacgccata    120
caggaatatg ggattaaagt taacttttgt tcatcaattt cagcttatga acttctaaaa    180
tatcaatttt acctttgaac ttatatgtta ttacccctt cgattgtggt atgttaatta     240
atatctgaat ctcagtcctt atgaaacttt tttatactgt cacaaacata tgaagtttta    300
ttgtaagttc ttagaaatca tctaaaaaga gtagtttgtt ggactattta ttttattttt    360
tcttattaag ttgttttcac gccatttcag taaaataact atagtgaata gagaatcaaa    420
cttctaatct taagttaagg tagtagggta tatgctaatt caataagata atccgtgatg    480
cttgacatct gacttaattg ttataagttt taaatttttt attgtaatat ttaaaatact    540
agtttttggt ttctaataaa gaaataattg aacaattaca aatatttata caaaattaaa    600
ctagaatata tgatcatttt ccttcgtgtt agaaaaaggg aaatatatgt gtgtatttat    660
acatattaga tattgtttta ctatattcca ttttcctcac gggaaatgga ggattgagtg    720
ggagataaac attgtcccca agagaattgg gaatggaaat gcaaatgaca tggccctcca    780
caaaattgtt cgcctaaaaa tgggctttct cacttctcac tccgcaagaa aaatatcgtt    840
tcccttcgaa ttcgggcaag atctcaaaac cacatgtttt tctttcttta tttttcaagc    900
ctacattatt tataaaaata taacttaagc agagaattat gtaaattcaa gtccattttt    960
```

```
cgcttcactt agctaaatca ttaacaaatc tgtaattttg ttcataaatt agctcaccaa   1020
ttatgtttta gcccactaag gcccattaga catttttatt agaaaaacat gaaccgttgg   1080
atcaagatgt gtgttttctt ttctttttct ttttattttt tttgggtttt ggtggatcaa   1140
ttcgtagctt tagcaaccta ttattatatg gagggaaagg gcgtattaat ctgttagcgc   1200
cgtccgggag tttagctttc ttccccgagc ctcggtctta tcccctaact ccaaaaccct   1260
agcccaaagg taatccactc cttccccctc cgctcttcat ctttttctat tcatcatctt   1320
taatctgttc tccctttttgg ttcttagatt cttcttttgt tggattcttt taatctttac   1380
tcatggttgg ccttgtaagt ttagacgacg tttttataca ttggttaatc ctgcttctct   1440
atctattcgc acgctagggt tttcctattg ttttctattc tgctctactt ctgcaaggtt   1500
gtgttcttct tcgttcaggt cccttttttt aaccgaaatt aaattaatgc aaattcgttt   1560
gtgcttctaa ttaggaagcc ttttggaaca tctcgacatt ttgattgctg catttcattt   1620
cgggtatatt tctatgattg aaggatgtgg gtctgttcac tgcatggtca ttacttatgc   1680
agctatgctt atcgagtcca ttatgtttgt gcaatctgtt tccggattca taatttttta   1740
gtaattgatc agtagatgaa aaaagatatt gtaatattcc ttgagtgttg caccagtctt   1800
ggtgggtatc tgctcctgct ctttgcttgt ggattttact tttattatat ctgtattatt   1860
cgaaatgttc tgttcttgtt ataacttata cccgaagatg tgttcctccc cgcgtctagc   1920
gttgtgggtt acttatgatg gacatggttt tgattctgtt tggtttgtgc agggtacc     1978
```

<210> SEQ ID NO 179
<211> LENGTH: 1263
<212> TYPE: DNA
<213> ORGANISM: Cucumis melo

<400> SEQUENCE: 179

```
aattctaaca actccggaac aaataattta gcatggattg aaatataaat cttcttgact     60
tgcaaaaaaa tcattgtaat ggtcttatgt tggttatagt tagggtatcg aaacgccata    120
caggaatatg ggattaaagt taacttttgt tcatcaattt cagcttatga acttctaaaa    180
tatcaatttt acctttgaac ttatatgtta ttaccccttt cgattgtggt atgttaatta    240
atatctgaat ctcagtcctt atgaaacttt tttatactgt cacaaacata tgaagtttta    300
ttgtaagttc ttagaaatca tctaaaaaga gtagtttgtt ggactattta ttttattttt    360
tcttattaag ttgttttcac gccatttcag taaaataact atagtgaata gagaatcaaa    420
cttctaatct taagttaagg tagtagggta tatgctaatt caataagata atccgtgatg    480
cttgacatct gacttaattg ttataagttt taaatttttt attgtaatat ttaaaatact    540
agtttttggt ttctaataaa gaaataattg aacaattaca aatatttata caaaattaaa    600
ctagaatata tgatcatttt ccttcgtgtt agaaaaaggg aaatatatgt gtgtatttat    660
acatattaga tattgtttta ctatattcca ttttcctcac gggaaatgga ggattgagtg    720
ggagataaac attgtcccca agagaattgg gaatggaaat gcaaatgaca tggccctcca    780
caaaattgtt cgcctaaaaa tgggctttct cacttctcac tccgcaagaa aaatatcgtt    840
tcccttcgaa ttcgggcaag atctcaaaac cacatgtttt tctttcttta tttttcaagc    900
ctacattatt tataaaaata taacttaagc agagaattat gtaaattcaa gtccattttt    960
cgcttcactt agctaaatca ttaacaaatc tgtaattttg ttcataaatt agctcaccaa   1020
ttatgtttta gcccactaag gcccattaga catttttatt agaaaaacat gaaccgttgg   1080
```

atcaagatgt gtgttttctt ttctttttct ttttattttt tttgggtttt ggtggatcaa 1140
ttcgtagctt tagcaaccta ttattatatg gagggaaagg gcgtattaat ctgttagcgc 1200
cgtccgggag tttagctttc ttccccgagc ctcggtctta tcccctaact ccaaaaccct 1260
agc 1263

<210> SEQ ID NO 180
<211> LENGTH: 715
<212> TYPE: DNA
<213> ORGANISM: Cucumis melo

<400> SEQUENCE: 180
ccaaaggtaa tccactcctt ccccctccgc tcttcatctt tttctattca tcatctttaa 60
tctgttctcc cttttggttc ttagattctt cttttgttgg attcttttaa tctttactca 120
tggttggcct tgtaagttta gacgacgttt ttatacattg gttaatcctg cttctctatc 180
tattcgcacg ctagggtttt cctattgttt tctattctgc tctacttctg caaggttgtg 240
ttcttcttcg ttcaggtccc tttttttaac cgaaattaaa ttaatgcaaa ttcgtttgtg 300
cttctaatta ggaagccttt tggaacatct cgacattttg attgctgcat ttcatttcgg 360
gtatatttct atgattgaag gatgtgggtc tgttcactgc atggtcatta cttatgcagc 420
tatgcttatc gagtccatta tgtttgtgca atctgtttcc ggattcataa ttttttagta 480
attgatcagt agatgaaaaa agatattgta atattccttg agtgttgcac cagtcttggt 540
gggtatctgc tcctgctctt tgcttgtgga ttttactttt attatatctg tattattcga 600
aatgttctgt tcttgttata acttataccc gaagatgtgt tcctccccgc gtctagcgtt 660
gtgggttact tatgatggac atggttttga ttctgtttgg tttgtgcagg gtacc 715

<210> SEQ ID NO 181
<211> LENGTH: 2000
<212> TYPE: DNA
<213> ORGANISM: Cucumis melo

<400> SEQUENCE: 181
aaataatttg tggattttat catattatgt accttagact ttgtaaggtt tataacacaa 60
gatgtggaga aatcccatga tgaacattgg acgttattat atcctttgaa actaaaaaca 120
aaggaaaaaa gacaaatggc tgagtataag aaaaagagaa gaaacaacca aaaagctaaa 180
atgtcatgct ctcatatgta acatatttga attgggattg atttcaagat gtattttaaa 240
ataatttaac acacgataaa ataattctaa caaactcaaa attactctta aacatttact 300
tgatatcttc gacataatga cttttgtttt aatacaactc aaaacataat taaggttggt 360
tttaaatgac aacaaacgaa aaactcgatt ctaatttcaa tactagtctt tgaaagccct 420
aaggagcgtg gttttgaatt gtatagcaag gtttcgaaaa ttttaatcat caaacaatag 480
gtatatttac ctgttcctca agtacagtta attcatagct acttgtcgtg cttcctacga 540
caacattgta agacttgcca cacactaatt gaagccgttg ttgaaggtag ttttccatgt 600
atagcttgaa tcgacggatg accaaagagg ttgaagaagg tttgaaaaat aggggaaggg 660
atatacaaag tttgagagtg agagagggag agaaatagaa atagaagaga ctgaaaaatg 720
taaaagaaag gatgaaaaaa tgtggggtaa acgcaaattg gatttttata gtagtatttt 780
gaaaatgcta tagaaaggct atgtatagta gtgcttccaa agttctatat gaatgagaca 840
aatcaaaata tattttttt gattaattaa ccccaaaaag actcataaaa aaatcttata 900
aatcccacta agatattgca tgttatatgt agtaaaattt atcgttcaaa taaaccttaa 960

```
acataattca aacgaagaaa gtaaaaattt gaatttctta tcttacatca ttcaaccaaa   1020

caatttccat ataagagatt aaacttctaa ctttaagaga gagatatcca gcatatgcaa   1080

cctaaaccaa cagtgacttt gctatatatt tgcacaaaat gtgggggaca aagttgtaat   1140

ttcggaatat caatgattaa agaaaaggta aaatttaaaa ttcggaagct tgacgtggca   1200

acacggaatg gtgatgatat ttccaactcc tcgcgacttt tagaagttgg cctcaccaac   1260

cgcatatccg cccctttgcc acgtgtcaga ctacaacaac ttccaacaat ttcctttaag   1320

aacaccaaat tatatcaata aatatttaac ttaaattaag aatatatttg ttacaatttt   1380

cctactgagt tagatagata gacagacttg tcaattaact aataagtcca aagtcaattt   1440

actcaacata gatacaattc taatttgagt gtgaaataca tattcaaatc aaaattatta   1500

ttaagaggaa aaactgattt gctttctcaa tttaaaatat aatattttga aaaagaaaca   1560

cacatgtatt atggttttca atatatttac tttcttagtc acctaatctc aaactaattt   1620

ttgaagaaat taaatatata tattatcatt tttattttct tggttatgat attggtatag   1680

aatcaacaaa actacaagtg tcctctcctc tgctatcgat ggggattaga ctctaaactt   1740

gtttagcgat tagtaattat atattagaaa aagtttatgt taatgtggac ccgacaatct   1800

caccaatagg ctcttcactt caccaacccc cgacccattc cctctaataa ttcgacacgg   1860

ctcatccccg gttcgaaccg ggccgacgtc ttcctattta acacacctcc atttcctctt   1920

ccctccgcaa cacaaacaga gacctcaccg gaaaatcaag ttaaagcaaa accaaagaga   1980

agcttcatca ctctccggaa                                                2000


<210> SEQ ID NO 182
<211> LENGTH: 2000
<212> TYPE: DNA
<213> ORGANISM: Cucumis melo

<400> SEQUENCE: 182

gcatcttatg gatgtagtca caacatattt atatggattt tctgataatg atatttatat     60

gaaagtccca aaaggattta agatacctaa aacatataaa tcaaattccc ataaactatg    120

ttcaataaag ttacagagat cattgtatgg attgaaaaaa tcatgacgaa tgtgatacaa    180

tcgcctgagt gaatatttgt taaaaaaata atatcaatat aattcaatat gtccatgcgt    240

ttttataaag aaatcaccgt caggatttgc tattataact gtatatgttg atgatttaaa    300

tataattgaa attttgaaga gttttcaaag gcaatagaat attaagaaag aatttgagat    360

gaaagatctc agaaaaataa aattttgtct tgattttcaa atcgagcatc tagtaaaagg    420

gatatttgtt catcaattaa cttatacaga gaaaatttta aaaagatttt atatagataa    480

aacacattca ttgaacattc taatgcaagt tcattcatta aatgtgaaga aagatatttt    540

tcgacgtcga gatgataatg aagaactcct tagtccagaa gtaccatacc ttaatacaat    600

tggtgcactt attttgtcaa taatcaagac cagatattgc attttctata aatttattag    660

ctagattcag ttctccaaca aaacaacatt ggaatgaagt taaacatata cttcgttatt    720

ttcgaggaac aattaatata agattatttt attcaaataa atcaaatttt aacctagtta    780

gttttgcata ttcttgattt ttatctgatc cacataaatc tagatctcaa acaggttatc    840

tattcacatg tggaggaact gctatatctt aacgatcagt gaaacaaatt accataacag    900

tcaactcttc aaaccgtgct gaaattctta caattcttga ggcattcatg aggctagcgg    960

agaatgaata tggttaaggt cgatgactca acacattcga aaattatgtg gtttgtcttc   1020
```

tagtaaactc cttccaacaa cattatacga agacaacaca acttgtatag ctcaaataaa 1080
atgaggttat attaaaagtg atagaacaaa acacatctca ccgaagtttt tctatactca 1140
tgatcttgaa gaaaatggtg acatcacagt acaaaaaatt tgttcaaaag ataatttggt 1200
agatttattt acaaaattat tacctactgc aacctttgaa aaattggtgc acaacattgg 1260
aacgcgacga cttagatatc tcaagtaatg ttacatctta cttgccaagt taactataca 1320
tagtgacatt tggtggagtt gtaagaaaca ctaatattgg agaaaaatcg aaagaaattg 1380
gaaaatatgg agaattgaat tttttttaga tttttcttat tttctaattt taggtttccg 1440
tattctgatt atgcctcatt ttcacaacat taataacttt aataagatga tttcttgggt 1500
taagggaaaa aaatcatttt tttagagttg cacgtacaaa aatattatca taacatatcg 1560
attataataa accaattcac cgtcaaccta acctaggtag agtttgagtt aaatgttaaa 1620
agaatatcca cccctcaaca ttgtaatccc aactaataaa tcagcaacct aaagtttttt 1680
ttaaaaaact aaaaagaaga gcaatatatt ttttttacta ttattttttt aaagagtgga 1740
tttatttatt aaattaaaaa atgaaaagaa gaaaatttgt tagtttgggt aatccgaaaa 1800
cccgattatt tgggcccgag aaaccgacgt tttgtttatt gttcctcacg gcaataagta 1860
atggcgtgaa tcgaccgcgt gcgcttcaag ctatctagac atttttatat cctccgatta 1920
gaaaccctaa ttcagattct ccgtattacc caccctggaa catctttgaa acgcgaaaag 1980
gtgacccgaa gaaacttgaa 2000

<210> SEQ ID NO 183
<211> LENGTH: 1989
<212> TYPE: DNA
<213> ORGANISM: Cucumis melo

<400> SEQUENCE: 183
attacttgaa cttaatccac atttatgtct ttatataaag ttcgaatact cataatatag 60
ccaagaaacc ttgtttattg gattttgagt tttatcataa gcaaatctct tatccaataa 120
caaattatta aacaacactt caacaataac tttattcaac aatatattag tttaacattc 180
acaaatcacg agtattagaa cataaaacgc aacaaagaat ggactaaggt actatattct 240
aacttaggtt gtttaggatt tccatatgtc aatgcttttg tgatttttga actagatttt 300
cttgttagat taattcaatt ctatttttaa atggcttaat atcttatttt cggatgcttg 360
gggattgcta gactaccgct ttgttgaagc aataagttaa atttgtttgt tacaggtatt 420
gatcaatcta acatagaatt gaatttgtat gaatatttag ttagacgctt gaaaactaat 480
tattctacca atgagccgta gatcttaatg caattgttat taatttgaac tttgtatgct 540
tctcatcgat taaatttata tcaagtagtt aattaggaca aatctattgg ctttttcatt 600
taattttgtt aagtaaaagc aacttagaat tttgaaaatg atgaacccat gatccaatac 660
attgaaagag aattttgttt aactcaaact aggattcttc tcacattgat ttcgtataat 720
ttaacttttt caatttatat caatcccccc agggtgaaaa aaatttgttt gaagaattca 780
tgtgctttct aaatctgatc tagacttgcc actaaaatta acttttgata tgtaatttgg 840
ttaaatattt gattcggatt tcgacgacaa acaattgatc aatgtggtat taaattctga 900
tctccatgta agaaatttac acattttcat aagttcaatg ttgacacaaa gagagtaaga 960
gcattttaaa aaaaaagata cttttaatct tttctaaaaa aacaccaaaa tgccattatg 1020
taaatgtaac ctaaataata aacatttaaa cttagaattc atgcaattag gctttgtatg 1080
ggacattgaa ttgattatta aaatcagtag ttatagaccg tgagttataa tggtttgtat 1140

```
tagaagcata aattatttta attttgatcg taatagcatg tatttgagat ataaattaat   1200

ttagtttggg tggcaaatag taaacagtaa agcaaaatat aaaaaaatga atttaaaata   1260

gtaagatttg taacaaatga ttaatactat aacaaacgtg gttttaaaat aacgttgatc   1320

gtagctaatt gaacattatt tattgtaaaa ttgagtgttt ttaatatttg gagcctcaaa   1380

cttcgggtgg atcaccacaa tataatcata ttcaaattta aaattttatt tttattataa   1440

atattgttaa tagatgctca ttatgggcca tctgtcactc cctccgtgca tatcctacct   1500

gaaacatcat atatcttaaa caatgtccat tgccatgtgt cactattttt acatcccatc   1560

cacttgacaa atatgttgaa gatgcctact tttttaggga tcatgtaatc tatctcatgc   1620

ttgtcaaatt gttcgataat agtgttacaa aaaatttagt aattattatt attatatttc   1680

ttcgatattt atgcttcata tgccattgtg ctctccattt ttaccatact taaaaaaatt   1740

tcttattata aatttttca aaaaaaaatt tactatatag tcatcatctt tattaaaatt   1800

aaaattgaga acctgatatt tttgatatta ataatttaaa atttgaatta atccacttta   1860

aaattattaa taatttattc gaatttgggc cttaaggaag agatacggaa acaaacccta   1920

gatcccatct atatataaat cgccacaaaa ccctaccttt ctctcagttt ctcgttttag   1980

ccggcaaaa                                                           1989
```

<210> SEQ ID NO 184
<211> LENGTH: 1463
<212> TYPE: DNA
<213> ORGANISM: Cucumis melo

<400> SEQUENCE: 184

```
ttttcttctt gatttgaaat tcttcctcct tcctgttgca aacaaaccca gatgaataat     60

cagacaaaaa aagcagcaaa tttgaagata tgcatatacg aagaagaaga agaaaaagag    120

agggaaggat aaggtaggag atagcttgag attacagcgt agaaaccgat cgaaccggag    180

atcaacggcg cgaattaggt caagaagaag tgagggtttt tatgaagaag aagtgagggt    240

ttttatgtgc cgatgaaaaa ccctacttct gtgttggtga tctaacgttg tttgatcggt    300

tcggtttttt tgagaatcga gtaccctcat tattattatt attattgtta ttattataag    360

tttgttgtaa gaattaataa attatttcaa aaattacaat ttttatttat atatagttta    420

aaaaatttta taattttttt aaataaattt cgaaatataa ggttggattt cttaaaaata    480

tatgaaaaaa gagatgaagt ttataaatta aaaatgaaat aaaaatagta agtttgtact    540

cttattctta tttacaattt aattttccat taaaatttta aattaaatag aaatataatt    600

aaaatcttaa attagataga aatataatta aaattttcag aatgtaaatt taaattagct    660

tagtgtatat ttaaaatata taagattgaa ataattgatt ttgtttatct aaatatttta    720

tattattatt tattgaataa atataattat atatggtaaa ttgttttgga taataagaaa    780

gtaaagatgg tatttatata tataattaac caaaatttaa gtttgttaaa aagaaaagtt    840

ttcaaaaata ttttttacg agtaattagg aaaaacccac attttacatc gaagtcatag    900

actgggtcta tgtcttcatt gccttgtcgt gtacccgatc cacgataacg cattatgaac    960

cgagtagatg acttaacttt ttgtaatagc ttttcttcta ccatattttt gacatttttt   1020

taaaagtaac attatttata aaaaaaaaat cgtagtttga tctcacatga aactattatt   1080

acatcattaa ctaatatatc tatatttaat gtagttttct tgacatgatt ttaatgctaa   1140

ttgaaatagt tacaattttt gtgtcccatt ttgtttagat caatatgact tcacgtatta   1200
```

tgacatatgg ggccatctta ccagaaattg gtgccaatga gaaaatgaat gtaccttaac 1260
caatggagca acccatgtga gccattgatg aacccaactt tcttggtttc ccatcttcta 1320
ttcatatgtc acaatacctt ctcttttctc attctatata tagactctaa acaaacaact 1380
aatctccaac ttcaaatctt tcacatattc tcattcaagc attgaagttt accacttcca 1440
aaaagattca atccaattta gcc 1463

<210> SEQ ID NO 185
<211> LENGTH: 2006
<212> TYPE: DNA
<213> ORGANISM: Cucumis melo

<400> SEQUENCE: 185
cagcgatctt cgtagaaact aattcaatgc tagctcatta tttgactttt ctcaggcaag 60
gctccgcgag gaagagaaaa ggtccaattt caggaaccaa gggcatggac aggttccggt 120
cagaagaagc tttttacgta aaccctttgc cagattgttt atgtcaagga gaattaccaa 180
atggaagtac gacttccatt ttcagatagt tcagtagaac atcaaagata aaatgctctt 240
agagagctca atgtatatgc aggcgaccac tcaacgtgtc accagctttg tacatccaat 300
aagccagcta cgatggaacg acggagtgtt tataacctga gttttggtag ttggcggagg 360
cggtgatggt ggtatagaag gaaggtcgag ggatggcaaa ccctttacgc caagtagtgg 420
aagggagtag ttggagatga acacattttg agaagtttcc aagatcactc catttggggg 480
agaggggatg ttggttattt agcacaattg ttttcatgtt ttagtaattt tatccaataa 540
tgagcgaggc attgaagcaa ttaaatttat ttttaatgat tttttcaccc ttccataggc 600
tttttctttt ttcttttcct tttagtttgc aaactttagc tccttttatc ggctgtcgaa 660 ctcattttttg aagttattga atgaaacaca gtttgggctg tgtcagatgg gtggtgaaat 720
tttatacatt ataattacta cataaaatga aatcatattg taattttcta tctatgccac 780 aattttttttt tattgcatca tgaggattaa attgtacgag tccaaatttg tacagtcatg 840
tttttaaagc tttcgagcat tgttactaat gcatggaaag gatcgattat caagtatcct 900
cccaacttca tgaaagttat tatttgtctt ctaaatttgt tttagaaaat gtttaattaa 960
ttatttgaga agaaagttta actaaatcct attggtttcc tctaaggttg tcatacttat 1020
ccaataacaa ttacgtttaa aatcaaaatt attctaatgg tataagacta atgttttaaa 1080
agcataaaat tgatgaggaa ggattggaag taatactatt tattttgaag gtaaacattc 1140
ttgaatgtct gtcctaaaat cactaatgtt ttcttagttt gagactttga gtcgttgaac 1200
ctctccatct ttataaaata taatacgagt ccttcacaat aacttaaaat atatactaaa 1260
tcctaattaa tgaaaaataa ataaataaaa ggtacaaaat cattaaagcc taaaaatcta 1320
ttactccttt aaaacttttc aagggtccct acaaccaatg agaaactacc acgtcatttt 1380
cacaatccgt tcagtgttta gaaaagtcaa atcgcaccgt ccatttatcc actcgtacca 1440
agtacggtag gaatctatct accgtccgat taagcacaaa gaagcacagt aaatgtcaat 1500
cgtgtccatc cgccgccata ccgcacatcc ttcgtccgac cggaaggccc tatataaagt 1560
cctttggttt tccgaatttc tacttcattc gcttttgaaa gatttcccaa tctcttcgtc 1620
ggccaaaatt ctctctcgct tctcaaccct tcttcggctt tttcatccag gtttgtttct 1680
cttctctttt ttcttccttt gttgttcttg gaatatgttt aatttcattt gtttttccat 1740
tcaatttcat gctagatttt acgattaggt tgattttctg ttcgtagatt gtaattgatg 1800
gttagggtta gctttttctc ccattccttc tggaatctgt ttcttgacct tcgaacttcg 1860

-continued ttgataaatc tttagaaaca tttacataac caaacaataa ttgaacaact cgtgttgtta 1920
tgcctatata atagcggtta ggaaactgga aacgccctta taattgaaat cgccttagaa 1980
atttgttttg attcatacag ggtacc 2006

<210> SEQ ID NO 186
<211> LENGTH: 1664
<212> TYPE: DNA
<213> ORGANISM: Cucumis melo

<400> SEQUENCE: 186
cagcgatctt cgtagaaact aattcaatgc tagctcatta tttgactttt ctcaggcaag 60
gctccgcgag gaagagaaaa ggtccaattt caggaaccaa gggcatggac aggttccggt 120
cagaagaagc tttttacgta aaccctttgc cagattgttt atgtcaagga gaattaccaa 180
atggaagtac gacttccatt ttcagatagt tcagtagaac atcaaagata aaatgctctt 240
agagagctca atgtatatgc aggcgaccac tcaacgtgtc accagctttg tacatccaat 300
aagccagcta cgatggaacg acggagtgtt tataacctga gttttggtag ttggcggagg 360
cggtgatggt ggtatagaag gaaggtcgag ggatggcaaa ccctttacgc caagtagtgg 420
aagggagtag ttggagatga acacattttg agaagtttcc aagatcactc catttggggg 480
agaggggatg ttggttattt agcacaattg ttttcatgtt ttagtaattt tatccaataa 540
tgagcgaggc attgaagcaa ttaaatttat ttttaatgat tttttcaccc ttccataggc 600
tttttctttt ttcttttcct tttagtttgc aaactttagc tccttttatc ggctgtcgaa 660
ctcatttttg aagttattga atgaaacaca gtttgggctg tgtcagatgg gtggtgaaat 720
tttatacatt ataattacta cataaaatga aatcatattg taattttcta tctatgccac 780
aatttttttt tattgcatca tgaggattaa attgtacgag tccaaatttg tacagtcatg 840
tttttaaagc tttcgagcat tgttactaat gcatggaaag gatcgattat caagtatcct 900
cccaacttca tgaaagttat tatttgtctt ctaaatttgt tttagaaaat gtttaattaa 960
ttatttgaga agaaagttta actaaatcct attggtttcc tctaaggttg tcatacttat 1020
ccaataacaa ttacgtttaa aatcaaaatt attctaatgg tataagacta atgttttaaa 1080
agcataaaat tgatgaggaa ggattggaag taatactatt tattttgaag gtaaacattc 1140
ttgaatgtct gtcctaaaat cactaatgtt ttcttagttt gagactttga gtcgttgaac 1200
ctctccatct ttataaaata taatacgagt ccttcacaat aacttaaaat atatactaaa 1260
tcctaattaa tgaaaaataa ataaataaaa ggtacaaaat cattaaagcc taaaaatcta 1320
ttactccttt aaaacttttc aagggtccct acaaccaatg agaaactacc acgtcatttt 1380
cacaatccgt tcagtgttta gaaaagtcaa atcgcaccgt ccatttatcc actcgtacca 1440
agtacggtag gaatctatct accgtccgat taagcacaaa gaagcacagt aaatgtcaat 1500
cgtgtccatc cgccgccata ccgcacatcc ttcgtccgac cggaaggccc tatataaagt 1560
cctttggttt tccgaatttc tacttcattc gcttttgaaa gatttcccaa tctcttcgtc 1620
ggccaaaatt ctctctcgct tctcaaccct tcttcggctt tttc 1664

<210> SEQ ID NO 187
<211> LENGTH: 342
<212> TYPE: DNA
<213> ORGANISM: Cucumis melo

<400> SEQUENCE: 187

```
atccaggttt gtttctcttc tcttttttct tcctttgttg ttcttggaat atgtttaatt      60

tcatttgttt ttccattcaa tttcatgcta gattttacga ttaggttgat tttctgttcg     120

tagattgtaa ttgatggtta gggttagctt tttctcccat tccttctgga atctgtttct     180

tgaccttcga acttcgttga taaatcttta gaaacattta cataaccaaa caataattga     240

acaactcgtg ttgttatgcc tatataatag cggttaggaa actggaaacg cccttataat     300

tgaaatcgcc ttagaaattt gttttgattc atacagggta cc                        342


<210> SEQ ID NO 188
<211> LENGTH: 2003
<212> TYPE: DNA
<213> ORGANISM: Cucumis melo

<400> SEQUENCE: 188

aactagacta gcgagtgcac aaccaaatta caaaatcctt aacagagaca accatctatc      60

tcctttaaag caacaataac atcaaccgaa ttagaatcca caatcagtaa agacgatgcc     120

gacaccaatg accaaaaccg atcaaatata gcttattacg gaccattact tcaacagtta     180

catcaacaaa aaaaaaaaaa ttaaacattg ctaataaaat ctgaaaatga ggaaaaagag     240

attaaaagtt ttgaagatag aaagaataaa tctgaaatgt tctaatttga tatataagaa     300

atatgaggta atatgacgaa agcattttga tagttttcac caactccctt tgtgaaagga     360

tacatccaac caattttaca atttctgttc aaattttgtc cacctaccct tctcttctgc     420

cccccaaggc tgctttcttt cttttattat ttgctaaatt accaaaaact attttcgaat     480

taaaccatct atttcaatta tatacgtcat tcgaatttta acttaattaa cattagtata     540

tgtttcggat caaggatagt ggtataaatc atcctaattt caatttgtat ttagaaaagt     600

tcaattatac ttaaaacttc taaaaatttt atattttaaa tttggatata aattaaattt     660

aagatttatg gaaggtaaat aattagagca aaacaaactt caaactatat ggaaaataga     720

aaaggaatat tttagccaaa caaaaacact tattatttta ttttgttttt ttgttttttt     780

tttaatttaa caattttttt ttttattggt tgaatgtgtt tctccactgg tgagtctcca     840

actttgacct gcaaagggtc tatatagcga gtttcacgag cacctaacca atatctgtgt     900

aataattccc atttttcttt catacccact tcatttgatc atctttttca caaccccgga     960

tctctaattc ttgggaattt gcctctttct cgatccattt ccaccgtaat tgaaaaatat    1020

tcaggtttga tttcttctgg gttttcattc aactgtctaa cttcattatg ccctttatgt    1080

gtttgttgaa agccccccac ccaccatcgt tcaatgcggt ttctttacct tttgttcggt    1140

ttcaacgatg atttagaagt tatagatgga tgctaattgt ttcgttgttg gtttgatcca    1200

ctgatctgcc tttgattggc ataaaaggag attctagatc ttgttttgat gttgtgattt    1260

atggatatta ttgttatagt cgtggaagtt tttcttgtcg ttctgcggta tatggttgtt    1320

ttattttttg agtggtaaat tgagcagatt gtgaactttt gggttttatg gtgaaagcat    1380

gaattagtaa atgtagagct gctgaaacaa aatggaggtt tgctagacct ctttgtgaat    1440

tcttaatggt cagcctccat cttaagaggc taagtccaaa aatttaaggc agtcttttgt    1500

tattgttaca aaggacaaga aataacagag gagttatttt aattgaatca agttggaaag    1560

aagtactact tcatgcttct ttcaaaagca ggtcaaagtg ctttaaagtc ttcttattta    1620

tttatttttt cctgaatcaa tttaaactaa tgatagaaag aagtgttttt taatgggtta    1680

ttataagtaa catcaatttt taaccattcc aaaagttaca tcaaattcat catagtgtga    1740

gtttacgaat tttggaagtt gtaattttaa gttaatactt cttttaagga aatgtacact    1800
```

ttgcatgttg tgttcataag ggtatttct ttgacaaacg cagcaaccac cccttaatga 1860
aaactacacc acggtggttg gtttttctt gttattttt tacttggaat ttacaataag 1920
ttgttatatt cggatatatg gcaaagcaga tatctgtttt tatccgaaac ctcataaatc 1980
ttgaatgtgc agcaggtaaa aac 2003

<210> SEQ ID NO 189
<211> LENGTH: 1024
<212> TYPE: DNA
<213> ORGANISM: Cucumis melo

<400> SEQUENCE: 189
tcattgatga agaaggaaac tttaagccaa ttcgacaact tatccattca acaactttcc 60
accttcagac attcagattc aactataata taacataaat tgatagtcaa gtctttttg 120 agacaaccat aaatcatctt agcttcgaga actgtcactt ccttaaattg gtgaatatat 180
cacattccat ccattcaaaa ctttgtttcg aactttactg tagttatgaa tcaataaatt 240
gggagagata ttgttaaaaa gagagagcat atttgtttct attatttact ctctcctaag 300
agagggttaa ttagtctata aatgatctat tcttctcgtc cattgaaatt ttgttatcct 360
aaatttatga atacttctac ccaaaataaa gacttttttt ttttttgaaa agtgtcaaaa 420
aaacataaag aaattgacaa aacattcatt tttagtggat tttttacgga cgtaaatagt 480
ttgtttttgt ttcttttaat aatacaattt tttttttactt taaaaaatat ttttgttata 540
aaaccaccgt atttttattc aattttaata aataaataaa tgaaagaata taaaaaagag 600
gaaggaaaaa gaagccaacg aaccaacggt tgccacgtat caaaggtcta aagtgcgcaa 660
aacgaggcct tcggaaacca aaatgcgtgg cttcaattgg agcaagtaaa catggaaacc 720
acgtccattg taacgcttcc tgatctcttc tttacaaccg ttggattcga gtactttttc 780
tcaacgatta acgactgagt ggacctccac ttgcttctgt tccacgcgcg tgggattgac 840
gtgtggtcca cgcaactctt ctcgatagga tcattcgaga acatccttta cttaaaccgc 900
ctctctctgc ctcaatttct cgtcacttcc ttctccttct ttacccttc cactgcggct 960 gattcttctt cgccttttat tctctcgtac gccgccatat tcttcacttc tttttccggc 1020
gaca 1024

<210> SEQ ID NO 190
<211> LENGTH: 2001
<212> TYPE: DNA
<213> ORGANISM: Cucumis melo

<400> SEQUENCE: 190
attcgtcttc gcattatcag taaatttatc attttaagag tttgttcttt tttaaaaaaa 60
attaatcatt tcgataaagt tggagaattc aaaaatttct ccaaataatt tataaaaact 120
ttcggttata tatcgaaaaa attaacatgg tattaaaacg atcataactc aattaacata 180
aacactccct ctcaacttta ataccaaatt tctttattaa cgcaaaattt aaaatttgtt 240
tttaaaattt tcacataaca taatagaaat acttttcttt atggcaaaaa tacaataatc 300
aaaattgatt gatggtgaca ggacaccaca caatattttt aaattttgaa tatacgaact 360
atataataag atatttatga gattcccatc ctaaagattc ctagagattt ccttgtgtac 420
aatattacac aagtatcttg gaagtccaaa gtcctgagaa aaaagctatg tataaagtaa 480
tagtgtttgt cgtaggaaat ttacttcatt cgtgtcatta gctttttatt gaaaaaaaaa 540

```
attaggtata tcttagtgaa tctcacttaa tcgttgtcga tagttattct tttaatatca    600
ttatatacta aaatataaca atattgaaaa gctaaaactg tatataaaaa aaatgttacc    660
tctaaacttt tatcgtttat ttaaaagata aatatattct ttcaaaactt acaatcaaca    720
tcctacgact atcattatag gtacaaatct tttcatgttt acacaaaaat tagattttta    780
aatggtgtaa tgatgatata taacgaaatt ttgaatgatt actatttgag gttaccattg    840
taattggtcg tgttgtttga aatttaattt tattagaaaa tttgtcaaaa gtagcaaaaa    900
tgaataaact atttaaactt taggataaaa tcaagtgtta tgagtttttg tctagtttat    960
atatttttat ttttattgaa aaccctttttc ctatcttttc attacttcaa aatagtttta   1020
aaatgtctat taaggctaaa gttagtataa ataaaatttc ggaaattttt tttcgaaaaa   1080
aattgataaa ttatttatat tttatattaa agtcaaaatt tattacgcgt agatgtttat   1140
caaattttct ttctttttgt tgataatttt ccaaaatttg gataattttt taaaatagta   1200
aaattattat aaaaatgaaa acaaactatt tataccttaa gcaagaaata ctaaaaaggc   1260
aaaaattcat ttacttcatg aagcgtaaaa attaaatatt ttaccacttt ttgttatttt   1320
ttaccatctc tatcaattat ttgtaaaaag aaaactacaa aattagatgt tttttctttt   1380
ttaaggttta atcaatatta aaatttctta aattggcaga caagttggtg ttggtaatta   1440
cgaataaatc ccgaattgac taaaaataaa ttcttctcca agtaaaatag acacgtggat   1500
gaagaaataa gtgaatcaaa ggcatccaca gttcaataaa tggaaaaaac tactttctgc   1560
tgactcattc ataagttttc ataaaatttc ataagaaagg ccaaagggct tatgaaagtg   1620
aatgtcatag cagtaaatga agcacagcgc cattgaaaga caactcaaat tgcatgcaaa   1680
cccacataat tattcaacaa acccacatca aatttcccat aaagatcaat tctttagggg   1740
gttcaattac ccaaaagtga ggtagttgaa aaccattaaa caacaagaaa tcaacaattt   1800
tgtaatttgt ttgtacagaa gtaagagata aaatcatcgt taaccattcc tttatttcgt   1860
aatacaaccc atcaaccatc tctctctctc tctctctctc tctctcggcc tttatctttc   1920
tcttcctcaa ttatttaagt actacccaag tgagctaaaa gcaagttcag tggacagtgt   1980
tgtaagaacc actacagaaa a                                              2001
```

<210> SEQ ID NO 191
<211> LENGTH: 4175
<212> TYPE: DNA
<213> ORGANISM: Cucumis melo

<400> SEQUENCE: 191

```
tagtttggtt cataggttat agtttccaaa tttgttaggc tatcattaat caaacacaat     60
acttctcttg taggatggct gccccctata gtactttttt aacttaggag aaggatataa    120
taattatatt ccttttagaa aatataataa taattgtgta gtgctttgat ataccttaaa    180
ttagctactc acgtttttag gaggaagctt ccgttgcttt tcatggtgtt atgatctttt    240
ttattttata aaggactgaa ctttaaaatt tctctttcat ctattttgga ttggattcca    300
tctattttat acgggaagtg aactctaaga tttctcttca cctattgtga atcggactcc    360
gtcatgtagg tcaagactac gacagataag aatagacttc cacgaaagaa agtggtcaat    420
cgagatggct atatttggct ctttcagctc aatttcttct tttttccttg catgttcttc    480
cgttggtaca tttcttgcac ttttttgtt ctcacatgac taatgtattc caagtttatc     540
attggcattg tgcctctttt aggcttgtaa actctcgatc caaaattatc taggacatat    600
gtttcctagt gaagaaatac tagtatattc cttatgtcaa tatgtcaaaa ttttcaattt    660
```

-continued

```
cttaaccttt gagtaaatca atattatatt tttatggagg ttatttataa ttggaaaaaa    720
gttacaccca tctcaaccct aattaacacc aaatgaaatt gtaccatgcg gcacaatatt    780
tttttgtgag ttttttgcaa agagaaacaa agtagcagac aaagaacaaa cattccccca    840
aaaacagcag agaataccta agagagaatg ctctctcgta aaaaataata cccaagaatc    900
ttcccaaaaa gagggagtaa aagagtccaa aacaaacgaa ccgaagattg acaagaaggg    960
cactctcgcc ctccactgcg ccgctaaatt gtaagaagca tattttcttg agttaacata   1020
ggaataggtg taactcaaga gaaatgtaat tcgtagaatt gaactttgta tattaattta   1080
tatggtgttg tagatacaat ctttagtatt tactcatttg gtgctttctc tcaaatacaa   1140
tttaaattta gaactttttg atcttcgatt ttcaggaagt tggagttgca aatcaattcg   1200
agtttcaatc tctggaattt aataaaagtt tgatcttcca agttttcaat ctttcagaag   1260
acgatgatct tgatatggat aaaaaattgc acatcatgag agctttttga agtttaaatc   1320
ttcaattctc tagagcttaa attcttcctt aaaccaaaga tcaccaaatg aatgacaaat   1380
gtctctattt atcgaaaaat ttcatagact tttagatggg cttaggcaca ttacttgttg   1440
ggcttggact tgggcttatt tgcttggcgg gctcatgctc gagcccatta tttctttggc   1500
ctatttttca tgaggggctt gaacttggtt gtatacgaaa aaacttgact acctaaatct   1560
aatcaaatta taatcatcac aattttgacg tgttacgatt taattggcca aaaattcttg   1620
ttcaacactt gtctctaatc attttcctat ataatttaac taaaatattt aactttaagt   1680
aacttaaaag atatagttta attcgaatca aaatacaaat acaatttcgt ctatctattc   1740
ccatcataaa tgttgattga gattcatatt ataaacttct ttcaggaaaa gaaagaggaa   1800
aattcaccta aaccacgttt tcctattttg gtaagaatcc ccaaaccata aatcattcca   1860
aaattatttt ttttagatta gaaaagaaaa aagaaaaaaa gaaattcaca tggcgtaaaa   1920
tttcagcccc gtgagatatt ttcgaacccc cagatacaat ctacaccgtg aaaacaaaat   1980
cggacggtgg ttgctataat gtccgtttag aggcaatggc agggatgaaa ttgccaacgc   2040
aagataagga acgaataaga gaaggacacg taagtacaag tttaggatgg gcgggcccac   2100
agccacaagt gccgttcgtg cttatataca agtcgctcat attcctagaa gtgtctccaa   2160
ataaaggaaa gaaaagttca ctcatagaga gaaagagaaa aataaagctt cgttgccggc   2220
gatctgaagg cggcggccat ttctctcggg agagagaaag agagagattg atagagcgga   2280
gagttcgagg ctctctcaaa cttcggtcct cttcttctct ttcaggtatc gttcttctct   2340
atcccttcgt attctgtttc ctcttttctc tttcttcgcc atcatgctct ttctcttgtt   2400
ttgtactcac tcaatgtgat tgactttatg ttgtttttct gttttatttt tccattaatg   2460
ctcgttgtaa tgtgtagatc tatgataaga tttgaattat tgctcattaa tgtgttgcat   2520
gcttttgatt tcattttaaa aacagagatt actttctcta tattgattaa atcgttggat   2580
tttaggttct tacagagttt gtaaacagtg atgttaagga ttgctgagat ttatgactga   2640
tgagagttag tgtttgtctt ttagcttgtc gttttcctct ttgaaatcac atggattcga   2700
tctggatatc tgggtttggc tcgtctgaaa tggctacact atagcatatt tgagtttgtg   2760
atgttgaaga tttgttaatt tcttggaaaa tcgggagttc gttttgtttt tcctcttttt   2820
acaggtttta ttgattggtt tattgatcgg cgatatctcg ttttcaactt ccgaaatgct   2880
atttttcata agaagaaatt gtggatgtct ttttctactc gattagagat ccttgaaact   2940
atgccaaaaa aaattggttc tttcaccaaa ttgtttttg tcgtttgtga tattaatgca    3000
```

ttttcttatt cttaattaag ttcaagtatt cttttattat tttttaatga tggttgttgt 3060
aatggttttt tcccttttac taaaagcttt ttccatgtga ttcaaaggtg tacttggggt 3120
ttcccggtct ttgttcccaa gtcaattagg atgggcgcca attcgatttt agcttctgta 3180
tcattggtgt atattctgtt ctggggagga aaaaaaaaaa gaaaaaaatc ttccgtccta 3240
cagtgtgctg agtaacaatt tgaccagcct tttctgccga aaactttttg aaattatttt 3300
ttaattgtga tttggtgaac ttaaattgtt ttaataaata aggtggattg aatcttaaca 3360
gaaacatcaa ataaaatcga gttttaaaaa aaaaacatat ttttagtgaa tgtttatttt 3420
atttaaaaga tctccatcag tcctgatgtt tcctagaaaa cttatacatc ataggtcttg 3480
attaacaaat ttggaggaag tcaataggtt attctttttt tctttttcca ttctagtttg 3540
aaacaatttt cttttctttt ttaacttaga aaataatggg tagctagaaa tatggaaatc 3600
aatgtatttt gggcttctcc ttgaaactgg agcagcggtc aatttctctt tcgtttgtat 3660
agatgtgata gaaatagaat gtttccttcg cttacggcat cagagagttg gaattggtct 3720
ttctcaacct caatatcaat taaatcaagt ttcgtcataa acaggttttt tttttcttcg 3780
tttcaaatgt ttggtagggt caaataattt gtaaaatacc tagccgtcca atatgataca 3840
aactggagga tttcacttgc tcttttaaat tacaaaaaat attttatcat tgatgttgcc 3900
tgtctgtgtt tatcttttct ctttccgcct caagtaggcg tctaattgtc ttggcaagtt 3960 ggtttttgt acttccgccc cttgtccttt ggcccttttg attaagtttt tcatttaatt 4020
ttctggtcgg cgtacgttga attattaggt ttgcatttaa tgtggtacct ggtgctttga 4080
ctcttatttg ataaggtatt ttgaagtcta aaacgttaaa ccctttgttt gatgtttatt 4140
tttttatcgt tccaggacaa tatcctttgg aaaaa 4175

<210> SEQ ID NO 192
<211> LENGTH: 1999
<212> TYPE: DNA
<213> ORGANISM: Cucumis melo

<400> SEQUENCE: 192
aaaagagtca tagtgaaaaa agctgagatc ataatagttt caccctaaac acaacttata 60
ataacacata ctatcataat atacacacca aacacagact ctatagtctt cactctaaac 120
gcagattaca atagtctgca ccccaaacgt agactattat aatcttctga ctattataat 180
actcttttca cttatcgccc caaacgtccc ctaagagaac aaagataggt tataaaagag 240
agatgagggt ttatattatg caacaagtat aaggttctag aacgatgtag tcttcaaagt 300
aacgaaagca ataggctaca cgagaaaaat atttttaaaa tatagtgctt tccctaaact 360
agatttcaat gacaaattat tataaaaaat agaatcatta atccaacatg gcttgcatgt 420
cacaccttgg ccaaaactga agacggatgt catactcgac ttcaatatat ttttttaatt 480
aattttcatg tgacaacaca taaatattta aaatttagat tgggttggat ttttttttcaa 540 gtgggtccca aaatactctt caaacccaaa ccaacccaac ttgtttaccc atctaataat 600
aacccaccag gttcaagaag acgaaccgaa ccgaaccgat ccggtctaac tttgtttcat 660
acttaagtcg aacttagcgg tacttttggt tcggttctcg gtttccccaa acagagccac 720
tcaaaattag atttagggtt ccgttcgcaa ttttcagcgc atttttattt gaatcggtcg 780
tttgttgaac acgttctctc tcagctggtt tagggttcat cgttctctct tctcgcgcta 840
tatctttctc tctctcaggt tcgtttcttt ctcttaggcc attttatcag aagatcctct 900
tcgttctccg attttctttc cgtgttcgcc ctcggtttct cagcagacgt aggaagtttg 960
gtttccgttt agtgaatctg tttggggtat tacgaatgat attttgtact gggctttccg 1020
catagtcttt ttctttctag gaatatatgc atctgagaat ttatttgttt ggcttttctt 1080
tataaagtat gaggacatat acatctcgat tgctaatcct tgattataat cttttttttt 1140
tctatgttgt ttgaatctgt tttttttttt ttaatttcaa taggtttttt gaatctaaaa 1200
atgtatttct tggatgaatt gcatactgtt gaattagaag tttattgatt agattgttga 1260
tatttgccct aagttccatg gataggtttg cgtctttcac cttttcgttt gctttttctt 1320
ttggctgacg acatcttaca tagcctctgc tctaaaaggt gccatgattt tttttcctgg 1380
ctttatctga gtttgcgcaa tttagatttg aagtgatgat ttgtctaaat ataaatatct 1440
atcggccata ctatttttg ttattttgag tttttcagga tgactgctag agaatgaaaa 1500
atcttgaaac attgtgtttt gaagttcaag gatcttgtag ttttgttctt ttctagacta 1560
tctcatttga tatagccctt taaatttaat caaaatttgt taatattcaa atcctcggac 1620
attttaatta tttatctaaa tagttgttta ggcattactc aggttgccca ctattttaag 1680
cttagaagcc tactctggtt gacctaaagt ttgcatgcta tttgccttat ttcgcacgac 1740
tctaaactgt tatagacatc ttttttcagc cttcaggtaa atgaacacaa aaaggagtga 1800
aagtctgact tctgtgtgat ggtcttttaa tcaattatag ggattaagat ggttttttta 1860
ttcattgtat aaatattaaa ttagaatgat gacaaccaat aatattaaaa ctgacaatgg 1920
aaggttcctt atattatttg gagtgtacat tacaacagcc tgattcttgg cttggcaggt 1980
tcctgatcac cttgtaaac 1999

<210> SEQ ID NO 193
<211> LENGTH: 2000
<212> TYPE: DNA
<213> ORGANISM: Cucumis melo

<400> SEQUENCE: 193
atttatttgt ttagagataa gacgcacatg agaatatgag atggattcca ctccactcac 60
actccaattt ctacctatcc tattactgtt tactattatc attccacccc tcgacccctc 120
attcttcttc tcaccttact tttttatgat ttactactac ttcattttgg atcacaatct 180
gatcaatgct gggtgggctg ccctcggcct gtcaccaggc ccagcccact tccaaattaa 240
acctcttggc ccaccgccca ttgtccccat cccattccat ttaatattcc caaccttccc 300
tttttctttc ccaatgcgat gcttctccaa tatacctttc ctgccctcca tgtttccttt 360
ttactgcttt cttatattta taacacacct tctacagtct tttggctggg aatgctgcgt 420
atgtgaatga gattcaagat ttcgttgatg ttatttgagt ctctatattc ataagttttg 480
ttcttagttt tctctagacc aactgcaaga gttagcgttc catatgctca taagtttcag 540
atttctgctg tgtggtttga agacagtcat cgatccatgg gtgaattcgg ctttttatta 600
ttattattat tattatttat tgttgtctta cttttctatt tgaatcttcc tatctttttt 660
actcattgtt ggactctaat aattcttgct aaacacaatc tccattttta ttggacattt 720
taaatcccat ctcaactcat aattttagtt accttccacc atcaccatat ccaaatccga 780
aataaactca aataaaatcc ttcacgtgca tgtgctctcc atatattttt tctacatggt 840
aaaaataaaa tgaaaacaat ctaaatttaa taaaataaca tatatggcag acttttattg 900
atgtagagac tgggtgttgt acaagaacag tgcagccaag aaaaaaaaaa tacttccaat 960
gaatcgtaca ttttaaggat tatgaaacta actagttcca accatttttt cacgaccacg 1020

-continued

```
tgcttgttaa acacgcaagt agaatcaaaa tgtgggcttc ttcgctttat ataactgtga   1080

atcattctcc aaaaagggaa ggggatctca ttccctaatt caataaagaa aaagaaaaat   1140

gctagcgaac ttcatccatc tcattccttt tacctatttc atgagatgcc cattgtatat   1200

aagtattttt ttttttattt cattttactt agtttactcc tcacctctaa aaaaaattag   1260

gagagtttgc taaatccatt ctcaaactta gctttatttt ttttaatttt atttaacctc   1320

gtcgtggatg ttaacctcaa atgtcagttc tttttattct atttattgat gttataattt   1380

actttaggat tccaatttta taaaaataag aatacaaata aagataaaga gtgtgaaagc   1440

cagaaagaaa aaaaaggaaa tcgtaatatg ggtaaaattg gtacaaattg ggtcccgtta   1500

aatattaact caaaaaatgc gagaaaatgg tagaaaagga aatagggggt aagagcaaag   1560

tagtggaagg agagcattga acatattctc tagtttttgc acttggatct aaacacgagg   1620

aattataggt ttattcattt actaattaca taaataggat tggattttaa aatttgaccg   1680

agtgattatg catatttgat agagttagaa aatagtggtg gggcaggtac aagttacaag   1740

taatgtataa gagatatgat gagcatatta ggaaactata gatttaaatt cgtccgtaaa   1800

taaataatta gaaatataat attcgagtgg aagggtatta gggttaggcg aaaccaattg   1860

cagttgcacc tataaaaccc cttttacgcc tccacccgct tcaacagcgg tctcggcgtc   1920

tacaactaca cactacacac tacacactac acactacaca gttgcagacc agaagcataa   1980

cgtaacgccg gtccacaaaa                                              2000
```

<210> SEQ ID NO 194
<211> LENGTH: 2000
<212> TYPE: DNA
<213> ORGANISM: Cucumis melo

<400> SEQUENCE: 194

```
tgaagagccg gaaaagcatg gcaaggtcaa ggcatttcag caagaatacg aggatgaatt     60

ctgggtttgt aagtccggtt cttcttcgga gttgtggttc gaatttcaaa cggccatgag    120

gagccctaca gcttaggaag cttcaggtct gagactctga ctccgacaga aattgctgat    180

ttttgtgtgt gttttgaata accattgtat gagtatgatt ggttgtatag gtttgaaatg    240

agggaaagtg atccatctcc ttgttgtctt tgcaggaaag gctcatattc gaccaagaac    300

gctttgtcat tgctttcgat aatcatagaa tccacaatgg tttggcatat tagcaaacaa    360

atcttcttta ggcattgcag acagaaaatt ggagagtaag ttattataat taaggattct    420

aaatgagtaa gaataataag atcaggcaaa gattggaaga actaaagcgt ttagtatttt    480

gtgtggtaca gaagaattgt aattagatac gtagtctaga gaagcagatg gtgagatttg    540

tgaaagacaa atgttagtgg agagtgaaga gtgtttctca acaaccgaca tagaaggatt    600

ctcagaaaat gagaaagatt tttattgcgc aaaatagctc ccatatcatc atatgccgtt    660

gccattccct ctggggttgc atgtaatgag taatggaaag ctgtagacag gctaacttca    720

ccctttgtct tgggtatagg gtgcattttt ggtcactcca ttttaagttt tctaataata    780

aaaggatgaa gaaaagatat tgaaaaacag ctcaggtttt aaagttgtca cacttgagaa    840

taatgcattt aacagttaga attttgcatc aacgtctttc aaatagaaaa gtaaaggaga    900

gtctagtttg agctggatag ctaaactggt ttaatcatat cttctatcaa gtggttagag    960

ttttagacct cccaacttta tatgtcgttg ccctaacaat gttgatggat gtttagtcct   1020

aagctctaac attgtccccg tatcatattt cataatagaa tgtactgagt aatggaaaac   1080

tagagaggta ggaagttgga cgaactttga atctatattg attttactat agtctttctt   1140
```

ccaagtctta atgagagctt tagctaaagt ttttcaaaaa ctcaaaagaa gtttttgttt 1200
tccaattctt cgatccatag attgtcaaga tggctataat atccttgaag ttaatagcct 1260
tcaaagtttc atagctttta tcctatgatc tttagaaatt caagagttat attctttaga 1320
actacagaac tttgatcttc gattcttcac ctcttccaga acctttatag tagagtttct 1380
tgaccttaca tgggcttggg attgggcctg gctacttatg ggcttagaga ttgaccttgg 1440
gtttaagcac attcgtttta cttggcccaa ttttcttaaa cttctgcaaa atcctaatta 1500
actaacacct caacaaaagt ccagtattaa atggggcata taaacaaaag ttaaacaaaa 1560
ttgtcgtaca gaatcctaat ttgctaacct cagcaaattt tatgccattc gtccttgtgt 1620
atctaattag tgttaatttg aggaaatata ataatataga cgtaggacgg atattggtat 1680
ttggtgcaac atcctccgaa ccaattcctg gaaagtaatt ggggcaacaa gataatgtta 1740
tcgtcagttt caagtgcaaa acttgccacg tggaacagcg gcaacatgat atctcaaata 1800
tggacctctc acccggtcaa gcttccacca ccaccaccac ctccgtattc taaaataaag 1860
tcaggaacaa gaacagacac accttaacaa aaccaatatt cttcatctct atctctctct 1920
catttcagca tagaagagag ctgagtaaaa ggaaaaaact tcaatcaaat ttgacagaga 1980
agagcccaag agaaaaccaa 2000

<210> SEQ ID NO 195
<211> LENGTH: 1400
<212> TYPE: DNA
<213> ORGANISM: Cucumis melo

<400> SEQUENCE: 195
tatatatatt aacttttaaa attttgaaaa cgtcatagat aaattatata caaaataaaa 60
agtttgatta tttacgaaag ttaaaaagtt tatccgaaag ttgactcaac gataaaaaca 120
ctaaatatca cttttagaga tgatgatatt atacataaac atacgaactt acgcgtcaaa 180
cttttatact aacacaagat caaaacaact ttgttgagta gtgagaattt tatctgctga 240
tatggttgaa acttgggaag caagcagagg aagttccatt cattaccaaa atccattttg 300
tattcatcaa aatatgaagt ttagcgactt gataaagtca agtcaagtgg tcctatcgat 360
ttgttaatgt caatgtttgg ttttgaattt gatacctatt agacaatgat atataatttt 420
aagtatggtt tacactgtga tgctttatat atttttaaat gtaaaatatt agaacttgta 480
atttcaataa attttaaaaa tgattttgtg ttatttcctt ttttaaattg aaatatcaat 540
gtatcaatat tgcgtcatag agtattgcaa cacaacctta tgttaaattg tttattgctt 600
attgctctaa ttcaactcct tcatcaaatg tgcacagaat ttaaacaaga aaaagagtag 660
gtgctttttt actaaaatat actaaaagct ttttatacca aatcttatga caaaatcatt 720
ccaacaaaat gactatttaa atataagatc gaatccctaa tttaaaaaaa aaaaaaaatc 780
aaagatgtta atttctatta ttaaactcac tttagcgtag ctaacaaaaa aaggaaaatg 840
agaggctaca aagcttgagc cctctgcctc cctttattgc attgtttgaa attagatcaa 900
tactttgtat ttttttcaaa atgaaaaatc gtacatagaa ttaattctat ggacaaaaaa 960
tcagagaagg aaataatcta gaataaaatt cgatttttaa cccaaaaaaa aaaaaaaaaa 1020
ctcgattctg atttttgtaa gcaatcaccc aaattaccat aaataaatgg tattcaatta 1080
ctcaattatg gatattttag aaatgataaa tttttattca taaactcttt tctttctctt 1140
tcaaaaagaa aaaaattagc ataaacttca atgacattta tttattcttc ttcgtttgga 1200
gtcaaaagtt taaattgagc atcagtccag cccaaaagcc cacgaagaag cccaagaatc 1260
ttcagctttt tcgttcaaac gtcccttttt ggtttataaa attaaagaaa ataaaaacta 1320
aatttatttg ttatttaaca aaacattttt ggttaagaca ttctctttga ttatttttct 1380
tccattcttc gtcgtcaatc 1400

<210> SEQ ID NO 196
<211> LENGTH: 2019
<212> TYPE: DNA
<213> ORGANISM: Cucumis melo

<400> SEQUENCE: 196
tttatattta tgaaaatgaa gtctctaaac aatttttcta ctcccaaatt tgttgatttt 60
tctgcctatt ctttatcggt gctttaaaaa atgaaaccaa atttcaaaac taaaaaaacc 120
aagcttttaa aaaaatgtta ggttattttt gaaattcaac taaatgttga actcttttac 180
ttattaaata ggcaaattat tgaaataaat ttagagcaag taagcttaat ttttaaaact 240
aatatactta ccaaatcgag gactaaaata ttcaaatact ctttaaaatt aagattaaca 300
ttaatcactt tgttatgttt aaaaagttgc agtgtcactt gaaccttttt aaattaatat 360
aatgaaaatg aatccaactc aatatatata atatctatat tattaatctc gatgtcagat 420
gtttgatacg cacatatctc aaaaattata cctcaactaa catcggtgca cgatgtatta 480
tttcgtgagg ataaaaatcg tttttagtat aaattgatgg aaagattatt tgaattactg 540
aaaaatgcac cggtacatta tttgaaactt ccccttcatt taaagaggct aatattagaa 600
aaagacacgc tgaggctatt tttacaatta atgtgggctg ttgacttggc ccagcccaaa 660
acataaaccc taaagtagca caaacaaacg cctctttctt cttgaaaccg catattaagc 720
gttttatcac ttctcaccac ctctcattcc tcctcttccg cacgttgttt cgctcctcaa 780
cgggagtgcc ttccctttgc tctccctcca ggttcttctt ccttctcatc tcatttccaa 840
gtaatttcat tccgtttctt ttctcttaat cgtatcttgt tcagactctt tcgcgttttt 900
ttttagttgc gccttaccag atctgtgttt tcactcgttt ctattcgata catgcttcca 960
agatccattt cttaatcgca tgtattcggt tgattggatg attgtctttt tgtaagtttt 1020
gattactttt ttggaatgga tcggttgaac caacggggtt taagtcgatg gaagtaggtt 1080
atgttaaaga tttgcttctt ttttatgaag atgtgtgtgt tcttttttct ttgctagatg 1140
atgttattat ttgattgttt taacagtcgt gttttgtttt tctgcagttt atagtcctcg 1200
gtcttttgaa gacttgtcaa gatggttagt acacctcttg tcatcgtgat tttgattgag 1260
tgatgtgtta agtgcttctt taggttacag ctaacgcgat tttttatatt caattgtgcc 1320
tgtgcaggtg aagtttacag cagaagagct ccgtcggatt atggactata agcataacat 1380
tcgtaatatg tctgttattg ctcacgtcga tcatggtaag ctacttagtt taagtttatt 1440
tatgccgagc gtctatttaa gaagattaac atcttagctt tcatttattg tttatttggt 1500
aagcatcgtt tctttttctc cgaggaactg tacatgtcag ttcacatgac aataaaacga 1560
tcttccttgg acattagttt ttgaagttca attagacgcc aaattttgtt ggttaaaaga 1620
tgcttgtgga gcatatggac ctaatggaat cagtactttt tgatggatgg acttgtcttt 1680
tgttctttta ttttcaaaag aaattgcatg tgcaattaca tcatctttga tcgaaagatt 1740
gggtaattgg gtaattgggg taaagacatg ttgtaaaaac taatgttaat tatcaattac 1800
cattatatac cttatttagt gcttatttat atcctttttc cccatttcag ggaagtccac 1860
tctcacagat tctcttgtgg ctgctgccgg tatcattgca caagaagttg ctggtgatgt 1920
acgaatgaca gatactcgtc aagatgaggc agagcgtggt atcaccatta aatctactgg 1980
aatctccctc tactatgagc agaagagctc cgtcggatt 2019

<210> SEQ ID NO 197
<211> LENGTH: 1999
<212> TYPE: DNA
<213> ORGANISM: Cucumis melo

<400> SEQUENCE: 197
aaaaggcgaa aaaaaagtta gcttcccgag aaggagaaga cgaggaagag tttgacttcc 60
cggggagata aagtttgtgt ctcgagggaa tctctaatct ggagttgacc gtcgacttat 120
gtgtcgagcc tggatttagt tgcatggtgc gacaaagcga taaggcggca tatgtaaagt 180
agtaattcaa aactagcggt taaagaaata atcagccaaa aaatttagta caaatacggg 240
tggaggccct aagtgaagtg ctgctattca gaggttttgg caaaagagtg caaagagttg 300
agttgtgcag agaaagtact aggtgaggag aggcgtttgg aaaagaaaag gatcaaacat 360
ttgcatgagt gatattctta aactaaacac tcttgtgtga gtgacttgcc taagctaaac 420
actcttgcat gagtaacttt cttaaactaa acgttttgta atgttttctt aatggattct 480
tttcgagtct gagttatgct taacacgttt tgtttctctc gtgttattgt tgttgttgtt 540
tgaaaagaga aaactattgt tttctatgtg ctgattgtga tgaatgtgtg cgaaccatta 600
gccttaatcc tatcaagtga atagtgatta tgtggtgtgt gcacataatg taaatgacat 660
tgtgtggatg gccagtgcaa caagaaatga atcagaaagc ttcccaaata ctgtgaatgg 720
agtgaacatc acactagctc aatggcaaga tattggcgat agtgaatcac aataggcttg 780
acaaggggaa ggattcatgt tcttggttga aaggaataag agaggctaat gtgagatttc 840
tgtgatttgc aaaatgaggc gttggaagac acgtttgaga aatgaaaacg aattagtgct 900
tgacttgtat tcctaaaaaa gttgtccaat atcttcaatc actaaatatt tgatgtgcct 960
aagttttcct tccttagttg ttgaggcgtt gaggccgagt aaggaaagat aagataatta 1020
tgacgttgaa aagctggtca agttatccat ctttggatgg tttaaagtta ttacatgtag 1080
ggagggttgc attccaattt tgtgtgtgag atgagtctta ttttcgagat gggttgctag 1140
gcgatcaagg agaagtataa gaaatgagtt cttatactct tgaacaactt gacacgaaga 1200
ataacatcct agtggatgaa ggaaggtgat ggaacttaaa gtttaggttt tatttttggc 1260
cttgtgataa aaaaaatgta attgtaaagt attagatcaa gtaataaaaa cagagttgtg 1320
ttttctattt ttgctgtgtt gggttgtgta tctttattgt gcttatggcc tagttgctaa 1380
agagttaagg ttattaccta aatgttttac ggtgtgttga gttgtaaaga tctcctgagt 1440
taaagttgga attttgtatt ggagattgtt ttgagaagtt tagcttacta attgtttaac 1500
tcattaggtg tctaagcgac acgcctcctt ttggtcgcat gaagtggcta gcagggtggg 1560
gcggaccggg gtggggtgtg ataataaacc taaaaaatca cccagataag cctaaattat 1620
acgttgaagt taaacttaca atttgattag aagaagaagg aatatctgat ttggacatga 1680
attaattaca aatacggcgc caatcataca aagcacatgt aagatcaacg cattctacac 1740
tcaatctcag ccgttgattg ctttcaatcc ttcaaaaaga aaaaaagaag ggcagttcgg 1800
gcagagtcat acctacccgt tgactataaa agcaactaca aatcgaaaac ctccatttct 1860
ccgttaccat tacagagaaa atcaaagaaa tttggcgttg agagattggg agagaggttt 1920
ctctttctag ggttgcttct tcttcttcat cctccattgt tgcaaatttc acttccttct 1980
cctcttgttc tcatctccc 1999

<210> SEQ ID NO 198
<211> LENGTH: 1578
<212> TYPE: DNA
<213> ORGANISM: Cucumis melo

<400> SEQUENCE: 198
atatatatat atataattta actaaataaa caaatgaaag aaaaaagtga gttcccattc 60
ggaaaatgca gatggatcca tttcttcaaa tattaaaaaa taaaaaaata aaataaaata 120
acttaaatat gcaaatagaa agaattttaa tttctggatt atccatatgg gacaattttt 180
aaaactcatt tattttattt tttttattta tttgattttg atatatctat ggggaaattt 240
ttcgtaataa ttttcgaaaa aatattgcaa tatatcattt gatcagatcg gtattattaa 300
atctctatca catttggtct taaattatcc aaagattcct ttaagataat ttagataacc 360
atctacagat cactactata atcaacaaaa ggaacaactt aaattattta aacaaattca 420
ttaatattag actttgtgct tcattagaaa atgatcttat cacaaccaca accatagtgg 480
tggtttaaaa ttttatttta aactcttatt agtattattt taattcatac ttaatcaaac 540
taattacttt aaaaaacata tatatataaa taagttaaat cattcccccct tatatctaaa 600 taacataaaa aaaaattgtt tactctacaa gaagtttgta tatatatatg ctcggtacta 660
tttagcatct ttataataaa atttctaaat caatttttta tatctcttta ttaaatgtat 720
agtcatcaaa aaatttaacg agataatgtg tcaaagattt attttattaa cgttcataaa 780
tatcaaatta tacttagctt ataattgaaa acatgttcga taaatataag taaataaaat 840
tttatttttt ttaaatatta caaaataaac taaataagtt ataaatatga caataaacat 900
tatatatttt attatattta taaatactta ataatttagt cgtttaaaat aattttctta 960
attttcaaaa catgtttcat atgttaataa taaataaatg gaaaaccttc caaaagaaga 1020
aaaaaagata tcttaaaatt taaaaattga gattttgagg atcaataatt aataaaagaa 1080
ggattaataa gggtgaaatt aaatcccaaa aagaaaattg aaaatgaaga aaagaaaagt 1140
gaagaaataa ttgaacgtgg gaagtggatt cgatgtctcc agagaacaag cgaaaggaga 1200
cgaaatccac ataatttgca cgttacgtgt ccctatcaac cgtagacacg tgtcaacatc 1260
tcaacaccct acgccgaatt gcttcgctgg atctggacgg tcatcggata acagcggcaa 1320
ccaattaata tttcccctta tatttcacag cctggccatg tccaccaatc acgttcaact 1380
attaattcat ttttcatttc ctttttcttt ttttttttaa ttcccctcaa ttattaccga 1440
caacctgttg tagccggtta accctaccct ccaacgttcc attataaggc ctagaaaatg 1500
gacgtgaaaa tggagtacta caaactacaa ttaattttaa agaattttaa ttttaaagtt 1560
ctctaattac tattagcc 1578

<210> SEQ ID NO 199
<211> LENGTH: 1023
<212> TYPE: DNA
<213> ORGANISM: Cucumis melo

<400> SEQUENCE: 199
ataataataa taaatacata atagtaataa taataaaaaa aataaaaaaa taataatagt 60
aatgaaaatc aatagaataa ttttaaaatc gggaaggaag tcgtgtacaa tccttgcacg 120
ttggagagtc aaatggccta agtggtgatg tggaagtcgt gtaccgggta cacgattttc 180
ctacaagtca ataataataa tatggttatt tttctagttt agggttcatg acaaaagatt 240

-continued gttcagtcga ctggatgtag acaaatctaa aaaataaatt aaaatctaat atgaaaacta 300
gttttaattt ccaaattatt aagggttgaa ttcgaccaat aaataataat aatacggtta 360
ttttgaaatt taggaaattg aataaagttg ttaaaatctt caagcaaatt gttaagcccc 420
gagatattaa gaagaggtaa taatagagga ttctatattt ataacatgtt aaaattaatt 480
gcaaactcat aaatgcatca cacagattaa caacatagga gggacttccg ataaaagtgc 540
aaatattgaa ataattacag ttcgcgaaca tgagtatttt aatattttat aaaatagtat 600
gcacgtgtat ttttgccaaa agaaaaaaag aatagatttt gccatttttc aaagtgactc 660
tcggttatat cttttatggc gattgtattt tatagcgtat gttgtttgta gttaacccat 720
ttctcattgg caaattcaat cgtgggccac aacgtttggg catagcttca atttggatta 780
actcaattat gtctgaatgg gttggactag ttcggactct tcggctgggc cagaatcaga 840
ttcgggccgc aatctgttca tttcacacct atatccaaac acccccaaaa tcgataccca 900
tcaaacccta actctcaata acccccatat ataaattcct tctttagggt tttttcatcc 960
tcatacactc tcaaacctcc ggtcattctc attttccctg ccgcttcttc aataacccta 1020
atc 1023

<210> SEQ ID NO 200
<211> LENGTH: 1654
<212> TYPE: DNA
<213> ORGANISM: Arabidopsis thaliana

<400> SEQUENCE: 200
tgatgattct tgttgttgta gttcttttta aaagtcccac ctgagcctct atagactctg 60
attctctttt aagttactat tttcaccgct ctctaataag gctcgtgatt ttttgggagc 120
catactgtat actcgccggc cctctcacga tgttgttcaa ttcacagact aaatttgatt 180
tatctatttc gccaaaacat aacttcatta aaaaatgttc tccaaataac taaacgaatt 240
aaataaaaga aacctttcat gtaaagttaa aggtatgaga ctttaagggc agttgctgaa 300
cattcgtaac acatgggaga acaatagaga aagttgaaaa gaaacgtagc atatagaaaa 360
attatctttg taaccaagtt gatttagaaa aatatcacta tttgtgaaaa atactagatc 420
agtttattat tacttttttt tttttgtata ttcacaaata tcatattcat atagaagaaa 480
ataaacaaag ttgtaaaaat ctggcattta aaataaaatt gaacacttca atttatttcc 540
tttcataata ataattttgg cataagatat ttgcaaattg atctggttcg gtatggtcga 600
caaaataatt ttccacgcta cccttccagc cgtccattca ctatttgccc tcaacgttac 660
caaataacgg tccagattcc tagggcaaga tctaacggtt agcaagtaaa gtcgtaccat 720
cagaaagaat aacaattctt tcacaaagta aacataacca acggttaaca agttcttagg 780
gttaaatcag taagatccaa cggatattaa attgcaaggc ccaaatagtt tttttgcagc 840
agataataac tcgtccccac tggcgagtga cgaccgagac tctgtgaccc tatttttcga 900
gacgataaaa gggcaaacaa tcgctctttt caaagctcgc ctcttcacca cagagaaaac 960
ttcgtctctc ttctctgctt cgccctctca tttcctgtga gataaaggcg gagtctctct 1020
ccagttattt tgctcatcca tcgattctta ggtatgactc gtttctctca gatctgtgat 1080
tctttataat ctcgtcgttc ttcaaatcat tgttatattc gtttcttcga tctgtgtttt 1140
ttagatctgt aaggtaaatg agacgtttcg atctgtagat ctgattgtta tattgataga 1200
ttatgttatc tgctttgctt aaagtccgat cggaatgttt tgtgctcatt gtcgaatatc 1260
tgatgtatcg gtttcataga tctgcttctt tttgtgcgtt tcgttgatct gataatcttc 1320
tagtgatcaa aatcgtttgg atctgttgac tttagtttaa aatgtatccg atctgatgtc 1380
gaggcttcat tattggaagt tgttattgtt gtaatcctga tttaagttgc tgttcttaaa 1440
tttatatgat ctttgcgtta taatatgaca tggtagatct tggttcatgg ttcactgttt 1500
tccaataaac ttggtttgtt tggttggata gcgttctgtg atacgaccat gtcttgtgtt 1560
ggataagaat tctctgaatt tccttggctg gtttgtagta tgttattcac gtctggtttc 1620
tcatcaatga ttatgtgatt ttgcagagtt cacc 1654

<210> SEQ ID NO 201
<211> LENGTH: 712
<212> TYPE: DNA
<213> ORGANISM: Artificial sequence
<220> FEATURE:
<221> NAME/KEY: misc_feature
<222> LOCATION: (1)..(712)
<223> OTHER INFORMATION: Chimeric transcriptional regulatory expression element.

<400> SEQUENCE: 201
ggtccgatgt gagacttttc aacaaagggt aatatccgga aacctcctcg gattccattg 60
cccagctatc tgtcacttta ttgtgaagat agtggaaaag gaaggtggct cctacaaatg 120
ccatcattgc gataaaggaa aggccatcgt tgaagatgcc tctgccgaca gtggtcccaa 180
agatggaccc ccacccacga ggagcatcgt ggaaaaagaa gacgttccaa ccacgtcttc 240
aaagcaagtg gattgatgtg atggtccgat tgagactttt caacaaaggg taatatccgg 300
aaacctcctc ggattccatt gcccagctat ctgtcacttt attgtgaaga tagtggaaaa 360
ggaaggtggc tcctacaaat gccatcattg cgataaagga aaggccatcg ttgaagatgc 420
ctctgccgac agtggtccca aagatggacc cccacccacg aggagcatcg tggaaaaaga 480
agacgttcca accacgtctt caaagcaagt ggattgatgt gatatctcca ctgacgtaag 540
ggatgacgca caatcccact atccttcgca agacccttcc tctatataag gaagttcatt 600
tcatttggag aggacactct agacagaaaa atttgctaca ttgtttcaca aacttcaaat 660
attattcatt tatttgtcag ctttcaaact ctttgtttct tgtttgttga tt 712

<210> SEQ ID NO 202
<211> LENGTH: 938
<212> TYPE: DNA
<213> ORGANISM: Arabidopsis thaliana

<400> SEQUENCE: 202
caaaagccga gccgataaat cctaagccga gcctaacttt agccgtaacc atcagtcacg 60
gctcccgggc taattcattt gaaccgaatc ataatcaacg gtttagatca aactcaaaac 120
aatctaacgg caacatagac gcgtcggtga gctaaaaaga gtgtgaaagc caggtcacca 180
tagcattgtc tctcccagat tttttatttg ggaaataata gaagaaatag aaaaaaataa 240
aagagtgaga aaaatcgtag agctatatat tcgcacatgt actcgtttcg ctttccttag 300
tgttagctgc tgccgctgtt gtttctcctc catttctcta tctttctctc tcgctgcttc 360
tcgaatcttc tgtatcatct tcttcttctt caaggtgagt ctctagatcc gttcgcttga 420
ttttgctgct cgttagtcgt tattgttgat tctctatgcc gatttcgcta gatctgttta 480
gcatgcgttg tggttttatg agaaaatctt tgttttgggg gttgcttgtt atgtgattcg 540
atccgtgctt gttggatcga tctgagctaa ttcttaaggt ttatgtgtta gatctatgga 600

-continued

```
gtttgaggat tcttctcgct tctgtcgatc tctcgctgtt atttttgttt ttttcagtga    660

agtgaagttg tttagttcga aatgacttcg tgtatgctcg attgatctgg ttttaatctt    720

cgatctgtta ggtgttgatg tttacaagtg aattctagtg ttttctcgtt gagatctgtg    780

aagtttgaac ctagttttct caataatcaa catatgaagc gatgtttgag tttcaataaa    840

cgctgctaat cttcgaaact aagttgtgat ctgattcatg tttacttcat gagcttatcc    900

aattcatttc ggtttcattt tacttttttt ttagtgaa                            938
```

<210> SEQ ID NO 203
<211> LENGTH: 633
<212> TYPE: DNA
<213> ORGANISM: Pisum sativum

<400> SEQUENCE: 203

```
agctttcgtt cgtatcatcg gtttcgacaa cgttcgtcaa gttcaatgca tcagtttcat     60

tgcgcacaca ccagaatcct actgagtttg agtattatgg cattgggaaa actgtttttc    120

ttgtaccatt tgttgtgctt gtaatttact gtgtttttta ttcggttttc gctatcgaac    180

tgtgaaatgg aaatggatgg agaagagtta atgaatgata tggtcctttt gttcattctc    240

aaattaatat tatttgtttt ttctcttatt tgttgtgtgt tgaatttgaa attataagag    300

atatgcaaac attttgtttt gagtaaaaat gtgtcaaatc gtggcctcta atgaccgaag    360

ttaatatgag gagtaaaaca cttgtagttg taccattatg cttattcact aggcaacaaa    420

tatattttca gacctagaaa agctgcaaat gttactgaat acaagtatgt cctcttgtgt    480

tttagacatt tatgaacttt cctttatgta attttccaga atccttgtca gattctaatc    540

attgctttat aattatagtt atactcatgg atttgtagtt gagtatgaaa atattttttta   600

atgcatttta tgacttgcca attgattgac aac                                 633
```

<210> SEQ ID NO 204
<211> LENGTH: 315
<212> TYPE: DNA
<213> ORGANISM: Gossypium barbadense

<400> SEQUENCE: 204

```
tgatcacctg tcgtacagta tttctacatt tgatgtgtga tttgtgaaga acatcaaaca     60

aaacaagcac tggctttaat atgatgataa gtattatggt aattaattaa ttggcaaaaa    120

caacaatgaa gctaaaattt tatttattga gccttgcggt taatttcttg tgatgatctt    180

ttttttttatt ttctaattat atatagtttc ctttgctttg aaatgctaaa ggtttgagag    240

agttatgctc tttttttctt cctctttctt ttttaacttt atcatacaaa ttttgaataa    300

aaatgtgagt acatt                                                     315
```

<210> SEQ ID NO 205
<211> LENGTH: 315
<212> TYPE: DNA
<213> ORGANISM: Gossypium barbadense

<400> SEQUENCE: 205

```
accatatgac actggtgcat gtgccatcat catgcagtaa tttcatggta tatcttaatt     60

atatggttaa taaaaaaaag atggtgagtg aataatgtgc gtgcattcct ccatgcacca    120

atggtgaatc tctttgcata catagagatt ctgaatgatt atagtttatg ttgtagtgaa    180

attaattttg aatgttgttt ttaaatttta atgtcacttg gcttgattta tgttttaacg    240

aagcttatgt tatgtatttt actttaatga tattgcatgt attgttaatt taacattgct    300
```

tgatcagtat actct 315

<210> SEQ ID NO 206
<211> LENGTH: 2001
<212> TYPE: DNA
<213> ORGANISM: Artificial sequence
<220> FEATURE:
<221> NAME/KEY: misc_feature
<222> LOCATION: (1)..(2001)
<223> OTHER INFORMATION: Codon redesigned coding sequence.

<400> SEQUENCE: 206
atggtccgtc ctgtagaaac cccaacccgt gaaatcaaaa aactcgacgg cctgtgggca 60
ttcagtctgg atcgcgaaaa ctgtggaatt gatcagcgtt ggtgggaaag cgcgttacaa 120
gaaagccggg caattgctgt gccaggcagt tttaacgatc agttcgccga tgcagatatt 180
cgtaattatg cgggcaacgt ctggtatcag cgcgaagtct ttataccgaa aggttgggca 240
ggccagcgta tcgtgctgcg tttcgatgcg gtcactcatt acggcaaagt gtgggtcaat 300
aatcaggaag tgatggagca tcagggcggc tatacgccat ttgaagccga tgtcacgccg 360
tatgttattg ccgggaaaag tgtacgtaag tttctgcttc tacctttgat atatatataa 420
taattatcat taattagtag taatataata tttcaaatat ttttttcaaa ataaaagaat 480
gtagtatata gcaattgctt ttctgtagtt tataagtgtg tatattttaa tttataactt 540
ttctaatata tgaccaaaat ttgttgatgt gcaggtatca ccgtttgtgt gaacaacgaa 600
ctgaactggc agactatccc gccgggaatg gtgattaccg acgaaaacgg caagaaaaag 660
cagtcttact tccatgattt ctttaactat gccggaatcc atcgcagcgt aatgctctac 720
accacgccga acacctgggt ggacgatatc accgtggtga cgcatgtcgc gcaagactgt 780
aaccacgcgt ctgttgactg gcaggtggtg gccaatggtg atgtcagcgt tgaactgcgt 840
gatgcggatc aacaggtggt tgcaactgga caaggcacta gcgggacttt gcaagtggtg 900
aatccgcacc tctggcaacc gggtgaaggt tatctctatg aactgtgcgt cacagccaaa 960
agccagacag agtgtgatat ctacccgctt cgcgtcggca tccggtcagt ggcagtgaag 1020
ggcgaacagt tcctgattaa ccacaaaccg ttctacttta ctggctttgg tcgtcatgaa 1080
gatgcggact tgcgtggcaa aggattcgat aacgtgctga tggtgcacga ccacgcatta 1140
atggactgga ttggggccaa ctcctaccgt acctcgcatt acccttacgc tgaagagatg 1200
ctcgactggg cagatgaaca tggcatcgtg gtgattgatg aaactgctgc tgtcggcttt 1260
aacctctctt taggcattgg tttcgaagcg ggcaacaagc cgaaagaact gtacagcgaa 1320
gaggcagtca acggggaaac tcagcaagcg cacttacagg cgattaaaga gctgatagcg 1380
cgtgacaaaa accacccaag cgtggtgatg tggagtattg ccaacgaacc ggatacccgt 1440
ccgcaaggtg cacgggaata tttcgcgcca ctggcggaag caacgcgtaa actcgacccg 1500
acgcgtccga tcacctgcgt caatgtaatg ttctgcgacg ctcacaccga taccatcagc 1560
gatctctttg atgtgctgtg cctgaaccgt tattacggat ggtatgtcca aagcggcgat 1620
ttggaaacgg cagagaaggt actggaaaaa gaacttctgg cctggcagga gaaactgcat 1680
cagccgatta tcatcaccga atacggcgtg gatacgttag ccgggctgca ctcaatgtac 1740
accgacatgt ggagtgaaga gtatcagtgt gcatggctgg atatgtatca ccgcgtcttt 1800
gatcgcgtca gcgccgtcgt cggtgaacag gtatggaatt tcgccgattt tgcgacctcg 1860
caaggcatat tgcgcgttgg cggtaacaag aaagggatct tcactcgcga ccgcaaaccg 1920
aagtcggcgg cttttctgct gcaaaaacgc tggactggca tgaacttcgg tgaaaaaccg 1980
cagcagggag gcaaacaatg a 2001

<210> SEQ ID NO 207
<211> LENGTH: 1653
<212> TYPE: DNA
<213> ORGANISM: Artificial sequence
<220> FEATURE:
<221> NAME/KEY: misc_feature
<222> LOCATION: (1)..(1653)
<223> OTHER INFORMATION: Codon redesinged coding sequence.

<400> SEQUENCE: 207
atggaagacg ccaaaaacat aaagaaaggc ccggcgccat tctatcctct agaggatgga 60
accgctggag agcaactgca taaggctatg aagagatacg ccctggttcc tggaacaatt 120
gcttttacag atgcacatat cgaggtgaac atcacgtacg cggaatactt cgaaatgtcc 180
gttcggttgg cagaagctat gaaacgatat gggctgaata caaatcacag aatcgtcgta 240
tgcagtgaaa actctcttca attctttatg ccggtgttgg gcgcgttatt tatcggagtt 300
gcagttgcgc ccgcgaacga catttataat gaacgtgaat tgctcaacag tatgaacatt 360
tcgcagccta ccgtagtgtt tgtttccaaa aaggggttgc aaaaaatttt gaacgtgcaa 420
aaaaaattac caataatcca gaaaattatt atcatggatt ctaaaacgga ttaccaggga 480
tttcagtcga tgtacacgtt cgtcacatct catctacctc ccggttttaa tgaatacgat 540
tttgtaccag agtcctttga tcgtgacaaa acaattgcac tgataatgaa ttcctctgga 600
tctactgggt tacctaaggg tgtggccctt ccgcatagaa ctgcctgcgt cagattctcg 660
catgccagag atcctatttt tggcaatcaa atcattccgg atactgcgat tttaagtgtt 720
gttccattcc atcacggttt tggaatgttt actacactcg gatatttgat atgtggattt 780
cgagtcgtct taatgtatag atttgaagaa gagctgtttt tacgatccct tcaggattac 840
aaaattcaaa gtgcgttgct agtaccaacc ctattttcat tcttcgccaa aagcactctg 900
attgacaaat acgatttatc taatttacac gaaattgctt ctgggggcgc acctctttcg 960
aaagaagtcg gggaagcggt tgcaaaacgc ttccatcttc cagggatacg acaaggatat 1020
gggctcactg agactacatc agctattctg attacacccg agggggatga taaaccgggc 1080
gcggtcggta aagttgttcc atttttttgaa gcgaaggttg tggatctgga taccgggaaa 1140
acgctgggcg ttaatcagag aggcgaatta tgtgtcagag gacctatgat tatgtccggt 1200
tatgtaaaca atccggaagc gaccaacgcc ttgattgaca aggatggatg gctacattct 1260
ggagacatag cttactggga cgaagacgaa cacttcttca tagttgaccg cttgaagtct 1320
ttaattaaat acaaaggata tcaggtggcc cccgctgaat tggaatcgat attgttacaa 1380
caccccaaca tcttcgacgc gggcgtggca ggtcttcccg acgatgacgc cggtgaactt 1440
cccgccgccg ttgttgtttt ggagcacgga aagacgatga cggaaaaaga gatcgtggat 1500
tacgtcgcca gtcaagtaac aaccgcgaaa aagttgcgcg gaggagttgt gtttgtggac 1560
gaagtaccga aaggtcttac cggaaaactc gacgcaagaa aaatcagaga gatcctcata 1620
aaggccaaga agggcggaaa gtccaaattg taa 1653

<210> SEQ ID NO 208
<211> LENGTH: 936
<212> TYPE: DNA
<213> ORGANISM: Artificial sequence
<220> FEATURE:
<221> NAME/KEY: misc_feature
<222> LOCATION: (1)..(936)
<223> OTHER INFORMATION: Codon redesigned coding sequence.

<400> SEQUENCE: 208
atggcttcca aggtgtacga ccccgagcaa cgcaaacgca tgatcactgg gcctcagtgg 60
tgggctcgct gcaagcaaat gaacgtgctg gactccttca tcaactacta tgattccgag 120
aagcacgccg agaacgccgt gatttttctg catggtaacg ctgcctccag ctacctgtgg 180
aggcacgtcg tgcctcacat cgagcccgtg gctagatgca tcatccctga tctgatcgga 240
atgggtaagt ccggcaagag cgggaatggc tcatatcgcc tcctggatca ctacaagtac 300
ctcaccgctt ggttcgagct gctgaacctt ccaaagaaaa tcatctttgt gggccacgac 360 tgggggggctt gtctggcctt tcactactcc tacgagcacc aagacaagat caaggccatc 420
gtccatgctg agagtgtcgt ggacgtgatc gagtcctggg acgagtggcc tgacatcgag 480
gaggatatcg ccctgatcaa gagcgaagag ggcgagaaaa tggtgcttga gaataacttc 540
ttcgtcgaga ccatgctccc aagcaagatc atgcggaaac tggagcctga ggagttcgct 600
gcctacctgg agccattcaa ggagaagggc gaggttagac ggcctaccct ctcctggcct 660
cgcgagatcc ctctcgttaa gggaggcaag cccgacgtcg tccagattgt ccgcaactac 720
aacgcctacc ttcgggccag cgacgatctg cctaagatgt tcatcgagtc cgaccctggg 780
ttcttttcca acgctattgt cgagggagct aagaagttcc ctaacaccga gttcgtgaag 840
gtgaagggcc tccacttcag ccaggaggac gctccagatg aaatgggtaa gtacatcaag 900
agcttcgtgg agcgcgtgct gaagaacgag cagtaa 936

<210> SEQ ID NO 209
<211> LENGTH: 253
<212> TYPE: DNA
<213> ORGANISM: Agrobacterium tumefaciens

<400> SEQUENCE: 209
gatcgttcaa acatttggca ataaagtttc ttaagattga atcctgttgc cggtcttgcg 60
atgattatca tataatttct gttgaattac gttaagcatg taataattaa catgtaatgc 120
atgacgttat ttatgagatg ggtttttatg attagagtcc cgcaattata catttaatac 180
gcgatagaaa acaaaatata gcgcgcaaac taggataaat tatcgcgcgc ggtgtcatct 240
atgttactag atc 253

<210> SEQ ID NO 210
<211> LENGTH: 622
<212> TYPE: DNA
<213> ORGANISM: Cauliflower mosaic virus

<400> SEQUENCE: 210
ggtccgattg agacttttca acaaagggta atatccggaa acctcctcgg attccattgc 60
ccagctatct gtcactttat tgtgaagata gtggaaaagg aaggtggctc ctacaaatgc 120
catcattgcg ataaaggaaa ggccatcgtt gaagatgcct ctgccgacag tggtcccaaa 180
gatggacccc cacccacgag gagcatcgtg gaaaaagaag acgttccaac cacgtcttca 240
aagcaagtgg attgatgtga tggtccgatt gagacttttc aacaaagggt aatatccgga 300
aacctcctcg gattccattg cccagctatc tgtcacttta ttgtgaagat agtggaaaag 360
gaaggtggct cctacaaatg ccatcattgc gataaaggaa aggccatcgt tgaagatgcc 420
tctgccgaca gtggtcccaa agatggaccc ccacccacga ggagcatcgt ggaaaaagaa 480
gacgttccaa ccacgtcttc aaagcaagtg gattgatgtg atatctccac tgacgtaagg 540
gatgacgcac aatcccacta tctagacgca agacccttcc tctatataag gaagttcatt 600
tcatttggag aggacacgct ga 622

<210> SEQ ID NO 211
<211> LENGTH: 1446
<212> TYPE: DNA
<213> ORGANISM: Cucumis melo

<400> SEQUENCE: 211
tcccttcagc cacttaacac ttaaaaatct taggaaactc catgggctcc tctttctcca 60
atgaaatttt gacatctgtg ttgttgatag ctcctatatc ctttgagaat ttgatataca 120
cctgtcattt gctgatttgt ggataactgt tagccttttg atattgatac gttccttttt 180
ttatgaattt ttgtaaatcc attcaatttt aatgctgtcg taaatgaaaa gccctttcat 240
taatgttgtt tatatacata ttttaaaatt aattcaataa caagtttagt tctgttagct 300
tctaggtttg tatctatttt atctattaaa ggtatgtttg ggcttcaggt tggaatggag 360
tagaattgaa tgggttgggg agtaaatttt ccattcaaca agttcaattt caaaatggct 420
aataagtttt gaactcaatt ttattttcaa taaattcctt aatttttttgt tccttgtttg 480 taaactattg acttattcga tatattttaa aattgaggta ttttaaaaaa ataatacaat 540
attaaaatta tttataaaat ataacaaaat ttatgtatag tttatttgaa aattttacta 600
tagtttcatt tttatattat tcctaaccat ttccatttaa aattatttca attatttctt 660
ttattaatat aattgaaatt tcatggattt attagacaca tgatttgaaa ttttatgggt 720
ttattaagta ttttctaaca caaaatcgct tccgcatcgt tttcaattca ttcagtaata 780
gaagtaattt tttaaaagaa ccaaatttgc caaattttga gttccataag gactctgaaa 840
actcattatg tctattactc ttcactaatt gtagagactt aaattcaaga taagagacac 900
taattgatga taattgccca aaaaataaaa ataaaaatgt ttcttcccca tcctcaacct 960
ccatgaattc acagagccca aagattaatt attgggcccc aattcctact catatatacc 1020
ttacagtccc tcaaagaaat cttaggaagt aatcaatttc tgtttattca agatgtagcc 1080
tcccaaaaga aaaatacatc acatcaaatt caaacaaaaa tatctacagc tagcaaaacc 1140
tcaaaccgtt aaaatttcaa gccacataaa tgaaattttc atctgaaaaa aggacaatct 1200
atctagacgt tagatttcag ccctaatatg aatctgaagc atttggtgga cgagaaagag 1260
ccatgtagga atgcatcaaa caaaggaaaa atctttgaac tccaatggga ttgaagatac 1320
agataccaat ggataagaat ctgttctctt tgcccactat ttaaactcac caaacccacc 1380
agtatcttcc tcaccacaaa atacattcca ccgttgatca caagccttat tccaccacct 1440
ccaaca 1446

<210> SEQ ID NO 212
<211> LENGTH: 2018
<212> TYPE: DNA
<213> ORGANISM: Cucumis melo

<400> SEQUENCE: 212
actattggag acgacgaagg aaaactctaa tgtgagctta gaattgaaga tggtgaacaa 60
ttgggagtct tttttaaaaa tctttcgtcg gtatattgaa atttcctttt acactcaaat 120
aacccccctt ttcacgcgtt caacgtcttc aaaccttcct ttttcaatta ttttttcgtt 180
tacattaatg acatttaggt aataagataa attagtggat tcttttgtga aaaatgttag 240

-continued

```
cccatttaag acttttatga aatatattag aaaaaaatca tatagcaatt tatattattc    300
tagttaaaag cccataatag aaactaaccc aacctaaagt aacgtaaaca ttcaataaga    360
gagacaaatt ttaaaataat ttctaattaa aaaaaaaatt gtcaagaccg tccgggtcgg    420
atccaaaata taacccgaac cggccggttt agcatctata taaatacacc tttagggttt    480
ttattctctc aagacttcac cgcatttcca cttctctgag gccacggtca gccattggag    540
cagctcaata atcctttgac tccctactac ggtaagtcga ccttactgct ttcggcttct    600
agtttttca atcctgtcat tagtcctttg gagttcttct gtacatttat gacgttttcg    660
gctcgtgttt tgtttcgcct gtatgtagtg ggtttttcga gttttgtttt tactttttt    720
tatacttgca ggaattagtt gaaatctatg tacttcatgc cttggataat actcttgatc    780
tgttgtgtta ttcaaaatga attgttttaa gatggtattt gagaatggtc atgtgagttt    840
tgcctacttg gttattaaaa tgaattgttt taggatggta tttgagaatg gtcttctggg    900
tatttggttg gaacctttgt gctctgctat gaattagggt gttctccccg ttttttttt    960
tttttttctt ttggttatta atatatcttt tatgactact tattcatata tgatatcttt   1020
tactcgtaaa ttttgactca tttgaaagtt ttatccttag tcctttctca ttcagggtgt   1080
aaaggtatgt tgttagggtt aaaatagcct atgcaggaaa gttctgtatt tgttctaatt   1140
attgcatttg tgtgcatttg tatctagttt atttcttgct gagagtatgc ttcattttt    1200
agtacacatc acttgtgcca ctttattata gttgcacatt tttgtttatg gagaggatga   1260
atagcattta gggatgtcaa ttttttattg agaaaaccct ctctcctact taagcttggg   1320
gaatttttgt tctaaatgtg gtaaacataa tacttcttct tattttaatt tgaatggaag   1380
gggaagacga atactaatat tttcaacgaa ccttcacaac tttttttttc ttatttagga   1440
agccatgttt ttcaaaattg tactgtgtga tccacatatt tatcgattat tagtgaatcg   1500
aataataatt agagttttat tggtataatt ttgaagttca gacttattac atttgtggaa   1560
agtttggtta caattttcaa ttttattgga atcctaagaa ctttgtgtta acatatattg   1620
agttttcttc tcttttttttt tactcattaa gttctctatt aggaatgttt ggttcaatgt   1680
cacatagtcg atagctaaga ccagtgaccc acaaagctat gattgaacga aaaacaagcc   1740
tttcacatct tggtaggaat ttgttatttc tcaatagatt tacagagctg tttcatgtga   1800
tcacaatttt tttctatttt tctgaagttc tctattagga atgggctatc tggttagttg   1860
cttttgagag aacatgtgga ttggtgttgc tcggtttcct tgcctttgta attttgtcct   1920
tggaaaaagc aaaatgatta ggtatcctga tatgcataac atgtttaagc caactagttc   1980
tcactttttt agtgcaaata attgatcttc aggaatcg                          2018
```

PLANT REGULATORY ELEMENTS AND USES THEREOF

REFERENCE TO RELATED APPLICATIONS

This application is a 371 National Stage application of International Application No. PCT/US2012/037561, filed May 11, 2012, which claims the benefit of U.S. provisional application No. 61/485,876, filed May 13, 2011 and is herein incorporated by reference in its entirety.

INCORPORATION OF SEQUENCE LISTING

The sequence listing that is contained in the file named "MONS304WO.txt", which is 463 kilobytes (as measured in Microsoft Windows®) and was created on May 9, 2012, is filed herewith by electronic submission and is incorporated by reference herein.

FIELD OF THE INVENTION

The invention relates to the field of plant molecular biology and plant genetic engineering, and DNA molecules useful for modulating gene expression in plants.

BACKGROUND

Regulatory elements are genetic elements that regulate gene activity by modulating the transcription of an operably linked transcribable polynucleotide molecule. Such elements include promoters, leaders, introns, and 3' untranslated regions and are useful in the field of plant molecular biology and plant genetic engineering.

SUMMARY OF THE INVENTION

The present invention provides novel gene regulatory elements such as promoters, leaders and introns derived from *Cucumis melo*, a plant species commonly referred to as muskmelon, for use in plants. The present invention also provides DNA constructs, transgenic plant cells, plants, and seeds comprising the regulatory elements. The sequences may be provided operably linked to a transcribable polynucleotide molecule which may be heterologous with respect to a regulatory sequence provided herein. The present invention also provides methods of making and using the regulatory elements, the DNA constructs comprising the regulatory elements, and the transgenic plant cells, plants, and seeds comprising the regulatory elements operably linked to a transcribable polynucleotide molecule.

Thus, in one aspect, the present invention provides a DNA molecule, such as a transcriptional regulatory expression element group, or promoter, or leader, or intron, comprising a polynucleotide sequence selected from the group consisting of a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In specific embodiments, a transcriptional regulatory expression element group, or promoter, or leader, or intron is at least 90 percent, at least 95 percent, at least 98 percent, or at least 99 percent identical to any of SEQ ID NOs: 1-199, 211 and 212. In particular embodiments, the heterologous transcribable polynucleotide molecule comprises a gene of agronomic interest, a gene capable of providing herbicide resistance in plants, or a gene capable of providing plant pest resistance in plants.

The invention also provides a transgenic plant cell containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. Further, the transcriptional regulatory expression element group, or promoter, or leader, or intron regulates the expression of a gene. The transgenic plant cell can be a monocotyledonous or dicotyledonous plant cell.

Further provided by the invention is a transgenic plant, or part of the transgenic plant containing a DNA molecule such as a transcriptional regulatory expression element group, or promoter, or leader, or intron, comprising a polynucleotide sequence selected from the group consisting of a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In specific embodiments, the transgenic plant may be a progeny plant of any generation that contains the transcriptional regulatory expression element group, or promoter, or leader, or intron.

Still further provided is a transgenic seed containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule.

In yet another aspect, the invention provides a method of producing a commodity product from the transgenic plant, transgenic plant part or transgenic seed which contains a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In one embodiment, the commodity product is protein concentrate, protein isolate, grain, starch, seeds, meal, flour, biomass, or seed oil.

In another aspect, the invention provides a commodity product comprising a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule.

In still yet another aspect, the invention provides a method of expressing a transcribable polynucleotide molecule in a transgenic plant using a DNA molecule such as a transcriptional regulatory expression element group, or promoter, or leader, or intron which has a DNA sequence which is at least 85 percent identical to that of any of SEQ ID NOs: 1-199, 211 and 212, or contains any of SEQ ID NOs: 1-199, 211 and 212, or consists of a fragment of any of SEQ ID NOs: 1-199, 211 and 212; and cultivating the transgenic plant.

BRIEF DESCRIPTION OF THE SEQUENCES

SEQ ID NOs: 1, 5, 7, 9, 11, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 159, 162, 167, 168, 172, 175, 176, 177, 178, 181, 182, 183, 184, 185, 188, 189, 190, 191, 192, 193, 194, 195, 196, 197, 198, 199, 211 and 212 are *Cucumis* transcriptional regulatory expression element groups or EXP sequences which are comprised of either a promoter element, operably linked to a leader element; or a promoter element, operably linked to a leader element and an intron element, or a promoter element, operably linked to a leader element, operably linked to an intron element, operably linked to a leader element.

SEQ ID NOs: 2, 6, 8, 10, 12, 163 and 169 are promoter elements.

SEQ ID NOs: 3, 164, 166 and 170 are leader sequences.

SEQ ID NOs: 4, 165 and 171 are intron sequences.

SEQ ID NOs: 157, 160, 173, 179 and 186 are sequences wherein a promoter is operably linked to a leader element.

SEQ ID NOs: 158, 161, 174, 180 and 187 are sequences wherein an intron is operably linked to a leader element.

BRIEF DESCRIPTION OF THE DRAWINGS

FIGS. 1*a*-1*f* depict alignment of promoter variant segments corresponding to promoter elements isolated from the *Cucumis melo*. In particular, FIGS. 1*a*-1*f* show alignment of the 2068 bp promoter sequence P-CUCme.Ubq1-1:1:15 (SEQ ID NO: 2), found in the transcriptional regulatory expression element group EXP-CUCme.Ubq1:1:1 (SEQ ID NO: 1), vs. promoter sequences derived via 5' deletions of the promoter, P-CUCme.Ubq1-1:1:15. Deletion, for instance of the 5' end of P-CUCme.Ubq1-1:1:15, produced the promoters, P-CUCme.Ubq1-1:1:16 (SEQ ID NO: 6) a 1459 bp promoter which is found within EXP-CUCme.Ubq1:1:2 (SEQ ID NO: 5); P-CUCme.Ubq1-1:1:17 (SEQ ID NO: 8), a 964 bp sequence comprised within EXP-CUCme.Ubq1:1:3 (SEQ ID NO: 7); P-CUCme.Ubq1-1:1:18 (SEQ ID NO: 10), a 479 bp sequence comprised within EXP-CUCme.Ubq1:1:4 (SEQ ID NO: 9); and P-CUCme.Ubq1-1:1:19 (SEQ ID NO: 12), a 173 bp sequence comprised within EXP-CUCme.Ubq1:1:5 (SEQ ID NO: 11).

DETAILED DESCRIPTION OF THE INVENTION

The invention disclosed herein provides polynucleotide molecules obtained from *Cucumis melo* having beneficial gene regulatory activity. The design, construction, and use of these polynucleotide molecules are described. The nucleotide sequences of these polynucleotide molecules are provided among SEQ ID NOs: 1-199, 211 and 212. These polynucleotide molecules are, for instance, capable of affecting the expression of an operably linked transcribable polynucleotide molecule in plant tissues, and therefore selectively regulating gene expression, or activity of an encoded gene product, in transgenic plants. The present invention also provides methods of modifying, producing, and using the same. The invention also provides compositions, transformed host cells, transgenic plants, and seeds containing the promoters and/or other disclosed nucleotide sequences, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term “DNA” or “DNA molecule” refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term “DNA sequence” refers to the nucleotide sequence of a DNA molecule.

As used herein, the term “isolated DNA molecule” refers to a DNA molecule at least partially separated from other molecules normally associated with it in its native or natural state. In one embodiment, the term “isolated” refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods are known in the to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein, the term “sequence identity” refers to the extent to which two optimally aligned polynucleotide sequences or two optimally aligned polypeptide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term “reference sequence” refers to a sequence provided as the polynucleotide sequences of SEQ ID NOs: 1-199, 211 and 212.

As used herein, the term “percent sequence identity” or “percent identity” or “% identity” is the identity fraction times 100. The “identity fraction” for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the invention is a DNA molecule comprising a sequence that when optimally aligned to a reference sequence, provided herein as SEQ ID NOs: 1-199, 211 and 212, has at least about 85 percent identity at least about 90 percent identity at least about 95 percent identity, at least about 96 percent identity, at least about 97 percent identity, at least about 98 percent identity, or at least about 99 percent identity to the reference sequence. In particular embodiments such sequences may be defined as having gene-regulatory activity or encoding a peptide that functions to localize an operably linked polypeptide within a cell.

Regulatory Elements

A regulatory element is a DNA molecule having gene regulatory activity, i.e. one that has the ability to affect the transcription and/or translation of an operably linked transcribable polynucleotide molecule. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group (EXP) may be comprised of expression elements, such as enhancers, promoters, leaders and introns, operably linked. Thus a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and further may be comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions are DNA molecules that have gene regulatory activity and play an integral part in the overall expression of genes in living cells. The term "regulatory element" refers to a DNA molecule having gene regulatory activity, i.e. one that has the ability to affect the transcription and/or translation of an operably linked transcribable polynucleotide molecule. Isolated regulatory elements, such as promoters and leaders that function in plants are therefore useful for modifying plant phenotypes through the methods of genetic engineering.

Regulatory elements may be characterized by their expression pattern effects (qualitatively and/or quantitatively), e.g. positive or negative effects and/or constitutive or other effects such as by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules. Promoters useful in practicing the present invention include any of SEQ ID NOs: 2, 6, 8, 10, 12, 163 and 169, or the promoter elements comprised within any of SEQ ID NOs: 13 through 199, 211 and 212, or fragments or variants thereof. In specific embodiments of the invention, such molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent sequence for recognition and binding of the RNA polymerase II complex for initiation of transcription.

In one embodiment, fragments of a promoter molecule are provided. Promoter fragments provide promoter activity, as described above, and may be useful alone or in combination with other promoters and promoter fragments, such as in constructing chimeric promoters. In specific embodiments, fragments of a promoter are provided comprising at least about 50, 95, 150, 250, 500, 750, or at least about 1000 contiguous nucleotides, or longer, of a polynucleotide molecule having promoter activity disclosed herein.

Compositions derived from any of the promoters presented as SEQ ID NOs: 2, 6, 8, 10, 12, 163 and 169, or the promoter elements comprised within SEQ ID NOs: 13 through 199, 211 and 212, such as internal or 5' deletions, for example, can be produced to improve or alter expression, including by removing elements that have either positive or negative effects on expression; duplicating elements that have positive or negative effects on expression; and/or duplicating or removing elements that have tissue or cell specific effects on expression. Compositions derived from any of the promoters presented as SEQ ID NOs: 2, 6, 8, 10, 12, 163 and 169, or the promoter elements comprised within SEQ ID NOs: 13 through 199, 211 and 212 comprised of 3' deletions in which the TATA box element or equivalent sequence thereof and downstream sequence is removed can be used, for example, to make enhancer elements. Further deletions can be made to remove any elements that have positive or negative; tissue specific; cell specific; or timing specific (such as, but not limited to, circadian rhythms)

effects on expression. Any of the promoters presented as SEQ ID NOs: 2, 6, 8, 10, 12, 163 and 169, or the promoter elements comprised within SEQ ID NOs: 13 through 199, 211 and 212, and fragments or enhancers derived there from can be used to make chimeric transcriptional regulatory element compositions comprised of any of the promoters presented as SEQ ID NOs: 2, 6, 8, 10, 12, 163 and 169, or the promoter elements comprised within SEQ ID NOs: 13 through 199, 211 and 212, and the fragments or enhancers derived therefrom operably linked to other enhancers and promoters. The efficacy of the modifications, duplications or deletions described herein on the desired expression aspects of a particular transgene may be tested empirically in stable and transient plant assays, such as those described in the working examples herein, so as to validate the results, which may vary depending upon the changes made and the goal of the change in the starting molecule.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. Leaders useful in practicing the present invention include SEQ ID NOs: 3, 164, 166 and 170, or the leader element comprised within SEQ ID NOs: 13 through 199, 211 and 212, or fragments or variants thereof. In specific embodiments, such sequences may be provided defined as being capable of acting as a leader in a host cell, including, for example, a transgenic plant cell. In one embodiment such sequences are decoded as comprising leader activity.

The leader sequences (5' UTR) presented as SEQ ID NOs: 3, 164, 166 and 170, or the leader element comprised within any of SEQ ID NOs: 13 through 199, 211 and 212 may be comprised of regulatory elements or may adopt secondary structures that can have an effect on transcription or translation of a transgene. The leader sequences presented as SEQ ID NOs: 3, 164, 166 and 170, or the leader element comprised within SEQ ID NOs: 13 through 199, 211 and 212 can be used in accordance with the invention to make chimeric regulatory elements that affect transcription or translation of a transgene. In addition, the leader sequences presented as SEQ ID NOs: 3, 164, 166 and 170, or the leader element comprised within any of SEQ ID NOs: 13 through 199, 211 and 212 can be used to make chimeric leader sequences that affect transcription or translation of a transgene.

The introduction of a foreign gene into a new plant host does not always result in a high expression of the incoming gene. Furthermore, if dealing with complex traits, it is sometimes necessary to modulate several genes with spatially or temporarily different expression pattern. Introns can principally provide such modulation. However, multiple use of the same intron in one transgenic plant has shown to exhibit disadvantages. In those cases it is necessary to have a collection of basic control elements for the construction of appropriate recombinant DNA elements. As the available collection of introns known in the art with expression enhancing properties is limited, alternatives are needed.

Compositions derived from any of the introns presented as SEQ ID NOs: 4, 165 and 171 or the intron element comprised within SEQ ID NOs: 13 through 199, 211 and 212 can be comprised of internal deletions or duplications of cis regulatory elements; and/or alterations of the 5' and 3' sequences comprising the intron/exon splice junctions can be used to improve expression or specificity of expression when operably linked to a promoter+leader or chimeric promoter+leader and coding sequence. Alterations of the 5' and 3' regions comprising the intron/exon splice junction can also be made to reduce the potential for introduction of false start and stop codons being produced in the resulting transcript after processing and splicing of the messenger RNA. The introns can be tested empirically as described in the working examples to determine the intron's effect on expression of a transgene.

In accordance with the invention a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants having a similar expression pattern to the original promoter.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box or equivalent sequence. A promoter may naturally comprise one or more enhancer elements that affect the transcription of an operably linked polynucleotide sequence. An isolated enhancer element may also be fused to a promoter to produce a chimeric promoter.cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron. This effect has been termed "intron mediated enhancement" (IME) of gene expression (Mascarenhas et al., (1990) *Plant Mol. Biol.* 15:913-920). Introns known to stimulate expression in plants have been identified in maize genes (e.g. tubA1, Adh1, Sh1, Ubi1 (Jeon et al. (2000) *Plant Physiol.* 123:1005-1014; Callis et al. (1987) *Genes Dev.* 1:1183-1200; Vasil et al. (1989) *Plant Physiol.* 91:1575-1579; Christiansen et al. (1992) *Plant Mol. Biol.* 18:675-689) and in rice genes (e.g. salt, tpi: McElroy et al., *Plant Cell* 2:163-171 (1990); Xu et al., *Plant Physiol.* 106:459-467 (1994)). Similarly, introns from dicotyledonous plant genes like those from *petunia* (e.g. rbcS), potato (e.g. st-ls1) and from *Arabidopsis thaliana* (e.g. ubq3 and pat1) have been found to elevate gene expression rates (Dean et al. (1989) *Plant Cell* 1:201-208; Leon et al. (1991) *Plant Physiol.* 95:968-972; Norris et al. (1993) *Plant Mol Biol* 21:895-906; Rose and Last (1997) *Plant J.* 11:455-464). It has been shown that deletions or mutations within the splice sites of an intron reduce gene expression, indicating that splicing might be needed for IME (Mascarenhas et al. (1990) *Plant Mol Biol.* 15:913-920; Clancy and Hannah (2002) *Plant Physiol.* 130:918-929). However, that splicing per se is not required for a certain IME in dicotyledonous plants has been shown by point mutations within the splice sites of the pat1 gene from *A. thaliana* (Rose and Beliakoff (2000) *Plant Physiol.* 122:535-542).

Enhancement of gene expression by introns is not a general phenomenon because some intron insertions into recombinant expression cassettes fail to enhance expression (e.g. introns from dicot genes (rbcS gene from pea, phaseolin gene from bean and the stls-1 gene from *Solanum tuberosum*) and introns from maize genes (adh1 gene the ninth intron, hsp81 gene the first intron)) (Chee et al. (1986) *Gene* 41:47-57; Kuhlemeier et al. (1988) *Mol Gen Genet* 212:405-411; Mascarenhas et al. (1990) *Plant Mol. Biol.* 15:913-920; Sinibaldi and Mettler (1992) In W E Cohn, K Moldave, eds, *Progress in Nucleic Acid Research and Molecular Biology*, Vol 42. Academic Press, New York, pp 229-257; Vancanneyt et al. 1990 *Mol. Gen. Genet.* 220:245-250). Therefore, not each intron can be employed in order to manipulate the gene expression level of non-endogenous genes or endogenous genes in transgenic plants. What characteristics or specific sequence features must be present in an intron sequence in order to enhance the expression rate of a given gene is not known in the prior art and therefore from the prior art it is not possible to predict whether a given plant intron, when used heterologously, will cause IME.

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is in composition similar, but not identical to, a first DNA molecule and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" can also encompass a regulatory element having a nucleotide sequence comprising a substitution, deletion and/or insertion of one or more nucleotides of a reference sequence, wherein the derivative regulatory element has more or less or equivalent transcriptional or translational activity than the corresponding parent regulatory molecule. The regulatory element "variants" may also encompass variants arising from mutations that naturally occur in bacterial and plant cell transformation. In the present invention, a polynucleotide sequence provided as SEQ ID NOs: 1-199, 211 and 212 may be used to create variants similar in composition, but not identical to, the polynucleotide sequence of the original regulatory element, while still maintaining the general functionality of, i.e. same or similar expression pattern, the original regulatory element. Production of such variants of the present invention is well within the ordinary skill of the art in light of the disclosure and is encompassed within the scope of the present invention. "Variants" of chimeric regulatory element comprise the same constituent elements as a reference chimeric regulatory element sequence but the constituent elements comprising the chimeric regulatory element may be operatively linked by various methods known in the art such as, restriction enzyme digestion and ligation, ligation independent cloning, modular assembly of PCR products during amplification, or direct chemical synthesis of the chimeric regulatory element as well as other methods known in the art. The resulting "variant" chimeric regulatory element is comprised of the same, or variants of the same, constituent elements as the reference sequence but differ in the sequence or sequences that are used to operably link the constituent elements. In the present invention, the polynucleotide sequences provided as SEQ ID NOs: 1-199, 211 and 212 each provide a reference sequence wherein the constituent elements of the reference sequence may be joined by methods known in the art and may consist of substitutions, deletions and/or insertions of one or more nucleotides or mutations that naturally occur in bacterial and plant cell transformation.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. The term includes an expression cassette isolated from any of the aforementioned molecules.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

The constructs of the present invention may be provided, in one embodiment, as double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells, permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known in the art of plant transformation can function in the present invention.

Methods are available for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells can be found in, for example, *Molecular Cloning: A Laboratory Manual,* 3rd Edition Volumes 1, 2, and 3 (2000) J. F. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908; 4,940,835; 4,769,061; and 4,757,011 in their entirety. These types of vectors have also been reviewed in the scientific literature (see, for example, Rodriguez, et al., *Vectors: A Survey of Molecular Cloning Vectors and Their Uses*, Butterworths, Boston, (1988) and Glick, et al., *Methods in Plant Molecular Biology and Biotechnology*, CRC Press, Boca Raton, Fla. (1993)). Typical vectors useful for expression of nucleic acids in higher plants are well known in the art and include vectors derived from the tumor-inducing (Ti) plasmid of *Agrobacterium tumefaciens* (Rogers, et al., Methods in Enzymology 153: 253-277 (1987)). Other recombinant vectors useful for plant transformation, including the pCaMVCN transfer control vector, have also been described in the scientific literature (see, for example, Fromm, et al., *Proc. Natl. Acad. Sci. USA* 82: 5824-5828 (1985)).

Various regulatory elements may be included in a construct including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3' transcription termination molecule.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus 35S transcript promoter (see, U.S. Pat. No. 5,352,605). The expression properties imparted by such operable linkages of heterologous elements is not necessarily additive of the elucidated properties of each promoter and leader, but rather is determined through empirical analysis of expression driven by the operably linked heterologous promoter and leader.

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Introns useful in practicing the present invention include SEQ ID NOs: 4, 165 and 171 or the intron element comprised within any of SEQ ID NOs: 13 through 199, 211 and 212.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules are the nopaline synthase 3' region (see, Fraley, et al., *Proc. Natl. Acad. Sci. USA,* 80: 4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806).

3' UTRs typically find beneficial use for the recombinant expression of specific genes. In animal systems, a machinery of 3' UTRs has been well defined (e.g. Zhao et al., *Microbiol Mol Biol Rev* 63:405-445 (1999); Proudfoot, *Nature* 322: 562-565 (1986); Kim et al., *Biotechnology Progress* 19:1620-1622 (2003); Yonaha and Proudfoot, *EMBO J.* 19:3770-3777 (2000); Cramer et al., *FEBS Letters* 498:179-182 (2001); Kuerstem and Goodwin, *Nature Reviews Genetics* 4:626-637 (2003)). Effective termination of RNA transcription is required to prevent unwanted transcription of trait-unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, *BioTechniques* 31:328-334 (2001). This may interfere with achieving adequate levels of expression, for instance in cases were strong gene expression from all cassettes is desired.

In plants, clearly defined polyadenylation signal sequences are not known. Hasegawa et al., *Plant J.* 33:1063-1072, (2003)) were not able to identify conserved polyadenylation signal sequences in both in vitro and in vivo systems in *Nicotiana sylvestris* and to determine the actual length of the primary (non-polyadenylated) transcript. A weak 3' UTR has the potential to generate read-through, which may affect the expression of the genes located in the neighboring expression cassettes (Padidam and Cao, *BioTechniques* 31:328-334 (2001)). Appropriate control of transcription termination can prevent read-through into sequences (e.g. other expression cassettes) localized downstream and can further allow efficient recycling of RNA polymerase, to improve gene expression. Efficient termination of transcription (release of RNA Polymerase II from the DNA) is pre-requisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, so that it is difficult to detect transcriptional termination sites by conventional methods. However, prediction of functional and efficient 3' UTRs by bioinformatics methods is difficult in that there are no conserved sequences which would allow easy prediction of an effective 3' UTR.

From a practical standpoint, it is typically beneficial that a 3' UTR used in a transgene cassette possesses the following characteristics. The 3' UTR should be able to efficiently and effectively terminate transcription of the transgene and prevent read-through of the transcript into any neighboring DNA sequence which can be comprised of another transgene cassette as in the case of multiple cassettes residing in one T-DNA, or the neighboring chromosomal DNA into which the T-DNA has inserted. The 3' UTR should not cause a reduction in the transcriptional activity imparted by the promoter, leader and introns that are used to drive expression of the transgene. In plant biotechnology, the 3' UTR is often used for priming of amplification reactions of reverse transcribed RNA extracted from the transformed plant and used to (1) assess the transcriptional activity or expression of the transgene cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from messenger RNA isolated from seed, flower and other tissues derived from Foxtail millet (*Setaria italica* (L.) Beauv). Libraries of cDNA are made from tissues isolated from selected plant species using flower tissue, seed, leaf and root. The resulting cDNAs are sequenced using various sequencing methods. The resulting ESTs are assembled into clusters using bioinformatics software such as clc_ref_assemble_complete version 2.01.37139 (CLC bio USA, Cambridge, Mass. 02142). Transcript abundance of each cluster is determined by counting the number of cDNA reads for each cluster. The identified 3' UTRs may be comprised of sequence derived from cDNA sequence as well as sequence derived from genomic DNA. The cDNA sequence is used to design primers, which are then used with GenomeWalker™ (Clontech Laboratories, Inc, Mountain View, Calif.) libraries constructed following the manufacturer's protocol to clone the 3' region of the corresponding genomic DNA sequence to provide a longer termination sequence. Analysis of relative transcript abundance either by direct counts or normalized counts of observed sequence reads for each tissue library can be used to infer properties about patters of expression. For example, some 3' UTRs may be found in transcripts seen in higher abundance in root tissue as opposed to leaf. This is suggestive that the transcript is highly expressed in root and that the properties of root expression may be attributable to the transcriptional regulation of the promoter, the lead, the introns or the 3' UTR. Empirical testing of 3' UTRs identified by the properties of expression within specific organs, tissues or cell types can result in the identification of 3' UTRs that enhance expression in those specific organs, tissues or cell types.

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. No. 5,188,642 and U.S. Pat. No. 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442 (1987)) or the *Petunia hybrida* EPSPS CTP (CTP4) (See, della-Cioppa et al., *Proc. Natl. Acad. Sci. USA* 83:6873-6877 (1986)) has been show to target heterologous EPSPS protein sequences to chloroplasts in transgenic plants (See, U.S. Pat. Nos. 5,627,061; 5,633,435; and 5,312,910 and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a regulatory element of the present invention, such as those provided as SEQ ID NOs: 1-199, 211 and 212, operably linked to a transcribable polynucleotide molecule so as to modulate transcription of the transcribable polynucleotide molecule at a desired level or in a desired pattern when the construct is integrated in the genome of a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule, double stranded RNA or other similar inhibitory RNA molecule in order to inhibit expression of a specific RNA molecule of interest in a target host cell.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type confers a desirable characteristic, such as associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a promoter of the present invention is incorporated into a construct such that the promoter is operably linked to a transcribable polynucleotide molecule that is a gene of agronomic interest. The expression of the gene of agronomic interest is desirable in order to confer an agronomically beneficial trait. A beneficial agronomic trait may be, for example, but is not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. RE37,543; 6,228,623; and 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding a RNA molecule that causes the targeted modulation of gene expression of an endogenous gene, for example via antisense (see e.g. U.S. Pat. No. 5,107,065); inhibitory RNA ("RNAi", including modulation of gene expression via miRNA-, siRNA-, trans-acting siRNA-, and phased sRNA-mediated mechanisms, e.g. as described in published applications US 2006/0200878 and US 2008/0066206, and in U.S. patent application Ser. No. 11/974,469); or cosuppression-mediated mechanisms. The RNA could also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US20070250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS described in U.S. Pat. No. 5,599,670), green fluorescent protein and variants thereof (GFP described in U.S. Pat. Nos. 5,491,084 and 6,146,826), proteins that confer antibiotic resistance, or proteins that confer herbicide tolerance. Useful antibiotic resistance markers include those encoding proteins conferring resistance to kanamycin (nptII), hygromycin B (aph IV), streptomycin or spectinomycin (aad, spec/strep) and gentamycin (aac3 and aacC4). Herbicides for which transgenic plant tolerance has been demonstrated and the method of the present invention can be applied, include, but are not limited to: amino-methyl-phosphonic acid, glyphosate, glufosinate, sulfonylureas, imidazolinones, bromoxynil, delapon, dicamba, cyclohezanedione, protoporphyrinogen oxidase inhibitors, and isoxasflutole herbicides. Transcribable polynucleotide molecules encoding proteins involved in herbicide tolerance include, but are not limited to, a transcribable polynucleotide molecule encoding 5-enolpyruvylshikimate-3-phosphate synthase (EPSPS for glyphosate tolerance described in U.S. Pat. Nos. 5,627,061; 5,633,435; 6,040,497; and 5,094,945); a transcribable polynucleotide molecule encoding a glyphosate oxidoreductase and a glyphosate-N-acetyl transferase (GOX described in U.S. Pat. No. 5,463,175; GAT described in U.S. Patent publication No. 20030083480, and dicamba monooxygenase U.S. Patent publication No. 20030135879); a transcribable polynucleotide molecule encoding bromoxynil nitrilase (Bxn for Bromoxynil tolerance described in U.S. Pat. No. 4,810,648); a transcribable polynucleotide molecule encoding phytoene desaturase (crtI) described in Misawa, et al., *Plant Journal* 4:833-840 (1993) and Misawa, et al., *Plant Journal* 6:481-489 (1994) for norflurazon tolerance; a transcribable polynucleotide molecule encoding acetohydroxyacid synthase (AHAS, aka ALS) described in Sathasiivan, et al., *Nucl. Acids Res.* 18:2188-2193 (1990) for tolerance to sulfonylurea herbicides; and the bar gene described in DeBlock, et al., *EMBO Journal* 6:2513-2519 (1987) for glufosinate and bialaphos tolerance. The promoter molecules of the present invention can express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g. by ELISA), small active enzymes which are detectable in extracellular solution (e.g, alpha-amylase, beta-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art and are encompassed by the present invention.

Cell Transformation

The invention is also directed to a method of producing transformed cells and plants which comprise a promoter operably linked to a transcribable polynucleotide molecule.

The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing polynucleic acid molecules into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.* 42: 205 (1991)).

Any transformation methods may be utilized to transform a host cell with one or more promoters and/or constructs of the present invention. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of CA, Davis, Calif., 50-98 (1960); Simmonds, *Principles of crop improvement*, Longman, Inc., NY, 369-399 (1979); Sneep and Hendriksen, *Plant breeding perspectives*, Wageningen (ed), Center for Agricultural Publishing and Documentation (1979); Fehr, *Soybeans: Improvement, Production and Uses,* 2nd Edition, Monograph, 16:249 (1987); Fehr, *Principles of variety development, Theory and Technique*, (Vol. 1) and *Crop* Species *Soybean* (Vol 2), Iowa State Univ., Macmillan Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used transgene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Identification and Cloning of Regulatory Elements

Novel transcriptional regulatory elements, or transcriptional regulatory expression element group (EXP) sequences were identified and isolated from genomic DNA of the dicot species *Cucumis melo* WSH-39-1070AN.

Transcriptional regulatory elements were selected based upon proprietary and public microarray data derived from transcriptional profiling experiments conducted in soybean (*Glycine max*) and *Arabidopsis* as well as homology based searches using known dicot sequences as query against proprietary *Cucumis melo* sequences.

Using the identified sequences, a bioinformatic analysis was conducted to identify regulatory elements within the amplified DNA, followed by identification of the transcriptional start site (TSS) and any bi-directionality, introns, or upstream coding sequence present in the sequence. Using the results of this analysis, regulatory elements were defined within the DNA sequences and primers designed to amplify the regulatory elements. The corresponding DNA molecule for each regulatory element was amplified using standard polymerase chain reaction conditions with primers containing unique restriction enzyme sites and genomic DNA isolated from *Cucumis melo*. The resulting DNA fragments were ligated into base plant expression vectors using standard restriction enzyme digestion of compatible restriction sites and DNA ligation methods.

Analysis of the regulatory element TSS and intron/exon splice junctions can be performed using transformed plant protoplasts. Briefly, the protoplasts are transformed with the plant expression vectors comprising the cloned DNA fragments operably linked to a heterologous transcribable polynucleotide molecule and the 5' RACE System for Rapid Amplification of cDNA Ends, Version 2.0 (Invtrogen, Carlsbad, Calif. 92008) is used to confirm the regulatory element TSS and intron/exon splice junctions by analyzing the sequence of the mRNA transcripts produced thereby.

Sequences encoding ubiquitin 1 transcriptional regulatory expression element groups (EXP) were analyzed as described above and each transcriptional regulatory expression element groups ("EXP's") was also broken down into the corresponding promoters, leaders and introns comprising each transcriptional regulatory expression element group. Sequences of the identified ubiquitin 1 transcriptional regulatory expression element groups ("EXP's") are provided herein as SEQ ID NOs: 1, 5, 7, 9 and 11 and is listed in Table 1 below. The corresponding ubiquitin 1 promoters are provided herein as SEQ ID NOs: 2, 6, 8, 10 and 12. The ubiquitin 1 leader and intron are herein provided as SEQ ID NOs: 3 and 4, respectively.

Sequences encoding other *Cucumis* transcriptional regulatory expression element groups or EXP sequences which are comprised of either a promoter element, operably linked to a leader element; or a promoter element, operably linked to a leader element and an intron element, or a promoter element, operably linked to a leader element, operably linked to an intron element, operably linked to a leader element are provided as SEQ ID NOs: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 159, 162, 167, 168, 172, 175, 176, 177, 178, 181, 182, 183, 184, 185, 188, 189, 190, 191, 192, 193, 194, 195, 196, 197, 198, 199, 211 and 212 and are also listed in Table 1 below. Additional promoter elements are provided as SEQ ID NOs: 163 and 169. Additional leader elements are provided as SEQ ID NOs: 164, 166 and 170. Additional intron elements are provided as SEQ ID NOs: 165 and 171. Elements wherein a promoter is operably linked to a leader element are provided as SEQ ID NOs: 157, 160, 173, 179 and 186. Elements wherein an intron is operably linked to a leader element are provided as SEQ ID NOs: 158, 161, 174, 180 and 187. With respect to the subset of sequences provided as SEQ ID NOs: 13 through 199, 211 and 212, these sequences were selected and cloned based upon the results of experiments such as transcript profiling or expression driven by promoters from homologous genes of a different species suggesting desirable patterns of expression such as constitutive expression, root expression, above ground expression or seed expression. The actual activity imparted by the *Cucumis* sequences is determined empirically and is not necessarily the same as that of a regulatory element derived from a homologous gene from a species other than *Cucumis melo* when used in a transformed plant host cell and whole transgenic plant.

TABLE 1

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| EXP-CUCme.Ubq1:1:1 | 1 | Ubiquitin 1 | EXP | 2611 | Promoter; Leader; Intron | 1-2068; 2069-2150; 2151-2608 |
| P-CUCme.Ubq1-1:1:15 | 2 | Ubiquitin 1 | P | 2068 | Promoter | |
| L-CUCme.Ubq1-1:1:1 | 3 | Ubiquitin 1 | L | 82 | Leader | |
| I-CUCme.Ubq1-1:1:1 | 4 | Ubiquitin 1 | I | 461 | Intron | |
| EXP-CUCme.Ubq1:1:2 | 5 | Ubiquitin 1 | EXP | 2002 | Promoter; Leader; Intron | 1-1459; 1460-1541; 1542-1999 |
| P-CUCme.Ubq1-1:1:16 | 6 | Ubiquitin 1 | P | 1459 | Promoter | |
| EXP-CUCme.Ubq1:1:3 | 7 | Ubiquitin 1 | EXP | 1507 | Promoter; Leader; Intron | 1-964; 965-1046; 1047-1504 |
| P-CUCme.Ubq1-1:1:17 | 8 | Ubiquitin 1 | P | 964 | Promoter | |
| EXP-CUCme.Ubq1:1:4 | 9 | Ubiquitin 1 | EXP | 1022 | Promoter; Leader; Intron | 1-479; 480-561; 562-1019 |
| P-CUCme.Ubq1-1:1:18 | 10 | Ubiquitin 1 | P | 479 | Promoter | |
| EXP-CUCme.Ubq1:1:5 | 11 | Ubiquitin 1 | EXP | 716 | Promoter; Leader; Intron | 1-173; 174-255; 256-713 |
| P-CUCme.Ubq1-1:1:19 | 12 | Ubiquitin 1 | P | 173 | Promoter | |
| P-CUCme.1-1:1:1 | 13 | Phosphatase 2A | EXP | 2000 | Promoter; Leader; Intron; Leader | Reverse compliment; see SEQ ID NO: 155 |
| P-CUCme.2-1:1:1 | 14 | Actin 1 | EXP | 2000 | Promoter; Leader; Intron; Leader | 1-964; 965-1028; 1029-1991; 1992-2003 |
| P-CUCme.3-1:1:3 | 15 | Actin 2 | EXP | 1990 | Promoter; Leader; Intron; Leader | 1-1243; 1244-1319; 1320-1982; 1983-1990 |
| P-CUCme.4-1:1:2 | 16 | Ubiquitin 2 | EXP | 2005 | Promoter; Leader; Intron; Leader | 1-1646; 1647-1704; 1705-2005; 2006-2008 |
| P-CUCme.5-1:1:2 | 17 | Ubiquitin 3 | EXP | 2004 | Promoter; Leader; Intron | 1-748; 749-819; 820-2004 |
| P-CUCme.6-1:1:1 | 18 | Tubulin beta chain | EXP | 1935 | Promoter; Leader; Intron; Leader | 1-1436; 1437-1482; 1483-1919; 1920-1935 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| P-CUCme.8-1:1:2 | 19 | Tubulin beta chain | EXP | 1606 | Promoter; Leader | 1-1527; 1528-1606 |
| P-CUCme.9-1:1:2 | 20 | Tubulin beta chain | EXP | 1487 | Promoter; Leader | 1-1384; 1385-1487 |
| P-CUCme.10-1:1:1 | 21 | Tubulin beta chain | EXP | 1448 | Promoter; Leader | 1-1363; 1364-1448 |
| P-CUCme.11-1:1:2 | 22 | Elongation Factor 1 alpha | EXP | 1235 | Promoter; Leader; Intron | 1-617; 618-677; 678-1213; 1214-1235 |
| P-CUCme.15-1:1:2 | 23 | Elongation Factor 1 alpha | EXP | 2003 | Promoter; Leader; Intron; Leader | 1-1330; 1331-1435; 1430-1975; 1976-2002 |
| P-CUCme.16a-1:1:2 | 24 | Ubiquitin 7 | EXP | 2015 | Promoter; Leader | |
| P-CUCme.16b-1:1:1 | 25 | Ubiquitin 6 | EXP | 2006 | Promoter; Leader | |
| P-CUCme.17-1:1:2 | 26 | ubiquitin-40S ribosomal protein S27a | EXP | 2017 | Promoter; Leader | 1-1969; 1970-2017 |
| P-CUCme.18-1:1:2 | 27 | ubiquitin-40S ribosomal protein S27a | EXP | 1353 | Promoter; Leader | 1-1308; 1309-1353 |
| P-CUCme.19-1:1:2 | 28 | Chloropyll a/b binding protein | EXP | 2005 | Promoter; Leader | 1-1960; 1961-2005 |
| P-CUCme.20-1:1:2 | 29 | Chloropyll a/b binding protein | EXP | 1445 | Promoter; Leader | 1-1390; 1391-1445 |
| P-CUCme.21-1:1:1 | 30 | Chloropyll a/b binding protein | EXP | 1282 | Promoter; Leader | 1-1233; 1234-1282 |
| P-CUCme.22-1:1:3 | 31 | Elongation Factor 4 alpha | EXP | 2002 | | |
| P-CUCme.24-1:1:2 | 32 | S-Adenosylmethionine Synthetase | EXP | 2003 | Promoter; Leader; Intron; Leader | 1-1067; 1068-1165; 1166-2001; 2002-2003 |
| P-CUCme.26-1:1:2 | 33 | Stress responsive protein | EXP | 1372 | Promoter; Leader; Intron; Leader | 1-577; 578-654; 655-1366; 1367-1372 |
| P-CUCme.28-1:1:2 | 34 | Ribosomal protein S5a | EXP | 1122 | | |
| P-CUCme.29-1:1:2 | 35 | Ribosomal protein S5a | EXP | 2017 | Promoter; Leader; Intron; Leader | 1-490; 491-571; 572-2012; 2013-2017 |
| CumMe_WSM_SF143981. G5150 | 36 | LHCB6 (LIGHT HARVESTING COMPLEX PSII SUBUNIT 6) | EXP | 2000 | | |
| CumMe_WSM_SF144839. G5080 | 37 | EIF2 GAMMA translation initiation factor | EXP | 1760 | | |
| CumMe_WSM_SF146040. G5050 | 38 | EIF2 translation initiation factor | EXP | 1767 | | |
| CumMe_WSM_SF16408. G5350 | 39 | elongation factor Tu | EXP | 2000 | | |
| CumMe_WSM_SF16429. G5670 | 40 | unknown protein | EXP | 2000 | | |
| CumMe_WSM_SF16444. G5140 | 41 | histone H4 | EXP | 2000 | Promoter; Leader | 1-1947; 1948-2000 |
| CumMe_WSM_SF16530. G6000 | 42 | HMGB2 (HIGH MOBILITY GROUP B 2) transcription factor | EXP | 2000 | | |
| CumMe_WSM_SF16553. G5090 | 43 | PBG1; threonine-type endopeptidase | EXP | 1115 | | |
| CumMe_WSM_SF16563. G5560 | 44 | ATARFB1A (ADP-ribosylation factor B1A) | EXP | 2000 | Promoter; Leader; Intron; Leader | 1-1329; 1330-1427; 1428-1988; 1989-2000 |
| CumMe_WSM_SF16675. G5720 | 45 | chromatin protein family | EXP | 2000 | | |
| CumMe_WSM_SF16920. G5650 | 46 | CSD1 (COPPER/ZINC SUPEROXIDE DISMUTASE 1) | EXP | 2000 | | |
| CumMe_WSM_SF16953. G5180 | 47 | SCE1 (SUMO CONJUGATION ENZYME 1); SUMO ligase | EXP | 2000 | | |
| CumMe_WSM_SF17051. G5470 | 48 | 60S ribosomal protein L9 (RPL90D) | EXP | 2000 | | |
| CumMe_WSM_SF17111. G5790 | 49 | ubiquinol-cytochrome C reductase complex ubiquinone-binding protein | EXP | 2000 | Promoter; Leader | 1-1895; 1896-2000 |
| CumMe_WSM_SF17142. G5920 | 50 | peptidyl-prolyl cis-trans isomerase, chloroplast | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF17190.G6200 | 51 | PRK (PHOSPHORIBULOKINASE) | EXP | 2000 | | |
| CumMe_WSM_SF17250.G5910 | 52 | LHCB5 (LIGHT HARVESTING COMPLEX OF PHOTOSYSTEM II 5) | EXP | 2000 | | |
| CumMe_WSM_SF17252.G7330 | 53 | nascent polypeptide-associated complex (NAC) domain-containing protein | EXP | 2000 | Promoter; Leader; Intron | 1-1195; 1196-1297; 1298-2000 |
| CumMe_WSM_SF17253.G5150 | 54 | RPS9 (RIBOSOMAL PROTEIN S9) | EXP | 1547 | | |
| CumMe_WSM_SF17322.G5110 | 55 | 60S ribosomal protein L22 (RPL22A) | EXP | 2000 | | |
| CumMe_WSM_SF17349.G5770 | 56 | PGRL1B (PGR5-Like B) | EXP | 2000 | | |
| CumMe_WSM_SF17357.G5630 | 57 | 40S ribosomal protein S10 (RPS10B) | EXP | 2000 | | |
| CumMe_WSM_SF17494.G5140 | 58 | MEE34 (maternal effect embryo arrest 34) | EXP | 1591 | | |
| CumMe_WSM_SF17524.G6410 | 59 | SUS2 (ABNORMAL SUSPENSOR 2) | EXP | 2000 | | |
| CumMe_WSM_SF17672.G5610 | 60 | PSAK (photosystem I subunit K) | EXP | 2000 | | |
| CumMe_WSM_SF17773.G6620 | 61 | aconitase C-terminal domain-containing protein | EXP | 2000 | | |
| CumMe_WSM_SF17866.G6050 | 62 | ATPDIL5-1 (PDI-like 5-1) | EXP | 2000 | | |
| CumMe_WSM_SF18004.G6600 | 63 | hydroxyproline-rich glycoprotein family protein | EXP | 2000 | | |
| CumMe_WSM_SF18045.G6670 | 64 | | EXP | 2000 | | |
| CumMe_WSM_SF18053.G5410 | 65 | endomembrane protein 70 | EXP | 2000 | | |
| CumMe_WSM_SF18287.G5380 | 66 | CP12-1 | EXP | 2000 | | |
| CumMe_WSM_SF18488.G5340 | 67 | caffeoyl-CoA 3-O-methyltransferase | EXP | 2000 | Promoter; Leader | 1-1923; 1924-2000 |
| CumMe_WSM_SF18504.G5090 | 68 | vacuolar ATP synthase subunit H family protein | EXP | 2000 | | |
| CumMe_WSM_SF18530.G5750 | 69 | GUN5 (GENOMES UNCOUPLED 5); magnesium chelatase | EXP | 2000 | | |
| CumMe_WSM_SF18536.G6480 | 70 | MBF1A (MULTIPROTEIN BRIDGING FACTOR 1A) transcription coactivator | EXP | 2000 | | |
| CumMe_WSM_SF18575.G6410 | 71 | unknown protein | EXP | 2000 | | |
| CumMe_WSM_SF18634.G5190 | 72 | 60S ribosomal protein L23 (RPL23A) | EXP | 2000 | Promoter; Leader | 1-1971; 1972-2000 |
| CumMe_WSM_SF18645.G5380 | 73 | GS2 (GLUTAMINE SYNTHETASE 2) | EXP | 2000 | | |
| CumMe_WSM_SF18716.G5860 | 74 | 40S ribosomal protein S12 (RPS12A); reverse compliment: Auxin-induced protein x10A-like | EXP | 2000 | Promoter; Leader | Reverse compliment; see SEQ ID NO: 184 |
| CumMe_WSM_SF18801.G5040 | 75 | | EXP | 2000 | | |
| CumMe_WSM_SF18806.G6220 | 76 | unknown protein | EXP | 2000 | | |
| CumMe_WSM_SF18850.G5630 | 77 | PAC1; threonine-type endopeptidase | EXP | 2000 | | |
| CumMe_WSM_SF18863.G7550 | 78 | ATP synthase gamma chain, mitochondrial (ATPC) | EXP | 2000 | | |
| CumMe_WSM_SF18986.G6110 | 79 | GER1 (GERMIN-LIKE PROTEIN 1); oxalate oxidase | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF19064.G5690 | 80 | histone H3.2 | EXP | 2000 | Promoter; Leader; Intron | 1-1581; 1582-1670; 1671-2000 |
| CumMe_WSM_SF19323.G5120 | 81 | chloroplast outer envelope GTP-binding protein, putative | EXP | 2000 | | |
| CumMe_WSM_SF19452.G5090 | 82 | glucan phosphorylase, putative | EXP | 1072 | | |
| CumMe_WSM_SF19631.G5170 | 83 | RuBisCO activase, putative | EXP | 1730 | | |
| CumMe_WSM_SF19647.G5760 | 84 | 6-phosphogluconate dehydrogenase family protein | EXP | 2000 | Promoter; Leader; Intron; Leader | 1-936; 937-1021; 1022-1992; 1993-2000 |
| CumMe_WSM_SF19839.G5090 | 85 | ATPDX1.1 (pyridoxine biosynthesis 1.1) | EXP | 1020 | Promoter; Leader | 1-928; 929-1020 |
| CumMe_WSM_SF19850.G5130 | 86 | HMGB2 (HIGH MOBILITY GROUP B 2) transcription factor | EXP | 2000 | | |
| CumMe_WSM_SF19902.G5260 | 87 | universal stress protein (USP) family protein/ early nodulin ENOD18 family protein | EXP | 2000 | | |
| CumMe_WSM_SF19992.G6100 | 88 | unknown protein | EXP | 2000 | | |
| CumMe_WSM_SF20132.G5560 | 89 | peroxidase 21 | EXP | 2000 | Promoter; Leader | 1-1962; 1963-2000 |
| CumMe_WSM_SF20147.G7910 | 90 | CSD1 (COPPER/ZINC SUPEROXIDE DISMUTASE 1) | EXP | 2000 | | |
| CumMe_WSM_SF20355.G5130 | 91 | ATP synthase family | EXP | 2000 | | |
| CumMe_WSM_SF20359.G5870 | 92 | NADH-ubiquinone oxidoreductase 20 kDa subunit, mitochondrial | EXP | 2000 | | |
| CumMe_WSM_SF20368.G5700 | 93 | PGR5 (proton gradient regulation 5) | EXP | 2000 | | |
| CumMe_WSM_SF20409.G5240 | 94 | elongation factor 1B alpha-subunit 1 (eEF1Balpha1) | EXP | 2000 | | |
| CumMe_WSM_SF20431.G6340 | 95 | DHS2 (3-deoxy-d-arabino-heptulosonate 7-phosphate synthase) | EXP | 2000 | | |
| CumMe_WSM_SF20505.G5440 | 96 | THIC (ThiaminC); ADP-ribose pyrophosphohydrolase | EXP | 1373 | | |
| CumMe_WSM_SF20509.G5920 | 97 | Y14; RNA binding/ protein binding | EXP | 2000 | | |
| CumMe_WSM_SF206458.G5970 | 98 | FAD2 (FATTY ACID DESATURASE 2) | EXP | 2000 | Promoter | 1-2000 |
| CumMe_WSM_SF206534.G5200 | 99 | unknown protein | EXP | 2000 | | |
| CumMe_WSM_SF20997.G6990 | 100 | ALD1 (AGD2-LIKE DEFENSE RESPONSE PROTEIN1) | EXP | 2000 | | |
| CumMe_WSM_SF21035.G5090 | 101 | sodium/calcium exchanger family protein | EXP | 1078 | | |
| CumMe_WSM_SF21117.G5370 | 102 | 30S ribosomal protein, putative | EXP | 2000 | | |
| CumMe_WSM_SF21141.G5630 | 103 | 40S ribosomal protein S24 (RPS24A) | EXP | 2000 | | |
| CumMe_WSM_SF21198.G5180 | 104 | | EXP | 1974 | | |
| CumMe_WSM_SF21366.G5980 | 105 | GRF12 (GENERAL REGULATORY FACTOR 12) | EXP | 2000 | | |
| CumMe_WSM_SF21828.G5150 | 106 | cpHsc70-1 (chloroplast heat shock protein 70-1) | EXP | 1643 | | |
| CumMe_WSM_SF21886.G5080 | 107 | NPQ4 (NONPHOTOCHEMICAL QUENCHING) | EXP | 2000 | | |
| CumMe_WSM_SF22008.G5670 | 108 | NAP1; 2 (NUCLEOSOME ASSEMBLY PROTEIN 1; 2) | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF22070.G5280 | 109 | fructose-bisphosphate aldolase, putative | EXP | 2000 | | |
| CumMe_WSM_SF22097.G5540 | 110 | APX3 (ASCORBATE PEROXIDASE 3) | EXP | 2000 | | |
| CumMe_WSM_SF22254.G5760 | 111 | 40S ribosomal protein S7 (RPS7B) | EXP | 2000 | | |
| CumMe_WSM_SF22275.G5780 | 112 | ribosomal protein L17 family protein | EXP | 1027 | | |
| CumMe_WSM_SF22355.G5310 | 113 | | EXP | 2000 | | |
| CumMe_WSM_SF22531.G5120 | 114 | eukaryotic translation initiation factor 1A, putative | EXP | 2000 | Promoter; Leader; Intron; Leader | 1-759; 760-858; 859-1979; 1980-2000 |
| CumMe_WSM_SF22870.G5370 | 115 | ATSARA1A (*ARABIDOPSIS THALIANA* SECRETION-ASSOCIATED RAS SUPER FAMILY 1) | EXP | 2000 | | |
| CumMe_WSM_SF22934.G5290 | 116 | T-complex protein 1 epsilon subunit, putative | EXP | 2000 | | |
| CumMe_WSM_SF23181.G5100 | 117 | CEV1 (CONSTITUTIVE EXPRESSION OF VSP 1) | EXP | 1025 | | |
| CumMe_WSM_SF23186.G6160 | 118 | ubiquinol-cytochrome C reductase complex 14 kDa protein, putative | EXP | 2000 | | |
| CumMe_WSM_SF23397.G5210 | 119 | RPL27 (RIBOSOMAL PROTEIN LARGE SUBUNIT 27) | EXP | 2000 | | |
| CumMe_WSM_SF23760.G5200 | 120 | NDPK1; ATP binding/nucleoside diphosphate kinase | EXP | 2000 | Promoter; Leader | 1-1901; 1902-2000 |
| CumMe_WSM_SF23906.G6180 | 121 | PSBX (photosystem II subunit X) | EXP | 2000 | | |
| CumMe_WSM_SF24040.G5450 | 122 | RPS17 (RIBOSOMAL PROTEIN S17) | EXP | 2000 | | |
| CumMe_WSM_SF24045.G5400 | 123 | EXL3 (EXORDIUM LIKE 3) | EXP | 2000 | | |
| CumMe_WSM_SF24117.G5600 | 124 | 60S ribosomal protein L26 (RPL26A) | EXP | 2000 | | |
| CumMe_WSM_SF25084.G5580 | 125 | | EXP | 2000 | | |
| CumMe_WSM_SF25141.G5160 | 126 | isocitrate dehydrogenase, putative | EXP | 1397 | Promoter; Leader | 1-1322; 1323-1397 |
| CumMe_WSM_SF25355.G5000 | 127 | LOS1; copper ion binding translation elongation factor | EXP | 2000 | Promoter; Leader; Intron; Leader; CDS | 1-734; 735-811; 812-1340; 1341-1360; 1361-2000 |
| CumMe_WSM_SF25370.G5000 | 128 | PSBP-1 (PHOTOSYSTEM II SUBUNIT P-1) | EXP | 1657 | | |
| CumMe_WSM_SF25455.G5370 | 129 | GLY3 (GLYOXALASE II 3) | EXP | 2000 | | |
| CumMe_WSM_SF25936.G5450 | 130 | mitochondrial substrate carrier family protein | EXP | 2000 | Promoter; Leader | 1-1878; 1879-2000 |
| CumMe_WSM_SF27080.G5510 | 131 | LIP1 (LIPOIC ACID SYNTHASE 1) | EXP | 2000 | | |
| CumMe_WSM_SF27222.G5150 | 132 | DRT112; copper ion binding/electron carrier | EXP | 2000 | | |
| CumMe_WSM_SF27957.G5450 | 133 | SMAP1 (SMALL ACIDIC PROTEIN 1) | EXP | 2000 | | |
| CumMe_WSM_SF28729.G5340 | 134 | RNA-binding protein cp29, putative | EXP | 1696 | | |
| CumMe_WSM_SF28805.G6200 | 135 | unknown protein | EXP | 2000 | | |
| CumMe_WSM_SF31264.G5380 | 136 | ATPH1 (*ARABIDOPSIS THALIANA* PLECKSTRIN HOMOLOGUE 1) | EXP | 2000 | | |
| CumMe_WSM_SF35856.G5150 | 137 | TIP4; 1 (tonoplast intrinsic protein 4; 1) | EXP | 1575 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF40859. G5250 | 138 | SMT2 (STEROL METHYLTRANSFERASE 2) | EXP | 2000 | | |
| CumMe_WSM_SF41124. G5080 | 139 | 40S ribosomal protein S2 (RPS2C) | EXP | 1006 | Promoter; Leader | 1-883; 884-1006 |
| CumMe_WSM_SF41128. G5410 | 140 | CRY2 (CRYPTOCHROME 2) | EXP | 2000 | | |
| CumMe_WSM_SF41254. G5160 | 141 | GDP-D-glucose Phosphorylase | EXP | 1556 | | |
| CumMe_WSM_SF41588. G5470 | 142 | PRPL11 (PLASTID RIBOSOMAL PROTEIN L11) | EXP | 2000 | | |
| CumMe_WSM_SF41644. G6400 | 143 | SHD (SHEPHERD) | EXP | 2000 | | |
| CumMe_WSM_SF41983. G5000 | 144 | catalytic/coenzyme binding | EXP | 1337 | | |
| CumMe_WSM_SF42075. G5100 | 145 | CPN60B (CHAPERONIN 60 BETA) | EXP | 2000 | | |
| CumMe_WSM_SF42141. G5110 | 146 | cathepsin B-like cysteine protease, putative | EXP | 1212 | | |
| CumMe_WSM_SF44933. G5290 | 147 | EBF1 (EIN3-BINDING F BOX PROTEIN 1) ubiquitin-protein ligase | EXP | 2000 | | |
| CumMe_WSM_SF44977. G5000 | 148 | PAP26 (PURPLE ACID PHOSPHATASE 26) | EXP | 1254 | | |
| CumMe_WSM_SF45441. G5510 | 149 | GAPA-2 (GLYCERALDEHYDE 3-PHOSPHATE DEHYDROGENASE A SUBUNIT 2) | EXP | 2000 | | |
| CumMe_WSM_SF45882. G5120 | 150 | fructose-1,6-bisphosphatase, putative | EXP | 1680 | | |
| CumMe_WSM_SF47806. G5070 | 151 | ATP synthase epsilon chain, mitochondrial | EXP | 1524 | | |
| CumMe_WSM_SF53106. G5190 | 152 | CPN60A (CHAPERONIN-60ALPHA) | EXP | 1851 | | |
| CumMe_WSM_SF65588. G5230 | 153 | vacuolar calcium-binding protein-related | EXP | 2000 | | |
| CumMe_WSM_SF9060. G5120 | 154 | APE2 (ACCLIMATION OF PHOTOSYNTHESIS TO ENVIRONMENT 2) | EXP | 1288 | | |
| P-CUCme.1-1:1:1rc | 155 | Phosphatase 2A | EXP | 2000 | Promoter; Leader; Intron; Leader | 1-1135; 1136-1249; 1250-1990; 1991-2000 |
| EXP-CUCme.4:1:1 | 156 | Ubiquitin 2 | EXP | 2011 | Promoter; Leader; Intron; Leader | 1-1646; 1647-1704; 1705-2005; 2006-2008 |
| P-CUCme.4-1:1:4 | 157 | Ubiquitin 2 | P; L | 1698 | Promoter; Leader | |
| I-CUCme.4-1:1:1 | 158 | Ubiquitin 2 | I; L | 313 | Intron; Leader | |
| EXP-CUCme.5:1:1 | 159 | Ubiquitin 3 | EXP | 2010 | Promoter; Leader; Intron; Leader | 1-748; 749-819; 820-2004; 2005-2007 |
| P-CUCme.5-1:1:3 | 160 | Ubiquitin 3 | P; L | 1107 | Promoter; Leader | |
| I-CUCme.5-1:1:1 | 161 | Ubiquitin 3 | I; L | 903 | Intron; Leader | |
| EXP-CUCme.eEF1a:1:1 | 162 | Elongation Factor 1 alpha | EXP | 1235 | Promoter; Leader; Intron; Leader | 1-617; 618-677; 678-1213; 1214-1235 |
| P-CUCme.eEF1a-1:1:1 | 163 | Elongation Factor 1 alpha | P | 617 | Promoter | |
| L-CUCme.eEF1a-1:1:1 | 164 | Elongation Factor 1 alpha | L | 54 | Leader | |
| I-CUCme.eEF1a-1:1:1 | 165 | Elongation Factor 1 alpha | I | 545 | Intron | |
| L-CUCme.eEF1a-1:1:2 | 166 | Elongation Factor 1 alpha | L | 19 | Leader | |
| P-CUCme.19-1:1:3 | 167 | Chloropyll a/b binding protein | EXP | 2003 | Promoter; Leader | 1-1958; 1959-2003 |
| EXP-CUCme.SAMS2:1:1 | 168 | S-Adenosylmethionine Synthetase | EXP | 2004 | Promoter; Leader; Intron | 1-1067; 1068-1165; 1166-2003 |
| P-CUCme.SAMS2-1:1:1 | 169 | S-Adenosylmethionine Synthetase | P | 1067 | Promoter | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| L-CUCme.SAMS2-1:1:1 | 170 | S-Adenosylmethionine Synthetase | L | 92 | Leader | |
| I-CUCme.SAMS2-1:1:1 | 171 | S-Adenosylmethionine Synthetase | I | 845 | Intron | |
| EXP-CUCme.29:1:1 | 172 | Ribosomal protein S5a | EXP | 2018 | Promoter; Leader; Intron; Leader | 1-490; 491-571; 572-2012; 2013-2018 |
| P-CUCme.29-1:1:4 | 173 | Ribosomal protein S5a | P; L | 565 | Promoter; Leader | |
| I-CUCme.29-1:1:1 | 174 | Ribosomal protein S5a | I; L | 1453 | Intron; Leader | |
| P-CUCme.CumMe_WSM_SF16444.G5140-1:1:1 | 175 | histone H4 | EXP | 1999 | Promoter; Leader; Intron | 1-1946; 947-1999 |
| P-CUCme.CumMe_WSM_SF16563.G5560-1:1:1 | 176 | ATARFB1A (ADP-ribosylation factor B1A) | EXP | 2004 | Promoter; Leader; Intron; Leader | 1-1331; 1332-1429; 1430-1992; 1993-2004 |
| P-CUCme.CumMe_WSM_SF17111.G5790-1:1:1 | 177 | ubiquinol-cytochrome C reductase complex ubiquinone-binding protein | EXP | 2005 | Promoter; Leader | 1-1901; 1902-2005 |
| EXP-CumMe.WSM_SF17252.G7330:1:1 | 178 | nascent polypeptide-associated complex (NAC) domain-containing protein | EXP | 1978 | Promoter; Leader; Intron; Leader | 1-1167; 1168-1269; 1270-1972; 1973-1975 |
| P-CUCme.WSM_SF17252.G7330-1:1:1 | 179 | nascent polypeptide-associated complex (NAC) domain-containing protein | P; L | 1263 | Promoter; Leader | |
| I-CUCme.WSM_SF17252.G7330-1:1:1 | 180 | nascent polypeptide-associated complex (NAC) domain-containing protein | I; L | 715 | Intron; Leader | |
| P-CUCme.CumMe_WSM_SF18488.G5340-1:1:1 | 181 | caffeoyl-CoA 3-O-methyltransferase | EXP | 2000 | Promoter; Leader | 1-923; 1924-2000 |
| P-CUCme.CumMe_WSM_SF18536.G6480-1:1:1 | 182 | MBF1A (MULTIPROTEIN BRIDGING FACTOR 1A) transcription coactivator | EXP | 2000 | Promoter; Leader; Intron | |
| P-CUCme.CumMe_WSM_SF18634.G5190-1:1:1 | 183 | 60S ribosomal protein L23 (RPL23A) | EXP | 1989 | Promoter; Leader | 1-1960; 1961-1989 |
| P-CUCme.CumMe_WSM_SF18716.G5860-1:1:1 | 184 | Auxin-induced prtoein X10A-like | EXP | 1463 | Promoter; Leader | 1-1392; 1393-1463 |
| EXP-CUCme.WSM_SF19064.G5690:1:1 | 185 | histone H3.2 | EXP | 2006 | Promoter; Leader; Intron; Leader | 1-1581; 1582-1670; 1671-2000; 2001-2003 |
| P-CUCme.WSM_SF19064.G5690-1:1:1 | 186 | histone H3.2 | P; L | 1664 | Promoter; Leader | |
| I-CUCme.WSM_SF19064.G5690-1:1:1 | 187 | histone H3.2 | I; L | 342 | Intron; Leader | |
| P-CUCme.CumMe_WSM_SF19647.G5760-1:1:1 | 188 | 6-phosphogluconate dehydrogenase family protein | EXP | 2003 | Promoter; Leader; Intron; Leader | 1-939; 940-1024; 1025-1995; 1996-2003 |
| P-CUCme.CumMe_WSM_SF19839.G5090-1:1:1 | 189 | ATPDX1.1 (pyridoxine biosynthesis 1.1) | EXP | 1024 | Promoter; Leader | 1-904; 905-1024 |
| P-CUCme.CumMe_WSM_SF20132.G5560-1:1:1 | 190 | peroxidase 21 | EXP | 2001 | Promoter; Leader | 1-1962; 1963-2001 |
| P-CUCme.CumMe_WSM_SF206458.G5970-1:1:1 | 191 | FAD2 (FATTY ACID DESATURASE 2) | EXP | 4175 | Promoter; Leader; Intron; Leader | 1-2171; 2172-2325; 2326-4155; 4156-4175 |
| P-CUCme.CumMe_WSM_SF22531.G5120-1:1:1 | 192 | eukaryotic translation initiation factor 1A, putative | EXP | 1999 | Promoter; Leader; Intron; Leader | 1-759; 760-858; 859-1978; 1979-1999 |
| P-CUCme.CumMe_WSM_SF23760.G5200-1:1:1 | 193 | NDPK1; ATP binding/nucleoside diphosphate kinase | EXP | 2000 | Promoter; Leader | 1-1901; 1902-2000 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| P-CUCme.CumMe_WSM_SF23906.G6180-1:1:1 | 194 | PSBX (photosystem II subunit X) | EXP | 2000 | Promoter; Leader | |
| P-CUCme.CumMe_WSM_SF25141.G5160-1:1:2 | 195 | isocitrate dehydrogenase, putative | EXP | 1400 | Promoter; Leader | 1-1325; 1326-1400 |
| P-CUCme.CumMe_WSM_SF25355.G5000-1:1:1 | 196 | LOS1; copper ion binding translation elongation factor | EXP | 2019 | Promoter; Leader; Intron; Leader; CDS | 1-734; 735-811; 812-1340; 1341-1360; 1361-2019 |
| P-CUCme.CumMe_WSM_SF25936.G5450-1:1:1 | 197 | mitochondrial substrate carrier family protein | EXP | 1999 | Promoter; Leader | 1-1877; 1878-1999 |
| P-CUCme.CumMe_WSM_SF35856.G5150-1:1:1 | 198 | TIP4; 1 (tonoplast intrinsic protein 4; 1) | EXP | 1578 | | |
| P-CUCme.CumMe_WSM_SF41124.G5080-1:1:1 | 199 | 40S ribosomal protein S2 (RPS2C) | EXP | 1023 | Promoter; Leader | 1-945; 946-1023 |
| P-CUCme.20-1:3 | 211 | Chloropyll a/b binding protein | EXP | 1446 | Promoter; Leader | 1-1390; 1391-1446 |
| EXP-CUCme.29:1:2 | 212 | Ribosomal protein S5a | EXP | 2018 | Promoter; Leader; Intron; Leader | 1-490; 491-571; 572-2011; 2013-2018 |

As shown in Table 1, for example, the transcriptional regulatory expression element group (EXP) designated EXP-CUCme.Ubq1:1:1 (SEQ ID NO: 1), with components isolated from *C. melo*, comprises a 2068 base pair sized (bp) promoter element, P-CUCme.Ubq1-1:1:15 (SEQ ID NO: 2), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:2 (SEQ ID NO: 5), with components isolated from *C. melo*, comprises a 1459 bp promoter element, P-CUCme.Ubq1-1:1:16 (SEQ ID NO: 6), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:3 (SEQ ID NO: 7), with components isolated from *C. melo*, comprises a 964 bp promoter element, P-CUCme.Ubq1-1:1:17 (SEQ ID NO: 8), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:4 (SEQ ID NO: 9), with components isolated from *C. melo*, comprises a 479 bp promoter element, P-CUCme.Ubq1-1:1:18 (SEQ ID NO: 10), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:5 (SEQ ID NO: 11), with components isolated from *C. melo*, comprises a 173 bp promoter element, P-CUCme.Ubq1-1:1:19 (SEQ ID NO: 12), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4).

An alignment of the ubiquitin 1 promoter sequences is provided in FIGS. 1*a*-1*f*. The promoter elements, P-CUCme.Ubq1-1:1:16 (SEQ ID NO: 6), P-CUCme.Ubq1-1:1:17 (SEQ ID NO: 8), P-CUCme.Ubq1-1:1:18 (SEQ ID NO: 10) and P-CUCme.Ubq1-1:1:19 (SEQ ID NO: 12) were built by introducing varying lengths of deletions from the 5' end of the promoter, P-CUCme.Ubq1-1:1:15 (SEQ ID NO: 2).

Example 2

Analysis of Regulatory Elements Driving GUS in Soy Cotyledon Protoplasts

Soybean cotyledon protoplasts were transformed with plant expression vectors containing a test transcriptional regulatory expression element group driving expression of the β-glucuronidase (GUS) transgene and compared to GUS expression in leaf protoplasts in which expression of GUS is driven by known constitutive promoters.

Expression of a transgene driven by EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) was compared with expression from known constitutive promoters. Each plant expression vector was comprised of a right border region from *Agrobacterium tumefaciens*, a first transgene cassette comprised of an EXP sequence or known constitutive promoter operably linked 5' to a coding sequence for β-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the *Arabidopsis* Actin 7 promoter) or the antibiotic, kanamycin and a left border region from *A. tumefaciens*. A promoterless control plant expression vector (pMON124912) served as a negative control for expression. The foregoing test and constitutive expression element groups were cloned into plant expression vectors as shown in Table 2 below.

TABLE 2

Plant expression vectors and corresponding expression element group and 3' UTR.

| Expression Vector | Regulatory Element | SEQ ID NO: | 3' UTR |
|---|---|---|---|
| pMON80585 | EXP-At.Atntt1:1:2 | 200 | T-Ps.RbcS2-E9-1:1:6 |
| pMON109584 | EXP-CaMV.35S-enh + Ph.DnaK:1:3 | 201 | T-Gb.E6-3b:1:1 |
| pMON118756 | EXP-At.Act7:1:11 | 202 | T-Gb.E6-3b:1:1 |
| pMON124912 | No promoter | | T-Gb.FbL2-1:1:1 |
| pMON138776 | EXP-CUCme.Ubq1:1:1 | 1 | T-Gb.FbL2-1:1:1 |
| pMON138777 | EXP-CUCme.Ubq1:1:2 | 5 | T-Gb.FbL2-1:1:1 |
| pMON138778 | EXP-CUCme.Ubq1:1:3 | 7 | T-Gb.FbL2-1:1:1 |
| pMON138779 | EXP-CUCme.Ubq1:1:4 | 9 | T-Gb.FbL2-1:1:1 |
| pMON138780 | EXP-CUCme.Ubq1:1:5 | 11 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 207), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 208), operably linked 5' to a 3' termination region from the *Agrobacterium tumefaciens* nopaline synthase gene.

The plant expression vectors, pMON80585, pMON109584, pMON118756, pMON124912, pMON138776, pMON138777, pMON138778, pMON138779 and pMON138780 were used to transform soybean cotyledon protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). Sample measurements were made using 3 or 4 replicates per transformation. The average GUS and luciferase values are presented in Table 3 below.

TABLE 3

Average GUS and luciferase expression values and GUS/luciferase ratios.

| Construct | Regulatory Element | SEQ ID NO: | Average GUS | Average FLuc | Average RLuc | GUS/ FLuc | GUS/ RLuc |
|---|---|---|---|---|---|---|---|
| pMON80585 | EXP-At.Atntt1:1:2 | 200 | 55173 | 6498 | 30503 | 8.49 | 1.81 |
| pMON109584 | EXP-CaMV.35S-enh + Ph.DnaK:1:3 | 200 | 24940 | 5050.75 | 35495 | 4.94 | 0.70 |
| pMON118756 | EXP-At.Act7:1:11 | 201 | 9871 | 6880 | 40850 | 1.43 | 0.24 |
| pMON124912 | No promoter | | 2000 | 11670 | 73187 | 0.17 | 0.03 |
| pMON138776 | EXP-CUCme.Ubq1:1:1 | 1 | 26972 | 6467.25 | 37200 | 4.17 | 0.73 |
| pMON138777 | EXP-CUCme.Ubq1:1:2 | 5 | 41307 | 5902.5 | 24396 | 7.00 | 1.69 |
| pMON138778 | EXP-CUCme.Ubq1:1:3 | 7 | 90140 | 10710.5 | 60983 | 8.42 | 1.48 |
| pMON138779 | EXP-CUCme.Ubq1:1:4 | 9 | 35526 | 5590 | 28001 | 6.36 | 1.27 |
| pMON138780 | EXP-CUCme.Ubq1:1:5 | 11 | 23298 | 4483.25 | 19075 | 5.20 | 1.22 |

To compare the relative activity of each promoter in soybean cotyledon protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 4 below shows the GUS to firefly luciferase (FLuc) ratios normalized with respect to EXP-At.Act7:1:11 and EXP-CaMV.35S-enh+Ph-.DnaK:1:3. Table 5 below shows the GUS to *renilla* luciferase (RLuc) ratios normalized with respect to EXP-At.Act7:1:11 and EXP-CaMV.35S-enh+Ph.DnaK:1:3.

TABLE 4

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh + Ph.DnaK:1:3 |
|---|---|---|---|---|
| pMON80585 | EXP-At.Atntt1:1:2 | 200 | 5.92 | 1.72 |
| pMON109584 | EXP-CaMV.35S-enh + Ph.DnaK:1:3 | 201 | 3.44 | 1.00 |
| pMON118756 | EXP-At.Act7:1:11 | 202 | 1.00 | 0.29 |
| pMON124912 | No promoter | | 0.12 | 0.03 |
| pMON138776 | EXP-CUCme.Ubq1:1:1 | 1 | 2.91 | 0.84 |
| pMON138777 | EXP-CUCme.Ubq1:1:2 | 5 | 4.88 | 1.42 |
| pMON138778 | EXP-CUCme.Ubq1:1:3 | 7 | 5.87 | 1.70 |
| pMON138779 | EXP-CUCme.Ubq1:1:4 | 9 | 4.43 | 1.29 |
| pMON138780 | EXP-CUCme.Ubq1:1:5 | 11 | 3.62 | 1.05 |

TABLE 5

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh + Ph.DnaK:1:3 |
|---|---|---|---|---|
| pMON80585 | EXP-At.Atntt1:1:2 | 200 | 7.49 | 2.57 |
| pMON109584 | EXP-CaMV.35S-enh + Ph.DnaK:1:3 | 201 | 2.91 | 1.00 |
| pMON118756 | EXP-At.Act7:1:11 | 202 | 1.00 | 0.34 |
| pMON124912 | No promoter | | 0.11 | 0.04 |
| pMON138776 | EXP-CUCme.Ubq1:1:1 | 1 | 3.00 | 1.03 |
| pMON138777 | EXP-CUCme.Ubq1:1:2 | 5 | 7.01 | 2.41 |
| pMON138778 | EXP-CUCme.Ubq1:1:3 | 7 | 6.12 | 2.10 |
| pMON138779 | EXP-CUCme.Ubq1:1:4 | 9 | 5.25 | 1.81 |
| pMON138780 | EXP-CUCme.Ubq1:1:5 | 11 | 5.05 | 1.74 |

As can be seen in Tables 4 and 5 above, each of the expression element groups EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) demonstrated the ability of driving transgene expression in soybean cotyledon protoplasts. Expression levels were greater than that of EXP-At.Act7:1:11 and was 2.9 to 5.8 (FLuc) or 3 to 7 (RLuc) fold higher than EXP-At.Act7:1:11 in this assay. Expression was equivalent or higher than expression observed for EXP-CaMV.35S-enh+Ph.DnaK:1:3. Expression levels were 0.8 to 1.7 (FLuc) or 1 to 2.4 (RLuc) fold higher than expression observed for EXP-CaMV.35S-enh+Ph.DnaK:1:3.

Example 3

Analysis of Regulatory Elements Driving GUS in Bombarded Soybean Leaves and Roots Soybean leaves and roots were transformed with plant expression vectors containing a test transcriptional regulatory expression element group driving expression of the β-glucuronidase (GUS) transgene and compared to GUS expression in roots and leaves in which expression of GUS is driven by known constitutive promoters.

Expression of a transgene driven by EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) was compared with expression from known constitutive promoters in particle bombarded soybean leaves and roots. The plant expression vectors used for transformation of leaves and roots was the same as those presented in Table 2 of Example 2 above.

The plant expression vectors, pMON80585, pMON109584, pMON118756, pMON124912, pMON138776, pMON138777, pMON138778, pMON138779 and pMON138780 were used to transform soybean leaves and roots using particle bombardment transformation methods.

Briefly, A3244 soybean seeds were surface sterilized and allowed to germinate in trays with a photoperiod of 16 hours light and 8 hours of darkness. After approximately 13 days, leaf and root tissue was harvested under sterile conditions from the seedlings and used for bombardment. The tissue samples were randomly placed on a petri dish containing plant culture medium. Ten micrograms of plasmid DNA was used to coat 0.6 micron gold particles (Catalog #165-2262 Bio-Rad, Hercules, Calif.) for bombardment. Macro-carriers were loaded with the DNA-coated gold particles (Catalog #165-2335 Bio-Rad, Hercules Calif.). A PDS 1000/He biolistic gun was used for transformation (Catalog #165-2257 Bio-Rad, Hercules Calif.). The bombarded root and leaf tissues were allowed to incubate in the dark for 24 hours at 26 degrees Celsius. Following this overnight incubation, the tissues were stained in solution for GUS expression overnight at 37 degrees Celsius. After staining overnight, the tissues were soaked in 70% ethanol overnight to remove chlorophyll and reveal the GUS staining. The tissues were then photographed and a rating scale, of "0","+" to "++++++" reflecting the level of GUS expression is assigned to each construct (0- no expression, + to +++++- low to high, respectively).

Expression of the GUS transgene demonstrated in each tissue is used to infer the relative potential level and specificity of each element's capacity to drive transgene expression in stably transformed corn plants. Average GUS expression ratings are provided in Table 6 below.

TABLE 6

GUS expression ratings for particle bombarded leaf and root.

| Construct | Regulatory Element | SEQ ID NO: | Leaf Expression Rating | Root Expression Rating |
|---|---|---|---|---|
| pMON80585 | EXP-At.Atntt1:1:2 | 200 | ++++ | ++ |
| pMON109584 | EXP-CaMV.35S-enh + Ph.DnaK:1:3 | 201 | +++++ | +++ |
| pMON118756 | EXP-At.Act7:1:11 | 202 | ++++ | ++ |
| pMON124912 | No promoter | | 0 | 0 |
| pMON138776 | EXP-CUCme.Ubq1:1:1 | 1 | ++++ | +++ |
| pMON138777 | EXP-CUCme.Ubq1:1:2 | 5 | +++ | ++ |
| pMON138778 | EXP-CUCme.Ubq1:1:3 | 7 | +++ | ++ |
| pMON138779 | EXP-CUCme.Ubq1:1:4 | 9 | +++ | ++ |
| pMON138780 | EXP-CUCme.Ubq1:1:5 | 11 | ++ | + |

As can be seen in Table 6 above, each of the expression element groups EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) demonstrated the ability of driving transgene expression in particle bombarded transformed leaf and root tissues.

Example 4

Analysis of Regulatory Elements Driving GUS in Soy Cotyledon Protoplasts

Soybean cotyledon protoplasts were transformed with plant expression vectors containing a test transcriptional regulatory expression element group driving expression of the β-glucuronidase (GUS) transgene and compared to GUS expression in leaf protoplasts in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups. Each plant expression vector was comprised of a right border region from *Agrobacterium tumefaciens*, a first transgene cassette comprised of a test promoter or known constitutive promoter operably linked 5' to a coding sequence for β-glucuronidase (GUS, SEQ ID NO: 206) containing a processable intron derived from the potato light-inducible tissue-specific ST-LS 1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the *Arabidopsis* Actin 7 promoter) or the antibiotic, kanamycin and a left border region from *A. tumefaciens*. A promoterless control plant expression vector (pMON 124912) served as a negative control for expression. The foregoing test and constitutive expression element groups were cloned into plant expression vectors as shown in Table 7 below.

TABLE 7

Plant expression vectors and corresponding expression element group and 3' UTR.

| Construct | Regulatory Element | SEQ ID NO: | 3' UTR |
|---|---|---|---|
| pMON80585 | EXP-At.Atntt1:1:2 | 200 | T-Ps.RbcS2-E9-1:1:6 |
| pMON109584 | EXP-CaMV.35S-enh + Ph.DnaK:1:3 | 201 | T-Gb.E6-3b:1:1 |
| pMON118756 | EXP-At.Act7:1:11 | 202 | T-Gb.E6-3b:1:1 |
| pMON124912 | Promoterless | | T-Gb.FbL2-1:1:1 |
| pMON140818 | P-CUCme.1-1:1:1rc | 155 | T-Gb.FbL2-1:1:1 |
| pMON140819 | P-CUCme.2-1:1:1 | 14 | T-Gb.FbL2-1:1:1 |
| pMON140820 | P-CUCme.3-1:1:3 | 15 | T-Gb.FbL2-1:1:1 |
| pMON140821 | EXP-CUCme.4:1:1 | 156 | T-Gb.FbL2-1:1:1 |
| pMON140822 | EXP-CUCme.5:1:1 | 159 | T-Gb.FbL2-1:1:1 |
| pMON140823 | P-CUCme.6-1:1:1 | 18 | T-Gb.FbL2-1:1:1 |
| pMON140824 | P-CUCme.8-1:1:2 | 19 | T-Gb.FbL2-1:1:1 |
| pMON140825 | P-CUCme.9-1:1:2 | 20 | T-Gb.FbL2-1:1:1 |
| pMON140826 | P-CUCme.10-1:1:1 | 21 | T-Gb.FbL2-1:1:1 |
| pMON140827 | EXP-CUCme.eEF1a:1:1 | 162 | T-Gb.FbL2-1:1:1 |
| pMON140828 | P-CUCme.15-1:1:2 | 23 | T-Gb.FbL2-1:1:1 |
| pMON140829 | P-CUCme.16a-1:1:2 | 24 | T-Gb.FbL2-1:1:1 |
| pMON140830 | P-CUCme.17-1:1:2 | 26 | T-Gb.FbL2-1:1:1 |
| pMON140831 | P-CUCme.18-1:1:2 | 27 | T-Gb.FbL2-1:1:1 |
| pMON140832 | P-CUCme.19-1:1:3 | 167 | T-Gb.FbL2-1:1:1 |
| pMON140833 | P-CUCme.20-1:3 | 211 | T-Gb.FbL2-1:1:1 |
| pMON140834 | P-CUCme.21-1:1:1 | 30 | T-Gb.FbL2-1:1:1 |

TABLE 7-continued

Plant expression vectors and corresponding expression element group and 3' UTR.

| Construct | Regulatory Element | SEQ ID NO: | 3' UTR |
|---|---|---|---|
| pMON140835 | P-CUCme.22-1:1:3 | 31 | T-Gb.FbL2-1:1:1 |
| pMON140836 | EXP-CUCme.SAMS2:1:1 | 168 | T-Gb.FbL2-1:1:1 |
| pMON140837 | P-CUCme.26-1:1:2 | 33 | T-Gb.FbL2-1:1:1 |
| pMON140838 | P-CUCme.28-1:1:2 | 34 | T-Gb.FbL2-1:1:1 |
| pMON140839 | EXP-CUCme.29:1:2 | 212 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 207), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 208), operably linked 5' to a 3' termination region from the *Agrobacterium tumefaciens* nopaline synthase gene.

The plant expression vectors, pMON80585, pMON109584, pMON118756, pMON124912, pMON140818, pMON140819, pMON140820, pMON140821, pMON140822, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform soybean cotyledon protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). Sample measurements were made using 3 or 4 replicates per transformation. The average GUS and luciferase values are presented in Table 8 below.

TABLE 8

Average GUS and luciferase expression values and GUS/luciferase ratios.

| Construct | Regulatory Element | SEQ ID NO: | Average GUS | Average FLuc | Average RLuc | GUS/FLuc | GUS/RLuc |
|---|---|---|---|---|---|---|---|
| pMON80585 | EXP-At.Atntt1:1:2 | 200 | 586 | 5220.7 | 8323 | 0.1100 | 0.0700 |
| pMON109584 | EXP-CaMV.35S-enh + Ph.DnaK:1:3 | 201 | 5768 | 4275 | 15098 | 1.3500 | 0.3800 |
| pMON118756 | EXP-At.Act7:1:11 | 202 | 773 | 7722 | 10545 | 0.1000 | 0.0700 |
| pMON124912 | Promoterless | | 48 | 9746.5 | 13905 | 0.0000 | 0.0000 |
| pMON140818 | P-CUCme.1-1:1:1rc | 155 | 194 | 4772 | 6363 | 0.0400 | 0.0300 |
| pMON140819 | P-CUCme.2-1:1:1 | 14 | 171 | 6855 | 10123 | 0.0200 | 0.0200 |
| pMON140820 | P-CUCme.3-1:1:3 | 15 | 37 | 7089.3 | 9593 | 0.0100 | 0.0000 |
| pMON140821 | EXP-CUCme.4:1:1 | 156 | 4211 | 7626.8 | 13935 | 0.5500 | 0.3000 |
| pMON140822 | EXP-CUCme.5:1:1 | 159 | 626 | 15609.3 | 21140 | 0.0400 | 0.0300 |
| pMON140823 | P-CUCme.6-1:1:1 | 18 | 331 | 15178.5 | 22818 | 0.0200 | 0.0100 |
| pMON140824 | P-CUCme.8-1:1:2 | 19 | 238 | 17514.5 | 28429 | 0.0100 | 0.0100 |
| pMON140825 | P-CUCme.9-1:1:2 | 20 | 510 | 13208 | 19567 | 0.0400 | 0.0300 |
| pMON140826 | P-CUCme.10-1:1:1 | 21 | 352 | 14805.3 | 22200 | 0.0200 | 0.0200 |
| pMON140827 | EXP-CUCme.eEF1a:1:1 | 162 | 724 | 9326.8 | 14476 | 0.0800 | 0.0500 |
| pMON140828 | P-CUCme.15-1:1:2 | 23 | 304 | 11798 | 17486 | 0.0300 | 0.0200 |
| pMON140829 | P-CUCme.16a-1:1:2 | 24 | 88 | 5429 | 9596 | 0.0200 | 0.0100 |
| pMON140830 | P-CUCme.17-1:1:2 | 26 | 180 | 10477.8 | 15291 | 0.0200 | 0.0100 |
| pMON140831 | P-CUCme.18-1:1:2 | 27 | 111 | 5059.3 | 6778 | 0.0200 | 0.0200 |
| pMON140832 | P-CUCme.19-1:1:3 | 167 | 121 | 3765 | 6032 | 0.0300 | 0.0200 |
| pMON140833 | P-CUCme.20-1:3 | 211 | 155 | 10458.8 | 14748 | 0.0100 | 0.0100 |
| pMON140834 | P-CUCme.21-1:1:1 | 30 | 582 | 7760 | 11440 | 0.0800 | 0.0500 |
| pMON140835 | P-CUCme.22-1:1:3 | 31 | 400 | 11393.8 | 18654 | 0.0400 | 0.0200 |
| pMON140836 | EXP-CUCme.SAMS2:1:1 | 168 | 568 | 9466.3 | 13962 | 0.0600 | 0.0400 |
| pMON140837 | P-CUCme.26-1:1:2 | 33 | 87 | 6683 | 8494 | 0.0100 | 0.0100 |
| pMON140838 | P-CUCme.28-1:1:2 | 34 | 171 | 19104.8 | 29619 | 0.0100 | 0.0100 |
| pMON140839 | EXP-CUCme.29:1:2 | 212 | 90 | 11247.3 | 15919 | 0.0100 | 0.0057 |

To compare the relative activity of each promoter in soybean cotyledon protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 9 below shows the GUS to firefly luciferase (FLuc) ratios normalized with respect to EXP-At.Act7:1:11 and EXP-CaMV.35S-enh+Ph.DnaK:1:3. Table 10 below shows the GUS to *renilla* luciferase (RLuc) ratios normalized with respect to EXP-At.Act7:1:11 and EXP-CaMV.35S-enh+Ph.DnaK:1:3.

TABLE 9

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh + Ph.DnaK:1:3 |
|---|---|---|---|---|
| pMON80585 | EXP-At.Atntt1:1:2 | 200 | 1.12 | 0.08 |
| pMON109584 | EXP-CaMV.35S-enh + Ph.DnaK:1:3 | 201 | 13.48 | 1.00 |
| pMON118756 | EXP-At.Act7:1:11 | 202 | 1.00 | 0.07 |
| pMON124912 | Promoterless | | 0.05 | 0.00 |
| pMON140818 | P-CUCme.1-1:1:1rc | 155 | 0.41 | 0.03 |
| pMON140819 | P-CUCme.2-1:1:1 | 14 | 0.25 | 0.02 |
| pMON140820 | P-CUCme.3-1:1:3 | 15 | 0.05 | 0.00 |
| pMON140821 | EXP-CUCme.4:1:1 | 156 | 5.52 | 0.41 |
| pMON140822 | EXP-CUCme.5:1:1 | 159 | 0.40 | 0.03 |
| pMON140823 | P-CUCme.6-1:1:1 | 18 | 0.22 | 0.02 |
| pMON140824 | P-CUCme.8-1:1:2 | 19 | 0.14 | 0.01 |
| pMON140825 | P-CUCme.9-1:1:2 | 20 | 0.39 | 0.03 |
| pMON140826 | P-CUCme.10-1:1:1 | 21 | 0.24 | 0.02 |
| pMON140827 | EXP-CUCme.eEF1a:1:1 | 162 | 0.78 | 0.06 |
| pMON140828 | P-CUCme.15-1:1:2 | 23 | 0.26 | 0.02 |
| pMON140829 | P-CUCme.16a-1:1:2 | 24 | 0.16 | 0.01 |
| pMON140830 | P-CUCme.17-1:1:2 | 26 | 0.17 | 0.01 |
| pMON140831 | P-CUCme.18-1:1:2 | 27 | 0.22 | 0.02 |
| pMON140832 | P-CUCme.19-1:1:3 | 167 | 0.32 | 0.02 |
| pMON140833 | P-CUCme.20-1:3 | 211 | 0.15 | 0.01 |
| pMON140834 | P-CUCme.21-1:1:1 | 30 | 0.75 | 0.06 |
| pMON140835 | P-CUCme.22-1:1:3 | 31 | 0.35 | 0.03 |
| pMON140836 | EXP-CUCme.SAMS2:1:1 | 168 | 0.60 | 0.04 |
| pMON140837 | P-CUCme.26-1:1:2 | 33 | 0.13 | 0.01 |
| pMON140838 | P-CUCme.28-1:1:2 | 34 | 0.09 | 0.01 |
| pMON140839 | EXP-CUCme.29:1:2 | 212 | 0.08 | 0.01 |

TABLE 10

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh + Ph.DnaK:1:3 |
|---|---|---|---|---|
| pMON80585 | EXP-At.Atntt1:1:2 | 200 | 0.96 | 0.18 |
| pMON109584 | EXP-CaMV.35S-enh + Ph.DnaK:1:3 | 201 | 5.21 | 1.00 |
| pMON118756 | EXP-At.Act7:1:11 | 202 | 1.00 | 0.19 |
| pMON124912 | Promoterless | | 0.05 | 0.01 |
| pMON140818 | P-CUCme.1-1:1:1rc | 155 | 0.42 | 0.08 |
| pMON140819 | P-CUCme.2-1:1:1 | 14 | 0.23 | 0.04 |
| pMON140820 | P-CUCme.3-1:1:3 | 15 | 0.05 | 0.01 |
| pMON140821 | EXP-CUCme.4:1:1 | 156 | 4.12 | 0.79 |
| pMON140822 | EXP-CUCme.5:1:1 | 159 | 0.40 | 0.08 |
| pMON140823 | P-CUCme.6-1:1:1 | 18 | 0.20 | 0.04 |
| pMON140824 | P-CUCme.8-1:1:2 | 19 | 0.11 | 0.02 |
| pMON140825 | P-CUCme.9-1:1:2 | 20 | 0.36 | 0.07 |
| pMON140826 | P-CUCme.10-1:1:1 | 21 | 0.22 | 0.04 |
| pMON140827 | EXP-CUCme.eEF1a:1:1 | 162 | 0.68 | 0.13 |
| pMON140828 | P-CUCme.15-1:1:2 | 23 | 0.24 | 0.05 |
| pMON140829 | P-CUCme.16a-1:1:2 | 24 | 0.13 | 0.02 |
| pMON140830 | P-CUCme.17-1:1:2 | 26 | 0.16 | 0.03 |
| pMON140831 | P-CUCme.18-1:1:2 | 27 | 0.22 | 0.04 |
| pMON140832 | P-CUCme.19-1:1:3 | 167 | 0.27 | 0.05 |
| pMON140833 | P-CUCme.20-1:3 | 211 | 0.14 | 0.03 |
| pMON140834 | P-CUCme.21-1:1:1 | 30 | 0.69 | 0.13 |
| pMON140835 | P-CUCme.22-1:1:3 | 31 | 0.29 | 0.06 |
| pMON140836 | EXP-CUCme.SAMS2:1:1 | 168 | 0.55 | 0.11 |

TABLE 10-continued

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh + Ph.DnaK:1:3 |
|---|---|---|---|---|
| pMON140837 | P-CUCme.26-1:1:2 | 33 | 0.14 | 0.03 |
| pMON140838 | P-CUCme.28-1:1:2 | 34 | 0.08 | 0.02 |
| pMON140839 | EXP-CUCme.29:1:2 | 212 | 0.08 | 0.01 |

As can be seen in Tables 9 and 10, most of the expression element groups tested, demonstrated the ability to drive transgene expression in soybean cotyledon protoplast cells. One expression element group, EXP-CUCme.4:1:1 (SEQ ID NO: 156) demonstrated levels of transgene expression higher than that of EXP-At.Act7:1:11 in this assay.

Example 5

Analysis of Regulatory Elements Driving GUS in Bombarded Soybean Leaves and Roots Soybean leaves and roots were transformed with plant expression vectors containing a test transcriptional regulatory expression element group driving expression of the β-glucuronidase (GUS) transgene and compared to GUS expression in roots and leaves in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups in particle bombarded soybean leaves and roots. The plant expression vectors used for transformation of leaves and roots was the same as those presented in Table 7 of Example 4 above.

The plant expression vectors, pMON80585, pMON109584, pMON118756, pMON124912, pMON140818, pMON140819, pMON140820, pMON140821, pMON140822, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform soybean leaves and roots using particle bombardment transformation methods.

Briefly, A3244 soybean seeds were surface sterilized and allowed to germinate in trays with a photoperiod of 16 hours light and 8 hours of darkness. After approximately 13 days, leaf and root tissue was harvested under sterile conditions from the seedlings and used for bombardment. The tissue samples were randomly placed on a petri dish containing plant culture medium. Ten micrograms of plasmid DNA was used to coat 0.6 micron gold particles (Catalog #165-2262 Bio-Rad, Hercules, Calif.) for bombardment. Macro-carriers were loaded with the DNA-coated gold particles (Catalog #165-2335 Bio-Rad, Hercules Calif.). A PDS 1000/He biolistic gun was used for transformation (Catalog #165-2257 Bio-Rad, Hercules Calif.). The bombarded root and leaf tissues were allowed to incubate in the dark for 24 hours at 26 degrees Celsius. Following this overnight incubation, the tissues were stained in solution for GUS expression overnight at 37 degrees Celsius. After staining overnight, the tissues were soaked in 70% ethanol overnight to remove chlorophyll and reveal the GUS staining. The tissues were then photographed and a rating scale of "0", "+" to "++++++" reflecting the level of GUS expression is assigned to each construct (0- no expression, + to ++++++- low to high, respectively).

Expression of the GUS transgene demonstrated in each tissue is used to infer the relative potential level and specificity of each element's capacity to drive transgene expression in stably transformed corn plants. Average GUS expression ratings are provided in Table 11 below.

TABLE 11

GUS expression ratings for particle bombarded leaf and root.

| Construct | Regulatory Element | SEQ ID NO: | Leaf Expression | Root Expression |
|---|---|---|---|---|
| pMON80585 | EXP-At.Atntt1:1:2 | 200 | +++ | +++ |
| pMON109584 | EXP-CaMV.35S-enh + Ph.DnaK:1:3 | 201 | +++++ | ++ |
| pMON118756 | EXP-At.Act7:1:11 | 202 | ++++ | +++ |
| pMON124912 | Promoterless | | 0 | 0 |
| pMON140818 | P-CUCme.1-1:1:1rc | 155 | +++ | + |
| pMON140819 | P-CUCme.2-1:1:1 | 14 | ++ | + |
| pMON140820 | P-CUCme.3-1:1:3 | 15 | 0 | 0 |
| pMON140821 | EXP-CUCme.4:1:1 | 156 | ++++++ | +++ |
| pMON140822 | EXP-CUCme.5:1:1 | 159 | ++ | + |
| pMON140823 | P-CUCme.6-1:1:1 | 18 | ++ | + |
| pMON140824 | P-CUCme.8-1:1:2 | 19 | + | + |
| pMON140825 | P-CUCme.9-1:1:2 | 20 | ++ | + |
| pMON140826 | P-CUCme.10-1:1:1 | 21 | +++ | +++ |
| pMON140827 | EXP-CUCme.eEF1a:1:1 | 162 | ++++ | +++ |
| pMON140828 | P-CUCme.15-1:1:2 | 23 | + | + |
| pMON140829 | P-CUCme.16a-1:1:2 | 24 | + | − |
| pMON140830 | P-CUCme.17-1:1:2 | 26 | ++++ | + |
| pMON140831 | P-CUCme.18-1:1:2 | 27 | +++ | + |
| pMON140832 | P-CUCme.19-1:1:3 | 167 | + | + |
| pMON140833 | P-CUCme.20-1:3 | 211 | + | + |
| pMON140834 | P-CUCme.21-1:1:1 | 30 | + | + |
| pMON140835 | P-CUCme.22-1:1:3 | 31 | ++++ | + |
| pMON140836 | EXP-CUCme.SAMS2:1:1 | 168 | +++++ | +++ |

TABLE 11-continued

GUS expression ratings for particle bombarded leaf and root.

| Construct | Regulatory Element | SEQ ID NO: | Leaf Expression | Root Expression |
|---|---|---|---|---|
| pMON140837 | P-CUCme.26-1:1:2 | 33 | + | + |
| pMON140838 | P-CUCme.28-1:1:2 | 34 | + | + |
| pMON140839 | EXP-CUCme.29:1:2 | 212 | + | + |

As can be seen in Table 11 above, all but one of the expression element groups demonstrated the ability to drive transgene expression in particle bombarded soybean leaf and root tissue. Two expression element groups, P-CUCme.28-1:1:2 (SEQ ID NO: 34) and EXP-CUCme.4:1:1 (SEQ ID NO: 156) demonstrated similar or higher levels of expression relative to expression driven by EXP-CaMV.35S-enh+Ph.DnaK:1:3 in this assay.

Example 6

Analysis of Regulatory Elements Driving GUS in Soy Cotyledon Protoplast Using Transgene Cassette Amplicons Soybean cotyledon protoplasts were transformed with transgene cassette amplicons containing a transcriptional regulatory expression element group driving expression of the β-glucuronidase (GUS) transgene and compared to GUS expression in leaf protoplasts in which expression of GUS is driven by known constitutive promoters. The transgene cassette amplicons were comprised of an EXP sequence, operably linked to a GUS coding sequence (GUS, SEQ ID NO: 206), operably linked to a 3' UTR (T-Gb.FbL2-1:1:1, SEQ ID NO: 205). Average GUS expression was compared to the control EXP elements, P-CaMV.35S-enh-1:1:102/L-CaMV.35S-1:1:2 (SEQ ID NO: 210) and EXP-At.Atntt1:1:2 (SEQ ID NO: 200).

A plasmid, for use in co-transformation and normalization of data was also used in a similar manner as that described above in Example 2. The transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209).

Table 12 below shows the mean GUS expression values conferred by each transgene amplicon. Table 13 below shows the GUS to firefly luciferase (FLuc) ratios normalized with respect to EXP-At.Atntt1:1:2 and P-CaMV.35S-enh-1:1:102/L-CaMV.35S-1:1:2

TABLE 12

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| No DNA | | | 0.00 | 0.00 | 0.00 |
| pMON124912 | No promoter | | 54.67 | 34905.00 | 0.00 |
| pMON33449 | P-CaMV.35S-enh-1:1:102/L-CaMV.35S-1:1:2 | 210 | 107064.67 | 21757.67 | 4.92 |
| pMON80585 | EXP-At.Atntt1:1:2 | 200 | 4962.33 | 40778.67 | 0.12 |
| 56969 | CumMe_WSM_SF16429.G5670 | 40 | 283.67 | 53452.00 | 0.01 |
| 56877 | P-CUCme.CumMe_WSM_SF16444.G5140-1:1:1 | 175 | 5297.67 | 46576.67 | 0.11 |
| 56749 | P-CUCme.CumMe_WSM_SF16563.G5560-1:1:1 | 176 | 280.67 | 41958.33 | 0.01 |
| 56918 | CumMe_WSM_SF17051.G5470 | 48 | 1088.00 | 36321.00 | 0.03 |
| 56849 | P-CUCme.CumMe_WSM_SF17111.G5790-1:1:1 | 177 | 196.00 | 48128.00 | 0.00 |
| 56754 | P-CUCme.WSM_SF17252.G7330-1:1:1 | 179 | 175.67 | 45427.00 | 0.00 |
| 56892 | CumMe_WSM_SF17349.G5770 | 56 | 34.00 | 38016.00 | 0.00 |
| 56477 | CumMe_WSM_SF17866.G6050 | 62 | 862.00 | 52203.33 | 0.02 |
| 56842 | P-CUCme.CumMe_WSM_SF18488.G5340-1:1:1 | 181 | 2892.67 | 49144.33 | 0.06 |
| 56852 | P-CUCme.CumMe_WSM_SF18536.G6480-1:1:1 | 182 | 3462.67 | 46549.33 | 0.07 |
| 56497 | CumMe_WSM_SF18575.G6410 | 71 | 92.67 | 47628.33 | 0.00 |
| 56847 | P-CUCme.CumMe_WSM_SF18634.G5190-1:1:1 | 183 | 122.33 | 36815.33 | 0.00 |
| 56746 | P-CUCme.CumMe_WSM_SF18716.G5860-1:1:1 | 184 | 14.33 | 62483.33 | 0.00 |
| 56883 | CumMe_WSM_SF18986.G6110 | 79 | 863.33 | 54379.33 | 0.02 |
| 56734 | EXP-CUCme.WSM_SF19064.G5690:1:1 | 185 | 142.00 | 46962.67 | 0.00 |
| 56912 | P-CUCme.CumMe_WSM_SF19647.G5760-1:1:1 | 188 | 7659.00 | 46935.67 | 0.16 |
| 56482 | P-CUCme.CumMe_WSM_SF19839.G5090-1:1:1 | 189 | 3279.00 | 37070.67 | 0.09 |
| 56963 | CumMe_WSM_SF19902.G5260 | 87 | 1629.00 | 55649.00 | 0.03 |
| 56747 | P-CUCme.CumMe_WSM_SF20132.G5560-1:1:1 | 190 | 340.33 | 40577.00 | 0.01 |
| 56479 | CumMe_WSM_SF20359.G5870 | 92 | 192.00 | 61341.67 | 0.00 |
| 56744 | CumMe_WSM_SF206458.G5970 | 98 | 154.67 | 33139.33 | 0.00 |
| 56948 | CumMe_WSM_SF206534.G5200 | 99 | 62.00 | 52118.00 | 0.00 |
| 56896 | CumMe_WSM_SF22008.G5670 | 108 | 1585.00 | 53540.00 | 0.03 |
| 56919 | CumMe_WSM_SF22275.G5780 | 112 | 8.33 | 48546.33 | 0.00 |
| 56967 | CumMe_WSM_SF22355.G5310 | 113 | 74.33 | 36202.67 | 0.00 |
| 56837 | P-CUCme.CumMe_WSM_SF22531.G5120-1:1:1 | 192 | 1526.67 | 52799.33 | 0.03 |
| 56940 | CumMe_WSM_SF22870.G5370 | 115 | 14.67 | 53663.33 | 0.00 |
| 56495 | P-CUCme.CumMe_WSM_SF23760.G5200-1:1:1 | 193 | 196.33 | 49870.67 | 0.00 |
| 56868 | P-CUCme.CumMe_WSM_SF23906.G6180-1:1:1 | 194 | 1584.33 | 42532.33 | 0.04 |
| 56998 | CumMe_WSM_SF24045.G5400 | 123 | 80.67 | 47553.00 | 0.00 |
| 56976 | P-CUCme.CumMe_WSM_SF25141.G5160-1:1:2 | 195 | 4506.00 | 57213.00 | 0.08 |
| 56742 | P-CUCme.CumMe_WSM_SF25355.G5000-1:1:1 | 196 | 4.00 | 41114.33 | 0.00 |
| 56915 | P-CUCme.CumMe_WSM_SF25936.G5450-1:1:1 | 197 | 965.33 | 34494.67 | 0.03 |
| 56854 | CumMe_WSM_SF28729.G5340 | 134 | 208.33 | 53956.00 | 0.00 |
| 56936 | CumMe_WSM_SF31264.G5380 | 136 | 292.67 | 42320.67 | 0.01 |
| 56863 | P-CUCme.CumMe_WSM_SF35856.G5150-1:1:1 | 198 | 125.00 | 48705.33 | 0.00 |

TABLE 12-continued

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| 56751 | P-CUCme.CumMe_WSM_SF41124.G5080-1:1:1 | 199 | 31.33 | 53595.00 | 0.00 |
| 56921 | CumMe_WSM_SF41254.G5160 | 141 | 11.67 | 52643.67 | 0.00 |
| 56884 | CumMe_WSM_SF42141.G5110 | 146 | 48.33 | 40556.67 | 0.00 |

TABLE 13

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| No DNA | | | 0.00 | 0.00 |
| pMON124912 | No promoter | | 0.01 | 0.00 |
| pMON33449 | P-CaMV.35S-enh-1:1:102/L-CaMV.35S-1:1:2 | 210 | 40.44 | 1.00 |
| pMON80585 | EXP-At.Atntt1:1:2 | 200 | 1.00 | 0.02 |
| 56969 | CumMe_WSM_SF16429.G5670 | 40 | 0.04 | 0.00 |
| 56877 | P-CUCme.CumMe_WSM_SF16444.G51140-1:1:1 | 175 | 0.93 | 0.02 |
| 56749 | P-CUCme.CumMe_WSM_SF16563.G5560-1:1:1 | 176 | 0.05 | 0.00 |
| 56918 | CumMe_WSM_SF17051.G5470 | 48 | 0.25 | 0.01 |
| 56849 | P-CUCme.CumMe_WSM_SF17111.G5790-1:1:1 | 177 | 0.03 | 0.00 |
| 56754 | P-CUCme.WSM_SF17252.G7330-1:1:1 | 179 | 0.03 | 0.00 |
| 56892 | CumMe_WSM_SF17349.G5770 | 56 | 0.01 | 0.00 |
| 56477 | CumMe_WSM_SF17866.G6050 | 62 | 0.14 | 0.00 |
| 56842 | P-CUCme.CumMe_WSM_SF18488.G5340-1:1:1 | 181 | 0.48 | 0.01 |
| 56852 | P-CUCme.CumMe_WSM_SF18536.G6480-1:1:1 | 182 | 0.61 | 0.02 |
| 56497 | CumMe_WSM_SF18575.G6410 | 71 | 0.02 | 0.00 |
| 56847 | P-CUCme.CumMe_WSM_SF18634.G5190-1:1:1 | 183 | 0.03 | 0.00 |
| 56746 | P-CUCme.CumMe_WSM_SF18716.G5860-1:1:1 | 184 | 0.00 | 0.00 |
| 56883 | CumMe_WSM_SF18986.G6110 | 79 | 0.13 | 0.00 |
| 56734 | EXP-CUCme.WSM_SF19064.G5690:1:1 | 185 | 0.02 | 0.00 |
| 56912 | P-CUCme.CumMe_WSM_SF19647.G5760-1:1:1 | 188 | 1.34 | 0.03 |
| 56482 | P-CUCme.CumMe_WSM_SF19839.G5090-1:1:1 | 189 | 0.73 | 0.02 |
| 56963 | CumMe_WSM_SF19902.G5260 | 87 | 0.24 | 0.01 |
| 56747 | P-CUCme.CumMe_WSM_SF20132.G5560-1:1:1 | 190 | 0.07 | 0.00 |
| 56479 | CumMe_WSM_SF20359.G5870 | 92 | 0.03 | 0.00 |
| 56744 | CumMe_WSM_SF206458.G5970 | 98 | 0.04 | 0.00 |
| 56948 | CumMe_WSM_SF206534.G5200 | 99 | 0.01 | 0.00 |
| 56896 | CumMe_WSM_SF22008.G5670 | 108 | 0.24 | 0.01 |
| 56919 | CumMe_WSM_SF22275.G5780 | 112 | 0.00 | 0.00 |
| 56967 | CumMe_WSM_SF22355.G5310 | 113 | 0.02 | 0.00 |
| 56837 | P-CUCme.CumMe_WSM_SF22531.G5120-1:1:1 | 192 | 0.24 | 0.01 |
| 56940 | CumMe_WSM_SF22870.G5370 | 115 | 0.00 | 0.00 |
| 56495 | P-CUCme.CumMe_WSM_SF23760.G5200-1:1:1 | 193 | 0.03 | 0.00 |
| 56868 | P-CUCme.CumMe_WSM_SF23906.G6180-1:1:1 | 194 | 0.31 | 0.01 |
| 56998 | CumMe_WSM_SF24045.G5400 | 123 | 0.01 | 0.00 |
| 56976 | P-CUCme.CumMe_WSM_SF25141.G5160-1:1:2 | 195 | 0.65 | 0.02 |
| 56742 | P-CUCme.CumMe_WSM_SF25355.G5000-1:1:1 | 196 | 0.00 | 0.00 |
| 56915 | P-CUCme.CumMe_WSM_SF25936.G5450-1:1:1 | 197 | 0.23 | 0.01 |
| 56854 | CumMe_WSM_SF28729.G5340 | 134 | 0.03 | 0.00 |
| 56936 | CumMe_WSM_SF31264.G5380 | 136 | 0.06 | 0.00 |
| 56863 | P-CUCme.CumMe_WSM_SF35856.G5150-1:1:1 | 198 | 0.02 | 0.00 |
| 56751 | P-CUCme.CumMe_WSM_SF41124.G5080-1:1:1 | 199 | 0.00 | 0.00 |
| 56921 | CumMe_WSM_SF41254.G5160 | 141 | 0.00 | 0.00 |
| 56884 | CumMe_WSM_SF42141.G5110 | 146 | 0.01 | 0.00 |

As can be seen in Table 12 above, not all EXP sequences demonstrated the ability to drive transgene expression when compared to the promoterless control. However, the EXP sequences, CumMe_WSM_SF16429.G5670 (SEQ ID NO: 40), P-CUCme.CumMe_WSM_SF16444.G5140-1:1:1 (SEQ ID NO: 175), P-CUCme.CumMe_WSM_SF16563.G5560-1:1:1 (SEQ ID NO: 176), CumMe_WSM_SF17051.G5470 (SEQ ID NO: 48), P-CUCme.CumMe_WSM_SF17111.G5790-1:1:1 (SEQ ID NO: 177), P-CUCme.WSM_SF17252.G7330-1:1:1 (SEQ ID NO: 179), CumMe_WSM_SF17866.G6050 (SEQ ID NO: 62), P-CUCme.CumMe_WSM_SF18488.G5340-1:1:1 (SEQ ID NO: 181), P-CUCme.CumMe_WSM_SF18536.G6480-1:1:1 (SEQ ID NO: 182), CumMe_WSM_SF18575.G6410 (SEQ ID NO: 71), P-CUCme.CumMe_WSM_SF18634.G5190-1:1:1 (SEQ ID NO: 183), CumMe_WSM_SF18986.G6110 (SEQ ID NO: 79), EXP-CUCme.WSM_SF19064.G5690:1:1 (SEQ ID NO: 185), P-CUCme.CumMe_WSM_SF19647.G5760-1:1:1 (SEQ ID NO: 188), P-CUCme.CumMe_WSM_SF19839.G5090-1:1:1 (SEQ ID NO: 189), CumMe_WSM_SF19902.G5260 (SEQ ID NO:

87), P-CUCme.CumMe_WSM_SF20132.G5560-1:1:1 (SEQ ID NO: 190), CumMe_WSM_SF20359.G5870 (SEQ ID NO: 92), CumMe_WSM_SF206458.G5970 (SEQ ID NO: 98), CumMe_WSM_SF206534.G5200 (SEQ ID NO: 99), CumMe_WSM_SF22008.G5670 (SEQ ID NO: 108), CumMe_WSM_SF22355.G5310 (SEQ ID NO: 113), P-CUCme.CumMe_WSM_SF22531.G5120-1:1:1 (SEQ ID NO: 192), EXP-CUCme.WSM_SF19064.G5690:1:1 (SEQ ID NO: 193), P-CUCme.CumMe_WSM_SF23906.G6180-1:1:1 (SEQ ID NO: 194), CumMe_WSM_SF24045.G5400 (SEQ ID NO: 123), P-CUCme.CumMe_WSM_SF25141.G5160-1:1:2 (SEQ ID NO: 195), P-CUCme.CumMe_WSM_SF25936.G5450-1:1:1 (SEQ ID NO: 197), CumMe_WSM_SF28729.G5340 (SEQ ID NO: 134), CumMe_WSM_SF31264.G5380 (SEQ ID NO: 136) and P-CUCme.CumMe_WSM_SF35856.G5150-1:1:1 (SEQ ID NO: 198) demonstrated the ability to drive trangene expression in soybean cotyledon protoplasts at a level similar or greater than EXP-At.Atntt1:1:2. As shown in Table 13 above, the EXP sequence P-CUCme.CumMe_WSM_SF19647.G5760-1:1:1 (SEQ ID NO: 188) demonstrated the ability to drive transgene expression in this assay at a level greater than EXP-At.Atntt1:1:2.

Example 7

Analysis of Regulatory Elements Driving GUS in Cotton Leaf Protoplasts

Cotton leaf protoplasts were transformed with plant expression vectors containing a test transcriptional regulatory expression element group driving expression of the β-glucuronidase (GUS) transgene and compared to GUS expression in leaf protoplasts in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups. Each plant expression vector was comprised of a right border region from *Agrobacterium tumefaciens*, a first transgene cassette comprised of a test promoter or known constitutive promoter operably linked 5' to a coding sequence for β-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the *Arabidopsis* Actin 7 promoter) or the antibiotic, kanamycin and a left border region from *A. tumefaciens*. A promoterless control plant expression vector (pMON124912) served as a negative control for expression. The foregoing test and constitutive expression element groups were cloned into plant expression vectors as shown in Table 14 below.

TABLE 14

Plant expression vectors and corresponding expression element group and 3' UTR.

| Construct | Regulatory Element | SEQ ID NO: | 3' UTR |
|---|---|---|---|
| pMON109584 | EXP-CaMV.35S-enh + Ph.DnaK:1:3 | 201 | T-Gb.E6-3b:1:1 |
| pMON118756 | EXP-At.Act7:1:11 | 202 | T-Gb.E6-3b:1:1 |
| pMON124912 | Promoterless | | T-Gb.FbL2-1:1:1 |
| pMON140818 | P-CUCme.1-1:1:1rc | 155 | T-Gb.FbL2-1:1:1 |
| pMON140819 | P-CUCme.2-1:1:1 | 14 | T-Gb.FbL2-1:1:1 |
| pMON140820 | P-CUCme.3-1:1:3 | 15 | T-Gb.FbL2-1:1:1 |
| pMON140821 | EXP-CUCme.4:1:1 | 156 | T-Gb.FbL2-1:1:1 |
| pMON140823 | P-CUCme.6-1:1:1 | 18 | T-Gb.FbL2-1:1:1 |
| pMON140824 | P-CUCme.8-1:1:2 | 19 | T-Gb.FbL2-1:1:1 |
| pMON140825 | P-CUCme.9-1:1:2 | 20 | T-Gb.FbL2-1:1:1 |
| pMON140826 | P-CUCme.10-1:1:1 | 21 | T-Gb.FbL2-1:1:1 |
| pMON140827 | EXP-CUCme.eEF1a:1:1 | 162 | T-Gb.FbL2-1:1:1 |
| pMON140828 | P-CUCme.15-1:1:2 | 23 | T-Gb.FbL2-1:1:1 |
| pMON140829 | P-CUCme.16a-1:1:2 | 24 | T-Gb.FbL2-1:1:1 |
| pMON140830 | P-CUCme.17-1:1:2 | 26 | T-Gb.FbL2-1:1:1 |
| pMON140831 | P-CUCme.18-1:1:2 | 27 | T-Gb.FbL2-1:1:1 |
| pMON140832 | P-CUCme.19-1:1:3 | 167 | T-Gb.FbL2-1:1:1 |
| pMON140833 | P-CUCme.20-1:3 | 211 | T-Gb.FbL2-1:1:1 |
| pMON140834 | P-CUCme.21-1:1:1 | 30 | T-Gb.FbL2-1:1:1 |
| pMON140835 | P-CUCme.22-1:1:3 | 31 | T-Gb.FbL2-1:1:1 |
| pMON140836 | EXP-CUCme.SAMS2:1:1 | 168 | T-Gb.FbL2-1:1:1 |
| pMON140837 | P-CUCme.26-1:1:2 | 33 | T-Gb.FbL2-1:1:1 |
| pMON140838 | P-CUCme.28-1:1:2 | 34 | T-Gb.FbL2-1:1:1 |
| pMON140839 | EXP-CUCme.29:1:2 | 212 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 206), operably linked 5' to a 3' termination region from the *Agrobacterium tumefaciens* nopaline synthase gene.

The plant expression vectors, pMON80585, pMON109584, pMON118756, pMON124912, pMON140818, pMON140819, pMON140820, pMON140821, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform cotton leaf protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). Sample measurements were made using 4 replicates per transformation. The average GUS and luciferase values are presented in Table 15 below.

TABLE 15

Average GUS and luciferase expression values and GUS/luciferase ratios.

| Construct | Regulatory Element | SEQ ID NO: | Average GUS | Average FLuc | Average RLuc | GUS/ FLuc | GUS/ RLuc |
|---|---|---|---|---|---|---|---|
| pMON109584 | EXP-CaMV.35S-enh + Ph.DnaK: 1:3 | 201 | 5322.8 | 14842.8 | 27990.5 | 0.3586 | 0.1902 |
| pMON118756 | EXP-At.Act7:1:11 | 202 | 1006.3 | 19746.8 | 25582.3 | 0.0510 | 0.0393 |
| pMON124912 | Promoterless | | 21 | 19248.5 | 25012 | 0.0011 | 0.0008 |
| PMON140818 | P-CUCme.1-1:1:1rc | 155 | 170.3 | 17796.8 | 22026.3 | 0.0096 | 0.0077 |
| pMON140819 | P-CUCme.2-1:1:1 | 14 | 34.8 | 16326.3 | 21407.5 | 0.0021 | 0.0016 |
| pMON140820 | P-CUCme.3-1:1:3 | 15 | 51.5 | 17356.8 | 21523.8 | 0.0030 | 0.0024 |
| pMON140821 | EXP-CUCme.4:1:1 | 156 | 3497.8 | 18745.3 | 26065.3 | 0.1866 | 0.1342 |
| pMON140823 | P-CUCme.6-1:1:1 | 18 | 40.8 | 19533.8 | 26361.5 | 0.0021 | 0.0015 |
| pMON140824 | P-CUCme.8-1:1:2 | 19 | 22 | 19701 | 26278 | 0.0011 | 0.0008 |
| pMON140825 | P-CUCme.9-1:1:2 | 20 | 372.5 | 21972.3 | 28755 | 0.0170 | 0.0130 |
| pMON140826 | P-CUCme.10-1:1:1 | 21 | 198 | 21362.8 | 28902 | 0.0093 | 0.0069 |
| pMON140827 | EXP-CUCme.eEF1a:1:1 | 162 | 725 | 21589 | 27635.3 | 0.0336 | 0.0262 |
| pMON140828 | P-CUCme.15-1:1:2 | 23 | 55.3 | 17706 | 28846 | 0.0031 | 0.0019 |
| pMON140829 | P-CUCme.16a-1:1:2 | 24 | 14 | 23289.5 | 30190 | 0.0006 | 0.0005 |
| PMON140830 | P-CUCme.17-1:1:2 | 26 | 155.5 | 23178.3 | 31602.8 | 0.0067 | 0.0049 |
| pMON140831 | P-CUCme.18-1:1:2 | 27 | 86.8 | 19085.8 | 22396.5 | 0.0045 | 0.0039 |
| pMON140832 | P-CUCme.19-1:1:3 | 167 | 130 | 21520.3 | 27270.5 | 0.0060 | 0.0048 |
| pMON140833 | P-CUCme.20-1:3 | 211 | 88.5 | 22223.8 | 30786 | 0.0040 | 0.0029 |
| pMON140834 | P-CUCme.21-1:1:1 | 30 | 98.5 | 18579 | 20506.3 | 0.0053 | 0.0048 |
| pMON140835 | P-CUCme.22-1:1:3 | 31 | 363 | 21780.3 | 28816.3 | 0.0167 | 0.0126 |
| PMON140836 | EXP-CUCme.SAMS2:1:1 | 168 | 515 | 17906 | 23031 | 0.0288 | 0.0224 |
| PMON140837 | P-CUCme.26-1:1:2 | 33 | 125 | 15529.3 | 15169.3 | 0.0080 | 0.0082 |
| pMON140838 | P-CUCme.28-1:1:2 | 34 | 115.8 | 17013.5 | 22236.5 | 0.0068 | 0.0052 |
| pMON140839 | EXP-CUCme.29:1:2 | 212 | 15.5 | 16370.3 | 20409 | 0.0009 | 0.0008 |

To compare the relative activity of each promoter in cotton leaf protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 16 below shows the GUS to firefly luciferase (FLuc) ratios normalized with respect to EXP-At.Act7:1:11 and EXP-CaMV.35S-enh+Ph.DnaK:1:3. Table 17 below shows the GUS to *renilla* luciferase (RLuc) ratios normalized with respect to EXP-At.Act7:1:11 and EXP-CaMV.35S-enh+Ph.DnaK:1:3.

TABLE 16

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh + Ph.DnaK:1:3 |
|---|---|---|---|---|
| pMON109584 | EXP-CaMV.35S-enh + Ph.DnaK:1:3 | 201 | 7.037 | 1.000 |
| pMON118756 | EXP-At.Act7:1:11 | 202 | 1.000 | 0.142 |
| pMON124912 | Promoterless | | 0.021 | 0.003 |
| pMON140818 | P-CUCme.1-1:1:1rc | 155 | 0.188 | 0.027 |
| pMON140819 | P-CUCme.2-1:1:1 | 14 | 0.042 | 0.006 |

TABLE 16-continued

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh + Ph.DnaK:1:3 |
|---|---|---|---|---|
| pMON140820 | P-CUCme.3-1:1:3 | 15 | 0.058 | 0.008 |
| pMON140821 | EXP-CUCme.4:1:1 | 156 | 3.662 | 0.520 |
| pMON140823 | P-CUCme.6-1:1:1 | 18 | 0.041 | 0.006 |
| pMON140824 | P-CUCme.8-1:1:2 | 19 | 0.022 | 0.003 |
| pMON140825 | P-CUCme.9-1:1:2 | 20 | 0.333 | 0.047 |
| pMON140826 | P-CUCme.10-1:1:1 | 21 | 0.182 | 0.026 |
| pMON140827 | EXP-CUCme.eEF1a:1:1 | 162 | 0.659 | 0.094 |
| pMON140828 | P-CUCme.15-1:1:2 | 23 | 0.061 | 0.009 |
| pMON140829 | P-CUCme.16a-1:1:2 | 24 | 0.012 | 0.002 |
| pMON140830 | P-CUCme.17-1:1:2 | 26 | 0.132 | 0.019 |
| pMON140831 | P-CUCme.18-1:1:2 | 27 | 0.089 | 0.013 |
| pMON140832 | P-CUCme.19-1:1:3 | 167 | 0.119 | 0.017 |
| pMON140833 | P-CUCme.20-1:3 | 211 | 0.078 | 0.011 |
| pMON140834 | P-CUCme.21-1:1:1 | 30 | 0.104 | 0.015 |
| pMON140835 | P-CUCme.22-1:1:3 | 31 | 0.327 | 0.046 |
| pMON140836 | EXP-CUCme.SAMS2:1:1 | 168 | 0.564 | 0.080 |
| pMON140837 | P-CUCme.26-1:1:2 | 33 | 0.158 | 0.022 |
| pMON140838 | P-CUCme.28-1:1:2 | 34 | 0.134 | 0.019 |
| pMON140839 | EXP-CUCme.29:1:2 | 212 | 0.019 | 0.003 |

TABLE 17

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh + Ph.DnaK:1:3 |
|---|---|---|---|---|
| pMON109584 | EXP-CaMV.35S-enh + Ph.DnaK:1:3 | 201 | 4.83 | 1.00 |
| pMON118756 | EXP-At.Act7:1:11 | 202 | 1.00 | 0.21 |
| pMON124912 | Promoterless | | 0.02 | 0.00 |
| pMON140818 | P-CUCme.1-1:1:1rc | 155 | 0.20 | 0.04 |
| pMON140819 | P-CUCme.2-1:1:1 | 14 | 0.04 | 0.01 |
| pMON140820 | P-CUCme.3-1:1:3 | 15 | 0.06 | 0.01 |
| pMON140821 | EXP-CUCme.4:1:1 | 156 | 3.41 | 0.71 |
| pMON140823 | P-CUCme.6-1:1:1 | 18 | 0.04 | 0.01 |
| pMON140824 | P-CUCme.8-1:1:2 | 19 | 0.02 | 0.00 |
| pMON140825 | P-CUCme.9-1:1:2 | 20 | 0.33 | 0.07 |
| pMON140826 | P-CUCme.10-1:1:1 | 21 | 0.17 | 0.04 |
| pMON140827 | EXP-CUCme.eEF1a:1:1 | 162 | 0.67 | 0.14 |
| pMON140828 | P-CUCme.15-1:1:2 | 23 | 0.05 | 0.01 |
| pMON140829 | P-CUCme.16a-1:1:2 | 24 | 0.01 | 0.00 |
| pMON140830 | P-CUCme.17-1:1:2 | 26 | 0.13 | 0.03 |
| pMON140831 | P-CUCme.18-1:1:2 | 27 | 0.10 | 0.02 |
| pMON140832 | P-CUCme.19-1:1:3 | 167 | 0.12 | 0.03 |
| pMON140833 | P-CUCme.20-1:3 | 211 | 0.07 | 0.02 |
| pMON140834 | P-CUCme.21-1:1:1 | 30 | 0.12 | 0.03 |
| pMON140835 | P-CUCme.22-1:1:3 | 31 | 0.32 | 0.07 |
| pMON140836 | EXP-CUCme.SAMS2:1:1 | 168 | 0.57 | 0.12 |
| pMON140837 | P-CUCme.26-1:1:2 | 33 | 0.21 | 0.04 |
| pMON140838 | P-CUCme.28-1:1:2 | 34 | 0.13 | 0.03 |
| pMON140839 | EXP-CUCme.29:1:2 | 212 | 0.02 | 0.00 |

As can be seen in Tables 16 and 17, most of the expression element groups tested, demonstrated the ability to drive transgene expression in cotton leaf protoplast cells. One expression element group, EXP-CUCme.4:1:1 (SEQ ID NO: 156) demonstrated levels of transgene expression higher than that of EXP-At.Act7:1:11 in this assay.

Example 8

Analysis of Regulatory Elements Driving GUS in Cotton Leaf Protoplasts using Transgene Cassette Amplicons Cotton leaf protoplasts were transformed with transgene cassette amplicons containing a transcriptional regulatory expression element group driving expression of the β-glucuronidase (GUS) transgene and compared to GUS expression in leaf protoplasts in which expression of GUS is driven by known constitutive promoters. The transgene cassette amplicons were comprised of an EXP sequence, operably linked to a GUS coding sequence (GUS, SEQ ID NO: 206), operably linked to a 3' UTR (T-Gb.FbL2-1:1:1, SEQ ID NO: 205). Average GUS expression was compared to the control EXP elements, P-CaMV.35S-enh-1:1:102/L-CaMV.35S-1:1:2 (SEQ ID NO: 210) and EXP-At.Atntt1:1:2 (SEQ ID NO: 200).

A plasmid, for use in co-transformation and normalization of data was also used in a similar manner as that described above in Example 2. The transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209).

Table 18 below shows the mean GUS expression values conferred by each transgene amplicon. Table 19 below shows the GUS to firefly luciferase (FLuc) ratios normalized with respect to EXP-At.Atntt1:1:2 and P-CaMV.35S-enh-1:1:102/L-CaMV.35S-1:1:2.

TABLE 18

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| Empty Vector | No DNA | | 32.8 | 14087.5 | 0.002 |
| pMON124912 | No promoter | | 12 | 20486.3 | 0.001 |
| pMON80585 | EXP-At.Atntt1:1:2 | 200 | 55.5 | 18811 | 0.003 |
| pMON33449 | P-CaMV.35S-enh-1:1:102/L-CaMV.35S-1:1:2 | 210 | 12472.5 | 19126.3 | 0.652 |
| 56741 | CumMe_WSM_SF143981.G5150 | 36 | 5.8 | 17449.5 | 0.000 |
| 56492 | CumMe_WSM_SF144839.G5080 | 37 | 27.5 | 16674 | 0.002 |
| 56877 | P-CUCme.CumMe_WSM_SF16444.G5140-1:1:1 | 175 | 96.3 | 17237.8 | 0.006 |
| 56485 | CumMe_WSM_SF16530.G6000 | 42 | 27.3 | 17858.5 | 0.002 |
| 56844 | CumMe_WSM_SF16953.G5180 | 47 | 22.3 | 19398.5 | 0.001 |
| 56500 | CumMe_WSM_SF17250.G5910 | 52 | 12.3 | 23980.3 | 0.001 |
| 56754 | P-CUCme.WSM_SF17252.G7330-1:1:1 | 179 | 16 | 13848.8 | 0.001 |
| 56740 | CumMe_WSM_SF17672.G5610 | 60 | 12 | 16646.8 | 0.001 |
| 56870 | CumMe_WSM_SF18287.G5380 | 66 | 39.3 | 13930.5 | 0.003 |
| 56478 | CumMe_WSM_SF18504.G5090 | 68 | 11.8 | 15830.5 | 0.001 |
| 56481 | CumMe_WSM_SF18530.G5750 | 69 | 6.5 | 15211.3 | 0.000 |
| 56498 | CumMe_WSM_SF18645.G5380 | 73 | 36 | 14569.8 | 0.002 |
| 56746 | P-CUCme.CumMe_WSM_SF18716.G5860-1:1:1 | 184 | 11 | 18054.5 | 0.001 |
| 56490 | CumMe_WSM_SF18801.G5040 | 75 | 21.5 | 14147.3 | 0.002 |
| 56488 | CumMe_WSM_SF19323.G5120 | 81 | 15.3 | 11985.3 | 0.001 |
| 56499 | CumMe_WSM_SF19631.G5170 | 83 | 12.5 | 20140.5 | 0.001 |
| 56482 | P-CUCme.CumMe_WSM_SF19839.G5090-1:1:1 | 189 | 75 | 18690.5 | 0.004 |
| 56489 | CumMe_WSM_SF19850.G5130 | 86 | 38.3 | 19756.5 | 0.002 |
| 56476 | CumMe_WSM_SF20355.G5130 | 91 | 10.5 | 27901.8 | 0.000 |
| 56895 | CumMe_WSM_SF20431.G6340 | 95 | 34.8 | 16283.8 | 0.002 |
| 56744 | CumMe_WSM_SF206458.G5970 | 98 | 11 | 19659 | 0.001 |
| 56480 | CumMe_WSM_SF21366.G5980 | 105 | 10.8 | 17367 | 0.001 |
| 56930 | CumMe_WSM_SF22070.G5280 | 109 | 25.3 | 14210.5 | 0.002 |
| 56484 | CumMe_WSM_SF23181.G5100 | 117 | 20.3 | 13506 | 0.002 |
| 56495 | P-CUCme.CumMe_WSM_SF23760.G5200-1:1:1 | 193 | 7.8 | 15138.5 | 0.001 |
| 56971 | CumMe_WSM_SF25084.G5580 | 125 | 16 | 16135.3 | 0.001 |
| 56742 | P-CUCme.CumMe_WSM_SF25355.G5000-1:1:1 | 196 | 18 | 13782.8 | 0.001 |
| 56494 | CumMe_WSM_SF25455.G5370 | 129 | 10.5 | 16089.8 | 0.001 |
| 56751 | P-CUCme.CumMe_WSM_SF41124.G5080-1:1:1 | 199 | 24.3 | 17884.3 | 0.001 |
| 56483 | CumMe_WSM_SF41644.G6400 | 143 | 14.5 | 13130.5 | 0.001 |
| 56904 | CumMe_WSM_SF44933.G5290 | 147 | 33 | 13369 | 0.002 |
| 56743 | CumMe_WSM_SF9060.G5120 | 154 | 11.3 | 15230.8 | 0.001 |

TABLE 19

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| Empty Vector | No DNA | | | |
| pMON124912 | No promoter | | | |
| pMON80585 | EXP-At.Atntt1:1:2 | 200 | 1.000 | 0.005 |
| pMON33449 | P-CaMV.35S-enh-1:1:102/L-CaMV.35S-1:1:2 | 210 | 221.025 | 1.000 |
| 56741 | CumMe_WSM_SF143981.G5150 | 36 | 0.113 | 0.001 |
| 56492 | CumMe_WSM_SF144839.G5080 | 37 | 0.559 | 0.003 |
| 56877 | P-CUCme.CumMe_WSM_SF16444.G5140-1:1:1 | 175 | 1.893 | 0.009 |
| 56485 | CumMe_WSM_SF16530.G6000 | 42 | 0.518 | 0.002 |
| 56844 | CumMe_WSM_SF16953.G5180 | 47 | 0.390 | 0.002 |
| 56500 | CumMe_WSM_SF17250.G5910 | 52 | 0.174 | 0.001 |
| 56754 | P-CUCme.WSM_SF17252.G7330-1:1:1 | 179 | 0.392 | 0.002 |
| 56740 | CumMe_WSM_SF17672.G5610 | 60 | 0.244 | 0.001 |
| 56870 | CumMe_WSM_SF18287.G5380 | 66 | 0.956 | 0.004 |
| 56478 | CumMe_WSM_SF18504.G5090 | 68 | 0.253 | 0.001 |
| 56481 | CumMe_WSM_SF18530.G5750 | 69 | 0.145 | 0.001 |
| 56498 | CumMe_WSM_SF18645.G5380 | 73 | 0.837 | 0.004 |
| 56746 | P-CUCme.CumMe_WSM_SF18716.G5860-1:1:1 | 184 | 0.207 | 0.001 |
| 56490 | CumMe_WSM_SF18801.G5040 | 75 | 0.515 | 0.002 |
| 56488 | CumMe_WSM_SF19323.G5120 | 81 | 0.433 | 0.002 |
| 56499 | CumMe_WSM_SF19631.G5170 | 83 | 0.210 | 0.001 |
| 56482 | P-CUCme.CumMe_WSM_SF19839.G5090-1:1:1 | 189 | 1.360 | 0.006 |
| 56489 | CumMe_WSM_SF19850.G5130 | 86 | 0.657 | 0.003 |
| 56476 | CumMe_WSM_SF20355.G5130 | 91 | 0.128 | 0.001 |
| 56895 | CumMe_WSM_SF20431.G6340 | 95 | 0.724 | 0.003 |
| 56744 | CumMe_WSM_SF206458.G5970 | 98 | 0.190 | 0.001 |
| 56480 | CumMe_WSM_SF21366.G5980 | 105 | 0.211 | 0.001 |
| 56930 | CumMe_WSM_SF22070.G5280 | 109 | 0.603 | 0.003 |
| 56484 | CumMe_WSM_SF23181.G5100 | 117 | 0.509 | 0.002 |
| 56495 | P-CUCme.CumMe_WSM_SF23760.G5200-1:1:1 | 193 | 0.175 | 0.001 |
| 56971 | CumMe_WSM_SF25084.G5580 | 125 | 0.336 | 0.002 |
| 56742 | P-CUCme.CumMe_WSM_SF25355.G5000-1:1:1 | 196 | 0.443 | 0.002 |
| 56494 | CumMe_WSM_SF25455.G5370 | 129 | 0.221 | 0.001 |
| 56751 | P-CUCme.CumMe_WSM_SF41124.G5080-1:1:1 | 199 | 0.461 | 0.002 |
| 56483 | CumMe_WSM_SF41644.G6400 | 143 | 0.374 | 0.002 |
| 56904 | CumMe_WSM_SF44933.G5290 | 147 | 0.837 | 0.004 |
| 56743 | CumMe_WSM_SF9060.G5120 | 154 | 0.251 | 0.001 |

As can be seen in Table 18 above, not all EXP sequences demonstrated the ability to drive transgene expression when compared to the promoterless control. However, the EXP sequences, P-CUCme.CumMe_WSM_SF16444.G5140-1:1:1 (SEQ ID NO: 175) and P-CUCme.CumMe_WSM_SF19839.G5090-1:1:1 (SEQ ID NO: 189) demonstrated the ability to drive trangene expression in soybean cotyledon protoplasts at a level similar or greater than EXP-At.Atntt1:1:2. As shown in Table 19 above, the EXP sequence, P-CUCme.CumMe_WSM_SF19839.G5090-1:1:1 (SEQ ID NO: 189) demonstrated the ability to drive transgene expression in this assay at a level greater than EXP-At.Atntt1:1:2.

Example 9

Analysis of Regulatory Elements Driving GUS in Stably Transformed Soybean

Soybean plants were transformed with plant expression vectors containing an EXP sequence driving expression of the β-glucuronidase (GUS) transgene.

Expression of the GUS transgene driven by EXP-CUCme.Ubq1:1:1 (SEQ ID NO: 1), EXP-CUCme.Ubq1:1:3 (SEQ ID NO: 7), P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), EXP-CUCme.SAMS2:1:1 (SEQ ID NO: 168), P-CUCme.26-1:1:2 (SEQ ID NO: 33), EXP-CUCme.29:1:2 (SEQ ID NO: 212), P-CUCme.CumMeWSM_SF25355.G5000-1:1:1 (SEQ ID NO: 196), P-CUCme.CumMe_WSM_SF17111.G5790-1:1:1 (SEQ ID NO: 177), P-CUCme.CumMe_WSM_SF22531.G5120-1:1:1 (SEQ ID NO: 192), P-CUCme.CumMe_WSM_SF18488.G5340-1:1:1 (SEQ ID NO: 181), P-CUCme.CumMe_WSM_SF23760.G5200-1:1:1 (SEQ ID NO: 193), EXP-CUCme.WSM_SF19064.G5690:1:1 (SEQ ID NO: 185), P-CUCme.WSM_SF17252.G7330-1:1:1 (SEQ ID NO: 179), P-CUCme.CumMe_WSM_SF18634.G5190-1:1:1 (SEQ ID NO: 183), P-CUCme.CumMe_WSM_SF19647.G5760-1:1:1 (SEQ ID NO: 188), P-CUCme.CumMe_WSM_SF25936.G5450-1:1:1 (SEQ ID NO: 197), P-CUCme.CumMe_WSM_SF19839.G5090-1:1:1 (SEQ ID NO: 189), CumMe_WSM_SF206458.G5970 (SEQ ID NO: 98) and P-CUCme.CumMe_WSM_SF18716.G5860-1:1:1 (SEQ ID NO: 184) assayed both qualitatively through inspection of stained tissue sections and quantitatively. Each plant expression vector was comprised of a right border region from *Agrobacterium tumefaciens*, a first transgene cassette comprised of an EXP sequence operably linked 5' to a coding sequence for β-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* FbLate-2 gene (T-Gb.FbL2-1:1:1, SEQ ID NO: 205); a second transgene selection cassette used for selection of transformed plant cells that conferred resistance to the herbicide glyphosate (driven by the *Arabidopsis* Actin 7 promoter) and a left border region from *A. tumefaciens.*

The foregoing EXP sequences were cloned into plant expression constructs as shown in Tables 20 through 23 below and used to transform soybean plants using an agrobacterium mediated transformation method.

Histochemical GUS analysis was used for qualitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues. The $R_0$ generation plants were inspected for expression in Vn5 Root, R1 Root, Vn5 Sink Leaf, Vn5 Source Leaf, R1 Source Leaf, R1 Petiole, Yellow Pod Embryo, Yellow Pod Cotyledon, R3 Immature Seed, R3 Pod, R5 Cotyledon and R1 Flower.

For quantitative analysis, total protein was extracted from selected tissues of transformed corn plants. One microgram of total protein was used with the fluorogenic substrate 4-methyleumbelliferyl-β-D-glucuronide (MUG) in a total reaction volume of 50 microliters. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm and emission 3 nm.

Tables 20 and 21 below show the mean quantitative expression levels measured in the $R_0$ generation plant tissues. Those tissued not assayed are shown as blank cells in both tables.

TABLE 20

Mean GUS expression in Vn5 Root, R1 Root, Vn5 Sink Leaf, Vn5 Source Leaf, R1 Source Leaf and R1 Petiole of $R_0$ generation transformed soybean plants

| Construct | Regulatory Element | SEQ ID NO: | Vn5_Root | R1_Root | Vn5_Sink_Leaf | Vn5_Source Leaf | R1_Source_Leaf | R1_Petiole |
|---|---|---|---|---|---|---|---|---|
| PMON138776 | EXP-CUCme.Ubq1:1:1 | 1 | 4 | | | | 4 | 4 |
| pMON138778 | EXP-CUCme.Ubq1:1:3 | 7 | 16 | | 1 | 2 | 13 | 23 |
| PMON140818 | P-CUCme.1-1:1:1rc | 155 | 48.21 | | 22.35 | 20.24 | 33.01 | 78.17 |
| pMON140819 | P-CUCme.2-1:1:1 | 14 | | | | | | |
| pMON140820 | P-CUCme.3-1:1:3 | 15 | | | | | | |
| pMON140821 | EXP-CUCme.4:1:1 | 156 | 96.82 | | 28.32 | 39.17 | 322.98 | 280.03 |
| pMON140822 | EXP-CUCme.5:1:1 | 159 | 28.88 | | | | 41.11 | |
| pMON140823 | P-CUCme.6-1:1:1 | 18 | 23.94 | | | | 32.14 | 30.22 |
| pMON140824 | P-CUCme.8-1:1:2 | 19 | | | | | | |
| pMON140825 | P-CUCme.9-1:1:2 | 20 | 22.06 | | | | 21.22 | 23.08 |
| pMON140826 | P-CUCme.10-1:1:1 | 21 | | | | | | |
| pMON140827 | EXP-CUCme.eEF1a:1:1 | 162 | 189.24 | 153.52 | 59.6 | 37.44 | 103.01 | 130.6 |
| pMON140828 | P-CUCme.15-1:1:2 | 23 | 30.53 | | | | | |
| pMON140830 | P-CUCme.17-1:1:2 | 26 | 51.62 | | 30.07 | 31.08 | 30.49 | 60.14 |
| PMON140831 | P-CUCme.18-1:1:2 | 27 | 57.38 | | | | | 30.03 |
| pMON140832 | P-CUCme.19-1:1:3 | 167 | 23.07 | | 50.21 | 59.73 | 65.58 | 137.42 |
| pMON140833 | P-CUCme.20-1:3 | 211 | 23.15 | | 61.6 | 118.76 | 502.55 | 119.46 |
| pMON140834 | P-CUCme.21-1:1:1 | 30 | | | | | 25.49 | |
| pMON140836 | EXP-CUCme.SAMS2:1:1 | 168 | 230.89 | 184.88 | 65.44 | 53.36 | 118.82 | 351.49 |
| pMON140837 | P-CUCme.26-1:1:2 | 33 | 56.21 | | 26.81 | 45.07 | 51.61 | 47.42 |
| pMON140839 | EXP-CUCme.29:1:2 | 212 | 82.17 | | 45.2 | 28.27 | 64.96 | 109.9 |
| pMON144926 | P-CUCme.CumMe_WSM_SF25355.G5000-1:1:1 | 196 | 28.53 | | | | | |

TABLE 20-continued

Mean GUS expression in Vn5 Root, R1 Root, Vn5 Sink Leaf, Vn5 Source Leaf, R1 Source Leaf and R1 Petiole of $R_0$ generation transformed soybean plants

| Construct | Regulatory Element | SEQ ID NO: | Vn5_Root | R1_Root | Vn5_Sink_Leaf | Vn5_Source Leaf | R1_Source_Leaf | R1_Petiole |
|---|---|---|---|---|---|---|---|---|
| pMON144927 | P-CUCme.CumMe_WSM_SF17111.05790-1:1:1 | 177 | 23.62 | | | | | |
| pMON144928 | P-CUCme.CumMe_WSM_SF22531.G5120-1:1:1 | 192 | 75.62 | | 23 | 20.46 | 21.78 | 39.77 |
| pMON144931 | P-CUCme.CumMe_WSM_SF18488.G5340-1:1:1 | 181 | 43.2 | | | | | 52.55 |
| pMON144933 | P-CUCme.CumMe_WSM_SF23760.G5200-1:1:1 | 193 | 25.61 | | 20.45 | 0 | 0 | 28.69 |
| pMON146941 | EXP-CUCme.WSM_SF19064.G5690:1:1 | 185 | 33.5 | | 0 | 0 | 24.27 | 47.82 |
| pMON144932 | P-CUCme.WSM_SF17252.G7330-1:1:1 | 179 | 32.54 | | 23.76 | 21.5 | 0 | 22.21 |
| pMON146940 | P-CUCme.CumMe_WSM_SF18634.G5190-1:1:1 | 183 | 0 | | 0 | 0 | 0 | 0 |
| pMON147340 | P-CUCme.CumMe_WSM_SF19647.G5760-1:1:1 | 188 | 28.9 | | 0 | 0 | 29.77 | 25.82 |
| pMON147342 | P-CUCme.CumMe_WSM_SF25936.G5450-1:1:1 | 197 | 50.15 | | 24.26 | 0 | 29.38 | 29.91 |
| pMON147343 | P-CUCme.CumMe_WSM_SF19839.G5090-1:1:1 | 189 | 36.05 | | 25.7 | 27.54 | 22.85 | 37.15 |
| pMON144929 | CumMe_WSM_SF206458.G5970 | 98 | | | | | | |
| PMON147304 | P-CUCme.CumMe_WSM_SF18716.G5860-1:1:1 | 184 | 35.01 | | 21.17 | 21.23 | 22 | 44.57 |

TABLE 21

Mean GUS expression in Yellow Pod Embryo, Yellow Pod Cotyledon, R3 Immature Seed, R3 Pod, R5 Cotyledon and R1 Flower of $R_0$ generation transformed soybean plants

| Construct | Regulatory Element | SEQ ID NO: | Yellow_Pod_Embryo | Yellow_Pod_Cotyledon |
|---|---|---|---|---|
| PMON138776 | EXP-CUCme.Ubq1:1:1 | 1 | 12 | 9 |
| PMON138778 | EXP-CUCme.Ubq1:1:3 | 7 | 3 | 1 |
| PMON140818 | P-CUCme.1-1:1:1rc | 155 | 100.79 | 117.5 |
| pMON140819 | P-CUCme.2-1:1:1 | 14 | | |
| pMON140820 | P-CUCme.3-1:1:3 | 15 | | |
| pMON140821 | EXP-CUCme.4:1:1 | 156 | 86.68 | 225.53 |
| pMON140822 | EXP-CUCme.5:1:1 | 159 | 21.48 | 32.27 |
| pMON140823 | P-CUCme.6-1:1:1 | 18 | 38.75 | |
| pMON140824 | P-CUCme.8-1:1:2 | 19 | | |
| pMON140825 | P-CUCme.9-1:1:2 | 20 | 132.04 | |
| pMON140826 | P-CUCme.10-1:1:1 | 21 | | |
| pMON140827 | EXP-CUCme.eEF1a:1:1 | 162 | 200.28 | 291.26 |
| pMON140828 | P-CUCme.15-1:1:2 | 23 | | |
| pMON140830 | P-CUCme.17-1:1:2 | 26 | 343.34 | 302.94 |
| pMON140831 | P-CUCme.18-1:1:2 | 27 | 103.17 | 135.97 |
| pMON140832 | P-CUCme.19-1:1:3 | 167 | 30.96 | 64.46 |
| pMON140833 | P-CUCme.20-1:3 | 211 | 174.62 | 524.88 |
| pMON140834 | P-CUCme.21-1:1:1 | 30 | | |
| pMON140836 | EXP-CUCme.SAMS2:1:1 | 168 | 110.23 | 159.43 |
| pMON140837 | P-CUCme.26-1:1:2 | 33 | 56.73 | 50.06 |
| pMON140839 | EXP-CUCme.29:1:2 | 212 | 251.76 | 237.2 |
| pMON144926 | P-CUCme.CumMe_WSM_SF25355.G5000-1:1:1 | 196 | | |

TABLE 21-continued

Mean GUS expression in Yellow Pod Embryo, Yellow Pod Cotyledon, R3 Immature Seed, R3 Pod, R5 Cotyledon and R1 Flower of $R_0$ generation transformed soybean plants

| | | | | |
|---|---|---|---|---|
| pMON144927 | P-CUCme.CumMe_WSM_SF17111 .G5790-1:1:1 | 177 | 58.84 | 28.94 |
| pMON144928 | P-CUCme.CumMe_WSM_SF22531.G5120-1:1:1 | 192 | 135.62 | 152.48 |
| pMON144931 | P-CUCme.CumMe_WSM_SF18488.G5340-1:1:1 | 181 | 866.94 | |
| pMON144933 | P-CUCme.CumMe_WSM_SF23760.G5200-1:1:1 | 193 | | |
| pMON146941 | EXP-CUCme.WSM_SF19064.G5690:1:1 | 185 | | |
| pMON144932 | P-CUCme.WSM_SF17252.G7330-1:1:1 | 179 | | |
| pMON146940 | P-CUCme.CumMe_WSM_SF18634.G5190-1:1:1 | 183 | | |
| pMON147340 | P-CUCme.CumMe_WSM_SF19647.G5760-1:1:1 | 188 | | |
| pMON147342 | P-CUCme.CumMe_WSM_SF25936.G5450-1:1:1 | 197 | | |
| pMON147343 | P-CUCme.CumMe_WSM_SF19839.G5090-1:1:1 | 189 | | |
| pMON144929 | CumMe_WSM_SF206458.G5970 | 98 | | |
| pMON147304 | P-CUCme.CumMe_WSM_SF18716.G5860-1:1:1 | 184 | | |

| Construct | R3_Immature_Seed | R3_Pod | R5_Cotyledon | R1_Flower |
|---|---|---|---|---|
| PMON138776 | 13 | 11 | 10 | 7 |
| PMON138778 | 13 | 9 | 13 | 27 |
| PMON140818 | 38.31 | 84.72 | 132.27 | 66.8 |
| pMON140819 | | | 20.35 | 36.18 |
| pMON140820 | | | | |
| pMON140821 | 105.62 | 342.07 | 119.08 | 184.92 |
| pMON140822 | 21.47 | 21.66 | | 36.88 |
| pMON140823 | 23.03 | | 25.32 | 58.7 |
| pMON140824 | | | 90.33 | 25.77 |
| pMON140825 | | 20.56 | 34.78 | |
| pMON140826 | | | 22.34 | |
| pMON140827 | 58.21 | 131.17 | 114.29 | 130.38 |
| pMON140828 | 142.24 | 26.2 | | |
| pMON140830 | 65.55 | 80.94 | 137.02 | 62.7 |
| pMON140831 | 30 | 34.62 | 88.14 | 23.73 |
| pMON140832 | | 316.66 | | 53.46 |
| pMON140833 | | 222.04 | 59.43 | 124.68 |
| pMON140834 | 28.15 | 20.52 | 23.89 | |
| pMON140836 | 61.99 | 248.96 | 49.17 | 224.24 |
| pMON140837 | 70 | 143.05 | 25.06 | 49.92 |
| pMON140839 | 49.16 | 89.28 | 114.92 | 57.84 |
| pMON144926 | 21.41 | | 22.23 | |
| pMON144927 | | | 20.97 | |
| pMON144928 | 30.45 | 51.71 | 129.72 | 42.2 |
| pMON144931 | 23.26 | 21.49 | | |
| pMON144933 | 29.03 | 34.9 | 69.63 | 24.42 |
| pMON146941 | 36.69 | 83.08 | 89.81 | 33.99 |
| pMON144932 | 34.29 | 39.89 | 113.83 | 0 |
| pMON146940 | 30.25 | 0 | 0 | 0 |
| pMON147340 | 25.73 | 28.28 | 24.04 | 23.35 |
| pMON147342 | 104.02 | 80.27 | 31.06 | 26.8 |
| pMON147343 | | | | 29.09 |
| pMON144929 | 24.42 | 25.33 | | |
| pMON147304 | | 283.49 | | 61.43 |

As can be seen in Tables 20 and 21, the EXP sequences, EXP-CUCme.Ubq1:1:1 (SEQ ID NO: 1), EXP-CUCme.Ubq1:1:3 (SEQ ID NO: 7), P-CUCme.1-1:1:1rc (SEQ ID NO: 155), P-CUCme.2-1:1:1 (SEQ ID NO: 14), EXP- CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), EXP-CUCme-.SAMS2:1:1 (SEQ ID NO: 168), P-CUCme.26-1:1:2 (SEQ ID NO: 33), EXP-CUCme.29:1:2 (SEQ ID NO: 212), P-CUCme.CumMe_WSM_SF25355.G5000-1:1:1 (SEQ ID NO: 196), P-CUCme.CumMe_WSM_SF17111.G5790-1:1:1 (SEQ ID NO: 177), P-CUCme.CumMe_WSM_SF22531.G5120-1:1:1 (SEQ ID NO: 192), P-CUCme.CumMe_WSM_SF18488.G5340-1:1:1 (SEQ ID NO: 181), P-CUCme.CumMe_WSM_SF23760.G5200-1:1:1 (SEQ ID NO: 193), EXP-CUCme.WSM_SF19064.G5690:1:1 (SEQ ID NO: 185), P-CUCme.WSM_SF17252.G7330-1:1:1 (SEQ ID NO: 179), P-CUCme.CumMe_WSM_SF18634.G5190-1:1:1 (SEQ ID NO: 183), P-CUCme.CumMe_WSM_SF19647.G5760-1:1:1 (SEQ ID NO: 188), P-CUCme.CumMe_WSM_SF25936.G5450-1:1:1 (SEQ ID NO: 197), P-CUCme.CumMe_WSM_SF19839.G5090-1:1:1 (SEQ ID NO: 189), CumMe_WSM_SF206458.G5970 (SEQ ID NO: 98) and P-CUCme.CumMe_WSM_SF18716.G5860-1:1:1 (SEQ ID NO: 184) demonstrated quantitatively the capacity to drive transgene expression in some or all tissues assayed, depending upon the EXP sequence used to drive expression.

Histological analysis of selected tissue sections provided further evidence of expression for many of the EXP sequences. EXP-CUCme.Ubq1:1:1 (SEQ ID NO: 1) and EXP-CUCme.Ubq1:1:3 (SEQ ID NO: 7) demonstrated a constitutive expression pattern with staining observed in all tissues, even though quantitative analysis showed fairly low levels of expression. This type of expression pattern can be most adventitious to driving expression of transgenes that require a low level of constitutive expression. Expression driven by P-CUCme.1-1:1:1rc (SEQ ID NO: 155) demonstrated expression in sink and source leaf vascular bundles and xylem and in the root cortex, phloem, xylem, endodermis, stele and tip. Expression driven by EXP-CUCme.4:1:1 (SEQ ID NO: 156) was observed in all tissues with the highest expression observed in the reproductive phase of the plant. Expression driven by P-CUCme.10-1:1:1 (SEQ ID NO: 21) was observed only in in V5 Sink Leaf and R1 Flower anthers. Expression driven by EXP-CUCme.eEF1a:1:1 (SEQ ID NO: 162) demonstrated a consititutive expression pattern with highest expression being observed in yellow pod embryo and cotyledon. The yellow pod embryo activity was 5 fold higher in the R1 generation than in the R0 generation (see Table 23 below). Expression driven by P-CUCme.15-1:1:2 (SEQ ID NO: 23), P-CUCme.17-1:1:2 (SEQ ID NO: 26) and P-CUCme.18-1:1:2 (SEQ ID NO: 27) demonstrated a constitutive level of expression histologically. Expression driven by P-CUCme.19-1:1:3 (SEQ ID NO: 167) demonstrated a constitutive pattern of expression histologically with the exception of the V5 root and R1 petiole. R3 pod showed the highest expression.

Expression driven by P-CUCme.20-1:3 (SEQ ID NO: 211) demonstrated a constitutive expression pattern histologically with the exception of expression in V5 root. Expression was highest in the R8 stage cotyledon. Expression driven by EXP-CUCme.SAMS2:1:1 (SEQ ID NO: 168) demonstrated a constitutive pattern of expression with expression observed histologically in all tissues. GUS expression was observed to increase in the R1 generation (see Tables 22 and 23 below). The R1 stage flowers and petioles demonstrated the highest levels of expression in soybean. Expression driven by P-CUCme.CumMe_WSM_SF22531.G5120-1:1:1 (SEQ ID NO: 192) demonstrated a constitutive pattern of expression histologically with highest expression in the R8 stage cotyledon and embryo. Expression driven by P-CUCme.CumMe_WSM_SF18488.G5340-1:1:1 (SEQ ID NO: 181) demonstrated a constitutive level of expression while quantitatively high expression was observed in the yellow pod embryo.

$R_0$ generation plants transformed with the plasmid constructs comprising EXP-CUCme.eEF1a:1:1 (SEQ ID NO: 162) and EXP-CUCme.SAMS2:1:1 (SEQ ID NO: 168) were allowed to set seed and the $R_1$ generation plants analyzed for GUS expression. The $R_1$ generation plants were analyzed for expression in Vn5 Root, Vn5 Sink Leaf, Vn5 Source Leaf, R1 Source Leaf, R1 Petiole Yellow Pod Embryo, Yellow Pod Cotyledon, R3 Immature Seed, R3 Pod, R5 Cotyledon and R1 Flower. Tables 22 and 23 show the mean GUS expression measured in each tissue of the $R_1$ generation transformed plants.

TABLE 22

Mean GUS expression in Vn5 Root, Vn5 Sink Leaf, Vn5 Source Leaf, R1 Source Leaf, R1 Petiole of $R_1$ generation transformed soybean plants

| Construct | Regulatory Element | SEQ ID NO: | Vn5_Root | Vn5_Sink_Leaf | Vn5_Source Leaf | R1_Source_Leaf | R1_Petiole |
|---|---|---|---|---|---|---|---|
| pMON140827 | EXP-CUCme.eEF1a:1:1 | 162 | 145.84 | 50.24 | 43.73 | 107.98 | 357.67 |
| PMON140836 | EXP-CUCme.SAMS2:1:1 | 168 | 260.41 | 65.52 | 51.12 | 129.86 | 623.42 |

TABLE 23

Mean GUS expression in Yellow Pod Embryo, Yellow Pod Cotyledon, R3 Immature Seed, R3 Pod, R5 Cotyledon, R1 Flower of $R_1$ generation transformed soybean plants

| Construct | Regulatory Element | SEQ ID NO: | Yellow_Pod_Embryo | Yellow_Pod_Cotyledon |
|---|---|---|---|---|
| pMON140827 | EXP-CUCme.eEF1a:1:1 | 162 | 1098.51 | 764.83 |
| pMON140836 | EXP-CUCme.SAMS2:1:1 | 168 | 219.04 | 291.58 |

| Construct | R3_Immature_Seed | R3_Pod | R5_Cotyledon | R1_Flower |
|---|---|---|---|---|
| pMON140827 | 288.77 | 214.6 | 459.62 | 394.77 |
| pMON140836 | 241.48 | 382.73 | 397.91 | 653.23 |

As can be seen in Tables 22 and 23 above expression driven in $R_1$ generation by EXP-CUCme.eEF1a:1:1 (SEQ ID NO: 162) and EXP-CUCme.SAMS2:1:1 (SEQ ID NO: 168) shows a constitutive level of expression with increase in expression observed in many tissues at $R_1$ generation relative to $R_0$ generation.

* * *

Having illustrated and described the principles of the present invention, it should be apparent to persons skilled in the art that the invention can be modified in arrangement and detail without departing from such principles. All modifications that are within the spirit and scope of the claims are intended to be included within the scope of the present invention. All publications and published patent documents cited herein are hereby incorporated by reference to the same extent as if each individual publication or patent application is specifically and individually indicated to be incorporated by reference.

What is claimed is:

1. A DNA molecule exhibiting a gene regulatory functional activity comprising a polynucleotide sequence selected from the group consisting of:
 - a) a sequence with at least 95 percent sequence identity to any one of SEQ ID NOs: 1, 2, 5, 6, 7, 8, 9, 10, 11, and 12, and exhibiting promoter activity;
 - b) a sequence comprising any one of SEQ ID NOs: 1, 2, 5, 6, 7, 8, 9, 10, 11, and 12;

and
 - c) a fragment of any one of SEQ ID NOs: 1, 2, 5, 6, 7, 8, 9, 10, and 11, wherein said fragment comprises SEQ ID NO: 12, and exhibiting promoter activity;

wherein said DNA molecule is operably linked to a heterologous transcribable polynucleotide molecule.

2. The DNA molecule of claim 1, wherein the heterologous transcribable polynucleotide molecule comprises a gene of agronomic interest.

3. The DNA molecule of claim 2, wherein the gene of agronomic interest confers herbicide tolerance in plants.

4. The DNA molecule of claim 2, wherein the gene of agronomic interest confers pest resistance in plants.

5. A transgenic plant cell comprising a DNA molecule exhibiting a gene regulatory functional activity comprising a polynucleotide sequence selected from the group consisting of:
 - a) a sequence with at least 95 percent sequence identity to any one of SEQ ID NOs: 1, 2, 5, 6, 7, 8, 9, 10, 11, and 12, and exhibiting promoter activity;

b) a sequence comprising any one of SEQ ID NOs: 1, 2, 5, 6, 7, 8, 9, 10, 11, and 12;

and c) a fragment of any one of SEQ ID NOs: 1, 2, 5, 6, 7, 8, 9, 10, and 11, wherein said fragment comprises SEQ ID NO: 12, and exhibiting promoter activity;

wherein said DNA molecule is operably linked to a heterologous transcribable polynucleotide molecule.

6. The transgenic plant cell of claim 5, wherein said transgenic plant cell is a monocotyledonous plant cell.

7. The transgenic plant cell of claim 5, wherein said transgenic plant cell is a dicotyledonous plant cell.

8. A transgenic plant, or part thereof, comprising a DNA molecule exhibiting a gene regulatory functional activity comprising a polynucleotide sequence selected from the group consisting of:

a) a sequence with at least 95 percent sequence identity to any one of SEQ ID NOs: 1, 2, 5, 6, 7, 8, 9, 10, 11, and 12, and exhibiting promoter activity;

b) a sequence comprising any one of SEQ ID NOs: 1, 2, 5, 6, 7, 8, 9, 10, 11, and 12;

and c) a fragment of any one of SEQ ID NOs: 1, 2, 5, 6, 7, 8, 9, 10, and 11, wherein said fragment comprises SEQ ID NO: 12, and exhibiting promoter activity;

wherein said DNA molecule is operably linked to a heterologous transcribable polynucleotide molecule.

9. A progeny plant of the transgenic plant of claim 8, or part thereof, wherein the progeny plant or part thereof comprises said DNA molecule exhibiting a gene regulatory functional activity.

10. A transgenic seed comprising a DNA molecule exhibiting a gene regulatory functional activity comprising a polynucleotide sequence selected from the group consisting of:

a) a sequence with at least 95 percent sequence identity to any one of SEQ ID NOs: 1, 2, 5, 6, 7, 8, 9, 10, 11, and 12, and exhibiting promoter activity;

b) a sequence comprising any one of SEQ ID NOs: 1, 2, 5, 6, 7, 8, 9, 10, 11, and 12;

and c) a fragment of any one of SEQ ID NOs: 1, 2, 5, 6, 7, 8, 9, 10, and 11, wherein said fragment comprises SEQ ID NO: 12, and exhibiting promoter activity;

wherein said DNA molecule is operably linked to a heterologous transcribable polynucleotide molecule.

11. A method of producing a commodity product comprising:

a) obtaining a transgenic plant or part thereof comprising a DNA molecule exhibiting a gene regulatory functional activity comprising a polynucleotide sequence selected from the group consisting of:

1) a sequence with at least 95 percent sequence identity to any one of SEQ ID NOs: 1, 2, 5, 6, 7, 8, 9, 10, 11, and 12, and exhibiting promoter activity;

2) a sequence comprising any one of SEQ ID NOs: 1, 2, 5, 6, 7, 8, 9, 10, 11, and 12;

and 3) a fragment of any one of SEQ ID NOs: 1, 2, 5, 6, 7, 8, 9, 10, and 11, wherein said fragment comprises SEQ ID NO: 12, and exhibiting promoter activity;

wherein said DNA molecule is operably linked to a heterologous transcribable polynucleotide molecule; and b) producing the commodity product from the transgenic plant or part thereof.

12. The method of claim 11, wherein the commodity product is protein concentrate, protein isolate, grain, starch, seeds, meal, flour, biomass, or seed oil.

13. A commodity product comprising a DNA molecule exhibiting a gene regulatory functional activity comprising a polynucleotide sequence selected from the group consisting of:

a) a sequence with at least 95 percent sequence identity to any one of SEQ ID NOs: 1, 2, 5, 6, 7, 8, 9, 10, 11, and 12, and exhibiting promoter activity;

b) a sequence comprising any one of SEQ ID NOs: 1, 2, 5, 6, 7, 8, 9, 10, 11, and 12;

and c) a fragment of any one of SEQ ID NOs: 1, 2, 5, 6, 7, 8, 9, 10, and 11, wherein said fragment comprises SEQ ID NO: 12, and exhibiting promoter activity;

wherein said DNA molecule is operably linked to a heterologous transcribable polynucleotide molecule.

14. A method of expressing a heterologous transcribable polynucleotide molecule comprising:

a) obtaining a transgenic plant comprising a DNA molecule exhibiting a gene regulatory functional activity comprising a polynucleotide sequence selected from the group consisting of:

1) a sequence with at least 95 percent sequence identity to any one of SEQ ID NOs: 1, 2, 5, 6, 7, 8, 9, 10, 11, and 12, and exhibiting promoter activity;

2) a sequence comprising any one of SEQ ID NOs: 1, 2, 5, 6, 7, 8, 9, 10, 11, and 12;

and 3) a fragment of any one of SEQ ID NOs: 1, 2, 5, 6, 7, 8, 9, 10, and 11, wherein said fragment comprises SEQ ID NO: 12, and exhibiting promoter activity;

wherein said DNA molecule 1s operably linked to the heterologous transcribable polynucleotide molecule; and b) cultivating said transgenic plant, wherein the heterologous transcribable polynucleotide is expressed.

* * * * *